(12) United States Patent
Singh et al.

(10) Patent No.: US 8,993,585 B2
(45) Date of Patent: Mar. 31, 2015

(54) CYCLIC AMINE SUBSTITUTED PYRIMIDINEDIAMINES AS PKC INHIBITORS

(75) Inventors: Rajinder Singh, Belmont, CA (US); Hui Li, Santa Clara, CA (US); Haoran Zhao, Foster City, CA (US); Donald Payan, Hillsborough, CA (US); Rao Kolluri, Foster City, CA (US); Kin Tso, San Francisco, CA (US); John Ramphal, Union City, CA (US); Shihai Gu, Union City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1620 days.

(21) Appl. No.: 12/175,441

(22) Filed: Jul. 17, 2008

(65) Prior Publication Data

US 2010/0130486 A1 May 27, 2010

Related U.S. Application Data

(60) Provisional application No. 60/950,309, filed on Jul. 17, 2007, provisional application No. 60/985,184, filed on Nov. 2, 2007, provisional application No. 61/049,750, filed on May 1, 2008.

(51) Int. Cl.
| | | |
|---|---|---|
| C07D 401/12 | (2006.01) | |
| C07D 239/48 | (2006.01) | |
| C07D 401/14 | (2006.01) | |
| C07D 407/14 | (2006.01) | |
| C07D 413/14 | (2006.01) | |
| C07D 417/14 | (2006.01) | |
| C07D 498/04 | (2006.01) | |

(52) U.S. Cl.
CPC ............ *C07D 401/12* (2013.01); *C07D 239/48* (2013.01); *C07D 401/14* (2013.01); *C07D 407/14* (2013.01); *C07D 413/14* (2013.01); *C07D 417/14* (2013.01); *C07D 498/04* (2013.01)
USPC .......................................... 514/275; 544/297

(58) Field of Classification Search
CPC .................................................... C07D 401/12
USPC .......................................... 514/275; 544/297
See application file for complete search history.

(56) References Cited

U.S. PATENT DOCUMENTS

| | | | |
|---|---|---|---|
| 5,958,935 | A | 9/1999 | Davis et al. |
| 6,235,746 | B1 | 5/2001 | Davis et al. |
| 6,908,920 | B2 | 6/2005 | Thomas et al. |
| 7,060,827 | B2 | 6/2006 | Singh et al. |
| 7,109,335 | B2 | 9/2006 | Kath et al. |
| 7,109,337 | B2 | 9/2006 | Kath et al. |
| 7,122,542 | B2 | 10/2006 | Singh et al. |
| 7,173,028 | B2 | 2/2007 | Dahmann et al. |
| 7,329,671 | B2 | 2/2008 | Singh et al. |
| 7,329,672 | B2 | 2/2008 | Singh et al. |
| 7,332,484 | B2 | 2/2008 | Singh et al. |
| 7,351,712 | B2 | 4/2008 | Kath et al. |
| 7,674,796 | B2 | 3/2010 | Kath et al. |
| 2003/0139435 | A1 | 7/2003 | Ahmed et al. |
| 2004/0029902 | A1 | 2/2004 | Singh et al. |
| 2005/0209230 | A1 | 9/2005 | Singh et al. |
| 2005/0234049 | A1 | 10/2005 | Singh et al. |
| 2005/0272753 | A1 | 12/2005 | Nagashima et al. |
| 2006/0058525 | A1 | 3/2006 | Singh et al. |
| 2006/0100211 | A1 | 5/2006 | Dahmann et al. |
| 2006/0135543 | A1 | 6/2006 | Singh et al. |
| 2006/0167254 | A1 | 7/2006 | Cooper et al. |
| 2006/0211657 | A1 | 9/2006 | Singh et al. |
| 2006/0234983 | A1 | 10/2006 | Singh et al. |
| 2006/0270694 | A1 | 11/2006 | Wong |
| 2006/0293311 | A1 | 12/2006 | Li et al. |
| 2007/0004626 | A1 | 1/2007 | Masuda et al. |
| 2007/0060603 | A1 | 3/2007 | Singh et al. |
| 2007/0117775 | A1 | 5/2007 | Payan |
| 2007/0129360 | A1 | 6/2007 | Bhamidipati et al. |
| 2007/0129362 | A1 | 6/2007 | Bhamidipati et al. |
| 2007/0167439 | A1 | 7/2007 | Singh et al. |
| 2007/0197782 | A1 | 8/2007 | Clough et al. |
| 2007/0203161 | A1 | 8/2007 | Argade et al. |
| 2007/0203162 | A1 | 8/2007 | Li et al. |
| 2007/0225321 | A1 | 9/2007 | Singh et al. |
| 2007/0225495 | A1 | 9/2007 | Singh et al. |
| 2007/0293494 | A1 | 12/2007 | Djung et al. |
| 2007/0293520 | A1 | 12/2007 | Singh et al. |

(Continued)

FOREIGN PATENT DOCUMENTS

| | | |
|---|---|---|
| CA | 2490888 | 1/2004 |
| CA | 2463989 A1 | 4/2004 |

(Continued)

OTHER PUBLICATIONS van De Waterbeemd H, Smith DA, Beaumont K, and Walker DK, "Property-based design: optimization of drug absorption and pharmacokinetics," Journal of Medicinal Chemistry, Apr. 2001,44(9), 1313-1333.*
Vippagunta SR, Brittain HG, and Grant D J, "Crystalline solids," Advanced Drug Delivery Reviews, May 2001,48(1), 3-26.*
U.S. Appl. No. 11/539,142, filed Oct. 5, 2006, Singh et al.
U.S. Appl. No. 11/539,074, filed Oct. 5, 2006, Singh et al.
U.S. Appl. No. 11/782,581, filed Jul. 24, 2007, Singh et al.
U.S. Appl. No. 11/875,772, filed Oct. 19, 2007, Li et al.
U.S. Appl. No. 11/943,506, filed Nov. 20, 2007, Bhamidipati et al.
U.S. Appl. No. 12/028,581, filed Feb. 8, 2008, Argade et al.
U.S. Appl. No. 12/030,031, filed Feb. 12, 2008, Li et al.
U.S. Appl. No. 12/053,382, filed Mar. 21, 2008, Atuegbu et al.

(Continued)

*Primary Examiner* — Paul Zarek
(74) *Attorney, Agent, or Firm* — Rudy J. Ng; Carol L. Francis; Bozicevic, Field & Francis LLP

(57) ABSTRACT

The invention encompasses compounds having formula I or II and the compositions and methods using these compounds in the treatment of conditions in which inhibition of PKC and PKD is therapeutically useful.

29 Claims, No Drawings

(56) References Cited

U.S. PATENT DOCUMENTS

| | | |
|---|---|---|
| 2007/0293521 A1 | 12/2007 | Singh et al. |
| 2007/0293522 A1 | 12/2007 | Singh et al. |
| 2007/0293523 A1 | 12/2007 | Singh et al. |
| 2007/0293524 A1 | 12/2007 | Singh et al. |
| 2007/0299095 A1 | 12/2007 | Singh et al. |
| 2008/0221089 A1 | 9/2008 | Argade et al. |

FOREIGN PATENT DOCUMENTS

| | | |
|---|---|---|
| EP | 2186803 | 5/2010 |
| WO | WO 97/19065 A1 | 5/1997 |
| WO | WO 03/032997 A1 | 4/2003 |
| WO | WO 03/063794 | 8/2003 |
| WO | WO 03/106451 | 12/2003 |
| WO | WO 2004/002964 A1 | 1/2004 |
| WO | WO 2004/014382 | 2/2004 |
| WO | WO 2004/056786 A2 | 7/2004 |
| WO | WO 2004/056807 | 7/2004 |
| WO | WO 2004/067516 | 8/2004 |
| WO | WO 2004/089913 | 10/2004 |
| WO | WO 2005/013996 | 2/2005 |
| WO | WO 2005/016893 | 2/2005 |
| WO | WO 2006/133426 | 12/2006 |
| WO | WO 2007/053452 | 5/2007 |
| WO | WO 2007/072158 | 6/2007 |
| WO | WO 2007/076427 | 7/2007 |
| WO | 2009056069 | 5/2009 |
| WO | 2009080694 | 7/2009 |

OTHER PUBLICATIONS

U.S. Appl. No. 12/053,438, filed Mar. 21, 2008, Li et al.
U.S. Appl. No. 12/175,441, filed Jul. 17, 2008, Singh et al.
U.S. Appl. No. 12/193,627, filed Aug. 18, 2008, Li et al.
U.S. Appl. No. 12/199,705, filed Aug. 27, 2008, Singh et al.
U.S. Appl. No. 12/268,235, filed Nov. 10, 2008, Singh et al.
U.S. Appl. No. 12/268,218, filed Nov. 10, 2008, Singh et al.
U.S. Appl. No. 12/273,357, filed Nov. 18, 2008, Singh et al.
U.S. Appl. No. 12/363,537, filed Jan. 30, 2009, Singh et al.
U.S. Appl. No. 12/260,886, filed Oct. 29, 2008, Cooper et al.

* cited by examiner

CYCLIC AMINE SUBSTITUTED PYRIMIDINEDIAMINES AS PKC INHIBITORS

CROSS-REFERENCE TO RELATED APPLICATIONS

This application claims the benefit of U.S. provisional patent application No. 60/950,309 filed 17 Jul. 2007, of U.S. provisional patent application No. 60/985,184, filed 2 Nov. 2007, and of U.S. provisional patent application No. 61/049,750, filed 1 May 2008, each of which is incorporated herein by reference in its entirety.

INTRODUCTION

1. Field

The present invention relates to compounds, prodrugs, and methods of using these compounds and prodrugs thereof in the treatment of conditions in which modulation or inhibition of Protein Kinase C (also known as PKC) is therapeutically useful. This invention also relates to pharmaceutical compositions comprising these compounds, methods of using these compounds in the treatment of various diseases and disorders, processes for preparing these compounds and intermediates useful in these processes.

2. Background

Protein kinases constitute a large family of structurally related enzymes that are responsible for the control of a variety of signal transduction processes within cells (see, e.g., Hardie and Hanks, *The Protein Kinase Facts Book*, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), *FASEB J.* 9:576-596; Knighton et al., (1991), *Science* 253:407-414; Hiles et al., (1992), *Cell* 70:419-429; Kunz et al., (1993), *Cell* 73:585-596; Garcia-Bustos et al., (1994), *EMBO J.* 13:2352-2361).

The Protein Kinase C family is a group of serine/threonine kinases including at least twelve related isoenzymes, including alpha, beta 1, beta 2, gamma, delta, epsilon, nu, lambda, mu, theta and zeta. When activated, the isozymes bind to membrane phospholipids or to membrane receptors and anchor the enzymes in a subcellular compartment (reviewed in Liu and Heckman, Cell. Signal, 1998, 10, 529-542). Protein Kinase C isozymes differ in number and expression level in different cell lines and tissues. The isoenzymes have been divided into three groups based on their differential expression patterns and cofactor requirements. The classical PKC enzymes (cPKC), including alpha, betel, beta 2 and gamma isozymes, require diacylglycerol (DAG), phosphatidylserine (PS) and calcium for activation. The novel PKC's (nPKC), including delta, epsilon, theta and eta isozymes, require DAG and PS but are calcium independent. The atypical PKC's (aPKC), including zeta, lambda/iota do not require calcium or DAG.

Protein kinase C's in general are commonly known to be related to cell proliferation, differentiation, metabolism, and apoptosis, and to have many roles in the radiation-induced cellular responses involving apoptosis. However, PKC-theta is primarily implicated in T cell activation and regulation of immune responses and in insulin resistance in skeletal muscle. PKC-epsilon and a related kinase, PKC-mu (or PKD1) are implicated in a variety of activities including sensitisation of the transient receptor potential vanilloid 4 (TRPV4), a neural ion channel involved in PAR-mediated pain.

In view of the numerous conditions that may benefit by treatment involving modulation of PKC it is immediately apparent that new compounds that modulate PKC and methods of using these compounds should provide substantial therapeutic benefits to a wide variety of patients. Provided herein are novel 2,4-pyrimidinediamine compounds for use in the treatment of conditions in which inhibition of PKC, is therapeutically useful.

SUMMARY OF THE INVENTION

One aspect of the invention provides compounds of formula I, solvates, N-oxides, prodrugs and therapeutically acceptable salts thereof:

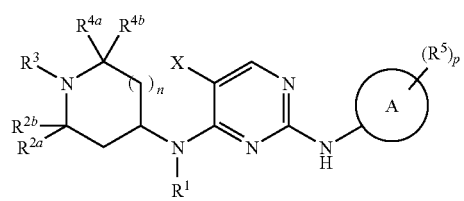

I wherein:
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;

$R^1$ is selected from the group consisting of hydrogen, lower alkyl, substituted lower alkyl, aryl, substituted aryl, heteroaryl, and substituted heteroaryl;

each $R^{2a}$, $R^{2b}$, $R^{4a}$ and $R^{4b}$ independently is selected from the group consisting of hydrogen and $C_{1-3}$ alkyl;

$R^3$ is selected from the group consisting of —Y, —C(O)—Y, —SO$_2$—Y, —(CH$_2$)$_m$—C(O)—Y, —CH=CH—C(O)—Y and —(CH$_2$)$_m$—NY$_2$, wherein each Y independently is hydrogen, hydroxy, oxy radical, alkoxy, alkyl, or substituted alkyl and m is 1, 2, or 3;

A is selected from the group consisting of bicyclic aryl, bicyclic heteroaryl, tricyclic aryl, tricyclic heteroaryl and

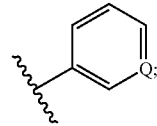

each $R^5$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;
n is an integer between 0 and 3;
p is an integer between 0 and 5; and
Q is N, N→O, or CR$^{7b}$;
provided that,
(1) when X is fluoro, n is zero or one, and A-(R$^5$)$_p$ is of the formula:

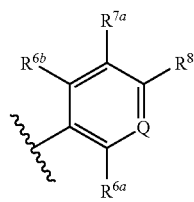

where each of R$^{6a}$, R$^{6b}$, R$^{7a}$, R$^{7b}$ and R$^8$ is independently R$^5$;
then
R$^{6a}$ or R$^{6b}$ is not hydrogen; or
R$^{7a}$ or R$^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or
R$^8$ is selected from the group consisting of substituted alkyl but not CF$_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and
(2) when A is tricyclic heteroaryl and X is halo, then at least one of R$^{2a}$, R$^{2b}$, R$^{4a}$ and R$^{4b}$ is not hydrogen; and
(3) when X is nitro, CF$_3$, or C(O)NH$_2$, then at least one of R$^{2a}$, R$^{2b}$, R$^{4a}$ and R$^{4b}$ is not hydrogen; and
(4) when X is bromo and R$^2$ is idolin-2-one-5-yl, then at least one of R$^{2a}$, R$^{2b}$, R$^{4a}$ and R$^{4b}$ is not hydrogen; and
(5) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

In one implementation, this invention relates to a compound of formula II, as well as solvates, prodrugs or therapeutically acceptable salts thereof:

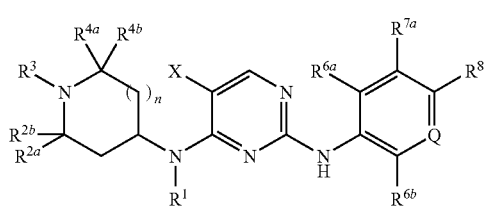

wherein:
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
Q is N, N→O, or CR$^{7b}$;
n is an integer between 0 and 3;
R$^1$ is selected from the group consisting of hydrogen, lower alkyl, substituted lower alkyl, aryl, substituted aryl, heteroaryl, and substituted heteroaryl;
R$^{2a}$, R$^{2b}$, R$^{4a}$ and R$^{4b}$ each independently is selected from the group consisting of hydrogen and C$_{1-3}$ alkyl;
R$^3$ is selected from the group consisting of —Y, —C(O)—Y, —SO$_2$—Y, —(CH$_2$)$_m$—C(O)—Y, —CH=CH—C(O)—Y and —(CH$_2$)$_m$—NY$_2$, wherein each Y independently is hydrogen, hydroxy, oxy radical, alkoxy, alkyl, or substituted alkyl and m is 1, 2, or 3;
each of R$^{6a}$, R$^{6b}$ R$^{7a}$, R$^{7b}$ and R$^8$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, sulfonyl, sulfonylamino, and aminosulfonyl;
provided that,
(1) when X is fluoro, and n is zero or one, then:
R$^{6a}$ or R$^{6b}$ is not hydrogen; or
R$^{7a}$ or R$^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or
R$^8$ is selected from the group consisting of substituted alkyl but not CF$_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and
(2) when X is nitro, CF$_3$, or C(O)NH$_2$, then at least one of R$^{2a}$, R$^{2b}$, R$^{4a}$ and R$^{4b}$ is not hydrogen; and
(3) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

Another embodiment of this invention relates to a method of inhibiting an activity of a Protein Kinase C theta, comprising contacting the Protein Kinase C theta with an amount of a compound effective to inhibit the activity of the Protein Kinase C theta wherein the compound is a compound of formula I as described above.

Another embodiment of this invention relates to a method of treating a disorder mediated by a Protein Kinase C theta, comprising administering to a patient in need thereof an amount of a compound effective to treat the disorder wherein the compound is a compound of formula I as described above.

Another embodiment of this invention relates to a compound selected from the group consisting of I-39, I-40, I-41, I-42, I-43, I-47, I-48, I-49, I-50, I-51, I-53, I-54, I-55, I-56, I-57, I-59, I-60, I-61, I-62, I-63, I-65, I-67, I-68, I-100, I-245; I-246, I-247, I-248, I-249, I-250, I-251, I-252, I-253, I-254, I-255, I-256, I-257, I-258, I-259, and I-260, or a solvate, N-oxide, prodrug or therapeutically acceptable salt thereof.

Another embodiment of this invention relates to a method of inhibiting an activity of a Protein Kinase C theta, comprising contacting the Protein Kinase C theta with an amount of a compound effective to inhibit the activity of the Protein Kinase C theta wherein the compound is selected from the group consisting of I-39, I-40, I-41, I-42, I-43, I-47, I-48, I-49, I-50, I-51, I-53, I-54, I-55, I-56, I-57, I-59, I-60, I-61, I-62, I-63, I-65, I-67, I-68, I-100, I-245; I-246, I-247, I-248, I-249, I-250, I-251, I-252, I-253, I-254, I-255, I-256, I-257, I-258, I-259, and I-260, or a solvate, N-oxide, prodrug or therapeutically acceptable salt thereof.

Another embodiment of this invention relates to a method of treating a disorder mediated by a Protein Kinase C theta, comprising administering to a patient in need thereof an amount of a compound effective to treat the disorder wherein the compound is selected from the group consisting of I-39, I-40, I-41, I-42, I-43, I-47, I-48, I-49, I-50, I-51, I-53, I-54, I-55, I-56, I-57, I-59, I-60, I-61, I-62, I-63, I-65, I-67, I-68, I-100, I-245; I-246, I-247, I-248, I-249, I-250, I-251, I-252, I-253, I-254, I-255, I-256, I-257, I-258, I-259, and I-260, or a solvate, N-oxide, prodrug or therapeutically acceptable salt thereof.

Another embodiment of this invention relates to a method of inhibiting an activity of a Protein Kinase C theta, comprising contacting the Protein Kinase C theta with an amount of a compound effective to inhibit the activity of the Protein Kinase C theta wherein the compound is a compound of formula I:

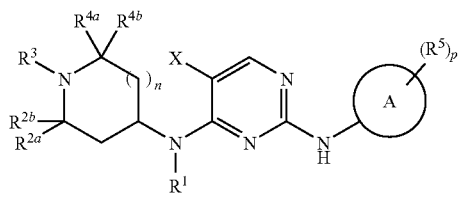

a solvate, N-oxide, prodrug or therapeutically acceptable salt thereof
wherein:
A is aryl or heteroaryl;
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
$R^1$ is selected from the group consisting of hydrogen, lower alkyl, substituted lower alkyl, aryl, substituted aryl, heteroaryl, and substituted heteroaryl;
$R^{2a}$, $R^{2b}$, $R^{4a}$ and $R^{4b}$ each independently is selected from the group consisting of hydrogen and $C_{1-3}$ alkyl;
$R^3$ is selected from the group consisting of —Y, —C(O)—Y, —SO$_2$—Y, —(CH$_2$)$_m$—C(O)—Y, —CH=CH—C(O)—Y and —(CH$_2$)$_m$—NY$_2$, wherein each Y independently is hydrogen, hydroxy, oxy radical, alkoxy, alkyl, or substituted alkyl and m is 1, 2, or 3;
each $R^5$ independently is selected from the group consisting of alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, sulfonyl, sulfonylamino, and aminosulfonyl;
n is an integer between 0 and 3; and
p is an integer between 0 and 5.

Another embodiment of this invention relates to a method of inhibiting an activity of a Protein Kinase C theta, comprising contacting the Protein Kinase C theta with an amount of a compound effective to inhibit the activity of the Protein Kinase C theta wherein the compound is a compound of formula I:

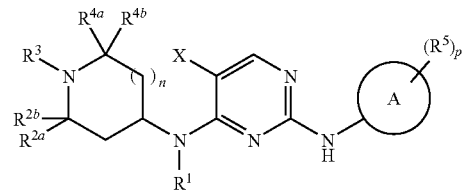

wherein:
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
$R^1$ is selected from the group consisting of hydrogen, lower alkyl, substituted lower alkyl, aryl, substituted aryl, heteroaryl, and substituted heteroaryl;
each $R^{2a}$, $R^{2b}$, $R^{4a}$ and $R^{4b}$ independently is selected from the group consisting of hydrogen and $C_{1-3}$ alkyl;
$R^3$ is selected from the group consisting of —Y, —C(O)—Y, —SO$_2$—Y, —(CH$_2$)$_m$—C(O)—Y, —CH=CH—C(O)—Y and —(CH$_2$)$_m$—NY$_2$, wherein each Y independently is hydrogen, hydroxy, oxy radical, alkoxy, alkyl, or substituted alkyl and m is 1, 2, or 3;
A is selected from the group consisting of bicyclic aryl, bicyclic heteroaryl, tricyclic aryl, tricyclic heteroaryl and

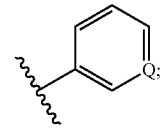

each $R^5$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;
n is an integer between 0 and 3;
p is an integer between 0 and 5; and
Q is N, N→O, or $CR^{7b}$;
provided that,
(1) when X is fluoro, n is zero or one, and A-($R^5$)$_p$ is of the formula:

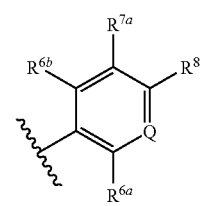

where each of $R^{6a}$, $R^{6b}$, $R^{7a}$, $R^{7b}$ and $R^8$ is independently $R^5$;
then
$R^{6a}$ or $R^{6b}$ is not hydrogen; or
$R^{7a}$ or $R^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or
$R^8$ is selected from the group consisting of substituted alkyl but not $CF_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and (2) when A is tricyclic heteroaryl and X is halo, then at least one of $R^{2a}$, $R^{2b}$, $R^{4a}$ and $R^{4b}$ is not hydrogen; and (3) when X is nitro, $CF_3$, or $C(O)NH_2$, then at least one of $R^{2a}$, $R^{2b}$, $R^{4a}$ and $R^{4b}$ is not hydrogen; and (4) when X is bromo and $R^2$ is idolin-2-one-5-yl, then at least one of $R^{2a}$, $R^{2b}$, $R^{4a}$ and $R^{4b}$ is not hydrogen; and (5) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

Another embodiment of this invention relates to a method of treating a disorder mediated by a Protein Kinase C theta, comprising administering to a patient in need thereof a therapeutically effective amount of a compound effective to treat the disorder wherein the compound is a compound of formula I:

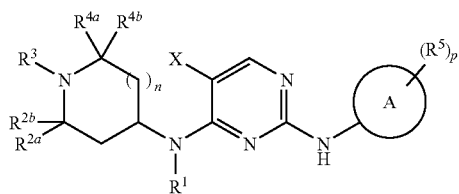

a solvate, N-oxide, prodrug or therapeutically acceptable salt thereof
wherein
A is aryl or heteroaryl;
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
$R^1$ is selected from the group consisting of hydrogen, lower alkyl, substituted lower alkyl, aryl, substituted aryl, heteroaryl, and substituted heteroaryl;
$R^{2a}$, $R^{2b}$, $R^{4a}$ and $R^{4b}$ each independently is selected from the group consisting of hydrogen and $C_{1-3}$ alkyl;
$R^3$ is selected from the group consisting of —Y, —C(O)—Y, —$SO_2$—Y, —$(CH_2)_m$—C(O)—Y, —CH═CH—C(O)—Y and —$(CH_2)_m$—$NY_2$, wherein each Y independently is hydrogen, hydroxy, oxy radical, alkoxy, alkyl, or substituted alkyl and m is 1, 2, or 3;
each $R^5$ independently is selected from the group consisting of alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, sulfonyl, sulfonylamino, and aminosulfonyl;
n is an integer between 0 and 3; and
p is an integer between 0 and 5.

Another embodiment of this invention relates to a method of treating a disorder mediated by a Protein Kinase C theta, comprising administering to a patient in need thereof a therapeutically effective amount of a compound effective to treat the disorder wherein the compound is a compound of formula I:

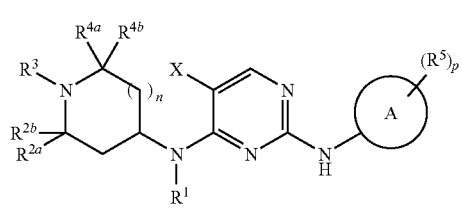

wherein:
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
$R^1$ is selected from the group consisting of hydrogen, lower alkyl, substituted lower alkyl, aryl, substituted aryl, heteroaryl, and substituted heteroaryl;
each $R^{2a}$, $R^{2b}$, $R^{4a}$ and $R^{4b}$ independently is selected from the group consisting of hydrogen and $C_{1-3}$ alkyl;
$R^3$ is selected from the group consisting of —Y, —C(O)—Y, —$SO_2$—Y, —$(CH_2)_m$—C(O)—Y, —CH═CH—C(O)—Y and —$(CH_2)_m$—$NY_2$, wherein each Y independently is hydrogen, hydroxy, oxy radical, alkoxy, alkyl, or substituted alkyl and m is 1, 2, or 3;
A is selected from the group consisting of bicyclic aryl, bicyclic heteroaryl, tricyclic aryl, tricyclic heteroaryl and

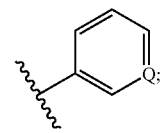

each $R^5$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;
n is an integer between 0 and 3;
p is an integer between 0 and 5; and
Q is N, N→O, or $CR^{7b}$;

provided that,
(1) when X is fluoro, n is zero or one, and A-(R⁵)ₚ is of the formula:

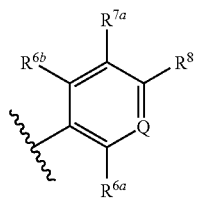

where each of $R^{6a}$, $R^{6b}$, $R^{7a}$, $R^{7b}$ and $R^8$ is independently $R^5$;
then
$R^{6a}$ or $R^{6b}$ is not hydrogen; or
$R^{7a}$ or $R^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or
$R^8$ is selected from the group consisting of substituted alkyl but not $CF_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and
(2) when A is tricyclic heteroaryl and X is halo, then at least one of $R^{2a}$, $R^{2b}$, $R^{4a}$ and $R^{4b}$ is not hydrogen; and
(3) when X is nitro, $CF_3$, or $C(O)NH_2$, then at least one of $R^{2a}$, $R^{2b}$, $R^{4a}$ and $R^{4b}$ is not hydrogen; and
(4) when X is bromo and $R^2$ is idolin-2-one-5-yl, then at least one of $R^{2a}$, $R^{2b}$, $R^{4a}$ and $R^{4b}$ is not hydrogen; and
(5) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

Another embodiment of this invention relates to a compound selected from the group consisting of:

I-9: N2-(4-Aminosulfonyl)phenyl-5-fluoro-N4-(1,2,2,6,6-pentamethylpiperidin-4-yl)-2,4-pyrimidinediamine;
I-10: N2-(3-Aminosulfonyl)phenyl-5-fluoro-N4-(1,2,2,6,6-pentamethylpiperidin-4-yl)-2,4-pyrimidinediamine;
I-11: N2-(3-Aminosulfonyl-4-methyl)phenyl-5-fluoro-N4-(1,2,2,6,6-pentamethylpiperidin-4-yl)-2,4-pyrimidinediamine;
I-12: N2-(3,5-Dimethyl)phenyl-5-fluoro-N4-(1,2,2,6,6-pentamethylpiperidin-4-yl)-2,4-pyrimidinediamine;
I-13: N2-(4-Aminosulfonyl)phenyl-5-methyl-N4-(1,2,2,6,6-pentamethylpiperidin-4-yl)-2,4-pyrimidinediamine;
I-14: N2-(3-Aminosulfonyl)phenyl-5-methyl-N4-(1,2,2,6,6-pentamethylpiperidin-4-yl)-2,4-pyrimidinediamine;
I-15: N2-(3-Aminosulfonyl-4-methyl)phenyl-5-methyl-N4-(1,2,2,6,6-pentamethylpiperidin-4-yl)-2,4-pyrimidinediamine;
I-16: 5-Methyl-N4-(1,2,2,6,6-pentamethylpiperidin-4-yl)-N2-(3,4,5-trimethoxy)phenyl-2,4-pyrimidinediamine;
I-17: N2-(3,5-Dimethyl)phenyl-5-methyl-N4-(1,2,2,6,6-pentamethylpiperidin-4-yl)-2,4-pyrimidinediamine;
I-18: N2-[4-(4-Ethylpiperazino)-3-methyl]phenyl-5-methyl-N4-(1,2,2,6,6-pentamethylpiperidin-4-yl)-2,4-pyrimidinediamine;
I-19: 5-Fluoro-N4-(1,2,2,6,6-pentamethylpiperidin-4-yl)-N2-(3,4,5-trimethoxy)phenyl-2,4-pyrimidinediamine;
I-20: N2-(3-Chloro-4-methoxy)phenyl-5-fluoro-N4-(1,2,2,6,6-pentamethylpiperidin-4-yl)-2,4-pyrimidinediamine;
I-21: N2-(3,4-Difluoro)phenyl-5-fluoro-N4-(1,2,2,6,6-pentamethylpiperidin-4-yl)-2,4-pyrimidinediamine;
I-22: N2-(3-Chloro-4-cyano)phenyl-5-fluoro-N4-(1,2,2,6,6-pentamethylpiperidin-4-yl)-2,4-pyrimidinediamine;
I-23: N2-(4-Aminocarbonyl)phenyl-5-fluoro-N4-(1,2,2,6,6-pentamethylpiperidin-4-yl)-2,4-pyrimidinediamine;
I-24: N2-(3-Aminocarbonyl)phenyl-5-fluoro-N4-(1,2,2,6,6-pentamethylpiperidin-4-yl)-2,4-pyrimidinediamine;
I-25: N2-(4-Cyano)phenyl-5-fluoro-N4-(1,2,2,6,6-pentamethylpiperidin-4-yl)-2,4-pyrimidinediamine;
I-26: N2-(3-Cyano)phenyl-5-fluoro-N4-(1,2,2,6,6-pentamethylpiperidin-4-yl)-2,4-pyrimidinediamine;
I-27: N2-(3-Chloro-4-methoxy)phenyl-5-methyl-N4-(1,2,2,6,6-pentamethylpiperidin-4-yl)-2,4-pyrimidinediamine;
I-28: N2-(3-Chloro-4-cyano)phenyl-5-methyl-N4-(1,2,2,6,6-pentamethylpiperidin-4-yl)-2,4-pyrimidinediamine;
I-29: N2-[3-Chloro-4-(4-methylpiperazino)]phenyl-5-methyl-N4-(1,2,2,6,6-pentamethylpiperidin-4-yl)-2,4-pyrimidinediamine;
I-30: 5-Methyl-N2-[4-(4-methylpiperazino)-3-trifluoromethyl]phenyl-N4-(1,2,2,6,6-pentamethylpiperidin-4-yl)-2,4-pyrimidinediamine;
I-31: 5-Chloro-N2-(3-chloro-4-methoxy)phenyl-N4-(1,2,2,6,6-pentamethylpiperidin-4-yl)-2,4-pyrimidinediamine;
I-32: N2-(3-Chloro-4-methoxy)phenyl-N4-(1,2,2,6,6-pentamethylpiperidin-4-yl)-5-trifluoromethyl-2,4-pyrimidinediamine;
I-33: N2-(3-Chloro-4-cyano)phenyl-N4-(1,2,2,6,6-pentamethylpiperidin-4-yl)-5-trifluoromethyl-2,4-pyrimidinediamine;
I-34: N2-[3-Chloro-4-(4-methylpiperazino)]phenyl-N4-(1,2,2,6,6-pentamethylpiperidin-4-yl)-5-trifluoromethyl-2,4-pyrimidinediamine;
I-35: 5-Chloro-N2-(3-chloro-4-cyano)phenyl-N4-(1,2,2,6,6-pentamethylpiperidin-4-yl)-2,4-pyrimidinediamine;
I-36: 5-Chloro-N2-[3-chloro-4-(4-methylpiperazino)]phenyl-N4-(1,2,2,6,6-pentamethylpiperidin-4-yl)-2,4-pyrimidinediamine;
I-37: 5-Chloro-N2-[4-(4-methylpiperazino)-3-trifluoromethyl]phenyl-N4-(1,2,2,6,6-pentamethylpiperidin-4-yl)-2,4-pyrimidinediamine;
I-38: N2-[4-(4-Methylpiperazino)-3-trifluoromethyl]phenyl-N4-(1,2,2,6,6-pentamethylpiperidin-4-yl)-5-trifluoromethyl-2,4-pyrimidinediamine;
I-39: 5-Fluoro-N2-[3-fluoro-4-(4-methylpiperazino)]phenyl-N4-(1,2,2,6,6-pentamethylpiperidin-4-yl)-2,4-pyrimidinediamine;
I-40: N2-[3,5-Difluoro-4-(4-methylpiperazino)]phenyl-5-fluoro-N4-(1,2,2,6,6-pentamethylpiperidin-4-yl)-2,4-pyrimidinediamine;
I-41: N2-[4-Chloro-3-(4-ethylpiperazino)]phenyl-5-fluoro-N4-(1,2,2,6,6-pentamethylpiperidin-4-yl)-2,4-pyrimidinediamine;
I-42: N2-[3-(4-Acylpiperazino)-4-chloro]phenyl-5-fluoro-N4-(1,2,2,6,6-pentamethylpiperidin-4-yl)-2,4-pyrimidinediamine;
I-43: N2-[4-Chloro-3-(4-methoxycarbonylpiperazino)]phenyl-5-fluoro-N4-(1,2,2,6,6-pentamethylpiperidin-4-yl)-2,4-pyrimidinediamine;
I-44: N2-[3-Chloro-4-(4-methylpiperazino)carbonyl]phenyl-5-fluoro-N4-(1,2,2,6,6-pentamethylpiperidin-4-yl)-2,4-pyrimidinediamine;
I-45: N2-[3-Chloro-4-(4-methylpiperazino)sulfonyl]phenyl-5-fluoro-N4-(1,2,2,6,6-pentamethylpiperidin-4-yl)-2,4-pyrimidinediamine;

I-46: N2-[3-Chloro-4-piperazinosulfonyl]phenyl-5-fluoro-N4-(1,2,2,6,6-pentamethylpiperidin-4-yl)-2,4-pyrimidinediamine;

I-47: 5-Fluoro-N2-[4-(4-methoxycarbonylpiperazino)-3-trifluoromethyl]phenyl-N4-(1,2,2,6,6-pentamethylpiperidin-4-yl)-2,4-pyrimidinediamine;

I-48: 5-Fluoro-N2-[4-(4-methylsulfonylpiperazino)-3-trifluoromethyl]phenyl-N4-(1,2,2,6,6-pentamethylpiperidin-4-yl)-2,4-pyrimidinediamine;

I-49: N2-[4-(4-Acylpiperazino)-3-trifluoromethyl]phenyl-5-fluoro-N4-(1,2,2,6,6-pentamethylpiperidin-4-yl)-2,4-pyrimidinediamine;

I-50: N2-[3-Chloro-4-(4,4-difluoropiperidinyl)]phenyl-5-fluoro-N4-(1,2,2,6,6-pentamethylpiperidin-4-yl)-2,4-pyrimidinediamine;

I-51: N2-[4-(4,4-Difluoropiperidinyl)-3-fluoro]phenyl-5-fluoro-N4-(1,2,2,6,6-pentamethylpiperidin-4-yl)-2,4-pyrimidinediamine;

I-52: 5-Fluoro-N2-[4-(4-methylpiperazino)methyl-3-trifluoromethyl]phenyl-N4-(1,2,2,6,6-pentamethylpiperidin-4-yl)-2,4-pyrimidinediamine;

I-53: N2-[3-Aminocarbonyl-4-(4-methylpiperazino)]phenyl-5-fluoro-N4-(1,2,2,6,6-pentamethylpiperidin-4-yl)-2,4-pyrimidinediamine;

I-54: 5-Fluoro-N2-[3-methylaminocarbonyl-4-(4-methylpiperazino)]phenyl-N4-(1,2,2,6,6-pentamethylpiperidin-4-yl)-2,4-pyrimidinediamine;

I-55: 5-Fluoro-N2-[3-methoxy-4-(4-methylpiperazino)]phenyl-N4-(1,2,2,6,6-pentamethylpiperidin-4-yl)-2,4-pyrimidinediamine;

I-56: N2-[4-Chloro-3-(4-propylpiperazino)]phenyl-5-fluoro-N4-(1,2,2,6,6-pentamethylpiperidin-4-yl)-2,4-pyrimidinediamine;

I-57: N2-[3-Chloro-4-(4-methylpiperazino)methyl]phenyl-5-fluoro-N4-(1,2,2,6,6-pentamethylpiperidin-4-yl)-2,4-pyrimidinediamine;

I-58: N2-(3-Chloro-4-methoxy)phenyl-5-fluoro-N4-methyl-N4-(1,2,2,6,6-pentamethylpiperidin-4-yl)-2,4-pyrimidinediamine;

I-59: 5-Fluoro-N4-methyl-N2-[4-(4-methylpiperazino)-3-trifluoromethyl]phenyl-N4-(1,2,2,6,6-pentamethylpiperidin-4-yl)-2,4-pyrimidinediamine;

I-60: N2-[3-Chloro-4-(4-methylpiperazino)]phenyl-5-fluoro-N4-methyl-N4-(1,2,2,6,6-pentamethylpiperidin-4-yl)-2,4-pyrimidinediamine;

I-61: N2-[3-Chloro-4-(4-methylsulfonylpiperazino)]phenyl-5-fluoro-N4-(1,2,2,6,6-pentamethylpiperidin-4-yl)-2,4-pyrimidinediamine;

I-62: N2-[3-Chloro-4-(4-methoxycarbonylpiperazino)]phenyl-5-fluoro-N4-(1,2,2,6,6-pentamethylpiperidin-4-yl)-2,4-pyrimidinediamine;

I-63: 5-Fluoro-N2-[3-hydroxymethyl-4-(4-methylpiperazino)]phenyl-N4-(1,2,2,6,6-pentamethylpiperidin-4-yl)-2,4-pyrimidinediamine;

I-64: 5-Fluoro-N2-[4-(4-methylpiperazino)carbonyl-3-trifluoromethyl]phenyl-N4-(1,2,2,6,6-pentamethylpiperidin-4-yl)-2,4-pyrimidinediamine;

I-65: N2-[4-Chloro-3-(4-methylpiperazino)]phenyl-5-fluoro-N4-(1,2,2,6,6-pentamethylpiperidin-4-yl)-2,4-pyrimidinediamine;

I-66: N2-(3-Cyano)phenyl-5-fluoro-N4-methyl-N4-(1,2,2,6,6-pentamethylpiperidin-4-yl)-2,4-pyrimidinediamine;

I-67: N2-[4-(4-Acylpiperazino)-3-chloro]phenyl-5-fluoro-N4-(1,2,2,6,6-pentamethylpiperidin-4-yl)-2,4-pyrimidinediamine;

I-68: N2-[4-Chloro-3-(4-methylsulfonylpiperazino)]phenyl-5-fluoro-N4-(1,2,2,6,6-pentamethylpiperidin-4-yl)-2,4-pyrimidinediamine;

I-69: N2-[3-(2-methylpyrimidin-4-yl)]phenyl-5-fluoro-N4-(1,2,2,6,6-pentamethylpiperidin-4-yl)-2,4-pyrimidinediamine;

I-70: N2-(3-Cyano)phenyl-5-fluoro-N4-(2,2,6,6-tetramethylpiperidin-4-yl)-2,4-pyrimidinediamine;

I-71: N2-(3-Chloro-4-methoxy)phenyl-5-nitro-N4-(1,2,2,6,6-pentamethylpiperidin-4-yl)-2,4-pyrimidinediamine;

I-72: N2-(3-Cyano)phenyl-5-nitro-N4-(1,2,2,6,6-pentamethylpiperidin-4-yl)-2,4-pyrimidinediamine;

I-73: N2-[3-Chloro-4-(4-methylsulfonylpiperazino)]phenyl-5-nitro-N4-(1,2,2,6,6-pentamethylpiperidin-4-yl)-2,4-pyrimidinediamine;

I-74: N2-[4-(4-Methylpiperazino)-3-trifluoromethyl]phenyl-5-nitro-N4-(1,2,2,6,6-pentamethylpiperidin-4-yl)-2,4-pyrimidinediamine;

I-75: 5-Nitro-N4-(1,2,2,6,6-pentamethylpiperidin-4-yl)-N2-(4-piperazino-3-trifluoromethyl)phenyl-2,4-pyrimidinediamine;

I-76: N2-[3-Chloro-4-(4-methylpiperazino)]phenyl-5-nitro-N4-(1,2,2,6,6-pentamethylpiperidin-4-yl)-2,4-pyrimidinediamine;

I-77: N2-(3-Chloro-4-piperazino)phenyl-5-nitro-N4-(1,2,2,6,6-pentamethylpiperidin-4-yl)-2,4-pyrimidinediamine;

I-78: N2-[4-(4-Methylsulfonylpiperazino)-3-trifluoromethyl]phenyl-5-nitro-N4-(1,2,2,6,6-pentamethylpiperidin-4-yl)-2,4-pyrimidinediamine;

I-79: 5-Fluoro-N4-(1,2,2,6,6-pentamethylpiperidin-4-yl)-N2-(3-pyridin-4-yl)phenyl-2,4-pyrimidinediamine;

I-80: N2-(3-Chloro-4-methoxy)phenyl-5-ethoxycarbonyl-N4-(1,2,2,6,6-pentamethylpiperidin-4-yl)-2,4-pyrimidinediamine;

I-81: N2-(3-Cyano)phenyl-5-ethoxycarbonyl-N4-(1,2,2,6,6-pentamethylpiperidin-4-yl)-2,4-pyrimidinediamine;

I-82: 5-Ethoxycarbonyl-N2-[4-(4-methylpiperazino)-3-trifluoromethyl]phenyl-N4-(1,2,2,6,6-pentamethylpiperidin-4-yl)-2,4-pyrimidinediamine;

I-83: 5-Ethoxycarbonyl-N2-[4-(4-methylsulfonylpiperazino)-3-trifluoromethyl]phenyl-N4-(1,2,2,6,6-pentamethylpiperidin-4-yl)-2,4-pyrimidinediamine;

I-84: N2-[3-Chloro-4-(4-methylsulfonylpiperazino)]phenyl-5-ethoxycarbonyl-N4-(1,2,2,6,6-pentamethylpiperidin-4-yl)-2,4-pyrimidinediamine;

I-85: 5-Aminocarbonyl-N2-(3-chloro-4-methoxy)phenyl-N4-(1,2,2,6,6-pentamethylpiperidin-4-yl)-2,4-pyrimidinediamine;

I-86: 5-Aminocarbonyl-N2-(3-cyano)phenyl-N4-(1,2,2,6,6-pentamethylpiperidin-4-yl)-2,4-pyrimidinediamine;

I-87: Mixture of N2-[3-Chloro-4-(4-methylsulfonylpiperazino)]phenyl-N4-(1,2,2,6,6-pentamethylpiperidin-4-yl)-5-trifluoromethyl-2,4-pyrimidinediamine and N4-[3-Chloro-4-(4-methylsulfonylpiperazino)]phenyl-N2-(1,2,2,6,6-pentamethylpiperidin-4-yl)-5-trifluoromethyl-2,4-pyrimidinediamine;

I-88: N2-[4-(4-Methylsulfonylpiperazino)-3-trifluoromethyl]phenyl-N4-(1,2,2,6,6-pentamethylpiperidin-4-yl)-5-trifluoromethyl-2,4-pyrimidinediamine;

I-89: N2-[3-Chloro-4-(4-methylpiperazino)]phenyl-5-ethoxycarbonyl-N4-(1,2,2,6,6-pentamethylpiperidin-4-yl)-2,4-pyrimidinediamine;

I-90: 5-Aminocarbonyl-N2-[4-(4-methylsulfonylpiperazino)-3-trifluoromethyl]phenyl-N4-(1,2,2,6,6-pentamethylpiperidin-4-yl)-2,4-pyrimidinediamine;

I-91: 5-Aminocarbonyl-N2-[3-chloro-4-(4-methylsulfonylpiperazino)]phenyl-N4-(1,2,2,6,6-pentamethylpiperidin-4-yl)-2,4-pyrimidinediamine;

I-92: N2-[3-Chloro-4-(4-methylsulfonylpiperazino)]phenyl-N4-(1,2,2,6,6-pentamethylpiperidin-4-yl)-5-trifluoromethyl-2,4-pyrimidinediamine;

I-93: N2-(3-Chloro-4-methoxy)phenyl-5-cyano-N4-(1,2,2,6,6-pentamethylpiperidin-4-yl)-2,4-pyrimidinediamine;

I-94: 5-Cyano-N2-[4-(4-methylpiperazino)-3-trifluoromethyl]phenyl-N4-(1,2,2,6,6-pentamethylpiperidin-4-yl)-2,4-pyrimidinediamine;

I-95: 5-Cyano-N2-[4-(4-methylsulfonylpiperazino)-3-trifluoromethyl]phenyl-N4-(1,2,2,6,6-pentamethylpiperidin-4-yl)-2,4-pyrimidinediamine;

I-96: 5-Fluoro-N4-(1,2,2,6,6-pentamethylpiperidin-4-yl)-N2-[4-(pyridin-4-yl)-3-trifluoromethyl]phenyl-2,4-pyrimidinediamine;

I-97: 5-Cyano-N2-(3-cyano)phenyl-N4-(1,2,2,6,6-pentamethylpiperidin-4-yl)-2,4-pyrimidinediamine;

I-98: 5-Aminocarbonyl-N2-[3-chloro-4-(4-methylpiperazino)]phenyl-N4-(1,2,2,6,6-pentamethylpiperidin-4-yl)-2,4-pyrimidinediamine;

I-99: N2-[3-Chloro-4-(pyridin-4-yl)]phenyl-5-fluoro-N4-(1,2,2,6,6-pentamethylpiperidin-4-yl)-2,4-pyrimidinediamine;

I-100: 5-Fluoro-N2-[3-(1,3-oxazol-5-yl)]phenyl-N4-(1,2,2,6,6-pentamethylpiperidin-4-yl)-2,4-pyrimidinediamine;

I-101: N2-[3-Chloro-4-(4-methylpiperazino)]phenyl-5-cyano-N4-(1,2,2,6,6-pentamethylpiperidin-4-yl)-2,4-pyrimidinediamine;

I-102: N2-[3-Chloro-4-(4-methylsulfonylpiperazino)]phenyl-5-cyano-N4-(1,2,2,6,6-pentamethylpiperidin-4-yl)-2,4-pyrimidinediamine;

I-103: N2-(3,5-Dichloro)phenyl-5-fluoro-N4-(1,2,2,6,6-pentamethylpiperidin-4-yl)-2,4-pyrimidinediamine;

I-104: N2-(3-Bromo)phenyl-5-fluoro-N4-(1,2,2,6,6-pentamethylpiperidin-4-yl)-2,4-pyrimidinediamine;

I-105: 5-Fluoro-N2-[3-(furan-3-yl)]phenyl-N4-(1,2,2,6,6-pentamethylpiperidin-4-yl)-2,4-pyrimidinediamine;

I-106: N2-[3-(Benzothiophen-2-yl)]phenyl-5-fluoro-N4-(1,2,2,6,6-pentamethylpiperidin-4-yl)-2,4-pyrimidinediamine;

I-107: 5-Fluoro-N4-(1,2,2,6,6-pentamethylpiperidin-4-yl)-N2-(3-pyridin-3-yl)phenyl-2,4-pyrimidinediamine;

I-108: N2-(4-Bromo)phenyl-5-fluoro-N4-(1,2,2,6,6-pentamethylpiperidin-4-yl)-2,4-pyrimidinediamine;

I-109: N2-(4-Bromo-3-trifluoromethyl)phenyl-5-fluoro-N4-(1,2,2,6,6-pentamethylpiperidin-4-yl)-2,4-pyrimidinediamine;

I-110: N2-(4-Bromo-3-fluoro)phenyl-5-fluoro-N4-(1,2,2,6,6-pentamethylpiperidin-4-yl)-2,4-pyrimidinediamine;

I-111: N2-(4-Bromo-3-methyl)phenyl-5-fluoro-N4-(1,2,2,6,6-pentamethylpiperidin-4-yl)-2,4-pyrimidinediamine;

I-112: 5-Fluoro-N4-(1,2,2,6,6-pentamethylpiperidin-4-yl)-N2-[4-(pyridin-3-yl)-3-trifluoromethyl]phenyl-2,4-pyrimidinediamine;

I-113: 5-Fluoro-N2-[4-(furan-3-yl)-3-trifluoromethyl]phenyl-N4-(1,2,2,6,6-pentamethylpiperidin-4-yl)-2,4-pyrimidinediamine;

I-114: N2-[4-(Benzothiophen-2-yl)-3-trifluoromethyl]phenyl-5-fluoro-N4-(1,2,2,6,6-pentamethylpiperidin-4-yl)-2,4-pyrimidinediamine;

I-115: 5-Fluoro-N2-[3-fluoro-4-(pyridin-4-yl)]phenyl-N4-(1,2,2,6,6-pentamethylpiperidin-4-yl)-2,4-pyrimidinediamine;

I-116: 5-Fluoro-N2-[4-(4-methylthiophen-2-yl)-3-trifluoromethyl]phenyl-N4-(1,2,2,6,6-pentamethylpiperidin-4-yl)-2,4-pyrimidinediamine;

I-117: N2-[4-Bromo-3,5-bis(trifluoromethyl)]phenyl-5-fluoro-N4-(1,2,2,6,6-pentamethylpiperidin-4-yl)-2,4-pyrimidinediamine;

I-118: 5-Fluoro-N2-[3-fluoro-4-(pyridin-3-yl)]phenyl-N4-(1,2,2,6,6-pentamethylpiperidin-4-yl)-2,4-pyrimidinediamine;

I-119: 5-Fluoro-N2-[3-fluoro-4-(furan-3-yl)]phenyl-N4-(1,2,2,6,6-pentamethylpiperidin-4-yl)-2,4-pyrimidinediamine;

I-120: 5-Fluoro-N2-[3-methyl-4-(pyridin-4-yl)]phenyl-N4-(1,2,2,6,6-pentamethylpiperidin-4-yl)-2,4-pyrimidinediamine;

I-121: 5-Fluoro-N2-[3-methyl-4-(pyridin-3-yl)]phenyl-N4-(1,2,2,6,6-pentamethylpiperidin-4-yl)-2,4-pyrimidinediamine;

I-122: 5-Fluoro-N2-[4-(furan-3-yl)-3-methyl]phenyl-N4-(1,2,2,6,6-pentamethylpiperidin-4-yl)-2,4-pyrimidinediamine;

I-123: 5-Fluoro-N4-(1,2,2,6,6-pentamethylpiperidin-4-yl)-N2-[4-(pyridin-4-yl)]phenyl-2,4-pyrimidinediamine;

I-124: 5-Fluoro-N4-(1,2,2,6,6-pentamethylpiperidin-4-yl)-N2-[4-(pyridin-3-yl)]phenyl-2,4-pyrimidinediamine;

I-125: 5-Fluoro-N2-[4-(furan-3-yl)]phenyl-N4-(1,2,2,6,6-pentamethylpiperidin-4-yl)-2,4-pyrimidinediamine;

I-126: 5-Fluoro-N2-[4-(1-methyl-1H-pyrazol-4-yl)-3-trifluoromethyl]phenyl-N4-(1,2,2,6,6-pentamethylpiperidin-4-yl)-2,4-pyrimidinediamine;

I-127: 5-Fluoro-N2-(3-fluoro-4-methoxy)phenyl-N4-(1,2,2,6,6-pentamethylpiperidin-4-yl)-2,4-pyrimidinediamine;

I-128: N2-(4-Chloro-3-cyano-5-ethyl)phenyl-5-fluoro-N4-(1,2,2,6,6-pentamethylpiperidin-4-yl)-2,4-pyrimidinediamine;

I-129: N2-(3,5-Dimethoxy)phenyl-5-fluoro-N4-(1,2,2,6,6-pentamethylpiperidin-4-yl)-2,4-pyrimidinediamine;

I-130: N2-(3,4-Dimethoxy)phenyl-5-fluoro-N4-(1,2,2,6,6-pentamethylpiperidin-4-yl)-2,4-pyrimidinediamine;

I-131: N2-(3,5-Dimethyl-4-methoxy)phenyl-5-fluoro-N4-(1,2,2,6,6-pentamethylpiperidin-4-yl)-2,4-pyrimidinediamine;

I-132: N2-[3-Cyano-4-(4-methylpiperazino)]phenyl-5-fluoro-N4-(1,2,2,6,6-pentamethylpiperidin-4-yl)-2,4-pyrimidinediamine;

I-133: N2-(4-Benzoylamino)phenyl-5-fluoro-N4-(1,2,2,6,6-pentamethylpiperidin-4-yl)-2,4-pyrimidinediamine;

I-134: N2-(4-Aminocarbonylmethoxy)phenyl-5-fluoro-N4-(1,2,2,6,6-pentamethylpiperidin-4-yl)-2,4-pyrimidinediamine;

I-135: 5-Fluoro-N2-(4-isopropoxycarbonylmethoxy)phenyl-N4-(1,2,2,6,6-pentamethylpiperidin-4-yl)-2,4-pyrimidinediamine;

I-136: 5-Fluoro-N2-(3-methylaminocarbonylmethoxy)phenyl-N4-(1,2,2,6,6-pentamethylpiperidin-4-yl)-2,4-pyrimidinediamine;

I-137: 5-Fluoro-N2-(4-isopropoxycarbonylamino)phenyl-N4-(1,2,2,6,6-pentamethylpiperidin-4-yl)-2,4-pyrimidinediamine;

I-138: N2-(3-Ethylaminocarbonylamino)phenyl-5-fluoro-N4-(1,2,2,6,6-pentamethylpiperidin-4-yl)-2,4-pyrimidinediamine;

I-139: 5-Fluoro-N2-(3-isopropoxycarbonylamino)phenyl-N4-(1,2,2,6,6-pentamethylpiperidin-4-yl)-2,4-pyrimidinediamine;

I-140: N2-(3-Cyano-4-fluoro)phenyl-5-fluoro-N4-(1,2,2,6,6-pentamethylpiperidin-4-yl)-2,4-pyrimidinediamine;

I-141: N2-(3,4-Dicyano)phenyl-5-fluoro-N4-(1,2,2,6,6-pentamethylpiperidin-4-yl)-2,4-pyrimidinediamine;

I-142: N2-(3-Cyano-4-methyl)phenyl-5-fluoro-N4-(1,2,2,6,6-pentamethylpiperidin-4-yl)-2,4-pyrimidinediamine;

I-143: 5-Fluoro-N2-[3-(1-methyl-1H-pyrazol-4-yl)]phenyl-N4-(1,2,2,6,6-pentamethylpiperidin-4-yl)-2,4-pyrimidinediamine;

I-144: 5-Fluoro-N2-[4-(1-methyl-1H-pyrazol-4-yl)]phenyl-N4-(1,2,2,6,6-pentamethylpiperidin-4-yl)-2,4-pyrimidinediamine;

I-145: 5-Fluoro-N2-(3-methoxy-5-trifluoromethyl)phenyl-N4-(1,2,2,6,6-pentamethylpiperidin-4-yl)-2,4-pyrimidinediamine;

I-146: N2-[3,5-Bis(trifluoromethyl)]phenyl-5-fluoro-N4-(1,2,2,6,6-pentamethylpiperidin-4-yl)-2,4-pyrimidinediamine;

I-147: 5-Fluoro-N2-(4-methoxy-3-trifluoromethyl)phenyl-N4-(1,2,2,6,6-pentamethylpiperidin-4-yl)-2,4-pyrimidinediamine;

I-148: N2-[3-Cyano-4-(1H-pyrrol-1-yl)]phenyl-5-fluoro-N4-(1,2,2,6,6-pentamethylpiperidin-4-yl)-2,4-pyrimidinediamine;

I-149: N2-(4-Ethylaminocarbonylamino)phenyl-5-fluoro-N4-(1,2,2,6,6-pentamethylpiperidin-4-yl)-2,4-pyrimidinediamine;

I-150: 5-Fluoro-N2-[3-fluoro-4-(1-methyl-1H-pyrazol-4-yl)]phenyl-N4-(1,2,2,6,6-pentamethylpiperidin-4-yl)-2,4-pyrimidinediamine;

I-151: 5-Fluoro-N2-[3-methyl-4-(1-methyl-1H-pyrazol-4-yl)]phenyl-N4-(1,2,2,6,6-pentamethylpiperidin-4-yl)-2,4-pyrimidinediamine;

I-152: N2-(4-Cyano-3-trifluoromethyl)phenyl-5-fluoro-N4-(1,2,2,6,6-pentamethylpiperidin-4-yl)-2,4-pyrimidinediamine;

I-153: N2-(4-Bromo-3-chloro)phenyl-5-fluoro-N4-(1,2,2,6,6-pentamethylpiperidin-4-yl)-2,4-pyrimidinediamine;

I-154: N2-[3-Chloro-4-(pyridin-3-yl)]phenyl-5-fluoro-N4-(1,2,2,6,6-pentamethylpiperidin-4-yl)-2,4-pyrimidinediamine;

I-155: N2-[3-Chloro-4-(furan-3-yl)]phenyl-5-fluoro-N4-(1,2,2,6,6-pentamethylpiperidin-4-yl)-2,4-pyrimidinediamine;

I-156: N2-[4-(Benzothiophen-2-yl)-3-chloro]phenyl-5-fluoro-N4-(1,2,2,6,6-pentamethylpiperidin-4-yl)-2,4-pyrimidinediamine;

I-157: N2-[3-Chloro-4-(1-methyl-1H-pyrazol-4-yl)]phenyl-5-fluoro-N4-(1,2,2,6,6-pentamethylpiperidin-4-yl)-2,4-pyrimidinediamine;

I-158: N2-(3-Bromo-4-fluoro)phenyl-5-fluoro-N4-(1,2,2,6,6-pentamethylpiperidin-4-yl)-2,4-pyrimidinediamine;

I-159: N2-(3-Bromo-4-methoxy)phenyl-5-fluoro-N4-(1,2,2,6,6-pentamethylpiperidin-4-yl)-2,4-pyrimidinediamine;

I-160: N2-(3-Bromo-4-methyl)phenyl-5-fluoro-N4-(1,2,2,6,6-pentamethylpiperidin-4-yl)-2,4-pyrimidinediamine;

I-161: N2-(4-Acetamido-3-trifluoromethyl)phenyl-5-fluoro-N4-(1,2,2,6,6-pentamethylpiperidin-4-yl)-2,4-pyrimidinediamine;

I-162: N2-(3-Bromo-5-trifluoromethyl)phenyl-5-fluoro-N4-(1,2,2,6,6-pentamethylpiperidin-4-yl)-2,4-pyrimidinediamine;

I-163: N2-(4-Chloro-3-cyano)phenyl-5-fluoro-N4-(1,2,2,6,6-pentamethylpiperidin-4-yl)-2,4-pyrimidinediamine;

I-164: N2-[3-Cyano-4-(4-methylsulfonylpiperazino)]phenyl-5-fluoro-N4-(1,2,2,6,6-pentamethylpiperidin-4-yl)-2,4-pyrimidinediamine;

I-165: 5-Chloro-N2-(4-chloro-3-cyano)phenyl-N4-(1,2,2,6,6-pentamethylpiperidin-4-yl)-2,4-pyrimidinediamine;

I-166: 5-Chloro-N2-(3-cyano-4-fluoro)phenyl-N4-(1,2,2,6,6-pentamethylpiperidin-4-yl)-2,4-pyrimidinediamine;

I-167: 5-Chloro-N2-[3-cyano-4-(1H-pyrrol-1-yl)]phenyl-N4-(1,2,2,6,6-pentamethylpiperidin-4-yl)-2,4-pyrimidinediamine;

I-168: 5-Chloro-N2-(3-cyano-4-methyl)phenyl-N4-(1,2,2,6,6-pentamethylpiperidin-4-yl)-2,4-pyrimidinediamine;

I-169: N2-(4-Chloro-3-cyano)phenyl-N4-(1,2,2,6,6-pentamethylpiperidin-4-yl)-5-trifluoromethyl-2,4-pyrimidinediamine;

I-170: N2-(3-Cyano-4-fluoro)phenyl-N4-(1,2,2,6,6-pentamethylpiperidin-4-yl)-5-trifluoromethyl-2,4-pyrimidinediamine;

I-171: N2-(3-Cyano-4-methyl)phenyl-N4-(1,2,2,6,6-pentamethylpiperidin-4-yl)-5-trifluoromethyl-2,4-pyrimidinediamine;

I-172: N2-[3-Cyano-4-(1H-pyrrol-1-yl)]phenyl-N4-(1,2,2,6,6-pentamethylpiperidin-4-yl)-5-trifluoromethyl-2,4-pyrimidinediamine;

I-173: N2-[4-(4-Cyclopropylsulfonylpiperazino)-3-trifluoromethyl]phenyl-5-fluoro-N4-(1,2,2,6,6-pentamethylpiperidin-4-yl)-2,4-pyrimidinediamine;

I-174: N2-[3-Chloro-4-(4-cyclopropylsulfonylpiperazino)]phenyl-5-fluoro-N4-(1,2,2,6,6-pentamethylpiperidin-4-yl)-2,4-pyrimidinediamine;

I-175: 5-Chloro-N2-[3-cyano-4-(4-methylsulfonylpiperazino)]phenyl-N4-(1,2,2,6,6-pentamethylpiperidin-4-yl)-2,4-pyrimidinediamine;

I-176: N2-[3-Cyano-4-(4-methylsulfonylpiperazino)]phenyl-N4-(1,2,2,6,6-pentamethylpiperidin-4-yl)-5-trifluoromethyl-2,4-pyrimidinediamine;

I-177: N2-(3-Bromo-4-trifluoromethoxy)phenyl-5-fluoro-N4-(1,2,2,6,6-pentamethylpiperidin-4-yl)-2,4-pyrimidinediamine;

I-178: N2-[3-Cyano-4-(4-methylpiperazino)]phenyl-N4-(1,2,2,6,6-pentamethylpiperidin-4-yl)-5-trifluoromethyl-2,4-pyrimidinediamine;

I-179: 5-Chloro-N2-[3-cyano-4-(4-methylpiperazino)]phenyl-N4-(1,2,2,6,6-pentamethylpiperidin-4-yl)-2,4-pyrimidinediamine;

I-180: 5-Fluoro-N2-[4-fluoro-3-(pyridin-3-yl)]phenyl-N4-(1,2,2,6,6-pentamethylpiperidin-4-yl)-2,4-pyrimidinediamine;

I-181: N2-[3-(Benzothiophen-2-yl)-4-fluoro]phenyl-5-fluoro-N4-(1,2,2,6,6-pentamethylpiperidin-4-yl)-2,4-pyrimidinediamine;

I-182: 5-Fluoro-N2-[4-fluoro-3-(1-methyl-1H-pyrazol-4-yl)]phenyl-N4-(1,2,2,6,6-pentamethylpiperidin-4-yl)-2,4-pyrimidinediamine;

I-183: 5-Fluoro-N2-[3-(furan-3-yl)-4-methoxy]phenyl-N4-(1,2,2,6,6-pentamethylpiperidin-4-yl)-2,4-pyrimidinediamine;

I-184: 5-Fluoro-N2-[4-methoxy-3-(1-methyl-1H-pyrazol-4-yl)]phenyl-N4-(1,2,2,6,6-pentamethylpiperidin-4-yl)-2,4-pyrimidinediamine;

I-185: N2-[3-Cyano-4-(pyridin-4-yl)]phenyl-5-fluoro-N4-(1,2,2,6,6-pentamethylpiperidin-4-yl)-2,4-pyrimidinediamine;

I-186: N2-[3-Cyano-4-(pyridin-3-yl)]phenyl-5-fluoro-N4-(1,2,2,6,6-pentamethylpiperidin-4-yl)-2,4-pyrimidinediamine;

I-187: 5-Fluoro-N2-[4-methyl-3-(pyridin-4-yl)]phenyl-N4-(1,2,2,6,6-pentamethylpiperidin-4-yl)-2,4-pyrimidinediamine;

I-188: 5-Fluoro-N2-[3-(furan-3-yl)-4-methyl]phenyl-N4-(1,2,2,6,6-pentamethylpiperidin-4-yl)-2,4-pyrimidinediamine;

I-189: N2-[3-(Benzothiophen-2-yl)-4-methyl]phenyl-5-fluoro-N4-(1,2,2,6,6-pentamethylpiperidin-4-yl)-2,4-pyrimidinediamine;

I-190: 5-Fluoro-N2-[4-methyl-3-(1-methyl-1H-pyrazol-4-yl)]phenyl-N4-(1,2,2,6,6-pentamethylpiperidin-4-yl)-2,4-pyrimidinediamine;

I-191: 5-Fluoro-N2-[4-fluoro-3-(pyridin-4-yl)]phenyl-N4-(1,2,2,6,6-pentamethylpiperidin-4-yl)-2,4-pyrimidinediamine;

I-192: 5-Fluoro-N2-[4-fluoro-3-(furan-3-yl)]phenyl-N4-(1,2,2,6,6-pentamethylpiperidin-4-yl)-2,4-pyrimidinediamine;

I-193: 5-Fluoro-N2-[4-methoxy-3-(pyridin-4-yl)]phenyl-N4-(1,2,2,6,6-pentamethylpiperidin-4-yl)-2,4-pyrimidinediamine;

I-194: 5-Fluoro-N2-[4-methoxy-3-(pyridin-3-yl)]phenyl-N4-(1,2,2,6,6-pentamethylpiperidin-4-yl)-2,4-pyrimidinediamine;

I-195: N2-[3-(Benzothiophen-2-yl)-4-methoxy]phenyl-5-fluoro-N4-(1,2,2,6,6-pentamethylpiperidin-4-yl)-2,4-pyrimidinediamine;

I-196: 5-Cyano-N2-[3-cyano-4-(4-methylsulfonylpiperazino)]phenyl-N4-(1,2,2,6,6-pentamethylpiperidin-4-yl)-2,4-pyrimidinediamine;

I-197: 5-Fluoro-N2-[4-methyl-3-(pyridin-3-yl)]phenyl-N4-(1,2,2,6,6-pentamethylpiperidin-4-yl)-2,4-pyrimidinediamine;

I-198: N2-(3-Cyano-4-morpholino)phenyl-5-fluoro-N4-(1,2,2,6,6-pentamethylpiperidin-4-yl)-2,4-pyrimidinediamine;

I-199: N2-(3-Cyano-4-thiomorpholino)phenyl-5-fluoro-N4-(1,2,2,6,6-pentamethylpiperidin-4-yl)-2,4-pyrimidinediamine;

I-200: N2-[3-Cyano-4-(pyrrolidin-1-yl)]phenyl-5-fluoro-N4-(1,2,2,6,6-pentamethylpiperidin-4-yl)-2,4-pyrimidinediamine;

I-201: 5-Fluoro-N4-(1,2,2,6,6-pentamethylpiperidin-4-yl)-N2-[3-(pyridin-4-yl)-5-trifluoromethyl]phenyl-2,4-pyrimidinediamine;

I-202: 5-Fluoro-N4-(1,2,2,6,6-pentamethylpiperidin-4-yl)-N2-[3-(pyridin-3-yl)-5-trifluoromethyl]phenyl-2,4-pyrimidinediamine;

I-203: 5-Fluoro-N2-[3-(furan-3-yl)-5-trifluoromethyl]phenyl-N4-(1,2,2,6,6-pentamethylpiperidin-4-yl)-2,4-pyrimidinediamine;

I-204: 5-Fluoro-N2-[3-(1-methyl-1H-pyrazol-4-yl)-5-trifluoromethyl]phenyl-N4-(1,2,2,6,6-pentamethylpiperidin-4-yl)-2,4-pyrimidinediamine;

I-205: N2-[3-(Benzothiophen-2-yl)-5-trifluoromethyl]phenyl-5-fluoro-N4-(1,2,2,6,6-pentamethylpiperidin-4-yl)-2,4-pyrimidinediamine;

I-206: 5-Cyano-N2-[3-cyano-4-(1H-pyrrol-1-yl)]phenyl-N4-(1,2,2,6,6-pentamethylpiperidin-4-yl)-2,4-pyrimidinediamine;

I-207: 5-Fluoro-N4-(1,2,2,6,6-pentamethylpiperidin-4-yl)-N2-[3-(pyridin-4-yl)-4-trifluoromethoxy]phenyl-2,4-pyrimidinediamine;

I-208: 5-Fluoro-N4-(1,2,2,6,6-pentamethylpiperidin-4-yl)-N2-[3-(pyridin-3-yl)-4-trifluoromethoxy]phenyl-2,4-pyrimidinediamine;

I-209: 5-Fluoro-N2-[3-(furan-3-yl)-4-trifluoromethoxy]phenyl-N4-(1,2,2,6,6-pentamethylpiperidin-4-yl)-2,4-pyrimidinediamine;

I-210: 5-Fluoro-N2-[3-(1-methyl-1H-pyrazol-4-yl)-4-trifluoromethoxy]phenyl-N4-(1,2,2,6,6-pentamethylpiperidin-4-yl)-2,4-pyrimidinediamine;

I-211: N2-[3-(Benzothiophen-2-yl)-4-trifluoromethoxy]phenyl-5-fluoro-N4-(1,2,2,6,6-pentamethylpiperidin-4-yl)-2,4-pyrimidinediamine;

I-212: N2-[3-(4-Acetylpiperazino)-4-trifluoromethyl]phenyl-5-fluoro-N4-(1,2,2,6,6-pentamethylpiperidin-4-yl)-2,4-pyrimidinediamine;

I-213: N4-(1-Acetyl-2,2,6,6-tetramethylpiperidin-4-yl)-N2-(3-chloro-4-methoxy)phenyl-5-fluoro-2,4-pyrimidinediamine;

I-214: 5-Fluoro-N2-[3-(4-methoxycarbonylpiperazino)-4-trifluoromethyl]phenyl-N4-(1,2,2,6,6-pentamethylpiperidin-4-yl)-2,4-pyrimidinediamine;

I-215: N4-(1-Acetyl-2,2,6,6-tetramethylpiperidin-4-yl)-5-fluoro-N2-[4-(4-methylsulfonylpiperazino)-3-trifluoromethyl]phenyl-2,4-pyrimidinediamine;

I-216: 5-Fluoro-N2-[3-(4-methylsulfonylpiperazino)-4-trifluoromethyl]phenyl-N4-(1,2,2,6,6-pentamethylpiperidin-4-yl)-2,4-pyrimidinediamine;

I-217: N4-(1-Acetyl-2,2,6,6-tetramethylpiperidin-4-yl)-N2-(3-cyanophenyl)-5-fluoro-2,4-pyrimidinediamine;

I-218: 5-Fluoro-N4-(1,2,2,6,6-pentamethylpiperidin-4-yl)-N2-[3-(4-propylpiperazino)-4-trifluoromethyl]phenyl-2,4-pyrimidinediamine;

I-219: N4-(1-Acetyl-2,2,6,6-tetramethylpiperidin-4-yl)-5-fluoro-N2-[4-(4-methylpiperazino)-3-trifluoromethyl]phenyl-2,4-pyrimidinediamine;

I-220: N2-[4-Chloro-3-(3,5-dimethyl-4-propylpiperazino)]phenyl-5-fluoro-N4-(1,2,2,6,6-pentamethylpiperidin-4-yl)-2,4-pyrimidinediamine;

I-221: 5-Fluoro-N2-[4-(1-methylpiperidin-4-yl)]phenyl-N4-(1,2,2,6,6-pentamethylpiperidin-4-yl)-2,4-pyrimidinediamine;

I-222: N2-[4-(2,6-Dimethyltetrahydropyran-4-yl)]phenyl-5-fluoro-N4-(1,2,2,6,6-pentamethylpiperidin-4-yl)-2,4-pyrimidinediamine;

I-223: 5-Fluoro-N4-(1,2,2,6,6-pentamethylpiperidin-4-yl)-N2-(3-trifluoromethoxy)phenyl-2,4-pyrimidinediamine;

I-224: 5-Fluoro-N2-[4-(4-morpholino)-3-trifluoromethyl]phenyl-N4-(1,2,2,6,6-pentamethylpiperidin-4-yl)-2,4-pyrimidinediamine;

I-225: N2-[4-(2,6-Dimethylmorpholino)-3-trifluoromethyl]phenyl-5-fluoro-N4-(1,2,2,6,6-pentamethylpiperidin-4-yl)-2,4-pyrimidinediamine;

I-226: N2-(3-Chloro-4-methoxy)phenyl-N4-(1,2,2,6,6-pentamethylpiperidin-4-yl)-2,4-pyrimidinediamine;

I-227: N2-(3-Cyanophenyl)-N4-(1,2,2,6,6-pentamethylpiperidin-4-yl)-2,4-pyrimidinediamine;

I-228: N2-[4-(4-Methylsulfonylpiperazino)-3-trifluoromethyl]phenyl-N4-(1,2,2,6,6-pentamethylpiperidin-4-yl)-2,4-pyrimidinediamine;

I-229: N2-[4-(4-Methylpiperazino)-3-trifluoromethyl]phenyl-N4-(1,2,2,6,6-pentamethylpiperidin-4-yl)-2,4-pyrimidinediamine;

I-230: N2-[4-(Cyclopropylaminocarbonyl)-3-trifluoromethyl]phenyl-5-fluoro-N4-(1,2,2,6,6-pentamethylpiperidin-4-yl)-2,4-pyrimidinediamine;

I-231: 5-Fluoro-N4-(1,2,2,6,6-pentamethylpiperidin-4-yl)-N2-(4-trifluoromethoxyphenyl)-2,4-pyrimidinediamine;

I-232: 5-Fluoro-N2-[4-(1-pyrrolidino)-3-trifluoromethyl]phenyl-N4-(1,2,2,6,6-pentamethylpiperidin-4-yl)-2,4-pyrimidinediamine;

I-233: 5-Fluoro-N4-(1,2,2,6,6-pentamethylpiperidin-4-yl)-N2-[4-(1-piperidino)-3-trifluoromethyl]phenyl-2,4-pyrimidinediamine;

I-234: N2-(3-Difluoromethoxyphenyl)-5-fluoro-N4-(1,2,2,6,6-pentamethylpiperidin-4-yl)-2,4-pyrimidinediamine;

I-235: N2-(3-Difluoromethoxy-4-morpholino)phenyl-5-fluoro-N4-(1,2,2,6,6-pentamethylpiperidin-4-yl)-2,4-pyrimidinediamine;

I-236: N2-[3-Difluoromethoxy-4-(4-methylpiperazino)]phenyl-5-fluoro-N4-(1,2,2,6,6-pentamethylpiperidin-4-yl)-2,4-pyrimidinediamine;

I-237: N2-(3-Difluoromethoxy-4-pyrrolidino)phenyl-5-fluoro-N4-(1,2,2,6,6-pentamethylpiperidin-4-yl)-2,4-pyrimidinediamine;

I-238: N2-[3-Difluoromethoxy-4-(4-methylsulfonylpiperazino)]phenyl-5-fluoro-N4-(1,2,2,6,6-pentamethylpiperidin-4-yl)-2,4-pyrimidinediamine;

I-239: N2-(3-Difluoromethoxy-4-methoxy)phenyl-5-fluoro-N4-(1,2,2,6,6-pentamethylpiperidin-4-yl)-2,4-pyrimidinediamine;

I-240: 5-Chloro-N4-(1,2,2,6,6-pentamethylpiperidin-4-yl)-N2-(3-trifluoromethoxyphenyl)-2,4-pyrimidinediamine;

I-241: 5-Chloro-N2-[4-(4-morpholino)-3-trifluoromethyl]phenyl-N4-(1,2,2,6,6-pentamethylpiperidin-4-yl)-2,4-pyrimidinediamine;

I-242: N4-(1,2,2,6,6-pentamethylpiperidin-4-yl)-N2-(3-trifluoromethoxyphenyl)-5-trifluoromethyl-2,4-pyrimidinediamine;

I-243: 5-Fluoro-N2-(3-methylsulfonylamino)phenyl-N4-(1,2,2,6,6-pentamethylpiperidin-4-yl)-2,4-pyrimidinediamine;

I-244: N2-[4-(4-methylsulfonylpiperazino)-3-trifluoromethyl]phenyl-5-fluoro-N4-(1,2,2,6,6-pentamethylpiperidin-4-yl)-2,4-pyrimidinediamine benzylate salt;

I-245: N2-[4-(4,4-Difluoropiperidin-1-yl)-3-trifluoromethyl]phenyl-5-fluoro-N4-(1,2,2,6,6-pentamethylpiperidin-4-yl)-2,4-pyrimidinediamine;

I-246: N2-[4-(4-Ethylpiperazino)-3-trifluoromethyl]phenyl-5-fluoro-N4-(1,2,2,6,6-pentamethylpiperidin-4-yl)-2,4-pyrimidinediamine;

I-247: 5-Fluoro-N4-(1,2,2,6,6-pentamethylpiperidin-4-yl)-N2-[4-(4-propylpiperazino)-3-trifluoromethyl]phenyl-2,4-pyrimidinediamine;

I-248: N2-[3-Chloro-4-(4-ethylpiperazino)]phenyl-5-fluoro-N4-(1,2,2,6,6-pentamethylpiperidin-4-yl)-2,4-pyrimidinediamine;

I-249: N2-[3-Chloro-4-(4-propylpiperazino)]phenyl-5-fluoro-N4-(1,2,2,6,6-pentamethylpiperidin-4-yl)-2,4-pyrimidinediamine;

I-250: N2-[4-Chloro-3-(3,4,5-trimethyl piperazino)]phenyl-5-fluoro-N4-(1,2,2,6,6-pentamethylpiperidin-4-yl)-2,4-pyrimidinediamine;

I-251: N2-[3-(4-Acyl-3,5-dimethylpiperazino)-4-chloro]phenyl-5-fluoro-N4-(1,2,2,6,6-pentamethylpiperidin-4-yl)-2,4-pyrimidinediamine;

I-252: 5-Fluoro-N2-(4-hydroxyl)phenyl-N4-(1,2,2,6,6-pentamethylpiperidin-4-yl)-2,4-pyrimidinediamine;

I-253: 5-Fluoro-N2-(3-hydroxyl)phenyl-N4-(1,2,2,6,6-pentamethylpiperidin-4-yl)-2,4-pyrimidinediamine;

I-254: N2-(3-Chloro-4-methoxy)phenyl-5-fluoro-N4-(2,2,6,6-tetramethylpiperidin-4-yl)-2,4-pyrimidinediamine;

I-255: 5-Fluoro-N2-[4-(4-methylpiperazino)-3-trifluoromethyl]phenyl-N4-(2,2,6,6-tetramethylpiperidin-4-yl)-2,4-pyrimidinediamine;

I-256: N2-[3-Chloro-4-(4-methylpiperazino)]phenyl-5-fluoro-N4-(2,2,6,6-tetramethylpiperidin-4-yl)-2,4-pyrimidinediamine;

I-257: 5-Fluoro-N2-[4-(4-methylsulfonylpiperazino)-3-trifluoromethyl]phenyl-N4-(2,2,6,6-tetramethylpiperidin-4-yl)-2,4-pyrimidinediamine;

I-258: N2-[3-Chloro-4-(4-methylsulfonylpiperazino)]phenyl-5-fluoro-N4-(2,2,6,6-tetramethylpiperidin-4-yl)-2,4-pyrimidinediamine;

I-259: 5-Fluoro-N4-(1,2,2,6,6-pentamethylpiperidin-4-yl)-N2-[3-trifluoromethyl-4-(1,3,5-trimethyl-3,7-diazabicyclo[3.3.1]nonan-7-yl)]phenyl-2,4-pyrimidinediamine;

I-260: 5-Fluoro-N4-(1,2,2,6,6-pentamethylpiperidin-4-yl)-N2-[4-(1,3,5-trimethyl-3,7-diazabicyclo[3.3.1]nonan-7-yl)]phenyl-2,4-pyrimidinediamine;

I-261: 5-Fluoro-N2-[4-morpholine-3-trifluoromethyl]phenyl-N4-(1,2,2,7,7-pentamethylazepan-4-yl)-2,4-pyrimidinediamine;

I-262: 5-Fluoro-N2-[3-chloro-4-methoxy]phenyl-N4-(1,2,2,7,7-pentamethylazepan-4-yl)-2,4-pyrimidinediamine;

I-263: 5-Fluoro-N2-[4-(methyl)-3-cyano]phenyl-N4-(1,2,2,7,7-pentamethylazepan-4-yl)-2,4-pyrimidinediamine;

I-264: 5-Fluoro-N2-[4-methylsulfonylpiperazin-lyl-3-trifluoromethyl]phenyl-N4-(1,2,2,7,7-pentamethylazepan-4-yl)-2,4-pyrimidinediamine;

I-265: 5-Fluoro-N2-[3,5-dichloro]phenyl-N4-(1,2,2,7,7-pentamethylazepan-4-yl)-2,4-pyrimidinediamine;

I-266: 5-Fluoro-N2-[3,4,5-trimethoxy]phenyl-N4-(1,2,2,7,7-pentamethylazepan-4-yl)-2,4-pyrimidinediamine;

I-267: 5-Fluoro-N2-[3,4-dimethoxy]phenyl-N4-(1,2,2,7,7-pentamethylazepan-4-yl)-2,4-pyrimidinediamine;

I-268: 5-Fluoro-N2-[4-methoxy-3-trifluoromethyl]phenyl-N4-(1,2,2,7,7-pentamethylazepan-4-yl)-2,4-pyrimidinediamine;

I-269: 5-Fluoro-N2-[3-methoxy]phenyl-N4-(1,2,2,7,7-pentamethylazepan-4-yl)-2,4-pyrimidinediamine;

I-270: 5-Fluoro-N2-[4-methylpiperizine-3-trifluoromethyl]phenyl-N4-(1,2,2,7,7-pentamethylazepan-4-yl)-2,4-pyrimidinediamine;

I-271: 5-Fluoro-N2-[6-morpholine-5-trifluoromethyl]pyridinyl-N4-(1,2,2,6,6-pentamethylpiperidin-4-yl)-2,4-pyrimidinediamine;

I-272: 5-Bromo-N2-[4-methoxy-3-trifluoromethyl]phenyl-N4-(1,2,2,6,6-pentamethylpiperidin-4-yl)-2,4-pyrimidinediamine;

I-273: 5-Fluoro-N2-[6-(4-methylpiperizine-1-yl)-5-trifluoromethyl]pyridine-3-yl]-N4-(1,2,2,6,6-pentamethylpiperidin-4-yl)-2,4-pyrimidinediamine;

I-274: 5-Bromo-N2-[3,4-dimethoxy]phenyl-N4-(1,2,2,6,6-pentamethylpiperidin-4-yl)-2,4-pyrimidinediamine;

I-275: 5-Bromo-N2-[3-trifluoromethoxy]phenyl-N4-(1,2,2,6,6-pentamethylpiperidin-4-yl)-2,4-pyrimidinediamine;

I-276: 5-Bromo-N2-[3,4,5-trimethoxy]phenyl-N4-(1,2,2,6,6-pentamethylpiperidin-4-yl)-2,4-pyrimidinediamine;

I-277: 5-Bromo-N2-[4-methyl-3-cyano]phenyl-N4-(1,2,2,6,6-pentamethylpiperidin-4-yl)-2,4-pyrimidinediamine;

I-278: 5-Fluoro-N2-(4-methyl-cyano)phenyl-N4-(1,2,2,5,5-pentamethylpyrrolidin-3-yl)-2,4-pyrimidinediamine;

I-279: 5-Fluoro-N2-(3,5-dichloro)phenyl-N4-(1,2,2,5,5-pentamethylpyrrolidin-3-yl)-2,4-pyrimidinediamine;

I-280: 5-Fluoro-N2-(3-chloro-4-methoxy)phenyl-N4-(1,2,2,5,5-pentamethylpyrrolidin-3-yl)-2,4-pyrimidinediamine;

I-281: 5-Fluoro-N2-(3,4-dimethoxy)phenyl-N4-(1,2,2,5,5-pentamethylpyrrolidin-3-yl)-2,4-pyrimidinediamine;

I-282: 5-Fluoro-N2-(3,4,5-trimethoxy)phenyl-N4-(1,2,2,5,5-pentamethylpyrrolidin-3-yl)-2,4-pyrimidinediamine;

I-283: 5-Fluoro-N2-(4-methoxy-3-trifluoromethyl)phenyl-N4-(1,2,2,5,5-pentamethylpyrrolidin-3-yl)-2,4-pyrimidinediamine;

I-284: 5-Fluoro-N2-(3-trifluoromethoxy)phenyl-N4-(1,2,2,5,5-pentamethylpyrrolidin-3-yl)-2,4-pyrimidinediamine;

I-285: 5-Fluoro-N2-[4-(4-methylpiperazin-1-yl)-3-(trifluoromethyl)]phenyl-N4-(1,2,2,5,5-pentamethylpyrrolidin-3-yl)-2,4-pyrimidinediamine;

I-286: 5-Fluoro-N2-[4-(4-methylsulfonyl)piperazin-1-yl)-3-(trifluoromethyl)]phenyl-N4-(1,2,2,5,5-pentamethylpyrrolidin-3-yl)-2,4-pyrimidinediamine;

I-287: 5-Fluoro-N2-[4-morpholino-3-(trifluoromethyl)]phenyl-N4-(1,2,2,5,5-pentamethylpyrrolidin-3-yl)-2,4-pyrimidinediamine;

I-288: 5-Fluoro-N2-[5-chloro-6-(4-methylpiperazin-1-yl)]pyridine-3-yl-N4-(1,2,2,6,6-pentamethylpiperidin-4-yl)-2,4-pyrimidinediamine;

I-289: 5-Fluoro-N2-[5-chloro-6-(4-(methylsulfonyl)piperazin-1-yl)]pyridin-3-yl-N4-(1,2,2,6,6-pentamethylpiperidin-4-yl)-2,4-pyrimidinediamine;

I-290: 5-Fluoro-N2-[5-chloro-6-(4-morpholino)]pyridine-3-yl-N4-(1,2,2,6,6-pentamethylpiperidin-4-yl)-2,4-pyrimidinediamine;

I-291: Methyl 3-[4-(2-(3,4-dimethoxyphenylamino)-5-fluoropyrimidine-4-ylamino)-2,2,6,6-tetramethylpiperidin-1-yl]propanoate;

I-292: Methyl 3-[4-(2-(3,5-dimethoxyphenylamino)-5-fluoropyrimidine-4-ylamino)-2,2,6,6-tetramethylpiperidin-1-yl]propanoate;

I-293: Methyl 3-[4-(2-(3-chloro-4-methoxyphenylamino)-5-fluoropyrimidine-4-ylamino)-2,2,6,6-tetramethylpiperidin-1-yl]propanoate;

I-294: Methyl 3-[4-(2-(3,5-dichlorophenylamino)-5-fluoropyrimidine-4-ylamino)-2,2,6,6-tetramethylpiperidin-1-yl]propanoate;

I-295: Methyl 3-[4-(2-(4-methoxy-3-trifluoromethyl)phenylamino)-5-fluoropyrimidine-4-ylamino)-2,2,6,6-tetramethylpiperidin-1-yl]propanoate;

I-296: Methyl 3-[4-(2-(3-cyano-4-methylphenylamino)-5-fluoropyrimidine-4-ylamino)-2,2,6,6-tetramethylpiperidin-1-yl]propanoate;

I-297: (E,Z)-Methyl 3-[4-(2-(3,4-dimethoxyphenylamino)-5-fluoropyrimidine-4-ylamino)-2,2,6,6-tetramethylpiperidin-1-yl]acrylate;

I-298: (E,Z)-Methyl 3-[4-(2-(3,5-dimethoxyphenylamino)-5-fluoropyrimidine-4-ylamino)-2,2,6,6-tetramethylpiperidin-1-yl]acrylate;

I-299: (E,Z)-Methyl 3-[4-(2-(3-chloro-4-methoxyphenylamino)-5-fluoropyrimidine-4-ylamino)-2,2,6,6-tetramethylpiperidin-1-yl]acrylate;

I-300: (E,Z)-Methyl 3-[4-(2-(3,5-dichlorophenylamino)-5-fluoropyrimidine-4-ylamino)-2,2,6,6-tetramethylpiperidin-1-yl]acrylate;

I-301: (E,Z)-Methyl 3-[4-(2-(4-methoxy-3-trifluoromethylphenylamino)-5-fluoropyrimidine-4-ylamino)-2,2,6,6-tetramethylpiperidin-1-yl]acrylate;

I-302: 3-[4-(2-(3,5-Dimethoxyphenylamino)-5-fluoropyrimidine-4-ylamino)-2,2,6,6-tetramethylpiperidin-1-yl]propanoicacid;

I-303: 3-[4-(2-(3-Chloro-4-methoxyphenylamino)-5-fluoropyrimidine-4-ylamino)-2,2,6,6-tetramethylpiperidin-1-yl]propanoicacid;

I-304: 3-[4-(2-(3,5-Dichlorophenylamino)-5-fluoropyrimidine-4-ylamino)-2,2,6,6-tetramethylpiperidin-1-yl]propanoicacid;

I-305: 3-[4-(2-(4-Methoxy-3-trifluoromethyl)phenylamino)-5-fluoropyrimidine-4-ylamino)-2,2,6,6-tetramethylpiperidin-1-yl]propanoicacid;

I-306: 3-[4-(2-(3-Cyano-4-methylphenylamino)-5-fluoropyrimidine-4-ylamino)-2,2,6,6-tetramethylpiperidin-1-yl]propanoicacid;

I-307: N2-(3,5-dimethoxyphenyl)-5-fluoro-N4-(1,2,2,6,6-pentamethylpiperidin-4-yl)pyrimidine-2,4-diamine;

I-308: N4-benzyl-N2-(3,5-dimethoxyphenyl)-5-fluoro-N4-(1,2,2,6,6-pentamethylpiperidin-4-yl)pyrimidine-2,4-diamine;

I-309: N4-benzyl-N2-(3-(difluoromethoxy)-4-methoxyphenyl)-5-fluoro-N4-(1,2,2,6,6-pentamethylpiperidin-4-yl)pyrimidine-2,4-diamine;

I-310: N4-benzyl-5-fluoro-N2-(4-(4-(methylsulfonyl)piperazin-1-yl)-3-(trifluoromethyl)phenyl)-N4-(1,2,2,6,6-pentamethylpiperidin-4-yl)pyrimidine-2,4-diamine;

I-311: N4-benzyl-5-fluoro-N2-(4-(4-methylpiperazin-1-yl)-3-(trifluoromethyl)phenyl)-N4-(1,2,2,6,6-pentamethylpiperidin-4-yl)pyrimidine-2,4-diamine;

I-312: N4-benzyl-5-fluoro-N2-(4-morpholino-3-(trifluoromethyl)phenyl)-N4-(1,2,2,6,6-pentamethylpiperidin-4-yl)pyrimidine-2,4-diamine;

I-313: 5-(4-(benzyl(1,2,2,6,6-pentamethylpiperidin-4-yl)amino)-5-fluoropyrimidin-2-ylamino)-2-methylbenzonitrile;

I-314: N2-(3,5-dimethoxyphenyl)-5-fluoro-N4-(naphthalen-2-ylmethyl)-N4-(1,2,2,6,6-pentamethylpiperidin-4-yl)pyrimidine-2,4-diamine;

I-315: 5-(5-fluoro-4-((naphthalen-2-ylmethyl)(1,2,2,6,6-pentamethylpiperidin-4-yl)amino)pyrimidin-2-ylamino)-2-methylbenzonitrile;

I-316: N2-(3-(difluoromethoxy)-4-methoxyphenyl)-5-fluoro-N4-(naphthalen-2-ylmethyl)-N4-(1,2,2,6,6-pentamethylpiperidin-4-yl)pyrimidine-2,4-diamine;

I-317: N4-(biphenyl-4-ylmethyl)-N2-(3,5-dimethoxyphenyl)-5-fluoro-N4-(1,2,2,6,6-pentamethylpiperidin-4-yl)pyrimidine-2,4-diamine;

I-318: 5-(4-((biphenyl-4-ylmethyl)(1,2,2,6,6-pentamethylpiperidin-4-yl)amino)-5-fluoropyrimidin-2-ylamino)-2-methylbenzonitrile;

I-319: N4-(biphenyl-4-ylmethyl)-N2-(3-(difluoromethoxy)-4-methoxyphenyl)-5-fluoro-N4-(1,2,2,6,6-pentamethylpiperidin-4-yl)pyrimidine-2,4-diamine;

I-320: 5-(5-fluoro-4-((1,2,2,6,6-pentamethylpiperidin-4-yl)(quinolin-2-ylmethyl)amino)pyrimidin-2-ylamino)-2-methylbenzonitrile;

I-321: N2-(3-(difluoromethoxy)-4-methoxyphenyl)-5-fluoro-N4-(1,2,2,6,6-pentamethylpiperidin-4-yl)-N4-(quinolin-2-ylmethyl)pyrimidine-2,4-diamine;

I-322: N2-(3,5-dimethoxyphenyl)-5-fluoro-N4-(1,2,2,6,6-pentamethylpiperidin-4-yl)-N4-(quinolin-2-ylmethyl)pyrimidine-2,4-diamine;

I-323: N4-((6-bromobenzo[d][1,3]dioxol-5-yl)methyl)-N2-(3,5-dimethoxyphenyl)-5-fluoro-N4-(1,2,2,6,6-pentamethylpiperidin-4-yl)pyrimidine-2,4-diamine;

I-324: 5-(4-(((6-bromobenzo[d][1,3]dioxol-5-yl)methyl)(1,2,2,6,6-pentamethylpiperidin-4-yl)amino)-5-fluoropyrimidin-2-ylamino)-2-methylbenzonitrile;

I-325: 4'-(((2-(3,5-dimethoxyphenylamino)-5-fluoropyrimidin-4-yl)(1,2,2,6,6-pentamethylpiperidin-4-yl)amino)methyl)biphenyl-2-carbonitrile;

I-326: 4'-(((2-(3-cyano-4-methylphenylamino)-5-fluoropyrimidin-4-yl)(1,2,2,6,6-pentamethylpiperidin-4-yl)amino)methyl)biphenyl-2-carbonitrile;

I-327: 5-Fluoro-N2-(3-hydroxyl)phenyl-N4-(1,2,2,6,6-pentamethylpiperidin-4-yl)-2,4-pyrimidinediamine;

I-328: 5-Fluoro-N2-[4-(furan-3-yl)-3-trifluoromethyl]phenyl-N4-(1,2,2,6,6-pentamethylpiperidin-4-yl)-2,4-pyrimidinediamine;

I-329: 5-Fluoro-N4-(1,2,2,6,6-pentamethylpiperidin-4-yl)-N2-(1,1,2,2-tetrafluoro-ethoxyphen-3-yl)-2,4-pyrimidinediamine;

I-330: N2-(4-Morpholino-3-trifluoromethyl)phenyl-N4-(1,2,2,6,6-pentamethylpiperidin-4-yl)-5-trifluoromethyl-2,4-pyrimidinediamine;

I-331: 5-Fluoro-N4-(1,2,2,6,6-pentamethylpiperidin-4-yl)-N2-(4-thiomorpholino-3-trifluoromethyl)phenyl-2,4-pyrimidinediamine;

I-332: N2-(3-Chloro-4-methyl)phenyl-5-fluoro-N4-(1,2,2,6,6-pentamethylpiperidin-4-yl)-2,4-pyrimidinediamine;

I-333: N2-(3-Chloro-4-fluoro)phenyl-5-fluoro-N4-(1,2,2,6,6-pentamethylpiperidin-4-yl)-2,4-pyrimidinediamine;

I-334: N2-(3-Chloro-4-trifluoromethoxy)phenyl-5-fluoro-N4-(1,2,2,6,6-pentamethylpiperidin-4-yl)-2,4-pyrimidinediamine;

I-335: N2-(3-Chloro-4-morpholino)phenyl-5-fluoro-N4-(1,2,2,6,6-pentamethylpiperidin-4-yl)-2,4-pyrimidinediamine;

I-336: N2-(3,4-Dichloro)phenyl-5-fluoro-N4-(1,2,2,6,6-pentamethylpiperidin-4-yl)-2,4-pyrimidinediamine;

I-337: N2-(3-Chloro-4-trifluoromethyl)phenyl-5-fluoro-N4-(1,2,2,6,6-pentamethylpiperidin-4-yl)-2,4-pyrimidinediamine;

I-338: N2-[3-Chloro-4-(pyrimin-2-yl)oxy]phenyl-5-fluoro-N4-(1,2,2,6,6-pentamethylpiperidin-4-yl)-2,4-pyrimidinediamine;

I-339: N2-[3-Chloro-4-(2-furoylamino)]phenyl-5-fluoro-N4-(1,2,2,6,6-pentamethylpiperidin-4-yl)-2,4-pyrimidinediamine;

I-340: 5-Chloro-N2-(3,5-dimethoxy)phenyl-N4-(1,2,2,6,6-pentamethylpiperidin-4-yl)-2,4-pyrimidinediamine;

I-341: 5-Chloro-N2-(3-difluoromethoxy-4-methoxy)phenyl-N4-(1,2,2,6,6-pentamethylpiperidin-4-yl)-2,4-pyrimidinediamine;

I-342: 5-Fluoro-N2-[3-methoxy-5-(1H-1,2,3,4-tetrazol-1-yl)]phenyl-N4-(1,2,2,6,6-pentamethylpiperidin-4-yl)-2,4-pyrimidinediamine;

I-343: 5-Fluoro-N2-(4-methoxy-3-trifluoromethoxy)phenyl-N4-(1,2,2,6,6-pentamethylpiperidin-4-yl)-2,4-pyrimidinediamine;

I-344: N2-(3,4-Bis-difluoromethoxy)phenyl-5-fluoro-N4-(1,2,2,6,6-pentamethylpiperidin-4-yl)-2,4-pyrimidinediamine;

I-345: 5-Fluoro-N2-(2-methoxypyrid-5-yl)-N4-(1,2,2,6,6-pentamethylpiperidin-4-yl)-2,4-pyrimidinediamine;

I-346: N2-(3-Chloro-4-isopropoxy)phenyl-5-fluoro-N4-(1,2,2,6,6-pentamethylpiperidin-4-yl)-2,4-pyrimidinediamine;

I-347: 5-Fluoro-N4-(1,2,2,6,6-pentamethylpiperidin-4-yl)-N2-(3,4,5-trifluoro)phenyl-2,4-pyrimidinediamine;

I-348: N2-[3-(2,5-Dimethyl-pyrrol-1-yl)-4-methoxy]phenyl-5-fluoro-N4-(1,2,2,6,6-pentamethylpiperidin-4-yl)-2,4-pyrimidinediamine;

I-349: 5-Fluoro-N2-[3-methoxy-4-(pyrrol-1-yl)]phenyl-N4-(1,2,2,6,6-pentamethylpiperidin-4-yl)-2,4-pyrimidinediamine;

I-350: N2-(3-Difluoromethoxy-4-methoxy)phenyl-N4-(1,2,2,6,6-pentamethylpiperidin-4-yl)-5-trifluoromethyl-2,4-pyrimidinediamine;

I-351: 5-Chloro-N2-[3-chloro-4-(2-furoylamino)]phenyl-N4-(1,2,2,6,6-pentamethylpiperidin-4-yl)-2,4-pyrimidinediamine;

I-352: 5-Chloro-N2-[4-(2-furoylamino)-3-methoxy]phenyl-N4-(1,2,2,6,6-pentamethylpiperidin-4-yl)-2,4-pyrimidinediamine;

I-353: N2-[3-methoxy-4-(2-furoylamino)]phenyl-N4-(1,2,2,6,6-pentamethylpiperidin-4-yl)-5-fluoro-2,4-pyrimidinediamine;

I-354: N2-(3,5-Difluoro)phenyl-5-fluoro-N4-(1,2,2,6,6-pentamethylpiperidin-4-yl)-2,4-pyrimidinediamine;

I-355: 5-Fluoro-N2-[4-(2-furoylamino)-3-trifluoromethyl]phenyl-N4-(1,2,2,6,6-pentamethylpiperidin-4-yl)-2,4-pyrimidinediamine;

I-356: N2-[3-Methoxy-5-(1,2,3,4-tetrazol-1-yl)]phenyl-N4-(1,2,2,6,6-pentamethylpiperidin-4-yl)-5-trifluoromethyl-2,4-pyrimidinediamine;

I-357: 5-Fluoro-N4-(1,2,2,6,6-pentamethylpiperidin-4-yl)-N2-(3-tetrazol-1-yl)phenyl-2,4-pyrimidinediamine;

I-358: 5-Fluoro-N2-[3-methoxy-5-(5-methyl-tetrazol-1-yl)]phenyl-N4-(1,2,2,6,6-pentamethylpiperidin-4-yl)-2,4-pyrimidinediamine;

I-359: N2-(3-Difluoromethoxy-4-methoxy)phenyl-5-fluoro-N4-(1,2,2,6,6-pentamethylpiperidin-4-yl)-2,4-pyrimidinediamine, citrate salt;

I-360: 5-Fluoro-N2-(3-isopropoxy-4-methoxy)phenyl-N4-(1,2,2,6,6-pentamethylpiperidin-4-yl)-2,4-pyrimidinediamine;

I-361: 5-Fluoro-N2-[4-(3,5-dimethylpyrazol-1-yl)-3-methoxy]phenyl-N4-(1,2,2,6,6-pentamethylpiperidin-4-yl)-2,4-pyrimidinediamine;

I-362: N2-{3-Chloro-4[2-(pyridine-2-yl)-ethylaminocarbonyl]}phenyl-5-fluoro-N4-(1,2,2,6,6-pentamethylpiperidin-4-yl)-2,4-pyrimidinediamine;

I-363: N2-(3,5-Dimethoxy)phenyl-N4-(1,2,2,6,6-pentamethylpiperidin-4-yl)-5-trifluoromethyl-2,4-pyrimidinediamine;

I-364: 5-Cyano-N2-(3,5-dimethoxy)phenyl-N4-(1,2,2,6,6-pentamethylpiperidin-4-yl)-2,4-pyrimidinediamine;

I-365: 5-Cyano-N2-[3-methoxy-5-(5-methyl-tetrazol-1-yl)]phenyl-N4-(1,2,2,6,6-pentamethylpiperidin-4-yl)-2,4-pyrimidinediamine;

I-366: 5-Cyano-N2-(3-difluoromethoxy-4-methoxy)phenyl-N4-(1,2,2,6,6-pentamethylpiperidin-4-yl)-2,4-pyrimidinediamine;

I-367: 5-Fluoro-N2-{4-[(pyridine-3-yl)methylaminocarbonyl]phenyl-N4-(1,2,2,6,6-pentamethylpiperidin-4-yl)-2,4-pyrimidinediamine;

I-368: N2-{3-Chloro-4-[2-(4-morpholino)ethoxy]}phenyl-5-fluoro-N4-(1,2,2,6,6-pentamethylpiperidin-4-yl)-2,4-pyrimidinediamine;

I-369: 5-Fluoro-N2-[4-methoxy-3-(1,3-oxazol-5-yl)]phenyl-N4-(1,2,2,6,6-pentamethylpiperidin-4-yl)-2,4-pyrimidinediamine;

I-370: N2-[3-Methoxy-5-(5-methyl-tetrazol-1-yl)]phenyl-N4-(1,2,2,6,6-pentamethylpiperidin-4-yl)-5-trifluoromethyl-2,4-pyrimidinediamine;

I-371: N2-(3,5-Dimethoxy)phenyl-5-fluoro-N4-(1H-2,2,6,6-tetramethylpiperidin-4-yl)-2,4-pyrimidinediamine;

I-372: 5-Fluoro-N2-[3-methoxy-5-(5-methyl-tetrazol-1-yl)]phenyl-N4-(1H-2,2,6,6-tetramethylpiperidin-4-yl)-2,4-pyrimidinediamine;

I-373: 5-Cyano-N2-{3-chloro-4-[2-(4-morpholino)ethoxy]}phenyl-N4-(1,2,2,6,6-pentamethylpiperidin-4-yl)-2,4-pyrimidinediamine;

I-374: N2-(3-methoxy-5-(5-methyl-1H-tetrazol-1-yl)phenyl)-5-methyl-N4-(1,2,2,6,6-pentamethylpiperidin-4-yl)-2,4-pyrimidinediamine;

I-375: N2-(3,5-bis(trifluoromethoxy)phenyl)-5-fluoro-N4-(2,2,6,6-tetramethylpiperidin-4-yl)-2,4-pyrimidinediamine;

I-376: 2-(3-(2,5-dimethyl-1H-pyrrol-1-yl)-4-methoxyphenylamino)-4-(1,2,2,6,6-pentamethylpiperidin-4-ylamino)pyrimidine-5-carbonitrile;

I-377: 2-(3-(difluoromethoxy)-4-methoxyphenylamino)-4-(2,2,6,6-tetramethylpiperidin-4-ylamino)pyrimidine-5-carbonitrile;

I-378: N2-[3,5-bis(2,2,2-trifluoroethoxy)]phenyl-5-fluoro-N4-(1,2,2,6,6-pentamethylpiperidin-4-yl)-2,4-pyrimidinediamine;

I-379: N2-(4,5-dimethoxy-2-methyl)phenyl-5-fluoro-N4-(2,2,6,6-tetramethylpiperidin-4-yl)-2,4-pyrimidinediamine;

I-380: N2-(4,5-dimethoxy-2-methyl)phenyl-5-fluoro-N4-(1,2,2,6,6-pentamethylpiperidin-4-yl)-2,4-pyrimidinediamine;

I-381: N2-(2-cyano-4,5-dimethoxy)phenyl-5-fluoro-N4-(1,2,2,6,6-pentamethylpiperidin-4-yl)-2,4-pyrimidinediamine;

I-382: N2-(2-cyano-4,5-dimethoxy)phenyl-5-fluoro-N4-(2,2,6,6-tetramethylpiperidin-4-yl)-2,4-pyrimidinediamine;

I-383: N2-(3,5-dihydroxy)phenyl-5-fluoro-N4-(2,2,6,6-tetramethylpiperidin-4-yl)-2,4-pyrimidinediamine;

I-384: N2-(3,5-dihydroxy)phenyl-5-fluoro-N4-(1,2,2,6,6-pentamethylpiperidin-4-yl)-2,4-pyrimidinediamine;

I-385: N2-[3,5-bis(2-methoxyethoxy)]phenyl-5-fluoro-N4-(1,2,2,6,6-pentamethylpiperidin-4-yl)-2,4-pyrimidinediamine;

I-386: N2-(2-chloro-4,5-dimethoxy)phenyl-5-fluoro-N4-(1,2,2,6,6-pentamethylpiperidin-4-yl)-2,4-pyrimidinediamine;

I-387: 5-aminocarbonyl-N2-[3-methoxy-5-(5-methyl-1H-tetrazol-1-yl)]phenyl-N4-(2,2,6,6-tetramethylpiperidin-4-yl)-2,4-pyrimidinediamine;

I-388: 5-fluoro-N2-[3-methoxy-5-(tetrazol-1-yl)]phenyl-N4-(2,2,6,6-tetramethylpiperidin-4-yl)-2,4-pyrimidinediamine;

I-389: 5-aminocarbonyl-N2-[3-methoxy-5-(tetrazol-1-yl)]phenyl-N4-(2,2,6,6-tetramethylpiperidin-4-yl)-2,4-pyrimidinediamine;

I-390: 5-aminocarbonyl-N2-[3-methoxy-5-(tetrazol-1-yl)]phenyl-N4-(1,2,2,6,6-pentamethylpiperidin-4-yl)-2,4-pyrimidinediamine;

I-391: 5-fluoro-N4-(2,2,6,6-tetramethylpiperidin-4-yl)-N2-[3-(tetrazol-1-yl)]phenyl-2,4-pyrimidinediamine;

I-392: 5-aminocarbonyl-N4-(2,2,6,6-tetramethylpiperidin-4-yl)-N2-[3-(tetrazol-1-yl)]phenyl-2,4-pyrimidinediamine;

I-393: 5-cyano-N4-(2,2,6,6-tetramethylpiperidin-4-yl)-N2-[3-(tetrazol-1-yl)]phenyl-2,4-pyrimidinediamine;

I-394: N2-[3,5-bis(2-methoxyethoxy)]phenyl-5-fluoro-N4-(2,2,6,6-tetramethylpiperidin-4-yl)-2,4-pyrimidinediamine;

I-395: 5-fluoro-N2-[4-methoxy-3-(5-propyl-1H-tetrazol-1-yl)]phenyl-N4-(1,2,2,6,6-pentamethylpiperidin-4-yl)-2,4-pyrimidinediamine;

I-396: 5-fluoro-N2-[3-(5-methyl-1H-tetrazol-1-yl)]phenyl-N4-(1,2,2,6,6-pentamethylpiperidin-4-yl)-2,4-pyrimidinediamine;

I-397: 5-fluoro-N2-[3-methyl-4-(1H-tetrazol-1-yl)]phenyl-N4-(1,2,2,6,6-pentamethylpiperidin-4-yl)-2,4-pyrimidinediamine;

I-398: 5-fluoro-N2-[4-methyl-3-(1H-tetrazol-1-yl)]phenyl-N4-(1,2,2,6,6-pentamethylpiperidin-4-yl)-2,4-pyrimidinediamine;

I-399: 5-fluoro-N2-[3-(5-methylthio-1H-tetrazol-1-yl)]phenyl-N4-(1,2,2,6,6-pentamethylpiperidin-4-yl)-2,4-pyrimidinediamine;

I-400: 5-fluoro-N2-[4-(1H-tetrazol-1-yl)]phenyl-N4-(1,2,2,6,6-pentamethylpiperidin-4-yl)-2,4-pyrimidinediamine;

I-401: 5-fluoro-N2-[4-methoxy-3-(2,2,2-trifluoroethoxy)]phenyl-N4-(1,2,2,6,6-pentamethylpiperidin-4-yl)-2,4-pyrimidinediamine;

I-402: 5-cyano-N2-[3-methoxy-5-(5-methyl-1H-tetrazol-1-yl)]phenyl-N4-(2,2,6,6-tetramethylpiperidin-4-yl)-2,4-pyrimidinediamine;

I-403: 5-cyano-N2-[3-methoxy-5-(1H-tetrazol-1-yl)]phenyl-N4-(2,2,6,6-tetramethylpiperidin-4-yl)-2,4-pyrimidinediamine;

I-404: 5-cyano-N2-[3-methoxy-5-(1H-tetrazol-1-yl)]phenyl-N4-(1,2,2,6,6-pentamethylpiperidin-4-yl)-2,4-pyrimidinediamine;

I-405: 5-cyano-N2-[3-(1H-tetrazol-1-yl)]phenyl-N4-(1,2,2,6,6-pentamethylpiperidin-4-yl)-2,4-pyrimidinediamine;

I-406: 5-aminocarbonyl-N2-[3,5-bis(2,2,2-trifluoroethoxy)]phenyl-N4-(1,2,2,6,6-pentamethylpiperidin-4-yl)-2,4-pyrimidinediamine;

I-407: 5-fluoro-N2-[3-methoxy-4-(5-methyl-1H-tetrazol-1-yl)]phenyl-N4-(1,2,2,6,6-pentamethylpiperidin-4-yl)-2,4-pyrimidinediamine;

I-408: 5-aminocarbonyl-N2-[3,5-bis(2,2,2-trifluoroethoxy)]phenyl-N4-(2,2,6,6-tetramethylpiperidin-4-yl)-2,4-pyrimidinediamine;

I-409: N2-[4-ethoxy-3-(5-ethyl-1H-tetrazol-1-yl)]phenyl-5-fluoro-N4-(1,2,2,6,6-pentamethylpiperidin-4-yl)-2,4-pyrimidinediamine;

I-410: N2-[3,4-bis(trifluoromethyl)]phenyl-5-fluoro-N4-(1,2,2,6,6-pentamethylpiperidin-4-yl)-2,4-pyrimidinediamine;

I-411: 5-cyano-N2-[3,5-bis(2,2,2-trifluoroethoxy)]phenyl-N4-(1,2,2,6,6-pentamethylpiperidin-4-yl)-2,4-pyrimidinediamine;

I-412: N2-[3-(cyclopropylaminocarbonylmethoxy)-4-methoxy]phenyl-5-fluoro-N4-(1,2,2,6,6-pentamethylpiperidin-4-yl)-2,4-pyrimidinediamine;

I-413: N2-[3-(2-methoxyethoxy)-4-methoxy]phenyl-5-fluoro-N4-(1,2,2,6,6-pentamethylpiperidin-4-yl)-2,4-pyrimidinediamine;

I-414: 5-fluoro-N2-[3-(5-methyl-1H-tetrazol-1-yl)]phenyl-N4-(2,2,6,6-tetramethylpiperidin-4-yl)-2,4-pyrimidinediamine;

I-415: N2-[4-ethoxy-3-(5-ethyl-1H-tetrazol-1-yl)]phenyl-5-fluoro-N4-(2,2,6,6-tetramethylpiperidin-4-yl)-2,4-pyrimidinediamine;

I-416: 5-fluoro-N2-[3-(5-methylthio-1H-tetrazol-1-yl)]phenyl-N4-(2,2,6,6-tetramethylpiperidin-4-yl)-2,4-pyrimidinediamine;

I-417: 5-fluoro-N2-[4-methoxy-3-(pyridin-4-ylmethoxy)]phenyl-N4-(1,2,2,6,6-pentamethylpiperidin-4-yl)-2,4-pyrimidinediamine;

I-418: 5-fluoro-N2-[4-methoxy-3-(pyridin-3-ylmethoxy)]phenyl-N4-(1,2,2,6,6-pentamethylpiperidin-4-yl)-2,4-pyrimidinediamine;

I-419: 5-cyano-N2-[3,5-bis(2,2,2-trifluoroethoxy)]phenyl-N4-(2,2,6,6-tetramethylpiperidin-4-yl)-2,4-pyrimidinediamine;

I-420: 5-aminocarbonyl-N2-[4-ethoxy-3-(5-ethyl-1H-tetrazol-1-yl)]phenyl-N4-(1,2,2,6,6-pentamethylpiperidin-4-yl)-2,4-pyrimidinediamine;

I-421: N2-{4-methoxy-3-[2-(N,N-dimethylamino)ethoxy]}phenyl-5-fluoro-N4-(1,2,2,6,6-pentamethylpiperidin-4-yl)-2,4-pyrimidinediamine;

I-422: 5-bromo-N2-(3,5-dimethoxyphenyl)-N4-(1,2,2,6,6-pentamethylpiperidin-4-yl)pyrimidine-2,4-diamine;

I-423: N2-(3,5-dimethoxyphenyl)-5-methoxy-N4-(1,2,2,6,6-pentamethylpiperidin-4-yl)pyrimidine-2,4-diamine;

I-424: 5-methoxy-N2-(3-methoxy-5-(5-methyl-1H-tetrazol-1-yl)phenyl)-N4-(1,2,2,6,6-pentamethylpiperidin-4-yl)pyrimidine-2,4-diamine;

I-425: N2-(3,5-dimethoxyphenyl)-5-methyl-N4-(1,2,2,6,6-pentamethylpiperidin-4-yl)pyrimidine-2,4-diamine;

I-426: 2-(6-(dimethylamino)pyridin-3-yl)-5-(5-fluoro-4-(1,2,2,6,6-pentamethylpiperidin-4-ylamino)pyrimidin-2-ylamino)benzonitrile;

I-427: 5-(5-fluoro-4-(1,2,2,6,6-pentamethylpiperidin-4-ylamino)pyrimidin-2-ylamino)-2-(6-morpholinopyridin-3-yl)benzonitrile;

I-428: 2-(6-(dimethylamino)pyridin-3-yl)-5-(5-fluoro-4-(2,2,6,6-tetramethylpiperidin-4-ylamino)pyrimidin-2-ylamino)benzonitrile;

I-429: 5-(5-fluoro-4-(2,2,6,6-tetramethylpiperidin-4-ylamino)pyrimidin-2-ylamino)-2-(6-morpholinopyridin-3-yl)benzonitrile;

I-430: N2-(3,5-dimethoxyphenyl)-N4-(1,2,2,6,6-pentamethylpiperidin-4-yl)-5-((trimethylsilyl)ethynyl)pyrimidine-2,4-diamine;

I-431: 5-fluoro-N2-(3-methoxy-5-(2-morpholinoethoxy)phenyl)-N4-(1,2,2,6,6-pentamethylpiperidin-4-yl)pyrimidine-2,4-diamine;

I-432: 5-fluoro-N2-(3-methoxy-5-(2-morpholinoethoxy)phenyl)-N4-(2,2,6,6-tetramethylpiperidin-4-yl)pyrimidine-2,4-diamine;

I-433: N2-(3,5-dimethoxyphenyl)-5-ethynyl-N4-(1,2,2,6,6-pentamethylpiperidin-4-yl)pyrimidine-2,4-diamine;

I-434: 5-fluoro-N2-(3-methoxy-5-(2-(pyrrolidin-1-yl)ethoxy)phenyl)-N4-(1,2,2,6,6-pentamethylpiperidin-4-yl)pyrimidine-2,4-diamine;

I-435: 5-fluoro-N2-(3-methoxy-5-(2-(pyrrolidin-1-yl)ethoxy)phenyl)-N4-(2,2,6,6-tetramethylpiperidin-4-yl)pyrimidine-2,4-diamine;

I-436: 3-(5-fluoro-4-(1,2,2,6,6-pentamethylpiperidin-4-ylamino)pyrimidin-2-ylamino)-5-methoxyphenol;

I-437: N2-(3-(2-(1H-pyrrol-1-yl)ethoxy)-5-methoxyphenyl)-5-fluoro-N4-(1,2,2,6,6-pentamethylpiperidin-4-yl)pyrimidine-2,4-diamine;

I-438: N2-(3-(2-(1H-pyrrol-1-yl)ethoxy)-5-methoxyphenyl)-5-fluoro-N4-(2,2,6,6-tetramethylpiperidin-4-yl)pyrimidine-2,4-diamine;

I-439: N2-(3-(2,5-dimethyl-1H-pyrrol-1-yl)-4-(2-morpholinoethoxy)phenyl)-5-fluoro-N4-(1,2,2,6,6-pentamethylpiperidin-4-yl)pyrimidine-2,4-diamine;

I-440: N2-(3-(2,5-dimethyl-1H-pyrrol-1-yl)-4-(2-(pyrrolidin-1-yl)ethoxy)phenyl)-5-fluoro-N4-(1,2,2,6,6-pentamethylpiperidin-4-yl)pyrimidine-2,4-diamine;

I-441: N2-(3-(2,5-dimethyl-1H-pyrrol-1-yl)-4-(2-morpholinoethoxy)phenyl)-5-fluoro-N4-(2,2,6,6-tetramethylpiperidin-4-yl)pyrimidine-2,4-diamine;

I-442: N2-(3-(2,5-dimethyl-1H-pyrrol-1-yl)-4-(2-(pyrrolidin-1-yl)ethoxy)phenyl)-5-fluoro-N4-(2,2,6,6-tetramethylpiperidin-4-yl)pyrimidine-2,4-diamine;

I-443: N2-(3-Fluoro-5-methoxy)phenyl-5-fluoro-N4-(1,2,2,6,6-pentamethylpiperidin-4-yl)-2,4-pyrimidinediamine;

I-444: N2-(3-Difluoromethoxy-4-methoxy)phenyl-5-fluoro-N4-(2,2,6,6-tetramethylpiperidin-4-yl)-2,4-pyrimidinediamine;

I-445: N2-{3-Chloro-4-[2-(4-morpholino)ethoxy]}phenyl-5-cyano-N4-(2,2,6,6-tetramethylpiperidin-4-yl)-2,4-pyrimidinediamine;

I-446: 5-Fluoro-N2-[3,5-dichloro]phenyl-N4-[1-(propionylhydrazine)-2,2,6,6-pentamethylpiperidin-4-yl]-2,4-pyrimidinediamine;

I-447: 5-Fluoro-N2-[3,5-dichloro]phenyl-N4-[1-(2-ethylamine)-2,2,6,6-pentamethylpiperidin-4-yl]-2,4-pyrimidinediamine;

I-448: 5-Amide-N2-{5-[2-(methylmorphine)-3-trifluoromethyl]pyridine}-N4-(1,2,2,6,6-pentamethylpiperidin-4-yl)-2,4-pyrimidinediamine;

I-449: 5-Fluoro-N2-{5-[2-(methylmorphine)-3-trifluoromethyl]pyridine}-N4-(2,2,6,6-tetramethylpiperidin-4-yl)-2,4-pyrimidinediamine;

I-450: 5-Fluoro-N2-[4-(methylmorphine)-3-cyano]phenyl-N4-(1,2,2,6,6-pentamethylpiperidin-4-yl)-2,4-pyrimidinediamine;

I-451: 5-Fluoro-N2-{5-[2-(methylmorphine)-3-cyano]pyridin}-N4-(2,2,6,6-tetramethylpiperidin-4-yl)-2,4-pyrimidinediamine;

I-452: 5-Cyano-N2-{5-[2-(methylmorphine)-3-trifluoromethyl]pyridine}-N4-(1,2,2,6,6-pentamethylpiperidin-4-yl)-2,4-pyrimidinediamine;

I-453: 3-(5-fluoro-4-(2,2,6,6-tetramethylpiperidin-4-ylamino)pyrimidin-2-ylamino)-5-methoxyphenol;

I-454: 5-fluoro-N2-[4-(5-methyl-1H-tetrazol-1-yl)]phenyl-N4-(1,2,2,6,6-pentamethylpiperidin-4-yl)-2,4-pyrimidinediamine;

I-455: 5-fluoro-N2-[4-methyl-3-(1H-tetrazol-1-yl)]phenyl-N4-(2,2,6,6-tetramethylpiperidin-4-yl)-2,4-pyrimidinediamine;

I-456: 5-aminocarbonyl-N2-[3-(5-methylthio-1H-tetrazol-1-yl)]phenyl-N4-(1,2,2,6,6-pentamethylpiperidin-4-yl)-2,4-pyrimidinediamine;

I-457: 5-aminocarbonyl-N2-[3-(5-methylthio-1H-tetrazol-1-yl)]phenyl-N4-(2,2,6,6-tetramethylpiperidin-4-yl)-2,4-pyrimidinediamine;

I-458: 5-fluoro-N2-{-4-[5-(furan-2-yl)-1H-tetrazol-1-yl]}phenyl-N4-(1,2,2,6,6-pentamethylpiperidin-4-yl)-2,4-pyrimidinediamine;

I-459: 5-cyano-N2-[4-methyl-3-(1H-tetrazol-1-yl)]phenyl-N4-(1,2,2,6,6-pentamethylpiperidin-4-yl)-2,4-pyrimidinediamine;

I-460: 5-cyano-N2-[4-ethoxy-3-(5-ethyl-1H-tetrazol-1-yl)]phenyl-N4-(1,2,2,6,6-pentamethylpiperidin-4-yl)-2,4-pyrimidinediamine;

I-461: 5-cyano-N2-[4-methyl-3-(1H-tetrazol-1-yl)]phenyl-N4-(2,2,6,6-tetramethylpiperidin-4-yl)-2,4-pyrimidinediamine;

I-462: 5-cyano-N2-[3-(5-methyl-1H-tetrazol-1-yl)]phenyl-N4-(1,2,2,6,6-pentamethylpiperidin-4-yl)-2,4-pyrimidinediamine;

I-463: 5-cyano-N2-[3-(5-methyl-1H-tetrazol-1-yl)]phenyl-N4-(2,2,6,6-tetramethylpiperidin-4-yl)-2,4-pyrimidinediamine;

I-464: 5-cyano-N2-[3-(5-methylthio-1H-tetrazol-1-yl)]phenyl-N4-(1,2,2,6,6-pentamethylpiperidin-4-yl)-2,4-pyrimidinediamine;

I-465: 5-cyano-N2-[3-(5-methylthio-1H-tetrazol-1-yl)]phenyl-N4-(2,2,6,6-tetramethylpiperidin-4-yl)-2,4-pyrimidinediamine;

I-466: 5-fluoro-N2-[4-fluoro-3-(1H-tetrazol-1-yl)]phenyl-N4-(1,2,2,6,6-pentamethylpiperidin-4-yl)-2,4-pyrimidinediamine;

I-467: 5-fluoro-N2-[4-fluoro-3-(1H-tetrazol-1-yl)]phenyl-N4-(2,2,6,6-tetramethylpiperidin-4-yl)-2,4-pyrimidinediamine;

I-468: 5-aminocarbonyl-N2-[4-fluoro-3-(1H-tetrazol-1-yl)]phenyl-N4-(1,2,2,6,6-pentamethylpiperidin-4-yl)-2,4-pyrimidinediamine;

I-469: 5-cyano-N2-[4-ethoxy-3-(5-ethyl-1H-tetrazol-1-yl)]phenyl-N4-(2,2,6,6-tetramethylpiperidin-4-yl)-2,4-pyrimidinediamine;

I-470: 5-Fluoro-N4-(1,2,2,6,6-pentamethylpiperidin-4-yl)-N2-[3-(tetrazol-5-yl)]phenyl-2,4-pyrimidinediamine;

I-471: 5-Fluoro-N4-(2,2,6,6-tetramethylpiperidin-4-yl)-N2-[3-(tetrazol-5-yl)]phenyl-2,4-pyrimidinediamine;

I-472: 5-Cyano-N2-[3-(2,5-dimethyl-pyrrol-1-yl)-4-methoxy]phenyl-N4-(1,2,2,6,6-pentamethylpiperidin-4-yl)-2,4-pyrimidinediamine;

I-473: 5-Cyano-N2-(3-difluoromethoxy-4-methoxy)phenyl-N4-(2,2,6,6-tetramethylpiperidin-4-yl)-2,4-pyrimidinediamine;

II-1: 5-Fluoro-N4-(1,2,2,6,6-pentamethylpiperidin-4-yl)-N2-(quinolin-6-yl)-2,4-pyrimidinediamine;

II-2: N2-(3,4-Dihydroquinolin-1H-2-one-6-yl)-5-fluoro-N4-(1,2,2,6,6-pentamethylpiperidin-4-yl)-2,4-pyrimidinediamine;

II-3: N2-(1H-Benzoxazin-3-one-6-yl)-5-fluoro-N4-(1,2,2,6,6-pentamethylpiperidin-4-yl)-2,4-pyrimidinediamine;

II-4: 5-Fluoro-N2-(1-methyl-3,4-dihydroquinolin-2-one-6-yl)-N4-(1,2,2,6,6-pentamethylpiperidin-4-yl)-2,4-pyrimidinediamine;

II-5: N2-(1-Ethyl-3,4-dihydroquinolin-2-one-6-yl)-5-fluoro-N4-(1,2,2,6,6-pentamethylpiperidin-4-yl)-2,4-pyrimidinediamine;

II-6: 5-Fluoro-N2-(4-methyl-2H-1,4-benzoxazin-3-one-7-yl)-N4-(1,2,2,6,6-pentamethylpiperidin-4-yl)-2,4-pyrimidinediamine;

II-7: 5-Fluoro-N2-(2-methylquinolin-6-yl)-N4-(1,2,2,6,6-pentamethylpiperidin-4-yl)-2,4-pyrimidinediamine;

II-8: N2-(2,2-Difluoro-4-methyl-2H-1,4-benzoxazin-3-one-7-yl)-5-fluoro-N4-(1,2,2,6,6-pentamethylpiperidin-4-yl)-2,4-pyrimidinediamine;

II-9: 5-Fluoro-N2-(2-methylbenzoimidazol-5-yl)-N4-(1,2,2,6,6-pentamethylpiperidin-4-yl)-2,4-pyrimidinediamine;

II-10: Methyl 3-[4-(2-(2,3-dihydrobenzo[b][1,4]dioxin-6-ylamino)-5-fluoropyrimidine-4-ylamino)-2,2,6,6-tetramethylpiperidin-1-yl]propanoate;

II-11: 5-Fluoro-N2-(4H-imidazo[2,1-c][1,4]-benzoxazin-7-yl)N4-(1,2,2,6,6-pentamethylpiperidin-4-yl)-2,4-pyrimidinediamine;

II-12: N2-(5-chlorobenzo[d]oxazol-2-yl)-5-fluoro-N4-(1,2,2,6,6-pentamethylpiperidin-4-yl)pyrimidine-2,4-diamine;

II-13: 5-fluoro-N4-(1,2,2,6,6-pentamethylpiperidin-4-yl)-N2-(5-(trifluoromethyl)-1,3,4-thiadiazol-2-yl)pyrimidine-2,4-diamine;

II-14: 5-fluoro-N2-(5-nitrothiazol-2-yl)-N4-(1,2,2,6,6-pentamethylpiperidin-4-yl)pyrimidine-2,4-diamine;

II-15: N2-(4-(4-chlorophenyl)thiazol-2-yl)-5-fluoro-N4-(1,2,2,6,6-pentamethylpiperidin-4-yl)pyrimidine-2,4-diamine;

II-16: N2-(benzo[d]thiazol-2-yl)-5-fluoro-N4-(1,2,2,6,6-pentamethylpiperidin-4-yl)pyrimidine-2,4-diamine;

II-17: 5-fluoro-N2-(6-nitrobenzo[d]thiazol-2-yl)-N4-(1,2,2,6,6-pentamethylpiperidin-4-yl)pyrimidine-2,4-diamine;

II-18: N2-(6-ethoxybenzo[d]thiazol-2-yl)-5-fluoro-N4-(1,2,2,6,6-pentamethylpiperidin-4-yl)pyrimidine-2,4-diamine;

II-19: 5-fluoro-N2-(4-methylbenzo[d]thiazol-2-yl)-N4-(1,2,2,6,6-pentamethylpiperidin-4-yl)pyrimidine-2,4-diamine;

II-20: 5-fluoro-N2-(4-methoxybenzo[d]thiazol-2-yl)-N4-(1,2,2,6,6-pentamethylpiperidin-4-yl)pyrimidine-2,4-diamine;

II-21: 5-fluoro-N2-(5-(methylthio)-1,3,4-thiadiazol-2-yl)-N4-(1,2,2,6,6-pentamethylpiperidin-4-yl)pyrimidine-2,4-diamine;

II-22: 2-(5-fluoro-4-(1,2,2,6,6-pentamethylpiperidin-4-ylamino)pyrimidin-2-ylamino)-1H-imidazole-4,5-dicarbonitrile;

II-23: 5-fluoro-N4-(1,2,2,6,6-pentamethylpiperidin-4-yl)-N2-(thiazolo[5,4-b]pyridin-2-yl)pyrimidine-2,4-diamine;

II-24: N2-(3,4-dihydro-2H-pyrido[3,2-b][1,4]oxazin-6-yl)-5-fluoro-N4-(1,2,2,6,6-pentamethylpiperidin-4-yl)pyrimidine-2,4-diamine;

II-25: N2-(2,2-Difluoro-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine;

II-26: N2-(2,2-Difluoro-4-methyl-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine;

II-27: N2-(2,2-Difluoro-4-ethyl-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine;

II-28: 5-Chloro-N2-(2,2-difluoro-4-methyl-2H-1,4-benzoxazin-3(4H)-one-7-yl)-N4-(1,2,2,6,6-pentamethylpiperidin-4-yl)-2,4-pyrimidinediamine;

II-29: N2-(3,4-Ethylenedioxy)phenyl-5-fluoro-N4-(1,2,2,6,6-pentamethylpiperidin-4-yl)-2,4-pyrimidinediamine;

II-30: 5-Fluoro-N2-(2-methyl-benzoxazol-5-yl)-N4-(1,2,2,6,6-pentamethylpiperidin-4-yl)-2,4-pyrimidinediamine;

II-31: N2-(2,2-Difluoro-4-ethyl-benzoxazin-3-one-7-yl)-5-fluoro-N4-(1,2,2,6,6-pentamethylpiperidin-4-yl)-2,4-pyrimidinediamine;

II-32: 5-Fluoro-N2-(3,4-methylenedioxy)phenyl-N4-(1,2,2,6,6-pentamethylpiperidin-4-yl)-2,4-pyrimidinediamine;

II-33: N2-(2,2-Dimethyl-1,4-benzoxazin-4H-3-one-7-yl)-5-fluoro-N4-(1,2,2,6,6-pentamethylpiperidin-4-yl)-2,4-pyrimidinediamine;

II-34: N2-(2,2-Dimethyl-4-methyl-1,4-benzoxazin-3-one-7-yl)-5-fluoro-N4-(1,2,2,6,6-pentamethylpiperidin-4-yl)-2,4-pyrimidinediamine;

II-35: N2-(2,2-Dimethyl-4-ethyl-1,4-benzoxazin-3-one-7-yl)-5-fluoro-N4-(1,2,2,6,6-pentamethylpiperidin-4-yl)-2,4-pyrimidinediamine;

II-36: 5-Fluoro-N2-(3-methyl-benzoxazol-2-one-6-yl)-N4-(1,2,2,6,6-pentamethylpiperidin-4-yl)-2,4-pyrimidinediamine;

II-37: N2-(2,2-Difluoro-1,3-benzodioxol-5-yl)-5-fluoro-N4-(1,2,2,6,6-pentamethylpiperidin-4-yl)-2,4-pyrimidinediamine;

II-38: 5-Fluoro-N2-(1H-indazol-5-yl)-N4-(1,2,2,6,6-pentamethylpiperidin-4-yl)-2,4-pyrimidinediamine;

II-39: 5-Fluoro-N2-(1-methyl-indazol-5-yl)-N4-(1,2,2,6,6-pentamethylpiperidin-4-yl)-2,4-pyrimidinediamine;

II-40: 5-Fluoro-N2-(1-H-indazol-6-yl)-N4-(1,2,2,6,6-pentamethylpiperidin-4-yl)-2,4-pyrimidinediamine;

II-41: 5-Fluoro-N2-(1-methyl-indazol-6-yl)-N4-(1,2,2,6,6-pentamethylpiperidin-4-yl)-2,4-pyrimidinediamine;

II-42: 5-Fluoro-N2-(3-aminocarboxylmethylene-benzoxazol-2-one-6-yl)-N4-(1,2,2,6,6-pentamethylpiperidin-4-yl)-2,4-pyrimidinediamine;

II-43: N2-(3,4-Dihydro-2H-1,5-benzodioxepin-7-yl)-5-fluoro-N4-(1,2,2,6,6-pentamethylpiperidin-4-yl)-2,4-pyrimidinediamine;

II-44: N2-(2,2-Dimethyl-4-isopropyl-1,4-benzoxazin-3-one-7-yl)-5-fluoro-N4-(1,2,2,6,6-pentamethylpiperidin-4-yl)-2,4-pyrimidinediamine;

II-45: 5-Cyano-N2-(2,2-dimethyl-4-ethyl-1,4-benzoxazin-3-one-7-yl)-N4-(1,2,2,6,6-pentamethylpiperidin-4-yl)-2,4-pyrimidinediamine;

II-46: N2-(3-Ethyl-benzoxazol-2-one-6-yl)-5-fluoro-N4-(1,2,2,6,6-pentamethylpiperidin-4-yl)-2,4-pyrimidinediamine;

II-47: 5-Fluoro-N2-(3-isopropyl-benzoxazol-2-one-6-yl)-N4-(1,2,2,6,6-pentamethylpiperidin-4-yl)-2,4-pyrimidinediamine;

II-48: N2-(2,2-Dimethyl-4-propyl-1,4-benzoxazin-3-one-7-yl)-5-fluoro-N4-(1,2,2,6,6-pentamethylpiperidin-4-yl)-2,4-pyrimidinediamine;

II-49: N2-{2,2-Dimethyl-4-[2-(N,N-dimethylamino)ethyl]-1,4-benzoxazin-3-one-7-yl}-5-fluoro-N4-(1,2,2,6,6-pentamethylpiperidin-4-yl)-2,4-pyrimidinediamine;

II-50: N2-[2,2-Dimethyl-4-ethyl-1,4-benzoxazin-3-one-7-yl]-N4-(1,2,2,6,6-pentamethylpiperidin-4-yl)-5-trifluoromethyl-2,4-pyrimidinediamine;

II-51: 5-Fluoro-N2-(1-methyl-2,3-dihydro-indol-5-yl)-N4-(1,2,2,6,6-pentamethylpiperidin-4-yl)-2,4-pyrimidinediamine;

II-52: 5-Fluoro-N2-(1-ethyl-2,3-dihydro-indol-5-yl)-N4-(1,2,2,6,6-pentamethylpiperidin-4-yl)-2,4-pyrimidinediamine;

II-53: 5-Fluoro-N2-(1-isopropyl-2,3-dihydro-indol-5-yl)-N4-(1,2,2,6,6-pentamethylpiperidin-4-yl)-2,4-pyrimidinediamine;

II-54: N2-(2,2-Dimethyl-4-N-methyl-2H-pyrido[3,2-b]-1,4-oxazin-3-one-7-yl)-5-fluoro-N4-(1,2,2,6,6-pentamethylpiperidin-4-yl)-2,4-pyrimidinediamine;

II-55: N2-(2,2-Dimethyl-4-N-ethyl-2H-pyrido[3,2-b]-1,4-oxazin-3-one-7-yl)-5-fluoro-N4-(1,2,2,6,6-pentamethylpiperidin-4-yl)-2,4-pyrimidinediamine;

II-56: N2-(1,3-Dimethyl-1,3-dihydro-benzoimidazol-2-one-5-yl)-5-fluoro-N4-(1,2,2,6,6-pentamethylpiperidin-4-yl)-2,4-pyrimidinediamine;

II-57: 5-Cyano-N2-(2,2-dimethyl-4-ethyl-1,4-benzoxazin-3-one-7-yl)-N4-(2,2,6,6-tetramethylpiperidin-4-yl)-2,4-pyrimidinediamine;

II-58: N2-(4-Ethyl-2H-1,4-benzoxazin-3-one-7-yl)-5-fluoro-N4-(1,2,2,6,6-pentamethylpiperidin-4-yl)-2,4-pyrimidinediamine;

II-59: 5-Fluoro-N2-(4-propyl-2H-1,4-benzoxazin-3-one-7-yl)-N4-(1,2,2,6,6-pentamethylpiperidin-4-yl)-2,4-pyrimidinediamine;

II-60: 5-Cyano-N2-(3,4-ethylenedioxy)phenyl-N4-(1,2,2,6,6-pentamethylpiperidin-4-yl)-2,4-pyrimidinediamine;

II-61: 5-Fluoro-N2-(4-isopropyl-2H-1,4-benzoxazin-3-one-7-yl)-N4-(1,2,2,6,6-pentamethylpiperidin-4-yl)-2,4-pyrimidinediamine;

II-62: N2-(2,2-Dimethyl-4-methyl-2H-1,4-benzothiazin-3-one-7-yl)-5-fluoro-N4-(1,2,2,6,6-pentamethylpiperidin-4-yl)-2,4-pyrimidinediamine;

II-63: N2-(2,2-Dimethyl-4-ethyl-1,4-benzothiazin-3-one-7-yl)-5-fluoro-N4-(1,2,2,6,6-pentamethylpiperidin-4-yl)-2,4-pyrimidinediamine;

II-64: N2-(2,2-Dimethyl-1,1-dioxide-4-methyl-1,4-benzothiazin-3-one-7-yl)-5-fluoro-N4-(1,2,2,6,6-pentamethylpiperidin-4-yl)-2,4-pyrimidinediamine;

II-65: 5-Cyano-N2-(2,2-difluoro-4-N-ethyl-2H-pyrido[3,2-b]-1,4-oxazin-3-one-7-yl)-N4-(1,2,2,6,6-pentamethylpiperidin-4-yl)-2,4-pyrimidinediamine;

II-66: N2-(2,2-Dimethyl-1,1-dioxide-4-ethyl-1,4-benzothiazin-3-one-7-yl)-5-fluoro-N4-(1,2,2,6,6-pentamethylpiperidin-4-yl)-2,4-pyrimidinediamine;

II-67: N2-(2,2-Dimethyl-1,1-dioxide-4-isopropyl-1,4-benzothiazin-3-one-7-yl)-5-fluoro-N4-(1,2,2,6,6-pentamethylpiperidin-4-yl)-2,4-pyrimidinediamine;

II-68: N2-(2,1-spiro-Cyclobutane-4-methyl-1,4-benzoxazin-3-one-7-yl)-5-fluoro-N4-(1,2,2,6,6-pentamethylpiperidin-4-yl)-2,4-pyrimidinediamine;

II-69: N2-(2,1-spiro-cyclobutane-4-ethyl-1,4-benzoxazin-3-one-7-yl)-5-fluoro-N4-(1,2,2,6,6-pentamethylpiperidin-4-yl)-2,4-pyrimidinediamine;

II-70: 5-Cyano-N2-(3-isopropyl-benzoxazol-2-one-6-yl)-N4-(1,2,2,6,6-pentamethylpiperidin-4-yl)-2,4-pyrimidinediamine;

II-71: 5-Cyano-N2-(4-ethyl-2H-1,4-benzoxazin-3-one-7-yl)-N4-(1,2,2,6,6-pentamethylpiperidin-4-yl)-2,4-pyrimidinediamine;

II-72: 5-Cyano-N2-(4-propyl-2H-1,4-benzoxazin-3-one-7-yl)-N4-(1,2,2,6,6-pentamethylpiperidin-4-yl)-2,4-pyrimidinediamine;

II-73: 5-Cyano-N2-(2,2-difluoro-4-N-ethyl-2H-pyrido[3,2-b]-1,4-oxazin-3-one-7-yl)-N4-(1H-2,2,6,6-tetramethylpiperidin-4-yl)-2,4-pyrimidinediamine;

II-74: 5-Cyano-N2-(2,2-dimethyl-4-isopropyl-1,4-benzoxazin-3-one-7-yl)-N4-(1,2,2,6,6-pentamethylpiperidin-4-yl)-2,4-pyrimidinediamine;

II-75: 5-Cyano-N2-(2,2-dimethyl-4-isopropyl-1,4-benzoxazin-3-one-7-yl)-N4-(1H-2,2,6,6-tetramethylpiperidin-4-yl)-2,4-pyrimidinediamine;

II-76: N2-(2,2-Dimethyl-4-cyclopropylmethylene-1,4-benzoxazin-3-one-7-yl)-5-fluoro-N4-(1,2,2,6,6-pentamethylpiperidin-4-yl)-2,4-pyrimidinediamine;

II-77: N2-(4-Cyclopropylmethylene-1,4-benzoxazin-3-one-7-yl)-5-fluoro-N4-(1,2,2,6,6-pentamethylpiperidin-4-yl)-2,4-pyrimidinediamine;

II-78: N2-[2,2-Dimethyl-4-(3-fluoropropyl)-1,4-benzoxazin-3-one-7-yl]-5-fluoro-N4-(1,2,2,6,6-pentamethylpiperidin-4-yl)-2,4-pyrimidinediamine;

II-79: 5-Cyano-N2-[2,2-dimethyl-4-(2-fluoroethyl)-1,4-benzoxazin-3-one-7-yl]-N4-(1,2,2,6,6-pentamethylpiperidin-4-yl)-2,4-pyrimidinediamine;

II-80: N2-[2,2-Dimethyl-4-(2-fluoroethyl)-1,4-benzoxazin-3-one-7-yl]-5-fluoro-N4-(1,2,2,6,6-pentamethylpiperidin-4-yl)-2,4-pyrimidinediamine;

II-81: 5-Cyano-N2-[2,2-dimethyl-4-(3-fluoropropyl)-1,4-benzoxazin-3-one-7-yl]-N4-(1,2,2,6,6-pentamethylpiperidin-4-yl)-2,4-pyrimidinediamine;

II-82: N2-[4-(2-fluoroethyl)-2H-1,4-benzoxazin-3-one-7-yl]-5-fluoro-N4-(1,2,2,6,6-pentamethylpiperidin-4-yl)-2,4-pyrimidinediamine;

II-83: (S)—N2-(2,3-dihydro-1H-inden-1-yl)-5-fluoro-N4-(1,2,2,6,6-pentamethylpiperidin-4-yl)pyrimidine-2,4-diamine;

II-84: (R)—N2-(2,3-dihydro-1H-inden-1-yl)-5-fluoro-N4-(1,2,2,6,6-pentamethylpiperidin-4-yl)pyrimidine-2,4-diamine;

II-85: N2-(5-Benzylamino-pyrid-2-yl)-N4-(1,2,2,6,6-pentamethylpiperidin-4-yl)-5-fluoro-2,4-pyrimidinediamine;

II-86: N4-benzyl-N2-(2,3-dihydrobenzo[b][1,4]dioxin-6-yl)-5-fluoro-N4-(1,2,2,6,6-pentamethylpiperidin-4-yl)pyrimidine-2,4-diamine;

II-87: N2-(2,3-dihydrobenzo[b][1,4]dioxin-6-yl)-5-fluoro-N4-(naphthalen-2-ylmethyl)-N4-(1,2,2,6,6-pentamethylpiperidin-4-yl)pyrimidine-2,4-diamine;

II-88: N4-(biphenyl-4-ylmethyl)-N2-(2,3-dihydrobenzo[b][1,4]dioxin-6-yl)-5-fluoro-N4-(1,2,2,6,6-pentamethylpiperidin-4-yl)pyrimidine-2,4-diamine;

II-89: N2-(2,3-dihydrobenzo[b][1,4]dioxin-6-yl)-5-fluoro-N4-(1,2,2,6,6-pentamethylpiperidin-4-yl)-N4-(quinolin-2-ylmethyl)pyrimidine-2,4-diamine;

II-90: N4-((6-bromobenzo[d][1,3]dioxol-5-yl)methyl)-N2-(2,3-dihydrobenzo[b][1,4]dioxin-6-yl)-5-fluoro-N4-(1,2,2,6,6-pentamethylpiperidin-4-yl)pyrimidine-2,4-diamine;

II-91: 4'-(((2-(2,3-dihydrobenzo[b][1,4]dioxin-6-ylamino)-5-fluoropyrimidin-4-yl)(1,2,2,6,6-pentamethylpiperidin-4-yl)amino)methyl)biphenyl-2-carbonitrile;

II-92: 5-fluoro-N4-(1,2,2,6,6-pentamethylpiperidin-4-yl)-N2-(2,2,3,3-tetrafluoro-2,3-dihydrobenzo[b][1,4]dioxin-6-yl)-2,4-pyrimidinediamine;

II-93: 7-(5-fluoro-4-(1,2,2,6,6-pentamethylpiperidin-4-ylamino)pyrimidin-2-ylamino)-4-(2-methoxyethyl)-2,2-dimethyl-2H-pyrido[3,2-b][1,4]oxazin-3(4H)-one;

II-94: 2-(4-(2-fluoroethyl)-3-oxo-3,4-dihydro-2H-benzo[b][1,4]oxazin-7-ylamino)-4-(1,2,2,6,6-pentamethylpiperidin-4-ylamino)pyrimidine-5-carbonitrile;

II-95: 2-(4-(2-fluoroethyl)-2,2-dimethyl-3-oxo-3,4-dihydro-2H-benzo[b][1,4]oxazin-7-ylamino)-4-(1,2,2,6,6-pentamethylpiperidin-4-ylamino)pyrimidine-5-carbonitrile;

II-96: 2-(3-(cyclopropylmethyl)-2-oxo-2,3-dihydrobenzo[d]oxazol-6-ylamino)-4-(1,2,2,6,6-pentamethylpiperidin-4-ylamino)pyrimidine-5-carbonitrile;

II-97: 2-(3-(cyclopropylmethyl)-2-oxo-2,3-dihydrobenzo[d]oxazol-6-ylamino)-4-(2,2,6,6-tetramethylpiperidin-4-ylamino)pyrimidine-5-carbonitrile;

II-98: 7-(5-fluoro-4-(1,2,2,6,6-pentamethylpiperidin-4-ylamino)pyrimidin-2-ylamino)-4-(2-fluoroethyl)-2H-benzo[b][1,4]oxazin-3(4H)-one;

II-99: N2-[3,4-dihydro-2,2-dimethyl-4-(2-methoxyethyl)-3-oxo-2H-pyrido[3,2-b]-1,4-oxazin-7-yl]phenyl-5-fluoro-N4-(2,2,6,6-tetramethylpiperidin-4-yl)-2,4-pyrimidinediamine;

II-100: 5-aminocarbonyl-N2-[3,4-dihydro-2,2-dimethyl-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-101: 5-aminocarbonyl-N2-[3,4-dihydro-2,2-dimethyl-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-102: N2-(2,2-dimethyl-benzo[1,3]dioxol-5-yl)-5-fluoro-N4-(2,2,6,6-tetramethylpiperidin-4-yl)-2,4-pyrimidinediamine;

II-103: N2-(2,2-dimethyl-benzo[1,3]dioxol-5-yl)-5-fluoro-N4-(1,2,2,6,6-pentamethylpiperidin-4-yl)-2,4-pyrimidinediamine;

II-104: N2-[3,4-dihydro-4-(2-methoxyethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine;

II-105: 5-aminocarbonyl-N2-[3,4-dihydro-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-106: 5-aminocarbonyl-N2-[3,4-dihydro-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-107: N2-[3,4-dihydro-4-(2-methoxyethyl)-3-oxo-2H-1,4-benzoxazin-7-yl]phenyl-5-fluoro-N4-(2,2,6,6-tetramethylpiperidin-4-yl)-2,4-pyrimidinediamine;

II-108: N2-[3,4-dihydro-4-(2-methoxyethyl)-3-oxo-2H-1,4-benzoxazin-7-yl]phenyl-5-fluoro-N4-(1,2,2,6,6-pentamethylpiperidin-4-yl)-2,4-pyrimidinediamine;

II-109: 5-aminocarbonyl-N2-[3,4-dihydro-4-(2-methoxyethyl)-3-oxo-2H-1,4-benzoxazin-7-yl]phenyl-N4-(2,2,6,6-tetramethylpiperidin-4-yl)-2,4-pyrimidinediamine;

II-110: 5-aminocarbonyl-N2-[3,4-dihydro-4-(2-methoxyethyl)-3-oxo-2H-1,4-benzoxazin-7-yl]phenyl-N4-(1,2,2,6,6-pentamethylpiperidin-4-yl)-2,4-pyrimidinediamine;

II-111: 5-cyano-N2-[3,4-dihydro-2,2-dimethyl-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-112: 5-cyano-N2-[3,4-dihydro-2,2-dimethyl-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-113: N2-[spiro(1,3-benzodioxole-2,1'-cyclopentan)-5-yl]-5-fluoro-N4-(1,2,2,6,6-pentamethylpiperidin-4-yl)-2,4-pyrimidinediamine;

II-114: N2-[spiro(1,3-benzodioxole-2,1'-cyclohexan)-5-yl]-5-fluoro-N4-(1,2,2,6,6-pentamethylpiperidin-4-yl)-2,4-pyrimidinediamine;

II-115: N2-(6-chloro-1,3-benzodioxol-5-yl)-5-fluoro-N4-(1,2,2,6,6-pentamethylpiperidin-4-yl)-2,4-pyrimidinediamine;

II-116: N2-(7-chloro-2,3-dihydro-1,4-benzodioxin-6-yl)-5-fluoro-N4-(1,2,2,6,6-pentamethylpiperidin-4-yl)-2,4-pyrimidinediamine;

II-117: 5-cyano-N2-[3,4-dihydro-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-118: 5-cyano-N2-[3,4-dihydro-4-(2-methoxyethyl)-3-oxo-2H-1,4-benzoxazin-7-yl]phenyl-N4-(2,2,6,6-tetramethylpiperidin-4-yl)-2,4-pyrimidinediamine;

II-119: 5-cyano-N2-[3,4-dihydro-4-(2-methoxyethyl)-3-oxo-2H-1,4-benzoxazin-7-yl]phenyl-N4-(1,2,2,6,6-pentamethylpiperidin-4-yl)-2,4-pyrimidinediamine;

II-120: N2-[spiro(1,3-benzodioxole-2,1'-cyclopentan)-5-yl]-5-fluoro-N4-(2,2,6,6-tetramethylpiperidin-4-yl)-2,4-pyrimidinediamine;

II-121: N2-[spiro(1,3-benzodioxole-2,1'-cyclohexan)-5-yl]-5-fluoro-N4-(2,2,6,6-tetramethylpiperidin-4-yl)-2,4-pyrimidinediamine;

II-122: N2-(6-bromo-2,2-difluoro-benzo[1,3]dioxol-5-yl)-5-fluoro-N4-(1,2,2,6,6-pentamethylpiperidin-4-yl)-2,4-pyrimidinediamine;

II-123: 5-fluoro-N2-(2,2,3,3,7-pentafluoro-2,3-dihydro-1,4-benzodioxin-6-yl)-N4-(1,2,2,6,6-pentamethylpiperidin-4-yl)-2,4-pyrimidinediamine;

II-124: N2-[3,4-dihydro-2,2-dimethyl-4-(2-fluoroethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine;

II-125: 5-aminocarbonyl-N2-[3,4-dihydro-2,2-dimethyl-4-(2-fluoroethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-126: N2-[3,4-dihydro-2,2-dimethyl-4-(2,2,2-trifluoroethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine;

II-127: 5-bromo-N2-(2,3-dihydrobenzo[b][1,4]dioxin-6-yl)-N4-(1,2,2,6,6-pentamethylpiperidin-4-yl)pyrimidine-2,4-diamine;

II-128: 7-(5-bromo-4-(1,2,2,6,6-pentamethylpiperidin-4-ylamino)pyrimidin-2-ylamino)-4-ethyl-2,2-dimethyl-2H-benzo[b][1,4]oxazin-3(4H)-one;

II-129: N2-(2,3-dihydrobenzo[b][1,4]dioxin-6-yl)-5-methoxy-N4-(1,2,2,6,6-pentamethylpiperidin-4-yl)pyrimidine-2,4-diamine;

II-130: 4-ethyl-7-(5-methoxy-4-(1,2,2,6,6-pentamethylpiperidin-4-ylamino)pyrimidin-2-ylamino)-2,2-dimethyl-2H-benzo[b][1,4]oxazin-3(4H)-one;

II-131: 5-fluoro-N2-(6-fluorobenzo[d]thiazol-2-yl)-N4-(1,2,2,6,6-pentamethylpiperidin-4-yl)pyrimidine-2,4-diamine;

II-132: N2-(4-(2,3-dihydrobenzo[b][1,4]dioxin-6-yl)thiazol-2-yl)-5-fluoro-N4-(1,2,2,6,6-pentamethylpiperidin-4-yl)pyrimidine-2,4-diamine;

II-133: 5-fluoro-N4-(1,2,2,6,6-pentamethylpiperidin-4-yl)-N2-(4-(4-(pyrrolidin-1-yl)phenyl)thiazol-2-yl)pyrimidine-2,4-diamine;

II-134: 5-fluoro-N4-(1,2,2,6,6-pentamethylpiperidin-4-yl)-N2-(4-(trifluoromethyl)oxazol-2-yl)pyrimidine-2,4-diamine;

II-135: N2-(4-(4-(diethylamino)phenyl)thiazol-2-yl)-5-fluoro-N4-(1,2,2,6,6-pentamethylpiperidin-4-yl)pyrimidine-2,4-diamine;

II-136: 5-fluoro-N4-(1,2,2,6,6-pentamethylpiperidin-4-yl)-N2-(4-(pyridin-3-yl)thiazol-2-yl)pyrimidine-2,4-diamine;

II-137: 5-fluoro-N2-(4-(3-fluoro-4-methoxyphenyl)thiazol-2-yl)-N4-(1,2,2,6,6-pentamethylpiperidin-4-yl)pyrimidine-2,4-diamine;

II-138: N2-(4-(3,4-dimethoxyphenyl)thiazol-2-yl)-5-fluoro-N4-(1,2,2,6,6-pentamethylpiperidin-4-yl)pyrimidine-2,4-diamine;

II-139: 5-fluoro-N4-(1,2,2,6,6-pentamethylpiperidin-4-yl)-N2-(4-(4-phenoxyphenyl)thiazol-2-yl)pyrimidine-2,4-diamine;

II-140: 5-fluoro-N4-(1,2,2,6,6-pentamethylpiperidin-4-yl)-N2-(4-(4-(trifluoromethyl)phenyl)thiazol-2-yl)pyrimidine-2,4-diamine;

II-141: N2-(4-(2,4-difluorophenyl)thiazol-2-yl)-5-fluoro-N4-(1,2,2,6,6-pentamethylpiperidin-4-yl)pyrimidine-2,4-diamine;

II-142: 4-chloro-N-(4-(2-(5-fluoro-4-(1,2,2,6,6-pentamethylpiperidin-4-ylamino)pyrimidin-2-ylamino)thiazol-4-yl)phenyl)benzenesulfonamide;

II-143: 2-(5-fluoro-4-(1,2,2,6,6-pentamethylpiperidin-4-ylamino)pyrimidin-2-ylamino)benzo[d]thiazole-6-carboxylic acid;

II-144: 5-fluoro-N2-(6-(methylsulfonyl)benzo[d]thiazol-2-yl)-N4-(1,2,2,6,6-pentamethylpiperidin-4-yl)pyrimidine-2,4-diamine;

II-145: 4-ethyl-2,2-dimethyl-7-(5-methyl-4-(1,2,2,6,6-pentamethylpiperidin-4-ylamino)pyrimidin-2-ylamino)-2H-benzo[b][1,4]oxazin-3(4H)-one;

II-146: N2-(2,3-dihydrobenzo[b][1,4]dioxin-6-yl)-5-methyl-N4-(1,2,2,6,6-pentamethylpiperidin-4-yl)pyrimidine-2,4-diamine;

II-147: 6-(5-fluoro-4-(1,2,2,6,6-pentamethylpiperidin-4-ylamino)pyrimidin-2-ylamino)quinazoline-2,4(1H,3H)-dione;

II-148: 5-(5-fluoro-4-(1,2,2,6,6-pentamethylpiperidin-4-ylamino)pyrimidin-2-ylamino)isoindoline-1,3-dione;

II-149: 5-(5-fluoro-4-(1,2,2,6,6-pentamethylpiperidin-4-ylamino)pyrimidin-2-ylamino)-2-methylisoindoline-1,3-dione;

II-150: N2-(2,3-dihydrobenzo[b][1,4]dioxin-6-yl)-N4-(1,2,2,6,6-pentamethylpiperidin-4-yl)-5-((trimethylsilyl)ethynyl)pyrimidine-2,4-diamine;

II-151: 4-ethyl-2,2-dimethyl-7-(4-(1,2,2,6,6-pentamethylpiperidin-4-ylamino)-5-((trimethylsilyl)ethynyl)pyrimidin-2-ylamino)-2H-benzo[b][1,4]oxazin-3(4H)-one;

II-152: 4-ethyl-7-(5-ethynyl-4-(1,2,2,6,6-pentamethylpiperidin-4-ylamino)pyrimidin-2-ylamino)-2,2-dimethyl-2H-benzo[b][1,4]oxazin-3(4H)-one;

II-153: 5-(5-fluoro-4-(2,2,6,6-tetramethylpiperidin-4-ylamino)pyrimidin-2-ylamino)-2-methylisoindoline-1,3-dione;

II-154: 6-(5-fluoro-4-(2,2,6,6-tetramethylpiperidin-4-ylamino)pyrimidin-2-ylamino)quinazoline-2,4(1H,3H)-dione;

II-155: 6-(5-fluoro-4-(2,2,6,6-tetramethylpiperidin-4-ylamino)pyrimidin-2-ylamino)-2,3-dihydrobenzo[b][1,4]dioxine-2-carboxylic acid;

II-156: N2-(2,3-dihydrobenzo[b][1,4]dioxin-6-yl)-5-ethynyl-N4-(1,2,2,6,6-pentamethylpiperidin-4-yl)pyrimidine-2,4-diamine;

II-157: 6-(5-fluoro-4-(1,2,2,6,6-pentamethylpiperidin-4-ylamino)pyrimidin-2-ylamino)-2,3-dihydrobenzo[b][1,4]dioxine-2-carboxylic acid;

II-158: (6-(5-fluoro-4-(1,2,2,6,6-pentamethylpiperidin-4-ylamino)pyrimidin-2-ylamino)-2,3-dihydrobenzo[b][1,4]dioxin-2-yl)(4-methylpiperazin-1-yl)methanone;

II-159: 6-(5-fluoro-4-(2,2,6,6-tetramethylpiperidin-4-ylamino)pyrimidin-2-ylamino)-2,3-dihydrobenzo[b][1,4]dioxine-2-carboxamide;

II-160: (6-(5-fluoro-4-(2,2,6,6-tetramethylpiperidin-4-ylamino)pyrimidin-2-ylamino)-2,3-dihydrobenzo[b][1,4]dioxin-2-yl)(4-methylpiperazin-1-yl)methanone;

II-161: 5-Cyano-N2-[4-(2-fluoroethyl)-2H-1,4-benzoxazin-3-one-7-yl]-N4-(1,2,2,6,6-pentamethylpiperidin-4-yl)-2,4-pyrimidinediamine;

II-162: 5-Cyano-N2-(3-isopropyl-benzoxazol-2-one-6-yl)-N4-(2,2,6,6-tetramethylpiperidin-4-yl)-2,4-pyrimidinediamine;

II-163: N2-(3-Cyclopropylmethylene-benzoxazol-2-one-6-yl)-5-fluoro-N4-(1,2,2,6,6-pentamethylpiperidin-4-yl)-2,4-pyrimidinediamine;

II-164: 5-Cyano-N2-[2,2-dimethyl-4-(2-fluoroethyl)-1,4-benzoxazin-3-one-7-yl]-N4-(2,2,6,6-tetramethylpiperidin-4-yl)-2,4-pyrimidinediamine;

II-165: N2-(2,1-spiro-cyclobutane-4-isopropyl-1,4-benzoxazin-3-one-7-yl)-5-fluoro-N4-(1,2,2,6,6-pentamethylpiperidin-4-yl)-2,4-pyrimidinediamine;

II-166: N2-(2,1-spiro-cyclobutane-4-propyl-1,4-benzoxazin-3-one-7-yl)-5-fluoro-N4-(1,2,2,6,6-pentamethylpiperidin-4-yl)-2,4-pyrimidinediamine;

II-167: 5-Fluoro-N2-{3-[2-(morpholino)ethyl]-benzoxazol-2-one-6-yl}-N4-(1,2,2,6,6-pentamethylpiperidin-4-yl)-2,4-pyrimidinediamine;

II-168: 5-Fluoro-N2-{3-[2-(morpholino)ethyl]-benzoxazol-2-one-6-yl}-N4-(2,2,6,6-tetramethylpiperidin-4-yl)-2,4-pyrimidinediamine;

II-169: 5-Cyano-N2-{3-[2-(morpholino)ethyl]-benzoxazol-2-one-6-yl}-N4-(1,2,2,6,6-pentamethylpiperidin-4-yl)-2,4-pyrimidinediamine;

II-170: 5-Cyano-N2-{3-[2-(morpholino)ethyl]-benzoxazol-2-one-6-yl}-N4-(2,2,6,6-tetramethylpiperidin-4-yl)-2,4-pyrimidinediamine;

II-171: 5-Cyano-N2-[4-(2-fluoroethyl)-2H-1,4-benzoxazin-3-one-7-yl]-N4-(2,2,6,6-tetramethylpiperidin-4-yl)-2,4-pyrimidinediamine;

II-172: 5-Fluoro-N2-[3-(2-fluoroethyl)-benzoxazol-2-one-6-yl]-N4-(1,2,2,6,6-pentamethylpiperidin-4-yl)-2,4-pyrimidinediamine;

II-173: N2-(3-Ethyl-benzoxazol-2-one-5-yl)-5-Fluoro-N4-(1,2,2,6,6-pentamethylpiperidin-4-yl)-2,4-pyrimidinediamine;

II-174: N2-(3-Ethyl-benzoxazol-2-one-5-yl)-5-fluoro-N4-(2,2,6,6-tetramethylpiperidin-4-yl)-2,4-pyrimidinediamine;

II-175: 5-Fluoro-N2-[7-Nitro-1,2,4-triazolo(3,4-c)][1,4]benzoxazin-N4-(1,2,2,6,6-pentamethylpiperidin-4-yl)-2,4-pyrimidinediamine;

II-176: 5-fluoro-N4-(1,2,2,6,6-pentamethylpiperidin-4-yl)-N2-(2,2,6-trifluoro-benzo[1,3]dioxol-5-yl)-2,4-pyrimidinediamine;

II-177: 5-cyano-N2-[3,4-dihydro-2,2-dimethyl-4-(2-fluoroethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-178: N2-[3,4-dihydro-2,2-dimethyl-4-(2-fluoroethyl)-3-oxo-2H-pyrido[3,2-b]-1,4-oxazin-7-yl]phenyl-5-fluoro-N4-(2,2,6,6-tetramethylpiperidin-4-yl)-2,4-pyrimidinediamine;

II-179: 5-Cyano-N2-(3-cyclopropylmethylene-benzoxazol-2-one-6-yl)-N4-(1,2,2,6,6-pentamethylpiperidin-4-yl)-2,4-pyrimidinediamine;

II-180: 5-Cyano-N2-(3-cyclopropylmethylene-benzoxazol-2-one-6-yl)-N4-(2,2,6,6-tetramethylpiperidin-4-yl)-2,4-pyrimidinediamine;

II-181: 5-Fluoro-N2-[4-(2-fluoroethyl)-2H-1,4-benzoxazin-3-one-7-yl]-N4-(2,2,6,6-tetramethylpiperidin-4-yl)-2,4-pyrimidinediamine;

III-1: N2-(3-Chloro-4-methoxy)phenyl-5-fluoro-N4-(1-methylpiperidin-4-yl)-2,4-pyrimidinediamine;

III-2: N2-(3-Cyano)phenyl-5-fluoro-N4-(1-methylpiperidin-4-yl)-2,4-pyrimidinediamine;

III-3: 5-Fluoro-N2-[4-(4-methylpiperazino)-3-trifluoromethyl]phenyl-N4-(1-methylpiperidin-4-yl)-2,4-pyrimidinediamine;

III-4: N2-[3-Chloro-4-(4-methylpiperazino)]phenyl-5-fluoro-N4-(1-methylpiperidin-4-yl)-2,4-pyrimidinediamine;

III-5: N2-(3-Chloro-4-methoxy)phenyl-5-fluoro-N4-[1-(2-hydroxyethyl)piperidin-4-yl]-2,4-pyrimidinediamine;

III-6: N2-(3-Cyano)phenyl-5-fluoro-N4-[1-(2-hydroxyethyl)piperidin-4-yl]-2,4-pyrimidinediamine;

III-7: 5-Fluoro-N4-[1-(2-hydroxyethyl)piperidin-4-yl]-N2-[4-(4-methylpiperazino)-3-trifluoromethyl]phenyl-2,4-pyrimidinediamine;

III-8: N2-[3-Chloro-4-(4-methylpiperazino)]phenyl-5-fluoro-N4-[1-(2-hydroxyethyl)piperidin-4-yl]-2,4-pyrimidinediamine;

III-9: N2-(3,5-dimethoxy)phenyl-5-fluoro-N4-[1-(pyridin-4-yl)methylpiperidin-4-yl]-2,4-pyrimidinediamine;

III-10: 5-fluoro-N2-[3-methoxy-5-(5-methyl-1H-tetrazol-1-yl)]phenyl-N4-[1-(pyridin-4-yl)methylpiperidin-4-yl]-2,4-pyrimidinediamine;

IV-1: 5-Fluoro-N2-[3-methoxy-5-(5-methyl-tetrazol-1-yl)]phenyl-N4-(1,2,6,-trimethylpiperidin-4-yl)-2,4-pyrimidinediamine, trans isomer;

IV-2: N2-(3,5-Dimethoxy)phenyl-6-methyl-N4-(1,2,2,6,6-pentamethylpiperidin-4-yl)-2,4-pyrimidinediamine;

IV-3: N2-[3-Chloro-4-(4-methylsulfonylpiperazino)]phenyl-6-methyl-N4-(1,2,2,6,6-pentamethylpiperidin-4-yl)-2,4-pyrimidinediamine;

IV-4: N2-[3-Chloro-4-(4-methylsulfonylpiperazino)]phenyl-N4-(4-diethylamino)cyclohexyl-5-fluoro-2,4-pyrimidinediamine;

IV-5: N2-(3-Chloro-4-methoxy)phenyl-N4-(4-diethylamino)cyclohexyl-5-fluoro-2,4-pyrimidinediamine;

IV-6: N2-(3-Cyano)phenyl-N4-(4-diethylamino)cyclohexyl-5-fluoro-2,4-pyrimidinediamine IV-7: N4-(4-Diethylamino)cyclohexyl-5-fluoro-N2-[4-(4-methylpiperazino)-3-trifluoromethyl]phenyl-2,4-pyrimidinediamine;

IV-8: N2-[3-Chloro-4-(4-methylpiperazino)]phenyl-N4-(4-diethylamino)cyclohexyl-5-fluoro-2,4-pyrimidinediamine; and IV-9: N4-(4-Diethylamino)cyclohexyl-5-fluoro-N2-[4-(4-methylsulfonylpiperazino)-3-trifluoromethyl]phenyl-2,4-pyrimidinediamine;

or a solvate, prodrug, or a pharmaceutically acceptable salt thereof.

DETAILED DESCRIPTION

A. Overview

The invention encompasses compounds having formula I or II and the compositions and methods using these compounds in the treatment of conditions in which inhibition of a PKC, particularly PKC-theta, PKC-epsilon or PKC-mu, is therapeutically useful.

B. Definitions

As used herein, the following definitions shall apply unless otherwise indicated.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). Also by way of example, a methyl group, an ethyl group, an n-propyl and an isopropyl group are all represented by the term $C_{1-3}$ alkyl. Likewise terms indicating larger numerical ranges of carbon atoms are representative of any linear or branched hydrocarbyl falling within the numerical range. This inclusiveness applies to other hydrocarbyl terms bearing such numerical ranges.

"Alkylene" refers to divalent saturated aliphatic hydrocarbyl groups preferably having from 1 to 6 and more preferably 1 to 3 carbon atoms that are either straight-chained or branched. This term is exemplified by groups such as methylene (—$CH_2$—), ethylene (—$CH_2CH_2$—), n-propylene (—$CH_2CH_2CH_2$—), iso-propylene (—$CH_2CH(CH_3)$—) or (—$CH(CH_3)CH_2$—), and the like.

"Substituted alkylene" refers to an alkylene group having from 1 to 3 hydrogens replaced with substituents as described for carbons in the definition of "substituted" below.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group $CH_3C(O)$—.

"Acylamino" refers to the groups —$NR^{20}C(O)$alkyl, —$NR^{20}C(O)$substituted alkyl, N $R^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group —NH$_2$.

"Aminocarbonyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR20C(O)NR21R22, wherein R20 is hydrogen or alkyl and R21 and R22 independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R21 and R22 are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{20}$C(S)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminocarbonyloxy" refers to the group —O—C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonyloxy" refers to the group —O—SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic; R$^{21}$ and R$^{22}$ are optionally joined together with the nitrogen bound thereto to form a heterocyclic or substituted heterocyclic group; and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{20}$—SO$_2$NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{30}$)NR$^{31}$R$^{32}$, wherein R$^{31}$ and R$^{32}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{31}$ and R$^{32}$ are optionally joined together with the nitrogen bound thereto to form a heterocyclic or substituted heterocyclic group. R$^{30}$ is selected from the group consisting of hydrogen, alkyl, substituted alkyl, alkenyl, substituted alkenyl, alkynyl, substituted alkynyl, cycloalkynyl, substituted cycloalkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, nitro, nitroso, hydroxy, alkoxy, cyano, —N=N—N-alkyl, —N=N—N-substituted alkyl, —N(alkyl)SO$_2$-alkyl, —N(alkyl)SO$_2$-substituted alkyl, —N=N=N-alkyl, —N=N=N— substituted alkyl, acyl, —SO$_2$-alkyl and —SO$_2$-substituted alkyl, wherein alkyl, substituted alkyl, alkenyl, substituted alkenyl, alkynyl, substituted alkynyl, cycloalkynyl, substituted cycloalkynyl, cycloalkyl, substituted cycloalkyl, cycloalkenyl, substituted cycloalkenyl, aryl, substituted aryl, heteroaryl, substituted heteroaryl, heterocyclic, substituted heterocyclic, nitro, nitroso, hydroxy, alkoxy, and cyano are as defined herein. One of R$^{31}$ and R$^{32}$ along with R$^{30}$ are optionally joined together with the nitrogens bound thereto and the intervening carbon of the guanidine group to form a cyclic amidine.

"Aryl" or "Ar" refers to a monovalent aromatic carbocyclic group of from 6 to 15 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, 9,10-dihydrophenanthrene, and the like), provided that the point of attachment is through an atom of the aromatic aryl group. Preferred aryl groups include phenyl and naphthyl.

"Aryloxy" refers to the group —O-aryl, wherein aryl is as defined herein, including, by way of example, phenoxy, naphthoxy, and the like.

"Arylthio" refers to the group —S-aryl, wherein aryl is as defined herein. In other embodiments, sulfur may be oxidized to —S(O)— or —SO$_2$— moieties. Depending on the pendant substitution, the sulfoxide may impart chirality to the molecule.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. Such groups are exemplified, for example, bi-vinyl, allyl, and but-3-en-1-yl. Included within this term are the cis and trans isomers or mixtures of these isomers.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

"Alkynyloxy" refers to the group —O-alkynyl, wherein alkynyl is as defined herein. Alkynyloxy includes, by way of example, ethynyloxy, propynyloxy, and the like.

"Carboxyl," "carboxy" or "carboxylate" refers to —CO$_2$H or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino" refers to the groups —NR—C(O)O-alkyl, —NR—C(O)O-substituted alkyl, —NR—C(O)O-alkenyl, —NR—C(O)O-substituted alkenyl, —NR—C(O)O-alkynyl, —NR—C(O)O-substituted alkynyl, —NR—C(O)O-aryl, —NR—C(O)O-substituted aryl, —NR—C(O)O-cycloalkyl, —NR—C(O)O-substituted cycloalkyl, —NR—C(O)O-cycloalkenyl, —NR—C(O)O-substituted cycloalkenyl, —NR—C(O)O-heteroaryl, —NR—C(O)O-substituted heteroaryl, —NR—C(O)O-heterocyclic, and —NR—C(O)O-substituted heterocyclic, wherein R is alkyl or hydrogen and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like.

"Cycloalkylalkyl" refers to a cycloalkyl-alkylene group, for example cyclopropyl-CH$_2$— where the cycloalkyl is bonded to the parent structure via an alkylene divalent linking group.

"Cycloalkenyl" refers to non-aromatic cyclic alkyl groups of from 3 to 10 carbon atoms having single or multiple rings and having at least one double bond and preferably from 1 to 2 double bonds.

"Cycloalkynyl" refers to non-aromatic cycloalkyl groups of from 5 to 10 carbon atoms having single or multiple rings and having at least one triple bond.

"Cycloalkylene" refers to divalent cycloalkyl groups, wherein cycloalkyl is as defined herein.

"Cycloalkoxy" refers to —O-cycloalkyl.

"Cycloalkylthio" refers to —S-cycloalkyl. In other embodiments, sulfur may be oxidized to —S(O)— or —SO$_2$— moieties. Depending on the pendant substitution, the sulfoxide may impart chirality to the molecule.

"Cycloalkenyloxy" refers to —O-cycloalkenyl.

"Cycloalkenylthio" refers to —S-cycloalkenyl. In other embodiments, sulfur may be oxidized to sulfinyl or sulfonyl moieties. Depending on the pendant substitution, the sulfoxide may impart chirality to the molecule.

"Guanidino" refers to the group —NHC(=NH)NH$_2$.

"Substituted guanidino" refers to the group —NR$^{33}$C(=NR$^{33}$)N(R$^{33}$)$_2$, wherein each R$^{33}$ independently is selected from the group consisting of hydrogen, alkyl, substituted alkyl, aryl, substituted aryl, heteroaryl, substituted heteroaryl, heterocyclic, and substituted heterocyclic; two R groups attached to a common guanidino nitrogen atom are optionally joined together with the nitrogen bound thereto to form a heterocyclic or substituted heterocyclic group, provided that at least one R is not hydrogen; and said substituents are as defined herein. Two R$^{33}$ groups on distinct nitrogens are optionally joined together with the nitrogens bound thereto and the intervening carbon of the guanidine group to form a cyclic guanidine.

"Halo" or "halogen" refers to fluoro, chloro, bromo, and iodo and is preferably fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen, and sulfur within the ring. Such heteroaryl groups can have a single ring (e.g., pyridinyl, imidazolyl or furyl) or multiple condensed rings (e.g., indolizinyl, quinolinyl, benzimidazolyl or benzothienyl), wherein the condensed rings may or may not be aromatic and/or contain a heteroatom, provided that the point of attachment is through an atom of the aromatic heteroaryl group. In one embodiment, the nitrogen and/or sulfur ring atom(s) of the heteroaryl group are optionally oxidized to provide for the N-oxide (N→O), sulfinyl, or sulfonyl moieties. Preferred heteroaryls include pyridinyl, pyrrolyl, indolyl, thiophenyl, and furanyl.

"Heteroaryloxy" refers to —O-heteroaryl.

"Heteroarylthio" refers to the group —S-heteroaryl. In other embodiments, sulfur may be oxidized to —S(O)— or —SO$_2$— moieties. The sulfoxide may exist as one or more stereoisomers.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In one embodiment, the nitrogen and/or sulfur atom(s) of the heterocyclic group are optionally oxidized to provide for the N-oxide, —S(O)—, or —SO$_2$— moieties.

"Heterocycloalkylalkyl" refers to a heterocyclyl group linked to the parent structure via an alkylene linker, for example (tetrahydrofuran-3-yl)methyl-:

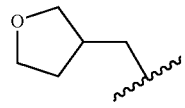 [SMILES: *CC1CCOC1]

Examples of heterocycle and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Heterocyclyloxy" refers to the group —O-heterocycyl.

"Heterocyclylthio" refers to the group —S-heterocycyl. In other embodiments, sulfur may be oxidized to —S(O)— or —SO$_2$— moieties. The sulfoxide may exist as one or more stereoisomers.

"Nitro" refers to the group —NO$_2$.

"Nitroso" refers to the group —NO.

"Oxo" refers to the atom (=O).

"Oxy radical" refers to —O. (also designated as →O), that is, a single bond oxygen radical. By way of example, N-oxides are nitrogens with an oxy radical. A specific example is where R$^{2a}$, R$^{2b}$, R$^{4a}$ and R$^{4b}$ are methyl, n is 1 and R$^3$ is oxy radical, that is, where the ring bearing R$^{2a}$, R$^{2b}$, R$^{4a}$, R$^{4b}$ and R$^3$ is 2,2,6,6-tetramethylpiperidin-N-oxide (commonly known as TEMPO).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cycloalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes groups such as methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cycloalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkenyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thiol" refers to the group —SH.

"Thioxo" refers to the atom (=S).

"Alkylthio" refers to the group —S-alkyl, wherein alkyl is as defined herein. In other embodiments, sulfur may be oxidized to —S(O)—. The sulfoxide may exist as one or more stereoisomers.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "substituted," when used to modify a specified group or radical, means that one or more hydrogen atoms of the specified group or radical are each, independently of one another, replaced with the same or different substituent groups as defined below. By way of example, a pyrrolidinyl group on a compound of the invention can be substituted or unsubstituted. A specific example of a substituted pyrrolidine is where $R^{2a}$, $R^{2b}$ are methyl, $R^3$, $R^{4a}$ and $R^{4b}$ are H, and n is 0, that is, where the ring bearing $R^{2a}$, $R^{2b}$, $R^3$, $R^{4a}$ and $R^{4b}$ is 2,2-dimethylpyrrolidinyl.

Substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2^-M^+$, —$SO_2OR^{70}$, —$OSO_2R^{70}$, —$OSO_2^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —OC(O)$R^{70}$, —OC(S)$R^{70}$, —OC(O)$O^-M^+$, —OC(O)$OR^{70}$, —OC(S)$OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means e.g. that one of the counter ions for such divalent alkali earth ions can be an ionized form of a compound of the invention and the other a typical counter ion such as chloride, or two ionized compounds of the invention can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

Substituent groups for hydrogens on nitrogen atoms in "substituted" heteroalkyl and cycloheteroalkyl groups are, unless otherwise specified, —$R^{60}$, —$O^-M^+$, —$OR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —OC(O)$R^{70}$, —OC(S)$R^{70}$, —OC(O)$OR^{70}$, —OC(S)$OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In a preferred embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to substituted aryl-(substituted aryl)-substituted aryl.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

"Patient" refers to human and non-human animals, especially mammals.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like.

"Prodrug" refers to a derivative of an active 4-pyrimidineamine compound (drug) that may require a transformation under the conditions of use, such as within the body, to release the active 2,4-pyrimidinediamine drug. Prodrugs are frequently, but not necessarily, pharmacologically inactive until converted into the active drug. Prodrugs are typically obtained by masking one or more functional groups in an active 2,4-pyrimidinediamine drug believed to be in part required for activity with a progroup (defined below) to form a promoiety which undergoes a transformation, such as cleavage, under the specified conditions of use to release the functional group, and hence the active 2,4-pyrimidinediamine drug. The cleavage of the promoiety may proceed spontaneously, such as by way of a hydrolysis reaction, or it can be catalyzed or induced by another agent, such as an enzyme, light, an acid or base, or a change of or exposure to a physical or environmental parameter, such as temperature. The agent can be endogenous to the conditions of use, such as an enzyme present in the cells to which the prodrug is administered or the acidic conditions of the stomach, or it can be supplied exogenously.

"Progroup" refers to a type of protecting group that, when used to mask a functional group within an active 2,4-pyrimidinediamine drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH3 comprises the progroup —C(O)CH3.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

Similarly, it is understood that the above definitions are not intended to include impermissible substitution patterns (e.g., methyl substituted with 5 fluoro groups). Such impermissible substitution patterns are easily recognized by a person having ordinary skill in the art.

C. Compounds of the Invention

This invention provides novel 2,4-pyrimidinediamine compounds, prodrugs of the compounds, methods of making the compounds and methods of using these compounds in the treatment of conditions in which inhibition of PKC is therapeutically useful. These conditions include, but are not limited to, pain (nociceptive and/or neuropathic), asthma, atopic dermatitis, allergic rhinitis, systemic anaphylaxis, hypersensitivity responses, drug allergies, insect sting allergies, dermatitis, eczema, urticaria, inflammatory bowel disease, Crohn's disease, ileitis, Celiac disease, nontropical Sprue, enteritis, enteropathy, colitis, eosinophilic gastroenteritis, ileoanal anastomosis, disorders of the skin, multiple sclerosis, systemic lupus erythermatosus, myasthenia gravis, juvenile onset diabetes, glomerulonephritis, autoimmune thyroiditis, Behcet's disease, graft rejection, stroke, cardiac ischemia, mastitis, vaginitis, cholecystitis, cholangitis, chronic bronchitis, chronic sinusitis, chronic inflammatory diseases of the lung, hypersensitivity pneumonitis, collagen diseases, sarcoidosis, vasculitis, spondyloarthropathies, scleroderma, atherosclerosis, restenosis, myositis pancreatitis, insulin-dependent diabetes mellitus, metabolic syndrome, autoimmune thrombocytopenia, rheumatoid arthritis, osteoarthritis, multiple sclerosis, inflammatory bowel disease, psoriasis, organ transplantation, graft vs. host disease, asthma, and chronic obstructive pulmonary disease. and the other conditions described herein. Given the severity of and suffering caused by these conditions, it is vital that new treatments are developed to treat these conditions.

In one embodiment, the present invention provides a compound of formula I, prodrugs, solvates, or pharmaceutically acceptable salts thereof:

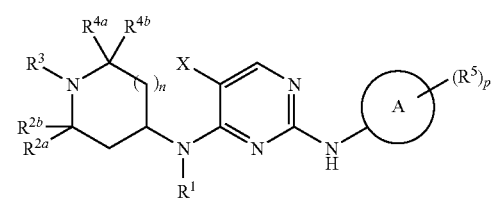

I wherein

X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;

$R^1$ is selected from the group consisting of hydrogen, lower alkyl, substituted lower alkyl, aryl, substituted aryl, heteroaryl, and substituted heteroaryl;

each $R^{2a}$, $R^{2b}$, $R^{4a}$ and $R^{4b}$ independently is selected from the group consisting of hydrogen and $C_{1-3}$ alkyl;

$R^3$ is selected from the group consisting of —Y, —C(O)—Y, —SO$_2$—Y, —(CH$_2$)$_m$—C(O)—Y, —CH═CH—C(O)—Y and —(CH$_2$)$_m$—NY$_2$, wherein each Y independently is hydrogen, hydroxy, oxy radical, alkoxy, alkyl, or substituted alkyl and m is 1, 2, or 3;

A is selected from the group consisting of bicyclic aryl, bicyclic heteroaryl, tricyclic aryl, tricyclic heteroaryl and

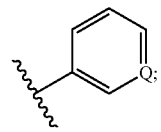

each $R^5$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;

n is an integer between 0 and 3;

p is an integer between 0 and 5; and

Q is N, N→O, or $CR^{7b}$;

provided that, (1) when X is fluoro, n is zero or one, and $A\text{-}(R^5)_p$ is of the formula:

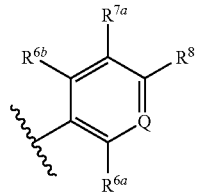

where each of $R^{6a}$, $R^{6b}$, $R^{7a}$, $R^{7b}$ and $R^8$ is independently $R^5$;

then $R^{6a}$ or $R^{6b}$ is not hydrogen; or $R^{7a}$ or $R^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or $R^8$ is selected from the group consisting of substituted alkyl but not $CF_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and (2) when A is tricyclic heteroaryl and X is halo, then at least one of $R^{2a}$, $R^{2b}$, $R^{4a}$ and $R^{4b}$ is not hydrogen; and (3) when X is nitro, $CF_3$, or $C(O)NH_2$, then at least one of $R^{2a}$, $R^{2b}$, $R^{4a}$ and $R^{4b}$ is not hydrogen; and (4) when X is bromo and $R^2$ is idolin-2-one-5-yl, then at least one of $R^{2a}$, $R^{2b}$, $R^{4a}$ and $R^{4b}$ is not hydrogen; and (5) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

In a preferred implementation, n is 1 and each of $R^{2a}$, $R^{2b}$, $R^3$, $R^{4a}$, and $R^{4b}$ is methyl.

In another embodiment, A is pyridyl. In another embodiment, A is phenyl.

In another embodiment, according to formula II, $R^{7a}$ or $R^{7b}$ is selected from the group consisting of cycloalkyl, substituted cycloalkyl, acyl, cyano, aminocarbonyl, sulfonyl, sulfonylamino, and aminosulfonyl.

In another embodiment, according to formula II, $R^8$ is selected from the group consisting of substituted alkyl not including $CF_3$ or an amino-substituted alkyl, substituted alkenyl, substituted alkynyl, cycloalkyl, substituted cycloalkyl, acyl, carboxyl, carboxyl ester, cyano, sulfonyl, and sulfonylamino.

In another embodiment, A is a bicyclic aryl or bicyclic heteroaryl selected from the group consisting of:

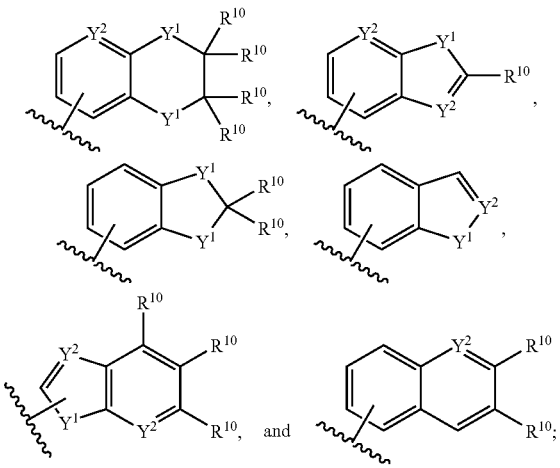

wherein
each $Y^1$ independently is selected from the group consisting of $—CH_2—$, $—O—$, $—NR^{11}—$, $—S—$, and $—S(O)_2—$;
each $Y^2$ independently is selected form the group consisting of $—CH=$ and $—N=$;
each $R^{10}$ independently is selected from the group consisting of hydrogen, alkyl, substituted alkyl, alkoxy, alkylthio, halo, cyano, and nitro, or two $R^{10}$ attached to the same carbon together form a $C_{4-6}$ cycloalkyl or an oxo group; and
each $R^{11}$ independently is selected from the group consisting of hydrogen, alkyl and substituted alkyl.

In another embodiment, A is a bicyclic aryl or bicyclic heteroaryl selected from the group consisting of:

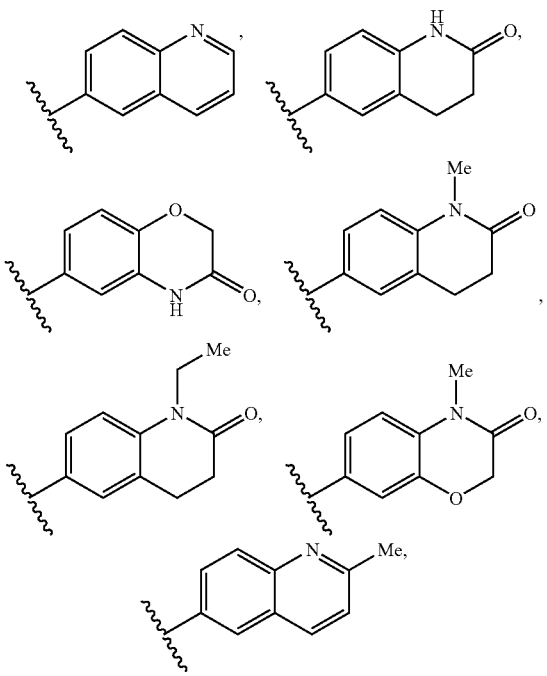

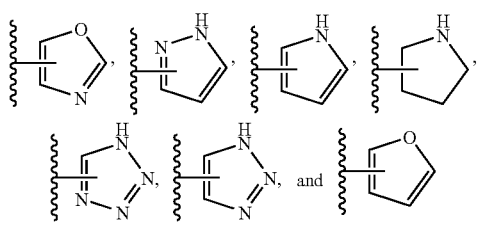

In a further particular embodiment, the methyl or ethyl group of the aforementioned bicyclic heteroaryls is substituted with one or more fluorine atoms.

In another embodiment, $R^{2a}$, $R^{2b}$, $R^{4a}$ and $R^{4b}$ each is hydrogen or methyl.

In another embodiment, X is methyl, substituted methyl or halo. In another embodiment, X is fluoro.

In another embodiment, $R^1$ is hydrogen.

In another embodiment, one $R^5$ is piperazinyl or substituted piperazinyl. In a preferred implementation, in compounds according to formula II, when one of $R^{6a}$, $R^{6b}$, $R^{7a}$, $R^{7b}$ and $R^8$ is piperazinyl or substituted piperazinyl, then X is not fluoro, or n is greater than one, or $R^{6a}$ or $R^{6b}$ is not hydrogen.

In yet another preferred embodiment, for compounds according to formula II, Q is C $R^{7b}$ (A is phenyl) and one of $R^{6a}$, $R^{6b}$, $R^{7a}$, $R^{7b}$ and $R^8$ is an optionally substituted five-membered heterocyclyl or heteroaryl moiety. More preferably, one of $R^{6a}$, $R^{6b}$, $R^{7a}$, $R^{7b}$ and $R^8$ is selected from the group consisting of tetrazolyl, substituted tetrazolyl, oxazolyl, substituted oxazolyl, furanyl, substituted suranyl, pyrazolyl, substituted pyrazolyl, pyrrolyl, substituted pyrrolyl, pyrrolidinyl, and substituted pyrrolidinyl. Even more preferably, one of $R^{6a}$, $R^{6b}$, $R^{7a}$, $R^{7b}$ and $R^8$ is tetrazol-1-yl or substituted tetrazol-5-yl. In a particularly preferred embodiment, the tetrazolyl moiety and the nitrogen at the 2-position of the pyrimidine which are oriented meta (i.e. 3- or 5-) on the phenyl (A). In another embodiment, when A is pyridyl (where Q is N), $R^{7a}$ is a tetrazolyl moiety.

In one embodiment, one of $R^{6a}$, $R^{6b}$, $R^{7a}$, $R^{7b}$ and $R^8$ is selected from the group consisting of

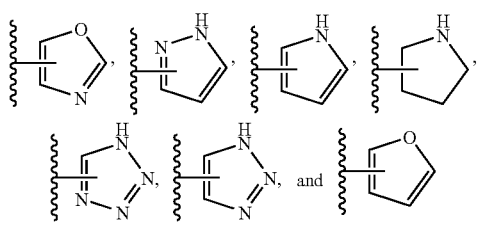

wherein one or more hydrogen atoms of the specified group or radical are each, independently of one another, replaced with the same or different substituent groups selected from the group consisting of halo, alkyl, substituted alkyl, alkoxy, substituted alkoxy, alkylthio, cycloalkyl, substituted cycloalkyl, heterocyclyl, substituted heterocyclyl, aryl, substituted aryl, heteroaryl and substituted heteroaryl. More preferably, the substituent is selected form the group consisting of halo, lower alkyl, methylthio and furanyl.

In another embodiment, the present invention provides a compound having the formula:

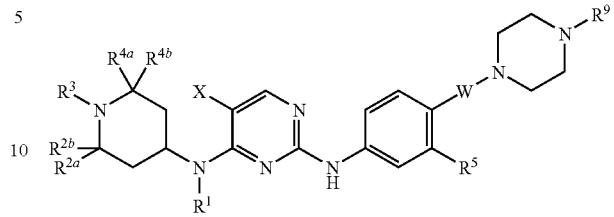

wherein W is a bond, —SO$_2$—, —C(O)—, or —CH$_2$—; and $R^9$ is selected from the group consisting of alkyl, substituted alkyl, sulfonyl, acyl, carboxyl and carboxyl ester.

In another embodiment, the present invention provides a compound having the formula:

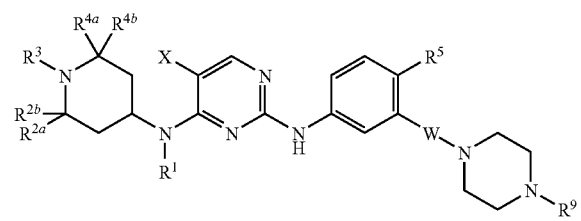

wherein W is a bond, —SO$_2$—, —C(O)—, or —CH$_2$—; and $R^9$ is selected from the group consisting of alkyl, substituted alkyl, sulfonyl, acyl, carboxyl and carboxyl ester.

In another embodiment, the present invention provides a compound of formula II:

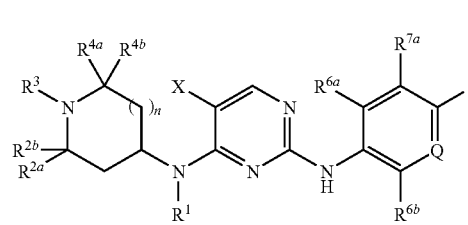

a solvate, N-oxide, prodrug or therapeutically acceptable salt thereof
wherein
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
Q is N, N→O, or CR$^{7b}$;
n is an integer between 0 and 3;
$R^1$ is selected from the group consisting of hydrogen, methyl and ethyl;
$R^{2a}$, $R^{2b}$, $R^{4a}$ and $R^{4b}$ each independently is selected from the group consisting of hydrogen and C$_{1-3}$ alkyl;
$R^3$ is selected from the group consisting of —Y, —C(O)—Y, —SO$_2$—Y, —(CH$_2$)$_m$—C(O)—Y, —CH═CH—C(O)—Y and —(CH$_2$)$_m$—NY$_2$, wherein each Y independently is hydrogen, hydroxy, oxy radical, alkoxy, alkyl, or substituted alkyl and m is 1, 2, or 3;

each of $R^{6a}$, $R^{6b}$ $R^{7a}$, $R^{7b}$, and $R^8$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, sulfonyl, sulfonylamino, and aminosulfonyl;

provided that, (1) when X is fluoro, and n is zero or one, then:
$R^{6a}$ or $R^{6b}$ is not hydrogen; or
$R^{7a}$ or $R^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or
$R^8$ is selected from the group consisting of substituted alkyl but not $CF_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and (2) when X is nitro, $CF_3$, or $C(O)NH_2$, then at least one of $R^{2a}$, $R^{2b}$, $R^{4a}$ and $R^{4b}$ is not hydrogen; and (3) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

In another embodiment, the present invention provides a compound selected from the group consisting of I-39, I-40, I-41, I-42, I-43, I-47, I-48, I-49, I-50, I-51, I-53, I-54, I-55, I-56, I-57, I-59, I-60, I-61, I-62, I-63, I-65, I-67, I-68, I-100, I-245; I-246, I-247, I-248, I-249, I-250, I-251, I-252, I-253, I-254, I-255, I-256, I-257, I-258, I-259, and I-260, or a solvate, N-oxide, prodrug or therapeutically acceptable salt thereof.

In another embodiment, the present invention does not include a compound selected from the group consisting of:
ethyl 4-(5-fluoro-2-(4-(4-methylpiperazin-1-yl)phenyl)pyrimidin-4-ylamino)piperidine-1-carboxylate;
5-fluoro-N2-(5-methyl-6-(4-methylpiperazin-1-yl)pyridin-3-yl)-N4-(1,2,2,6,6-pentamethylpiperidin-4-yl)pyrimidin-2,4-diamine;
N2-(6-(4-ethylpiperazin-1-yl)pyridin-3-yl)-5-fluoro-N4-(1,2,2,6,6-pentamethylpiperidin-4-yl)pyrimidin-2,4-diamine;
5-fluoro-N2-(4-(4-methylpiperazin-1-yl)-3-(trifluoromethyl)phenyl)-N4-(1,2,2,6,6-pentamethylpiperidin-4-yl)pyrimidin-2,4-diamine;
5-fluoro-N2-(3-methyl-4-(4-methylpiperazin-1-yl)phenyl)-N4-(1,2,2,6,6-pentamethylpiperidin-4-yl)pyrimidin-2,4-diamine;
N2-(3-chloro-4-(4-methylpiperazin-1-yl)phenyl)-5-fluoro-N4-(1,2,2,6,6-pentamethylpiperidin-4-yl)pyrimidin-2,4-diamine;
5-fluoro-N2-(3-(4-methylpiperazin-1-yl)phenyl)-N4-(1,2,2,6,6-pentamethylpiperidin-4-yl)pyrimidin-2,4-diamine;
5-fluoro-N2-(4-(4-methylpiperazin-1-yl)phenyl)-N4-(1,2,2,6,6-pentamethylpiperidin-4-yl)pyrimidin-2,4-diamine;
1-{4-[(5-fluoro-4-{[1-(2,2,2-trifluoroethyl)piperidin-4-yl]amino}pyrimidin-2-yl)amino]-11-azatricyclo[6.2.1.0$^{2,7}$]undeca-2,4,6-trien-11-yl}ethanone;
5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine;
ethyl 4-(2-(6-(4-ethylpiperazin-1-yl)pyridin-3-ylamino)-5-fluoropyrimidin-4-ylamino)piperidine-1-carboxylate;
ethyl 4-(5-fluoro-2-(6-(4-methylpiperazin-1-yl)pyridin-3-ylamino)pyrimidin-4-ylamino)piperidine-1-carboxylate;
ethyl 4-(5-fluoro-2-(4-(4-methylpiperazin-1-yl)-3-(trifluoromethyl)phenylamino)pyrimidin-4-ylamino)piperidine-1-carboxylate;
ethyl 4-(5-fluoro-2-(3-methyl-4-(4-methylpiperazin-1-yl)phenylamino)pyrimidin-4-ylamino)piperidine-1-carboxylate;
ethyl 4-(2-(3-chloro-4-(4-methylpiperazin-1-yl)phenylamino)-5-fluoropyrimidin-4-ylamino)piperidine-1-carboxylate; and
ethyl 4-(5-fluoro-2-(3-(4-methylpiperazin-1-yl)phenylamino)pyrimidin-4-ylamino)piperidine-1-carboxylate.

In another embodiment, the present invention provides a compound selected from the group consisting of:

I-9: N2-(4-Aminosulfonyl)phenyl-5-fluoro-N4-(1,2,2,6,6-pentamethylpiperidin-4-yl)-2,4-pyrimidinediamine;
I-10: N2-(3-Aminosulfonyl)phenyl-5-fluoro-N4-(1,2,2,6,6-pentamethylpiperidin-4-yl)-2,4-pyrimidinediamine;
I-11: N2-(3-Aminosulfonyl-4-methyl)phenyl-5-fluoro-N4-(1,2,2,6,6-pentamethylpiperidin-4-yl)-2,4-pyrimidinediamine;
I-12: N2-(3,5-Dimethyl)phenyl-5-fluoro-N4-(1,2,2,6,6-pentamethylpiperidin-4-yl)-2,4-pyrimidinediamine;
I-13: N2-(4-Aminosulfonyl)phenyl-5-methyl-N4-(1,2,2,6,6-pentamethylpiperidin-4-yl)-2,4-pyrimidinediamine;
I-14: N2-(3-Aminosulfonyl)phenyl-5-methyl-N4-(1,2,2,6,6-pentamethylpiperidin-4-yl)-2,4-pyrimidinediamine;
I-15: N2-(3-Aminosulfonyl-4-methyl)phenyl-5-methyl-N4-(1,2,2,6,6-pentamethylpiperidin-4-yl)-2,4-pyrimidinediamine;
I-16: 5-Methyl-N4-(1,2,2,6,6-pentamethylpiperidin-4-yl)-N2-(3,4,5-trimethoxy)phenyl-2,4-pyrimidinediamine;
I-17: N2-(3,5-Dimethyl)phenyl-5-methyl-N4-(1,2,2,6,6-pentamethylpiperidin-4-yl)-2,4-pyrimidinediamine;
I-18: N2-[4-(4-Ethylpiperazino)-3-methyl]phenyl-5-methyl-N4-(1,2,2,6,6-pentamethylpiperidin-4-yl)-2,4-pyrimidinediamine;
I-19: 5-Fluoro-N4-(1,2,2,6,6-pentamethylpiperidin-4-yl)-N2-(3,4,5-trimethoxy)phenyl-2,4-pyrimidinediamine;
I-20: N2-(3-Chloro-4-methoxy)phenyl-5-fluoro-N4-(1,2,2,6,6-pentamethylpiperidin-4-yl)-2,4-pyrimidinediamine;
I-21: N2-(3,4-Difluoro)phenyl-5-fluoro-N4-(1,2,2,6,6-pentamethylpiperidin-4-yl)-2,4-pyrimidinediamine;
I-22: N2-(3-Chloro-4-cyano)phenyl-5-fluoro-N4-(1,2,2,6,6-pentamethylpiperidin-4-yl)-2,4-pyrimidinediamine;
I-23: N2-(4-Aminocarbonyl)phenyl-5-fluoro-N4-(1,2,2,6,6-pentamethylpiperidin-4-yl)-2,4-pyrimidinediamine;
I-24: N2-(3-Aminocarbonyl)phenyl-5-fluoro-N4-(1,2,2,6,6-pentamethylpiperidin-4-yl)-2,4-pyrimidinediamine;
I-25: N2-(4-Cyano)phenyl-5-fluoro-N4-(1,2,2,6,6-pentamethylpiperidin-4-yl)-2,4-pyrimidinediamine;
I-26: N2-(3-Cyano)phenyl-5-fluoro-N4-(1,2,2,6,6-pentamethylpiperidin-4-yl)-2,4-pyrimidinediamine;
I-27: N2-(3-Chloro-4-methoxy)phenyl-5-methyl-N4-(1,2,2,6,6-pentamethylpiperidin-4-yl)-2,4-pyrimidinediamine;
I-28: N2-(3-Chloro-4-cyano)phenyl-5-methyl-N4-(1,2,2,6,6-pentamethylpiperidin-4-yl)-2,4-pyrimidinediamine;
I-29: N2-[3-Chloro-4-(4-methylpiperazino)]phenyl-5-methyl-N4-(1,2,2,6,6-pentamethylpiperidin-4-yl)-2,4-pyrimidinediamine;
I-30: 5-Methyl-N2-[4-(4-methylpiperazino)-3-trifluoromethyl]phenyl-N4-(1,2,2,6,6-pentamethylpiperidin-4-yl)-2,4-pyrimidinediamine;

I-31: 5-Chloro-N2-(3-chloro-4-methoxy)phenyl-N4-(1,2,2,6,6-pentamethylpiperidin-4-yl)-2,4-pyrimidinediamine;

I-32: N2-(3-Chloro-4-methoxy)phenyl-N4-(1,2,2,6,6-pentamethylpiperidin-4-yl)-5-trifluoromethyl-2,4-pyrimidinediamine;

I-33: N2-(3-Chloro-4-cyano)phenyl-N4-(1,2,2,6,6-pentamethylpiperidin-4-yl)-5-trifluoromethyl-2,4-pyrimidinediamine;

I-34: N2-[3-Chloro-4-(4-methylpiperazino)]phenyl-N4-(1,2,2,6,6-pentamethylpiperidin-4-yl)-5-trifluoromethyl-2,4-pyrimidinediamine;

I-35: 5-Chloro-N2-(3-chloro-4-cyano)phenyl-N4-(1,2,2,6,6-pentamethylpiperidin-4-yl)-2,4-pyrimidinediamine;

I-36: 5-Chloro-N2-[3-chloro-4-(4-methylpiperazino)]phenyl-N4-(1,2,2,6,6-pentamethylpiperidin-4-yl)-2,4-pyrimidinediamine;

I-37: 5-Chloro-N2-[4-(4-methylpiperazino)-3-trifluoromethyl]phenyl-N4-(1,2,2,6,6-pentamethylpiperidin-4-yl)-2,4-pyrimidinediamine;

I-38: N2-[4-(4-Methylpiperazino)-3-trifluoromethyl]phenyl-N4-(1,2,2,6,6-pentamethylpiperidin-4-yl)-5-trifluoromethyl-2,4-pyrimidinediamine;

I-39: 5-Fluoro-N2-[3-fluoro-4-(4-methylpiperazino)]phenyl-N4-(1,2,2,6,6-pentamethylpiperidin-4-yl)-2,4-pyrimidinediamine;

I-40: N2-[3,5-Difluoro-4-(4-methylpiperazino)]phenyl-5-fluoro-N4-(1,2,2,6,6-pentamethylpiperidin-4-yl)-2,4-pyrimidinediamine;

I-41: N2-[4-Chloro-3-(4-ethylpiperazino)]phenyl-5-fluoro-N4-(1,2,2,6,6-pentamethylpiperidin-4-yl)-2,4-pyrimidinediamine;

I-42: N2-[3-(4-Acylpiperazino)-4-chloro]phenyl-5-fluoro-N4-(1,2,2,6,6-pentamethylpiperidin-4-yl)-2,4-pyrimidinediamine;

I-43: N2-[4-Chloro-3-(4-methoxycarbonylpiperazino)]phenyl-5-fluoro-N4-(1,2,2,6,6-pentamethylpiperidin-4-yl)-2,4-pyrimidinediamine;

I-44: N2-[3-Chloro-4-(4-methylpiperazino)carbonyl]phenyl-5-fluoro-N4-(1,2,2,6,6-pentamethylpiperidin-4-yl)-2,4-pyrimidinediamine;

I-45: N2-[3-Chloro-4-(4-methylpiperazino)sulfonyl]phenyl-5-fluoro-N4-(1,2,2,6,6-pentamethylpiperidin-4-yl)-2,4-pyrimidinediamine;

I-46: N2-[3-Chloro-4-piperazinosulfonyl]phenyl-5-fluoro-N4-(1,2,2,6,6-pentamethylpiperidin-4-yl)-2,4-pyrimidinediamine;

I-47: 5-Fluoro-N2-[4-(4-methoxycarbonylpiperazino)-3-trifluoromethyl]phenyl-N4-(1,2,2,6,6-pentamethylpiperidin-4-yl)-2,4-pyrimidinediamine;

I-48: 5-Fluoro-N2-[4-(4-methylsulfonylpiperazino)-3-trifluoromethyl]phenyl-N4-(1,2,2,6,6-pentamethylpiperidin-4-yl)-2,4-pyrimidinediamine;

I-49: N2-[4-(4-Acylpiperazino)-3-trifluoromethyl]phenyl-5-fluoro-N4-(1,2,2,6,6-pentamethylpiperidin-4-yl)-2,4-pyrimidinediamine;

I-50: N2-[3-Chloro-4-(4,4-difluoropiperidinyl)]phenyl-5-fluoro-N4-(1,2,2,6,6-pentamethylpiperidin-4-yl)-2,4-pyrimidinediamine;

I-51: N2-[4-(4,4-Difluoropiperidinyl)-3-fluoro]phenyl-5-fluoro-N4-(1,2,2,6,6-pentamethylpiperidin-4-yl)-2,4-pyrimidinediamine;

I-52: 5-Fluoro-N2-[4-(4-methylpiperazino)methyl-3-trifluoromethyl]phenyl-N4-(1,2,2,6,6-pentamethylpiperidin-4-yl)-2,4-pyrimidinediamine;

I-53: N2-[3-Aminocarbonyl-4-(4-methylpiperazino)]phenyl-5-fluoro-N4-(1,2,2,6,6-pentamethylpiperidin-4-yl)-2,4-pyrimidinediamine;

I-54: 5-Fluoro-N2-[3-methylaminocarbonyl-4-(4-methylpiperazino)]phenyl-N4-(1,2,2,6,6-pentamethylpiperidin-4-yl)-2,4-pyrimidinediamine;

I-55: 5-Fluoro-N2-[3-methoxy-4-(4-methylpiperazino)]phenyl-N4-(1,2,2,6,6-pentamethylpiperidin-4-yl)-2,4-pyrimidinediamine;

I-56: N2-[4-Chloro-3-(4-propylpiperazino)]phenyl-5-fluoro-N4-(1,2,2,6,6-pentamethylpiperidin-4-yl)-2,4-pyrimidinediamine;

I-57: N2-[3-Chloro-4-(4-methylpiperazino)methyl]phenyl-5-fluoro-N4-(1,2,2,6,6-pentamethylpiperidin-4-yl)-2,4-pyrimidinediamine;

I-58: N2-(3-Chloro-4-methoxy)phenyl-5-fluoro-N4-methyl-N4-(1,2,2,6,6-pentamethylpiperidin-4-yl)-2,4-pyrimidinediamine;

I-59: 5-Fluoro-N4-methyl-N2-[4-(4-methylpiperazino)-3-trifluoromethyl]phenyl-N4-(1,2,2,6,6-pentamethylpiperidin-4-yl)-2,4-pyrimidinediamine;

I-60: N2-[3-Chloro-4-(4-methylpiperazino)]phenyl-5-fluoro-N4-methyl-N4-(1,2,2,6,6-pentamethylpiperidin-4-yl)-2,4-pyrimidinediamine;

I-61: N2-[3-Chloro-4-(4-methylsulfonylpiperazino)]phenyl-5-fluoro-N4-(1,2,2,6,6-pentamethylpiperidin-4-yl)-2,4-pyrimidinediamine;

I-62: N2-[3-Chloro-4-(4-methoxycarbonylpiperazino)]phenyl-5-fluoro-N4-(1,2,2,6,6-pentamethylpiperidin-4-yl)-2,4-pyrimidinediamine;

I-63: 5-Fluoro-N2-[3-hydroxymethyl-4-(4-methylpiperazino)]phenyl-N4-(1,2,2,6,6-pentamethylpiperidin-4-yl)-2,4-pyrimidinediamine;

I-64: 5-Fluoro-N2-[4-(4-methylpiperazino)carbonyl-3-trifluoromethyl]phenyl-N4-(1,2,2,6,6-pentamethylpiperidin-4-yl)-2,4-pyrimidinediamine;

I-65: N2-[4-Chloro-3-(4-methylpiperazino)]phenyl-5-fluoro-N4-(1,2,2,6,6-pentamethylpiperidin-4-yl)-2,4-pyrimidinediamine;

I-66: N2-(3-Cyano)phenyl-5-fluoro-N4-methyl-N4-(1,2,2,6,6-pentamethylpiperidin-4-yl)-2,4-pyrimidinediamine;

I-67: N2-[4-(4-Acylpiperazino)-3-chloro]phenyl-5-fluoro-N4-(1,2,2,6,6-pentamethylpiperidin-4-yl)-2,4-pyrimidinediamine;

I-68: N2-[4-Chloro-3-(4-methylsulfonylpiperazino)]phenyl-5-fluoro-N4-(1,2,2,6,6-pentamethylpiperidin-4-yl)-2,4-pyrimidinediamine;

I-69: N2-[3-(2-methylpyrimidin-4-yl)]phenyl-5-fluoro-N4-(1,2,2,6,6-pentamethylpiperidin-4-yl)-2,4-pyrimidinediamine;

I-70: N2-(3-Cyano)phenyl-5-fluoro-N4-(2,2,6,6-tetramethylpiperidin-4-yl)-2,4-pyrimidinediamine;

I-71: N2-(3-Chloro-4-methoxy)phenyl-5-nitro-N4-(1,2,2,6,6-pentamethylpiperidin-4-yl)-2,4-pyrimidinediamine;

I-72: N2-(3-Cyano)phenyl-5-nitro-N4-(1,2,2,6,6-pentamethylpiperidin-4-yl)-2,4-pyrimidinediamine;

I-73: N2-[3-Chloro-4-(4-methylsulfonylpiperazino)]phenyl-5-nitro-N4-(1,2,2,6,6-pentamethylpiperidin-4-yl)-2,4-pyrimidinediamine;

I-74: N2-[4-(4-Methylpiperazino)-3-trifluoromethyl]phenyl-5-nitro-N4-(1,2,2,6,6-pentamethylpiperidin-4-yl)-2,4-pyrimidinediamine;

I-75: 5-Nitro-N4-(1,2,2,6,6-pentamethylpiperidin-4-yl)-N2-(4-piperazino-3-trifluoromethyl)phenyl-2,4-pyrimidinediamine;

I-76: N2-[3-Chloro-4-(4-methylpiperazino)]phenyl-5-nitro-N4-(1,2,2,6,6-pentamethylpiperidin-4-yl)-2,4-pyrimidinediamine;

I-77: N2-(3-Chloro-4-piperazino)phenyl-5-nitro-N4-(1,2,2,6,6-pentamethylpiperidin-4-yl)-2,4-pyrimidinediamine;

I-78: N2-[4-(4-Methylsulfonylpiperazino)-3-trifluoromethyl]phenyl-5-nitro-N4-(1,2,2,6,6-pentamethylpiperidin-4-yl)-2,4-pyrimidinediamine;

I-79: 5-Fluoro-N4-(1,2,2,6,6-pentamethylpiperidin-4-yl)-N2-(3-pyridin-4-yl)phenyl-2,4-pyrimidinediamine;

I-80: N2-(3-Chloro-4-methoxy)phenyl-5-ethoxycarbonyl-N4-(1,2,2,6,6-pentamethylpiperidin-4-yl)-2,4-pyrimidinediamine;

I-81: N2-(3-Cyano)phenyl-5-ethoxycarbonyl-N4-(1,2,2,6,6-pentamethylpiperidin-4-yl)-2,4-pyrimidinediamine;

I-82: 5-Ethoxycarbonyl-N2-[4-(4-methylpiperazino)-3-trifluoromethyl]phenyl-N4-(1,2,2,6,6-pentamethylpiperidin-4-yl)-2,4-pyrimidinediamine;

I-83: 5-Ethoxycarbonyl-N2-[4-(4-methylsulfonylpiperazino)-3-trifluoromethyl]phenyl-N4-(1,2,2,6,6-pentamethylpiperidin-4-yl)-2,4-pyrimidinediamine;

I-84: N2-[3-Chloro-4-(4-methylsulfonylpiperazino)]phenyl-5-ethoxycarbonyl-N4-(1,2,2,6,6-pentamethylpiperidin-4-yl)-2,4-pyrimidinediamine;

I-85: 5-Aminocarbonyl-N2-(3-chloro-4-methoxy)phenyl-N4-(1,2,2,6,6-pentamethylpiperidin-4-yl)-2,4-pyrimidinediamine;

I-86: 5-Aminocarbonyl-N2-(3-cyano)phenyl-N4-(1,2,2,6,6-pentamethylpiperidin-4-yl)-2,4-pyrimidinediamine;

I-87: Mixture of N2-[3-Chloro-4-(4-methylsulfonylpiperazino)]phenyl-N4-(1,2,2,6,6-pentamethylpiperidin-4-yl)-5-trifluoromethyl-2,4-pyrimidinediamine and N4-[3-Chloro-4-(4-methylsulfonylpiperazino)]phenyl-N2-(1,2,2,6,6-pentamethylpiperidin-4-yl)-5-trifluoromethyl-2,4-pyrimidinediamine;

I-88: N2-[4-(4-Methylsulfonylpiperazino)-3-trifluoromethyl]phenyl-N4-(1,2,2,6,6-pentamethylpiperidin-4-yl)-5-trifluoromethyl-2,4-pyrimidinediamine;

I-89: N2-[3-Chloro-4-(4-methylpiperazino)]phenyl-5-ethoxycarbonyl-N4-(1,2,2,6,6-pentamethylpiperidin-4-yl)-2,4-pyrimidinediamine;

I-90: 5-Aminocarbonyl-N2-[4-(4-methylsulfonylpiperazino)-3-trifluoromethyl]phenyl-N4-(1,2,2,6,6-pentamethylpiperidin-4-yl)-2,4-pyrimidinediamine;

I-91: 5-Aminocarbonyl-N2-[3-chloro-4-(4-methylsulfonylpiperazino)]phenyl-N4-(1,2,2,6,6-pentamethylpiperidin-4-yl)-2,4-pyrimidinediamine;

I-92: N2-[3-Chloro-4-(4-methylsulfonylpiperazino)]phenyl-N4-(1,2,2,6,6-pentamethylpiperidin-4-yl)-5-trifluoromethyl-2,4-pyrimidinediamine;

I-93: N2-(3-Chloro-4-methoxy)phenyl-5-cyano-N4-(1,2,2,6,6-pentamethylpiperidin-4-yl)-2,4-pyrimidinediamine;

I-94: 5-Cyano-N2-[4-(4-methylpiperazino)-3-trifluoromethyl]phenyl-N4-(1,2,2,6,6-pentamethylpiperidin-4-yl)-2,4-pyrimidinediamine;

I-95: 5-Cyano-N2-[4-(4-methylsulfonylpiperazino)-3-trifluoromethyl]phenyl-N4-(1,2,2,6,6-pentamethylpiperidin-4-yl)-2,4-pyrimidinediamine;

I-96: 5-Fluoro-N4-(1,2,2,6,6-pentamethylpiperidin-4-yl)-N2-[4-(pyridin-4-yl)-3-trifluoromethyl]phenyl-2,4-pyrimidinediamine;

I-97: 5-Cyano-N2-(3-cyano)phenyl-N4-(1,2,2,6,6-pentamethylpiperidin-4-yl)-2,4-pyrimidinediamine;

I-98: 5-Aminocarbonyl-N2-[3-chloro-4-(4-methylpiperazino)]phenyl-N4-(1,2,2,6,6-pentamethylpiperidin-4-yl)-2,4-pyrimidinediamine;

I-99: N2-[3-Chloro-4-(pyridin-4-yl)]phenyl-5-fluoro-N4-(1,2,2,6,6-pentamethylpiperidin-4-yl)-2,4-pyrimidinediamine;

I-100: 5-Fluoro-N2-[3-(1,3-oxazol-5-yl)]phenyl-N4-(1,2,2,6,6-pentamethylpiperidin-4-yl)-2,4-pyrimidinediamine;

I-101: N2-[3-Chloro-4-(4-methylpiperazino)]phenyl-5-cyano-N4-(1,2,2,6,6-pentamethylpiperidin-4-yl)-2,4-pyrimidinediamine;

I-102: N2-[3-Chloro-4-(4-methylsulfonylpiperazino)]phenyl-5-cyano-N4-(1,2,2,6,6-pentamethylpiperidin-4-yl)-2,4-pyrimidinediamine;

I-103: N2-(3,5-Dichloro)phenyl-5-fluoro-N4-(1,2,2,6,6-pentamethylpiperidin-4-yl)-2,4-pyrimidinediamine;

I-104: N2-(3-Bromo)phenyl-5-fluoro-N4-(1,2,2,6,6-pentamethylpiperidin-4-yl)-2,4-pyrimidinediamine;

I-105: 5-Fluoro-N2-[3-(furan-3-yl)]phenyl-N4-(1,2,2,6,6-pentamethylpiperidin-4-yl)-2,4-pyrimidinediamine;

I-106: N2-[3-(Benzothiophen-2-yl)]phenyl-5-fluoro-N4-(1,2,2,6,6-pentamethylpiperidin-4-yl)-2,4-pyrimidinediamine;

I-107: 5-Fluoro-N4-(1,2,2,6,6-pentamethylpiperidin-4-yl)-N2-(3-pyridin-3-yl)phenyl-2,4-pyrimidinediamine;

I-108: N2-(4-Bromo)phenyl-5-fluoro-N4-(1,2,2,6,6-pentamethylpiperidin-4-yl)-2,4-pyrimidinediamine;

I-109: N2-(4-Bromo-3-trifluoromethyl)phenyl-5-fluoro-N4-(1,2,2,6,6-pentamethylpiperidin-4-yl)-2,4-pyrimidinediamine;

I-110: N2-(4-Bromo-3-fluoro)phenyl-5-fluoro-N4-(1,2,2,6,6-pentamethylpiperidin-4-yl)-2,4-pyrimidinediamine;

I-111: N2-(4-Bromo-3-methyl)phenyl-5-fluoro-N4-(1,2,2,6,6-pentamethylpiperidin-4-yl)-2,4-pyrimidinediamine;

I-112: 5-Fluoro-N4-(1,2,2,6,6-pentamethylpiperidin-4-yl)-N2-[4-(pyridin-3-yl)-3-trifluoromethyl]phenyl-2,4-pyrimidinediamine;

I-113: 5-Fluoro-N2-[4-(furan-3-yl)-3-trifluoromethyl]phenyl-N4-(1,2,2,6,6-pentamethylpiperidin-4-yl)-2,4-pyrimidinediamine;

I-114: N2-[4-(Benzothiophen-2-yl)-3-trifluoromethyl]phenyl-5-fluoro-N4-(1,2,2,6,6-pentamethylpiperidin-4-yl)-2,4-pyrimidinediamine;

I-115: 5-Fluoro-N2-[3-fluoro-4-(pyridin-4-yl)]phenyl-N4-(1,2,2,6,6-pentamethylpiperidin-4-yl)-2,4-pyrimidinediamine;

I-116: 5-Fluoro-N2-[4-(4-methylthiophen-2-yl)-3-trifluoromethyl]phenyl-N4-(1,2,2,6,6-pentamethylpiperidin-4-yl)-2,4-pyrimidinediamine;

I-117: N2-[4-Bromo-3,5-bis(trifluoromethyl)]phenyl-5-fluoro-N4-(1,2,2,6,6-pentamethylpiperidin-4-yl)-2,4-pyrimidinediamine;

I-118: 5-Fluoro-N2-[3-fluoro-4-(pyridin-3-yl)]phenyl-N4-(1,2,2,6,6-pentamethylpiperidin-4-yl)-2,4-pyrimidinediamine;

I-119: 5-Fluoro-N2-[3-fluoro-4-(furan-3-yl)]phenyl-N4-(1,2,2,6,6-pentamethylpiperidin-4-yl)-2,4-pyrimidinediamine;

I-120: 5-Fluoro-N2-[3-methyl-4-(pyridin-4-yl)]phenyl-N4-(1,2,2,6,6-pentamethylpiperidin-4-yl)-2,4-pyrimidinediamine;

I-121: 5-Fluoro-N2-[3-methyl-4-(pyridin-3-yl)]phenyl-N4-(1,2,2,6,6-pentamethylpiperidin-4-yl)-2,4-pyrimidinediamine;

I-122: 5-Fluoro-N2-[4-(furan-3-yl)-3-methyl]phenyl-N4-(1,2,2,6,6-pentamethylpiperidin-4-yl)-2,4-pyrimidinediamine;

I-123: 5-Fluoro-N4-(1,2,2,6,6-pentamethylpiperidin-4-yl)-N2-[4-(pyridin-4-yl)]phenyl-2,4-pyrimidinediamine;

I-124: 5-Fluoro-N4-(1,2,2,6,6-pentamethylpiperidin-4-yl)-N2-[4-(pyridin-3-yl)]phenyl-2,4-pyrimidinediamine;

I-125: 5-Fluoro-N2-[4-(furan-3-yl)]phenyl-N4-(1,2,2,6,6-pentamethylpiperidin-4-yl)-2,4-pyrimidinediamine;

I-126: 5-Fluoro-N2-[4-(1-methyl-1H-pyrazol-4-yl)-3-trifluoromethyl]phenyl-N4-(1,2,2,6,6-pentamethylpiperidin-4-yl)-2,4-pyrimidinediamine;

I-127: 5-Fluoro-N2-(3-fluoro-4-methoxy)phenyl-N4-(1,2,2,6,6-pentamethylpiperidin-4-yl)-2,4-pyrimidinediamine;

I-128: N2-(4-Chloro-3-cyano-5-ethyl)phenyl-5-fluoro-N4-(1,2,2,6,6-pentamethylpiperidin-4-yl)-2,4-pyrimidinediamine;

I-129: N2-(3,5-Dimethoxy)phenyl-5-fluoro-N4-(1,2,2,6,6-pentamethylpiperidin-4-yl)-2,4-pyrimidinediamine;

I-130: N2-(3,4-Dimethoxy)phenyl-5-fluoro-N4-(1,2,2,6,6-pentamethylpiperidin-4-yl)-2,4-pyrimidinediamine;

I-131: N2-(3,5-Dimethyl-4-methoxy)phenyl-5-fluoro-N4-(1,2,2,6,6-pentamethylpiperidin-4-yl)-2,4-pyrimidinediamine;

I-132: N2-[3-Cyano-4-(4-methylpiperazino)]phenyl-5-fluoro-N4-(1,2,2,6,6-pentamethylpiperidin-4-yl)-2,4-pyrimidinediamine;

I-133: N2-(4-Benzoylamino)phenyl-5-fluoro-N4-(1,2,2,6,6-pentamethylpiperidin-4-yl)-2,4-pyrimidinediamine;

I-134: N2-(4-Aminocarbonylmethoxy)phenyl-5-fluoro-N4-(1,2,2,6,6-pentamethylpiperidin-4-yl)-2,4-pyrimidinediamine;

I-135: 5-Fluoro-N2-(4-isopropoxycarbonylmethoxy)phenyl-N4-(1,2,2,6,6-pentamethylpiperidin-4-yl)-2,4-pyrimidinediamine;

I-136: 5-Fluoro-N2-(3-methylaminocarbonylmethoxy)phenyl-N4-(1,2,2,6,6-pentamethylpiperidin-4-yl)-2,4-pyrimidinediamine;

I-137: 5-Fluoro-N2-(4-isopropoxycarbonylamino)phenyl-N4-(1,2,2,6,6-pentamethylpiperidin-4-yl)-2,4-pyrimidinediamine;

I-138: N2-(3-Ethylaminocarbonylamino)phenyl-5-fluoro-N4-(1,2,2,6,6-pentamethylpiperidin-4-yl)-2,4-pyrimidinediamine;

I-139: 5-Fluoro-N2-(3-isopropoxycarbonylamino)phenyl-N4-(1,2,2,6,6-pentamethylpiperidin-4-yl)-2,4-pyrimidinediamine;

I-140: N2-(3-Cyano-4-fluoro)phenyl-5-fluoro-N4-(1,2,2,6,6-pentamethylpiperidin-4-yl)-2,4-pyrimidinediamine;

I-141: N2-(3,4-Dicyano)phenyl-5-fluoro-N4-(1,2,2,6,6-pentamethylpiperidin-4-yl)-2,4-pyrimidinediamine;

I-142: N2-(3-Cyano-4-methyl)phenyl-5-fluoro-N4-(1,2,2,6,6-pentamethylpiperidin-4-yl)-2,4-pyrimidinediamine;

I-143: 5-Fluoro-N2-[3-(1-methyl-1H-pyrazol-4-yl)]phenyl-N4-(1,2,2,6,6-pentamethylpiperidin-4-yl)-2,4-pyrimidinediamine;

I-144: 5-Fluoro-N2-[4-(1-methyl-1H-pyrazol-4-yl)]phenyl-N4-(1,2,2,6,6-pentamethylpiperidin-4-yl)-2,4-pyrimidinediamine;

I-145: 5-Fluoro-N2-(3-methoxy-5-trifluoromethyl)phenyl-N4-(1,2,2,6,6-pentamethylpiperidin-4-yl)-2,4-pyrimidinediamine;

I-146: N2-[3,5-Bis(trifluoromethyl)]phenyl-5-fluoro-N4-(1,2,2,6,6-pentamethylpiperidin-4-yl)-2,4-pyrimidinediamine;

I-147: 5-Fluoro-N2-(4-methoxy-3-trifluoromethyl)phenyl-N4-(1,2,2,6,6-pentamethylpiperidin-4-yl)-2,4-pyrimidinediamine;

I-148: N2-[3-Cyano-4-(1H-pyrrol-1-yl)]phenyl-5-fluoro-N4-(1,2,2,6,6-pentamethylpiperidin-4-yl)-2,4-pyrimidinediamine;

I-149: N2-(4-Ethylaminocarbonylamino)phenyl-5-fluoro-N4-(1,2,2,6,6-pentamethylpiperidin-4-yl)-2,4-pyrimidinediamine;

I-150: 5-Fluoro-N2-[3-fluoro-4-(1-methyl-1H-pyrazol-4-yl)]phenyl-N4-(1,2,2,6,6-pentamethylpiperidin-4-yl)-2,4-pyrimidinediamine;

I-151: 5-Fluoro-N2-[3-methyl-4-(1-methyl-1H-pyrazol-4-yl)]phenyl-N4-(1,2,2,6,6-pentamethylpiperidin-4-yl)-2,4-pyrimidinediamine;

I-152: N2-(4-Cyano-3-trifluoromethyl)phenyl-5-fluoro-N4-(1,2,2,6,6-pentamethylpiperidin-4-yl)-2,4-pyrimidinediamine;

I-153: N2-(4-Bromo-3-chloro)phenyl-5-fluoro-N4-(1,2,2,6,6-pentamethylpiperidin-4-yl)-2,4-pyrimidinediamine;

I-154: N2-[3-Chloro-4-(pyridin-3-yl)]phenyl-5-fluoro-N4-(1,2,2,6,6-pentamethylpiperidin-4-yl)-2,4-pyrimidinediamine;

I-155: N2-[3-Chloro-4-(furan-3-yl)]phenyl-5-fluoro-N4-(1,2,2,6,6-pentamethylpiperidin-4-yl)-2,4-pyrimidinediamine;

I-156: N2-[4-(Benzothiophen-2-yl)-3-chloro]phenyl-5-fluoro-N4-(1,2,2,6,6-pentamethylpiperidin-4-yl)-2,4-pyrimidinediamine;

I-157: N2-[3-Chloro-4-(1-methyl-1H-pyrazol-4-yl)]phenyl-5-fluoro-N4-(1,2,2,6,6-pentamethylpiperidin-4-yl)-2,4-pyrimidinediamine;

I-158: N2-(3-Bromo-4-fluoro)phenyl-5-fluoro-N4-(1,2,2,6,6-pentamethylpiperidin-4-yl)-2,4-pyrimidinediamine;

I-159: N2-(3-Bromo-4-methoxy)phenyl-5-fluoro-N4-(1,2,2,6,6-pentamethylpiperidin-4-yl)-2,4-pyrimidinediamine;

I-160: N2-(3-Bromo-4-methyl)phenyl-5-fluoro-N4-(1,2,2,6,6-pentamethylpiperidin-4-yl)-2,4-pyrimidinediamine;

I-161: N2-(4-Acetamido-3-trifluoromethyl)phenyl-5-fluoro-N4-(1,2,2,6,6-pentamethylpiperidin-4-yl)-2,4-pyrimidinediamine;

I-162: N2-(3-Bromo-5-trifluoromethyl)phenyl-5-fluoro-N4-(1,2,2,6,6-pentamethylpiperidin-4-yl)-2,4-pyrimidinediamine;

I-163: N2-(4-Chloro-3-cyano)phenyl-5-fluoro-N4-(1,2,2,6,6-pentamethylpiperidin-4-yl)-2,4-pyrimidinediamine;

I-164: N2-[3-Cyano-4-(4-methylsulfonylpiperazino)]phenyl-5-fluoro-N4-(1,2,2,6,6-pentamethylpiperidin-4-yl)-2,4-pyrimidinediamine;

I-165: 5-Chloro-N2-(4-chloro-3-cyano)phenyl-N4-(1,2,2,6,6-pentamethylpiperidin-4-yl)-2,4-pyrimidinediamine;

I-166: 5-Chloro-N2-(3-cyano-4-fluoro)phenyl-N4-(1,2,2,6,6-pentamethylpiperidin-4-yl)-2,4-pyrimidinediamine;

I-167: 5-Chloro-N2-[3-cyano-4-(1H-pyrrol-1-yl)]phenyl-N4-(1,2,2,6,6-pentamethylpiperidin-4-yl)-2,4-pyrimidinediamine;

I-168: 5-Chloro-N2-(3-cyano-4-methyl)phenyl-N4-(1,2,2,6,6-pentamethylpiperidin-4-yl)-2,4-pyrimidinediamine;

I-169: N2-(4-Chloro-3-cyano)phenyl-N4-(1,2,2,6,6-pentamethylpiperidin-4-yl)-5-trifluoromethyl-2,4-pyrimidinediamine;

I-170: N2-(3-Cyano-4-fluoro)phenyl-N4-(1,2,2,6,6-pentamethylpiperidin-4-yl)-5-trifluoromethyl-2,4-pyrimidinediamine;

I-171: N2-(3-Cyano-4-methyl)phenyl-N4-(1,2,2,6,6-pentamethylpiperidin-4-yl)-5-trifluoromethyl-2,4-pyrimidinediamine;

I-172: N2-[3-Cyano-4-(1H-pyrrol-1-yl)]phenyl-N4-(1,2,2,6,6-pentamethylpiperidin-4-yl)-5-trifluoromethyl-2,4-pyrimidinediamine;

I-173: N2-[4-(4-Cyclopropylsulfonylpiperazino)-3-trifluoromethyl]phenyl-5-fluoro-N4-(1,2,2,6,6-pentamethylpiperidin-4-yl)-2,4-pyrimidinediamine;

I-174: N2-[3-Chloro-4-(4-cyclopropylsulfonylpiperazino)]phenyl-5-fluoro-N4-(1,2,2,6,6-pentamethylpiperidin-4-yl)-2,4-pyrimidinediamine;

I-175: 5-Chloro-N2-[3-cyano-4-(4-methylsulfonylpiperazino)]phenyl-N4-(1,2,2,6,6-pentamethylpiperidin-4-yl)-2,4-pyrimidinediamine;

I-176: N2-[3-Cyano-4-(4-methylsulfonylpiperazino)]phenyl-N4-(1,2,2,6,6-pentamethylpiperidin-4-yl)-5-trifluoromethyl-2,4-pyrimidinediamine;

I-177: N2-(3-Bromo-4-trifluoromethoxy)phenyl-5-fluoro-N4-(1,2,2,6,6-pentamethylpiperidin-4-yl)-2,4-pyrimidinediamine;

I-178: N2-[3-Cyano-4-(4-methylpiperazino)]phenyl-N4-(1,2,2,6,6-pentamethylpiperidin-4-yl)-5-trifluoromethyl-2,4-pyrimidinediamine;

I-179: 5-Chloro-N2-[3-cyano-4-(4-methylpiperazino)]phenyl-N4-(1,2,2,6,6-pentamethylpiperidin-4-yl)-2,4-pyrimidinediamine;

I-180: 5-Fluoro-N2-[4-fluoro-3-(pyridin-3-yl)]phenyl-N4-(1,2,2,6,6-pentamethylpiperidin-4-yl)-2,4-pyrimidinediamine;

I-181: N2-[3-(Benzothiophen-2-yl)-4-fluoro]phenyl-5-fluoro-N4-(1,2,2,6,6-pentamethylpiperidin-4-yl)-2,4-pyrimidinediamine;

I-182: 5-Fluoro-N2-[4-fluoro-3-(1-methyl-1H-pyrazol-4-yl)]phenyl-N4-(1,2,2,6,6-pentamethylpiperidin-4-yl)-2,4-pyrimidinediamine;

I-183: 5-Fluoro-N2-[3-(furan-3-yl)-4-methoxy]phenyl-N4-(1,2,2,6,6-pentamethylpiperidin-4-yl)-2,4-pyrimidinediamine;

I-184: 5-Fluoro-N2-[4-methoxy-3-(1-methyl-1H-pyrazol-4-yl)]phenyl-N4-(1,2,2,6,6-pentamethylpiperidin-4-yl)-2,4-pyrimidinediamine;

I-185: N2-[3-Cyano-4-(pyridin-4-yl)]phenyl-5-fluoro-N4-(1,2,2,6,6-pentamethylpiperidin-4-yl)-2,4-pyrimidinediamine;

I-186: N2-[3-Cyano-4-(pyridin-3-yl)]phenyl-5-fluoro-N4-(1,2,2,6,6-pentamethylpiperidin-4-yl)-2,4-pyrimidinediamine;

I-187: 5-Fluoro-N2-[4-methyl-3-(pyridin-4-yl)]phenyl-N4-(1,2,2,6,6-pentamethylpiperidin-4-yl)-2,4-pyrimidinediamine;

I-188: 5-Fluoro-N2-[3-(furan-3-yl)-4-methyl]phenyl-N4-(1,2,2,6,6-pentamethylpiperidin-4-yl)-2,4-pyrimidinediamine;

I-189: N2-[3-(Benzothiophen-2-yl)-4-methyl]phenyl-5-fluoro-N4-(1,2,2,6,6-pentamethylpiperidin-4-yl)-2,4-pyrimidinediamine;

I-190: 5-Fluoro-N2-[4-methyl-3-(1-methyl-1H-pyrazol-4-yl)]phenyl-N4-(1,2,2,6,6-pentamethylpiperidin-4-yl)-2,4-pyrimidinediamine;

I-191: 5-Fluoro-N2-[4-fluoro-3-(pyridin-4-yl)]phenyl-N4-(1,2,2,6,6-pentamethylpiperidin-4-yl)-2,4-pyrimidinediamine;

I-192: 5-Fluoro-N2-[4-fluoro-3-(furan-3-yl)]phenyl-N4-(1,2,2,6,6-pentamethylpiperidin-4-yl)-2,4-pyrimidinediamine;

I-193: 5-Fluoro-N2-[4-methoxy-3-(pyridin-4-yl)]phenyl-N4-(1,2,2,6,6-pentamethylpiperidin-4-yl)-2,4-pyrimidinediamine;

I-194: 5-Fluoro-N2-[4-methoxy-3-(pyridin-3-yl)]phenyl-N4-(1,2,2,6,6-pentamethylpiperidin-4-yl)-2,4-pyrimidinediamine;

I-195: N2-[3-(Benzothiophen-2-yl)-4-methoxy]phenyl-5-fluoro-N4-(1,2,2,6,6-pentamethylpiperidin-4-yl)-2,4-pyrimidinediamine;

I-196: 5-Cyano-N2-[3-cyano-4-(4-methylsulfonylpiperazino)]phenyl-N4-(1,2,2,6,6-pentamethylpiperidin-4-yl)-2,4-pyrimidinediamine;

I-197: 5-Fluoro-N2-[4-methyl-3-(pyridin-3-yl)]phenyl-N4-(1,2,2,6,6-pentamethylpiperidin-4-yl)-2,4-pyrimidinediamine;

I-198: N2-(3-Cyano-4-morpholino)phenyl-5-fluoro-N4-(1,2,2,6,6-pentamethylpiperidin-4-yl)-2,4-pyrimidinediamine;

I-199: N2-(3-Cyano-4-thiomorpholino)phenyl-5-fluoro-N4-(1,2,2,6,6-pentamethylpiperidin-4-yl)-2,4-pyrimidinediamine;

I-200: N2-[3-Cyano-4-(pyrrolidin-1-yl)]phenyl-5-fluoro-N4-(1,2,2,6,6-pentamethylpiperidin-4-yl)-2,4-pyrimidinediamine;

I-201: 5-Fluoro-N4-(1,2,2,6,6-pentamethylpiperidin-4-yl)-N2-[3-(pyridin-4-yl)-5-trifluoromethyl]phenyl-2,4-pyrimidinediamine;

I-202: 5-Fluoro-N4-(1,2,2,6,6-pentamethylpiperidin-4-yl)-N2-[3-(pyridin-3-yl)-5-trifluoromethyl]phenyl-2,4-pyrimidinediamine;

I-203: 5-Fluoro-N2-[3-(furan-3-yl)-5-trifluoromethyl]phenyl-N4-(1,2,2,6,6-pentamethylpiperidin-4-yl)-2,4-pyrimidinediamine;

I-204: 5-Fluoro-N2-[3-(1-methyl-1H-pyrazol-4-yl)-5-trifluoromethyl]phenyl-N4-(1,2,2,6,6-pentamethylpiperidin-4-yl)-2,4-pyrimidinediamine;

I-205: N2-[3-(Benzothiophen-2-yl)-5-trifluoromethyl]phenyl-5-fluoro-N4-(1,2,2,6,6-pentamethylpiperidin-4-yl)-2,4-pyrimidinediamine;

I-206: 5-Cyano-N2-[3-cyano-4-(1H-pyrrol-1-yl)]phenyl-N4-(1,2,2,6,6-pentamethylpiperidin-4-yl)-2,4-pyrimidinediamine;

I-207: 5-Fluoro-N4-(1,2,2,6,6-pentamethylpiperidin-4-yl)-N2-[3-(pyridin-4-yl)-4-trifluoromethoxy]phenyl-2,4-pyrimidinediamine;

I-208: 5-Fluoro-N4-(1,2,2,6,6-pentamethylpiperidin-4-yl)-N2-[3-(pyridin-3-yl)-4-trifluoromethoxy]phenyl-2,4-pyrimidinediamine;

I-209: 5-Fluoro-N2-[3-(furan-3-yl)-4-trifluoromethoxy]phenyl-N4-(1,2,2,6,6-pentamethylpiperidin-4-yl)-2,4-pyrimidinediamine;

I-210: 5-Fluoro-N2-[3-(1-methyl-1H-pyrazol-4-yl)-4-trifluoromethoxy]phenyl-N4-(1,2,2,6,6-pentamethylpiperidin-4-yl)-2,4-pyrimidinediamine;

I-211: N2-[3-(Benzothiophen-2-yl)-4-trifluoromethoxy]phenyl-5-fluoro-N4-(1,2,2,6,6-pentamethylpiperidin-4-yl)-2,4-pyrimidinediamine;

I-212: N2-[3-(4-Acetylpiperazino)-4-trifluoromethyl]phenyl-5-fluoro-N4-(1,2,2,6,6-pentamethylpiperidin-4-yl)-2,4-pyrimidinediamine;

I-213: N4-(1-Acetyl-2,2,6,6-tetramethylpiperidin-4-yl)-N2-(3-chloro-4-methoxy)phenyl-5-fluoro-2,4-pyrimidinediamine;

I-214: 5-Fluoro-N2-[3-(4-methoxycarbonylpiperazino)-4-trifluoromethyl]phenyl-N4-(1,2,2,6,6-pentamethylpiperidin-4-yl)-2,4-pyrimidinediamine;

I-215: N4-(1-Acetyl-2,2,6,6-tetramethylpiperidin-4-yl)-5-fluoro-N2-[4-(4-methylsulfonylpiperazino)-3-trifluoromethyl]phenyl-2,4-pyrimidinediamine;

I-216: 5-Fluoro-N2-[3-(4-methylsulfonylpiperazino)-4-trifluoromethyl]phenyl-N4-(1,2,2,6,6-pentamethylpiperidin-4-yl)-2,4-pyrimidinediamine;

I-217: N4-(1-Acetyl-2,2,6,6-tetramethylpiperidin-4-yl)-N2-(3-cyanophenyl)-5-fluoro-2,4-pyrimidinediamine;

I-218: 5-Fluoro-N4-(1,2,2,6,6-pentamethylpiperidin-4-yl)-N2-[3-(4-propylpiperazino)-4-trifluoromethyl]phenyl-2,4-pyrimidinediamine;

I-219: N4-(1-Acetyl-2,2,6,6-tetramethylpiperidin-4-yl)-5-fluoro-N2-[4-(4-methylpiperazino)-3-trifluoromethyl]phenyl-2,4-pyrimidinediamine;

I-220: N2-[4-Chloro-3-(3,5-dimethyl-4-propylpiperazino)]phenyl-5-fluoro-N4-(1,2,2,6,6-pentamethylpiperidin-4-yl)-2,4-pyrimidinediamine;

I-221: 5-Fluoro-N2-[4-(1-methylpiperidin-4-yl)]phenyl-N4-(1,2,2,6,6-pentamethylpiperidin-4-yl)-2,4-pyrimidinediamine;

I-222: N2-[4-(2,6-Dimethyltetrahydropyran-4-yl)]phenyl-5-fluoro-N4-(1,2,2,6,6-pentamethylpiperidin-4-yl)-2,4-pyrimidinediamine;

I-223: 5-Fluoro-N4-(1,2,2,6,6-pentamethylpiperidin-4-yl)-N2-(3-trifluoromethoxy)phenyl-2,4-pyrimidinediamine;

I-224: 5-Fluoro-N2-[4-(4-morpholino)-3-trifluoromethyl]phenyl-N4-(1,2,2,6,6-pentamethylpiperidin-4-yl)-2,4-pyrimidinediamine;

I-225: N2-[4-(2,6-Dimethylmorpholino)-3-trifluoromethyl]phenyl-5-fluoro-N4-(1,2,2,6,6-pentamethylpiperidin-4-yl)-2,4-pyrimidinediamine;

I-226: N2-(3-Chloro-4-methoxy)phenyl-N4-(1,2,2,6,6-pentamethylpiperidin-4-yl)-2,4-pyrimidinediamine;

I-227: N2-(3-Cyanophenyl)-N4-(1,2,2,6,6-pentamethylpiperidin-4-yl)-2,4-pyrimidinediamine;

I-228: N2-[4-(4-Methylsulfonylpiperazino)-3-trifluoromethyl]phenyl-N4-(1,2,2,6,6-pentamethylpiperidin-4-yl)-2,4-pyrimidinediamine;

I-229: N2-[4-(4-Methylpiperazino)-3-trifluoromethyl]phenyl-N4-(1,2,2,6,6-pentamethylpiperidin-4-yl)-2,4-pyrimidinediamine;

I-230: N2-[4-(Cyclopropylaminocarbonyl)-3-trifluoromethyl]phenyl-5-fluoro-N4-(1,2,2,6,6-pentamethylpiperidin-4-yl)-2,4-pyrimidinediamine;

I-231: 5-Fluoro-N4-(1,2,2,6,6-pentamethylpiperidin-4-yl)-N2-(4-trifluoromethoxyphenyl)-2,4-pyrimidinediamine;

I-232: 5-Fluoro-N2-[4-(1-pyrrolidino)-3-trifluoromethyl]phenyl-N4-(1,2,2,6,6-pentamethylpiperidin-4-yl)-2,4-pyrimidinediamine;

I-233: 5-Fluoro-N4-(1,2,2,6,6-pentamethylpiperidin-4-yl)-N2-[4-(1-piperidino)-3-trifluoromethyl]phenyl-2,4-pyrimidinediamine;

I-234: N2-(3-Difluoromethoxyphenyl)-5-fluoro-N4-(1,2,2,6,6-pentamethylpiperidin-4-yl)-2,4-pyrimidinediamine;

I-235: N2-(3-Difluoromethoxy-4-morpholino)phenyl-5-fluoro-N4-(1,2,2,6,6-pentamethylpiperidin-4-yl)-2,4-pyrimidinediamine;

I-236: N2-[3-Difluoromethoxy-4-(4-methylpiperazino)]phenyl-5-fluoro-N4-(1,2,2,6,6-pentamethylpiperidin-4-yl)-2,4-pyrimidinediamine;

I-237: N2-(3-Difluoromethoxy-4-pyrrolidino)phenyl-5-fluoro-N4-(1,2,2,6,6-pentamethylpiperidin-4-yl)-2,4-pyrimidinediamine;

I-238: N2-[3-Difluoromethoxy-4-(4-methylsulfonylpiperazino)]phenyl-5-fluoro-N4-(1,2,2,6,6-pentamethylpiperidin-4-yl)-2,4-pyrimidinediamine;

I-239: N2-(3-Difluoromethoxy-4-methoxy)phenyl-5-fluoro-N4-(1,2,2,6,6-pentamethylpiperidin-4-yl)-2,4-pyrimidinediamine;

I-240: 5-Chloro-N4-(1,2,2,6,6-pentamethylpiperidin-4-yl)-N2-(3-trifluoromethoxyphenyl)-2,4-pyrimidinediamine;

I-241: 5-Chloro-N2-[4-(4-morpholino)-3-trifluoromethyl]phenyl-N4-(1,2,2,6,6-pentamethylpiperidin-4-yl)-2,4-pyrimidinediamine;

I-242: N4-(1,2,2,6,6-pentamethylpiperidin-4-yl)-N2-(3-trifluoromethoxyphenyl)-5-trifluoromethyl-2,4-pyrimidinediamine;

I-243: 5-Fluoro-N2-(3-methylsulfonylamino)phenyl-N4-(1,2,2,6,6-pentamethylpiperidin-4-yl)-2,4-pyrimidinediamine;

I-244: N2-[4-(4-methylsulfonylpiperazino)-3-trifluoromethyl]phenyl-5-fluoro-N4-(1,2,2,6,6-pentamethylpiperidin-4-yl)-2,4-pyrimidinediamine benzylate salt;

I-245: N2-[4-(4,4-Difluoropiperidin-1-yl)-3-trifluoromethyl]phenyl-5-fluoro-N4-(1,2,2,6,6-pentamethylpiperidin-4-yl)-2,4-pyrimidinediamine;

I-246: N2-[4-(4-Ethylpiperazino)-3-trifluoromethyl]phenyl-5-fluoro-N4-(1,2,2,6,6-pentamethylpiperidin-4-yl)-2,4-pyrimidinediamine;

I-247: 5-Fluoro-N4-(1,2,2,6,6-pentamethylpiperidin-4-yl)-N2-[4-(4-propylpiperazino)-3-trifluoromethyl]phenyl-2,4-pyrimidinediamine;

I-248: N2-[3-Chloro-4-(4-ethylpiperazino)]phenyl-5-fluoro-N4-(1,2,2,6,6-pentamethylpiperidin-4-yl)-2,4-pyrimidinediamine;

I-249: N2-[3-Chloro-4-(4-propylpiperazino)]phenyl-5-fluoro-N4-(1,2,2,6,6-pentamethylpiperidin-4-yl)-2,4-pyrimidinediamine;

I-250: N2-[4-Chloro-3-(3,4,5-trimethylpiperazino)]phenyl-5-fluoro-N4-(1,2,2,6,6-pentamethylpiperidin-4-yl)-2,4-pyrimidinediamine;

I-251: N2-[3-(4-Acyl-3,5-dimethylpiperazino)-4-chloro]phenyl-5-fluoro-N4-(1,2,2,6,6-pentamethylpiperidin-4-yl)-2,4-pyrimidinediamine;

I-252: 5-Fluoro-N2-(4-hydroxyl)phenyl-N4-(1,2,2,6,6-pentamethylpiperidin-4-yl)-2,4-pyrimidinediamine;

I-253: 5-Fluoro-N2-(3-hydroxyl)phenyl-N4-(1,2,2,6,6-pentamethylpiperidin-4-yl)-2,4-pyrimidinediamine;

I-254: N2-(3-Chloro-4-methoxy)phenyl-5-fluoro-N4-(2,2,6,6-tetramethylpiperidin-4-yl)-2,4-pyrimidinediamine;

I-255: 5-Fluoro-N2-[4-(4-methylpiperazino)-3-trifluoromethyl]phenyl-N4-(2,2,6,6-tetramethylpiperidin-4-yl)-2,4-pyrimidinediamine;

I-256: N2-[3-Chloro-4-(4-methylpiperazino)]phenyl-5-fluoro-N4-(2,2,6,6-tetramethylpiperidin-4-yl)-2,4-pyrimidinediamine;

I-257: 5-Fluoro-N2-[4-(4-methylsulfonylpiperazino)-3-trifluoromethyl]phenyl-N4-(2,2,6,6-tetramethylpiperidin-4-yl)-2,4-pyrimidinediamine;

I-258: N2-[3-Chloro-4-(4-methylsulfonylpiperazino)]phenyl-5-fluoro-N4-(2,2,6,6-tetramethylpiperidin-4-yl)-2,4-pyrimidinediamine;

I-259: 5-Fluoro-N4-(1,2,2,6,6-pentamethylpiperidin-4-yl)-N2-[3-trifluoromethyl-4-(1,3,5-trimethyl-3,7-diazabicyclo[3.3.1]nonan-7-yl)]phenyl-2,4-pyrimidinediamine;

I-260: 5-Fluoro-N4-(1,2,2,6,6-pentamethylpiperidin-4-yl)-N2-[4-(1,3,5-trimethyl-3,7-diazabicyclo[3.3.1]nonan-7-yl)]phenyl-2,4-pyrimidinediamine;

I-261: 5-Fluoro-N2-[4-morpholine-3-trifluoromethyl]phenyl-N4-(1,2,2,7,7-pentamethylazepan-4-yl)-2,4-pyrimidinediamine;

I-262: 5-Fluoro-N2-[3-chloro-4-methoxy]phenyl-N4-(1,2,2,7,7-pentamethylazepan-4-yl)-2,4-pyrimidinediamine;

I-263: 5-Fluoro-N2-[4-(methyl)-3-cyano]phenyl-N4-(1,2,2,7,7-pentamethylazepan-4-yl)-2,4-pyrimidinediamine;

I-264: 5-Fluoro-N2-[4-methylsulfonylpiperazin-1-yl-3-trifluoromethyl]phenyl-N4-(1,2,2,7,7-pentamethylazepan-4-yl)-2,4-pyrimidinediamine;

I-265: 5-Fluoro-N2-[3,5-dichloro]phenyl-N4-(1,2,2,7,7-pentamethylazepan-4-yl)-2,4-pyrimidinediamine;

I-266: 5-Fluoro-N2-[3,4,5-trimethoxy]phenyl-N4-(1,2,2,7,7-pentamethylazepan-4-yl)-2,4-pyrimidinediamine;

I-267: 5-Fluoro-N2-[3,4-dimethoxy]phenyl-N4-(1,2,2,7,7-pentamethylazepan-4-yl)-2,4-pyrimidinediamine;

I-268: 5-Fluoro-N2-[4-methoxy-3-trifluoromethyl]phenyl-N4-(1,2,2,7,7-pentamethylazepan-4-yl)-2,4-pyrimidinediamine;
I-269: 5-Fluoro-N2-[3-methoxy]phenyl-N4-(1,2,2,7,7-pentamethylazepan-4-yl)-2,4-pyrimidinediamine;
I-270: 5-Fluoro-N2-[4-methylpiperizine-3-trifluoromethyl]phenyl-N4-(1,2,2,7,7-pentamethylazepan-4-yl)-2,4-pyrimidinediamine;
I-271: 5-Fluoro-N2-[6-morpholine-5-trifluoromethyl]pyridinyl-N4-(1,2,2,6,6-pentamethylpiperidin-4-yl)-2,4-pyrimidinediamine;
I-272: 5-Bromo-N2-[4-methoxy-3-trifluoromethyl]phenyl-N4-(1,2,2,6,6-pentamethylpiperidin-4-yl)-2,4-pyrimidinediamine;
I-273: 5-Fluoro-N2-[6-(4-methylpiperizin-1-yl)-5-trifluoromethyl]pyridine-3-yl]-N4-(1,2,2,6,6-pentamethylpiperidin-4-yl)-2,4-pyrimidinediamine;
I-274: 5-Bromo-N2-[3,4-dimethoxy]phenyl-N4-(1,2,2,6,6-pentamethylpiperidin-4-yl)-2,4-pyrimidinediamine;
I-275: 5-Bromo-N2-[3-trifluoromethoxy]phenyl-N4-(1,2,2,6,6-pentamethylpiperidin-4-yl)-2,4-pyrimidinediamine;
I-276: 5-Bromo-N2-[3,4,5-trimethoxy]phenyl-N4-(1,2,2,6,6-pentamethylpiperidin-4-yl)-2,4-pyrimidinediamine;
I-277: 5-Bromo-N2-[4-methyl-3-cyano]phenyl-N4-(1,2,2,6,6-pentamethylpiperidin-4-yl)-2,4-pyrimidinediamine;
I-278: 5-Fluoro-N2-(4-methyl-cyano)phenyl-N4-(1,2,2,5,5-pentamethylpyrrolidin-3-yl)-2,4-pyrimidinediamine;
I-279: 5-Fluoro-N2-(3,5-dichloro) phenyl-N4-(1,2,2,5,5-pentamethylpyrrolidin-3-yl)-2,4-pyrimidinediamine;
I-280: 5-Fluoro-N2-(3-chloro-4-methoxy)phenyl-N4-(1,2,2,5,5-pentamethylpyrrolidin-3-yl)-2,4-pyrimidinediamine;
I-281: 5-Fluoro-N2-(3,4-dimethoxy)phenyl-N4-(1,2,2,5,5-pentamethylpyrrolidin-3-yl)-2,4-pyrimidinediamine;
I-282: 5-Fluoro-N2-(3,4,5-trimethoxy)phenyl-N4-(1,2,2,5,5-pentamethylpyrrolidin-3-yl)-2,4-pyrimidinediamine;
I-283: 5-Fluoro-N2-(4-methoxy-3-trifluoromethyl)phenyl-N4-(1,2,2,5,5-pentamethylpyrrolidin-3-yl)-2,4-pyrimidinediamine;
I-284: 5-Fluoro-N2-(3-trifluoromethoxy)phenyl-N4-(1,2,2,5,5-pentamethylpyrrolidin-3-yl)-2,4-pyrimidinediamine;
I-285: 5-Fluoro-N2-[4-(4-methylpiperazin-1-yl)-3-(trifluoromethyl)]phenyl-N4-(1,2,2,5,5-pentamethylpyrrolidin-3-yl)-2,4-pyrimidinediamine;
I-286: 5-Fluoro-N2-[4-(4-methylsulfonyl)piperazin-1-yl)-3-(trifluoromethyl)]phenyl-N4-(1,2,2,5,5-pentamethylpyrrolidin-3-yl)-2,4-pyrimidinediamine;
I-287: 5-Fluoro-N2-[4-morpholino-3-(trifluoromethyl)]phenyl-N4-(1,2,2,5,5-pentamethylpyrrolidin-3-yl)-2,4-pyrimidinediamine;
I-288: 5-Fluoro-N2-[5-chloro-6-(4-methylpiperazin-1-yl)]pyridine-3-yl-N4-(1,2,2,6,6-pentamethylpiperidin-4-yl)-2,4-pyrimidinediamine;
I-289: 5-Fluoro-N2-[5-chloro-6-(4-(methylsulfonyl)piperazin-1-yl)]pyridin-3-yl-N4-(1,2,2,6,6-pentamethylpiperidin-4-yl)-2,4-pyrimidinediamine;
I-290: 5-Fluoro-N2-[5-chloro-6-(4-morpholino)]pyridine-3-yl-N4-(1,2,2,6,6-pentamethylpiperidin-4-yl)-2,4-pyrimidinediamine;
I-291: Methyl 2-[4-(2-(3,4-dimethoxyphenylamino)-5-fluoropyrimidine-4-ylamino)-2,2,6,6-tetramethylpiperidin-1-yl]propanoate;
I-292: Methyl 2-[4-(2-(3,5-dimethoxyphenylamino)-5-fluoropyrimidine-4-ylamino)-2,2,6,6-tetramethylpiperidin-1-yl]propanoate;
I-293: Methyl 3-[4-(2-(3-chloro-4-methoxyphenylamino)-5-fluoropyrimidine-4-ylamino)-2,2,6,6-tetramethylpiperidin-1-yl]propanoate;
I-294: Methyl 2-[4-(2-(3,5-dichlorophenylamino)-5-fluoropyrimidine-4-ylamino)-2,2,6,6-tetramethylpiperidin-1-yl]propanoate;
I-295: Methyl 2-[4-(2-(4-methoxy-3-trifluoromethyl)phenylamino)-5-fluoropyrimidine-4-ylamino)-2,2,6,6-tetramethylpiperidin-1-yl]propanoate;
I-296: Methyl 3-[4-(2-(3-cyano-4-methylphenylamino)-5-fluoropyrimidine-4-ylamino)-2,2,6,6-tetramethylpiperidin-1-yl]propanoate;
I-297: (E,Z)-Methyl 2-[4-(2-(3,4-dimethoxyphenylamino)-5-fluoropyrimidine-4-ylamino)-2,2,6,6-tetramethylpiperidin-1-yl]acrylate;
I-298: (E,Z)-Methyl 2-[4-(2-(3,5-dimethoxyphenylamino)-5-fluoropyrimidine-4-ylamino)-2,2,6,6-tetramethylpiperidin-1-yl]acrylate;
I-299: (E,Z)-Methyl 3-[4-(2-(3-chloro-4-methoxyphenylamino)-5-fluoropyrimidine-4-ylamino)-2,2,6,6-tetramethylpiperidin-1-yl]acrylate;
I-300: (E,Z)-Methyl 2-[4-(2-(3,5-dichlorophenylamino)-5-fluoropyrimidine-4-ylamino)-2,2,6,6-tetramethylpiperidin-1-yl]acrylate;
I-301: (E,Z)-Methyl 2-[4-(2-(4-methoxy-3-trifluoromethylphenylamino)-5-fluoropyrimidine-4-ylamino)-2,2,6,6-tetramethylpiperidin-1-yl]acrylate;
I-302: 3-[4-(2-(3,5-Dimethoxyphenylamino)-5-fluoropyrimidine-4-ylamino)-2,2,6,6-tetramethylpiperidin-1-yl]propanoicacid;
I-303: 3-[4-(2-(3-Chloro-4-methoxyphenylamino)-5-fluoropyrimidine-4-ylamino)-2,2,6,6-tetramethylpiperidin-1-yl]propanoicacid;
I-304: 3-[4-(2-(3,5-Dichlorophenylamino)-5-fluoropyrimidine-4-ylamino)-2,2,6,6-tetramethylpiperidin-1-yl]propanoicacid;
I-305: 3-[4-(2-(4-Methoxy-3-trifluoromethyl)phenylamino)-5-fluoropyrimidine-4-ylamino)-2,2,6,6-tetramethylpiperidin-1-yl]propanoicacid;
I-306: 3-[4-(2-(3-Cyano-4-methylphenylamino)-5-fluoropyrimidine-4-ylamino)-2,2,6,6-tetramethylpiperidin-1-yl]propanoicacid;
I-307: N2-(3,5-dimethoxyphenyl)-5-fluoro-N4-(1,2,2,6,6-pentamethylpiperidin-4-yl)pyrimidine-2,4-diamine;
I-308: N4-benzyl-N2-(3,5-dimethoxyphenyl)-5-fluoro-N4-(1,2,2,6,6-pentamethylpiperidin-4-yl)pyrimidine-2,4-diamine;
I-309: N4-benzyl-N2-(3-(difluoromethoxy)-4-methoxyphenyl)-5-fluoro-N4-(1,2,2,6,6-pentamethylpiperidin-4-yl)pyrimidine-2,4-diamine;
I-310: N4-benzyl-5-fluoro-N2-(4-(4-(methylsulfonyl)piperazin-1-yl)-3-(trifluoromethyl)phenyl)-N4-(1,2,2,6,6-pentamethylpiperidin-4-yl)pyrimidine-2,4-diamine;
I-311: N4-benzyl-5-fluoro-N2-(4-(4-methylpiperazin-1-yl)-3-(trifluoromethyl)phenyl)-N4-(1,2,2,6,6-pentamethylpiperidin-4-yl)pyrimidine-2,4-diamine;
I-312: N4-benzyl-5-fluoro-N2-(4-morpholino-3-(trifluoromethyl)phenyl)-N4-(1,2,2,6,6-pentamethylpiperidin-4-yl)pyrimidine-2,4-diamine;
I-313: 5-(4-(benzyl(1,2,2,6,6-pentamethylpiperidin-4-yl)amino)-5-fluoropyrimidin-2-ylamino)-2-methylbenzonitrile;
I-314: N2-(3,5-dimethoxyphenyl)-5-fluoro-N4-(naphthalen-2-ylmethyl)-N4-(1,2,2,6,6-pentamethylpiperidin-4-yl)pyrimidine-2,4-diamine;
I-315: 5-(5-fluoro-4-((naphthalen-2-ylmethyl)(1,2,2,6,6-pentamethylpiperidin-4-yl)amino)pyrimidin-2-ylamino)-2-methylbenzonitrile;

I-316: N2-(3-(difluoromethoxy)-4-methoxyphenyl)-5-fluoro-N4-(naphthalen-2-ylmethyl)-N4-(1,2,2,6,6-pentamethylpiperidin-4-yl)pyrimidine-2,4-diamine;

I-317: N4-(biphenyl-4-ylmethyl)-N2-(3,5-dimethoxyphenyl)-5-fluoro-N4-(1,2,2,6,6-pentamethylpiperidin-4-yl)pyrimidine-2,4-diamine;

I-318: 5-(4-((biphenyl-4-ylmethyl)(1,2,2,6,6-pentamethylpiperidin-4-yl)amino)-5-fluoropyrimidin-2-ylamino)-2-methylbenzonitrile;

I-319: N4-(biphenyl-4-ylmethyl)-N2-(3-(difluoromethoxy)-4-methoxyphenyl)-5-fluoro-N4-(1,2,2,6,6-pentamethylpiperidin-4-yl)pyrimidine-2,4-diamine;

I-320: 5-(5-fluoro-4-((1,2,2,6,6-pentamethylpiperidin-4-yl)(quinolin-2-ylmethyl)amino)pyrimidin-2-ylamino)-2-methylbenzonitrile;

I-321: N2-(3-(difluoromethoxy)-4-methoxyphenyl)-5-fluoro-N4-(1,2,2,6,6-pentamethylpiperidin-4-yl)-N4-(quinolin-2-ylmethyl)pyrimidine-2,4-diamine;

I-322: N2-(3,5-dimethoxyphenyl)-5-fluoro-N4-(1,2,2,6,6-pentamethylpiperidin-4-yl)-N4-(quinolin-2-ylmethyl)pyrimidine-2,4-diamine;

I-323: N4-((6-bromobenzo[d][1,3]dioxol-5-yl)methyl)-N2-(3,5-dimethoxyphenyl)-5-fluoro-N4-(1,2,2,6,6-pentamethylpiperidin-4-yl)pyrimidine-2,4-diamine;

I-324: 5-(4-(((6-bromobenzo[d][1,3]dioxol-5-yl)methyl)(1,2,2,6,6-pentamethylpiperidin-4-yl)amino)-5-fluoropyrimidin-2-ylamino)-2-methylbenzonitrile;

I-325: 4'-(((2-(3,5-dimethoxyphenylamino)-5-fluoropyrimidin-4-yl)(1,2,2,6,6-pentamethylpiperidin-4-yl)amino)methyl)biphenyl-2-carbonitrile;

I-326: 4'-(((2-(3-cyano-4-methylphenylamino)-5-fluoropyrimidin-4-yl)(1,2,2,6,6-pentamethylpiperidin-4-yl)amino)methyl)biphenyl-2-carbonitrile;

I-327: 5-Fluoro-N2-(3-hydroxy)phenyl-N4-(1,2,2,6,6-pentamethylpiperidin-4-yl)-2,4-pyrimidinediamine;

I-328: 5-Fluoro-N2-[4-(furan-3-yl)-3-trifluoromethyl]phenyl-N4-(1,2,2,6,6-pentamethylpiperidin-4-yl)-2,4-pyrimidinediamine;

I-329: 5-Fluoro-N4-(1,2,2,6,6-pentamethylpiperidin-4-yl)-N2-(1,1,2,2-tetrafluoro-ethoxyphen-3-yl)-2,4-pyrimidinediamine;

I-330: N2-(4-Morpholino-3-trifluoromethyl)phenyl-N4-(1,2,2,6,6-pentamethylpiperidin-4-yl)-5-trifluoromethyl-2,4-pyrimidinediamine;

I-331: 5-Fluoro-N4-(1,2,2,6,6-pentamethylpiperidin-4-yl)-N2-(4-thiomorpholino-3-trifluoromethyl)phenyl-2,4-pyrimidinediamine;

I-332: N2-(3-Chloro-4-methyl)phenyl-5-fluoro-N4-(1,2,2,6,6-pentamethylpiperidin-4-yl)-2,4-pyrimidinediamine;

I-333: N2-(3-Chloro-4-fluoro)phenyl-5-fluoro-N4-(1,2,2,6,6-pentamethylpiperidin-4-yl)-2,4-pyrimidinediamine;

I-334: N2-(3-Chloro-4-trifluoromethoxy)phenyl-5-fluoro-N4-(1,2,2,6,6-pentamethylpiperidin-4-yl)-2,4-pyrimidinediamine;

I-335: N2-(3-Chloro-4-morpholino)phenyl-5-fluoro-N4-(1,2,2,6,6-pentamethylpiperidin-4-yl)-2,4-pyrimidinediamine;

I-336: N2-(3,4-Dichloro)phenyl-5-fluoro-N4-(1,2,2,6,6-pentamethylpiperidin-4-yl)-2,4-pyrimidinediamine;

I-337: N2-(3-Chloro-4-trifluoromethyl)phenyl-5-fluoro-N4-(1,2,2,6,6-pentamethylpiperidin-4-yl)-2,4-pyrimidinediamine;

I-338: N2-[3-Chloro-4-(pyrimin-2-yl)oxy]phenyl-5-fluoro-N4-(1,2,2,6,6-pentamethylpiperidin-4-yl)-2,4-pyrimidinediamine;

I-339: N2-[3-Chloro-4-(2-furoylamino)]phenyl-5-fluoro-N4-(1,2,2,6,6-pentamethylpiperidin-4-yl)-2,4-pyrimidinediamine;

I-340: 5-Chloro-N2-(3,5-dimethoxy)phenyl-N4-(1,2,2,6,6-pentamethylpiperidin-4-yl)-2,4-pyrimidinediamine;

I-341: 5-Chloro-N2-(3-difluoromethoxy-4-methoxy)phenyl-N4-(1,2,2,6,6-pentamethylpiperidin-4-yl)-2,4-pyrimidinediamine;

I-342: 5-Fluoro-N2-[3-methoxy-5-(1H-1,2,3,4-tetrazol-1-yl)]phenyl-N4-(1,2,2,6,6-pentamethylpiperidin-4-yl)-2,4-pyrimidinediamine;

I-343: 5-Fluoro-N2-(4-methoxy-3-trifluoromethoxy)phenyl-N4-(1,2,2,6,6-pentamethylpiperidin-4-yl)-2,4-pyrimidinediamine;

I-344: N2-(3,4-Bis-difluoromethoxy)phenyl-5-fluoro-N4-(1,2,2,6,6-pentamethylpiperidin-4-yl)-2,4-pyrimidinediamine;

I-345: 5-Fluoro-N2-(2-methoxypyrid-5-yl)-N4-(1,2,2,6,6-pentamethylpiperidin-4-yl)-2,4-pyrimidinediamine;

I-346: N2-(3-Chloro-4-isopropoxy)phenyl-5-fluoro-N4-(1,2,2,6,6-pentamethylpiperidin-4-yl)-2,4-pyrimidinediamine;

I-347: 5-Fluoro-N4-(1,2,2,6,6-pentamethylpiperidin-4-yl)-N2-(3,4,5-trifluoro)phenyl-2,4-pyrimidinediamine;

I-348: N2-[3-(2,5-Dimethyl-pyrrol-1-yl)-4-methoxy]phenyl-5-fluoro-N4-(1,2,2,6,6-pentamethylpiperidin-4-yl)-2,4-pyrimidinediamine;

I-349: 5-Fluoro-N2-[3-methoxy-4-(pyrrol-1-yl)]phenyl-N4-(1,2,2,6,6-pentamethylpiperidin-4-yl)-2,4-pyrimidinediamine;

I-350: N2-(3-Difluoromethoxy-4-methoxy)phenyl-N4-(1,2,2,6,6-pentamethylpiperidin-4-yl)-5-trifluoromethyl-2,4-pyrimidinediamine;

I-351: 5-Chloro-N2-[3-chloro-4-(2-furoylamino)]phenyl-N4-(1,2,2,6,6-pentamethylpiperidin-4-yl)-2,4-pyrimidinediamine;

I-352: 5-Chloro-N2-[4-(2-furoylamino)-3-methoxy]phenyl-N4-(1,2,2,6,6-pentamethylpiperidin-4-yl)-2,4-pyrimidinediamine;

I-353: N2-[3-methoxy-4-(2-furoylamino)]phenyl-N4-(1,2,2,6,6-pentamethylpiperidin-4-yl)-5-fluoro-2,4-pyrimidinediamine;

I-354: N2-(3,5-Difluoro)phenyl-5-fluoro-N4-(1,2,2,6,6-pentamethylpiperidin-4-yl)-2,4-pyrimidinediamine;

I-355: 5-Fluoro-N2-[4-(2-furoylamino)-3-trifluoromethyl]phenyl-N4-(1,2,2,6,6-pentamethylpiperidin-4-yl)-2,4-pyrimidinediamine;

I-356: N2-[3-Methoxy-5-(1,2,3,4-tetrazol-1-yl)]phenyl-N4-(1,2,2,6,6-pentamethylpiperidin-4-yl)-5-trifluoromethyl-2,4-pyrimidinediamine;

I-357: 5-Fluoro-N4-(1,2,2,6,6-pentamethylpiperidin-4-yl)-N2-(3-tetrazol-1-yl)phenyl-2,4-pyrimidinediamine;

I-358: 5-Fluoro-N2-[3-methoxy-5-(5-methyl-tetrazol-1-yl)]phenyl-N4-(1,2,2,6,6-pentamethylpiperidin-4-yl)-2,4-pyrimidinediamine;

I-359: N2-(3-Difluoromethoxy-4-methoxy)phenyl-5-fluoro-N4-(1,2,2,6,6-pentamethylpiperidin-4-yl)-2,4-pyrimidinediamine, citrate salt;

I-360: 5-Fluoro-N2-(3-isopropoxy-4-methoxy)phenyl-N4-(1,2,2,6,6-pentamethylpiperidin-4-yl)-2,4-pyrimidinediamine;

I-361: 5-Fluoro-N2-[4-(3,5-dimethylpyrazol-1-yl)-3-methoxy]phenyl-N4-(1,2,2,6,6-pentamethylpiperidin-4-yl)-2,4-pyrimidinediamine;

I-362: N2-{3-Chloro-4-[2-(pyridine-2-yl)-ethylaminocarbonyl]}phenyl-5-fluoro-N4-(1,2,2,6,6-pentamethylpiperidin-4-yl)-2,4-pyrimidinediamine;

I-363: N2-(3,5-Dimethoxy)phenyl-N4-(1,2,2,6,6-pentamethylpiperidin-4-yl)-5-trifluoromethyl-2,4-pyrimidinediamine;

I-364: 5-Cyano-N2-(3,5-dimethoxy)phenyl-N4-(1,2,2,6,6-pentamethylpiperidin-4-yl)-2,4-pyrimidinediamine;

I-365: 5-Cyano-N2-[3-methoxy-5-(5-methyl-tetrazol-1-yl)]phenyl-N4-(1,2,2,6,6-pentamethylpiperidin-4-yl)-2,4-pyrimidinediamine;

I-366: 5-Cyano-N2-(3-difluoromethoxy-4-methoxy)phenyl-N4-(1,2,2,6,6-pentamethylpiperidin-4-yl)-2,4-pyrimidinediamine;

I-367: 5-Fluoro-N2-{4-[(pyridine-3-yl)methylaminocarbonyl]phenyl-N4-(1,2,2,6,6-pentamethylpiperidin-4-yl)-2,4-pyrimidinediamine;

I-368: N2-{3-Chloro-4-[2-(4-morpholino)ethoxy]}phenyl-5-fluoro-N4-(1,2,2,6,6-pentamethylpiperidin-4-yl)-2,4-pyrimidinediamine;

I-369: 5-Fluoro-N2-[4-methoxy-3-(1,3-oxazol-5-yl)]phenyl-N4-(1,2,2,6,6-pentamethylpiperidin-4-yl)-2,4-pyrimidinediamine;

I-370: N2-[3-Methoxy-5-(5-methyl-tetrazol-1-yl)]phenyl-N4-(1,2,2,6,6-pentamethylpiperidin-4-yl)-5-trifluoromethyl-2,4-pyrimidinediamine;

I-371: N2-(3,5-Dimethoxy)phenyl-5-fluoro-N4-(1H-2,2,6,6-tetramethylpiperidin-4-yl)-2,4-pyrimidinediamine;

I-372: 5-Fluoro-N2-[3-methoxy-5-(5-methyl-tetrazol-1-yl)]phenyl-N4-(1H-2,2,6,6-tetramethylpiperidin-4-yl)-2,4-pyrimidinediamine;

I-373: 5-Cyano-N2-{3-chloro-4-[2-(4-morpholino)ethoxy]}phenyl-N4-(1,2,2,6,6-pentamethylpiperidin-4-yl)-2,4-pyrimidinediamine;

I-374: N2-(3-methoxy-5-(5-methyl-1H-tetrazol-1-yl)phenyl)-5-methyl-N4-(1,2,2,6,6-pentamethylpiperidin-4-yl)-2,4-pyrimidinediamine;

I-375: N2-(3,5-bis(trifluoromethoxy)phenyl)-5-fluoro-N4-(2,2,6,6-tetramethylpiperidin-4-yl)-2,4-pyrimidinediamine;

I-376: 2-(3-(2,5-dimethyl-1H-pyrrol-1-yl)-4-methoxyphenylamino)-4-(1,2,2,6,6-pentamethylpiperidin-4-ylamino)pyrimidine-5-carbonitrile;

I-377: 2-(3-(difluoromethoxy)-4-methoxyphenylamino)-4-(2,2,6,6-tetramethylpiperidin-4-ylamino)pyrimidine-5-carbonitrile;

I-378: N2-[3,5-bis(2,2,2-trifluoroethoxy)]phenyl-5-fluoro-N4-(1,2,2,6,6-pentamethylpiperidin-4-yl)-2,4-pyrimidinediamine;

I-379: N2-(4,5-dimethoxy-2-methyl)phenyl-5-fluoro-N4-(2,2,6,6-tetramethylpiperidin-4-yl)-2,4-pyrimidinediamine;

I-380: N2-(4,5-dimethoxy-2-methyl)phenyl-5-fluoro-N4-(1,2,2,6,6-pentamethylpiperidin-4-yl)-2,4-pyrimidinediamine;

I-381: N2-(2-cyano-4,5-dimethoxy)phenyl-5-fluoro-N4-(1,2,2,6,6-pentamethylpiperidin-4-yl)-2,4-pyrimidinediamine;

I-382: N2-(2-cyano-4,5-dimethoxy)phenyl-5-fluoro-N4-(2,2,6,6-tetramethylpiperidin-4-yl)-2,4-pyrimidinediamine;

I-383: N2-(3,5-dihydroxy)phenyl-5-fluoro-N4-(2,2,6,6-tetramethylpiperidin-4-yl)-2,4-pyrimidinediamine;

I-384: N2-(3,5-dihydroxy)phenyl-5-fluoro-N4-(1,2,2,6,6-pentamethylpiperidin-4-yl)-2,4-pyrimidinediamine;

I-385: N2-[3,5-bis(2-methoxyethoxy)]phenyl-5-fluoro-N4-(1,2,2,6,6-pentamethylpiperidin-4-yl)-2,4-pyrimidinediamine;

I-386: N2-(2-chloro-4,5-dimethoxy)phenyl-5-fluoro-N4-(1,2,2,6,6-pentamethylpiperidin-4-yl)-2,4-pyrimidinediamine;

I-387: 5-aminocarbonyl-N2-[3-methoxy-5-(5-methyl-1H-tetrazol-1-yl)]phenyl-N4-(2,2,6,6-tetramethylpiperidin-4-yl)-2,4-pyrimidinediamine;

I-388: 5-fluoro-N2-[3-methoxy-5-(tetrazol-1-yl)]phenyl-N4-(2,2,6,6-tetramethylpiperidin-4-yl)-2,4-pyrimidinediamine;

I-389: 5-aminocarbonyl-N2-[3-methoxy-5-(tetrazol-1-yl)]phenyl-N4-(2,2,6,6-tetramethylpiperidin-4-yl)-2,4-pyrimidinediamine;

I-390: 5-aminocarbonyl-N2-[3-methoxy-5-(tetrazol-1-yl)]phenyl-N4-(1,2,2,6,6-pentamethylpiperidin-4-yl)-2,4-pyrimidinediamine;

I-391: 5-fluoro-N4-(2,2,6,6-tetramethylpiperidin-4-yl)-N2-[3-(tetrazol-1-yl)]phenyl-2,4-pyrimidinediamine;

I-392: 5-aminocarbonyl-N4-(2,2,6,6-tetramethylpiperidin-4-yl)-N2-[3-(tetrazol-1-yl)]phenyl-2,4-pyrimidinediamine;

I-393: 5-cyano-N4-(2,2,6,6-tetramethylpiperidin-4-yl)-N2-[3-(tetrazol-1-yl)]phenyl-2,4-pyrimidinediamine;

I-394: N2-[3,5-bis(2-methoxyethoxy)]phenyl-5-fluoro-N4-(2,2,6,6-tetramethylpiperidin-4-yl)-2,4-pyrimidinediamine;

I-395: 5-fluoro-N2-[4-methoxy-3-(5-propyl-1H-tetrazol-1-yl)]phenyl-N4-(1,2,2,6,6-pentamethylpiperidin-4-yl)-2,4-pyrimidinediamine;

I-396: 5-fluoro-N2-[3-(5-methyl-1H-tetrazol-1-yl)]phenyl-N4-(1,2,2,6,6-pentamethylpiperidin-4-yl)-2,4-pyrimidinediamine;

I-397: 5-fluoro-N2-[3-methyl-4-(1H-tetrazol-1-yl)]phenyl-N4-(1,2,2,6,6-pentamethylpiperidin-4-yl)-2,4-pyrimidinediamine;

I-398: 5-fluoro-N2-[4-methyl-3-(1H-tetrazol-1-yl)]phenyl-N4-(1,2,2,6,6-pentamethylpiperidin-4-yl)-2,4-pyrimidinediamine;

I-399: 5-fluoro-N2-[3-(5-methylthio-1H-tetrazol-1-yl)]phenyl-N4-(1,2,2,6,6-pentamethylpiperidin-4-yl)-2,4-pyrimidinediamine;

I-400: 5-fluoro-N2-[4-(1H-tetrazol-1-yl)]phenyl-N4-(1,2,2,6,6-pentamethylpiperidin-4-yl)-2,4-pyrimidinediamine;

I-401: 5-fluoro-N2-[4-methoxy-3-(2,2,2-trifluoroethoxy)]phenyl-N4-(1,2,2,6,6-pentamethylpiperidin-4-yl)-2,4-pyrimidinediamine;

I-402: 5-cyano-N2-[3-methoxy-5-(5-methyl-1H-tetrazol-1-yl)]phenyl-N4-(2,2,6,6-tetramethylpiperidin-4-yl)-2,4-pyrimidinediamine;

I-403: 5-cyano-N2-[3-methoxy-5-(1H-tetrazol-1-yl)]phenyl-N4-(2,2,6,6-tetramethylpiperidin-4-yl)-2,4-pyrimidinediamine;

I-404: 5-cyano-N2-[3-methoxy-5-(1H-tetrazol-1-yl)]phenyl-N4-(1,2,2,6,6-pentamethylpiperidin-4-yl)-2,4-pyrimidinediamine;

I-405: 5-cyano-N2-[3-(1H-tetrazol-1-yl)]phenyl-N4-(1,2,2,6,6-pentamethylpiperidin-4-yl)-2,4-pyrimidinediamine;

I-406: 5-aminocarbonyl-N2-[3,5-bis(2,2,2-trifluoroethoxy)]phenyl-N4-(1,2,2,6,6-pentamethylpiperidin-4-yl)-2,4-pyrimidinediamine;

I-407: 5-fluoro-N2-[3-methoxy-4-(5-methyl-1H-tetrazol-1-yl)]phenyl-N4-(1,2,2,6,6-pentamethylpiperidin-4-yl)-2,4-pyrimidinediamine;

I-408: 5-aminocarbonyl-N2-[3,5-bis(2,2,2-trifluoroethoxy)]phenyl-N4-(2,2,6,6-tetramethylpiperidin-4-yl)-2,4-pyrimidinediamine;

I-409: N2-[4-ethoxy-3-(5-ethyl-1H-tetrazol-1-yl)]phenyl-5-fluoro-N4-(1,2,2,6,6-pentamethylpiperidin-4-yl)-2,4-pyrimidinediamine;

I-410: N2-[3,4-bis(trifluoromethyl)]phenyl-5-fluoro-N4-(1,2,2,6,6-pentamethylpiperidin-4-yl)-2,4-pyrimidinediamine;

I-411: 5-cyano-N2-[3,5-bis(2,2,2-trifluoroethoxy)]phenyl-N4-(1,2,2,6,6-pentamethylpiperidin-4-yl)-2,4-pyrimidinediamine;

I-412: N2-[3-(cyclopropylaminocarbonylmethoxy)-4-methoxy]phenyl-5-fluoro-N4-(1,2,2,6,6-pentamethylpiperidin-4-yl)-2,4-pyrimidinediamine;

I-413: N2-[3-(2-methoxyethoxy)-4-methoxy]phenyl-5-fluoro-N4-(1,2,2,6,6-pentamethylpiperidin-4-yl)-2,4-pyrimidinediamine;

I-414: 5-fluoro-N2-[3-(5-methyl-1H-tetrazol-1-yl)]phenyl-N4-(2,2,6,6-tetramethylpiperidin-4-yl)-2,4-pyrimidinediamine;

I-415: N2-[4-ethoxy-3-(5-ethyl-1H-tetrazol-1-yl)]phenyl-5-fluoro-N4-(2,2,6,6-tetramethylpiperidin-4-yl)-2,4-pyrimidinediamine;

I-416: 5-fluoro-N2-[3-(5-methylthio-1H-tetrazol-1-yl)]phenyl-N4-(2,2,6,6-tetramethylpiperidin-4-yl)-2,4-pyrimidinediamine;

I-417: 5-fluoro-N2-[4-methoxy-3-(pyridin-4-ylmethoxy)]phenyl-N4-(1,2,2,6,6-pentamethylpiperidin-4-yl)-2,4-pyrimidinediamine;

I-418: 5-fluoro-N2-[4-methoxy-3-(pyridin-3-ylmethoxy)]phenyl-N4-(1,2,2,6,6-pentamethylpiperidin-4-yl)-2,4-pyrimidinediamine;

I-419: 5-cyano-N2-[3,5-bis(2,2,2-trifluoroethoxy)]phenyl-N4-(2,2,6,6-tetramethylpiperidin-4-yl)-2,4-pyrimidinediamine;

I-420: 5-aminocarbonyl-N2-[4-ethoxy-3-(5-ethyl-1H-tetrazol-1-yl)]phenyl-N4-(1,2,2,6,6-pentamethylpiperidin-4-yl)-2,4-pyrimidinediamine;

I-421: N2-{4-methoxy-3-[2-(N,N-dimethylamino)ethoxy]}phenyl-5-fluoro-N4-(1,2,2,6,6-pentamethylpiperidin-4-yl)-2,4-pyrimidinediamine;

I-422: 5-bromo-N2-(3,5-dimethoxyphenyl)-N4-(1,2,2,6,6-pentamethylpiperidin-4-yl)pyrimidine-2,4-diamine;

I-423: N2-(3,5-dimethoxyphenyl)-5-methoxy-N4-(1,2,2,6,6-pentamethylpiperidin-4-yl)pyrimidine-2,4-diamine;

I-424: 5-methoxy-N2-(3-methoxy-5-(5-methyl-1H-tetrazol-1-yl)phenyl)-N4-(1,2,2,6,6-pentamethylpiperidin-4-yl)pyrimidine-2,4-diamine;

I-425: N2-(3,5-dimethoxyphenyl)-5-methyl-N4-(1,2,2,6,6-pentamethylpiperidin-4-yl)pyrimidine-2,4-diamine;

I-426: 2-(6-(dimethylamino)pyridin-3-yl)-5-(5-fluoro-4-(1,2,2,6,6-pentamethylpiperidin-4-ylamino)pyrimidin-2-ylamino)benzonitrile;

I-427: 5-(5-fluoro-4-(1,2,2,6,6-pentamethylpiperidin-4-ylamino)pyrimidin-2-ylamino)-2-(6-morpholinopyridin-3-yl)benzonitrile;

I-428: 2-(6-(dimethylamino)pyridin-3-yl)-5-(5-fluoro-4-(2,2,6,6-tetramethylpiperidin-4-ylamino)pyrimidin-2-ylamino)benzonitrile;

I-429: 5-(5-fluoro-4-(2,2,6,6-tetramethylpiperidin-4-ylamino)pyrimidin-2-ylamino)-2-(6-morpholinopyridin-3-yl)benzonitrile;

I-430: N2-(3,5-dimethoxyphenyl)-N4-(1,2,2,6,6-pentamethylpiperidin-4-yl)-5-((trimethylsilyl)ethynyl)pyrimidine-2,4-diamine;

I-431: 5-fluoro-N2-(3-methoxy-5-(2-morpholinoethoxy)phenyl)-N4-(1,2,2,6,6-pentamethylpiperidin-4-yl)pyrimidine-2,4-diamine;

I-432: 5-fluoro-N2-(3-methoxy-5-(2-morpholinoethoxy)phenyl)-N4-(2,2,6,6-tetramethylpiperidin-4-yl)pyrimidine-2,4-diamine;

I-433: N2-(3,5-dimethoxyphenyl)-5-ethynyl-N4-(1,2,2,6,6-pentamethylpiperidin-4-yl)pyrimidine-2,4-diamine;

I-434: 5-fluoro-N2-(3-methoxy-5-(2-(pyrrolidin-1-yl)ethoxy)phenyl)-N4-(1,2,2,6,6-pentamethylpiperidin-4-yl)pyrimidine-2,4-diamine;

I-435: 5-fluoro-N2-(3-methoxy-5-(2-(pyrrolidin-1-yl)ethoxy)phenyl)-N4-(2,2,6,6-tetramethylpiperidin-4-yl)pyrimidine-2,4-diamine;

I-436: 3-(5-fluoro-4-(1,2,2,6,6-pentamethylpiperidin-4-ylamino)pyrimidin-2-ylamino)-5-methoxyphenol;

I-437: N2-(3-(2-(1H-pyrrol-1-yl)ethoxy)-5-methoxyphenyl)-5-fluoro-N4-(1,2,2,6,6-pentamethylpiperidin-4-yl)pyrimidine-2,4-diamine;

I-438: N2-(3-(2-(1H-pyrrol-1-yl)ethoxy)-5-methoxyphenyl)-5-fluoro-N4-(2,2,6,6-tetramethylpiperidin-4-yl)pyrimidine-2,4-diamine;

I-439: N2-(3-(2,5-dimethyl-1H-pyrrol-1-yl)-4-(2-morpholinoethoxy)phenyl)-5-fluoro-N4-(1,2,2,6,6-pentamethylpiperidin-4-yl)pyrimidine-2,4-diamine;

I-440: N2-(3-(2,5-dimethyl-1H-pyrrol-1-yl)-4-(2-(pyrrolidin-1-yl)ethoxy)phenyl)-5-fluoro-N4-(1,2,2,6,6-pentamethylpiperidin-4-yl)pyrimidine-2,4-diamine;

I-441: N2-(3-(2,5-dimethyl-1H-pyrrol-1-yl)-4-(2-morpholinoethoxy)phenyl)-5-fluoro-N4-(2,2,6,6-tetramethylpiperidin-4-yl)pyrimidine-2,4-diamine;

I-442: N2-(3-(2,5-dimethyl-1H-pyrrol-1-yl)-4-(2-(pyrrolidin-1-yl)ethoxy)phenyl)-5-fluoro-N4-(2,2,6,6-tetramethylpiperidin-4-yl)pyrimidine-2,4-diamine;

I-443: N2-(3-Fluoro-5-methoxy)phenyl-5-fluoro-N4-(1,2,2,6,6-pentamethylpiperidin-4-yl)-2,4-pyrimidinediamine;

I-444: N2-(3-Difluoromethoxy-4-methoxy)phenyl-5-fluoro-N4-(2,2,6,6-tetramethylpiperidin-4-yl)-2,4-pyrimidinediamine;

I-445: N2-{3-Chloro-4-[2-(4-morpholino)ethoxy]}phenyl-5-cyano-N4-(2,2,6,6-tetramethylpiperidin-4-yl)-2,4-pyrimidinediamine;

I-446: 5-Fluoro-N2-[3,5-dichloro]phenyl-N4-[1-(propionylhydrazine)-2,2,6,6-pentamethylpiperidin-4-yl]-2,4-pyrimidinediamine;

I-447: 5-Fluoro-N2-[3,5-dichloro]phenyl-N4-[1-(2-ethylamine)-2,2,6,6-pentamethylpiperidin-4-yl]-2,4-pyrimidinediamine;

I-448: 5-Amide-N2-{5-[2-(methylmorphine)-3-trifluoromethyl]pyridine}-N4-(1,2,2,6,6-pentamethylpiperidin-4-yl)-2,4-pyrimidinediamine;

I-449: 5-Fluoro-N2-{5-[2-(methylmorphine)-3-trifluoromethyl]pyridine}-N4-(2,2,6,6-tetramethylpiperidin-4-yl)-2,4-pyrimidinediamine;

I-450: 5-Fluoro-N2-[4-(methylmorphine)-3-cyano]phenyl-N4-(1,2,2,6,6-pentamethylpiperidin-4-yl)-2,4-pyrimidinediamine;

I-451: 5-Fluoro-N2-{5-[2-(methylmorphine)-3-cyano]pyridin}-N4-(2,2,6,6-tetramethylpiperidin-4-yl)-2,4-pyrimidinediamine;

I-452: 5-Cyano-N2-{5-[2-(methylmorphine)-3-trifluoromethyl]pyridine}-N4-(1,2,2,6,6-pentamethylpiperidin-4-yl)-2,4-pyrimidinediamine;

I-453: 3-(5-fluoro-4-(2,2,6,6-tetramethylpiperidin-4-ylamino)pyrimidin-2-ylamino)-5-methoxyphenol;

I-454: 5-fluoro-N2-[4-(5-methyl-1H-tetrazol-1-yl)]phenyl-N4-(1,2,2,6,6-pentamethylpiperidin-4-yl)-2,4-pyrimidinediamine;

I-455: 5-fluoro-N2-[4-methyl-3-(1H-tetrazol-1-yl)]phenyl-N4-(2,2,6,6-tetramethylpiperidin-4-yl)-2,4-pyrimidinediamine;

I-456: 5-aminocarbonyl-N2-[3-(5-methylthio-1H-tetrazol-1-yl)]phenyl-N4-(1,2,2,6,6-pentamethylpiperidin-4-yl)-2,4-pyrimidinediamine;

I-457: 5-aminocarbonyl-N2-[3-(5-methylthio-1H-tetrazol-1-yl)]phenyl-N4-(2,2,6,6-tetramethylpiperidin-4-yl)-2,4-pyrimidinediamine;

I-458: 5-fluoro-N2-{-4-[5-(furan-2-yl)-1H-tetrazol-1-yl]}phenyl-N4-(1,2,2,6,6-pentamethylpiperidin-4-yl)-2,4-pyrimidinediamine;

I-459: 5-cyano-N2-[4-methyl-3-(1H-tetrazol-1-yl)]phenyl-N4-(1,2,2,6,6-pentamethylpiperidin-4-yl)-2,4-pyrimidinediamine;

I-460: 5-cyano-N2-[4-ethoxy-3-(5-ethyl-1H-tetrazol-1-yl)]phenyl-N4-(1,2,2,6,6-pentamethylpiperidin-4-yl)-2,4-pyrimidinediamine;

I-461: 5-cyano-N2-[4-methyl-3-(1H-tetrazol-1-yl)]phenyl-N4-(2,2,6,6-tetramethylpiperidin-4-yl)-2,4-pyrimidinediamine;

I-462: 5-cyano-N2-[3-(5-methyl-1H-tetrazol-1-yl)]phenyl-N4-(1,2,2,6,6-pentamethylpiperidin-4-yl)-2,4-pyrimidinediamine;

I-463: 5-cyano-N2-[3-(5-methyl-1H-tetrazol-1-yl)]phenyl-N4-(2,2,6,6-tetramethylpiperidin-4-yl)-2,4-pyrimidinediamine;

I-464: 5-cyano-N2-[3-(5-methylthio-1H-tetrazol-1-yl)]phenyl-N4-(1,2,2,6,6-pentamethylpiperidin-4-yl)-2,4-pyrimidinediamine;

I-465: 5-cyano-N2-[3-(5-methylthio-1H-tetrazol-1-yl)]phenyl-N4-(2,2,6,6-tetramethylpiperidin-4-yl)-2,4-pyrimidinediamine;

I-466: 5-fluoro-N2-[4-fluoro-3-(1H-tetrazol-1-yl)]phenyl-N4-(1,2,2,6,6-pentamethylpiperidin-4-yl)-2,4-pyrimidinediamine;

I-467: 5-fluoro-N2-[4-fluoro-3-(1H-tetrazol-1-yl)]phenyl-N4-(2,2,6,6-tetramethylpiperidin-4-yl)-2,4-pyrimidinediamine;

I-468: 5-aminocarbonyl-N2-[4-fluoro-3-(1H-tetrazol-1-yl)]phenyl-N4-(1,2,2,6,6-pentamethylpiperidin-4-yl)-2,4-pyrimidinediamine;

I-469: 5-cyano-N2-[4-ethoxy-3-(5-ethyl-1H-tetrazol-1-yl)]phenyl-N4-(2,2,6,6-tetramethylpiperidin-4-yl)-2,4-pyrimidinediamine;

I-470: 5-Fluoro-N4-(1,2,2,6,6-pentamethylpiperidin-4-yl)-N2-[3-(tetrazol-5-yl)]phenyl-2,4-pyrimidinediamine;

I-471: 5-Fluoro-N4-(2,2,6,6-tetramethylpiperidin-4-yl)-N2-[3-(tetrazol-5-yl)]phenyl-2,4-pyrimidinediamine;

I-472: 5-Cyano-N2-[3-(2,5-dimethyl-pyrrol-1-yl)-4-methoxy]phenyl-N4-(1,2,2,6,6-pentamethylpiperidin-4-yl)-2,4-pyrimidinediamine;

I-473: 5-Cyano-N2-(3-difluoromethoxy-4-methoxy)phenyl-N4-(2,2,6,6-tetramethylpiperidin-4-yl)-2,4-pyrimidinediamine;

II-1: 5-Fluoro-N4-(1,2,2,6,6-pentamethylpiperidin-4-yl)-N2-(quinolin-6-yl)-2,4-pyrimidinediamine;

II-2: N2-(3,4-Dihydroquinolin-1H-2-one-6-yl)-5-fluoro-N4-(1,2,2,6,6-pentamethylpiperidin-4-yl)-2,4-pyrimidinediamine;

II-3: N2-(1H-Benzoxazin-3-one-6-yl)-5-fluoro-N4-(1,2,2,6,6-pentamethylpiperidin-4-yl)-2,4-pyrimidinediamine;

II-4: 5-Fluoro-N2-(1-methyl-3,4-dihydroquinolin-2-one-6-yl)-N4-(1,2,2,6,6-pentamethylpiperidin-4-yl)-2,4-pyrimidinediamine;

II-5: N2-(1-Ethyl-3,4-dihydroquinolin-2-one-6-yl)-5-fluoro-N4-(1,2,2,6,6-pentamethylpiperidin-4-yl)-2,4-pyrimidinediamine;

II-6: 5-Fluoro-N2-(4-methyl-2H-1,4-benzoxazin-3-one-7-yl)-N4-(1,2,2,6,6-pentamethylpiperidin-4-yl)-2,4-pyrimidinediamine;

II-7: 5-Fluoro-N2-(2-methylquinolin-6-yl)-N4-(1,2,2,6,6-pentamethylpiperidin-4-yl)-2,4-pyrimidinediamine;

II-8: N2-(2,2-Difluoro-4-methyl-2H-1,4-benzoxazin-3-one-7-yl)-5-fluoro-N4-(1,2,2,6,6-pentamethylpiperidin-4-yl)-2,4-pyrimidinediamine;

II-9: 5-Fluoro-N2-(2-methylbenzoimidazol-5-yl)-N4-(1,2,2,6,6-pentamethylpiperidin-4-yl)-2,4-pyrimidinediamine;

II-10: Methyl 3-[4-(2-(2,3-dihydrobenzo[b][1,4]dioxin-6-ylamino)-5-fluoropyrimidine-4-ylamino)-2,2,6,6-tetramethylpiperidin-1-yl]propanoate;

II-11: 5-Fluoro-N2-(4H-imidazo[2,1-c][1,4]-benzoxazin-7-yl)N4-(1,2,2,6,6-pentamethylpiperidin-4-yl)-2,4-pyrimidinediamine;

II-12: N2-(5-chlorobenzo[d]oxazol-2-yl)-5-fluoro-N4-(1,2,2,6,6-pentamethylpiperidin-4-yl)pyrimidine-2,4-diamine;

II-13: 5-fluoro-N4-(1,2,2,6,6-pentamethylpiperidin-4-yl)-N2-(5-(trifluoromethyl)-1,3,4-thiadiazol-2-yl)pyrimidine-2,4-diamine;

II-14: 5-fluoro-N2-(5-nitrothiazol-2-yl)-N4-(1,2,2,6,6-pentamethylpiperidin-4-yl)pyrimidine-2,4-diamine;

II-15: N2-(4-(4-chlorophenyl)thiazol-2-yl)-5-fluoro-N4-(1,2,2,6,6-pentamethylpiperidin-4-yl)pyrimidine-2,4-diamine;

II-16: N2-(benzo[d]thiazol-2-yl)-5-fluoro-N4-(1,2,2,6,6-pentamethylpiperidin-4-yl)pyrimidine-2,4-diamine;

II-17: 5-fluoro-N2-(6-nitrobenzo[d]thiazol-2-yl)-N4-(1,2,2,6,6-pentamethylpiperidin-4-yl)pyrimidine-2,4-diamine;

II-18: N2-(6-ethoxybenzo[d]thiazol-2-yl)-5-fluoro-N4-(1,2,2,6,6-pentamethylpiperidin-4-yl)pyrimidine-2,4-diamine;

II-19: 5-fluoro-N2-(4-methylbenzo[d]thiazol-2-yl)-N4-(1,2,2,6,6-pentamethylpiperidin-4-yl)pyrimidine-2,4-diamine;

II-20: 5-fluoro-N2-(4-methoxybenzo[d]thiazol-2-yl)-N4-(1,2,2,6,6-pentamethylpiperidin-4-yl)pyrimidine-2,4-diamine;

II-21: 5-fluoro-N2-(5-(methylthio)-1,3,4-thiadiazol-2-yl)-N4-(1,2,2,6,6-pentamethylpiperidin-4-yl)pyrimidine-2,4-diamine;

II-22: 2-(5-fluoro-4-(1,2,2,6,6-pentamethylpiperidin-4-ylamino)pyrimidin-2-ylamino)-1H-imidazole-4,5-dicarbonitrile;

II-23: 5-fluoro-N4-(1,2,2,6,6-pentamethylpiperidin-4-yl)-N2-(thiazolo[5,4-b]pyridin-2-yl)pyrimidine-2,4-diamine;

II-24: N2-(3,4-dihydro-2H-pyrido[3,2-b][1,4]oxazin-6-yl)-5-fluoro-N4-(1,2,2,6,6-pentamethylpiperidin-4-yl)pyrimidine-2,4-diamine;

II-25: N2-(2,2-Difluoro-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine;

II-26: N2-(2,2-Difluoro-4-methyl-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine;

II-27: N2-(2,2-Difluoro-4-ethyl-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine;

II-28: 5-Chloro-N2-(2,2-difluoro-4-methyl-2H-1,4-benzoxazin-3(4H)-one-7-yl)-N4-(1,2,2,6,6-pentamethylpiperidin-4-yl)-2,4-pyrimidinediamine;

II-29: N2-(3,4-Ethylenedioxy)phenyl-5-fluoro-N4-(1,2,2,6,6-pentamethylpiperidin-4-yl)-2,4-pyrimidinediamine;

II-30: 5-Fluoro-N2-(2-methyl-benzoxazol-5-yl)-N4-(1,2,2,6,6-pentamethylpiperidin-4-yl)-2,4-pyrimidinediamine;

II-31: N2-(2,2-Difluoro-4-ethyl-benzoxazin-3-one-7-yl)-5-fluoro-N4-(1,2,2,6,6-pentamethylpiperidin-4-yl)-2,4-pyrimidinediamine;

II-32: 5-Fluoro-N2-(3,4-methylenedioxy)phenyl-N4-(1,2,2,6,6-pentamethylpiperidin-4-yl)-2,4-pyrimidinediamine;

II-33: N2-(2,2-Dimethyl-1,4-benzoxazin-4H-3-one-7-yl)-5-fluoro-N4-(1,2,2,6,6-pentamethylpiperidin-4-yl)-2,4-pyrimidinediamine;

II-34: N2-(2,2-Dimethyl-4-methyl-1,4-benzoxazin-3-one-7-yl)-5-fluoro-N4-(1,2,2,6,6-pentamethylpiperidin-4-yl)-2,4-pyrimidinediamine;

II-35: N2-(2,2-Dimethyl-4-ethyl-1,4-benzoxazin-3-one-7-yl)-5-fluoro-N4-(1,2,2,6,6-pentamethylpiperidin-4-yl)-2,4-pyrimidinediamine;

II-36: 5-Fluoro-N2-(3-methyl-benzoxazol-2-one-6-yl)-N4-(1,2,2,6,6-pentamethylpiperidin-4-yl)-2,4-pyrimidinediamine;

II-37: N2-(2,2-Difluoro-1,3-benzodioxol-5-yl)-5-fluoro-N4-(1,2,2,6,6-pentamethylpiperidin-4-yl)-2,4-pyrimidinediamine;

II-38: 5-Fluoro-N2-(1H-indazol-5-yl)-N4-(1,2,2,6,6-pentamethylpiperidin-4-yl)-2,4-pyrimidinediamine;

II-39: 5-Fluoro-N2-(1-methyl-indazol-5-yl)-N4-(1,2,2,6,6-pentamethylpiperidin-4-yl)-2,4-pyrimidinediamine;

II-40: 5-Fluoro-N2-(1-H-indazol-6-yl)-N4-(1,2,2,6,6-pentamethylpiperidin-4-yl)-2,4-pyrimidinediamine;

II-41: 5-Fluoro-N2-(1-methyl-indazol-6-yl)-N4-(1,2,2,6,6-pentamethylpiperidin-4-yl)-2,4-pyrimidinediamine;

II-42: 5-Fluoro-N2-(3-aminocarboxylmethylene-benzoxazol-2-one-6-yl)-N4-(1,2,2,6,6-pentamethylpiperidin-4-yl)-2,4-pyrimidinediamine;

II-43: N2-(3,4-Dihydro-2H-1,5-benzodioxepin-7-yl)-5-fluoro-N4-(1,2,2,6,6-pentamethylpiperidin-4-yl)-2,4-pyrimidinediamine;

II-44: N2-(2,2-Dimethyl-4-isopropyl-1,4-benzoxazin-3-one-7-yl)-5-fluoro-N4-(1,2,2,6,6-pentamethylpiperidin-4-yl)-2,4-pyrimidinediamine;

II-45: 5-Cyano-N2-(2,2-dimethyl-4-ethyl-1,4-benzoxazin-3-one-7-yl)-N4-(1,2,2,6,6-pentamethylpiperidin-4-yl)-2,4-pyrimidinediamine;

II-46: N2-(3-Ethyl-benzoxazol-2-one-6-yl)-5-fluoro-N4-(1,2,2,6,6-pentamethylpiperidin-4-yl)-2,4-pyrimidinediamine;

II-47: 5-Fluoro-N2-(3-isopropyl-benzoxazol-2-one-6-yl)-N4-(1,2,2,6,6-pentamethylpiperidin-4-yl)-2,4-pyrimidinediamine;

II-48: N2-(2,2-Dimethyl-4-propyl-1,4-benzoxazin-3-one-7-yl)-5-fluoro-N4-(1,2,2,6,6-pentamethylpiperidin-4-yl)-2,4-pyrimidinediamine;

II-49: N2-{2,2-Dimethyl-4-[2-(N,N-dimethylamino)ethyl]-1,4-benzoxazin-3-one-7-yl}-5-fluoro-N4-(1,2,2,6,6-pentamethylpiperidin-4-yl)-2,4-pyrimidinediamine;

II-50: N2-[2,2-Dimethyl-4-ethyl-1,4-benzoxazin-3-one-7-yl]-N4-(1,2,2,6,6-pentamethylpiperidin-4-yl)-5-trifluoromethyl-2,4-pyrimidinediamine;

II-51: 5-Fluoro-N2-(1-methyl-2,3-dihydro-indol-5-yl)-N4-(1,2,2,6,6-pentamethylpiperidin-4-yl)-2,4-pyrimidinediamine;

II-52: 5-Fluoro-N2-(1-ethyl-2,3-dihydro-indol-5-yl)-N4-(1,2,2,6,6-pentamethylpiperidin-4-yl)-2,4-pyrimidinediamine;

II-53: 5-Fluoro-N2-(1-isopropyl-2,3-dihydro-indol-5-yl)-N4-(1,2,2,6,6-pentamethylpiperidin-4-yl)-2,4-pyrimidinediamine;

II-54: N2-(2,2-Dimethyl-4-N-methyl-2H-pyrido[3,2-b]-1,4-oxazin-3-one-7-yl)-5-fluoro-N4-(1,2,2,6,6-pentamethylpiperidin-4-yl)-2,4-pyrimidinediamine;

II-55: N2-(2,2-Dimethyl-4-N-ethyl-2H-pyrido[3,2-b]-1,4-oxazin-3-one-7-yl)-5-fluoro-N4-(1,2,2,6,6-pentamethylpiperidin-4-yl)-2,4-pyrimidinediamine;

II-56: N2-(1,3-Dimethyl-1,3-dihydro-benzoimidazol-2-one-5-yl)-5-fluoro-N4-(1,2,2,6,6-pentamethylpiperidin-4-yl)-2,4-pyrimidinediamine;

II-57: 5-Cyano-N2-(2,2-dimethyl-4-ethyl-1,4-benzoxazin-3-one-7-yl)-N4-(2,2,6,6-tetramethylpiperidin-4-yl)-2,4-pyrimidinediamine;

II-58: N2-(4-Ethyl-2H-1,4-benzoxazin-3-one-7-yl)-5-fluoro-N4-(1,2,2,6,6-pentamethylpiperidin-4-yl)-2,4-pyrimidinediamine;

II-59: 5-Fluoro-N2-(4-propyl-2H-1,4-benzoxazin-3-one-7-yl)-N4-(1,2,2,6,6-pentamethylpiperidin-4-yl)-2,4-pyrimidinediamine;

II-60: 5-Cyano-N2-(3,4-ethylenedioxy)phenyl-N4-(1,2,2,6,6-pentamethylpiperidin-4-yl)-2,4-pyrimidinediamine;

II-61: 5-Fluoro-N2-(4-isopropyl-2H-1,4-benzoxazin-3-one-7-yl)-N4-(1,2,2,6,6-pentamethylpiperidin-4-yl)-2,4-pyrimidinediamine;

II-62: N2-(2,2-Dimethyl-4-methyl-2H-1,4-benzothiazin-3-one-7-yl)-5-fluoro-N4-(1,2,2,6,6-pentamethylpiperidin-4-yl)-2,4-pyrimidinediamine;

II-63: N2-(2,2-Dimethyl-4-ethyl-1,4-benzothiazin-3-one-7-yl)-5-fluoro-N4-(1,2,2,6,6-pentamethylpiperidin-4-yl)-2,4-pyrimidinediamine;

II-64: N2-(2,2-Dimethyl-1,1-dioxide-4-methyl-1,4-benzothiazin-3-one-7-yl)-5-fluoro-N4-(1,2,2,6,6-pentamethylpiperidin-4-yl)-2,4-pyrimidinediamine;

II-65: 5-Cyano-N2-(2,2-difluoro-4-N-ethyl-2H-pyrido[3,2-b]-1,4-oxazin-3-one-7-yl)-N4-(1,2,2,6,6-pentamethylpiperidin-4-yl)-2,4-pyrimidinediamine;

II-66: N2-(2,2-Dimethyl-1,1-dioxide-4-ethyl-1,4-benzothiazin-3-one-7-yl)-5-fluoro-N4-(1,2,2,6,6-pentamethylpiperidin-4-yl)-2,4-pyrimidinediamine;

II-67: N2-(2,2-Dimethyl-1,1-dioxide-4-isopropyl-1,4-benzothiazin-3-one-7-yl)-5-fluoro-N4-(1,2,2,6,6-pentamethylpiperidin-4-yl)-2,4-pyrimidinediamine;

II-68: N2-(2,1-spiro-Cyclobutane-4-methyl-1,4-benzoxazin-3-one-7-yl)-5-fluoro-N4-(1,2,2,6,6-pentamethylpiperidin-4-yl)-2,4-pyrimidinediamine;

II-69: N2-(2,1-spiro-cyclobutane-4-ethyl-1,4-benzoxazin-3-one-7-yl)-5-fluoro-N4-(1,2,2,6,6-pentamethylpiperidin-4-yl)-2,4-pyrimidinediamine;

II-70: 5-Cyano-N2-(3-isopropyl-benzoxazol-2-one-6-yl)-N4-(1,2,2,6,6-pentamethylpiperidin-4-yl)-2,4-pyrimidinediamine;

II-71: 5-Cyano-N2-(4-ethyl-2H-1,4-benzoxazin-3-one-7-yl)-N4-(1,2,2,6,6-pentamethylpiperidin-4-yl)-2,4-pyrimidinediamine;

II-72: 5-Cyano-N2-(4-propyl-2H-1,4-benzoxazin-3-one-7-yl)-N4-(1,2,2,6,6-pentamethylpiperidin-4-yl)-2,4-pyrimidinediamine;

II-73: 5-Cyano-N2-(2,2-difluoro-4-N-ethyl-2H-pyrido[3,2-b]-1,4-oxazin-3-one-7-yl)-N4-(1H-2,2,6,6-tetramethylpiperidin-4-yl)-2,4-pyrimidinediamine;

II-74: 5-Cyano-N2-(2,2-dimethyl-4-isopropyl-1,4-benzoxazin-3-one-7-yl)-N4-(1,2,2,6,6-pentamethylpiperidin-4-yl)-2,4-pyrimidinediamine;

II-75: 5-Cyano-N2-(2,2-dimethyl-4-isopropyl-1,4-benzoxazin-3-one-7-yl)-N4-(1H-2,2,6,6-tetramethylpiperidin-4-yl)-2,4-pyrimidinediamine;

II-76: N2-(2,2-Dimethyl-4-cyclopropylmethylene-1,4-benzoxazin-3-one-7-yl)-5-fluoro-N4-(1,2,2,6,6-pentamethylpiperidin-4-yl)-2,4-pyrimidinediamine;

II-77: N2-(4-Cyclopropylmethylene-1,4-benzoxazin-3-one-7-yl)-5-fluoro-N4-(1,2,2,6,6-pentamethylpiperidin-4-yl)-2,4-pyrimidinediamine;

II-78: N2-[2,2-Dimethyl-4-(3-fluoropropyl)-1,4-benzoxazin-3-one-7-yl]-5-fluoro-N4-(1,2,2,6,6-pentamethylpiperidin-4-yl)-2,4-pyrimidinediamine;

II-79: 5-Cyano-N2-[2,2-dimethyl-4-(2-fluoroethyl)-1,4-benzoxazin-3-one-7-yl]-N4-(1,2,2,6,6-pentamethylpiperidin-4-yl)-2,4-pyrimidinediamine;

II-80: N2-[2,2-Dimethyl-4-(2-fluoroethyl)-1,4-benzoxazin-3-one-7-yl]-5-fluoro-N4-(1,2,2,6,6-pentamethylpiperidin-4-yl)-2,4-pyrimidinediamine;

II-81: 5-Cyano-N2-[2,2-dimethyl-4-(3-fluoropropyl)-1,4-benzoxazin-3-one-7-yl]-N4-(1,2,2,6,6-pentamethylpiperidin-4-yl)-2,4-pyrimidinediamine;

II-82: N2-[4-(2-fluoroethyl)-2H-1,4-benzoxazin-3-one-7-yl]-5-fluoro-N4-(1,2,2,6,6-pentamethylpiperidin-4-yl)-2,4-pyrimidinediamine;

II-83: (S)—N2-(2,3-dihydro-1H-inden-1-yl)-5-fluoro-N4-(1,2,2,6,6-pentamethylpiperidin-4-yl)pyrimidine-2,4-diamine;

II-84: (R)—N2-(2,3-dihydro-1H-inden-1-yl)-5-fluoro-N4-(1,2,2,6,6-pentamethylpiperidin-4-yl)pyrimidine-2,4-diamine;

II-85: N2-(5-Benzylamino-pyrid-2-yl)-N4-(1,2,2,6,6-pentamethylpiperidin-4-yl)-5-fluoro-2,4-pyrimidinediamine;

II-86: N4-benzyl-N2-(2,3-dihydrobenzo[b][1,4]dioxin-6-yl)-5-fluoro-N4-(1,2,2,6,6-pentamethylpiperidin-4-yl)pyrimidine-2,4-diamine;

II-87: N2-(2,3-dihydrobenzo[b][1,4]dioxin-6-yl)-5-fluoro-N4-(naphthalen-2-ylmethyl)-N4-(1,2,2,6,6-pentamethylpiperidin-4-yl)pyrimidine-2,4-diamine;

II-88: N4-(biphenyl-4-ylmethyl)-N2-(2,3-dihydrobenzo[b][1,4]dioxin-6-yl)-5-fluoro-N4-(1,2,2,6,6-pentamethylpiperidin-4-yl)pyrimidine-2,4-diamine;

II-89: N2-(2,3-dihydrobenzo[b][1,4]dioxin-6-yl)-5-fluoro-N4-(1,2,2,6,6-pentamethylpiperidin-4-yl)-N4-(quinolin-2-ylmethyl)pyrimidine-2,4-diamine;

II-90: N4-((6-bromobenzo[d][1,3]dioxol-5-yl)methyl)-N2-(2,3-dihydrobenzo[b][1,4]dioxin-6-yl)-5-fluoro-N4-(1,2,2,6,6-pentamethylpiperidin-4-yl)pyrimidine-2,4-diamine;

II-91: 4'-(((2-(2,3-dihydrobenzo[b][1,4]dioxin-6-ylamino)-5-fluoropyrimidin-4-yl)(1,2,2,6,6-pentamethylpiperidin-4-yl)amino)methyl)biphenyl-2-carbonitrile;

II-92: 5-fluoro-N4-(1,2,2,6,6-pentamethylpiperidin-4-yl)-N2-(2,2,3,3-tetrafluoro-2,3-dihydrobenzo[b][1,4]dioxin-6-yl)-2,4-pyrimidinediamine;

II-93: 7-(5-fluoro-4-(1,2,2,6,6-pentamethylpiperidin-4-ylamino)pyrimidin-2-ylamino)-4-(2-methoxyethyl)-2,2-dimethyl-2H-pyrido[3,2-b][1,4]oxazin-3(4H)-one;

II-94: 2-(4-(2-fluoroethyl)-3-oxo-3,4-dihydro-2H-benzo[b][1,4]oxazin-7-ylamino)-4-(1,2,2,6,6-pentamethylpiperidin-4-ylamino)pyrimidine-5-carbonitrile;

II-95: 2-(4-(2-fluoroethyl)-2,2-dimethyl-3-oxo-3,4-dihydro-2H-benzo[b][1,4]oxazin-7-ylamino)-4-(1,2,2,6,6-pentamethylpiperidin-4-ylamino)pyrimidine-5-carbonitrile;

II-96: 2-(3-(cyclopropylmethyl)-2-oxo-2,3-dihydrobenzo[d]oxazol-6-ylamino)-4-(1,2,2,6,6-pentamethylpiperidin-4-ylamino)pyrimidine-5-carbonitrile;

II-97: 2-(3-(cyclopropylmethyl)-2-oxo-2,3-dihydrobenzo[d]oxazol-6-ylamino)-4-(2,2,6,6-tetramethylpiperidin-4-ylamino)pyrimidine-5-carbonitrile;

II-98: 7-(5-fluoro-4-(1,2,2,6,6-pentamethylpiperidin-4-ylamino)pyrimidin-2-ylamino)-4-(2-fluoroethyl)-2H-benzo[b][1,4]oxazin-3(4H)-one;

II-99: N2-[3,4-dihydro-2,2-dimethyl-4-(2-methoxyethyl)-3-oxo-2H-pyrido[3,2-b]-1,4-oxazin-7-yl]phenyl-5-fluoro-N4-(2,2,6,6-tetramethylpiperidin-4-yl)-2,4-pyrimidinediamine;

II-100: 5-aminocarbonyl-N2-[3,4-dihydro-2,2-dimethyl-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-101: 5-aminocarbonyl-N2-[3,4-dihydro-2,2-dimethyl-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-102: N2-(2,2-dimethyl-benzo[1,3]dioxol-5-yl)-5-fluoro-N4-(2,2,6,6-tetramethylpiperidin-4-yl)-2,4-pyrimidinediamine;

II-103: N2-(2,2-dimethyl-benzo[1,3]dioxol-5-yl)-5-fluoro-N4-(1,2,2,6,6-pentamethylpiperidin-4-yl)-2,4-pyrimidinediamine;

II-104: N2-[3,4-dihydro-4-(2-methoxyethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine;

II-105: 5-aminocarbonyl-N2-[3,4-dihydro-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-106: 5-aminocarbonyl-N2-[3,4-dihydro-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-107: N2-[3,4-dihydro-4-(2-methoxyethyl)-3-oxo-2H-1,4-benzoxazin-7-yl]phenyl-5-fluoro-N4-(2,2,6,6-tetramethylpiperidin-4-yl)-2,4-pyrimidinediamine;

II-108: N2-[3,4-dihydro-4-(2-methoxyethyl)-3-oxo-2H-1,4-benzoxazin-7-yl]phenyl-5-fluoro-N4-(1,2,2,6,6-pentamethylpiperidin-4-yl)-2,4-pyrimidinediamine;

II-109: 5-aminocarbonyl-N2-[3,4-dihydro-4-(2-methoxyethyl)-3-oxo-2H-1,4-benzoxazin-7-yl]phenyl-N4-(2,2,6,6-tetramethylpiperidin-4-yl)-2,4-pyrimidinediamine;

II-110: 5-aminocarbonyl-N2-[3,4-dihydro-4-(2-methoxyethyl)-3-oxo-2H-1,4-benzoxazin-7-yl]phenyl-N4-(1,2,2,6,6-pentamethylpiperidin-4-yl)-2,4-pyrimidinediamine;

II-111: 5-cyano-N2-[3,4-dihydro-2,2-dimethyl-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-112: 5-cyano-N2-[3,4-dihydro-2,2-dimethyl-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-113: N2-[spiro(1,3-benzodioxole-2,1'-cyclopentan)-5-yl]-5-fluoro-N4-(1,2,2,6,6-pentamethylpiperidin-4-yl)-2,4-pyrimidinediamine;

II-114: N2-[spiro(1,3-benzodioxole-2,1'-cyclohexan)-5-yl]-5-fluoro-N4-(1,2,2,6,6-pentamethylpiperidin-4-yl)-2,4-pyrimidinediamine;

II-115: N2-(6-chloro-1,3-benzodioxol-5-yl)-5-fluoro-N4-(1,2,2,6,6-pentamethylpiperidin-4-yl)-2,4-pyrimidinediamine;

II-116: N2-(7-chloro-2,3-dihydro-1,4-benzodioxin-6-yl)-5-fluoro-N4-(1,2,2,6,6-pentamethylpiperidin-4-yl)-2,4-pyrimidinediamine;

II-117: 5-cyano-N2-[3,4-dihydro-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine;

II-118: 5-cyano-N2-[3,4-dihydro-4-(2-methoxyethyl)-3-oxo-2H-1,4-benzoxazin-7-yl]phenyl-N4-(2,2,6,6-tetramethylpiperidin-4-yl)-2,4-pyrimidinediamine;

II-119: 5-cyano-N2-[3,4-dihydro-4-(2-methoxyethyl)-3-oxo-2H-1,4-benzoxazin-7-yl]phenyl-N4-(1,2,2,6,6-pentamethylpiperidin-4-yl)-2,4-pyrimidinediamine;

II-120: N2-[spiro(1,3-benzodioxole-2,1'-cyclopentan)-5-yl]-5-fluoro-N4-(2,2,6,6-tetramethylpiperidin-4-yl)-2,4-pyrimidinediamine;

II-121: N2-[spiro(1,3-benzodioxole-2,1'-cyclohexan)-5-yl]-5-fluoro-N4-(2,2,6,6-tetramethylpiperidin-4-yl)-2,4-pyrimidinediamine;

II-122: N2-(6-bromo-2,2-difluoro-benzo[1,3]dioxol-5-yl)-5-fluoro-N4-(1,2,2,6,6-pentamethylpiperidin-4-yl)-2,4-pyrimidinediamine;

II-123: 5-fluoro-N2-(2,2,3,3,7-pentafluoro-2,3-dihydro-1,4-benzodioxin-6-yl)-N4-(1,2,2,6,6-pentamethylpiperidin-4-yl)-2,4-pyrimidinediamine;

II-124: N2-[3,4-dihydro-2,2-dimethyl-4-(2-fluoroethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine;

II-125: 5-aminocarbonyl-N2-[3,4-dihydro-2,2-dimethyl-4-(2-fluoroethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-126: N2-[3,4-dihydro-2,2-dimethyl-4-(2,2,2-trifluoroethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine;

II-127: 5-bromo-N2-(2,3-dihydrobenzo[b][1,4]dioxin-6-yl)-N4-(1,2,2,6,6-pentamethylpiperidin-4-yl)pyrimidine-2,4-diamine;

II-128: 7-(5-bromo-4-(1,2,2,6,6-pentamethylpiperidin-4-ylamino)pyrimidin-2-ylamino)-4-ethyl-2,2-dimethyl-2H-benzo[b][1,4]oxazin-3(4H)-one;

II-129: N2-(2,3-dihydrobenzo[b][1,4]dioxin-6-yl)-5-methoxy-N4-(1,2,2,6,6-pentamethylpiperidin-4-yl)pyrimidine-2,4-diamine;

II-130: 4-ethyl-7-(5-methoxy-4-(1,2,2,6,6-pentamethylpiperidin-4-ylamino)pyrimidin-2-ylamino)-2,2-dimethyl-2H-benzo[b][1,4]oxazin-3(4H)-one;

II-131: 5-fluoro-N2-(6-fluorobenzo[d]thiazol-2-yl)-N4-(1,2,2,6,6-pentamethylpiperidin-4-yl)pyrimidine-2,4-diamine;

II-132: N2-(4-(2,3-dihydrobenzo[b][1,4]dioxin-6-yl)thiazol-2-yl)-5-fluoro-N4-(1,2,2,6,6-pentamethylpiperidin-4-yl)pyrimidine-2,4-diamine;

II-133: 5-fluoro-N4-(1,2,2,6,6-pentamethylpiperidin-4-yl)-N2-(4-(4-(pyrrolidin-1-yl)phenyl)thiazol-2-yl)pyrimidine-2,4-diamine;

II-134: 5-fluoro-N4-(1,2,2,6,6-pentamethylpiperidin-4-yl)-N2-(4-(trifluoromethyl)oxazol-2-yl)pyrimidine-2,4-diamine;

II-135: N2-(4-(4-(diethylamino)phenyl)thiazol-2-yl)-5-fluoro-N4-(1,2,2,6,6-pentamethylpiperidin-4-yl)pyrimidine-2,4-diamine;

II-136: 5-fluoro-N4-(1,2,2,6,6-pentamethylpiperidin-4-yl)-N2-(4-(pyridin-3-yl)thiazol-2-yl)pyrimidine-2,4-diamine;

II-137: 5-fluoro-N2-(4-(3-fluoro-4-methoxyphenyl)thiazol-2-yl)-N4-(1,2,2,6,6-pentamethylpiperidin-4-yl)pyrimidine-2,4-diamine;

II-138: N2-(4-(3,4-dimethoxyphenyl)thiazol-2-yl)-5-fluoro-N4-(1,2,2,6,6-pentamethylpiperidin-4-yl)pyrimidine-2,4-diamine;

II-139: 5-fluoro-N4-(1,2,2,6,6-pentamethylpiperidin-4-yl)-N2-(4-(4-phenoxyphenyl)thiazol-2-yl)pyrimidine-2,4-diamine;

II-140: 5-fluoro-N4-(1,2,2,6,6-pentamethylpiperidin-4-yl)-N2-(4-(4-(trifluoromethyl)phenyl)thiazol-2-yl)pyrimidine-2,4-diamine;

II-141: N2-(4-(2,4-difluorophenyl)thiazol-2-yl)-5-fluoro-N4-(1,2,2,6,6-pentamethylpiperidin-4-yl)pyrimidine-2,4-diamine;

II-142: 4-chloro-N-(4-(2-(5-fluoro-4-(1,2,2,6,6-pentamethylpiperidin-4-ylamino)pyrimidin-2-ylamino)thiazol-4-yl)phenyl)benzenesulfonamide;

II-143: 2-(5-fluoro-4-(1,2,2,6,6-pentamethylpiperidin-4-ylamino)pyrimidin-2-ylamino)benzo[d]thiazole-6-carboxylic acid;

II-144: 5-fluoro-N2-(6-(methylsulfonyl)benzo[d]thiazol-2-yl)-N4-(1,2,2,6,6-pentamethylpiperidin-4-yl)pyrimidine-2,4-diamine;

II-145: 4-ethyl-2,2-dimethyl-7-(5-methyl-4-(1,2,2,6,6-pentamethylpiperidin-4-ylamino)pyrimidin-2-ylamino)-2H-benzo[b][1,4]oxazin-3(4H)-one;

II-146: N2-(2,3-dihydrobenzo[b][1,4]dioxin-6-yl)-5-methyl-N4-(1,2,2,6,6-pentamethylpiperidin-4-yl)pyrimidine-2,4-diamine;

II-147: 6-(5-fluoro-4-(1,2,2,6,6-pentamethylpiperidin-4-ylamino)pyrimidin-2-ylamino)quinazoline-2,4(1H,3H)-dione;

II-148: 5-(5-fluoro-4-(1,2,2,6,6-pentamethylpiperidin-4-ylamino)pyrimidin-2-ylamino)isoindoline-1,3-dione;

II-149: 5-(5-fluoro-4-(1,2,2,6,6-pentamethylpiperidin-4-ylamino)pyrimidin-2-ylamino)-2-methylisoindoline-1,3-dione;

II-150: N2-(2,3-dihydrobenzo[b][1,4]dioxin-6-yl)-N4-(1,2,2,6,6-pentamethylpiperidin-4-yl)-5-((trimethylsilyl)ethynyl)pyrimidine-2,4-diamine;

II-151: 4-ethyl-2,2-dimethyl-7-(4-(1,2,2,6,6-pentamethylpiperidin-4-ylamino)-5-((trimethylsilyl)ethynyl)pyrimidin-2-ylamino)-2H-benzo[b][1,4]oxazin-3(4H)-one;

II-152: 4-ethyl-7-(5-ethynyl-4-(1,2,2,6,6-pentamethylpiperidin-4-ylamino)pyrimidin-2-ylamino)-2,2-dimethyl-2H-benzo[b][1,4]oxazin-3(4H)-one;

II-153: 5-(5-fluoro-4-(2,2,6,6-tetramethylpiperidin-4-ylamino)pyrimidin-2-ylamino)-2-methylisoindoline-1,3-dione;

II-154: 6-(5-fluoro-4-(2,2,6,6-tetramethylpiperidin-4-ylamino)pyrimidin-2-ylamino)quinazoline-2,4(1H,3H)-dione;

II-155: 6-(5-fluoro-4-(1,2,2,6,6-pentamethylpiperidin-4-ylamino)pyrimidin-2-ylamino)-2,3-dihydrobenzo[b][1,4]dioxine-2-carboxylic acid;

II-156: N2-(2,3-dihydrobenzo[b][1,4]dioxin-6-yl)-5-ethynyl-N4-(1,2,2,6,6-pentamethylpiperidin-4-yl)pyrimidine-2,4-diamine;

II-157: 6-(5-fluoro-4-(1,2,2,6,6-pentamethylpiperidin-4-ylamino)pyrimidin-2-ylamino)-2,3-dihydrobenzo[b][1,4]dioxine-2-carboxylic acid;

II-158: (6-(5-fluoro-4-(1,2,2,6,6-pentamethylpiperidin-4-ylamino)pyrimidin-2-ylamino)-2,3-dihydrobenzo[b][1,4]dioxin-2-yl)(4-methylpiperazin-1-yl)methanone;

II-159: 6-(5-fluoro-4-(2,2,6,6-tetramethylpiperidin-4-ylamino)pyrimidin-2-ylamino)-2,3-dihydrobenzo[b][1,4]dioxine-2-carboxamide;

II-160: (6-(5-fluoro-4-(2,2,6,6-tetramethylpiperidin-4-ylamino)pyrimidin-2-ylamino)-2,3-dihydrobenzo[b][1,4]dioxin-2-yl)(4-methylpiperazin-1-yl)methanone;

II-161: 5-Cyano-N2-[4-(2-fluoroethyl)-2H-1,4-benzoxazin-3-one-7-yl]-N4-(1,2,2,6,6-pentamethylpiperidin-4-yl)-2,4-pyrimidinediamine;

II-162: 5-Cyano-N2-(3-isopropyl-benzoxazol-2-one-6-yl)-N4-(2,2,6,6-tetramethylpiperidin-4-yl)-2,4-pyrimidinediamine;

II-163: N2-(3-Cyclopropylmethylene-benzoxazol-2-one-6-yl)-5-fluoro-N4-(1,2,2,6,6-pentamethylpiperidin-4-yl)-2,4-pyrimidinediamine;

II-164: 5-Cyano-N2-[2,2-dimethyl-4-(2-fluoroethyl)-1,4-benzoxazin-3-one-7-yl]-N4-(2,2,6,6-tetramethylpiperidin-4-yl)-2,4-pyrimidinediamine;

II-165: N2-(2,1-spiro-cyclobutane-4-isopropyl-1,4-benzoxazin-3-one-7-yl)-5-fluoro-N4-(1,2,2,6,6-pentamethylpiperidin-4-yl)-2,4-pyrimidinediamine;

II-166: N2-(2,1-spiro-cyclobutane-4-propyl-1,4-benzoxazin-3-one-7-yl)-5-fluoro-N4-(1,2,2,6,6-pentamethylpiperidin-4-yl)-2,4-pyrimidinediamine;

II-167: 5-Fluoro-N2-{3-[2-(morpholino)ethyl]-benzoxazol-2-one-6-yl}-N4-(1,2,2,6,6-pentamethylpiperidin-4-yl)-2,4-pyrimidinediamine;

II-168: 5-Fluoro-N2-{3-[2-(morpholino)ethyl]-benzoxazol-2-one-6-yl}-N4-(2,2,6,6-tetramethylpiperidin-4-yl)-2,4-pyrimidinediamine;

II-169: 5-Cyano-N2-{3-[2-(morpholino)ethyl]-benzoxazol-2-one-6-yl}-N4-(1,2,2,6,6-pentamethylpiperidin-4-yl)-2,4-pyrimidinediamine;

II-170: 5-Cyano-N2-{3-[2-(morpholino)ethyl]-benzoxazol-2-one-6-yl}-N4-(2,2,6,6-tetramethylpiperidin-4-yl)-2,4-pyrimidinediamine;

II-171: 5-Cyano-N2-[4-(2-fluoroethyl)-2H-1,4-benzoxazin-3-one-7-yl]-N4-(2,2,6,6-tetramethylpiperidin-4-yl)-2,4-pyrimidinediamine;

II-172: 5-Fluoro-N2-[3-(2-fluoroethyl)-benzoxazol-2-one-6-yl]-N4-(1,2,2,6,6-pentamethylpiperidin-4-yl)-2,4-pyrimidinediamine;

II-173: N2-(3-Ethyl-benzoxazol-2-one-5-yl)-5-Fluoro-N4-(1,2,2,6,6-pentamethylpiperidin-4-yl)-2,4-pyrimidinediamine;

II-174: N2-(3-Ethyl-benzoxazol-2-one-5-yl)-5-fluoro-N4-(2,2,6,6-tetramethylpiperidin-4-yl)-2,4-pyrimidinediamine;

II-175: 5-Fluoro-N2-[7-Nitro-1,2,4-triazolo(3,4-c)][1,4]-benzoxazin-N4-(1,2,2,6,6-pentamethylpiperidin-4-yl)-2,4-pyrimidinediamine;

II-176: 5-fluoro-N4-(1,2,2,6,6-pentamethylpiperidin-4-yl)-N2-(2,2,6-trifluoro-benzo[1,3]dioxol-5-yl)-2,4-pyrimidinediamine;

II-177: 5-cyano-N2-[3,4-dihydro-2,2-dimethyl-4-(2-fluoroethyl)-3-oxo-2H-pyrido[3,2-b]-1,4-oxazin-7-yl]phenyl-N4-(2,2,6,6-tetramethylpiperidin-4-yl)-2,4-pyrimidinediamine;

II-178: N2-[3,4-dihydro-2,2-dimethyl-4-(2-fluoroethyl)-3-oxo-2H-pyrido[3,2-b]-1,4-oxazin-7-yl]phenyl-5-fluoro-N4-(2,2,6,6-tetramethylpiperidin-4-yl)-2,4-pyrimidinediamine;

II-179: 5-Cyano-N2-(3-cyclopropylmethylene-benzoxazol-2-one-6-yl)-N4-(1,2,2,6,6-pentamethylpiperidin-4-yl)-2,4-pyrimidinediamine;

II-180: 5-Cyano-N2-(3-cyclopropylmethylene-benzoxazol-2-one-6-yl)-N4-(2,2,6,6-tetramethylpiperidin-4-yl)-2,4-pyrimidinediamine;

II-181: 5-Fluoro-N2-[4-(2-fluoroethyl)-2H-1,4-benzoxazin-3-one-7-yl]-N4-(2,2,6,6-tetramethylpiperidin-4-yl)-2,4-pyrimidinediamine;

III-1: N2-(3-Chloro-4-methoxy)phenyl-5-fluoro-N4-(1-methylpiperidin-4-yl)-2,4-pyrimidinediamine;

III-2: N2-(3-Cyano)phenyl-5-fluoro-N4-(1-methylpiperidin-4-yl)-2,4-pyrimidinediamine;

III-3: 5-Fluoro-N2-[4-(4-methylpiperazino)-3-trifluoromethyl]phenyl-N4-(1-methylpiperidin-4-yl)-2,4-pyrimidinediamine;

III-4: N2-[3-Chloro-4-(4-methylpiperazino)]phenyl-5-fluoro-N4-(1-methylpiperidin-4-yl)-2,4-pyrimidinediamine;

III-5: N2-(3-Chloro-4-methoxy)phenyl-5-fluoro-N4-[1-(2-hydroxyethyl)piperidin-4-yl]-2,4-pyrimidinediamine;

III-6: N2-(3-Cyano)phenyl-5-fluoro-N4-[1-(2-hydroxyethyl)piperidin-4-yl]-2,4-pyrimidinediamine;

III-7: 5-Fluoro-N4-[1-(2-hydroxyethyl)piperidin-4-yl]-N2-[4-(4-methylpiperazino)-3-trifluoromethyl]phenyl-2,4-pyrimidinediamine;

III-8: N2-[3-Chloro-4-(4-methylpiperazino)]phenyl-5-fluoro-N4-[1-(2-hydroxyethyl)piperidin-4-yl]-2,4-pyrimidinediamine;

III-9: N2-(3,5-dimethoxy)phenyl-5-fluoro-N4-[1-(pyridin-4-yl)methylpiperidin-4-yl]-2,4-pyrimidinediamine;

III-10: 5-fluoro-N2-[3-methoxy-5-(5-methyl-1H-tetrazol-1-yl)]phenyl-N4-[1-(pyridin-4-yl)methylpiperidin-4-yl]-2,4-pyrimidinediamine;

IV-1: 5-Fluoro-N2-[3-methoxy-5-(5-methyl-tetrazol-1-yl)]phenyl-N4-(1,2,6,-trimethylpiperidin-4-yl)-2,4-pyrimidinediamine, trans isomer;

IV-2: N2-(3,5-Dimethoxy)phenyl-6-methyl-N4-(1,2,2,6,6-pentamethylpiperidin-4-yl)-2,4-pyrimidinediamine; and IV-3: N2-[3-Chloro-4-(4-methylsulfonylpiperazino)]phenyl-6-methyl-N4-(1,2,2,6,6-pentamethylpiperidin-4-yl)-2,4-pyrimidinediamine;

IV-4: N2-[3-Chloro-4-(4-methylsulfonylpiperazino)]phenyl-N4-(4-diethylamino)cyclohexyl-5-fluoro-2,4-pyrimidinediamine;

IV-5: N2-(3-Chloro-4-methoxy)phenyl-N4-(4-diethylamino)cyclohexyl-5-fluoro-2,4-pyrimidinediamine;

IV-6: N2-(3-Cyano)phenyl-N4-(4-diethylamino)cyclohexyl-5-fluoro-2,4-pyrimidinediamine;

IV-7: N4-(4-Diethylamino)cyclohexyl-5-fluoro-N2-[4-(4-methylpiperazino)-3-trifluoromethyl]phenyl-2,4-pyrimidinediamine;

IV-8: N2-[3-Chloro-4-(4-methylpiperazino)]phenyl-N4-(4-diethylamino)cyclohexyl-5-fluoro-2,4-pyrimidinediamine;

IV-9: N4-(4-Diethylamino)cyclohexyl-5-fluoro-N2-[4-(4-methylsulfonylpiperazino)-3-trifluoromethyl]phenyl-2,4-pyrimidinediamine;

or a solvate, N-oxide, prodrug, or a pharmaceutically acceptable salt thereof.

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. Indeed, many of the 2,4-pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-pyrimidinediamine compounds that include ester moieties can be considered prodrugs of their corresponding carboxylic acid, regardless of whether the ester form is pharmacologically active.

The mechanism by which the progroup(s) metabolizes is not critical, and can be caused by, for example, hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-substituted pyrimidinediamine, can employ progroups including such esters. Alternatively, the progroups can be designed to metabolize in the presence of enzymes such as esterases, amidases, lipolases, phosphatases including ATPases and kinase etc. Progroups including linkages capable of metabolizing in vivo are well known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

In the prodrugs, any available functional moiety can be masked with a progroup to yield a prodrug. Functional groups within the 2,4-pyrimidinediamine compounds that can be masked with progroups for inclusion in a promoiety include, but are not limited to, amines (primary and secondary), hydroxyls, sulfanyls (thiols), carboxyls, etc. A wide variety of progroups, as well as the resultant promoieties, suitable for masking functional groups in active 2,4-pyrimidinediamine compounds to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Other specific examples of suitable progroups and their respective promoieties will be apparent to those of skill in the art. All of these progroups, alone or in combinations, can be included in the prodrugs.

In some embodiments of the 2,4-pyrimidinediamine compounds and methods of using the compounds, the progroup(s) can be attached to any available primary or secondary amine, including, for example, the N2 nitrogen atom of the 2,4 pyrimidinediamine moiety, the N4 nitrogen atom of the 2,4 pyrimidinediamine moiety, and/or a primary or secondary nitrogen atom included in a substituent on the 2,4 pyrimidinediamine compound.

In particular embodiments of the 2,4-pyrimidinediamine compounds and methods of using the compounds, the prodrugs described herein are 2,4-pyrimidinediamine compounds that are substituted at the N4 nitrogen of the 2,4 pyrimidinediamine moiety with a substituted or unsubstituted nitrogen containing bicyclic ring that includes at least one progroup at one or more of: the nitrogen atom(s) of the bicyclic ring, the N2 nitrogen of the 2,4 pyrimidinediamine moiety and/or the N4 nitrogen of the 2,4 pyrimidinediamine moiety.

As noted above, the identity of the progroup is not critical, provided that it can be metabolized under the desired conditions of use, for example under the acidic conditions found in the stomach and/or by enzymes found in vivo, to yield a the biologically active group, e.g., the 2,4-substituted pyrimidinediamines as described herein. Thus, skilled artisans will appreciate that the progroup can comprise virtually any known or later discovered hydroxyl, amine or thiol protecting group. Non limiting examples of suitable protecting groups can be found, for example, in *Protective Groups in Organic Synthesis*, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport mediated intestinal absorption, protection against fast metabolism (slow release prodrugs), tissue selective delivery, passive enrichment in target tissues, targeting specific transporters, etc. Groups capable of imparting prodrugs with these characteristics are well known, and are described, for example, in Ettmayer et al., 2004, *J. Med. Chem.* 47(10):2393-2404, the disclosure of which is incorporated by reference. All of the various groups described in these references can be utilized in the prodrugs described herein.

As noted above, progroup(s) may also be selected to increase the water solubility of the prodrug as compared to the active drug. Thus the progroup(s) may include or can be a group(s) suitable for imparting drug molecules with improved water solubility. Such groups are well known, and include, by way of example and not limitation, hydrophilic groups such as alkyl, aryl, arylalkyl, or heterocyclyl groups substituted with one or more of an amine, alcohol, a carboxylic acid, a phosphorous acid, a sulfoxide, a sugar, an amino acid, a thiol, a polyol, an ether, a thioether, and a quaternary ammonium salt.

The suitability of any particular progroup for a desired mode of administration can be confirmed in biochemical assays. For example, if a prodrug is to be administered by injection into a particular tissue or organ, and the identities of the various enzyme(s) expressed in the tissue or organ are known, the particular prodrug can be tested for metabolism in biochemical assays with the isolated enzyme(s). Alternatively, the particular prodrug can be tested for metabolism to the active 2,4-pyrimidinediamine compound with tissue and/or organ extracts. Using tissue and/or organ extracts can be of particular convenience when the identity(ies) of the enzymes expressed in the target tissues or organs are unknown, or in instances when the isolated enzymes are not conveniently available. Skilled artisans will be able to readily select progroups having metabolic properties (such as kinetics) suitable for particular applications using such in vitro tests. Of course, specific prodrugs could also be tested for suitable metabolism in vitro animal models.

Numerous references teach the use and synthesis of prodrugs, including, for example, Ettmayer et al., ibid and Bungaard et al., (1989) *J. Med. Chem.* 32(12): 2503-2507. Additionally, the preparation and use of prodrugs of 2,4-pyrimidinediamines is specifically taught in U.S. Provisional Patent Application 60/654,620, filed Feb. 18, 2005, entitled "Pyrimidinediamine Prodrugs and their Uses," U.S. patent application Ser. No. 11/337,049, filed 19 Jan. 2006, published as US 2006-0211657A1, U.S. patent application Ser. No. 11/453,731, filed 14 Jun. 2006, published as US 2006-0234983A1, and U.S. patent application Ser. No. 11/567,717, filed 6 Dec. 2006, published as US 2007-0129360 A1, the disclosures of which is hereby incorporated by reference in its entirety.

One of ordinary skill in the art will appreciate that many of the compounds and prodrugs thereof, as well as the various compound species specifically described and/or illustrated herein, may exhibit the phenomena of tautomerism, conformational isomerism, geometric isomerism and/or optical isomerism. For example, the compounds and prodrugs of the invention may include one or more chiral centers and/or double bonds and as a consequence may exist as stereoisomers, such as double-bond isomers (i.e., geometric isomers), enantiomers and diastereomers and mixtures thereof, such as racemic mixtures. As another example, the compounds and prodrugs of the invention may exist in several tautomeric forms, including the enol form, the keto form and mixtures thereof. As the various compound names, formulae and compound drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds or prodrugs having one or more of the utilities described herein, as well as mixtures of these various different isomeric forms. In cases of limited rotation around the 2,4-pyrimidinediamine core structure, atropisomers are also possible and are also specifically included in the compounds of the invention. It is intended that the compounds encompassed herein are, with the exception of forms of isomerism, chemically stable and able to be isolated.

Depending upon the nature of the various substituents, the 2,4-pyrimidinediamine compounds and prodrugs of the invention can be in the form of salts. Such salts include salts suitable for pharmaceutical uses ("pharmaceutically-acceptable salts"), salts suitable for veterinary uses, etc. Such salts can be derived from acids or bases, as is well-known in the art.

In one embodiment, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethanedisulfonic acid, 2-hydroxyethanesulfonic acid, etc.), arylsulfonic acids (e.g., benzenesulfonic acid, 4 chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, triethylamine, ammonia, etc.).

The 2,4-pyrimidinediamine compounds and prodrugs thereof, as well as the salts thereof, may also be in the form of hydrates, solvates and N-oxides, as are well-known in the art.

In another embodiment, this invention provides a compound, or stereoisomer, tautomer, N-oxide, prodrug, solvate, or pharmaceutically acceptable salt thereof, selected from Tables I-IV.

TABLE I

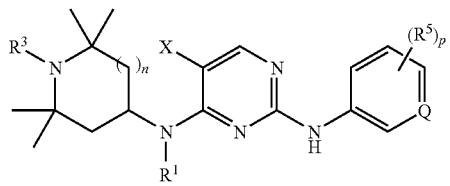

| # | $(R^5)_p$ | n | $R^1$ | $R^3$ | X | Q |
|---|---|---|---|---|---|---|
| I-1 | 4-(4-methylpiperazin-1-yl)- | 1 | H | Me | F | CH |
| I-2 | 3-(4-methylpiperazin-1-yl)- | 1 | H | Me | F | CH |
| I-3 | 3-Cl-4-(4-methylpiperazin-1-yl)- | 1 | H | Me | F | CH |
| I-4 | 3-Me-4-(4-methylpiperazin-1-yl)- | 1 | H | Me | F | CH |
| I-5 | 3-$CF_3$-4-(4-methylpiperazin-1-yl)- | 1 | H | Me | F | CH |
| I-6 | 4-(4-ethylpiperazin-1-yl)- | 1 | H | Me | F | N |
| I-7 | 3-Me-4-(4-methylpiperazin-1-yl)- | 1 | H | Me | F | N |
| I-8 | 2-Me-4-(4-methylpiperazin-1-yl)- | 1 | H | Me | F | N |
| I-9 | 4-$SO_2NH_2$ | 1 | H | Me | F | CH |
| I-10 | 3-$SO_2NH_2$ | 1 | H | Me | F | CH |
| I-11 | 3-$SO_2NH_2$-4-Me | 1 | H | Me | F | CH |
| I-12 | 3,5-di-Me | 1 | H | Me | F | CH |
| I-13 | 4-$SO_2NH_2$ | 1 | H | Me | Me | CH |
| I-14 | 3-$SO_2NH_2$ | 1 | H | Me | Me | CH |
| I-15 | 3-$SO_2NH_2$-4-Me | 1 | H | Me | Me | CH |
| I-16 | 3,4,5-tri-OMe | 1 | H | Me | Me | CH |
| I-17 | 3,5-di-Me | 1 | H | Me | Me | CH |
| I-18 | 3-Me-4-(4-ethylpiperazin-1-yl)- | 1 | H | Me | Me | CH |
| I-19 | 3,4,5-tri-OMe | 1 | H | Me | F | CH |
| I-20 | 3-Cl-4-OMe | 1 | H | Me | F | CH |
| I-21 | 3,4-di-F | 1 | H | Me | F | CH |
| I-22 | 3-Cl-4-CN | 1 | H | Me | F | CH |
| I-23 | 4-$CONH_2$ | 1 | H | Me | F | CH |

TABLE I-continued

| # | (R⁵)ₚ | n | R¹ | R³ | X | Q |
|---|---|---|---|---|---|---|
| I-24 | 3-CONH₂ | 1 | H | Me | F | CH |
| I-25 | 4-CN | 1 | H | Me | F | CH |
| I-26 | 3-CN | 1 | H | Me | F | CH |
| I-27 | 3-Cl-4-OMe | 1 | H | Me | Me | CH |
| I-28 | 3-Cl-4-CN | 1 | H | Me | Me | CH |
| I-29 | 3-Cl-4-(4-methylpiperazin-1-yl)- | 1 | H | Me | Me | CH |
| I-30 | 3-CF₃-4-(4-methylpiperazin-1-yl)- | 1 | H | Me | Me | CH |
| I-31 | 3-Cl-4-OMe | 1 | H | Me | Cl | CH |
| I-32 | 3-Cl-4-OMe | 1 | H | Me | CF₃ | CH |
| I-33 | 3-Cl-4-CN | 1 | H | Me | CF₃ | CH |
| I-34 | 3-Cl-4-(4-methylpiperazin-1-yl)- | 1 | H | Me | CF₃ | CH |
| I-35 | 3-Cl-4-CN | 1 | H | Me | Cl | CH |
| I-36 | 3-Cl-4-(4-methylpiperazin-1-yl)- | 1 | H | Me | Cl | CH |
| I-37 | 3-CF₃-4-(4-methylpiperazin-1-yl)- | 1 | H | Me | Cl | CH |
| I-38 | 3-CF₃-4-(4-methylpiperazin-1-yl)- | 1 | H | Me | CF₃ | CH |
| I-39 | 3-F-4-(4-methylpiperazin-1-yl)- | 1 | H | Me | F | CH |
| I-40 | 3,5-di-F-4-(4-methylpiperazin-1-yl)- | 1 | H | Me | F | CH |
| I-41 | 4-Cl-3-(4-ethylpiperazin-1-yl)- | 1 | H | Me | F | CH |
| I-42 | 4-Cl-3-(4-acetylpiperazin-1-yl)- | 1 | H | Me | F | CH |
| I-43 | 4-Cl-3-(4-methoxycarbonyl-piperazin-1-yl)- | 1 | H | Me | F | CH |
| I-44 | 3-Cl-4-(4-methylpiperazin-1-carbonyl)- | 1 | H | Me | F | CH |
| I-45 | 3-Cl-4-(4-methylpiperazin-1-sulfonyl)- | 1 | H | Me | F | CH |
| I-46 | 3-Cl-4-(piperazin-1-sulfonyl)- | 1 | H | Me | F | CH |
| I-47 | 3-CF₃-4-(4-methoxycarbonyl-piperazin-1-yl)- | 1 | H | Me | F | CH |
| I-48 | 3-CF₃-4-(4-methylsulfonyl-piperazin-1-yl)- | 1 | H | Me | F | CH |
| I-49 | 3-CF₃-4-(4-acetylpiperazin-1-yl)- | 1 | H | Me | F | CH |
| I-50 | 3-Cl-4-(4,4-di-F-piperidin-1-yl)- | 1 | H | Me | F | CH |
| I-51 | 3-F-4-(4,4-di-F-piperidin-1-yl)- | 1 | H | Me | F | CH |
| I-52 | 3-CF₃-4-(4-methylpiperazin-1-methyl)- | 1 | H | Me | F | CH |
| I-53 | 3-CONH₂-4-(4-methylpiperazin-1-yl)- | 1 | H | Me | F | CH |
| I-54 | 3-CONHMe-4-(4-methylpiperazin-1-yl)- | 1 | H | Me | F | CH |
| I-55 | 3-OMe-4-(4-methylpiperazin-1-yl)- | 1 | H | Me | F | CH |
| I-56 | 4-Cl-3-(4-propylpiperazin-1-yl)- | 1 | H | Me | F | CH |
| I-57 | 3-Cl-4-(4-methylpiperazin-1-methyl)- | 1 | H | Me | F | CH |
| I-58 | 3-Cl-4-OMe | 1 | Me | Me | F | CH |
| I-59 | 3-CF₃-4-(4-methylpiperazin-1-yl)- | 1 | Me | Me | F | CH |
| I-60 | 3-Cl-4-(4-methylpiperazin-1-yl)- | 1 | Me | Me | F | CH |
| I-61 | 3-Cl-4-(4-methylsulfonyl-piperazin-1-yl)- | 1 | H | Me | F | CH |
| I-62 | 3-Cl-4-(4-methoxycarbonyl-piperazin-1-yl)- | 1 | H | Me | F | CH |
| I-63 | 3-hydroxymethyl-4-(4-methylpiperazin-1-yl- | 1 | H | Me | F | CH |
| I-64 | 3-CF₃-4-(4-methylpiperazin-1-carbonyl)- | 1 | H | Me | F | CH |
| I-65 | 4-Cl-3-(4-methylpiperazin-1-yl)- | 1 | H | Me | F | CH |
| I-66 | 3-CN | 1 | Me | Me | F | CH |
| I-67 | 3-Cl-4-(4-acetylpiperazin-1-yl)- | 1 | H | Me | F | CH |
| I-68 | 4-Cl-3-(4-methylsulfonyl-piperazin-1-yl)- | 1 | H | Me | F | CH |
| I-69 | 3-(2-methylpyrimidin-4-yl)- | 1 | H | Me | F | CH |
| I-70 | 3-CN | 1 | H | H | F | CH |
| I-71 | 3-Cl-4-OMe | 1 | H | Me | NO₂ | CH |
| I-72 | 3-CN | 1 | H | Me | NO₂ | CH |
| I-73 | 3-Cl-4-(4-methylsulfonylpiperazin-1-yl)- | 1 | H | Me | NO₂ | CH |
| I-74 | 3-CF₃-4-(4-methylpiperazin-1-yl)- | 1 | H | Me | NO₂ | CH |
| I-75 | 3-CF₃-4-(4-piperazin-1-yl)- | 1 | H | Me | NO₂ | CH |
| I-76 | 3-Cl-4-(4-methylpiperazin-1-yl)- | 1 | H | Me | NO₂ | CH |
| I-77 | 3-chloro-4-(piperazin-1-yl)- | 1 | H | Me | NO₂ | CH |
| I-78 | 3-CF₃-4-(4-methylsulfonylpiperazin-1-yl)- | 1 | H | Me | NO₂ | CH |
| I-79 | 4-(pyridin-4-yl)- | 1 | H | Me | F | CH |
| I-80 | 3-Cl-4-OMe | 1 | H | Me | COOEt | CH |
| I-81 | 3-CN | 1 | H | Me | COOEt | CH |
| I-82 | 3-CF₃-4-(4-methylpiperazin-1-yl)- | 1 | H | Me | COOEt | CH |
| I-83 | 3-CF₃-4-(4-methylsulfonylpiperazin-1-yl)- | 1 | H | Me | COOEt | CH |
| I-84 | 3-Cl-4-(4-methylsulfonylpiperazin-1-yl)- | 1 | H | Me | COOEt | CH |
| I-85 | 3-Cl-4-OMe | 1 | H | Me | CONH₂ | CH |
| I-86 | 3-CN | 1 | H | Me | CONH₂ | CH |
| I-87 | 3-Cl-4-(4-methylsulfonylpiperazin-1-yl)- | 1 | H | Me | CF₃ | CH |
| I-88 | 3-CF₃-4-(4-methylpiperazin-1-yl)- | 1 | H | Me | CF₃ | CH |
| I-89 | 3-Cl-4-(4-methylpiperazin-1-yl)- | 1 | H | Me | COOEt | CH |
| I-90 | 3-CF₃-4-(4-methylsulfonylpiperazin-1-yl)- | 1 | H | Me | CONH₂ | CH |
| I-91 | 3-Cl-4-(4-methylsulfonylpiperazin-1-yl)- | 1 | H | Me | CONH₂ | CH |

TABLE I-continued

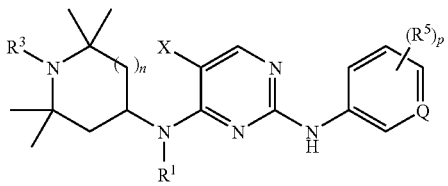

| # | (R⁵)ₚ | n | R¹ | R³ | X | Q |
|---|---|---|---|---|---|---|
| I-92 | 3-Cl-4-(4-methylsulfonylpiperazin-1-yl)- | 1 | H | Me | CF₃ | CH |
| I-93 | 3-Cl-4-OMe | 1 | H | Me | CN | CH |
| I-94 | 3-CF₃-4-(4-methylpiperazin-1-yl)- | 1 | H | Me | CN | CH |
| I-95 | 3-CF₃-4-(4-methylsulfonylpiperazin-1-yl)- | 1 | H | Me | CN | CH |
| I-96 | 3-CF₃-4-(pyridin-4-yl)- | 1 | H | Me | F | CH |
| I-97 | 3-CN | 1 | H | Me | CN | CH |
| I-98 | 3-Cl-4-(4-methylpiperazin-1-yl)- | 1 | H | Me | CONH₂ | CH |
| I-99 | 3-Cl-4-(pyridin-4-yl)- | 1 | H | Me | F | CH |
| I-100 | 3-(oxazol-5-yl)- | 1 | H | Me | F | CH |
| I-101 | 3-Cl-4-(4-methylpiperazin-1-yl)- | 1 | H | Me | CN | CH |
| I-102 | 3-Cl-4-(4-methylsulfonylpiperazin-1-yl)- | 1 | H | Me | CN | CH |
| I-103 | 3,5-di-Cl | 1 | H | Me | F | CH |
| I-104 | 3-Br | 1 | H | Me | F | CH |
| I-105 | 3-(furan-3-yl)- | 1 | H | Me | F | CH |
| I-106 | 3-(benzo[b]thiophen-2-yl)- | 1 | H | Me | F | CH |
| I-107 | 3-(pyridin-3-yl)- | 1 | H | Me | F | CH |
| I-108 | 4-Br | 1 | H | Me | F | CH |
| I-109 | 4-Br-3-CF₃ | 1 | H | Me | F | CH |
| I-110 | 4-Br-3-F | 1 | H | Me | F | CH |
| I-111 | 4-Br-3-Me | 1 | H | Me | F | CH |
| I-112 | 3-CF₃-4-(pyridin-3-yl)- | 1 | H | Me | F | CH |
| I-113 | 3-CF₃-4-(furan-3-yl)- | 1 | H | Me | F | CH |
| I-114 | 3-CF₃-4-((benzo[b]thiophen-2-yl)-)- | 1 | H | Me | F | CH |
| I-115 | 3-F-4-(pyridin-4-yl)- | 1 | H | Me | F | CH |
| I-116 | 3-CF₃-4-(4-methylthiophen-2-yl)- | 1 | H | Me | F | CH |
| I-117 | 4-Br-3,5-di-CF₃ | 1 | H | Me | F | CH |
| I-118 | 3-F-4-(pyridin-3-yl)- | 1 | H | Me | F | CH |
| I-119 | 3-F-4-(furan-3-yl)- | 1 | H | Me | F | CH |
| I-120 | 3-Me-4-(pyridin-4-yl)- | 1 | H | Me | F | CH |
| I-121 | 3-Me-4-(pyridin-3-yl)- | 1 | H | Me | F | CH |
| I-122 | 3-Me-4-(furan-3-yl)- | 1 | H | Me | F | CH |
| I-123 | 4-(pyridin-4-yl)- | 1 | H | Me | F | CH |
| I-124 | 4-(pyridin-3-yl)- | 1 | H | Me | F | CH |
| I-125 | 4-(furan-3-yl)- | 1 | H | Me | F | CH |
| I-126 | 3-CF₃-4-(1-methylpyrazol-4-yl)- | 1 | H | Me | F | CH |
| I-127 | 3-F-4-OMe | 1 | H | Me | F | CH |
| I-128 | 4-Cl-3-CN-5-Et | 1 | H | Me | F | CH |
| I-129 | 3,5-di-OMe | 1 | H | Me | F | CH |
| I-130 | 3,4-di-OMe | 1 | H | Me | F | CH |
| I-131 | 3,5-di-Me-4-OMe | 1 | H | Me | F | CH |
| I-132 | 3-CN-4-(4-methylpiperazin-1-yl)- | 1 | H | Me | F | CH |
| I-133 | 4-NHC(O)Ph | 1 | H | Me | F | CH |
| I-134 | 4-OCH₂C(O)NH₂ | 1 | H | Me | F | CH |
| I-135 | 4-OCH₂C(O)OCHMe₂ | 1 | H | Me | F | CH |
| I-136 | 4-OCH₂C(O)NHMe | 1 | H | Me | F | CH |
| I-137 | 4-NHC(O)OCHMe₂ | 1 | H | Me | F | CH |
| I-138 | 3-NHC(O)NHEt | 1 | H | Me | F | CH |
| I-139 | 3-NHC(O)OCHMe₂ | 1 | H | Me | F | CH |
| I-140 | 3-CN-4-F | 1 | H | Me | F | CH |
| I-141 | 3,4-di-CN | 1 | H | Me | F | CH |
| I-142 | 3-CN-4-Me | 1 | H | Me | F | CH |
| I-143 | 3-(1-methylpyrazol-4-yl)- | 1 | H | Me | F | CH |
| I-144 | 4-(1-methylpyrazol-4-yl)- | 1 | H | Me | F | CH |
| I-145 | 3-CF₃-5-OMe | 1 | H | Me | F | CH |
| I-146 | 3,5-di-CF₃ | 1 | H | Me | F | CH |
| I-147 | 3-CF₃-4-OMe | 1 | H | Me | F | CH |
| I-148 | 3-CN-4-(pyrrol-1-yl)- | 1 | H | Me | F | CH |
| I-149 | 4-NHC(O)NHEt | 1 | H | Me | F | CH |
| I-150 | 3-F-4-(1-methylpyrazol-4-yl)- | 1 | H | Me | F | CH |
| I-151 | 3-Me-4-(1-methylpyrazol-4-yl)- | 1 | H | Me | F | CH |
| I-152 | 3-CF₃-4-CN | 1 | H | Me | F | CH |
| I-153 | 4-Br-3-Cl | 1 | H | Me | F | CH |
| I-154 | 3-Cl-4-(pyridin-3-yl)- | 1 | H | Me | F | CH |
| I-155 | 3-Cl-4-(furan-3-yl)- | 1 | H | Me | F | CH |
| I-156 | 3-Cl-4-((benzo[b]thiophen-2-yl)-)- | 1 | H | Me | F | CH |
| I-157 | 3-Cl-4-(1-methylpyrazol-4-yl)- | 1 | H | Me | F | CH |
| I-158 | 3-Br-4-F | 1 | H | Me | F | CH |
| I-159 | 3-Br-4-OMe | 1 | H | Me | F | CH |

TABLE I-continued

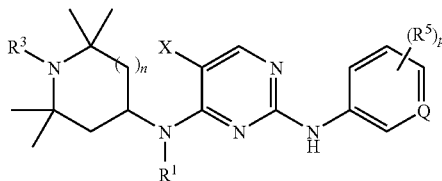

| # | (R⁵)ₚ | n | R¹ | R³ | X | Q |
|---|---|---|---|---|---|---|
| I-160 | 3-Br-4-Me | 1 | H | Me | F | CH |
| I-161 | 3-CF₃-4-NHC(O)Me | 1 | H | Me | F | CH |
| I-162 | 3-Br-S-CF₃ | 1 | H | Me | F | CH |
| I-163 | 4-Cl-3-CN | 1 | H | Me | F | CH |
| I-164 | 3-CN-4-(4-methylsulfonylpiperazin-1-yl)- | 1 | H | Me | F | CH |
| I-165 | 4-Cl-3-CN | 1 | H | Me | Cl | CH |
| I-166 | 3-CN-4-F | 1 | H | Me | Cl | CH |
| I-167 | 3-CN-4-(pyrrol-1-yl)- | 1 | H | Me | Cl | CH |
| I-168 | 3-CN-4-Me | 1 | H | Me | Cl | CH |
| I-169 | 3-CN-4-OI | 1 | H | Me | CF₃ | CH |
| I-170 | 3-CN-4-F | 1 | H | Me | CF₃ | CH |
| I-171 | 3-CN-4-Me | 1 | H | Me | CF₃ | CH |
| I-172 | 3-CN-4-(pyrrol-1-yl)- | 1 | H | Me | CF₃ | CH |
| I-173 | 3-CF₃-4-(4-cyclopropylsulfonylpiperazin-1-yl)- | 1 | H | Me | F | CH |
| I-174 | 3-Cl-4-(4-cyclopropylsulfonylpiperazin-1-yl)- | 1 | H | Me | F | CH |
| I-175 | 3-CN-4-(4-methylsulfonylpiperazin-1-yl)- | 1 | H | Me | Cl | CH |
| I-176 | 3-CN-4-(4-methylsulfonylpiperazin-1-yl)- | 1 | H | Me | CF₃ | CH |
| I-177 | 3-Br-4-OCF₃ | 1 | H | Me | F | CH |
| I-178 | 3-CN-4-(4-methylpiperazin-1-yl)- | 1 | H | Me | CF₃ | CH |
| I-179 | 3-CN-4-(4-methylpiperazin-1-yl)- | 1 | H | Me | Cl | CH |
| I-180 | 4-F-3-(pyridin-3-yl)- | 1 | H | Me | F | CH |
| I-181 | 3-(benzo[b]thiophen-2-yl)-4-F | 1 | H | Me | F | CH |
| I-182 | 4-F-3-(1-methylpyrazol-4-yl)- | 1 | H | Me | F | CH |
| I-183 | 3-(furan-3-yl)-4-OMe | 1 | H | Me | F | CH |
| I-184 | 4-OMe-3-(1-methylpyrazol-4-yl)- | 1 | H | Me | F | CH |
| I-185 | 3-CN-4-(pyridin-4-yl)- | 1 | H | Me | F | CH |
| I-186 | 3-CN-4-(pyridin-3-yl)- | 1 | H | Me | F | CH |
| I-187 | 4-Me-3-(pyridin-4-yl)- | 1 | H | Me | F | CH |
| I-188 | 3-(furan-3-yl)-4-Me | 1 | H | Me | F | CH |
| I-189 | 3-(benzo[b]thiophen-2-yl)-4-Me | 1 | H | Me | F | CH |
| I-190 | 4-Me-3-(1-methylpyrazol-4-yl)- | 1 | H | Me | F | CH |
| I-191 | 4-F-3-(pyridin-4-yl)- | 1 | H | Me | F | CH |
| I-192 | 4-F-3-(furan-3-yl)- | 1 | H | Me | F | CH |
| I-193 | 4-OMe-3-(pyridin-4-yl)- | 1 | H | Me | F | CH |
| I-194 | 4-OMe-3-(pyridin-3-yl)- | 1 | H | Me | F | CH |
| I-195 | 3-(benzo[b]thiophen-2-yl)-4-OMe | 1 | H | Me | F | CH |
| I-196 | 3-CN-4-(4-methylsulfonylpiperazin-1-yl)- | 1 | H | Me | CN | CH |
| I-197 | 3-Me-4-(4-pyridin-3-yl)- | 1 | H | Me | CN | CH |
| I-198 | 3-CN-4-(4-morpholin-1-yl)- | 1 | H | Me | F | CH |
| I-199 | 3-CN-4-(4-thiomorpholin-1-yl)- | 1 | H | Me | F | CH |
| I-200 | 3-CN-4-(4-pyrrolidin-1-yl)- | 1 | H | Me | F | CH |
| I-201 | 3-(pyridin-4-yl)-5-CF₃— | 1 | H | Me | F | CH |
| I-202 | 3-(pyridin-3-yl)-5-CF₃— | 1 | H | Me | F | CH |
| I-203 | 3-(furan-3-yl)-5-CF₃— | 1 | H | Me | F | CH |
| I-204 | 3-(1-methylpyrazol-4-yl)-5-CF₃— | 1 | H | Me | F | CH |
| I-205 | 3-(benzo[b]thiophen-2-yl)-5-CF₃— | 1 | H | Me | F | CH |
| I-206 | 3-CN-4-(4-pyrrol-1-yl)- | 1 | H | Me | F | CH |
| I-207 | 3-(pyridin-4-yl)-4-OCF₃— | 1 | H | Me | F | CH |
| I-208 | 3-(pyridin-3-yl)-4-OCF₃— | 1 | H | Me | F | CH |
| I-209 | 3-(furan-3-yl)-4-OCF₃— | 1 | H | Me | F | CH |
| I-210 | 3-(1-methylpyrazol-4-yl)-4-OCF₃— | 1 | H | Me | F | CH |
| I-211 | 3-(benzo[b]thiophen-2-yl)-4-OCF₃— | 1 | H | Me | F | CH |
| I-212 | 4-CF₃-3-(4-acetylpiperazin-1-yl)- | 1 | H | Me | F | CH |
| I-213 | 3-Cl-4-OMe | 1 | H | C(O)Me | F | CH |
| I-214 | 4-CF₃-3-(4-methoxycarbonylpiperazin-1-yl)- | 1 | H | Me | F | CH |
| I-215 | 3-CF₃-4-(4-methylsulfonylpiperazin-1-yl)- | 1 | H | C(O)Me | F | CH |
| I-216 | 4-CF₃-3-(4-methylsulfonylpiperazin-1-yl)- | 1 | H | Me | F | CH |
| I-217 | 3-CN | 1 | H | C(O)Me | F | CH |
| I-218 | 4-CF₃-3-(4-n-propylpiperazin-1-yl)- | 1 | H | Me | F | CH |
| I-219 | 3-CF₃-4-(4-methylpiperazin-1-yl)- | 1 | H | C(O)Me | F | CH |
| I-220 | 4-Cl-3-(4-n-propyl-3,5-dimethylpiperazin-1-yl)- | 1 | H | Me | F | CH |
| I-221 | 4-(1-methylpiperidin-4-yl)- | 1 | H | Me | F | CH |
| I-222 | 3-Me-4-(3,5-dimethylmorpholin-1-yl)- | 1 | H | Me | F | CH |
| I-223 | 3-OCF₃ | 1 | H | Me | F | CH |
| I-224 | 3-CF₃-4-(morpholin-1-yl)- | 1 | H | Me | F | CH |
| I-225 | 3-CF₃-4-(3,5-dimethylmorpholin-1-yl)- | 1 | H | Me | F | CH |
| I-226 | 3-Cl-4-OMe | 1 | H | Me | H | CH |
| I-227 | 3-CN | 1 | H | Me | H | CH |

TABLE I-continued

| # | (R$^5$)$_p$ | n | R$^1$ | R$^3$ | X | Q |
|---|---|---|---|---|---|---|
| I-228 | 3-CF$_3$-4-(4-methylsulfonylpiperazin-1-yl)- | 1 | H | Me | H | CH |
| I-229 | 3-CF$_3$-4-(4-methylpiperazin-1-yl)- | 1 | H | Me | H | CH |
| I-230 | 3-CF$_3$-4-(4-cyclopropylaminocarbonyl)- | 1 | H | Me | F | CH |
| I-231 | 4-OCF$_3$ | 1 | H | Me | F | CH |
| I-232 | 3-CF$_3$-4-(pyrrolidin-1-yl)- | 1 | H | Me | F | CH |
| I-233 | 3-CF$_3$-4-(piperidin-1-yl)- | 1 | H | Me | F | CH |
| I-234 | 3-OCF$_2$H | 1 | H | Me | F | CH |
| I-235 | 3-OCF$_2$H-4-(morpholin-1-yl)- | 1 | H | Me | F | CH |
| I-236 | 3-OCF$_2$H-4-(4-methylpiperazin-1-yl)- | 1 | H | Me | F | CH |
| I-237 | 3-OCF$_2$H-4-(pyrrolidin-1-yl)- | 1 | H | Me | F | CH |
| I-238 | 3-OCF$_2$H-4-(4-methylsufonylpiperazin-1-yl)- | 1 | H | Me | F | CH |
| I-239 | 3-OCF$_2$H-4-OMe | 1 | H | Me | F | CH |
| I-240 | 3-OCF$_3$ | 1 | H | Me | Cl | CH |
| I-241 | 3-CF$_3$-4-(morpholin-1-yl)- | 1 | H | Me | Cl | CH |
| I-242 | 3-OCF$_3$ | 1 | H | Me | CF$_3$ | CH |
| I-243 | 3-NHSO$_2$Me | 1 | H | Me | F | CH |
| I-244 | 3-CF$_3$-4-(4-methylsufonylpiperazin-1-yl)- | 1 | H | Me | F | CH |
| I-245 | 3-CF$_3$-4-(4,4-difluoropiperidin-1-yl)- | 1 | H | Me | F | CH |
| I-246 | 3-CF$_3$-4-(4-ethylpiperazin-1-yl)- | 1 | H | Me | F | CH |
| I-247 | 3-CF$_3$-4-(4-propylpiperazin-1-yl)- | 1 | H | Me | F | CH |
| I-248 | 3-Cl-4-(4-ethylpiperazin-1-yl)- | 1 | H | Me | F | CH |
| I-249 | 3-Cl-4-(4-propylpiperazin-1-yl)- | 1 | H | Me | F | CH |
| I-250 | 4-Cl-3-(3,4,5-trimethylpiperazin-1-yl)- | 1 | H | Me | F | CH |
| I-251 | 4-Cl-3-(3,5-dimethyl-4-acetylpiperazin-1-yl)- | 1 | H | Me | F | CH |
| I-252 | 4-OH | 1 | H | Me | F | CH |
| I-253 | 3-OH | 1 | H | Me | F | CH |
| I-254 | 3-Cl-4OMe | 1 | H | Me | F | CH |
| I-255 | 3-CF$_3$-4-(4-methylpiperazin-1-yl)- | 1 | H | Me | F | CH |
| I-256 | 3-Cl-4-(4-methylpiperazin-1-yl)- | 1 | H | Me | F | CH |
| I-257 | 3-CF$_3$-4-(4-methylsulfonylpiperazin-1-yl)- | 1 | H | Me | F | CH |
| I-258 | 3-Cl-4-(4-methylsulfonylpiperazin-1-yl)- | 1 | H | Me | F | CH |
| I-259 | 3-CF$_3$-4-(1,3,5-trimethyl-3,7-diazabicyclo[3.3.1]nonan-7-yl)- | 1 | H | Me | F | CH |
| I-260 | 4-(1,3,5-trimethyl-3,7-diazabicyclo[3.3.1]nonan-7-yl) | 1 | H | Me | F | CH |
| I-261 | 3-trifluoromethyl-4-morpholino | 2 | H | Me | F | CH |
| I-262 | 3-chloro-4-methoxy | 2 | H | Me | F | CH |
| I-263 | 3-cyano-4-methyl | 2 | H | Me | F | CH |
| I-264 | 3-trifluoromethyl-4-(4-(methylsulfonyl)piperazin-1-yl)- | 2 | H | Me | F | CH |
| I-265 | 3,5-dichloro | 2 | H | Me | F | CH |
| I-266 | 3,4,5-trimethoxy | 2 | H | Me | F | CH |
| I-267 | 3,4-dimethoxy | 2 | H | Me | F | CH |
| I-268 | 3-trifluoromethyl-4-methoxy | 2 | H | Me | F | CH |
| I-269 | 3-methoxy | 2 | H | Me | F | CH |
| I-270 | 3-trifluoromethyl-4-(4-methylpiperizin-1-yl)- | 2 | H | Me | F | CH |
| I-271 | 4-morpholino-5-trifluoromethyl- | 1 | H | Me | F | N |
| I-272 | 3-trifluoromethyl-4-morpholino | 1 | H | Me | Br | CH |
| I-273 | 3-trifluoromethyl-4-(4-methylpiperizin-1-yl)- | 1 | H | Me | F | CH |
| I-274 | 3,4-dimethoxy- | 1 | H | Me | Br | CH |
| I-275 | 3-trifluoromethoxy- | 1 | H | Me | Br | CH |
| I-276 | 3,4,5-trimethoxy- | 1 | H | Me | Br | CH |
| I-277 | 4-methyl-3-cyano- | 1 | H | Me | Br | CH |
| I-278 | 4-methyl-3-cyano- | 0 | H | Me | F | CH |
| I-279 | 3,5-dichloro | 0 | H | Me | F | CH |
| I-280 | 3-chloro-4-methoxy | 0 | H | Me | F | CH |
| I-281 | 3,4-dimethoxy | 0 | H | Me | F | CH |
| I-282 | 3,4,5-trimethoxy | 0 | H | Me | F | CH |
| I-283 | 4-methoxy-3-trifluoromethyl | 0 | H | Me | F | CH |
| I-284 | 3-trifluoromethoxy | 0 | H | Me | F | CH |
| I-285 | 4-(4-methylpiperazin-1-yl)-3-trifluoromethyl- | 0 | H | Me | F | CH |
| I-286 | 4-(4-methylsulfonyl)piperazin-1-yl)-3-trifluoromethyl | 0 | H | Me | F | CH |
| I-287 | 4-morpholino-3-trifluoromethyl- | 0 | H | Me | F | CH |
| I-288 | 5-chloro-6-(4-methylpiperazin-1-yl) | 1 | H | Me | F | N |
| I-289 | 5-chloro-6-(4-(methylsulfonyl)piperazin-1-yl) | 1 | H | Me | F | N |
| I-290 | 5-chloro-6-(4-morpholino) | 1 | H | Me | F | N |
| I-291 | 3,4-dimethoxy | 1 | H | —(CH$_2$)$_2$C(O)OCH$_3$ | F | CH |
| I-292 | 3,5-dimethoxy | 1 | H | —(CH$_2$)$_2$C(O)OCH$_3$ | F | CH |
| I-293 | 3-chloro-4-methoxy | 1 | H | —(CH$_2$)$_2$C(O)OCH$_3$ | F | CH |
| I-294 | 3,5-dichloro | 1 | H | —(CH$_2$)$_2$C(O)OCH$_3$ | F | CH |
| I-295 | 4-methoxy-3-trifluoromethyl | 1 | H | —(CH$_2$)$_2$C(O)OCH$_3$ | F | CH |

TABLE I-continued

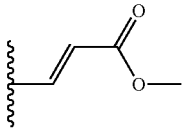

| # | (R⁵)ₚ | n | R¹ | R³ | X | Q |
|---|---|---|---|---|---|---|
| I-296 | 3-cyano-4-methyl | 1 | H | —(CH₂)₂C(O)OCH₃ | F | CH |
| I-297 | 3,4-dimethoxy | 1 | H | 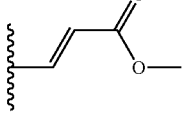 | F | CH |
| I-298 | 3,5-dimethoxy | 1 | H | 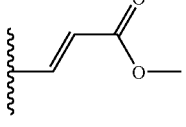 | F | CH |
| I-299 | 3-chloro-4-methyl | 1 | H | 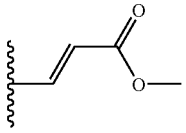 [SMILES: */C=C/C(=O)OC] | F | CH |
| I-300 | 3,5-dichloro | 1 | H |  | F | CH |
| I-301 | 4-methoxy-3-trifluoromethyl | 1 | H | F | CH | |
| I-302 | 3,5-dimethoxy | 1 | H | —(CH₂)₂C(O)OH | F | CH |
| I-303 | 3-chloro-4-methoxy | 1 | H | —(CH₂)₂C(O)OH | F | CH |
| I-304 | 3,5-dichloro | 1 | H | —(CH₂)₂C(O)OH | F | CH |
| I-305 | 4-methoxy-3-trifluoromethyl | 1 | H | —(CH₂)₂C(O)OH | F | CH |
| I-306 | 3-cyano-4-methyl | 1 | H | —(CH₂)₂C(O)OH | F | CH |
| I-307 | 3,5-dimethoxy | 1 | H | Me | F | CH |
| I-308 | 3,5-dimethoxy | 1 | benzyl | Me | F | CH |
| I-309 | 3-difluoromethoxy-4-methoxy | 1 | benzyl | Me | F | CH |
| I-310 | 4-(4-(methylsulfonyl)piperazin-1-yl)-3-trifluoromethyl | 1 | benzyl | Me | F | CH |
| I-311 | 4-(4-methylpiperazin-1-yl)-3-trifluoromethyl | 1 | benzyl | Me | F | CH |
| I-312 | 4-morpholino-3-trifluoromethyl | 1 | benzyl | Me | F | CH |
| I-313 | 3-cyano-4-methyl | 1 | benzyl | Me | F | CH |
| I-314 | 3,5-dimethoxy | 1 | naphthalen-2-ylmethyl | Me | F | CH |
| I-315 | 3-cyano-4-methyl | 1 | naphthalen-2-ylmethyl | Me | F | CH |
| I-316 | 3-difluoromethyl-4-methoxy | 1 | naphthalen-2-ylmethyl | Me | F | CH |
| I-317 | 3,5-dimethoxy | 1 | biphenyl-4-ylmethyl | Me | F | CH |
| I-318 | 3-cyano-4-methyl | 1 | biphenyl-4-ylmethyl | Me | F | CH |
| I-319 | 3-difluoromethyl-4-methoxy | 1 | biphenyl-4-ylmethyl | Me | F | CH |
| I-320 | 3-cyano-4-methyl | 1 | quinolin-2-ylmethyl | Me | F | CH |
| I-321 | 3-difluoromethyl-4-methoxy | 1 | quinolin-2-ylmethyl | Me | F | CH |
| I-322 | 3,5-dimethoxy | 1 | quinolin-2-ylmethyl | Me | F | CH |
| I-323 | 3,5-dimethoxy | 1 | 6-bromobenzo[d][1,3]dioxol-5-yl | Me | F | CH |
| I-324 | 3-cyano-4-methyl | 1 | 6-bromobenzo[d][1,3]dioxol-5-yl | Me | F | CH |
| I-325 | 3,5-dimethoxy | 1 | 3'-cyano-biphenyl-4-yl | Me | F | CH |
| I-326 | 3-cyano-4-methyl | 1 | 3'-cyano-biphenyl-4-yl | Me | F | CH |
| I-327 | 3-hydroxyl | 1 | H | Me | F | CH |
| I-328 | 4-(furan-3-yl)-3-trifluoromethyl | 1 | H | Me | F | CH |
| I-329 | 1,1,2,2-tetrafluoro-ethoxy | 1 | H | Me | F | CH |
| I-330 | 4-morpholino-3-trifluoromethyl | 1 | H | Me | CF₃ | CH |
| I-331 | 4-thiomorpholino-3-trifluoromethyl | 1 | H | Me | F | CH |
| I-332 | 3-chloro-4-methyl | 1 | H | Me | F | CH |
| I-333 | 3-chloro-4-fluoro | 1 | H | Me | F | CH |
| I-334 | 3-chloro-4-trifluoromethoxy | 1 | H | Me | F | CH |
| I-335 | 3-chloro-4-morpholino | 1 | H | Me | F | CH |

TABLE I-continued

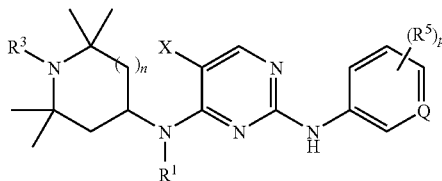

| # | $(R^5)_p$ | n | $R^1$ | $R^3$ | X | Q |
|---|---|---|---|---|---|---|
| I-336 | 3,4-dichloro | 1 | H | Me | F | CH |
| I-337 | 3-chloro-4-trifluoromethyl | 1 | H | Me | F | CH |
| I-338 | 3-chloro-4-(pyrimidin-2-yl)oxy | 1 | H | Me | F | CH |
| I-339 | 3-Chloro-4-(2-furoylamino) | 1 | H | Me | F | CH |
| I-340 | 3,5-dimethoxy | 1 | H | Me | Cl | CH |
| I-341 | 3-difluoromethoxy-4-methoxy | 1 | H | Me | Cl | CH |
| I-342 | 3-methoxy-5-(1H-1,2,3,4-tetrazol-1-yl | 1 | H | Me | F | CH |
| I-343 | 4-methoxy-3-trifluoromethoxy | 1 | H | Me | F | CH |
| I-344 | 3,4-bis-difluoromethoxy | 1 | H | Me | F | CH |
| I-345 | 4-methoxy | 1 | H | Me | F | N |
| I-346 | 3-chloro-4-isopropoxy | 1 | H | Me | F | CH |
| I-347 | 3,4,5-trifluoro | 1 | H | Me | F | CH |
| I-348 | 3-(2,5-Dimethyl-pyrrol-1-yl)-4-methoxy | 1 | H | Me | F | CH |
| I-349 | 3-methoxy-4-(pyrrol-1-yl) | 1 | H | Me | F | CH |
| I-350 | 3-difluoromethoxy-4-methoxy | 1 | H | Me | $CF_3$ | CH |
| I-351 | 3-chloro-4-(2-furoylamino) | 1 | H | Me | Cl | CH |
| I-352 | 3-methoxy-4-(2-furoylamino) | 1 | H | Me | Cl | CH |
| I-353 | 3-methoxy-4-(2-furoylamino) | 1 | H | Me | F | CH |
| I-354 | 3,5-dichloro | 1 | H | Me | F | CH |
| I-355 | 3-trifluoromethyl-4-(2-furoylamino) | 1 | H | Me | F | CH |
| I-356 | 3-methoxy-5-(1,2,3,4-tetrazol-1-yl) | 1 | H | Me | $CF_3$ | CH |
| I-357 | 3-tetrazol-1-yl | 1 | H | Me | F | CH |
| I-358 | 3-methoxy-5-(5-methyl-tetrazol-1-yl) | 1 | H | Me | F | CH |
| I-359 | 3-difluoromethoxy-4-methoxy | 1 | H | Me | F | CH |
| I-360 | 3-isopropoxy-4-methoxy | 1 | H | Me | F | CH |
| I-361 | 4-(3,5-dimethylpyrazol-1-yl)-3-methoxy | 1 | H | Me | F | CH |
| I-362 | 3-chloro-4[2-(pyridin-2-yl)-ethylaminocarbonyl] | 1 | H | Me | F | CH |
| I-363 | 3,5-dimethoxy | 1 | H | Me | $CF_3$ | CH |
| I-364 | 3,5-dimethoxy | 1 | H | Me | cyano | CH |
| I-365 | 3-methoxy-5-(5-methyl-tetrazol-1-yl) | 1 | H | Me | cyano | CH |
| I-366 | 3-difluoromethoxy-4-methoxy | 1 | H | Me | cyano | CH |
| I-367 | 4-[(pyridin-3-yl)methylaminocarbonyl] | 1 | H | Me | F | CH |
| I-368 | 3-chloro-4-[2-(4-morpholino)ethoxy] | 1 | H | Me | F | CH |
| I-369 | 4-methoxy-3-(1,3-oxazol-5-yl) | 1 | H | Me | F | CH |
| I-370 | 3-methoxy-5-(5-methyl-tetrazol-1-yl) | 1 | H | Me | $CF_3$ | CH |
| I-371 | 3,5-dimethoxy | 1 | H | H | F | CH |
| I-372 | 3-methoxy-5-(5-methyl-tetrazol-1-yl) | 1 | H | H | F | CH |
| I-373 | 3-chloro-4-[2-(4-morpholino)ethoxy] | 1 | H | Me | cyano | CH |
| I-374 | 3-methoxy-5-(5-methyl-1H-1,2,3-triazol-1-yl) | 1 | H | Me | Me | CH |
| I-375 | 3,5-bis(2,2,2-trifluoroethoxy) | 1 | H | H | F | CH |
| I-376 | 3-(2,5-dimethyl-1H-pyrrol-1-yl)-4-methoxy | 1 | H | Me | cyano | CH |
| I-377 | 3-(2,2-difluoroethoxy)-4-methoxy | 1 | H | H | cyano | CH |
| I-378 | 3,5-bis(2,2,2,-trifluoroethoxy) | 1 | H | methyl | F | CH |
| I-379 | 2-methyl-4,5-dimethoxy | 1 | H | H | F | CH |
| I-380 | 2-methyl-4,5-dimethoxy | 1 | H | methyl | F | CH |
| I-381 | 2-cyano-4,5-dimethoxy | 1 | H | methyl | F | CH |
| I-382 | 2-cyano-4,5-dimethoxy | 1 | H | H | F | CH |
| I-383 | 3,5-dihydroxy | 1 | H | H | F | CH |
| I-384 | 3,5-dihydroxy | 1 | H | methyl | F | CH |
| I-385 | 3,5-di(2-methoxyethoxy) | 1 | H | methyl | F | CH |
| I-386 | 2-cloro-4,5-dimethoxy | 1 | H | methyl | F | CH |
| I-387 | 3-(5-methyl-1H-tetrazol-1-yl)-5-methoxy | 1 | H | H | $C(O)NH_2$ | CH |
| I-388 | 3-(1H-tetrazol-1-yl)-5-methoxy | 1 | H | H | F | CH |
| I-389 | 3-(1H-tetrazol-1-yl)-5-methoxy | 1 | H | H | $C(O)NH_2$ | CH |
| I-390 | 3-(1H-tetrazol-1-yl)-5-methoxy | 1 | H | methyl | $C(O)NH_2$ | CH |
| I-391 | 3-(1H-tetrazol-1-yl) | 1 | H | H | F | CH |
| I-392 | 3-(1H-tetrazol-1-yl) | 1 | H | H | $C(O)NH_2$ | CH |
| I-387 | 3-(5-methyl-1H-tetrazol-1-yl)-5-methoxy | 1 | H | H | $C(O)NH_2$ | CH |
| I-393 | 3-(1H-tetrazol-1-yl) | 1 | H | H | cyano | CH |
| I-387 | 3-(5-methyl-1H-tetrazol-1-yl)-5-methoxy | 1 | H | H | $C(O)NH_2$ | CH |
| I-394 | 3,5-di(2-methoxyethoxy) | 1 | H | H | F | CH |
| I-395 | 3-(5-propyl-1H-tetrazol-1-yl)-4-methoxy | 1 | H | methyl | F | CH |
| I-396 | 3-(5-methyl-1H-tetrazol-1-yl) | 1 | H | methyl | F | CH |
| I-397 | 3-methyl-4-(1H-tetrazol-1-yl) | 1 | H | methyl | F | CH |
| I-398 | 4-methyl-3-(1H-tetrazol-1-yl) | 1 | H | methyl | F | CH |
| I-399 | 3-(5-(methylthio)-1H-tetrazol-1-yl) | 1 | H | methyl | F | CH |
| I-400 | 4-(1H-tetrazol-1-yl) | 1 | H | methyl | F | CH |
| I-401 | 3-(2,2,2-trifluoroethoxy)-4-methoxy | 1 | H | methyl | F | CH |

TABLE I-continued

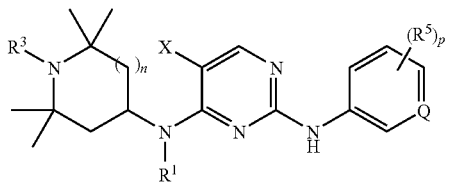

| # | (R⁵)ₚ | n | R¹ | R³ | X | Q |
|---|---|---|---|---|---|---|
| I-402 | 3-(5-methyl-1H-tetrazol-1-yl)-5-methoxy | 1 | H | H | cyano | CH |
| I-403 | 3-(1H-tetrazol-1-yl)-5-methoxy | 1 | H | H | cyano | CH |
| I-404 | 3-(1H-tetrazol-1-yl)-5-methoxy | 1 | H | methyl | cyano | CH |
| I-405 | 3-(1H-tetrazol-1-yl) | 1 | H | methyl | cyano | CH |
| I-406 | 3,5-bis(2,2,2,-trifluoroethoxy) | 1 | H | methyl | C(O)NH₂ | CH |
| I-407 | 4-(5-methyl-1H-tetrazol-1-yl)-3-methoxy | 1 | H | methyl | F | CH |
| I-408 | 3,5-bis(2,2,2,-trifluoroethoxy) | 1 | H | H | C(O)NH₂ | CH |
| I-409 | 3-(5-ethyl-1H-tetrazol-1-yl)-4-ethoxy | 1 | H | methyl | F | CH |
| I-410 | 3,4-di(trifluoromethyl) | 1 | H | methyl | F | CH |
| I-411 | 3,5-bis(2,2,2,-trifluoroethoxy) | 1 | H | methyl | cyano | CH |
| I-412 | 3-(2-(cyclopropylamino)-2-oxoethoxy)-4-methoxy | 1 | H | methyl | F | CH |
| I-413 | 3-methoxyethoxy-4-methoxy | 1 | H | methyl | F | CH |
| I-414 | 3-(5-methyl-1H-tetrazol-1-yl) | 1 | H | H | F | CH |
| I-415 | 3-(5-ethyl-1H-tetrazol-1-yl)-4-ethoxy | 1 | H | H | F | CH |
| I-416 | 3-(5-(methylthio)-1H-tetrazol-1-yl) | 1 | H | H | F | CH |
| I-417 | 3-(pyridin-4-ylmethoxy)-4-methoxy | 1 | H | methyl | F | CH |
| I-418 | 3-(pyridin-3-ylmethoxy)-4-methoxy | 1 | H | methyl | F | CH |
| I-419 | 3,5-bis(2,2,2,-trifluoroethoxy) | 1 | H | H | cyano | CH |
| I-420 | 3-(5-ethyl-1H-tetrazol-1-yl)-4-ethoxy | 1 | H | methyl | C(O)NH₂ | CH |
| I-421 | 3-(2-(dimethylamino)ethoxy)-4-methoxy | 1 | H | methyl | F | CH |
| I-422 | 3,5-dimethoxy | 1 | H | methyl | Br | CH |
| I-423 | 3,5-dimethoxy | 1 | H | methyl | methoxy | CH |
| I-424 | 3-(5-methyl-1H-tetrazol-1-yl)-5-methoxy | 1 | H | methyl | methoxy | CH |
| I-425 | 3,5-dimethoxy | 1 | H | methyl | methyl | CH |
| I-426 | 4-(6-(dimethylamino)pyridin-3-yl)-3-cyano | 1 | H | methyl | F | CH |
| I-427 | 4-(6-morpholinopyridin-3-yl)-3-cyano | 1 | H | methyl | F | CH |
| I-428 | 4-(6-(dimethylamino)pyridin-3-yl)-3-cyano | 1 | H | H | F | CH |
| I-429 | 4-(6-morpholinopyridin-3-yl)-3-cyano | 1 | H | H | F | CH |
| I-430 | 3,5-dimethoxy | 1 | H | methyl | C≡CSi(CH₃)₃ | CH |
| I-431 | 3-(2-morpholinoethoxy)-5-methoxy | 1 | H | methyl | F | CH |
| I-432 | 3-(2-morpholinoethoxy)-5-methoxy | 1 | H | H | F | CH |
| I-433 | 3,5-dimethoxy | 1 | H | methyl | —C≡CH | CH |
| I-434 | 3-(2-(pyrrolidin-1-yl)ethoxy-5-methoxy | 1 | H | methyl | F | CH |
| I-435 | 3-(2-(pyrrolidin-1-yl)ethoxy-5-methoxy | 1 | H | H | F | CH |
| I-436 | 3-methoxy-5-hydroxy | 1 | H | methyl | F | CH |
| I-437 | 3-(2-(1H-pyrrol-1-yl)ethoxy-5-methoxy | 1 | H | methyl | F | CH |
| I-438 | 3-(2-(1H-pyrrol-1-yl)ethoxy-5-methoxy | 1 | H | H | F | CH |
| I-439 | 3-(2,5-dimethyl-1H-pyrrol-1-yl)-4-(2-morpholinoethoxy) | 1 | H | methyl | F | CH |
| I-440 | 3-(2,5-dimethyl-1H-pyrrol-1-yl)-4-(2-(pyrrolidin-1-yl)ethoxy) | 1 | H | methyl | F | CH |
| I-441 | 3-(2,5-dimethyl-1H-pyrrol-1-yl)-4-(2-morpholinoethoxy) | 1 | H | H | F | CH |
| I-442 | 3-(2,5-dimethyl-1H-pyrrol-1-yl)-4-(2-(pyrrolidin-1-yl)ethoxy) | 1 | H | H | F | CH |
| I-443 | 3-fluoro-5-methoxy | 1 | H | methyl | F | CH |
| I-444 | 3-difluromethoxy-4-methoxy | 1 | H | H | F | CH |
| I-445 | 3-chloro-4-(2-morpholinoethoxy) | 1 | H | H | cyano | CH |
| I-446 | 3,5-dichloro | 1 | H | 3-hydrazinyl-3-oxopropyl | F | CH |
| I-447 | 3,5-dichloro | 1 | H | 2-aminoethyl | F | CH |
| I-448 | 4-(4-methylpiperazin-1-yl-3-trifluoromethyl | 1 | H | methyl | C(O)NH₂ | CH |
| I-449 | 4-(4-methylpiperazin-1-yl-3-trifluoromethyl | 1 | H | H | F | CH |
| I-450 | 4-(4-methylpiperazin-1-yl)-3-cyano | 1 | H | methyl | F | CH |
| I-451 | 4-(4-methylpiperazin-1-yl)-3-cyano | 1 | H | H | F | CH |
| I-452 | 4-(4-methylpiperazin-1-yl)-3-trifluoromethyl | 1 | H | methyl | cyano | CH |
| I-453 | 3-hydroxy-5-methoxy | 1 | H | H | F | CH |
| I-454 | 4-(5-methyl-1H-tetrazol-1-yl) | 1 | H | H | F | CH |
| I-455 | 3-(1H-tetrazol-1-yl)-4-methyl | 1 | H | methyl | F | CH |
| I-456 | 3-(5-(methylthio)-1H-tetrazol-1-yl) | 1 | H | methyl | C(O)NH₂ | CH |
| I-457 | 3-(5-(methylthio)-1H-tetrazol-1-yl) | 1 | H | H | C(O)NH₂ | CH |
| I-458 | 4-(5-(furan-2-yl)-1H-tetrazol-1-yl) | 1 | H | methyl | F | CH |
| I-459 | 3-(1H-tetrazol-1-yl)-4-methyl | 1 | H | methyl | cyano | CH |
| I-460 | 3-(5-ethyl-1H-tetrazol-1-yl)-4-ethoxy | 1 | H | methyl | cyano | CH |
| I-461 | 3-(1H-tetrazol-1-yl)-4-methyl | 1 | H | H | cyano | CH |
| I-462 | 3-(5-methyl-1H-tetrazol-1-yl) | 1 | H | methyl | cyano | CH |
| I-463 | 3-(5-methyl-1H-tetrazol-1-yl) | 1 | H | H | cyano | CH |
| I-464 | 3-(5-(methylthio)-1H-tetrazol-1-yl) | 1 | H | methyl | cyano | CH |
| I-465 | 3-(5-(methylthio)-1H-tetrazol-1-yl) | 1 | H | H | cyano | CH |
| I-466 | 3-(1H-tetrazol-1-yl)-4-fluoro | 1 | H | methyl | F | CH |
| I-467 | 3-(1H-tetrazol-1-yl)-4-fluoro | 1 | H | H | F | CH |
| I-468 | 3-(1H-tetrazol-1-yl)-4-fluoro | 1 | H | methyl | C(O)NH₂ | CH |

TABLE I-continued

| # | (R⁵)ₚ | n | R¹ | R³ | X | Q |
|---|---|---|---|---|---|---|
| I-469 | 3-(5-ethyl-1H-tetrazol-1-yl)-4-ethoxy | 1 | H | H | cyano | CH |
| I-470 | 3-(1H-tetrazol-5-yl) | 1 | H | methyl | F | CH |
| I-471 | 3-(1H-tetrazol-5-yl) | 1 | H | H | F | CH |
| I-472 | 3-(2,5-dimethyl-1H-pyrrol-1-yl-4-methoxy | 1 | H | methyl | cyano | CH |
| I-473 | 3-difluoromethoxy-4-methoxy | 1 | H | H | cyano | CH |

TABLE II

| # | A | R³ | R¹ | X |
|---|---|---|---|---|
| II-1 | quinolin-6-yl | Me | H | F |
| II-2 | 3,4-dihydroquinolin-2(1H)-one-6-yl | Me | H | F |
| II-3 | 3-oxo-3,4-dihydro-2H-benzo[b][1,4]oxazin-6-yl | Me | H | F |
| II-4 | 1-methyl-3,4-dihydroquinolin-2(1H)-one-6-yl | Me | H | F |
| II-5 | 1-ethyl-3,4-dihydroquinolin-2(1H)-one-6-yl | Me | H | F |

TABLE II-continued

| # | A | R³ | R¹ | X |
|---|---|----|----|---|
| II-6 | 4-methyl-3-oxo-3,4-dihydro-2H-benzo[b][1,4]oxazin-7-yl | Me | H | F |
| II-7 | 2-methylquinolin-6-yl | Me | H | F |
| II-8 | 2,2-difluoro-4-methyl-3-oxo-3,4-dihydro-2H-benzo[b][1,4]oxazin-7-yl | Me | H | F |
| II-9 | 2-methyl-1H-benzo[d]imidazol-6-yl | Me | H | F |
| II-10 | 2,3-dihydrobenzo[b][1,4]dioxin-6-yl | —(CH₂)₂C(O)OCH₃ | H | F |
| II-11 | benzo[b]imidazo[2,1-d][1,4]oxazin-7-yl | Me | H | F |
| II-12 | 5-chlorobenzo[d]oxazol-2-yl | Me | H | F |
| II-13 | 5-(trifluoromethyl)-1,3,4-thiadiazol-2-yl | Me | H | F |
| II-14 | 5-nitrothiazol-2-yl | Me | H | F |

TABLE II-continued

| # | A | R³ | R¹ | X |
|---|---|----|----|---|
| II-15 | 4-(4-chlorophenyl)thiazol-2-yl | Me | H | F |
| II-16 | benzothiazol-2-yl | Me | H | F |
| II-17 | 6-nitrobenzothiazol-2-yl | Me | H | F |
| II-18 | 6-ethoxybenzothiazol-2-yl | Me | H | F |
| II-19 | 4-methylbenzothiazol-2-yl | Me | H | F |
| II-20 | 4-methoxybenzothiazol-2-yl | Me | H | F |
| II-21 | 5-(methylthio)-1,3,4-thiadiazol-2-yl | Me | H | F |
| II-22 | 4,5-dicyano-1H-imidazol-2-yl | Me | H | F |

TABLE II-continued
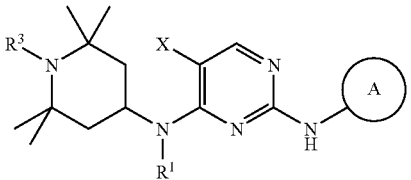
| # | A | R³ | R¹ | X |
|---|---|----|----|---|
| II-23 | 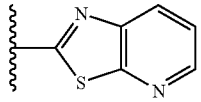 [SMILES: *c1nc2cccnc2s1] | Me | H | F |
| II-24 | 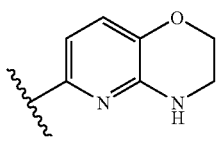 [SMILES: *c1ccc2c(n1)NCCO2] | Me | H | F |
| II-25 | 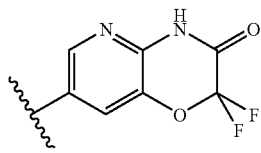 [SMILES: *c1cnc2c(c1)OC(F)(F)C(=O)N2] | Me | H | F |
| II-26 | 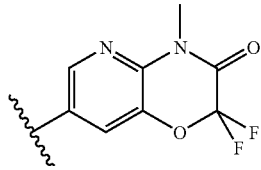 [SMILES: *c1cnc2c(c1)OC(F)(F)C(=O)N2C] | Me | H | F |
| II-27 | 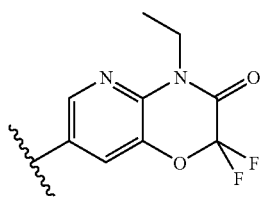 [SMILES: *c1cnc2c(c1)OC(F)(F)C(=O)N2CC] | Me | H | F |
| II-28 | 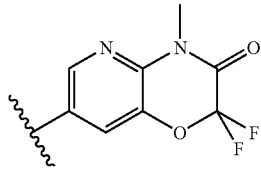 [SMILES: *c1cnc2c(c1)OC(F)(F)C(=O)N2C] | Me | H | Cl |
| II-29 | 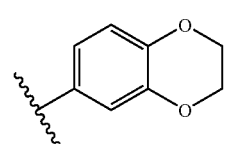 [SMILES: *c1ccc2c(c1)OCCO2] | Me | H | F |
| II-30 | 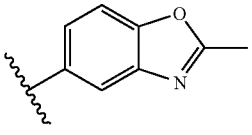 [SMILES: *c1ccc2oc(C)nc2c1] | Me | H | F |

TABLE II-continued

| # | A | R³ | R¹ | X |
|---|---|----|----|----|
| II-31 | 4-ethyl-2,2-difluoro-benzo[1,4]oxazin-3-one-7-yl | Me | H | F |
| II-32 | benzo[1,3]dioxol-5-yl | Me | H | F |
| II-33 | 2,2-dimethyl-benzo[1,4]oxazin-3(4H)-one-7-yl | Me | H | F |
| II-34 | 2,2,4-trimethyl-benzo[1,4]oxazin-3-one-7-yl | Me | H | F |
| II-35 | 4-ethyl-2,2-dimethyl-benzo[1,4]oxazin-3-one-7-yl | Me | H | F |
| II-36 | 3-methyl-benzoxazol-2(3H)-one-6-yl | Me | H | F |
| II-37 | 2,2-difluoro-benzo[1,3]dioxol-5-yl | Me | H | F |
| II-38 | 1H-indazol-5-yl | Me | H | F |

TABLE II-continued
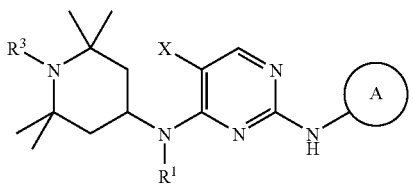
| # | A | R³ | R¹ | X |
|---|---|----|----|---|
| II-39 | 1-methylindazol-5-yl | Me | H | F |
| II-40 | 1H-indazol-6-yl | Me | H | F |
| II-41 | 1-methylindazol-6-yl | Me | H | F |
| II-42 | 3-(carbamoylmethyl)-2-oxo-benzoxazol-6-yl | Me | H | F |
| II-43 | 3,4-dihydro-2H-1,5-benzodioxepin-7-yl | Me | H | F |
| II-44 | 1-isopropyl-3,3-dimethyl-2-oxo-1,2,3,4-tetrahydroquinoxalin-6-yl | Me | H | F |
| II-45 | 4-ethyl-2,2-dimethyl-3-oxo-3,4-dihydro-2H-benzo[b][1,4]oxazin-7-yl | Me | H | cyano |

TABLE II-continued
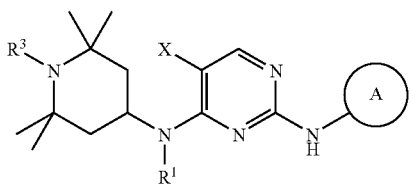
| # | A | R³ | R¹ | X |
|---|---|---|---|---|
| II-46 | 3-ethyl-2-oxo-benzoxazol-6-yl | Me | H | F |
| II-47 | 3-isopropyl-2-oxo-benzoxazol-6-yl | Me | H | F |
| II-48 | 4-propyl-2,2-dimethyl-3-oxo-benzo[1,4]oxazin-7-yl | Me | H | F |
| II-49 | 4-(2-dimethylaminoethyl)-2,2-dimethyl-3-oxo-benzo[1,4]oxazin-7-yl | Me | H | F |
| II-50 | 4-ethyl-2,2-dimethyl-3-oxo-benzo[1,4]oxazin-7-yl | Me | H | $CF_3$ |
| II-51 | 1-methyl-2,3-dihydro-1H-indol-5-yl | Me | H | F |

TABLE II-continued

| # | A | R³ | R¹ | X |
|---|---|----|----|---|
| II-52 | (1-ethyl-2,3-dihydro-1H-indol-5-yl) | Me | H | F |
| II-53 | (1-isopropyl-2,3-dihydro-1H-indol-5-yl) | Me | H | F |
| II-54 | (4,2,2-trimethyl-3-oxo-3,4-dihydro-2H-pyrido[3,2-b][1,4]oxazin-7-yl) | Me | H | F |
| II-55 | (4-ethyl-2,2-dimethyl-3-oxo-3,4-dihydro-2H-pyrido[3,2-b][1,4]oxazin-7-yl) | Me | H | F |
| II-56 | (1,3-dimethyl-2-oxo-2,3-dihydro-1H-benzimidazol-5-yl) | Me | H | F |
| II-57 | (4-ethyl-2,2-dimethyl-3-oxo-3,4-dihydro-2H-benzo[1,4]oxazin-7-yl) | H | H | cyano |
| II-58 | (4-ethyl-3-oxo-3,4-dihydro-2H-benzo[1,4]oxazin-7-yl) | Me | H | F |

TABLE II-continued

| # | A | R³ | R¹ | X |
|---|---|----|----|---|
| II-59 | 7-(4-propyl-3-oxo-benzo[1,4]oxazinyl) | Me | H | F |
| II-60 | 6-(2,3-dihydrobenzo[1,4]dioxinyl) | Me | H | cyano |
| II-61 | 7-(4-isopropyl-3-oxo-benzo[1,4]oxazinyl) | Me | H | F |
| II-62 | 7-(4-methyl-2,2-dimethyl-3-oxo-benzo[1,4]thiazinyl) | Me | H | F |
| II-63 | 7-(4-ethyl-2,2-dimethyl-3-oxo-benzo[1,4]thiazinyl) | Me | H | F |
| II-64 | 7-(4-methyl-2,2-dimethyl-3-oxo-benzo[1,4]thiazinyl 1,1-dioxide) | Me | H | F |
| II-65 | 7-(4-ethyl-2-fluoro-3-oxo-pyrido[1,4]oxazinyl) | Me | H | cyano |

TABLE II-continued

| # | A | R³ | R¹ | X |
|---|---|----|----|---|
| II-66 | | Me | H | F |
| II-67 | | Me | H | F |
| II-68 | | Me | H | F |
| II-69 | | Me | H | F |
| II-70 | | Me | H | cyano |
| II-71 | | Me | H | cyano |

TABLE II-continued
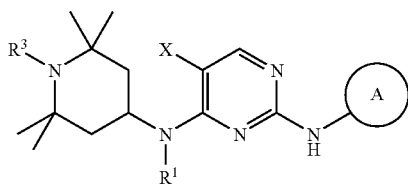
| # | A | R³ | R¹ | X |
|---|---|----|----|---|
| II-72 | (4-propyl-3-oxo-benzo[1,4]oxazin-7-yl) | Me | H | cyano |
| II-73 | (4-ethyl-2,2-difluoro-3-oxo-pyrido[1,4]oxazin-7-yl) | H | H | cyano |
| II-74 | (4-isopropyl-2,2-dimethyl-3-oxo-benzo[1,4]oxazin-7-yl) | Me | H | cyano |
| II-75 | (4-isopropyl-2,2-dimethyl-3-oxo-benzo[1,4]oxazin-7-yl) | H | H | cyano |
| II-76 | (4-cyclopropylmethyl-2,2-dimethyl-3-oxo-benzo[1,4]oxazin-7-yl) | Me | H | F |
| II-77 | (4-cyclopropylmethyl-3-oxo-benzo[1,4]oxazin-7-yl) | Me | H | F |

TABLE II-continued

| # | A | R³ | R¹ | X |
|---|---|----|----|---|
| II-78 | (4-(3-fluoropropyl)-2,2-dimethyl-3-oxo-3,4-dihydro-2H-benzo[b][1,4]oxazin-7-yl) | Me | H | F |
| II-79 | (4-(2-fluoroethyl)-2,2-dimethyl-3-oxo-3,4-dihydro-2H-benzo[b][1,4]oxazin-7-yl) | Me | H | cyano |
| II-80 | (4-(2-fluoroethyl)-2,2-dimethyl-3-oxo-3,4-dihydro-2H-benzo[b][1,4]oxazin-7-yl) | Me | H | F |
| II-81 | (4-(3-fluoropropyl)-2,2-dimethyl-3-oxo-3,4-dihydro-2H-benzo[b][1,4]oxazin-7-yl) | Me | H | cyano |
| II-82 | (4-(2-fluoroethyl)-3-oxo-3,4-dihydro-2H-benzo[b][1,4]oxazin-7-yl) | Me | H | F |
| II-83 | (2,3-dihydro-1H-inden-1-yl) | Me | H | F |
| II-84 | (2,3-dihydro-1H-inden-1-yl) | Me | H | F |

TABLE II-continued

| # | A | R³ | R¹ | X |
|---|---|----|----|---|
| II-85 | (6-(benzylamino)pyridin-3-yl... 5-position) | Me | H | F |
| II-86 | 2,3-dihydrobenzo[b][1,4]dioxin-6-yl | Me | benzyl | F |
| II-87 | 2,3-dihydrobenzo[b][1,4]dioxin-6-yl | Me | naphthalen-2-ylmethyl | F |
| II-88 | 2,3-dihydrobenzo[b][1,4]dioxin-6-yl | Me | biphenyl-4-ylmethyl | F |
| II-89 | 2,3-dihydrobenzo[b][1,4]dioxin-6-yl | Me | quinolin-2-ylmethyl | F |
| II-90 | 2,3-dihydrobenzo[b][1,4]dioxin-6-yl | Me | 6-bromobenzo[d][1,3]dioxol-5-yl | F |
| II-91 | 2,3-dihydrobenzo[b][1,4]dioxin-6-yl | Me | 3'-cyano-biphenyl-4-yl | F |
| II-92 | 2,2,3,3-tetrafluoro-2,3-dihydrobenzo[b][1,4]dioxin-6-yl | Me | H | F |

TABLE II-continued

| # | A | R³ | R¹ | X |
|---|---|---|---|---|
| II-93 | (3-(2-methoxyethyl)-2,2-dimethyl-2H-pyrido[3,2-b][1,4]oxazin-3(4H)-one-7-yl) | Me | H | F |
| II-94 | (4-(2-fluoroethyl)-2H-pyrido[3,2-b][1,4]oxazin-3(4H)-one-7-yl) | Me | H | cyano |
| II-95 | (4-(2-fluoroethyl)-2,2-dimethyl-2H-pyrido[3,2-b][1,4]oxazin-3(4H)-one-7-yl) | H | H | cyano |
| II-96 | (3-(cyclopropylmethyl)benzo[d]oxazol-2(3H)-one-6-yl) | Me | H | cyano |
| II-97 | (3-(cyclopropylmethyl)benzo[d]oxazol-2(3H)-one-6-yl) | H | H | cyano |

TABLE II-continued
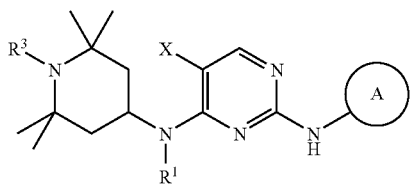
| # | A | R³ | R¹ | X |
|---|---|----|----|---|
| II-98 | (2-fluoroethyl pyrido-oxazinone) | H | H | F |
| II-99 | (methoxyethyl dimethyl pyrido-oxazinone) | H | H | F |
| II-100 | (methoxyethyl dimethyl pyrido-oxazinone) | H | H | —C(O)NH2 |
| II-101 | (methoxyethyl dimethyl pyrido-oxazinone) | Me | H | —C(O)NH2 |
| II-102 | (dimethyl benzodioxole) | H | H | F |
| II-103 | (dimethyl benzodioxole) | Me | H | F |
| II-104 | (methoxyethyl pyrido-oxazinone) | Me | H | F |

TABLE II-continued

| # | A | R³ | R¹ | X |
|---|---|----|----|---|
| II-105 | pyrido-benzoxazinone with N-CH₂CH₂OMe | H | H | —C(O)NH2 |
| II-106 | pyrido-benzoxazinone with N-CH₂CH₂OMe | Me | H | —C(O)NH2 |
| II-107 | benzoxazinone with N-CH₂CH₂OMe | H | H | F |
| II-108 | benzoxazinone with N-CH₂CH₂OMe | Me | H | F |
| II-109 | benzoxazinone with N-CH₂CH₂OMe | H | H | —C(O)NH2 |
| II-110 | benzoxazinone with N-CH₂CH₂OMe | Me | H | —C(O)NH2 |

TABLE II-continued

| # | A | R³ | R¹ | X |
|---|---|---|---|---|
| II-111 | (methoxyethyl-substituted pyrido-oxazinone) | H | H | cyano |
| II-112 | (methoxyethyl-substituted pyrido-oxazinone) | Me | H | cyano |
| II-113 | (benzodioxole spirocyclopentane) | Me | H | F |
| II-114 | (benzodioxole spirocyclohexane) | Me | H | F |
| II-115 | (chloro-benzodioxole) | Me | H | F |
| II-114 | (benzodioxole spirocyclopentane) | Me | H | F |
| II-116 | (chloro-benzodioxane) | Me | H | F |
| II-117 | (methoxyethyl-substituted pyrido-oxazinone) | Me | H | cyano |

TABLE II-continued

| # | A | R³ | R¹ | X |
|---|---|----|----|---|
| II-118 | (4-(2-methoxyethyl)-3-oxo-3,4-dihydro-2H-benzo[b][1,4]oxazin-7-yl) | H | H | cyano |
| II-119 | (4-(2-methoxyethyl)-3-oxo-3,4-dihydro-2H-benzo[b][1,4]oxazin-7-yl) | Me | H | cyano |
| II-120 | spiro[benzo[d][1,3]dioxole-2,1'-cyclopentane]-5-yl | H | H | F |
| II-121 | spiro[benzo[d][1,3]dioxole-2,1'-cyclohexane]-5-yl | H | H | F |
| II-122 | 6-bromo-2,2-difluorobenzo[d][1,3]dioxol-5-yl | Me | H | F |
| II-123 | 7-fluoro-2,2,3,3-tetrafluoro-2,3-dihydrobenzo[b][1,4]dioxin-6-yl | Me | H | F |
| II-124 | 4-(2-fluoroethyl)-2,2-dimethyl-3-oxo-3,4-dihydro-2H-pyrido[3,2-b][1,4]oxazin-6-yl | Me | H | F |
| II-125 | 4-(2-fluoroethyl)-2,2-dimethyl-3-oxo-3,4-dihydro-2H-pyrido[3,2-b][1,4]oxazin-6-yl | H | H | —C(O)NH2 |

TABLE II-continued

| # | A | R³ | R¹ | X |
|---|---|---|---|---|
| II-126 | 7-yl of 4-(2,2,2-trifluoroethyl)-2,2-dimethyl-pyrido[3,2-b][1,4]oxazin-3(4H)-one | Me | H | F |
| II-127 | 2,3-dihydro-1,4-benzodioxin-6-yl | Me | H | Br |
| II-128 | 7-yl of 4-ethyl-2,2-dimethyl-2H-benzo[b][1,4]oxazin-3(4H)-one | Me | H | Br |
| II-129 | 2,3-dihydro-1,4-benzodioxin-6-yl | Me | H | methoxy |
| II-130 | 7-yl of 4-ethyl-2,2-dimethyl-2H-benzo[b][1,4]oxazin-3(4H)-one | Me | H | methoxy |
| II-131 | 6-fluorobenzo[d]thiazol-2-yl | Me | H | F |
| II-132 | 4-(2,3-dihydrobenzo[b][1,4]dioxin-6-yl)thiazol-2-yl | Me | H | F |
| II-133 | 4-(4-(pyrrolidin-1-yl)phenyl)thiazol-2-yl | Me | H | F |

TABLE II-continued
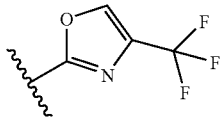 [SMILES: *c1nc(C(F)(F)F)co1]
| # | A | R³ | R¹ | X |
|---|---|----|----|---|
| II-134 | 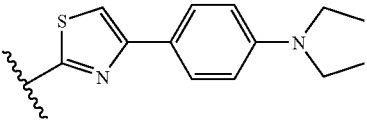 [SMILES: *c1nc(-c2ccc(N(CC)CC)cc2)cs1] | Me | H | F |
| II-135 | 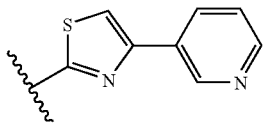 [SMILES: *c1nc(-c2cccnc2)cs1] | Me | H | F |
| II-136 | 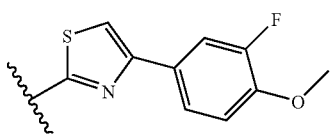 [SMILES: *c1nc(-c2ccc(OC)c(F)c2)cs1] | Me | H | F |
| II-137 | 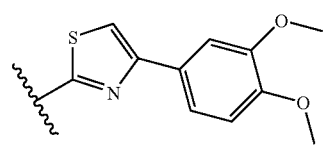 [SMILES: *c1nc(-c2ccc(OC)c(OC)c2)cs1] | Me | H | F |
| II-138 | 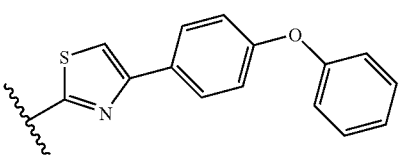 [SMILES: *c1nc(-c2ccc(Oc3ccccc3)cc2)cs1] | Me | H | F |
| II-139 | 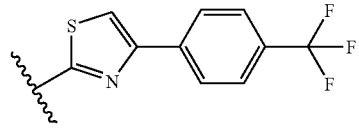 | Me | H | F |
| II-140 |  | Me | H | F |
| II-141 | 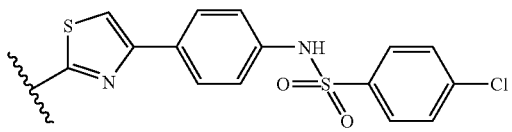 [SMILES: *c1nc(-c2ccc(NS(=O)(=O)c3ccc(Cl)cc3)cc2)cs1] | Me | H | F |
| II-142 | | Me | H | F |

TABLE II-continued
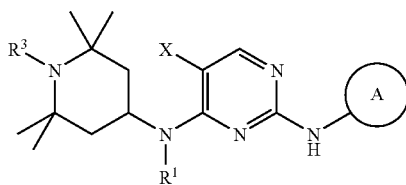
| # | A | R³ | R¹ | X |
|---|---|---|---|---|
| II-143 | benzothiazol-2-yl-6-carboxylic acid | Me | H | F |
| I-144 | 6-(methylsulfonyl)benzothiazol-2-yl | Me | H | F |
| II-145 | 4-ethyl-2,2-dimethyl-3-oxo-3,4-dihydro-2H-benzo[b][1,4]oxazin-7-yl | Me | H | methyl |
| II-146 | 2,3-dihydrobenzo[b][1,4]dioxin-6-yl | Me | H | methyl |
| II-147 | 2,4-dioxo-1,2,3,4-tetrahydroquinazolin-6-yl | Me | H | F |
| II-148 | 1,3-dioxoisoindolin-5-yl | Me | H | F |
| II-149 | 2-methyl-1,3-dioxoisoindolin-5-yl | Me | H | F |
| II-150 | 2,3-dihydrobenzo[b][1,4]dioxin-6-yl | Me | H | C≡CSi(CH₃)₃ |

TABLE II-continued

| # | A | R³ | R¹ | X |
|---|---|----|----|----|
| II-151 | 4-ethyl-2,2-dimethyl-3-oxo-benzoxazine | Me | H | C≡CSi(CH₃)₃ |
| II-152 | 4-ethyl-2,2-dimethyl-3-oxo-benzoxazine | Me | H | C≡CH |
| II-153 | N-methyl phthalimide | H | H | F |
| II-154 | quinazoline-2,4-dione | H | H | F |
| II-155 | benzodioxine-carboxylic acid | H | H | F |
| II-156 | benzodioxine | Me | H | C≡CH |
| II-157 | benzodioxine-carboxylic acid | Me | H | F |

TABLE II-continued

| # | A | R³ | R¹ | X |
|---|---|---|---|---|
| II-158 | (2,3-dihydro-1,4-benzodioxin-6-yl with 2-(4-methylpiperazin-1-yl)carbonyl) | Me | H | F |
| II-159 | (2,3-dihydro-1,4-benzodioxin-6-yl with 2-carboxamide) | H | H | F |
| II-160 | (2,3-dihydro-1,4-benzodioxin-6-yl with 2-(4-methylpiperazin-1-yl)carbonyl) | H | H | F |
| II-161 | (4-(2-fluoroethyl)-3-oxo-3,4-dihydro-2H-benzo[b][1,4]oxazin-7-yl) | Me | H | cyano |
| II-162 | (3-isopropyl-2-oxo-2,3-dihydrobenzo[d]oxazol-6-yl) | H | H | cyano |
| II-163 | (3-cyclopropyl-2-oxo-2,3-dihydrobenzo[d]oxazol-6-yl) | Me | H | F |

TABLE II-continued

| # | A | R³ | R¹ | X |
|---|---|----|----|---|
| II-164 | (2-fluoroethyl-N, 2,2-dimethyl-benzoxazin-3-one) | H | H | cyano |
| II-165 | (isopropyl-N, spirocyclobutyl-benzoxazin-3-one) | Me | H | F |
| II-166 | (propyl-N, spirocyclobutyl-benzoxazin-3-one) | Me | H | F |
| II-167 | (morpholinoethyl-benzoxazol-2-one) | Me | H | F |
| II-168 | (morpholinoethyl-benzoxazol-2-one) | H | H | F |
| II-169 | (morpholinoethyl-benzoxazol-2-one) | H | methyl | cyano |
| II-170 | (morpholinoethyl-benzoxazol-2-one) | H | H | cyano |
| II-171 | (2-fluoroethyl-benzoxazin-3-one) | H | H | cyano |

TABLE II-continued

| # | A | R³ | R¹ | X |
|---|---|----|----|---|
| II-172 | 6-(3-(2-fluoroethyl)-2-oxobenzoxazol-6-yl) | Me | H | F |
| II-173 | 5-(3-ethyl-2-oxobenzoxazol-5-yl) | Me | H | F |
| II-174 | 5-(3-ethyl-2-oxobenzoxazol-5-yl) | H | H | F |
| II-175 | benzo[triazolo]oxazine | Me | H | F |
| II-176 | 2,2,5-trifluorobenzodioxole | Me | H | F |
| II-177 | 4-(2-fluoroethyl)-2,2-dimethyl-pyrido-oxazinone | H | H | cyano |
| II-178 | 4-(2-fluoroethyl)-2,2-dimethyl-pyrido-oxazinone | H | H | F |
| II-179 | 3-(cyclopropylmethyl)-2-oxobenzoxazol-6-yl | Me | H | cyano |

TABLE II-continued

| # | A | R³ | R¹ | X |
|---|---|----|----|---|
| II-180 | (6-(cyclopropylmethyl)-2-oxo-2,3-dihydrobenzo[d]oxazol-5-yl) | H | H | cyano |
| II-181 | (4-(2-fluoroethyl)-2,2-dimethyl-3-oxo-3,4-dihydro-2H-benzo[b][1,4]oxazin-7-yl) | H | H | F |

TABLE III

| # | (R⁵)$_p$ | R³ |
|---|----------|-----|
| III-1 | 3-Cl-4-OMe | Me |
| III-2 | 3-CN | Me |
| III-3 | 3-CF₃-4-(4-methylpiperazin-1-yl)- | Me |
| III-4 | 3-Cl-4-(4-methylpiperazin-1-yl)- | Me |
| III-5 | 3-Cl-4-OMe | CH₂CH₂OH |
| III-6 | 3-CN | CH₂CH₂OH |
| III-7 | 3-CF₃-4-(4-methylpiperazin-1-yl)- | CH₂CH₂OH |
| III-8 | 3-Cl-4-(4-methylpiperazin-1-yl)- | CH₂CH₂OH |
| III-9 | 3,5-dimethoxy | pyridin-4-ylmethyl |
| III-10 | 3-(1H-tetrazol-1-yl)-5-methoxy | pyridin-4-ylmethyl |

TABLE IV

IV-1
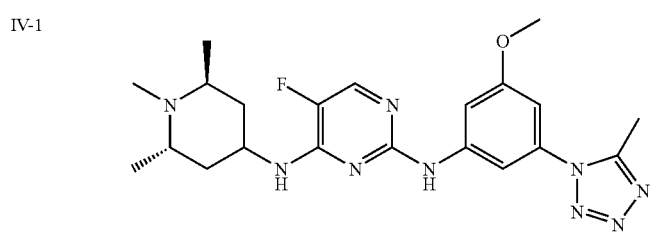

IV-2
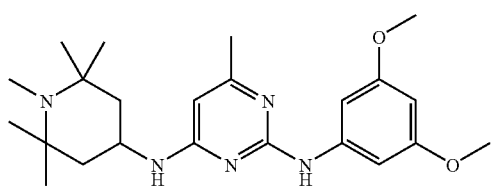

TABLE IV-continued
IV-3
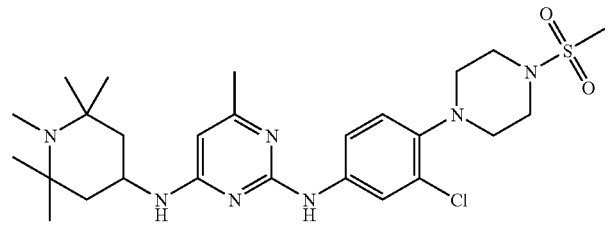
IV-4
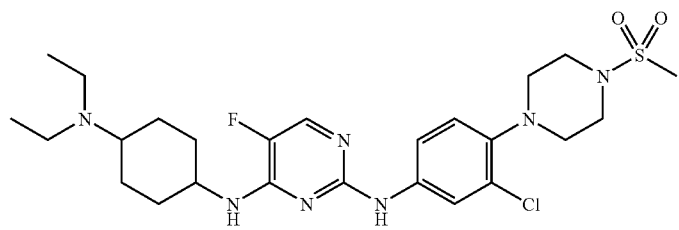 [SMILES: CCN(CC)C1CCC(Nc2nc(Nc3ccc(N4CCN(S(C)(=O)=O)CC4)c(Cl)c3)ncc2F)CC1]
IV-5
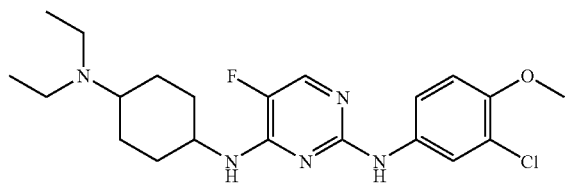 [SMILES: CCN(CC)C1CCC(Nc2nc(Nc3ccc(OC)c(Cl)c3)ncc2F)CC1]
IV-6
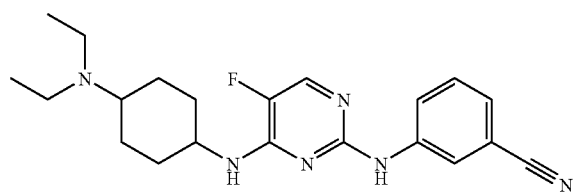 [SMILES: CCN(CC)C1CCC(Nc2nc(Nc3cccc(C#N)c3)ncc2F)CC1]
IV-7
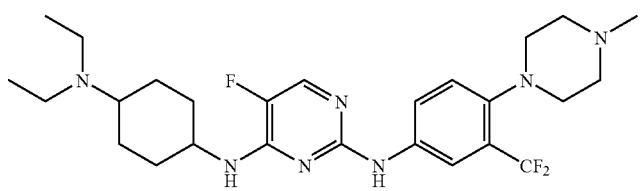 [SMILES: CCN(CC)C1CCC(Nc2nc(Nc3ccc(N4CCN(C)CC4)c(Cl)c3)ncc2F)CC1]
IV-8
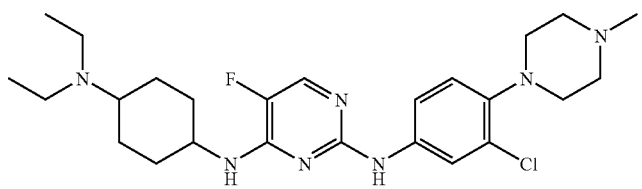
IV-9
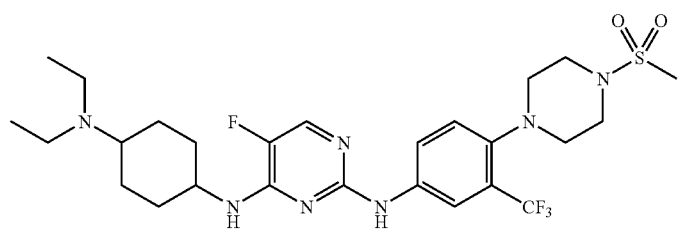

D. Methods of the Invention

Protein Kinase C theta (also known as PKC-theta, PKCT, PRKCT, nPKC-theta and PRKCQ) is a member of the nPKC sub-family. It has a restricted expression pattern, found predominantly in T cells and skeletal muscle. Upon T cell activation, a supramolecular activation complex (SMAC) forms at the site of contact between the T cell and antigen presenting cell (APC). PKC-theta is the only PKC isoform found to localize at the SMAC (C. Monks et al., *Nature,* 1997, 385, 83), placing it in proximity with other signaling enzymes that mediate T cell activation processes. In another study (G. Baier-Bitterlich et al., *Mol. Cell. Biol.,* 1996, 16, 842) the role of PKC-theta in the activation of AP-1, a transcription factor important in the activation of the IL-2 gene, was confirmed. In unstimulated T cells, constitutively active PKC-theta stimulated AP-1 activity while in cells with dominant negative PKC-theta, AP-1 activity was not induced upon activation by PMA. Other studies showed that PKC-theta, via activation of I-kappa-B kinase beta, mediates activation of NF-kappa-B induced by T cell receptor/CD28 co-stimulation (N. Coudronniere et al., *Proc. Nat. Acad. Sci. U.S.A.,* 2000, 97, 3394; X. Lin et al., *Mol. Cell. Biol.,* 2000, 20, 2933). Proliferation of peripheral T cells from PKC-theta knockout mice, in response to T cell receptor (TCR)/CD28 stimulation was greatly diminished compared to T cells from wild type mice. In addition, the amount of IL-2 released from the T cells was also greatly reduced (Z. Sun et al., *Nature,* 2000, 404, 402). Otherwise, the PKC-theta knockout mice seemed normal and were fertile.

PKC-theta, one of the novel serine/threonine Protein Kinase C isoforms (nPKC), is expressed ubiquitously in tissues with the highest levels found in hematopoietic cell lines, including T-cells and thymocytes (Baier et al., *J. Biol. Chem.,* 1993, 268, 4997-5004; Keenan et al., Immunology, 1997, 90, 557-563; Meller et al., *Cell. Immunol.,* 1999, 193, 185-193; Wang et al., *Biochem. Biophys. Res. Commun.,* 1993, 191, 240-246). This isozyme has been shown to be specifically responsible for antigen driven activation events in peripheral T cells. PKC-theta is not required for the development of T cells in the thymus, as PKC-theta knock-out mice develop normal numbers of peripheral T cells. However, when these mice are challenged with an antigen, they fail to make a T cell response.

It has been well established that T cells play an important role in regulating the immune response (Powrie and Coffman, *Immunolog Today,* 1993, 14, 270). Indeed, activation of T cells is often the initiating event in immunological disorders. Following activation of the T-cell receptor (TCR), there is an influx of calcium that is required for T cell activation. Upon activation, T cells produce cytokines, including IL-2, leading to T cell proliferation, differentiation, and effector function. Clinical studies with inhibitors of IL-2 have shown that interference with T cell activation and proliferation effectively suppresses immune response in vivo (Waldmann, *Immunology Today,* 1993, 14, 264). Accordingly, agents, such as PKC-theta inhibitors, that dampen T lymphocyte activation and subsequent cytokine production are therapeutically useful for selectively suppressing the immune response in a patient in need of such immunosuppression and therefore are useful in treating immunological disorders such as autoimmune and inflammatory diseases.

In addition, PKC-theta activation has been shown to be associated with insulin resistance in skeletal muscle (M. E. Griffen et al., *Diabetes,* 1999, 48, 1270). Therefore inhibitors of PKC-theta can also be useful for treating type II diabetes.

The present invention provides 2,4-pyrimidinediamine compounds and prodrugs thereof, as described herein, for use in therapy for the conditions as described herein. The present invention further provides use of the compounds of the present invention in the manufacture of a medicament for the treatment of conditions in which inhibition of PKC-theta can be therapeutically useful. Conditions in which inhibition of PKC-theta can be therapeutically useful include, but are not limited to, asthma, atopic dermatitis, allergic rhinitis, systemic anaphylaxis, hypersensitivity responses, drug allergies, insect sting allergies, dermatitis, eczema, urticaria, inflammatory bowel disease, Crohn's disease, ileitis, Celiac disease, nontropical Sprue, enteritis, enteropathy, colitis, eosinophilic gastroenteritis, ileoanal anastomosis, disorders of the skin, multiple sclerosis, systemic lupus erythermatosus, myasthenia gravis, juvenile onset diabetes, glomerulonephritis, autoimmune thyroiditis, Behcet's disease, graft rejection, stroke, cardiac ischemia, mastitis, vaginitis, cholecystitis, cholangitis, chronic bronchitis, chronic sinusitis, chronic inflammatory diseases of the lung, hypersensitivity pneumonitis, collagen diseases, sarcoidosis, vasculitis, spondyloarthropathies, scleroderma, atherosclerosis, restenosis, myositis pancreatitis, insulin-dependent diabetes mellitus, metabolic syndrome, autoimmune thrombocytopenia, rheumatoid arthritis, osteoarthritis, multiple sclerosis, inflammatory bowel disease, psoriasis, organ transplantation, graft vs. host disease, asthma, and chronic obstructive pulmonary disease and the other conditions described herein. Given the severity of and suffering caused by these conditions, it is vital that new treatments are developed to treat these conditions.

Exacerbated sensitivity to mechanical stimuli that are normally innocuous or mildly painful (mechanical allodynia and hyperalgesia) occurs during inflammation and underlies painful diseases. Proteases that are generated during inflammation and disease cleave protease-activated receptors (PARs), a family of four G-protein-coupled receptors, on afferent nerves to cause mechanical hyperalgesia in the skin and intestine. One mechanism for PAR-mediated hyperalgesia involves sensitization of the ion channel transient receptor potential vanilloidI-4 (TRPVI-4). PAR2-agonist was shown to sensitize TRPV4-dependent Ca2+ signals and currents in primary dorsal root ganglion (DRG) neurons and TRPV4-dependent release of neuropeptides from dorsal horn of rat spinal cord. In addition, intraplantar injection of PAR2 agonist caused mechanical hyperalgesia in mice and sensitized pain responses to the TRPV4 agonists whereas deletion of TRPV4 prevented PAR2 agonist-induced mechanical hyperalgesia and sensitization. Antagonists of phospholipase C-β and protein kinases A, PKC and PKD inhibited PAR2-induced sensitization of TRPV4. This novel mechanism, by which PAR2 activates a series of enzymes including PKCε and PKD1 to sensitize TRPV4-dependent release of nociceptive peptides and induce mechanical hyperalgesia, indicates that inhibitors of PKCε and PKD1 may be useful therapies for a variety of inflammatory and painful conditions.

Protein Kinase C epsilon is one of the novel PKC (nPKC) isozymes which response to DAG but not to calcium. Protein Kinase C-mu (also known as PKD1) encodes a cytosolic serine-threonine kinase that belongs to the Protein kinase D (PKD) family, which is part of the CAMK group of kinases. PKD family is composed of three mammalian homologs (PKD1/PKCmu, PKD2, and PKD3/PKCnu) encoded by distinct genes. PKDs are ubiquitously expressed at varying levels in different tissues. Similar to PKCs, PKDs have two cysteine-rich, DAG/PMA-binding C1 domains at the N-terminus, a central Pleckstrin-homology (PH) domain, and a conserved kinase domain at the C-terminus. Like many kinases, PKD kinase activity is negatively regulated by intramolecular interactions. Various studies have shown that stimulus-dependent binding of lipids (phosphatidylserine and DAG) to C1 domains, protein binding to or tyrosine phosphorylation of the PH domain, and phosphorylation of serine residues in the activation loop of the kinase domain can release the kinase from autoinhibition.

PKD isoforms are effectors of nPKCs in signaling cascades controlled by DAG. DAG regulates the intracellular localization of PKD and also activates PKD through nPKC by phosphorylation. Depending on the cellular context or activating stimulus, all four isoforms in the nPKC family have been shown to directly phosphorylate the activation loop serine residues. Important discoveries have been made regarding the roles of PKDs in regulating cell growth, gene expression, survival, motility, Golgi vesicle fission and trafficking, and lymphocyte biology in response to reactive oxygen species, growth factors, activators of GPCRs, and stimulators of antigen receptor complexes.

As noted previously, numerous conditions can be treated using the 2,4-substituted pyrimidinediamine compounds, prodrugs thereof, and methods of treatment as described herein. As used herein, "Treating" or "treatment" of a disease in a patient refers to (1) preventing the disease from occurring in a patient that is predisposed or does not yet display symptoms of the disease; (2) inhibiting the disease or arresting its development; or (3) ameliorating or causing regression of the disease. As well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease, state, and remission (whether partial or total), whether detectable or undetectable. Preferred are compounds that are potent and can be administered locally at very low doses, thus minimizing systemic adverse effects.

The compounds described herein are potent and selective inhibitors of PKC. As a consequence of this activity, the compounds can be used in a variety of in vitro, in vivo and ex vivo contexts to inhibit PKC activity.

In another embodiment, the present invention provides a method of inhibiting an activity of a Protein Kinase C, comprising contacting the Protein Kinase C with an amount of a compound effective to inhibit the activity of the Protein Kinase C wherein the compound is a compound of formula II:

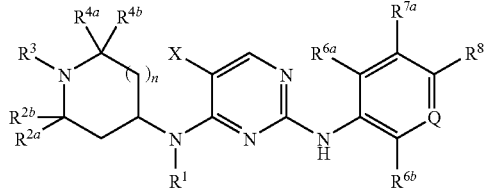

a solvate, N-oxide, prodrug or therapeutically acceptable salt thereof
wherein
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
Q is N, N→O, or $CR^{7b}$;
n is an integer between 0 and 3;
$R^1$ is selected from the group consisting of hydrogen, methyl and ethyl;
$R^{2a}$, $R^{2b}$, $R^{4a}$ and $R^{4b}$ each independently is selected from the group consisting of hydrogen and $C_{1-3}$ alkyl;
$R^3$ is selected from the group consisting of —Y, —C(O)—Y, —$SO_2$—Y, —$(CH_2)_m$—C(O)—Y, —CH=CH—C(O)—Y and —$(CH_2)_m$—$NY_2$, wherein each Y independently is hydrogen, hydroxy, oxy radical, alkoxy, alkyl, or substituted alkyl and m is 1, 2, or 3;
each of $R^{6a}$, $R^{6b}$ $R^{7a}$, $R^{7b}$, and $R^8$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, sulfonyl, sulfonylamino, and aminosulfonyl;
provided that,
(1) when X is fluoro, and n is zero or one, then:
$R^{6a}$ or $R^{6b}$ is not hydrogen; or
$R^{7a}$ or $R^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or
$R^8$ is selected from the group consisting of substituted alkyl but not $CF_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and
(2) when X is nitro, $CF_3$, or $C(O)NH_2$, then at least one of $R^{2a}$, $R^{2b}$, $R^{4a}$ and $R^{4b}$ is not hydrogen; and
(3) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

In another embodiment, the present invention provides a method of treating a disorder mediated by a Protein Kinase C, comprising administering to a patient in need thereof an amount of a compound effective to treat the disorder wherein the compound is a compound of formula II:

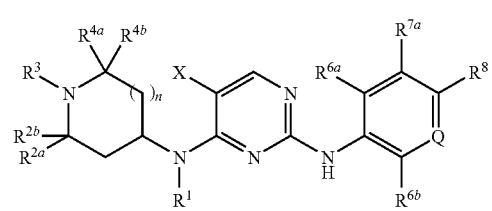

a solvate, N-oxide, prodrug or therapeutically acceptable salt thereof
wherein
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;

Q is N, N→O, or $CR^{7b}$;

n is an integer between 0 and 3;

$R^1$ is selected from the group consisting of hydrogen, methyl and ethyl;

$R^{2a}$, $R^{2b}$, $R^{4a}$ and $R^{4b}$ each independently is selected from the group consisting of hydrogen and $C_{1-3}$ alkyl;

$R^3$ is selected from the group consisting of —Y, —C(O)—Y, —$SO_2$—Y, —$(CH_2)_m$—C(O)—Y, —CH=CH—C(O)—Y and —$(CH_2)_m$—$NY_2$, wherein each Y independently is hydrogen, hydroxy, oxy radical, alkoxy, alkyl, or substituted alkyl and m is 1, 2, or 3;

each of $R^{6a}$, $R^{6b}$, $R^{7a}$, $R^{7b}$, and $R^8$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, sulfonyl, sulfonylamino, and aminosulfonyl;

provided that, (1) when X is fluoro, and n is zero or one, then:

$R^{6a}$ or $R^{6b}$ is not hydrogen; or $R^{7a}$ or $R^{7b}$ is selected from the group consisting of cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, and substituted heteroaryl; or $R^8$ is selected from the group consisting of substituted alkyl but not $CF_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, and substituted aryl; and (2) when X is nitro, $CF_3$, or $C(O)NH_2$, then at least one of $R^{2a}$, $R^{2b}$, $R^{4a}$ and $R^{4b}$ is not hydrogen; and (3) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

In another embodiment, the present invention provides a method of inhibiting an activity of a Protein Kinase C, comprising contacting the Protein Kinase C with an amount of a compound effective to inhibit the activity of the Protein C theta wherein the compound is selected from the group consisting of I-39, I-40, I-41, I-42, I-43, I-47, I-48, I-49, I-50, I-51, I-53, I-54, I-55, I-56, I-57, I-59, I-60, I-61, I-62, I-63, I-65, I-67, I-68, I-100, I-245; I-246, I-247, I-248, I-249, I-250, I-251, I-252, I-253, I-254, I-255, I-256, I-257, I-258, I-259, and I-260, or a solvate, N-oxide, prodrug or therapeutically acceptable salt thereof. Preferably the Protein Kinase C is PKC-theta and PKC-epsilon, or PKC-mu.

In another embodiment, the present invention provides a method of treating a disorder mediated by a Protein Kinase C, comprising administering to a patient in need thereof an amount of a compound effective to treat the disorder wherein the compound is selected from the group consisting of I-39, I-40, I-41, I-42, I-43, I-47, I-48, I-49, I-50, I-51, I-53, I-54, I-55, I-56, I-57, I-59, I-60, I-61, I-62, I-63, I-65, I-67, I-68, I-100, I-245; I-246, I-247, I-248, I-249, I-250, I-251, I-252, I-253, I-254, I-255, I-256, I-257, I-258, I-259, and I-260, or a solvate, N-oxide, prodrug or therapeutically acceptable salt thereof.

In another embodiment, the present invention provides a method of inhibiting an activity of a Protein Kinase C, comprising contacting the Protein Kinase C with an amount of a compound effective to inhibit the activity of the Protein Kinase C wherein the compound is a compound of formula I:

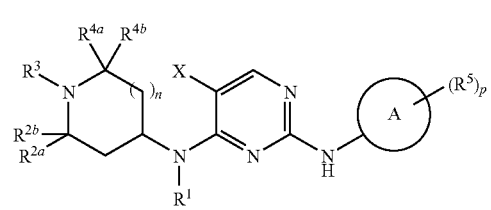

a solvate, N-oxide, prodrug or therapeutically acceptable salt thereof wherein:

X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;

$R^1$ is selected from the group consisting of hydrogen, lower alkyl, substituted lower alkyl, aryl, substituted aryl, heteroaryl, and substituted heteroaryl;

each $R^{2a}$, $R^{2b}$, $R^{4a}$ and $R^{4b}$ independently is selected from the group consisting of hydrogen and $C_{1-3}$ alkyl;

$R^3$ is selected from the group consisting of —Y, —C(O)—Y, —$SO_2$—Y, —$(CH_2)_m$—C(O)—Y, —CH=CH—C(O)—Y and —$(CH_2)_m$—$NY_2$, wherein each Y independently is hydrogen, hydroxy, oxy radical or substituted alkyl and m is 1, 2, or 3;

A is selected from the group consisting of bicyclic aryl, bicyclic heteroaryl, tricyclic aryl, tricyclic heteroaryl and

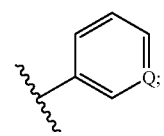

each $R^5$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;

n is an integer between 0 and 3;

p is an integer between 0 and 5; and

Q is N, N→O, or $CR^{7b}$;

provided that, when A is tricyclic heteroaryl and X is fluoro, then at least one of $R^{2a}$, $R^{2b}$, $R^{4a}$ and $R^{4b}$ is not hydrogen.

In one embodiment, the method further comprises contacting the Protein Kinase C with the compound in a cell. In another embodiment, said contacting occurs in vivo. In another embodiment, said contacting occurs in vitro.

In another embodiment, the present invention provides a method of treating a disorder mediated by a Protein Kinase C, comprising administering to a patient in need thereof a therapeutically effective amount of a compound effective to treat the disorder wherein the compound is a compound of formula I:

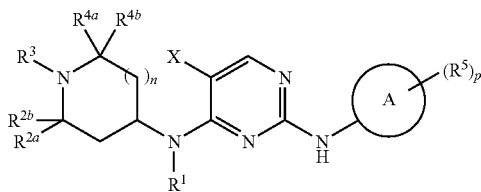

a solvate, N-oxide, prodrug or therapeutically acceptable salt thereof
wherein:
X is selected from the group consisting of alkyl, substituted alkyl, hydroxy, alkoxy, substituted alkoxy, amino, substituted amino, aminocarbonyl, carboxyl, carboxyl ester, cyano, halo, nitro, alkenyl, substituted alkenyl, alkynyl, substituted alkynyl, and trihalomethyl;
$R^1$ is selected from the group consisting of hydrogen, lower alkyl, substituted lower alkyl, aryl, substituted aryl, heteroaryl, and substituted heteroaryl;
each $R^{2a}$, $R^{2b}$, $R^{4a}$ and $R^{4b}$ independently is selected from the group consisting of hydrogen and $C_{1-3}$ alkyl;
$R^3$ is selected from the group consisting of —Y, —C(O)—Y, —SO$_2$—Y, —(CH$_2$)$_m$—C(O)—Y, —CH=CH—C(O)—Y and —(CH$_2$)$_m$—NY$_2$, wherein each Y independently is hydrogen, hydroxy, oxy radical or substituted alkyl and m is 1, 2, or 3;
A is selected from the group consisting of bicyclic aryl, bicyclic heteroaryl, tricyclic aryl, tricyclic heteroaryl and

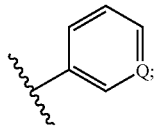

each $R^5$ independently is selected from the group consisting of hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;
n is an integer between 0 and 3;
p is an integer between 0 and 5; and
Q is N, N→O, or CR$^{7b}$;
provided that,
when A is tricyclic heteroaryl and X is fluoro, then at least one of $R^{2a}$, $R^{2b}$, $R^{4a}$ and $R^{4b}$ is not hydrogen.
In yet another embodiment, the disorder mediated by a protein kinase is a cancer where a PKC-family kinase such as PKC alpha or PKC-theta is activated or overexpressed, such as T cell leukemia, thymoma, T and B cell lymphoma (such as diffuse large B cell lymphoma or transformed (CD20+) indolent lymphoma), colon carcinoma, colorectal cancer, breast cancer, prostate cancer, pancreatic cancer (e.g. adenocarcinoma of the pancreas), ovarian cancer (e.g. ovarian epithelial or primary peritoneal carcinoma) and lung carcinoma (e.g., non-small cell lung cancer or small-cell lung cancer), or cancers where PKC-family kinase activity facilitates tumor growth or survival or provides resistance to chemotherapeutic drugs or radiation. The present compounds also may have a therapeutic effect in solid tumors such as brain, breast, ovarian, gastric, non small-cell lung cancer, small-cell lung cancer, gastric, hepatocellular, colon and renal cell cancer by decreasing the number of intratumoral vessels.

In another embodiment, the present invention provides a method of treating a disorder mediated by a Protein Kinase C theta, comprising administering to a patient in need thereof a therapeutically effective amount of a compound effective to treat the disorder wherein the compound is selected from the compounds of this invention, as described above. In another embodiment, the method further comprises administering the compound in combination with an antibody. In a preferred embodiment, the antibody is an anti-Her2 antibody. In another embodiment, the disorder mediated by a Protein Kinase C theta is an inflammatory or immune disorder. In another embodiment, the disorder mediated by a Protein Kinase C theta is selected from the group consisting of asthma, atopic dermatitis, allergic rhinitis, systemic anaphylaxis, hypersensitivity responses, drug allergies, insect sting allergies, dermatitis, eczema, urticaria, inflammatory bowel disease, Crohn's disease, ileitis, Celiac disease, nontropical Sprue, enteritis, enteropathy, colitis, eosinophilic gastroenteritis, ileoanal anastomosis, disorders of the skin, multiple sclerosis, systemic lupus erythermatosus, myasthenia gravis, juvenile onset diabetes, glomerulonephritis, autoimmune thyroiditis, Behcet's disease, graft rejection, stroke, cardiac ischemia, mastitis, vaginitis, cholecystitis, cholangitis, chronic bronchitis, chronic sinusitis, chronic inflammatory diseases of the lung, hypersensitivity pneumonitis, collagen diseases, sarcoidosis, vasculitis, spondyloarthropathies, scleroderma, atherosclerosis, restenosis, myositis pancreatitis, insulin-dependent diabetes mellitus, autoimmune thrombocytopenia, rheumatoid arthritis, osteoarthritis, multiple sclerosis, inflammatory bowel disease, psoriasis, organ transplantation, graft vs. host disease, asthma, and chronic obstructive pulmonary disease. In another embodiment, the disorder mediated by a Protein Kinase C theta is osteoarthritis, multiple sclerosis, psoriasis, organ transplantation, asthma, and insulin-dependent diabetes. In another embodiment, the disorder mediated by a Protein Kinase C theta is a metabolic disorder. In a preferred embodiment, the metabolic disorder is selected from the group consisting of insulin-dependent diabetes, and insulin resistance, metabolic syndrome, and type II diabetes.

In another embodiment, the 2,4-pyrimidinediamine compounds described herein can be used to treat and/or prevent many aspects of transplant rejection, and are particularly useful in the treatment and/or prevention of rejection reactions that are mediated, at least in part, by T-cells, such as HVGR or GVHR. The 2,4-pyrimidinediamine compounds can also be used to treat and/or prevent chronic rejection in transplant recipients and, in particular, in renal transplant recipients. The compound can also be administered to a tissue or an organ prior to transplanting the tissue or organ in the transplant recipient. Such administration may occur in vivo (e.g., by administering the compound to the donor) or ex vivo (e.g., by applying the compound to the tissue or organ after removal from the donor but before placing the tissue or organ in the recipient).

In another embodiment, the present invention provides a method of treating a disorder mediated by a Protein Kinase C, comprising:
 a) selecting a patient with a disorder mediated by the Protein Kinase C; and
 b) administering to the patient a therapeutically effective amount of a compound of this invention, as described above. Preferably, the Protein Kinase C is PKC-theta and PKC-epsilon, or PKC-mu.

In yet another embodiment, the present invention provides a method of producing an anti-nociceptive effect in a mammal which comprises administering to said mammal an analgetically effective amount of a 2,4,-pyrimidinediamine compound as disclosed herein.

E. Pharmaceutical Compositions of the Invention

Pharmaceutical compositions comprising the 2,4-pyrimidinediamine compounds described herein (or prodrugs thereof) can be manufactured by means of conventional mixing, dissolving, granulating, dragee-making, levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

The 2,4-pyrimidinediamine compound or prodrug can be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed.

In one embodiment, this invention provides a pharmaceutical formulation comprising a compound selected from the compounds of this invention, as described above.

The compounds can be provided in a variety of formulations and dosages. The compounds can be provided in a pharmaceutically acceptable form including, where the compound or prodrug can be formulated in the pharmaceutical compositions per se, or in the form of a hydrate, solvate, N-oxide or pharmaceutically acceptable salt, as described herein. Typically, such salts are more soluble in aqueous solutions than the corresponding free acids and bases, but salts having lower solubility than the corresponding free acids and bases may also be formed. It is to be understood that reference to the compound, 2,4-pyrimidinediamine compound, or "active" in discussions of formulations is also intended to include, where appropriate as known to those of skill in the art, formulation of the prodrugs of the 2,4-pyrimidinediamine compounds.

In one embodiment, the compounds are provided as non-toxic pharmaceutically acceptable salts, as noted previously. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention can be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope solvates of the 2,4-pyrimidinediamine compounds and salts thereof, for example, hydrates.

The 2,4-pyrimidinediamine compounds may have one or more asymmetric centers, and may accordingly exist both as enantiomers and as diastereomers. It is to be understood that all such isomers and mixtures thereof are encompassed within the scope of the present invention.

The 2,4-pyrimidinediamine compounds can be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds of the invention can be effective in humans.

The pharmaceutical compositions for the administration of the 2,4-pyrimidinediamine compounds may conveniently be presented in dosage unit form and can be prepared by any of the methods well known in the art of pharmacy. The pharmaceutical compositions can be, for example, prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired therapeutic effect. For example, pharmaceutical compositions of the invention may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) of this invention or prodrug(s) can be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection can be presented in unit dosage form, e.g., in ampules or in multidose containers, and may contain added preservatives.

Alternatively, the injectable formulation can be provided in powder form for reconstitution with a suitable vehicle, including but not limited to sterile pyrogen free water, buffer, dextrose solution, etc., before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars, films or enteric coatings. Additionally, the pharmaceutical compositions containing the 2,4-substituted pyrimidinediamine as active ingredient or prodrug thereof in a form suitable for oral use, may also include, for example, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient (including prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch, or alginic acid); binding agents (e.g. starch, gelatin or acacia); and lubricating agents (e.g. magnesium stearate, stearic acid or talc). The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and 4,265,874 to form osmotic therapeutic tablets for control release. The pharmaceutical compositions of the invention may also be in the form of oil-in-water emulsions.

Liquid preparations for oral administration may take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, Cremophore™ or fractionated vegetable oils); and preservatives (e.g., methyl or propyl p hydroxybenzoates or sorbic acid). The preparations may also contain buffer salts, preservatives, flavoring, coloring and sweetening agents as appropriate.

Preparations for oral administration can be suitably formulated to give controlled release of the active compound or prodrug, as is well known.

For buccal administration, the compositions may take the form of tablets or lozenges formulated in conventional manner.

For rectal and vaginal routes of administration, the active compound(s) can be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

The pharmaceutical compositions can be in the form of a sterile injectable aqueous or oleagenous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that can be employed are water, Ringer's solution and isotonic sodium chloride solution. The 2,4-pyrimidinediamine compounds may also be administered in the form of suppositories for rectal or urethral administration of the drug. In particular embodiments, the compounds can be formulated as urethral suppositories, for example, for use in the treatment of fertility conditions, particularly in males, e.g., for the treatment of testicular dysfunction.

According to the invention, 2,4-pyrimidinediamine compounds can be used for manufacturing a composition or medicament, including medicaments suitable for rectal or urethral administration. The invention also relates to methods for manufacturing compositions including 2,4-pyrimidinediamine compounds in a form that is suitable for urethral or rectal administration, including suppositories.

For topical use, creams, ointments, jellies, gels, solutions or suspensions, etc., containing the 2,4-pyrimidinediamine compounds can be employed. In certain embodiments, the 2,4-pyrimidinediamine compounds can be formulated for topical administration with polyethylene glycol (PEG). These formulations may optionally comprise additional pharmaceutically acceptable ingredients such as diluents, stabilizers and/or adjuvants. In particular embodiments, the topical formulations are formulated for the treatment of allergic conditions and/or skin conditions including psoriasis, contact dermatitis and atopic dermatitis, among others described herein.

According to the invention, 2,4-pyrimidinediamine compounds can be used for manufacturing a composition or medicament, including medicaments suitable for topical administration. The invention also relates to methods for manufacturing compositions including 2,4-pyrimidinediamine compounds in a form that is suitable for topical administration.

According to the present invention, 2,4-pyrimidinediamine compounds can also be delivered by any of a variety of inhalation devices and methods known in the art, including, for example: U.S. Pat. No. 6,241,969; U.S. Pat. No. 6,060,069; U.S. Pat. No. 6,238,647; U.S. Pat. No. 6,335,316; U.S. Pat. No. 5,364,838; U.S. Pat. No. 5,672,581; WO96/32149; WO95/24183; U.S. Pat. No. 5,654,007; U.S. Pat. No. 5,404,871; U.S. Pat. No. 5,672,581; U.S. Pat. No. 5,743,250; U.S. Pat. No. 5,419,315; U.S. Pat. No. 5,558,085; WO98/33480; U.S. Pat. No. 5,364,833; U.S. Pat. No. 5,320,094; U.S. Pat.

No. 5,780,014; U.S. Pat. Nos. 5,658,878; 5,518,998; 5,506,203; U.S. Pat. No. 5,661,130; U.S. Pat. No. 5,655,523; U.S. Pat. No. 5,645,051; U.S. Pat. No. 5,622,166; U.S. Pat. No. 5,577,497; U.S. Pat. No. 5,492,112; U.S. Pat. No. 5,327,883; U.S. Pat. No. 5,277,195; U.S. Pat. Pub. No. 20010041190; U.S. Pat. Pub. No. 20020006901; and U.S. Pat. Pub. No. 20020034477.

Included among the devices which can be used to administer particular examples of the 2,4-pyrimidinediamine compounds are those well-known in the art, such as, metered dose inhalers, liquid nebulizers, dry powder inhalers, sprayers, thermal vaporizers, and the like. Other suitable technology for administration of particular 2,4-pyrimidinediamine compounds includes electrohydrodynamic aerosolizers.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, Del.), Rotahaler (Glaxo, Research Triangle Park, N.C.), Diskus (Glaxo, Research Triangle Park, N.C.), the Ultravent nebulizer (Mallinckrodt), the Acorn II nebulizer (Marquest Medical Products, Totowa, N.J.) the Ventolin metered dose inhaler (Glaxo, Research Triangle Park, N.C.), or the like. In one embodiment, 2,4-pyrimidinediamine compounds can be delivered by a dry powder inhaler or a sprayer.

As those skilled in the art will recognize, the formulation of 2,4-pyrimidinediamine compounds, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of 2,4-pyrimidinediamine compounds in the aerosol. For example, shorter periods of administration can be used at higher concentrations of 2,4-pyrimidinediamine compounds in the nebulizer solution. Devices such as metered dose inhalers can produce higher aerosol concentrations, and can be operated for shorter periods to deliver the desired amount of 2,4-pyrimidinediamine compounds in some embodiments. Devices such as dry powder inhalers deliver active agent until a given charge of agent is expelled from the device. In this type of inhaler, the amount of 2,4-pyrimidinediamine compounds in a given quantity of the powder determines the dose delivered in a single administration. The formulation of 2,4-pyrimidinediamine is selected to yield the desired particle size in the chosen inhalation device.

Formulations of 2,4-pyrimidinediamine compounds for administration from a dry powder inhaler may typically include a finely divided dry powder containing 2,4-pyrimidinediamine compounds, but the powder can also include a bulking agent, buffer, carrier, excipient, another additive, or the like. Additives can be included in a dry powder formulation of 2,4-pyrimidinediamine compounds, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like.

The present invention also relates to a pharmaceutical composition including 2,4-pyrimidinediamine compounds suitable for administration by inhalation. According to the invention, 2,4-pyrimidinediamine compounds can be used for manufacturing a composition or medicament, including medicaments suitable for administration by inhalation. The invention also relates to methods for manufacturing compositions including 2,4-pyrimidinediamine compounds in a form that is suitable for administration, including administration by inhalation. For example, a dry powder formulation can be manufactured in several ways, using conventional techniques, such as described in any of the publications mentioned above and incorporated expressly herein by reference, and for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. And a liquid formulation can be manufactured by dissolving the 2,4-pyrimidinediamine compounds in a suitable solvent, such as water, at an appropriate pH, including buffers or other excipients.

Pharmaceutical compositions comprising the 2,4-pyrimidinediamine compounds described herein (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

For ocular administration, the 2,4-pyrimidinediamine compound(s) or prodrug(s) can be formulated as a solution, emulsion, suspension, etc. suitable for administration to the eye. A variety of vehicles suitable for administering compounds to the eye are known in the art. Specific non-limiting examples are described in U.S. Pat. No. 6,261,547; U.S. Pat. No. 6,197,934; U.S. Pat. No. 6,056,950; U.S. Pat. No. 5,800,807; U.S. Pat. No. 5,776,445; U.S. Pat. No. 5,698,219; U.S. Pat. No. 5,521,222; U.S. Pat. No. 5,403,841; U.S. Pat. No. 5,077,033; U.S. Pat. No. 4,882,150; and U.S. Pat. No. 4,738,851.

For prolonged delivery, the 2,4-pyrimidinediamine compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device can be accompanied by instructions for administration.

The 2,4-pyrimidinediamine compound(s) or prodrug(s) described herein, or compositions thereof, will generally be used in an amount effective to achieve the intended result, for example in an amount effective to treat or prevent the particular condition being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. As another specific example, therapeutic benefit in the context of transplantation rejection includes the ability to alleviate an acute rejection episode, such as for example, HVGR or GVHR, or the ability to prolong the time period between onset of acute rejection episodes and/or onset of chronic rejection. Therapeutic benefit also includes halting or slowing the progression of the disease, regardless of whether improvement is realized.

The amount of compound administered will depend upon a variety of factors, including, for example, the particular condition being treated, the mode of administration, the severity of the condition being treated and the age and weight of the patient, the bioavailability of the particular active compound, etc. Determination of an effective dosage is well within the capabilities of those skilled in the art.

As known by those of skill in the art, the preferred dosage of 2,4-pyrimidinediamine compounds will also depend on the age, weight, general health and severity of the condition of the individual being treated. Dosage may also need to be tailored to the sex of the individual and/or where administered by inhalation, the lung capacity of the individual. Dosage may also be tailored to individuals suffering from more than one condition or those individuals who have additional conditions which affect lung capacity and the ability to breathe normally, for example, emphysema, bronchitis, pneumonia, respiratory infections, etc. Dosage, and frequency of administration of the compounds or prodrugs thereof, will also depend on whether the compounds are formulated for treatment of acute episodes of a condition or for the prophylactic treatment of a disorder. For example, acute episodes of allergic conditions, including allergy-related asthma, transplant rejection, etc. A skilled practitioner will be able to determine the optimal dose for a particular individual.

For prophylactic administration, the compound can be administered to a patient at risk of developing one of the previously described conditions. For example, if it is unknown whether a patient is allergic to a particular drug, the compound can be administered prior to administration of the drug to avoid or ameliorate an allergic response to the drug. Alternatively, prophylactic administration can be applied to avoid the onset of symptoms in a patient diagnosed with the underlying disorder. For example, a compound can be administered to an allergy sufferer prior to expected exposure to the allergen. Compounds may also be administered prophylactically to healthy individuals who are repeatedly exposed to agents known to one of the above-described maladies to prevent the onset of the disorder. For example, a compound can be administered to a healthy individual who is repeatedly exposed to an allergen known to induce allergies, such as latex, in an effort to prevent the individual from developing an allergy. Alternatively, a compound can be administered to a patient suffering from asthma prior to partaking in activities which trigger asthma attacks to lessen the severity of, or avoid altogether, an asthmatic episode.

In the context of transplant rejection, the compound can be administered while the patient is not having an acute rejection reaction to avoid the onset of rejection and/or prior to the appearance of clinical indications of chronic rejection. The compound can be administered systemically to the patient as well as administered to the tissue or organ prior to transplanting the tissue or organ in the patient.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, etc. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an $IC_{50}$ of the particular compound as measured in as in vitro assay. Calculating dosages to achieve such circulating blood or serum concentrations taking into account the bioavailability of the particular compound is well within the capabilities of skilled artisans. For guidance, the reader is referred to Fingl & Woodbury, "*General Principles*," In: Goodman and Gilman's *The Pharmaceutical Basis of Therapeutics*, Chapter 1, pp. 1-46, latest edition, Pergamagon Press, and the references cited therein.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) *Allergy* 50(21 Suppl):6-9, discussion 34-38 and Tumas et al., (2001), *J. Allergy Clin. Immunol.* 107(6): 1025-1033. Suitable animal models of allergic rhinitis are described in Szelenyi et al., (2000), *Arzneimittelforschung* 50(11):1037-42; Kawaguchi et al., (1994), *Clin. Exp. Allergy* 24(3):238-244 and Sugimoto et al., (2000), *Immunopharmacology* 48(1):I-7. Suitable animal models of allergic conjunctivitis are described in Carreras et al., (1993), *Br. J. Opthalmol.* 77(8):509-514; Saiga et al., (1992), *Ophthalmic Res.* 24(1):45-50; and Kunert et al., (2001), *Invest. Opthalmol. Vis. Sci.* 42(11):2483-2489. Suitable animal models of systemic mastocytosis are described in O'Keefe et al., (1987), *J. Vet. Intern. Med.* 1(2):75-80 and Bean-Knudsen et al., (1989), *Vet. Pathol.* 26(1):90-92. Suitable animal models of hyper IgE syndrome are described in Claman et al., (1990), *Clin. Immunol. Immunopathol.* 56(1):46-53. Suitable animal models of B-cell lymphoma are described in Hough et al., (1998), *Proc. Natl. Acad. Sci. USA* 95:13853-13858 and Hakim et al., (1996), *J. Immunol.* 157(12):5503-5511. Suitable animal models of atopic disorders such as atopic dermatitis, atopic eczema and atopic asthma are described in Chan et al., (2001), *J. Invest. Dermatol.* 117(4):977-983 and Suto et al., (1999), *Int. Arch. Allergy Immunol.* 120(Suppl 1):70-75. Suitable animal models of transplant rejection, such as models of HVGR are described in O'Shea et al., (2004), *Nature Reviews Drug Discovery* 3:555-564; Cetkovic-Curlje & Tibbles, (2004), *Current Pharmaceutical Design* 10:1767-1784; and Chengelian et al., (2003), *Science* 302:875-878. Ordinarily skilled artisans can routinely adapt such information to determine dosages suitable for human administration.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The foregoing disclosure pertaining to the dosage requirements for the 2,4-substituted pyrimidinediamine compounds is pertinent to dosages required for prodrugs, with the realization, apparent to the skilled artisan, that the amount of prodrug(s) administered will also depend upon a variety of factors, including, for example, the bioavailability of the particular prodrug(s) the conversation rate and efficiency into active drug compound under the selected route of administration, etc. Determination of an effective dosage of prodrug(s) for a particular use and mode of administration is well within the capabilities of those skilled in the art.

Effective dosages can be estimated initially from in vitro activity and metabolism assays. For example, an initial dosage of prodrug for use in animals can be formulated to achieve a circulating blood or serum concentration of the metabolite active compound that is at or above an $IC_{50}$ of the particular compound as measured in as in vitro assay, such as the in vitro CHMC or BMMC and other in vitro assays described in U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO2004/014382), U.S. application Ser. No. 10/903,263 filed Jul. 30, 2004 (US2005-0234049A1) and international application Serial No. PCT/US2004/24716 (WO005/016893). Calculating dosages to achieve such circulating blood or serum concentrations taking into account the bioavailability of the particular prodrug via the desired route of administration is well within the capabilities of skilled artisans. For guidance, the reader is referred to Fingl & Woodbury, "General Principles," In: Goodman and Gilman's *The Pharmaceutical Basis of Therapeutics*, Chapter 1, pp. 146, latest edition, Pagamonon Press, and the references cited therein.

Also provided are kits for administration of the 2,4-substituted pyrimidinediamine, prodrug thereof or pharmaceutical formulations comprising the compound, that may include a dosage amount of at least one 2,4-pyrimidinediamine or a composition comprising at least one 2,4-pyrimidinediamine as disclosed herein. Kits may further comprise suitable packaging and/or instructions for use of the compound. Kits may also comprise a means for the delivery of the at least one 2,4-pyrimidinediamine or compositions comprising at least one 2,4-substituted pyrimidinediamine, such as an inhaler, spray dispenser (e.g. nasal spray), syringe for injection or pressure pack for capsules, tables, suppositories, or other device as described herein.

Additionally, the compounds of the present invention can be assembled in the form of kits. The kit provides the compound and reagents to prepare a composition for administration. The composition can be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In one embodiment, the therapeutic agents are immunosuppressant or anti-allergen compounds. These compounds can be provided in a separate form, or mixed with the compounds of the present invention.

The kits will include appropriate instructions for preparation and administration of the composition, side effects of the compositions, and any other relevant information. The instructions can be in any suitable format, including, but not limited to, printed matter, videotape, computer readable disk, or optical disc.

In one embodiment, this invention provides a kit comprising a compound selected from the compounds of this invention, packaging, and instructions for use.

Kits may also be provided that contain sufficient dosages of the 2,4-pyrimidinediamine or composition to provide effective treatment for an individual for an extended period, such as a week, 2 weeks, 3, weeks, 4 weeks, 6 weeks or 8 weeks or more.

It will be appreciated by one of skill in the art that the embodiments summarized above may be used together in any suitable combination to generate additional embodiments not expressly recited above, and that such embodiments are considered to be part of the present invention.

F. General Synthesis of the Compounds of the Invention

The 2,4-pyrimidinediamine compounds and prodrugs of the invention can be synthesized via a variety of different synthetic routes using commercially available starting materials and/or starting materials prepared by conventional synthetic methods. Suitable exemplary methods that can be routinely adapted to synthesize the 2,4-pyrimidinediamine compounds and prodrugs of the invention are found in U.S. Pat. No. 5,958,935, the disclosure of which is incorporated herein by reference. Specific examples describing the synthesis of numerous 2,4-pyrimidinediamine compounds and prodrugs, as well as intermediates therefore, are described in the U.S. publication No. US2004/0029902A1, the contents of which are incorporated herein by reference. Suitable exemplary methods that can be routinely used and/or adapted to synthesize active 2,4-pyrimidinediamine compounds can also be found in WO 03/063794, U.S. application Ser. No. 10/631,029 filed Jul. 29, 2003, WO2004/014382, U.S. publication No. 2005-0234049 A1, and WO005/016893, the disclosures of which are incorporated herein by reference. All of the compounds described herein (including prodrugs) can be prepared by routine adaptation of these methods.

Exemplary synthetic methods for the 2,4-substituted pyrimidinediamines described herein are described below. Those of skill in the art will also be able to readily adapt these methods for the synthesis of specific 2,4-substituted pyrimidinediamines as described herein.

A variety of exemplary synthetic routes that can be used to synthesize the 2,4-pyrimidinediamine compounds of the invention are described in Schemes I-VII, below. These methods can be routinely adapted to synthesize the 2,4-pyrimidinediamine compounds and prodrugs described herein.

In one exemplary embodiment, the compounds can be synthesized from substituted or unsubstituted uracils as illustrated in Scheme I, below:

typically obtained. The regioselectivity of the reaction can also be controlled by adjusting the solvent and other synthetic conditions (such as temperature), as is well-known in the art.

The reactions depicted in Scheme I may proceed more quickly when the reaction mixtures are heated via microwave. When heating in this fashion, the following conditions can be used: heat to 175° C. in ethanol for 5-20 min. in a Smith Reactor (Personal Chemistry, Uppsala, Sweden) in a sealed tube (at 20 bar pressure).

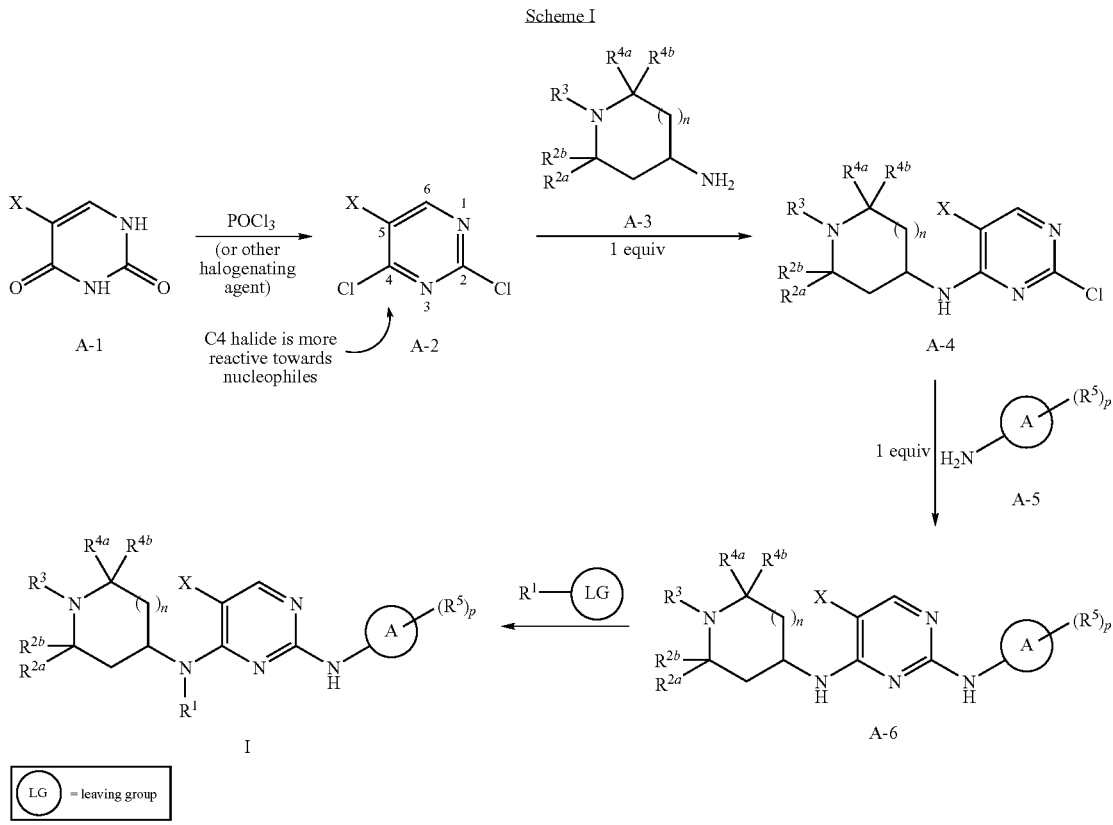

In Scheme I, ring A, $R^1$, $R^{2a}$, $R^{2b}$, $R^3$, $R^{4a}$, $R^{4b}$, $(R^5)_p$, n, and X are as defined herein. According to Scheme I, uracil A-1 is dehalogenated at the 2- and 4-positions using a standard dehydrating-halogenating agent such as POCl3 (or other standard halogenating agent) under standard conditions to yield 2,4 dichloropyrimidine A-2. Depending upon the X substituent, in pyrimidinediamine A-2, the chloride at the C4 position is more reactive towards nucleophiles than the chloride at the C2 position. This differential reactivity can be exploited by first reacting 2,4 dichloropyrimidine A-2 with one equivalent of amine A-3, yielding 4N-substituted-2-chloro-4-pyrimidineamine A-4, followed by amine A-5 to yield a 2,4-pyrimidinediamine derivative A-6, where N4 nitrogen can be selectively alkylated e.g. using an alkylating agent employing a leaving group "LG", to give compounds of formula I.

Typically, the C4 halide is more reactive towards nucleophiles, as illustrated in Scheme I. However, as will be recognized by skilled artisans, the identity of the X substituent may alter this reactivity. For example, when X is trifluoromethyl, a 50:50 mixture of 4N-substituted-4-pyrimidineamine A-4 and the corresponding 2N-substituted-2-pyrimidineamine is The uracil A-1 starting materials can be purchased from commercial sources or prepared using standard techniques of organic chemistry. Commercially available uracils that can be used as starting materials in Scheme I include, by way of example and not limitation, uracil (Aldrich #13,078-8; CAS Registry 66-22-8); 5 bromouracil (Aldrich #85,247-3; CAS Registry 51-20-7; 5 fluorouracil (Aldrich #85,847-1; CAS Registry 51-21-8); 5 iodouracil (Aldrich #85,785-8; CAS Registry 696-07-1); 5 nitrouracil (Aldrich #85,276-7; CAS Registry 611-08-5); 5 (trifluoromethyl)-uracil (Aldrich #22,327-1; CAS Registry 54-20-6). Additional 5-substituted uracils are available from General Intermediates of Canada, Inc., Edmonton, Calif. and/or Interchim, Cedex, France, or can be prepared using standard techniques. Myriad textbook references teaching suitable synthetic methods are provided infra.

Amines A-3 and A-5 can be purchased from commercial sources or, alternatively, can be synthesized utilizing standard techniques. For example, suitable amines can be synthesized from nitro precursors using standard chemistry. See also Vogel, 1989, Practical Organic Chemistry, Addison Wesley Longman, Ltd. and John Wiley & Sons, Inc. Representative examples of commercially available A-3 amines include, but are not limited to, the structures shown in the following Table V.

TABLE V

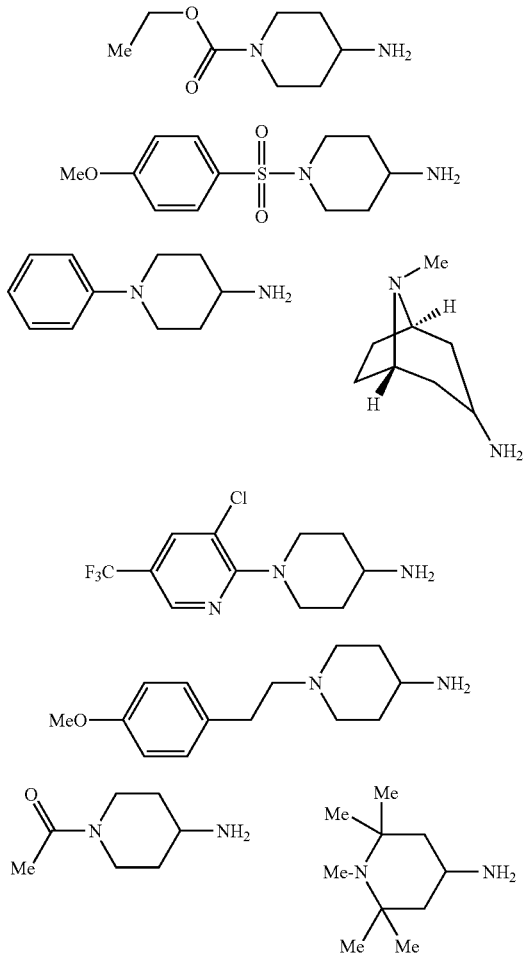

TABLE V-continued

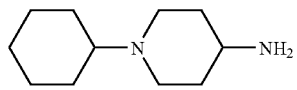

Skilled artisans will recognize that in some instances, amines A-3 and A-5 and/or substituent X on uracil A-1 may include functional groups that require protection during synthesis. The exact identity of any protecting group(s) used will depend upon the identity of the functional group being protected, and will be apparent to those of skill in the art. Guidance for selecting appropriate protecting groups, as well as synthetic strategies for their attachment and removal, can be found, for example, in Greene & Wuts, *Protective Groups in Organic Synthesis*, 3d Edition, John Wiley & Sons, Inc., New York (1999) and the references cited therein (hereinafter "Greene & Wuts").

Thus, protecting group refers to a group of atoms that, when attached to a reactive functional group in a molecule, mask, reduce or prevent the reactivity of the functional group. Typically, a protecting group can be selectively removed as desired during the course of a synthesis. Examples of protecting groups can be found in Greene and Wuts, as mentioned above, and additionally, in Harrison et al., Compendium of Synthetic Organic Methods, Vols. 1 8, 1971 1996, John Wiley & Sons, NY. Representative amino protecting groups include, but are not limited to, formyl, acetyl, trifluoroacetyl, benzyl, benzyloxycarbonyl ("CBZ"), tert butoxycarbonyl ("Boc"), trimethylsilyl ("TMS"), 2 trimethylsilyl ethanesulfonyl ("TES"), trityl and substituted trityl groups, allyloxycarbonyl, 9 fluorenylmethyloxycarbonyl ("FMOC"), nitro veratryloxycarbonyl ("NVOC") and the like. Representative hydroxyl protecting groups include, but are not limited to, those where the hydroxyl group is either acylated to form acetate and benzoate esters or alkylated to form benzyl and trityl ethers, as well as alkyl ethers, tetrahydropyranyl ethers, trialkylsilyl ethers (e.g., TMS or TIPPS groups) and allyl ethers.

A specific embodiment of Scheme I utilizing 5-fluorouracil (Aldrich #32,937-1) as a starting material is illustrated in Scheme Ia, below:

Scheme Ia

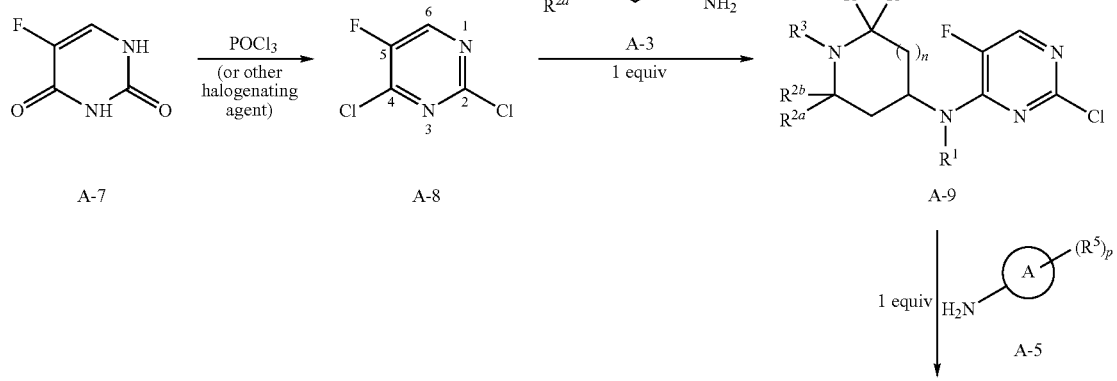

-continued

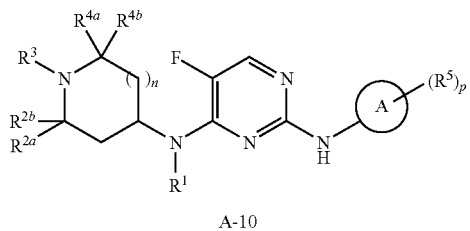

A-10

In Scheme Ia, ring A, $R^1$, $R^{2a}$, $R^{2b}$, $R^3$, $R^{4a}$, $R^{4b}$, $(R^5)_p$, and n are as previously defined for Scheme I. Asymmetric 2N,4N-disubstituted-5-fluoro-2,4-pyrimidinediamine A-10 can be obtained by reacting 2,4-dichloro-5-fluoropyrimidine A-8 with one equivalent of amine A-3 (to yield 2-chloro-N4-substituted-5-fluoro-4-pyrimidineamine A-9) followed by one or more equivalents of amine A-5.

In another exemplary embodiment, the 2,4 pyrimidinediamine compounds of the invention can be synthesized from substituted or unsubstituted cytosines as illustrated in Schemes IIa and IIb, below:

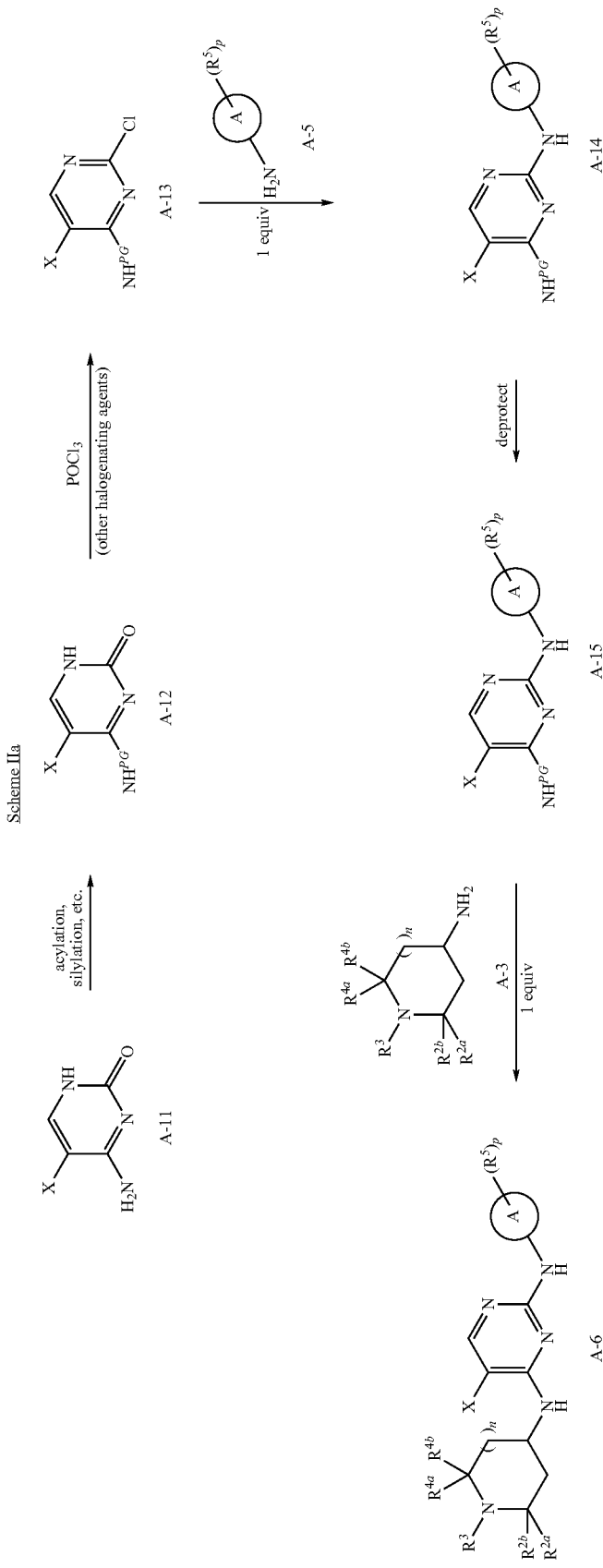

In Scheme IIa, ring A, $R^{2a}$, $R^{2b}$, $R^3$, $R^{4a}$, $R^{4b}$, $(R^5)_p$, n, and X are as previously defined for Scheme I and PG represents a protecting group. Referring to Scheme IIa, the C4 exocyclic amine of cytosine A-11 is first protected with a suitable protecting group PG to yield N4-protected cytosine A-12. For specific guidance regarding protecting groups useful in this context, see Vorbrüggen and Ruh-Pohlenz, 2001, Handbook of Nucleoside Synthesis, John Wiley & Sons, NY, pp. I-631 ("Vorbrüggen"). Protected cytosine A-12 is halogenated at the C2 position using a standard halogenation reagent under standard conditions to yield 2 chloro 4N protected 4 pyrimidineamine A-13. Reaction with amine A-5 gives A-14, which on deprotection of the C4 exocyclic amine, gives A-15. Reaction of A-15 with amine A-3 yields 2,4 pyrimidinediamine derivative A-6.

described, deprotected (in the case of N4 substituted cytosine A-19) and reacted with amine A-5 to yield a 2,4 pyrimidinediamine A-6.

Commercially-available cytosines that can be used as starting materials in Schemes IIa and IIb include, but are not limited to, cytosine (Aldrich #14,201-8; CAS Registry 71-30-7); N4 acetylcytosine (Aldrich #37,791-0; CAS Registry 14631-20-0); 5 fluorocytosine (Aldrich #27,159-4; CAS Registry 2022-85-7); and 5 (trifluoromethyl)-cytosine. Other suitable cytosines useful as starting materials in Schemes IIa are available from General Intermediates of Canada, Inc., Edmonton, Calif. and/or Interchim, Cedex, France, or can be

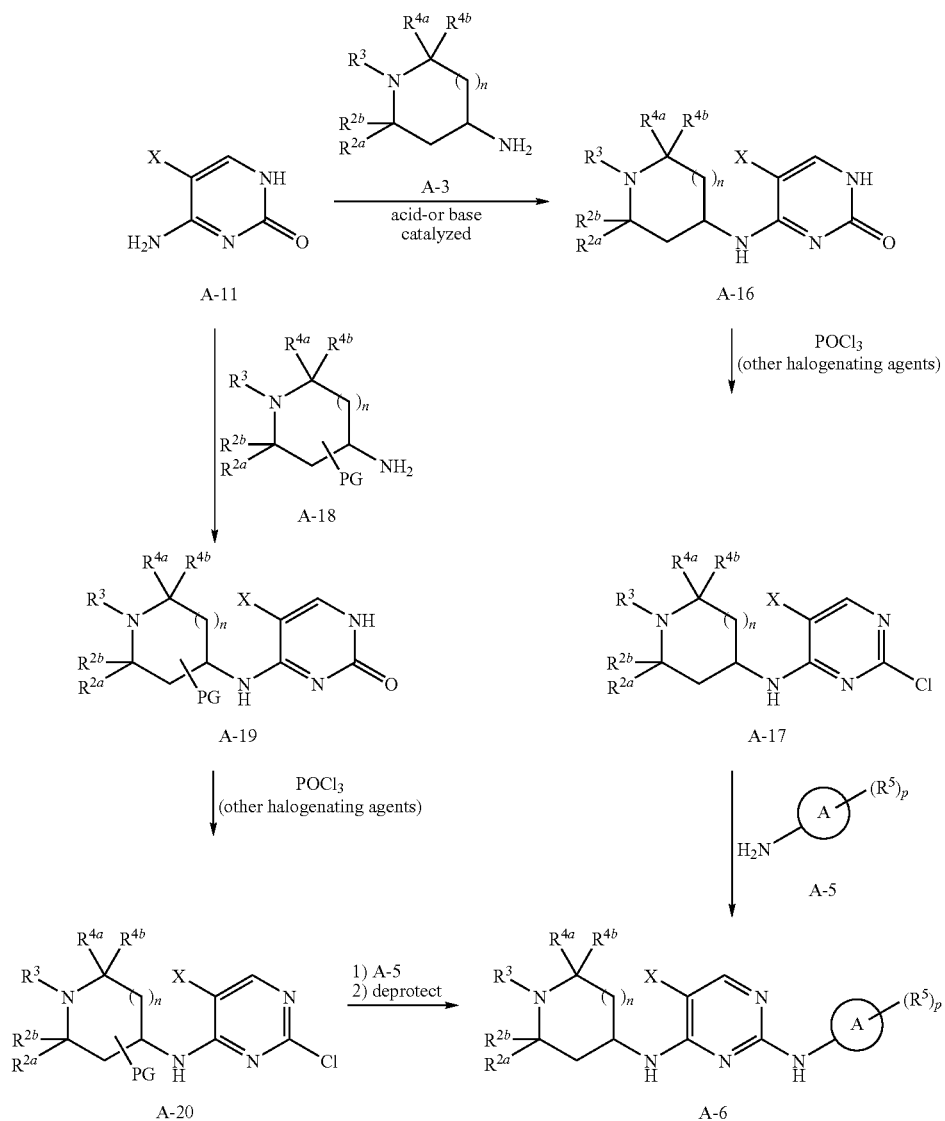

In Scheme IIb, ring A, $R^{2a}$, $R^{2b}$, $R^3$, $R^{4a}$, $R^{4b}$, $(R^5)_p$, n, and X are as previously defined for Scheme I and PG represents a protecting group. Referring to Scheme IIb, cytosine A-11 can be reacted with amine A-3 or protected amine A-18 to yield N4 substituted cytosine A-16 or A-19, respectively. These substituted cytosines can then be halogenated as previously prepared using standard techniques. Myriad textbook references teaching suitable synthetic methods are provided infra.

In still another exemplary embodiment, the 2,4 pyrimidinediamine compounds of the invention can be synthesized from substituted or unsubstituted 2 amino 4 pyrimidinols as illustrated in Scheme III, below:

Scheme III

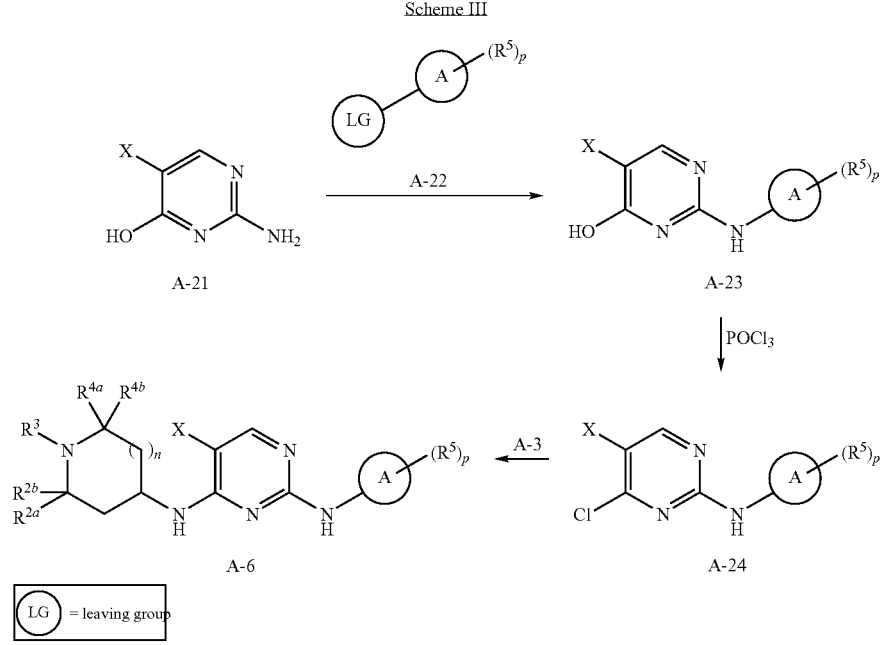

In Scheme III, ring A, $R^{2a}$, $R^{2b}$, $R^3$, $R^{4a}$, $R^{4b}$, $(R^5)_p$, n, and X are as previously defined for Scheme I and LG is a leaving group as discussed in more detail in connection with Scheme IV, infra. Referring to Scheme III, 2 amino 4 pyrimidinol A-21 is reacted with arylating agent A-22 to yield N2 substituted 4 pyrimidinol A-23, which is then halogenated as previously described to yield N2 substituted 4 halo 2 pyrimidineamine A-24. Further reaction with amine A-3 affords a 2,4 pyrimidinediamine derivative A-6.

Suitable commercially-available 2 amino 4 pyrimidinols A-21 that can be used as starting materials in Scheme III are available from General Intermediates of Canada, Inc., Edmonton, Calif. and/or Interchim, Cedex, France, or can be prepared using standard techniques. Myriad textbook references teaching suitable synthetic methods are provided infra.

Alternatively, the 2,4-pyrimidinediamine compounds of the invention can be prepared from substituted or unsubstituted 4 amino 2 pyrimidinols as illustrated in Scheme IV, below:

Scheme IV

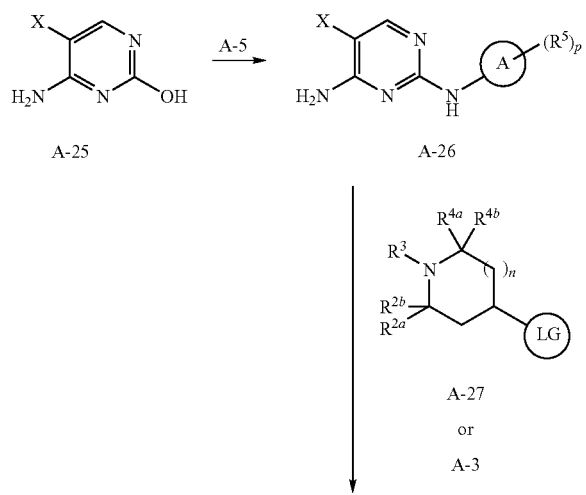

-continued

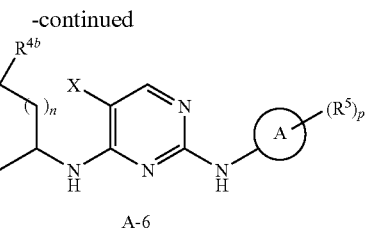

In Scheme IV, ring A, $R^{2a}$, $R^{2b}$, $R^3$, $R^{4a}$, $R^{4b}$, $(R^5)_p$, n, and X are as previously defined for Scheme I. Referring to Scheme IV, the C2-hydroxyl of 4 amino 2 pyrimidinol A-25 is more reactive towards nucleophiles than the C4 amino such that reaction with amine A-5 yields N2 substituted 2,4 pyrimidinediamine A-26. Subsequent reaction with compound A-27, which includes a suitable leaving group, or amine A-3 yields a 2,4 pyrimidinediamine derivative A-6. Compound A-27 may include virtually any leaving group that can be displaced by the C4 amino of N2 substituted 2,4 pyrimidinediamine A-26. Suitable leaving groups include, but are not limited to, halogens, methanesulfonyloxy (mesyloxy; "OMs"), trifluoromethanesulfonyloxy ("OTf") and p-toluenesulfonyloxy (tosyloxy; "OTs"), benzene sulfonyloxy ("besylate") and m-nitro benzene sulfonyloxy ("nosylate"). Other suitable leaving groups will be apparent to those of skill in the art.

Substituted 4-amino-2-pyrimidinol starting materials can be obtained commercially or synthesized using standard techniques. Myriad textbook references teaching suitable synthetic methods are provided infra.

In still another exemplary embodiment, the 2,4 pyrimidinediamine compounds of the invention can be prepared from 2 chloro 4 aminopyrimidines or 2 amino 4 chloropyrimidines as illustrated in Scheme V, below:

Scheme V

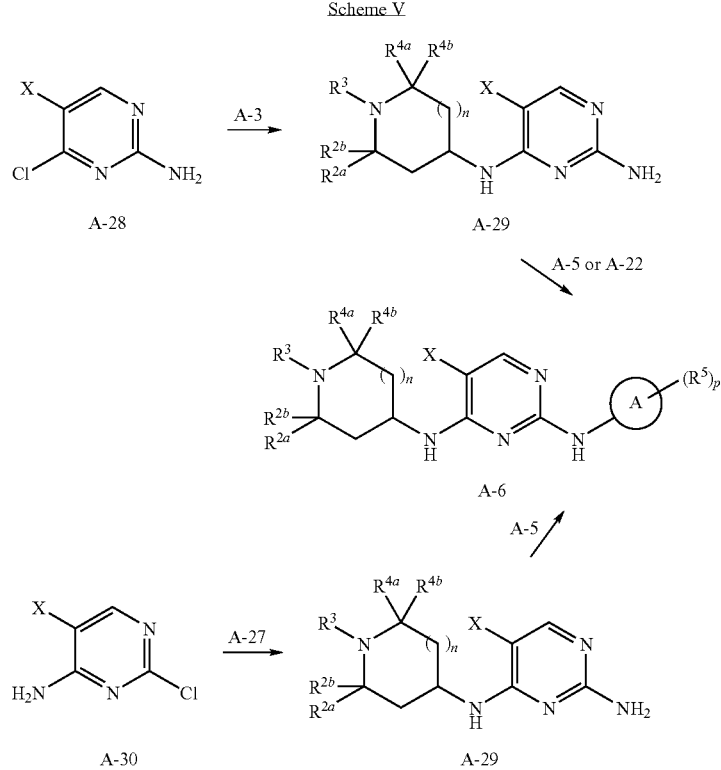

In Scheme V, ring A, $R^{2a}$, $R^{2b}$, $R^3$, $R^{4a}$, $R^{4b}$, $(R^5)_p$, n, and X are as defined for Scheme I and leaving group is as defined for Scheme IV. Referring to Scheme V, 2 amino 4 chloropyrimidine A-28 is reacted with amine A-3 to yield 4N substituted 2,4 pyrimidinediamine A-29 which, following reaction with compound A-22 or amine A-5, yields a N2,N4-2,4 pyrimidinediamine derivative A-6. Alternatively, 2 chloro 4 amino-pyrimidine A-30 can be reacted with compound A-27 to give compound A-29 which on reaction with amine A-5 yields A-6.

A variety of pyrimidines A-28 and A-30 suitable for use as starting materials in Scheme V are commercially available from General Intermediates of Canada, Inc., Edmonton, Calif. and/or Interchim, Cedex, France, or can be prepared using standard techniques. Myriad textbook references teaching suitable synthetic methods are provided infra.

Alternatively, 4-chloro-2-pyrimidineamines A-28 can be prepared as illustrated in Scheme Va:

Scheme Va

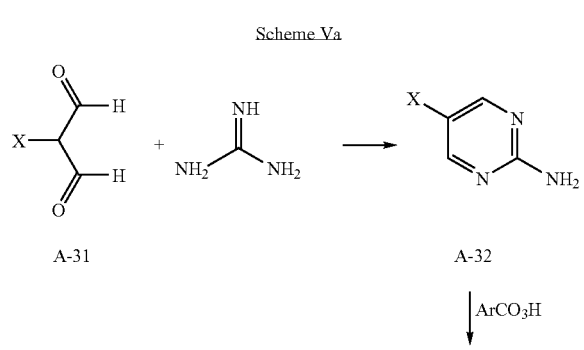

-continued

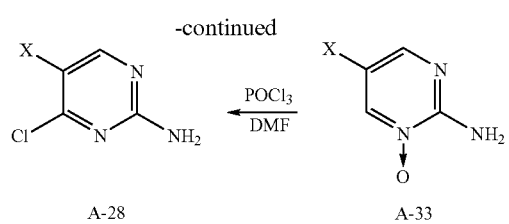

In Scheme Va, X is as previously defined for Scheme I. In Scheme Va, dialdehyde A-31 is reacted with guanidine to yield 2-pyrimidineamine A-32. Reaction with a peracid such as m-chloroperbenzoic acid, trifluoroperacetic acid or urea hydrogen peroxide complex yields N-oxide A-33, which is then halogenated to give 4-chloro-2-pyrimidineamine A-28. The corresponding 4-halo-2-pyrimidineamines can be obtained by using suitable halogenation reagents.

In yet another exemplary embodiment, the 2,4 pyrimidinediamine compounds of the invention can be prepared from substituted or unsubstituted uridines as illustrated in Scheme VI, below:

Scheme VI

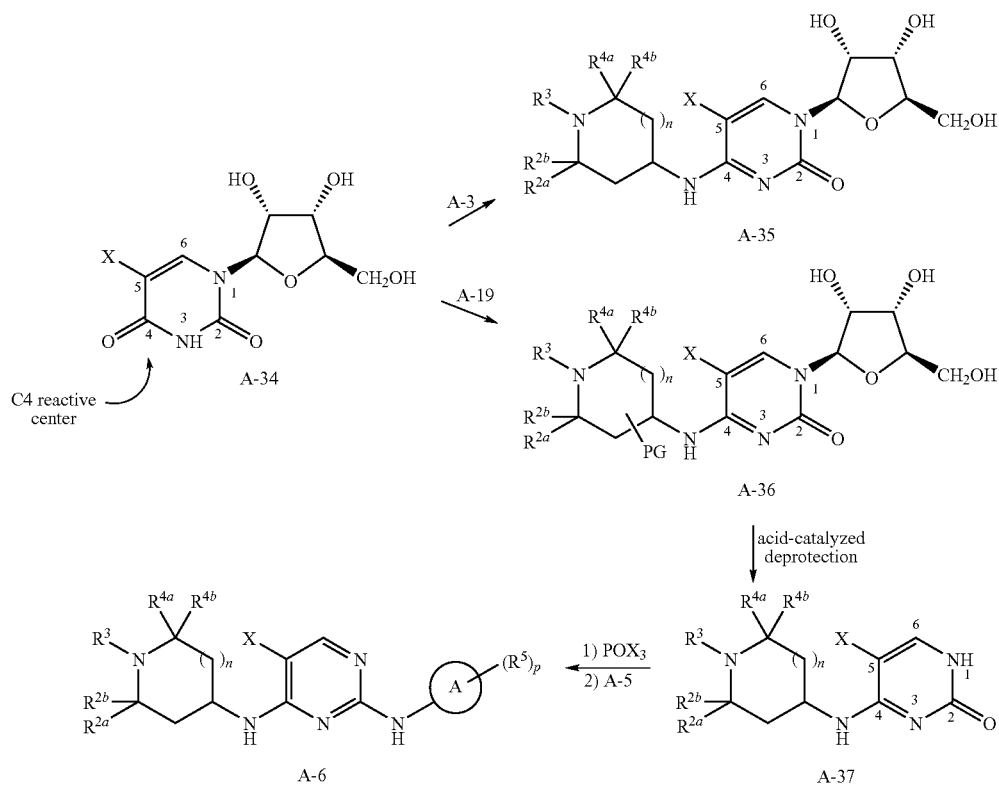

In Scheme VI, ring A, $R^{2a}$, $R^{2b}$, $R^3$, $R^{4a}$, $R^{4b}$, $(R^5)_p$, n, and X are as previously defined for Scheme I and PG represents a protecting group, as discussed in connection with Scheme IIb. According to Scheme VI, uridine A-34 has a C4 reactive center such that reaction with amine A-3 or protected amine A-19 yields N4 substituted cytidine A-35 or A-36, respectively. Acid-catalyzed deprotection of N4 substituted A-35 or A-36 (when "PG" represents an acid-labile protecting group) yields N4 substituted cytosine A-37, which can be subsequently halogenated at the C2 position and reacted with amine A-5 to yield a 2,4 pyrimidinediamine derivative A-6.

Cytidines may also be used as starting materials in an analogous manner, as illustrated in Scheme VII, below:

Scheme VII

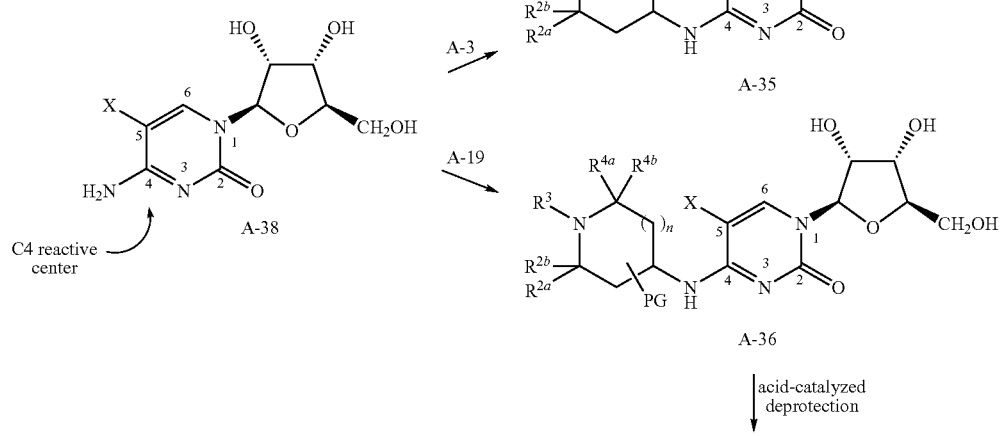

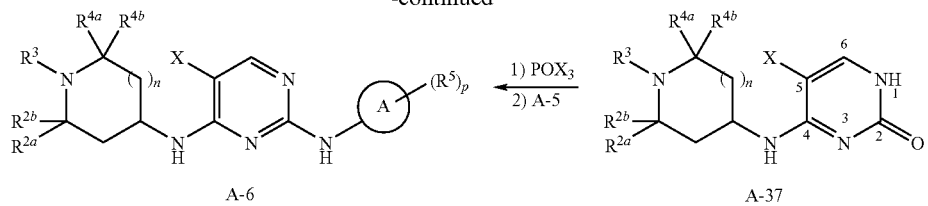

In Scheme VII, ring A, $R^1$, $R^{2a}$, $R^{2b}$, $R^3$, $R^{4a}$, $R^{4b}$, $(R^5)_p$, n, and X are as previously defined in Scheme I and PG represents a protecting group as discussed above. Referring to Scheme VII, like uridine A-34, cytidine A-38 has a C4 reactive center such that reaction with amine A-3 or protected amine A-19 yields N4 substituted cytidine A-35 or A-36, respectively. These cytidines A-35 and A-36 are then treated as previously described for Scheme VI to yield a 2,4 pyrimidinediamine derivative A-6.

Although Schemes VI and VII are exemplified with ribosylnucleosides, skilled artisans will appreciate that the corresponding 2' deoxyribo and 2',3' dideoxyribo nucleosides, as well as nucleosides including sugars or sugar analogs other than ribose, would also work.

Numerous uridines and cytidines useful as starting materials in Schemes VI and VII are known in the art, and include, by way of example and not limitation, 5 trifluoromethyl-2' deoxycytidine (Chem. Sources #ABCR F07669; CAS Registry 66,384-66-5); 5 bromouridine (Chem. Sources Int'l 2000; CAS Registry 957-75-5); 5 iodo 2' deoxyuridine (Aldrich #I-775-6; CAS Registry 54-42-2); 5 fluorouridine (Aldrich #32,937-1; CAS Registry 316-46-1); 5 iodouridine (Aldrich #85,259-7; CAS Registry 1024-99-3); 5 (trifluoromethyl)uridine (Chem. Sources Int'l 2000; CAS Registry 70-00-8); 5 trifluoromethyl 2' deoxyuridine (Chem. Sources Int'l 2000; CAS Registry 70-00-8). Additional uridines and cytidines that can be used as starting materials in Schemes VI and VII are available from General Intermediates of Canada, Inc., Edmonton, Calif. and/or Interchim, Cedex, France, or can be prepared using standard techniques. Myriad textbook references teaching suitable synthetic methods are provided infra.

Although many of the synthetic schemes discussed above do not illustrate the use of protecting groups, skilled artisans will recognize that in some instances certain substituents, such as, for example, $R^2$ and/or $R^4$, may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the above-described methods. Alternatively, such prodrugs can be prepared by reacting a suitably protected 2,4-pyrimidinediamine 6 with a suitable progroup. Conditions for carrying out such reactions and for deprotecting the product to yield a prodrugs as described herein are well-known.

Myriad references teaching methods useful for synthesizing pyrimidines generally, as well as starting materials described in Schemes I-VII, are known in the art. For specific guidance, the reader is referred to Brown, D. J., "The Pyrimidines", in The Chemistry of Heterocyclic Compounds, Volume 16 (Weissberger, A., Ed.), 1962, Interscience Publishers, (A Division of John Wiley & Sons), New York ("Brown I"); Brown, D. J., "The Pyrimidines", in The Chemistry of Heterocyclic Compounds, Volume 16, Supplement I (Weissberger, A. and Taylor, E. C., Ed.), 1970, Wiley-Interscience, (A Division of John Wiley & Sons), New York (Brown II"); Brown, D. J., "The Pyrimidines", in The Chemistry of Heterocyclic Compounds, Volume 16, Supplement II (Weissberger, A. and Taylor, E. C., Ed.), 1985, An Interscience Publication (John Wiley & Sons), New York ("Brown III"); Brown, D. J., "The Pyrimidines" in The Chemistry of Heterocyclic Compounds, Volume 52 (Weissberger, A. and Taylor, E. C., Ed.), 1994, John Wiley & Sons, Inc., New York, pp. I-1509 (Brown IV"); Kenner, G. W. and Todd, A., in Heterocyclic Compounds, Volume 6, (Elderfield, R. C., Ed.), 1957, John Wiley, New York, Chapter 7 (pyrimidines); Paquette, L. A., Principles of Modern Heterocyclic Chemistry, 1968, W. A. Benjamin, Inc., New York, pp. I-401 (uracil synthesis pp. 313, 315; pyrimidinediamine synthesis pp. 313-316; amino pyrimidinediamine synthesis pp. 315); Joule, J. A., Mills, K. and Smith, G. F., Heterocyclic Chemistry, 3rd Edition, 1995, Chapman and Hall, London, UK, pp. 1-516; Vorbrüggen, H. and Ruh-Pohlenz, C., Handbook of Nucleoside Synthesis, John Wiley & Sons, New York, 2001, pp. I-631 (protection of pyrimidines by acylation pp. 90-91; silylation of pyrimidines pp. 91-93); Joule, J. A., Mills, K. and Smith, G. F., Heterocyclic Chemistry, 4th Edition, 2000, Blackwell Science, Ltd, Oxford, UK, pp. I-589; and Comprehensive Organic Synthesis, Volumes I-9 (Trost, B. M. and Fleming, I., Ed.), 1991, Pergamon Press, Oxford, UK.

Those of skill in the art will appreciate that the 2,4-pyrimidinediamine compounds described herein may include functional groups that can be masked with progroups to create prodrugs. Such prodrugs are usually, but need not be, pharmacologically inactive until converted into their active drug form. Indeed, many of the 2,4-pyrimidinediamine compounds described in this invention include promoieties that are hydrolyzable or otherwise cleavable under conditions of use. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, 2,4-pyrimidinediamine compounds that include ester moieties can be considered prodrugs of their corresponding carboxylic acid, regardless of whether the ester form is pharmacologically active.

The mechanism by which the progroup(s) metabolizes is not critical, and can be caused by, for example, hydrolysis under the acidic conditions of the stomach, as described above, and/or by enzymes present in the digestive tract and/or tissues or organs of the body. Indeed, the progroup(s) can be selected to metabolize at a particular site within the body. For example, many esters are cleaved under the acidic conditions found in the stomach. Prodrugs designed to cleave chemically in the stomach to the active 2,4-pyrimidinediamine can employ progroups including such esters. Alternatively, the progroups can be designed to metabolize in the presence of enzymes such as esterases, amidases, lipolases, phosphatases including ATPases and kinase etc. Progroups including linkages capable of metabolizing in vivo are well known, and include, by way of example and not limitation, ethers, thioethers, silylethers, silylthioethers, esters, thioesters, carbonates, thiocarbonates, carbamates, thiocarbamates, ureas, thioureas, carboxamides, etc. In some instances, a "precursor" group that is oxidized by oxidative enzymes such as, for example, cytochrome P450 of the liver, to a metabolizable group, can be selected.

In the prodrugs, any available functional moiety can be masked with a progroup to yield a prodrug. Functional groups within the 2,4-pyrimidinediamine compounds that can be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, can be included in the prodrugs.

In some embodiments of the 2,4-pyrimidinediamine compounds and methods of using the compounds, the progroup(s) can be attached to any available primary or secondary amine, including, for example, the N2 nitrogen atom of the 2,4 pyrimidinediamine moiety, the N4 nitrogen atom of the 2,4 pyrimidinediamine moiety, and/or a primary or secondary nitrogen atom included in a substituent on the 2,4 pyrimidinediamine compound.

In particular embodiments of the 2,4-pyrimidinediamine compounds and methods of using the compounds, the prodrugs described herein are 2,4-pyrimidinediamine compounds that are substituted at the N4 nitrogen of the 2,4 pyrimidinediamine moiety with a substituted or unsubstituted nitrogen containing bicyclic ring that includes at least one progroup at one or more of: the nitrogen atom(s) of the bicyclic ring, the N2 nitrogen of the 2,4 pyrimidinediamine moiety and/or the N4 nitrogen of the 2,4 pyrimidinediamine moiety.

As noted above, the identity of the progroup is not critical, provided that it can be metabolized under the desired conditions of use, for example under the acidic conditions found in the stomach and/or by enzymes found in vivo, to yield a the biologically active group, e.g., the 2,4-substituted pyrimidinediamines as described herein. Thus, skilled artisans will appreciate that the progroup can comprise virtually any known or later discovered hydroxyl, amine or thiol protecting group. Non-limiting examples of suitable protecting groups can be found, for example, in Protective Groups in Organic Synthesis, Greene & Wuts, 2nd Ed., John Wiley & Sons, New York, 1991 (especially pages 10-142 (alcohols, 277-308 (thiols) and 309-405 (amines) the disclosure of which is incorporated herein by reference).

Additionally, the identity of the progroup(s) can also be selected so as to impart the prodrug with desirable characteristics. For example, lipophilic groups can be used to decrease water solubility and hydrophilic groups can be used to increase water solubility. In this way, prodrugs specifically tailored for selected modes of administration can be obtained. The progroup can also be designed to impart the prodrug with other properties, such as, for example, improved passive intestinal absorption, improved transport mediated intestinal absorption, protection against fast metabolism (slow release prodrugs), tissue selective delivery, passive enrichment in target tissues, targeting specific transporters, etc. Groups capable of imparting prodrugs with these characteristics are well known, and are described, for example, in Ettmayer et al., 2004, J. Med. Chem. 47(10):2393-2404, the disclosure of which is incorporated by reference. All of the various groups described in these references can be utilized in the prodrugs described herein.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In the examples below as well as throughout the application, the following abbreviations have the following meanings. If not defined, the terms have their generally accepted meanings.

mL=milliliter
s=singlet
d=doublet
t=triplet
q=quartet
m=multiplet
dd=doublet of doublets
br=broad
nM=nanomolar
µg=microgram
ng=nanogram
MS=mass spectrum or mass spectrometry
LC=liquid chromatography
DMSO=dimethylsulfoxide
µL=microliter
mM=millimolar
rpm=revolutions per minute
LAH=lithium aluminum hydride
HEPES=N-(2-hydroxyethyl)-piperazine-N'-2-ethanesulfonic acid
EGTA=Ethylene glycol-bis(beta-aminoethyl ether)-N,N,N',N'-tetraacetic acid
BRIJ-35=polyoxyethyleneglycol dodecyl ether detergent

A. Example 1

I-5: 5-Fluoro-N2-[4-(4-methylpiperazino)-3-trifluoromethyl]phenyl-N4-(1,2,2,6,6-pentamethylpiperidin-4-yl)-2,4-pyrimidinediamine 2-Fluoro-5-nitrobenzotrifluoride (2 g) and 1-methylpiperazine (2 mL) were dissolved in methanol (5 mL). The yellow solution was stirred at rt overnight. The reaction mixture was diluted with water (100 mL) and extracted with ethyl acetate (2×100 mL). The organic solutions were evaporated to give 2-(4-methyl piperazino)-5-nitrobenzotrifluoride.

2-(4-Methylpiperazino)-5-nitrobenzotrifluoride was dissolved in methanol (100 mL) and to the solution was added 10% Pd—C. The reaction mixture was reacted under hydrogen atmosphere (~40 psi) for 1 h. The catalyst was filtered off over cellite and washed with methanol. The filtrate was evaporated to give [4-(4-methylpiperazino)-3-trifluoromethyl]aniline (2.25 g, 91% in two steps). $^1$H NMR (DMSO-d6): δ 2.19 (s, 3H), 2.38 (br, 4H), 2.70 (t, J=4.5 Hz, 4H), 5.31 (br, 2H), 6.73 (dd, J=2.4, 8.7 Hz, 1H), 6.78 (d, J=2.7 Hz, 1H), 7.20 (d, J=8.1 Hz, 1H).

4-Amino-1,2,2,6,6-pentamethylpiperidine (1 g) and 2,6-dichloro-5-fluoropyrimidine (1.5 g) were dissolved in methanol (10 mL). The reaction solution was stirred at rt overnight. The reaction solution was evaporated and crystallized from ethyl acetate and hexanes to give 2-chloro-5-fluoro-N4-(1,2,2,6,6-pentamethylpiperidin-4-yl)-4-pyrimidineamine HCl salt (1.65 g, 93%). 1H NMR (DMSO-d6): δ 1.38 (s, 6H), 1.48 (s, 6H), 2.02 (m, 4H), 2.68 (d, J=4.8 Hz, 3H), 4.33 (br, 1H), 8.10 (d, J=3.3 Hz, 1H), 8.32 (d, J=6.9 Hz, 1H), 9.66 (br, 1H).

2-Chloro-5-fluoro-N4-(1,2,2,6,6-pentamethylpiperidin-4-yl)-4-pyrimidineamine (300 mg) and [4-(4-methylpiperazino)-3-trifluoromethyl]aniline (300 mg) were suspended in isopropanol (1 mL) and TFA (5 drops). The solution was heated at 100° C. overnight, then cooled to room temperature. The solution was evaporated and purified by flash column chromatography (2.0 M NH$_3$/MeOH in dichloromethane=2, 4, 6, 10%) to give 5-fluoro-N2-[4-(4-methylpiperazino)-3-trifluoromethyl]phenyl-N4-(1,2,2,6,6-pentamethylpiperidin-4-yl)-2,4-pyrimidinediamine (440 mg, 84%). $^1$H NMR (DMSO-d6): δ 1.04 (s, 6H), 1.07 (s, 6H), 1.44 (t, J=11.7 Hz, 2H), 1.68 (d, J=9.9 Hz, 2H), 2.18 (s, 3H), 2.20 (s, 3H), 2.41 (br, 4H), 2.76 (t, J=4.2 Hz, 4H), 4.29 (br, 1H), 7.16 (d, J=8.4 Hz, 1H), 7.32 (d, J=8.4 Hz, 1H), 7.75 (d, J=2.1 Hz, 1H), 7.84 (d, J=3.6 Hz, 1H), 8.07 (d, J=8.7 Hz, 1H), 9.13 (s, 1H); 19F NMR (282 MHz, DMSO-d6): δ–165.87, –59.89; LCMS: purity: 100%; MS (m/e): 524.43 (MH+).

The following compounds were made in a similar fashion to the example 1 or by methods described herein or known to skilled artisans.

I-1: 5-Fluoro-N2-[4-(4-methylpiperazino)phenyl]-N4-(1,2,2,6,6-pentamethylpiperidin-4-yl)-2,4-pyrimidinediamine LCMS: purity: 95.14%; MS (m/e): 456.63 (MH+); $^1$H NMR (DMSO-d$_6$): δ 1.067 (s, 6H), 1.074 (s, 6H), 1.45 (t, J=12.0 Hz, 2H), 1.68 (d, J=9.3 Hz, 2H), 2.19 (s, 3H), 2.20 (s, 3H), 2.42 (t, J=4.8 Hz, 4H), 2.98 (t, J=4.8 Hz, 4H), 4.34 (br, 1H), 6.74 (d, J=9.0 Hz, 2H), 7.06 (d, J=7.2 Hz, 1H), 7.50 (d, J=9.0 Hz, 2H), 7.76 (d, J=3.9 Hz, 1H), 8.70 (s, 1H); $^{19}$F NMR (282 MHz, DMSO-d$_6$): δ–167.90.

I-2: 5-Fluoro-N2-[3-(4-methylpiperazino)phenyl]N4-(1,2,2,6,6-pentamethylpiperidin-4-yl)-2,4-pyrimidinediamine LCMS: purity: 95%; MS (m/e): 456.30 (MH+); $^1$H NMR (DMSO-d$_6$): δ 1.07 (s, 12H), 1.46 (t, J=12.0 Hz, 2H), 1.69 (d, J=9.9 Hz, 2H), 2.18 (s, 3H), 2.20 (s, 3H), 2.42 (t, J=4.5 Hz, 4H), 3.05 (t, J=3.9 Hz, 4H), 4.36 (br, 1H), 6.46 (d, J=8.1 Hz, 1H), 6.87 (s, 1H), 6.94 (t, J=8.1 Hz, 1H), 7.12 (d, J=8.7 Hz, 1H), 7.58 (d, J=8.1 Hz, 1H), 7.80 (d, J=3.9 Hz, 1H), 8.71 (s, 1H); $^{19}$F NMR (282 MHz, DMSO-d$_6$): δ–166.98.

I-3: N2-[3-Chloro-4-(4-methylpiperazino)]phenyl-5-fluoro-N4-(1,2,2,6,6-pentamethylpiperidin-4-yl)-2,4-pyrimidinediamine LCMS: purity: 97.41%; MS (m/e): 490.10 (MH+); $^1$H NMR (DMSO-d$_6$): δ 1.07 (s, 12H), 1.45 (t, J=12.0 Hz, 2H), 1.67 (d, J=11.4 Hz, 2H), 2.18 (s, 3H), 2.21 (s, 3H), 2.45 (br, 4H), 2.85 (br, 4H), 4.32 (br, 1H), 6.95 (d, J=9.0 Hz, 1H), 7.16 (d, J=8.1 Hz, 1H), 7.57 (d, J=8.4 Hz, 1H), 7.72 (d, J=1.8 Hz, 1H), 7.82 (d, J=3.6 Hz, 1H), 8.98 (s, 1H); $^{19}$F NMR (282 MHz, DMSO-d$_6$): δ–166.42.

I-4: 5-Fluoro-N2-[3-methyl-4-(4-methylpiperazino) phenyl]-N4-(1,2,2,6,6-pentamethylpiperidin-4-yl)-2,4-pyrimidinediamine LCMS: purity: 100%; MS (m/e): 470.29 (MH+); $^1$H NMR (DMSO-d$_6$): δ 1.05 (s, 6H), 1.07 (s, 6H), 1.44 (t, J=12.0 Hz, 2H), 1.67 (d, J=8.4 Hz, 2H), 2.17 (s, 3H), 2.18 (s, 3H), 2.21 (s, 3H), 2.43 (br, 4H), 2.73 (t, J=4.5 Hz, 4H), 4.34 (br, 1H), 6.81 (d, J=8.7 Hz, 1H), 7.06 (d, J=7.5 Hz, 1H), 7.22 (d, J=2.4 Hz, 1H), 7.60 (dd, J=2.1, 8.4 Hz, 1H), 7.78 (d, J=3.9 Hz, 1H), 8.70 (s, 1H); $^{19}$F NMR (282 MHz, DMSO-d$_6$): δ–167.47.

I-6: N2-[2-(4-Ethylpiperazino)pyrid-5-yl]-5-fluoro-N4-(1,2,2,6,6-pentamethylpiperidin-4-yl)-2,4-pyrimidinediamine LCMS: purity: 99.58%; MS (m/e): 471.73 (MH+); $^1$H NMR (DMSO-d$_6$): δ 1.02 (s, 6H), 1.04 (t, 3H), 1.06 (s, 6H), 1.42 (t, J=12.3 Hz, 2H), 1.66 (d, J=8.7 Hz, 2H), 2.17 (s, 3H), 2.33 (q, J=7.2 Hz, 2H), 2.42 (t, J=4.8 Hz, 4H), 4.29 (br, 1H), 6.64 (d, J=9.0 Hz, 1H), 7.07 (d, J=7.8 Hz, 1H), 7.76 (d, J=3.3 Hz, 1H), 7.78 (d, J=2.1 Hz, 1H), 8.34 (d, J=2.7 Hz, 1H), 8.66 (s, 1H); $^{19}$F NMR (282 MHz, DMSO-d$_6$): δ–167.81.

I-7: 5-Fluoro-N2-[2-(4-methylpiperazino)-3-methylpyrid-5-yl]-N4-(1,2,2,6,6-pentamethylpiperidin-4-yl)-2,4-pyrimidinediamine LCMS: purity: 95.56%; MS (m/e): 471.26 (MH+); $^1$H NMR (DMSO-d$_6$): δ 1.03 (s, 6H), 1.06 (s, 6H), 1.43 (t, J=12.0 Hz, 2H), 1.66 (d, J=8.7 Hz, 2H), 2.17 (s, 6H), 2.21 (s, 3H), 2.43 (t, 4H), 2.92 (t, J=4.5 Hz, 4H), 4.33 (br, 1H), 7.11 (d, J=8.1 Hz, 1H), 7.62 (d, 1H), 7.79 (d, J=3.9 Hz, 1H), 8.41 (d, J=2.4 Hz, 1H), 8.77 (s, 1H); $^{19}$F NMR (282 MHz, DMSO-d$_6$): δ–167.12.

I-8: 5-Fluoro-N2-[2-(4-methylpiperazino)-4-methylpyrid-5-yl]-N4-(1,2,2,6,6-pentamethylpiperidin-4-yl)-2,4-pyrimidinediamine LCMS: purity: 98%; MS (m/e): 471.22 (MH+); $^1$H NMR (DMSO-d$_6$): δ 0.80 (s, 6H), 1.00 (s, 6H), 1.31 (t, J=12.9 Hz, 2H), 1.51 (d, J=9.6 Hz, 2H), 2.08 (s, 3H), 2.11 (s, 3H), 2.19 (s, 3H), 2.36 (t, J=4.5 Hz, 4H), 4.08 (br, 1H), 6.60 (s, 1H), 6.94 (d, J=7.8 Hz, 1H), 7.68 (d, J=3.9 Hz, 1H), 7.90 (s, 1H), 7.97 (s, 1H); $^{19}$F NMR (282 MHz, DMSO-d$_6$): δ–169.50.

I-9: N2-(4-Aminosulfonyl)phenyl-5-fluoro-N4-(1,2,2,6,6-pentamethylpiperidin-4-yl)-2,4-pyrimidinediamine LCMS: purity: 99.48%; MS (m/e): 436.87 (MH+); $^1$H NMR (DMSO-d$_6$): δ 1.40 (s, 6H), 1.48 (s, 6H), 2.04 (d, J=5.4 Hz, 4H), 2.71 (d, J=5.1 Hz, 3H), 4.47 (br, 1H), 7.19 (s, 2H), 7.65 (d, J=8.7 Hz, 2H), 7.78 (d, J=8.7 Hz, 2H), 8.05 (d, J=4.5 Hz, 1H), 8.23 (br, 1H), 9.57 (br, 1H), 9.92 (br, 1H); $^{19}$F NMR (282 MHz, DMSO-d$_6$): δ–163.24.

I-10: N2-(3-Aminosulfonyl)phenyl-5-fluoro-N4-(1,2,2,6,6-pentamethylpiperidin-4-yl)-2,4-pyrimidinediamine LCMS: purity: 89.05%; MS (m/e): 437.20 (MH+); $^1$H NMR (DMSO-d$_6$): δ 1.33 (s, 6H), 1.46 (s, 6H), 2.00 (d, J=7.8

Hz, 4H), 2.67 (d, J=4.8 Hz, 3H), 4.42 (m, 1H), 7.32 (s, 2H), 7.42 (d, J=4.5 Hz, 2H), 7.90 (m, 2H), 8.06 (d, J=3.3 Hz, 1H), 8.33 (br, 1H), 9.59 (br, 1H), 9.88 (br, 1H); $^{19}$F NMR (282 MHz, DMSO-d$_6$): δ−163.28.

I-11: N2-(3-Aminosulfonyl-4-methyl)phenyl-5-fluoro-N4-(1,2,2,6,6-pentamethylpiperidin-4-yl)-2,4-pyrimidinediamine LCMS: purity: 99.46%; MS (m/e): 451.20 (MH+); $^1$H NMR (DMSO-d$_6$): δ 1.29 (s, 6H), 1.46 (s, 6H), 2.02 (m, 4H), 2.52 (s, 3H), 2.66 (d, J=5.1 Hz, 3H), 4.37 (m, 1H), 7.24 (d, J=8.7 Hz, 1H), 7.34 (s, 2H), 7.78 (d, J=8.1 Hz, 1H), 7.89 (s, 1H), 8.10 (d, J=4.2 Hz, 1H), 8.69 (br, 1H), 9.80 (br, 1H), 10.11 (br, 1H); $^{19}$F NMR (282 MHz, DMSO-d$_6$): δ−162.54.

I-12: N2-(3,5-Dimethyl)phenyl-5-fluoro-N4-(1,2,2,6,6-pentamethylpiperidin-4-yl)-2,4-pyrimidinediamine LCMS: purity: 99.38%; MS (m/e): 386.18 (MH+); $^1$H NMR (DMSO-d$_6$): δ 1.05 (s, 6H), 1.06 (s, 6H), 1.45 (t, J=12.3 Hz, 2H), 1.66 (d, J=9.3 Hz, 2H), 2.18 (s, 9H), 4.36 (m, 1H), 6.48 (s, 1H), 7.08 (d, J=8.1 Hz, 1H), 7.24 (s, 2H), 7.81 (d, J=3.6 Hz, 1H), 8.72 (br, 1H); $^{19}$F NMR (282 MHz, DMSO-d$_6$): δ−166.83.

I-13: N2-(4-Aminosulfonyl)phenyl-5-methyl-N4-(1,2,2,6,6-pentamethylpiperidin-4-yl)-2,4-pyrimidinediamine LCMS: purity: 90.52%; MS (m/e): 432.98 (MH+); $^1$H NMR (DMSO-d$_6$): δ 1.10 (s, 6H), 1.12 (s, 6H), 1.51 (t, J=12.0 Hz, 2H), 1.73 (d, J=9.9 Hz, 2H), 1.91 (s, 3H), 2.21 (s, 3H), 4.46 (m, 1H), 6.24 (d, J=8.7 Hz, 1H), 7.10 (s, 2H), 7.57 (d, J=8.4 Hz, 2H), 7.67 (s, 1H), 7.89 (d, J=8.4 Hz, 2H), 9.29 (s, 1H).

I-14: N2-(3-Aminosulfonyl)phenyl-5-methyl-N4-(1,2,2,6,6-pentamethylpiperidin-4-yl)-2,4-pyrimidinediamine LCMS: purity: 87.94%; MS (m/e): 432.90 (MH+); $^1$H NMR (DMSO-d$_6$): δ 1.09 (s, 12H), 1.48 (t, J=11.4 Hz, 2H), 1.71 (d, J=11.4 Hz, 2H), 1.90 (s, 3H), 2.20 (s, 3H), 4.45 (m, 1H), 6.17 (d, J=7.8 Hz, 1H), 7.23 (s, 2H), 7.27 (m, 2H), 7.65 (s, 1H), 7.86 (s, 1H), 8.30 (d, 1H), 9.10 (s, 1H).

I-15: N2-(3-Aminosulfonyl-4-methyl)phenyl-5-methyl-N4-(1,2,2,6,6-pentamethylpiperidin-4-yl)-2,4-pyrimidinediamine LCMS: purity: 99.43%; MS (m/e): 446.98 (MH+); $^1$H NMR (DMSO-d$_6$): δ 1.09 (s, 6H), 1.42 (s, 6H), 1.90 (m, 4H), 4.44 (m, 1H), 6.12 (br, 1H), 7.09 (br, 1H), 7.20 (s, 2H), 7.63 (br, 1H), 7.93 (br, 2H), 8.19 (br, 1H), 8.97 (br, 1H).

I-16: 5-Methyl-N4-(1,2,2,6,6-pentamethylpiperidin-4-yl)-N2-(3,4,5-trimethoxy)phenyl-2,4-pyrimidinediamine LCMS: purity: 97.51%; MS (m/e): 444.11 (MH+); $^1$H NMR (DMSO-d$_6$): δ 1.39 (s, 6H), 1.40 (s, 6H), 1.77 (t, J=12.3 Hz, 2H), 1.90 (s, 3H), 2.04 (d, J=12.3 Hz, 2H), 2.74 (d, J=4.2 Hz, 3H), 3.59 (s, 3H), 3.71 (s, 6H), 4.54 (m, 1H), 6.48 (br, 1H), 7.00 (s, 2H), 7.67 (s, 1H), 8.49 (br, 1H), 8.54 (br, 1H).

I-17: N2-(3,5-Dimethyl)phenyl-5-methyl-N4-(1,2,2,6,6-pentamethylpiperidin-4-yl)-2,4-pyrimidinediamine LCMS: purity: 98.45%; MS (m/e): 382.21 (MH+); $^1$H NMR (DMSO-d$_6$): δ 1.06 (s, 12H), 1.45 (t, 2H), 1.67 (d, 2H), 1.88 (s, 3H), 2.18 (s, 9H), 4.47 (m, 1H), 5.98 (br, 1H), 6.45 (s, 1H), 7.26 (s, 2H), 7.61 (s, 1H), 8.46 (s, 1H).

I-18: N2-[4-(4-Ethylpiperazino)-3-methyl]phenyl-5-methyl-N4-(1,2,2,6,6-pentamethylpiperidin-4-yl)-2,4-pyrimidinediamine LCMS: purity: 97.97%; MS (m/e): 480.33 (MH+); $^1$H NMR (DMSO-d$_6$): δ 1.01 (t, J=6.9 Hz, 3H), 1.07 (s, 12H), 1.45 (t, J=12.9 Hz, 2H), 1.69 (d, J=11.7 Hz, 2H), 1.86 (s, 3H), 2.16 (s, 3H), 2.19 (s, 3H), 2.36 (q, J=7.5 Hz, 2H), 2.73 (br, 4H), 4.46 (br, 1H), 6.00 (d, 1H), 6.81 (d, J=8.4 Hz, 1H), 7.19 (s, 1H), 7.57 (s, 1H), 7.70 (d, J=7.2 Hz, 1H), 8.48 (s, 1H).

I-19: 5-Fluoro-N4-(1,2,2,6,6-pentamethylpiperidin-4-yl)-N2-(3,4,5-trimethoxy)phenyl-2,4-pyrimidinediamine LCMS: purity: 95.49%; MS (m/e): 447.92 (MH+); $^1$H NMR (DMSO-d$_6$): δ 1.02 (s, 6H), 1.05 (s, 6H), 1.41 (t, J=12.3 Hz, 2H), 1.65 (d, J=12.0 Hz, 2H), 2.16 (s, 3H), 3.57 (s, 3H), 3.70 (s, 6H), 4.32 (m, 1H), 7.01 (s, 2H), 7.06 (d, J=9.0 Hz, 1H), 7.80 (d, J=3.6 Hz, 1H), 8.61 (s, 1H); $^{19}$F NMR (282 MHz, DMSO-d$_6$): δ−166.67.

I-20: N2-(3-Chloro-4-methoxy)phenyl-5-fluoro-N4-(1,2,2,6,6-pentamethylpiperidin-4-yl)-2,4-pyrimidinediamine LCMS: purity: 95.99%; MS (m/e): 421.89 (MH+); $^1$H NMR (DMSO-d$_6$): δ 1.06 (s, 12H), 1.44 (t, J=11.7 Hz, 2H), 1.67 (d, J=10.5 Hz, 2H), 2.17 (s, 3H), 3.75 (s, 3H), 4.35 (m, 1H), 6.93 (d, J=9.0 Hz, 1H), 7.14 (d, J=8.4 Hz, 1H), 7.55 (d, J=8.4 Hz, 1H), 7.75 (d, J=2.7 Hz, 1H), 7.81 (d, J=3.9 Hz, 1H), 8.91 (s, 1H); $^{19}$F NMR (282 MHz, DMSO-d$_6$): δ−166.67.

I-21: N2-(3,4-Difluoro)phenyl-5-fluoro-N4-(1,2,2,6,6-pentamethylpiperidin-4-yl)-2,4-pyrimidinediamine LCMS: purity: 99.62%; MS (m/e): 394.39 (MH+); $^1$H NMR (DMSO-d$_6$): δ 1.06 (s, 12H), 1.46 (t, J=12.0 Hz, 2H), 1.67 (d, J=10.5 Hz, 2H), 2.17 (s, 3H), 4.36 (m, 1H), 7.16-7.29 (m, 3H), 7.84 (d, J=3.9 Hz, 1H), 7.90 (m, 1H), 9.22 (s, 1H); $^{19}$F NMR (282 MHz, DMSO-d$_6$): δ−165.79, −149.09, −137.90.

I-22: N2-(3-Chloro-4-cyano)phenyl-5-fluoro-N4-(1,2,2,6,6-pentamethylpiperidin-4-yl)-2,4-pyrimidinediamine LCMS: purity: 97.90%; MS (m/e): 417.06 (MH+); $^1$H NMR (DMSO-d$_6$): δ 1.08 (s, 12H), 1.48 (t, 2H), 1.69 (d, J=12.9 Hz, 2H), 2.19 (s, 3H), 4.36 (m, 1H), 7.42 (d, 1H), 7.68 (d, J=8.4 Hz, 1H), 7.78 (d, 1H), 7.95 (s, 1H), 8.04 (s, 1H), 9.80 (s, 1H); $^{19}$F NMR (282 MHz, DMSO-d$_6$): δ−163.24.

I-23: N2-(4-Aminocarbonyl)phenyl-5-fluoro-N4-(1,2,2,6,6-pentamethylpiperidin-4-yl)-2,4-pyrimidinediamine LCMS: purity: 98.74%; MS (m/e): 400.93 (MH+); $^1$H NMR (DMSO-d$_6$): δ 1.42 (s, 6H), 1.46 (s, 6H), 2.04 (m, 4H), 2.72 (d, J=5.1 Hz, 3H), 4.52 (m, 1H), 7.17 (br, 1H), 7.68 (d, J=8.7 Hz, 2H), 7.75 (d, J=9.0 Hz, 2H), 7.77 (br, 1H), 8.03 (d, J=3.9 Hz, 1H), 8.17 (s, 1H), 9.34 (s, 1H), 9.75 (s, 1H).

I-24: N2-(3-Aminocarbonyl)phenyl-5-fluoro-N4-(1, 2,2,6,6-pentamethylpiperidin-4-yl)-2,4-pyrimidinediamine LCMS: purity: 94.94%; MS (m/e): 401.46 (MH+); $^1$H NMR (DMSO-$d_6$): δ 1.06 (s, 6H), 1.07 (s, 6H), 1.45 (t, J=11.4 Hz, 2H), 1.69 (d, J=11.7 Hz, 2H), 2.18 (s, 3H), 4.36 (m, 1H), 7.12 (s, 1H), 7.16 (d, J=8.1 Hz, 1H), 7.20 (s, 1H), 7.31 (d, J=7.8 Hz, 1H), 7.77 (s, 1H), 7.83 (d, J=3.9 Hz, 1H), 7.87 (s, 1H), 8.04 (d, J=7.2 Hz, 1H), 9.04 (s, 1H); $^{19}$F NMR (282 MHz, DMSO-$d_6$): δ−166.33.

I-25: N2-(4-Cyano)phenyl-5-fluoro-N4-(1,2,2,6,6-pentamethylpiperidin-4-yl)-2,4-pyrimidinediamine LCMS: purity: 99.76%; MS (m/e): 383.19 (MH+); $^1$H NMR (DMSO-$d_6$): δ 1.09 (s, 12H), 1.48 (t, J=12.0 Hz, 2H), 1.71 (d, J=9.9 Hz, 2H), 2.20 (s, 3H), 4.34 (m, 1H), 7.37 (d, J=7.8 Hz, 1H), 7.55 (d, J=8.7 Hz, 2H), 7.88 (d, J=9.0 Hz, 2H), 7.91 (s, 1H), 9.64 (s, 1H); $^{19}$F NMR (282 MHz, DMSO-$d_6$): δ−164.32.

I-26: N2-(3-Cyano)phenyl-5-fluoro-N4-(1,2,2,6,6-pentamethylpiperidin-4-yl)-2,4-pyrimidinediamine LCMS: purity: 97.94%; MS (m/e): 383.31 (MH+); $^1$H NMR (DMSO-$d_6$): δ 1.08 (s, 12H), 1.47 (t, J=12.0 Hz, 2H), 1.69 (d, J=9.9 Hz, 2H), 2.18 (s, 3H), 4.37 (m, 1H), 7.26 (d, J=7.8 Hz, 1H), 7.28 (s, 1H), 7.35 (t, J=8.1 Hz, 1H), 7.88 (d, J=3.3 Hz, 1H), 7.99 (d, J=8.1 Hz, 1H), 8.04 (s, 1H), 9.35 (s, 1H); $^{19}$F NMR (282 MHz, DMSO-$d_6$): δ−165.12.

I-27: N2-(3-Chloro-4-methoxy)phenyl-5-methyl-N4-(1,2,2,6,6-pentamethylpiperidin-4-yl)-2,4-pyrimidinediamine LCMS: purity: 99.22%; MS (m/e): 418.08 (MH+); $^1$H NMR (DMSO-$d_6$): δ 1.08 (s, 12H), 1.43 (m, 2H), 1.68 (m, 2H), 1.89 (s, 3H), 2.19 (s, 3H), 3.76 (s, 3H), 4.44 (m, 1H), 6.08 (d, 1H), 6.92 (d, J=9.3 Hz, 1H), 7.62 (br, 2H), 7.76 (d, J=2.7 Hz, 1H), 8.70 (s, 1H).

I-28: N2-(3-Chloro-4-cyano)phenyl-5-methyl-N4-(1, 2,2,6,6-pentamethylpiperidin-4-yl)-2,4-pyrimidinediamine LCMS: purity: 100%; MS (m/e): 413.04 (MH+); $^1$H NMR (DMSO-$d_6$): δ 1.09 (s, 12H), 1.48 (t, J=12.3 Hz, 2H), 1.70 (d, J=11.4 Hz, 2H), 1.92 (s, 3H), 2.19 (s, 3H), 4.39 (m, 1H), 6.32 (d, J=8.4 Hz, 1H), 7.64 (d, J=8.7 Hz, 1H), 7.72 (s, 1H), 7.85 (d, J=9.0 Hz, 1H), 8.04 (s, 1H), 9.61 (s, 1H).

I-29: N2-[3-Chloro-4-(4-methylpiperazino)]phenyl-5-methyl-N4-(1,2,2,6,6-pentamethylpiperidin-4-yl)-2,4-pyrimidinediamine LCMS: purity: 98.24%; MS (m/e): 486.28 (MH+); $^1$H NMR (DMSO-$d_6$): δ 1.08 (s, 12H), 1.45 (t, J=12.0 Hz, 2H), 1.69 (d, J=12.6 Hz, 2H), 1.88 (s, 3H), 2.18 (s, 3H), 2.20 (s, 3H), 2.44 (br, 4H), 2.85 (br, 4H), 4.41 (br, 1H), 6.08 (d, J=8.1 Hz, 1H), 6.94 (d, J=8.7 Hz, 1H), 7.61 (s, 1H), 7.63 (dd, J=2.4, 8.7 Hz, 1H), 7.72 (d, J=2.4 Hz, 1H), 8.76 (s, 1H).

I-30: 5-Methyl-N2-[4-(4-methylpiperazino)-3-trifluoromethyl]phenyl-N4-(1,2,2,6,6-pentamethylpiperidin-4-yl)-2,4-pyrimidinediamine LCMS: purity: 96.99%; MS (m/e): 520.50 (MH+); $^1$H NMR (DMSO-$d_6$): δ 1.05 (s, 6H), 1.07 (s, 6H), 1.45 (t, J=11.7 Hz, 2H), 1.69 (d, J=10.5 Hz, 2H), 1.89 (s, 3H), 2.18 (s, 3H), 2.20 (s, 3H), 2.41 (br, 4H), 2.75 (t, J=4.2 Hz, 4H), 4.37 (br, 1H), 6.11 (d, J=8.1 Hz, 1H), 7.31 (d, J=8.7 Hz, 1H), 7.63 (s, 1H), 7.74 (d, J=2.4 Hz, 1H), 8.15 (d, J=9.6 Hz, 1H), 8.95 (s, 1H); $^{19}$F NMR (282 MHz, DMSO-$d_6$): δ−59.87.

I-31: 5-Chloro-N2-(3-chloro-4-methoxy)phenyl-N4-(1,2,2,6,6-pentamethylpiperidin-4-yl)-2,4-pyrimidinediamine LCMS: purity: 99.72%; MS (m/e): 440.05 (MH+); $^1$H NMR (DMSO-$d_6$): δ 1.07 (s, 6H), 1.08 (s, 6H), 1.53 (t, J=12.9 Hz, 2H), 1.64 (m, 2H), 2.19 (s, 3H), 3.76 (s, 3H), 4.40 (m, 1H), 6.63 (d, 1H), 6.94 (d, J=9.0 Hz, 1H), 7.56 (dd, J=2.7, 9.3 Hz, 1H), 7.69 (d, J=2.4 Hz, 1H), 7.89 (s, 1H), 9.07 (s, 1H).

I-32: N2-(3-Chloro-4-methoxy)phenyl-N4-(1,2,2,6,6-pentamethylpiperidin-4-yl)-5-trifluoromethyl-2,4-pyrimidinediamine LCMS: purity: 97.51%; MS (m/e): 472.18 (MH+); $^1$H NMR (DMSO-$d_6$): δ 1.27 (s, 6H), 1.32 (s, 6H), 1.87 (m, 4H), 2.62 (s, 3H), 3.79 (s, 3H), 4.64 (m, 1H), 6.80 (d, 1H), 7.01 (d, J=9.3 Hz, 1H), 7.48 (d, J=8.7 Hz, 1H), 7.62 (br, 1H), 8.19 (s, 1H), 9.50 (s, 1H); $^{19}$F NMR (282 MHz, DMSO-$d_6$): δ−60.58.

I-33: N2-(3-Chloro-4-cyano)phenyl-N4-(1,2,2,6,6-pentamethylpiperidin-4-yl)-5-trifluoromethyl-2,4-pyrimidinediamine)

LCMS: purity: 100%; MS (m/e): 467.19 (MH+); $^1$H NMR (DMSO-$d_6$): δ 1.22 (s, 12H), 1.80 (m, 4H), 2.43 (s, 3H), 4.59 (m, 1H), 6.87 (d, 1H), 7.76 (d, J=8.1 Hz, 1H), 7.86 (d, J=8.4 Hz, 1H), 7.98 (s, 1H), 8.30 (s, 1H), 10.20 (s, 1H); $^{19}$F NMR (282 MHz, DMSO-$d_6$): δ−61.32.

I-34: N2-[3-Chloro-4-(4-methylpiperazino)]phenyl-N4-(1,2,2,6,6-pentamethylpiperidin-4-yl)-5-trifluoromethyl-2,4-pyrimidinediamine LCMS: purity: 96.46%; MS (m/e): 540.17 (MH+); $^1$H NMR (DMSO-$d_6$): δ 1.35 (s, 6H), 1.38 (s, 6H), 1.95 (m, 4H), 2.72 (s, 4H), 2.74 (s, 3H), 2.16 (br, 7H), 4.68 (br, 1H), 6.92 (d, J=7.5 Hz, 1H), 7.09 (d, J=9.3 Hz, 1H), 7.52 (d, J=8.4 Hz, 1H), 7.70 (br, 1H), 8.22 (s, 1H), 9.59 (br, 1H); $^{19}$F NMR (282 MHz, DMSO-$d_6$): δ−60.67.

I-35: 5-Chloro-N2-(3-chloro-4-cyano)phenyl-N4-(1,2,2,6,6-pentamethylpiperidin-4-yl)-2,4-pyrimidinediamine LCMS: purity: 96.59%; MS (m/e): 433.00 (MH+); $^1$H NMR (DMSO-$d_6$): δ 1.08 (s, 12H), 1.57 (t, J=11.1 Hz, 2H), 1.65 (m, 2H), 2.19 (s, 3H), 4.38 (m, 1H), 6.91 (d, J=7.8 Hz, 1H), 7.69 (d, J=8.7 Hz, 1H), 7.84 (d, J=9.0 Hz, 1H), 7.99 (d, J=1.8 Hz, 1H), 8.03 (s, 1H), 9.90 (s, 1H).

I-36: 5-Chloro-N2-[3-chloro-4-(4-methylpiperazino)]phenyl-N4-(1,2,2,6,6-pentamethylpiperidin-4-yl)-2,4-pyrimidinediamine LCMS: purity: 84.78%; MS (m/e): 506.20 (MH+); $^1$H NMR (DMSO-$d_6$): δ 1.06 (s, 12H), 1.53 (t, J=11.7 Hz, 2H), 1.62 (m, 2H), 2.18 (s, 3H), 2.21 (s, 3H), 2.45 (br, 4H), 2.86 (br, 4H), 4.38 (br, 1H), 6.66 (d, 1H), 6.96 (d, J=9.0 Hz, 1H), 7.60 (d, J=9.3 Hz, 1H), 7.65 (s, 1H), 7.89 (d, J=1.5 Hz, 1H), 9.14 (s, 1H).

I-37: 5-Chloro-N2-[4-(4-methylpiperazino)-3-trifluoromethyl]phenyl-N4-(1,2,2,6,6-pentamethylpiperidin-4-yl)-2,4-pyrimidinediamine LCMS: purity: 94.83%; MS (m/e): 540.24 (MH+); $^1$H NMR (DMSO-$d_6$): δ 1.03 (s, 6H), 1.07 (s, 6H), 1.52 (m, 2H), 1.63 (m, 2H), 2.18 (s, 3H), 2.20 (s, 3H), 2.42 (br, 4H), 2.76 (t, 4H), 4.36 (br, 1H), 6.70 (d, 1H), 7.34 (d, J=8.7 Hz, 1H), 7.70 (s, 1H), 7.92 (s, 1H), 8.08 (d, J=8.7 Hz, 1H), 9.30 (s, 1H); $^{19}$F NMR (282 MHz, DMSO-$d_6$): δ−59.93.

I-38: N2-[4-(4-Methylpiperazino)-3-trifluoromethyl]phenyl-N4-(1,2,2,6,6-pentamethylpiperidin-4-yl)-5-trifluoromethyl-2,4-pyrimidinediamine LCMS: purity: 100%; MS (m/e): 574.54 (MH+); $^1$H NMR (DMSO-$d_6$): δ 1.32 (s, 6H), 1.38 (s, 6H), 1.94 (m, 4H), 2.64 (s, 3H), 2.71 (br, 4H), 2.97 (br, 4H), 4.63 (br, 1H), 6.97 (br, 1H), 7.46 (d, 1H), 7.76 (br, 1H), 7.99 (d, J=9.3 Hz, 1H), 8.24 (s, 1H), 8.52 (br, 1H), 9.69 (br, 1H); $^{19}$F NMR (282 MHz, DMSO-$d_6$): δ−60.02, −60.79.

I-39: 5-Fluoro-N2-[3-fluoro-4-(4-methylpiperazino)]phenyl-N4-(1,2,2,6,6-pentamethylpiperidin-4-yl)-2,4-pyrimidinediamine LCMS: purity: 87.87%; MS (m/e): 473.97 (MH+); $^1$H NMR (DMSO-$d_6$): δ 1.07 (s, 12H), 1.46 (t, J=12.0 Hz, 2H), 1.67 (d, J=9.9 Hz, 2H), 2.18 (s, 3H), 2.20 (s, 3H), 2.43 (br, 4H), 2.88 (br, 4H), 4.35 (br, 1H), 6.83 (t, J=9.3 Hz, 1H), 7.17 (d, J=7.8 Hz, 1H), 7.25 (d, J=9.3 Hz, 1H), 7.64 (d, J=15.3 Hz, 1H), 7.81 (d, J=3.6 Hz, 1H), 9.00 (s, 1H); $^{19}$F NMR (282 MHz, DMSO-$d_6$): δ−166.69.

I-40: N2-[3,5-Difluoro-4-(4-methylpiperazino)]phenyl-5-fluoro-N4-(1,2,2,6,6-pentamethylpiperidin-4-yl)-2,4-pyrimidinediamine LCMS: purity: 95.84%; MS (m/e): 492.55 (MH+); $^1$H NMR (DMSO-$d_6$): δ 1.07 (s, 12H), 1.47 (t, J=11.7 Hz, 2H), 1.67 (d, J=12.6 Hz, 2H), 2.19 (s, 6H), 2.38 (br, 4H), 2.97 (br, 4H), 4.34 (br, 1H), 7.27 (d, J=8.7 Hz, 1H), 7.36 (d, J=12.0 Hz, 2H), 7.85 (d, J=3.9 Hz, 1H), 9.25 (s, 1H); $^{19}$F NMR (282 MHz, DMSO-$d_6$): δ−119.86, −165.44.

I-41: N2-[4-Chloro-3-(4-ethylpiperazino)]phenyl-5-fluoro-N4-(1,2,2,6,6-pentamethylpiperidin-4-yl)-2,4-pyrimidinediamine LCMS: purity: 91.29%; MS (m/e): 504.15 (MH+); $^1$H NMR (DMSO-$d_6$): δ 1.02 (t, J=6.9 Hz, 3H), 1.08 (s, 12H), 1.46 (t, J=12.0 Hz, 2H), 1.68 (d, J=10.8 Hz, 2H), 2.18 (s, 3H), 2.37 (q, J=6.9 Hz, 2H), 2.92 (br, 4H), 4.36 (br, 1H), 7.06 (d, J=9.3 Hz, 1H), 7.15 (s, 1H), 7.18 (d, 1H), 7.82 (m, 2H), 9.01 (s, 1H); $^{19}$F NMR (282 MHz, DMSO-$d_6$): δ−166.17.

I-42: N2-[3-(4-Acylpiperazino)-4-chloro]phenyl-5-fluoro-N4-(1,2,2,6,6-pentamethylpiperidin-4-yl)-2,4-pyrimidinediamine LCMS: purity: 100%; MS (m/e): 518.26 (MH+); $^1$H NMR (DMSO-$d_6$): δ 1.08 (s, 12H), 1.46 (t, J=11.4 Hz, 2H), 1.69 (d, J=10.5 Hz, 2H), 2.03 (s, 3H), 2.19 (s, 3H), 2.86 (t, 2H), 2.92 (t, 2H), 3.57 (t, 4H), 4.35 (br, 1H), 7.10 (d, J=8.7 Hz, 1H), 7.16 (s, 1H), 7.20 (d, J=8.1 Hz, 1H), 7.84 (m, 2H), 9.02 (s, 1H); $^{19}$F NMR (282 MHz, DMSO-$d_6$): δ−166.06.

I-43: N2-[4-Chloro-3-(4-methoxycarbonylpiperazino)]phenyl-5-fluoro-N4-(1,2,2,6,6-pentamethylpiperidin-4-yl)-2,4-pyrimidinediamine LCMS: purity: 100%; MS (m/e): 534.24 (MH+); $^1$H NMR (DMSO-$d_6$): δ 1.07 (s, 12H), 1.46 (t, J=12.0 Hz, 2H), 1.69 (d, J=10.5 Hz, 2H), 2.18 (s, 3H), 2.88 (t, 4H), 3.50 (t, 4H), 3.61 (s, 3H), 4.36 (br, 1H), 7.09 (d, J=8.7 Hz, 1H), 7.16 (s, 1H), 7.20 (d, J=7.8 Hz, 1H), 7.83 (m, 2H), 9.02 (s, 1H); $^{19}$F NMR (282 MHz, DMSO-$d_6$): δ−166.04.

I-44: N2-[3-Chloro-4-(4-methylpiperazino)carbonyl]phenyl-5-fluoro-N4-(1,2,2,6,6-pentamethylpiperidin-4-yl)-2,4-pyrimidinediamine LCMS: purity: 87.76%; MS (m/e): 518.28 (MH+); $^1$H NMR (DMSO-$d_6$): δ 1.06 (s, 12H), 1.46 (t, J=11.4 Hz, 2H), 1.68 (d, J=10.2 Hz, 2H), 2.16 (s, 6H), 2.32 (br, 2H), 3.11 (br, 2H), 3.58 (br, 2H), 4.33 (br, 1H), 7.07 (d, J=8.1 Hz, 1H), 7.25 (d, 1H), 7.71 (d, J=8.4 Hz, 1H), 7.79 (s, 1H), 7.87 (d, J=3.6 Hz, 1H), 9.33 (s, 1H); $^{19}$F NMR (282 MHz, DMSO-$d_6$): δ−165.12.

I-45: N2-[3-Chloro-4-(4-methylpiperazino)sulfonyl]phenyl-5-fluoro-N4-(1,2,2,6,6-pentamethylpiperidin-4-yl)-2,4-pyrimidinediamine LCMS: purity: 98.98%; MS (m/e): 554.13 (MH+); $^1$H NMR (DMSO-$d_6$): δ 1.40 (s, 6H), 1.44 (s, 6H), 1.82 (t, 2H), 2.10 (d, J=14.1 Hz, 2H), 2.74 (br, 4H), 3.09 (br, 4H), 4.48 (br, 1H), 7.75 (m, 3H), 7.96 (s, 1H), 8.02 (d, J=3.3 Hz, 1H), 8.59 (br, 1H), 9.76 (s, 1H); $^{19}$F NMR (282 MHz, DMSO-$d_6$): δ−163.36.

I-46: N2-[3-Chloro-4-piperazinosulfonyl]phenyl-5-fluoro-N4-(1,2,2,6,6-pentamethylpiperidin-4-yl)-2,4-pyrimidinediamine LCMS: purity: 99.38%; MS (m/e): 540.03 (MH+); $^1$H NMR (DMSO-$d_6$): δ 1.34 (br, 12H), 3.04 (br, 4H), 3.65 (br, 4H), 4.28 (br, 1H), 6.31 (s, 1H), 6.53 (d, J=10.5 Hz, 1H), 6.66 (s, 1H), 7.54 (d, J=8.7 Hz, 1H), 7.78 (s, 1H).

I-47: 5-Fluoro-N2-[4-(4-methoxycarbonylpiperazino)-3-trifluoromethyl]phenyl-N4-(1,2,2,6,6-pentamethylpiperidin-4-yl)-2,4-pyrimidinediamine LCMS: purity: 98.79%; MS (m/e): 568.51 (MH+); $^1$H NMR (DMSO-$d_6$): δ 1.07 (s, 12H), 1.50 (br, 2H), 1.68 (br, 2H), 2.18 (s, 3H), 2.73 (t, 4H), 3.45 (t, 4H), 3.61 (s, 3H), 4.31 (br, 1H), 7.19 (br, 1H), 7.34 (d, J=8.7 Hz, 1H), 7.79 (s, 1H), 7.86 (d, 1H), 8.06 (d, J=7.2 Hz, 1H), 9.17 (s, 1H); $^{19}$F NMR (282 MHz, DMSO-$d_6$): δ−59.83, −165.73.

I-48: 5-Fluoro-N2-[4-(4-methylsulfonylpiperazino)-3-trifluoromethyl]phenyl-N4-(1,2,2,6,6-pentamethylpiperidin-4-yl)-2,4-pyrimidinediamine LCMS: purity: 100%; MS (m/e): 588.49 (MH+); $^1$H NMR (DMSO-$d_6$): δ 1.04 (s, 6H), 1.07 (s, 6H), 1.44 (t, J=12.0 Hz, 2H), 1.68 (d, J=10.2 Hz, 2H), 2.18 (s, 3H), 2.86 (t, 4H), 2.93 (s, 3H), 3.19 (t, 4H), 4.32 (br, 1H), 7.19 (d, J=7.2 Hz, 1H), 7.40 (d, J=8.1 Hz, 1H), 7.80 (s, 1H), 7.85 (d, 1H), 8.08 (d, J=9.3 Hz, 1H), 9.18 (s, 1H); $^{19}$F NMR (282 MHz, DMSO-d$_6$): δ−59.87, −165.68.

I-49: N2-[4-(4-Acylpiperazino)-3-trifluoromethyl]phenyl-5-fluoro-N4-(1,2,2,6,6-pentamethylpiperidin-4-yl)-2,4-pyrimidinediamine LCMS: purity: 97.82%; MS (m/e): 552.45 (MH+); $^1$H NMR (DMSO-d$_6$): δ 1.23 (s, 12H), 1.61 (br, 2H), 1.88 (br, 2H), 2.02 (s, 3H), 2.70 (t, 2H), 2.76 (t, 2H), 3.50 (t, 4H), 4.35 (br, 1H), 7.34 (d, J=8.4 Hz, 1H), 7.36 (br, 1H), 7.78 (s, 1H), 7.88 (d, J=3.9 Hz, 1H), 8.03 (d, 1H), 9.21 (s, 1H); $^{19}$F NMR (282 MHz, DMSO-d$_6$): δ−59.85, −165.64.

I-50: N2-[3-Chloro-4-(4,4-difluoropiperidinyl)]phenyl-5-fluoro-N4-(1,2,2,6,6-pentamethylpiperidin-4-yl)-2,4-pyrimidinediamine LCMS: purity: 96.77%; MS (m/e): 511.22 (MH+); $^1$H NMR (DMSO-d$_6$): δ 1.20 (s, 12H), 1.59 (t, 2H), 1.82 (d, 2H), 2.09 (m, 4H), 2.41 (br, 3H), 2.96 (t, 4H), 4.38 (br, 1H), 7.02 (d, J=8.7 Hz, 1H), 7.33 (br, 1H), 7.55 (d, J=8.4 Hz, 1H), 7.78 (d, 1H), 7.86 (d, J=3.9 Hz, 1H), 9.05 (s, 1H); $^{19}$F NMR (282 MHz, DMSO-d$_6$): δ−166.18.

I-51: N2-[4-(4,4-Difluoropiperidinyl)-3-fluoro]phenyl-5-fluoro-N4-(1,2,2,6,6-pentamethylpiperidin-4-yl)-2,4-pyrimidinediamine LCMS: purity: 96.28%; MS (m/e): 495.43 (MH+); $^1$H NMR (DMSO-d$_6$): δ 1.28 (s, 12H), 1.67 (br, 2H), 1.90 (br, 2H), 2.08 (m, 4H), 3.00 (t, 4H), 4.43 (br, 1H), 6.93 (t, J=9.3 Hz, 1H), 7.24 (d, J=8.4 Hz, 1H), 7.41 (br, 1H), 7.67 (d, J=13.5 Hz, 1H), 7.88 (d, 1H), 9.09 (s, 1H); $^{19}$F NMR (282 MHz, DMSO-d$_6$): δ−122.41, −166.37.

I-52: 5-Fluoro-N2-[4-(4-methylpiperazino)methyl-3-trifluoromethyl]phenyl-N4-(1,2,2,6,6-pentamethylpiperidin-4-yl)-2,4-pyrimidinediamine LCMS: purity: 90.35%; MS (m/e): 538.62 (MH+).

I-53: N2-[3-Aminocarbonyl-4-(4-methylpiperazino)]phenyl-5-fluoro-N4-(1,2,2,6,6-pentamethylpiperidin-4-yl)-2,4-pyrimidinediamine LCMS: purity: 99.31%; MS (m/e): 499.52 (MH+); $^1$H NMR (DMSO-d$_6$): δ 1.38 (s, 6H), 1.39 (s, 6H), 1.79 (t, J=12.6 Hz, 2H), 2.06 (d, J=12.0 Hz, 2H), 2.71 (d, J=4.5 Hz, 3H), 2.85 (s, 3H), 2.96 (t, J=12.9 Hz, 2H), 3.17 (t, 2H), 3.52 (t, 4H), 4.42 (br, 1H), 7.06 (d, J=9.0 Hz, 1H), 7.51 (s, 1H), 7.63 (d, 1H), 7.70 (d, J=9.3 Hz, 1H), 7.92 (d, J=3.9 Hz, 1H), 7.96 (s, 1H), 8.22 (s, 1H), 8.66 (br, 1H), 9.15 (s, 1H), 9.88 (br, 1H); $^{19}$F NMR (282 MHz, DMSO-d$_6$): δ−165.88.

I-54: 5-Fluoro-N2-[3-methylaminocarbonyl-4-(4-methylpiperazino)]phenyl-N4-(1,2,2,6,6-pentamethylpiperidin-4-yl)-2,4-pyrimidinediamine LCMS: purity: 98.96%; MS (m/e): 513.56 (MH+); $^1$H NMR (DMSO-d$_6$): δ 1.38 (s, 6H), 1.39 (s, 6H), 1.79 (t, J=12.6 Hz, 2H), 2.06 (d, J=7.8 Hz, 2H), 2.72 (d, J=3.9 Hz, 3H), 2.83 (d, J=4.8 Hz, 3H), 2.87 (s, 3H), 2.96 (t, J=12.0 Hz, 2H), 3.15 (m, 6H), 4.43 (br, 1H), 7.06 (d, J=8.7 Hz, 1H), 7.60 (d, J=5.7 Hz, 1H), 7.67 (d, J=8.1 Hz, 1H), 7.91 (d, J=3.6 Hz, 1H), 7.98 (s, 1H), 8.66 (s, 1H), 8.67 (s, 1H), 9.15 (s, 1H), 9.87 (br, 1H); $^{19}$F NMR (282 MHz, DMSO-d$_6$): δ−165.88.

I-55: 5-Fluoro-N2-[3-methoxy-4-(4-methylpiperazino)]phenyl-N4-(1,2,2,6,6-pentamethylpiperidin-4-yl)-2,4-pyrimidinediamine LCMS: purity: 98.48%; MS (m/e): 486.72 (MH+); $^1$H NMR (DMSO-d$_6$): δ 1.40 (s, 12H), 1.81 (t, J=12.9 Hz, 2H), 2.06 (d, J=11.4 Hz, 2H), 2.74 (d, 3H), 2.86 (s, 3H), 3.19 (m, 2H), 3.35-3.49 (m, 6H), 3.74 (s, 3H), 4.45 (br, 1H), 6.75 (d, J=8.1 Hz, 1H), 7.12 (s, 1H), 7.36 (d, J=7.5 Hz, 1H), 7.65 (br, 1H), 7.90 (d, J=3.6 Hz, 1H), 8.67 (s, 1H), 8.92 (s, 1H), 9.69 (br, 1H).

I-56: N2-[4-Chloro-3-(4-propylpiperazino)]phenyl-5-fluoro-N4-(1,2,2,6,6-pentamethylpiperidin-4-yl)-2,4-pyrimidinediamine LCMS: purity: 99.76%; MS (m/e): 518.30 (MH+); $^1$H NMR (DMSO-d$_6$): δ 0.92 (t, J=7.2 Hz, 3H), 1.41 (s, 6H), 1.44 (s, 6H), 1.68 (m, J=7.5 Hz, 2H), 1.82 (t, J=12.9 Hz, 2H), 2.08 (d, J=10.5 Hz, 2H), 2.75 (s, 3H), 3.09 (t, 4H), 4.46 (br, 1H), 7.18 (d, J=8.7 Hz, 1H), 7.22 (s, 1H), 7.61 (d, J=7.8 Hz, 1H), 7.80 (d, J=9.3 Hz, 1H), 7.91 (d, J=3.6 Hz, 1H), 8.72 (br, 1H), 9.12 (s, 1H); $^{19}$F NMR (282 MHz, DMSO-d$_6$): δ−165.61.

I-57: N2-[3-Chloro-4-(4-methylpiperazino)methyl]phenyl-5-fluoro-N4-(1,2,2,6,6-pentamethylpiperidin-4-yl)-2,4-pyrimidinediamine LCMS: purity: 86.88%; MS (m/e): 504.09 (MH+).

I-58: N2-(3-Chloro-4-methoxy)phenyl-5-fluoro-N4-methyl-N4-(1,2,2,6,6-pentamethylpiperidin-4-yl)-2,4-pyrimidinediamine LCMS: purity: 99.24%; MS (m/e): 436.12 (MH+); $^1$H NMR (DMSO-d$_6$): δ 1.32 (s, 6H), 1.38 (s, 6H), 1.83 (d, J=11.4 Hz, 2H), 2.03 (t, J=12.3 Hz, 2H), 2.67 (s, 3H), 2.98 (d, J=2.7 Hz, 3H), 3.78 (s, 3H), 4.78 (t, 1H), 7.00 (d, J=8.7 Hz, 1H), 7.45 (dd, J=2.7, 9.0 Hz, 1H), 7.72 (d, J=2.4 Hz, 1H), 7.98 (d, J=6.9 Hz, 1H), 8.98 (s, 1H); $^{19}$F NMR (282 MHz, DMSO-d$_6$): δ−158.70.

I-59: 5-Fluoro-N4-methyl-N2-[4-(4-methylpiperazino)-3-trifluoromethyl]phenyl-N4-(1,2,2,6,6-pentamethylpiperidin-4-yl)-2,4-pyrimidinediamine LCMS: purity: 95.10%; MS (m/e): 538.45 (MH+); $^1$H NMR (DMSO-d$_6$): δ 1.35 (s, 6H), 1.39 (s, 6H), 1.90 (m, 2H), 2.06 (m, 2H), 2.69 (s, 3H), 2.95 (s, 3H), 2.99 (br, 4H), 4.73 (br, 1H), 7.43 (d, J=8.4 Hz, 1H), 7.85 (d, J=8.4 Hz, 1H), 8.04 (m, 2H), 9.35 (s, 1H); $^{19}$F NMR (282 MHz, DMSO-d$_6$): δ−157.53, −59.96.

I-60: N2-[3-Chloro-4-(4-methylpiperazino)]phenyl-5-fluoro-N4-methyl-N4-(1,2,2,6,6-pentamethylpiperidin-4-yl)-2,4-pyrimidinediamine LCMS: purity: 98.86%; MS (m/e): 504.26 (MH+); $^1$H NMR (DMSO-d$_6$): δ 1.34 (s, 6H), 1.38 (s, 6H), 1.85 (d, J=11.4 Hz, 2H), 2.06 (t, J=12.6 Hz, 2H), 2.64 (s, 3H), 2.68 (s, 4H), 2.99 (d, J=2.4 Hz, 3H), 3.03 (br, 4H), 4.78 (t, 1H), 7.07 (d, J=9.0 Hz, 1H), 7.50 (d, J=9.0 Hz, 1H), 7.79 (s, 1H), 8.00 (d, J=7.2 Hz, 1H), 9.11 (s, 1H); $^{19}$F NMR (282 MHz, DMSO-d$_6$): δ−158.15.

I-61: N2-[3-Chloro-4-(4-methylsulfonylpiperazino)]phenyl-5-fluoro-N4-(1,2,2,6,6-pentamethylpiperidin-4-yl)-2,4-pyrimidinediamine LCMS: purity: 99.56%; MS (m/e): 554.20 (MH+); $^1$H NMR (DMSO-d$_6$): δ 1.08 (s, 12H), 1.46 (t, J=12.0 Hz, 2H), 1.68 (d, J=10.5 Hz, 2H), 2.18 (s, 3H), 2.93 (s, 3H), 2.96 (t, 4H), 3.25 (t, 4H), 4.33 (br, 1H), 7.01 (d, J=8.7 Hz, 1H), 7.18 (d, J=8.4 Hz, 1H), 7.60 (d, J=9.3 Hz, 1H), 7.79 (s, 1H), 7.83 (d, J=3.9 Hz, 1H), 9.04 (s, 1H); $^{19}$F NMR (282 MHz, DMSO-d$_6$): δ−166.22.

I-62: N2-[3-Chloro-4-(4-methoxycarbonylpiperazino)]phenyl-5-fluoro-N4-(1,2,2,6,6-pentamethylpiperidin-4-yl)-2,4-pyrimidinediamine LCMS: purity: 99.79%; MS (m/e): 534.24 (MH+); $^1$H NMR (DMSO-d$_6$): δ 1.07 (s, 12H), 1.46 (t, J=12.0 Hz, 2H), 1.68 (d, J=9.3 Hz, 2H), 2.18 (s, 3H), 2.82 (t, 4H), 3.49 (t, 4H), 3.61 (s, 3H), 4.33 (br, 1H), 6.96 (d, J=8.7 Hz, 1H), 7.17 (d, J=8.1 Hz, 1H), 7.60 (d, J=9.0 Hz, 1H), 7.78 (s, 1H), 7.83 (d, J=3.6 Hz, 1H), 9.02 (s, 1H); $^{19}$F NMR (282 MHz, DMSO-d$_6$): δ−166.28.

I-63: 5-Fluoro-N2-[3-hydroxymethyl-4-(4-methylpiperazino)]phenyl-N4-(1,2,2,6,6-pentamethylpiperidin-4-yl)-2,4-pyrimidinediamine LCMS: purity: 82.75%; MS (m/e): 486.55 (MH+); $^1$H NMR (DMSO-d$_6$): δ 1.40 (s, 12H), 1.79 (t, J=12.6 Hz, 2H), 2.07 (d, J=13.2 Hz, 2H), 2.73 (s, 3H), 2.87 (s, 3H), 2.93 (m, 2H), 3.08-3.19 (m, 6H), 4.50 (br, 1H), 4.51 (s, 2H), 6.92 (d, J=8.4 Hz, 1H), 7.57 (m, 2H), 7.89 (d, J=2.7 Hz, 1H), 8.64 (s, 1H), 8.98 (s, 1H), 9.71 (br, 1H); $^{19}$F NMR (282 MHz, DMSO-d$_6$): δ−166.58.

I-64: 5-Fluoro-N2-[4-(4-methylpiperazino)carbonyl-3-trifluoromethyl]phenyl-N4-(1,2,2,6,6-pentamethylpiperidin-4-yl)-2,4-pyrimidinediamine LCMS: purity: 97.98%; MS (m/e): 552.48 (MH+); $^1$H NMR (DMSO-d$_6$): δ 1.37 (s, 12H), 1.76 (br, 2H), 2.05 (d, J=13.8 Hz, 2H), 2.21 (s, 3H), 2.67 (s, 3H), 3.11 (br, 4H), 3.58 (br, 4H), 4.43 (br, 1H), 7.21 (d, J=8.1 Hz, 1H), 7.62 (d, 1H), 7.90 (s, 1H), 7.97 (d, J=3.9 Hz, 1H), 8.16 (d, J=8.1 Hz, 1H), 9.46 (s, 1H); $^{19}$F NMR (282 MHz, DMSO-d$_6$): δ−59.44, −164.59.

I-65: N2-[4-Chloro-3-(4-methylpiperazino)]phenyl-5-fluoro-N4-(1,2,2,6,6-pentamethylpiperidin-4-yl)-2,4-pyrimidinediamine LCMS: purity: 99.81%; MS (m/e): 490.23 (MH+); $^1$H NMR (DMSO-d$_6$): δ 1.42 (s, 6H), 1.44 (s, 6H), 1.83 (t, J=12.9 Hz, 2H), 2.08 (d, J=13.2 Hz, 2H), 2.75 (d, J=4.5 Hz, 3H), 2.88 (s, 3H), 2.92 (m, 2H), 3.22 (m, 2H), 3.41 (d, J=12.9 Hz, 2H), 3.54 (d, J=12.0 Hz, 2H), 4.46 (br, 1H), 7.19 (d, J=8.7 Hz, 1H), 7.21 (s, 1H), 7.65 (d, J=7.8 Hz, 1H), 7.81 (d, J=8.4 Hz, 1H), 7.93 (d, J=3.6 Hz, 1H), 8.71 (br, 1H), 9.14 (s, 1H), 9.85 (br, 1H); $^{19}$F NMR (282 MHz, DMSO-d$_6$): δ−165.51.

I-66: N2-(3-Cyano)phenyl-5-fluoro-N4-methyl-N4-(1,2,2,6,6-pentamethylpiperidin-4-yl)-2,4-pyrimidinediamine LCMS: purity: 99.82%; MS (m/e): 396.89 (MH+); $^1$H NMR (DMSO-d$_6$): δ 1.04 (s, 6H), 1.11 (s, 6H), 1.56 (d, 2H), 1.70 (t, J=11.7 Hz, 2H), 2.17 (s, 3H), 3.00 (s, 3H), 4.60 (t, 1H), 7.29 (d, J=8.1 Hz, 1H), 7.40 (t, J=7.8 Hz, 1H), 7.92 (d, J=6.9 Hz, 1H), 8.01 (d, J=7.2 Hz, 1H), 8.11 (s, 1H), 9.42 (s, 1H); $^{19}$F NMR (282 MHz, DMSO-d$_6$): δ−156.96.

I-67: N2-[4-(4-Acylpiperazino)-3-chloro]phenyl-5-fluoro-N4-(1,2,2,6,6-pentamethylpiperidin-4-yl)-2,4-pyrimidinediamine LCMS: purity: 95.04%; MS (m/e): 518.26 (MH+); $^1$H NMR (DMSO-d$_6$): δ 1.33 (s, 6H), 1.34 (s, 6H), 1.72 (t, J=12.6 Hz, 2H), 1.96 (m, 2H), 2.03 (s, 3H), 2.61 (s, 3H), 2.80 (t, 2H), 2.86 (t, 2H), 3.55 (t, 4H), 4.43 (br, 1H), 6.98 (d, J=8.7 Hz, 1H), 7.45 (d, 1H), 7.54 (dd, J=2.1, 8.7 Hz, 1H), 7.76 (d, J=2.1 Hz, 1H), 7.89 (d, J=3.9 Hz, 1H), 9.07 (s, 1H); $^{19}$F NMR (282 MHz, DMSO-d$_6$): δ−166.15.

I-68: N2-[4-Chloro-3-(4-methylsulfonylpiperazino)]phenyl-5-fluoro-N4-(1,2,2,6,6-pentamethylpiperidin-4-yl)-2,4-pyrimidinediamine LCMS: purity: 99.84%; MS (m/e): 554.20 (MH+); $^1$H NMR (DMSO-d$_6$): δ 1.25 (s, 12H), 1.64 (t, J=12.6 Hz, 2H), 1.89 (d, J=13.5 Hz, 2H), 2.18 (s, 3H), 2.94 (s, 3H), 3.02 (t, 4H), 3.27 (t, 4H), 4.40 (br, 1H), 7.14 (d, J=8.7 Hz, 1H), 7.22 (s, 1H), 7.39 (d, J=6.9 Hz, 1H), 7.81 (d, J=8.4 Hz, 1H), 7.89 (d, J=3.6 Hz, 1H), 9.06 (s, 1H); $^{19}$F NMR (282 MHz, DMSO-d$_6$): δ−165.93.

I-69: N2-[3-(2-methylpyrimidin-4-yl)]phenyl-5-fluoro-N4-(1,2,2,6,6-pentamethylpiperidin-4-yl)-2,4-pyrimidinediamine LCMS: purity: 96.54%; MS (m/e): 450.56 (MH+); $^1$H NMR (DMSO-d$_6$): δ 1.29 (s, 6H), 1.37 (s, 6H), 1.78 (t, J=12.6 Hz, 2H), 2.06 (d, J=11.1 Hz, 2H), 2.67 (s, 3H), 2.70 (d, J=4.8 Hz, 3H), 4.46 (br, 1H), 7.35 (t, J=7.8 Hz, 1H), 7.64 (m, 2H), 7.74 (d, J=5.4 Hz, 1H), 7.95 (d, J=3.9 Hz, 1H), 8.01 (d, J=8.4 Hz, 1H), 8.18 (s, 1H), 8.59 (br, 1H), 8.71 (d, J=5.7 Hz, 1H), 9.27 (s, 1H); $^{19}$F NMR (282 MHz, DMSO-d$_6$): δ−165.82.

I-70: N2-(3-Cyano)phenyl-5-fluoro-N4-(2,2,6,6-tetramethylpiperidin-4-yl)-2,4-pyrimidinediamine LCMS: purity: 99.65%; MS (m/e): 369.34 (MH+); $^1$H NMR (DMSO-d$_6$): δ 1.40 (s, 6H), 1.46 (s, 6H), 1.64 (t, J=12.6 Hz, 2H), 1.94 (d, J=11.1 Hz, 2H), 4.49 (br, 1H), 7.34 (d, J=7.2 Hz, 1H), 7.42 (t, J=8.1 Hz, 1H), 7.87 (d, J=7.8 Hz, 2H), 8.01 (d, J=3.9 Hz, 2H), 9.03 (d, J=11.1 Hz, 1H), 9.65 (s, 1H); $^{19}$F NMR (282 MHz, DMSO-d$_6$): δ−164.12.

I-71: N2-(3-Chloro-4-methoxy)phenyl-5-nitro-N4-(1,2,2,6,6-pentamethylpiperidin-4-yl)-2,4-pyrimidinediamine LCMS: purity: 99.20%; MS (m/e): 449.02 (MH+); $^1$H NMR (DMSO-d$_6$): δ 1.29 (s, 6H), 1.44 (s, 6H), 2.04 (m, 4H), 2.68 (d, J=4.2 Hz, 3H), 3.81 (s, 3H), 4.57 (m, 1H), 7.06 (d, J=8.4 Hz, 1H), 7.53 (d, J=8.7 Hz, 1H), 7.66 (s, 1H), 8.46 (d, J=8.1 Hz, 1H), 8.97 (s, 1H), 9.56 (br, 1H), 10.35 (s, 1H).

I-72: N2-(3-Cyano)phenyl-5-nitro-N4-(1,2,2,6,6-pentamethylpiperidin-4-yl)-2,4-pyrimidinediamine LCMS: purity: 98.16%; MS (m/e): 410.12 (MH+); $^1$H NMR (DMSO-d$_6$): δ 1.36 (s, 6H), 1.45 (s, 6H), 2.08 (br, 4H), 2.69 (d, J=4.5 Hz, 3H), 4.63 (m, 1H), 7.52 (m, 2H), 7.98 (d, J=7.8 Hz, 1H), 8.05 (s, 1H), 8.51 (d, J=6.6 Hz, 1H), 9.03 (s, 1H), 9.42 (br, 1H), 10.65 (br, 1H).

I-73: N2-[3-Chloro-4-(4-methylsulfonylpiperazino)]phenyl-5-nitro-N4-(1,2,2,6,6-pentamethylpiperidin-4-yl)-2,4-pyrimidinediamine LCMS: purity: 94.77%; MS (m/e): 581.10 (MH+); $^1$H NMR (DMSO-d$_6$): δ 1.32 (s, 6H), 1.43 (s, 6H), 2.05 (m, 4H), 2.70 (d, J=3.9 Hz, 3H), 2.94 (s, 3H), 3.00 (t, 4H), 3.27 (t, 3H), 4.60 (m, 1H), 7.11 (d, J=8.1 Hz, 1H), 7.64 (m, 2H), 8.48 (d, J=7.5 Hz, 1H), 8.99 (s, 1H), 9.23 (br, 1H), 10.42 (s, 1H).

I-74: N2-[4-(4-Methylpiperazino)-3-trifluoromethyl]phenyl-5-nitro-N4-(1,2,2,6,6-pentamethylpiperidin-4-yl)-2,4-pyrimidinediamine LCMS: purity: 98.43%; MS (m/e): 551.48 (MH+); $^1$H NMR (DMSO-d$_6$): δ 1.03 (s, 3H), 1.09 (s, 3H), 1.13 (s, 6H), 1.57 (m, 2H), 1.82 (d, J=10.8 Hz, 2H), 2.24 (s, 3H), 2.27 (s, 3H), 2.53 (br, 4H), 2.80 (t, 4H), 4.45 (br, 1H), 7.46 (d, J=9.3 Hz, 1H), 7.70 (s, 1H), 8.11 (s, 1H), 8.40 (br, 1H), 8.98 (s, 1H), 10.47 (br, 1H); $^{19}$F NMR (282 MHz, DMSO-d$_6$): δ−59.98.

I-75: 5-Nitro-N4-(1,2,2,6,6-pentamethylpiperidin-4-yl)-N2-(4-piperazino-3-trifluoromethyl)phenyl-2,4-pyrimidinediamine LCMS: purity: 88.30%; MS (m/e): 537.46 (MH+); $^1$H NMR (DMSO-d$_6$): δ 1.05 (s, 6H), 1.10 (s, 6H), 1.48 (t, J=11.7 Hz, 2H), 1.86 (d, J=10.8 Hz, 2H), 2.19 (s, 3H), 2.52 (br, 4H), 2.78 (t, 4H), 4.37 (br, 1H), 5.37 (br, 1H), 6.72 (d, J=9.0 Hz, 1H), 6.80 (s, 1H), 7.23 (d, J=8.7 Hz, 1H), 8.17 (d, J=6.9 Hz, 1H), 8.91 (s, 1H); $^{19}$F NMR (282 MHz, DMSO-d$_6$): δ−60.13.

I-76: N2-[3-Chloro-4-(4-methylpiperazino)]phenyl-5-nitro-N4-(1,2,2,6,6-pentamethylpiperidin-4-yl)-2,4-pyrimidinediamine LCMS: purity: 96.74%; MS (m/e): 517.12 (MH+); $^1$H NMR (DMSO-d$_6$): δ 1.06 (s, 6H), 1.10 (s, 6H), 1.57 (m, 2H), 1.80 (d, J=11.1 Hz, 2H), 2.23 (s, 6H), 2.52 (br, 4H), 2.91 (t, 4H), 4.50 (br, 1H), 7.06 (d, J=8.4 Hz, 1H), 7.63 (m, 2H), 8.12 (s, 1H), 8.39 (br, 1H), 8.95 (s, 1H), 10.34 (br, 1H).

I-77: N2-(3-Chloro-4-piperazino)phenyl-5-nitro-N4-(1,2,2,6,6-pentamethylpiperidin-4-yl)-2,4-pyrimidinediamine LCMS: purity: 85%; MS (m/e): 503.20 (MH+); $^1$H NMR (DMSO-d$_6$): δ 1.07 (s, 6H), 1.10 (s, 6H), 1.48 (t, J=11.4 Hz, 2H), 1.86 (d, J=12.3 Hz, 2H), 2.20 (s, 3H), 2.85 (br, 2H), 2.98 (br, 2H), 4.40 (br, 1H), 5.05 (br, 1H), 6.45 (d, J=9.0 Hz, 1H), 6.61 (s, 1H), 6.88 (d, J=9.0 Hz, 1H), 8.21 (br, 1H), 8.92 (s, 1H).

I-78: N2-[4-(4-Methylsulfonylpiperazino)-3-trifluoromethyl]phenyl-5-nitro-N4-(1,2,2,6,6-pentamethylpiperidin-4-yl)-2,4-pyrimidinediamine LCMS: purity: 90.54%; MS (m/e): 615.19 (MH+); $^1$H NMR (DMSO-d$_6$): δ 1.02 (s, 6H), 1.11 (s, 6H), 1.54 (t, J=11.4 Hz, 2H), 1.81 (d, J=10.2 Hz, 2H), 2.25 (s, 3H), 2.89 (br, 4H), 2.93 (s, 3H), 3.21 (br, 4H), 4.44 (br, 1H), 7.50 (d, J=9.0 Hz, 1H), 7.73 (s, 1H), 8.11 (s, 1H), 8.39 (br, 1H), 8.98 (s, 1H), 10.49 (br, 1H); $^{19}$F NMR (282 MHz, DMSO-d$_6$): δ−59.98.

I-79: 5-Fluoro-N4-(1,2,2,6,6-pentamethylpiperidin-4-yl)-N2-(3-pyridin-4-yl)phenyl-2,4-pyrimidinediamine LCMS: purity: 96.09%; MS (m/e): 434.79 (MH+); $^1$H NMR (DMSO-d$_6$): δ 0.94 (s, 6H), 1.05 (s, 6H), 1.44 (t, J=13.8 Hz, 2H), 1.67 (d, J=10.2 Hz, 2H), 2.14 (s, 3H), 4.34 (br, 1H), 7.26 (m, 3H), 7.58 (d, J=5.1 Hz, 2H), 7.82 (s, 1H), 7.87 (d, 1H), 8.00 (d, 1H), 8.60 (d, J=4.8 Hz, 2H), 9.11 (s, 1H); $^{19}$F NMR (282 MHz, DMSO-d$_6$): δ−166.20.

I-80: N2-(3-Chloro-4-methoxy)phenyl-5-ethoxycarbonyl-N4-(1,2,2,6,6-pentamethylpiperidin-4-yl)-2,4-pyrimidinediamine LCMS: purity: 96.48%; MS (m/e): 475.83 (MH+); $^1$H NMR (DMSO-d$_6$): δ 1.24 (s, 12H), 1.29 (t, J=7.2 Hz, 3H), 1.51 (t, 2H), 2.01 (d, J=14.1 Hz, 2H), 3.79 (s, 3H), 4.23 (q, J=7.2 Hz, 2H), 4.43 (m, 1H), 7.01 (d, J=8.4 Hz, 1H), 7.59 (d, J=9.3 Hz, 1H), 7.72 (s, 1H), 8.11 (s, 1H), 8.55 (s, 1H), 9.78 (br, 1H).

I-81: N2-(3-Cyano)phenyl-5-ethoxycarbonyl-N4-(1,2,2,6,6-pentamethylpiperidin-4-yl)-2,4-pyrimidinediamine LCMS: purity: 86.59%; MS (m/e): 436.93 (MH+); $^1$H NMR (DMSO-d$_6$): δ 1.16 (s, 12H), 1.30 (t, J=6.3 Hz, 3H), 1.42 (t, 2H), 1.90 (d, 2H), 2.33 (s, 3H), 4.24 (q, J=6.9 Hz, 2H), 4.41 (m, 1H), 7.42 (d, 2H), 8.06 (br, 2H), 8.11 (m, 1H), 8.60 (s, 1H), 10.10 (br, 1H).

I-82: 5-Ethoxycarbonyl-N2-[4-(4-methylpiperazino)-3-trifluoromethyl]phenyl-N4-(1,2,2,6,6-pentamethylpiperidin-4-yl)-2,4-pyrimidinediamine LCMS: purity: 96.93%; MS (m/e): 577.92 (MH+); $^1$H NMR (DMSO-d$_6$): δ 1.04 (s, 6H), 1.08 (s, 6H), 1.29 (t, J=6.9 Hz, 3H), 1.31 (t, J=10.5 Hz, 2H), 1.84 (d, J=12.3 Hz, 2H), 2.21 (s, 6H), 2.43 (t, 4H), 2.78 (t, 4H), 4.23 (q, J=6.9 Hz, 2H), 4.30 (br, 1H), 7.36 (d, 1H), 7.73 (br, 1H), 8.06 (d, 1H), 8.13 (s, 1H), 8.56 (s, 1H), 9.91 (br, 1H); $^{19}$F NMR (282 MHz, DMSO-d$_6$): δ−59.94.

I-83: 5-Ethoxycarbonyl-N2-[4-(4-methylsulfonylpiperazino)-3-trifluoromethyl]phenyl-N4-(1,2,2,6,6-pentamethylpiperidin-4-yl)-2,4-pyrimidinediamine LCMS: purity: 98.99%; MS (m/e): 642.23 (MH+); $^1$H NMR (DMSO-d$_6$): δ 1.11 (s, 6H), 1.14 (s, 6H), 1.29 (t, J=6.9 Hz, 3H), 1.38 (t, J=12.6 Hz, 2H), 1.91 (d, J=10.8 Hz, 2H), 2.31 (s, 3H), 2.88 (t, 4H), 2.94 (s, 3H), 3.21 (t, 4H), 4.23 (q, J=6.9 Hz, 2H), 4.34 (br, 1H), 7.46 (d, J=9.0 Hz, 1H), 7.76 (br, 1H), 8.08 (d, J=7.2 Hz, 1H), 8.16 (d, J=7.8 Hz, 1H), 8.57 (s, 1H), 9.96 (br, 1H); $^{19}$F NMR (282 MHz, DMSO-d$_6$): δ−59.94.

I-84: N2-[3-Chloro-4-(4-methylsulfonylpiperazino)]phenyl-5-ethoxycarbonyl-N4-(1,2,2,6,6-pentamethylpiperidin-4-yl)-2,4-pyrimidinediamine LCMS: purity: 97.85%; MS (m/e): 608.12 (MH+); $^1$H NMR (DMSO-d$_6$): δ 1.13 (s, 12H), 1.29 (t, J=6.9 Hz, 3H), 1.36 (t, J=11.1 Hz, 2H), 1.88 (d, J=12.3 Hz, 2H), 2.28 (s, 3H), 2.93 (s, 3H), 2.98 (t, 4H), 3.26 (t, 4H), 4.22 (q, J=6.9 Hz, 2H), 4.41 (br, 1H), 7.05 (d, J=8.4 Hz, 1H), 7.73 (m, 2H), 8.09 (d, 1H), 8.55 (s, 1H), 9.82 (br, 1H).

I-85: 5-Aminocarbonyl-N2-(3-chloro-4-methoxy)phenyl-N4-(1,2,2,6,6-pentamethylpiperidin-4-yl)-2,4-pyrimidinediamine LCMS: purity: 92.84%; MS (m/e): 446.76 (MH+).

I-86: 5-Aminocarbonyl-N2-(3-cyano)phenyl-N4-(1,2,2,6,6-pentamethylpiperidin-4-yl)-2,4-pyrimidinediamine LCMS: purity: 80.88%; MS (m/e): 408.14 (MH+); $^1$H NMR (DMSO-d$_6$): δ 0.86 (s, 6H), 0.88 (s, 6H), 1.84 (m, 4H), 3.71 (d, J=7.2 Hz, 3H), 4.42 (m, 1H), 7.39 (m, 2H), 8.10 (m, 2H), 8.56 (s, 1H), 9.24 (br, 1H), 9.80 (br, 1H).

I-87: Mixture of N2-[3-Chloro-4-(4-methylsulfonylpiperazino)]phenyl-N4-(1,2,2,6,6-pentamethylpiperidin-4-yl)-5-trifluoromethyl-2,4-pyrimidinediamine and N4-[3-Chloro-4-(4-methylsulfonylpiperazino)]phenyl-N2-(1,2,2,6,6-pentamethylpiperidin-4-yl)-5-trifluoromethyl-2,4-pyrimidinediamine LCMS: purity: 95.28%; MS (m/e): 604.00 (MH+); $^1$H NMR (DMSO-d$_6$): δ 1.05 (s, 6H), 1.08 (s, 6H), 1.28 (t, J=11.1 Hz, 2H), 1.58 (m, 2H), 2.18 and 2.21 (s, 3H), 2.93 (s, 3H), 2.98 (t, 4H), 3.26 (t, 4H), 3.88 (br, 1H), 4.51 (br, 1H), 6.38 (d, J=7.2 Hz, 1H), 7.05 (t, J=8.7 Hz, 2H), 7.36 (d, 1H), 7.47 (s, 1H), 7.64 (d, 2H), 8.16 (s, 1H), 8.42 (s, 1H), 9.54 (s, 1H); $^{19}$F NMR (282 MHz, DMSO-d$_6$): δ−60.76, −59.38.

I-88: N2-[4-(4-Methylsulfonylpiperazino)-3-trifluoromethyl]phenyl-N4-(1,2,2,6,6-pentamethylpiperidin-4-yl)-5-trifluoromethyl-2,4-pyrimidinediamine LCMS: purity: 98.14%; MS (m/e): 638.20 (MH+); $^1$H NMR (DMSO-d$_6$): δ 1.34 (s, 12H), 1.91 (br, 4H), 2.88 (t, 4H), 2.93 (s, 3H), 3.21 (t, 4H), 4.62 (br, 1H), 7.49 (d, 1H), 7.67 (br, 1H), 8.03 (d, 1H), 8.22 (s, 1H), 9.74 (br, 1H); $^{19}$F NMR (282 MHz, DMSO-d$_6$): δ−59.94, −60.77.

I-89: N2-[3-Chloro-4-(4-methylpiperazino)]phenyl-5-ethoxycarbonyl-N4-(1,2,2,6,6-pentamethylpiperidin-4-yl)-2,4-pyrimidinediamine LCMS: purity: 88.90%; MS (m/e): 544.20 (MH+); $^1$H NMR (DMSO-d$_6$): δ 1.29 (t, J=6.9 Hz, 3H), 1.32 (s, 12H), 1.62 (t, 2H), 2.07 (d, 2H), 2.40 (s, 3H), 2.62 (br, 2H), 2.71 (br, 2H), 2.96 (t, 4H), 4.23 (q, J=7.2 Hz, 2H), 4.49 (br, 1H), 6.51 (s, 1H), 7.05 (d, J=9.9 Hz, 1H), 7.60 (d, 1H), 7.72 (br, 1H), 8.57 (s, 1H), 9.86 (br, 1H).

I-90: 5-Aminocarbonyl-N2-[4-(4-methylsulfonylpiperazino)-3-trifluoromethyl]phenyl-N4-(1,2,2,6,6-pentamethylpiperidin-4-yl)-2,4-pyrimidinediamine LCMS: purity: 92.16%; MS (m/e): 613.01 (MH+); $^1$H NMR (DMSO-d$_6$): δ 1.22 (s, 12H), 1.41 (m, 2H), 1.96 (m, 2H), 2.88 (t, 4H), 2.93 (s, 3H), 3.16 (d, 3H), 3.20 (t, 4H), 4.09 (br, 1H), 6.51 (s, 1H), 7.44 (br, 1H), 7.80 (br, 1H), 8.11 (br, 1H), 8.53 (s, 1H), 9.14 (br, 1H), 9.66 (br, 1H); $^{19}$F NMR (282 MHz, DMSO-d$_6$): δ−59.90.

I-91: 5-Aminocarbonyl-N2-[3-chloro-4-(4-methylsulfonylpiperazino)]phenyl-N4-(1,2,2,6,6-pentamethylpiperidin-4-yl)-2,4-pyrimidinediamine LCMS: purity: 82.23%; MS (m/e): 579.18 (MH+); $^1$H NMR (DMSO-d$_6$): δ 1.26 (s, 12H), 1.46 (t, 2H), 2.02 (d, J=12.9 Hz, 2H), 2.93 (s, 3H), 2.98 (t, 4H), 3.25 (t, 4H), 4.41 (br, 1H), 6.51 (br, 1H), 7.15 (d, J=8.4 Hz, 1H), 7.77 (br, 1H), 8.22 (s, 1H), 8.51 (s, 1H), 9.16 (br, 1H), 9.53 (br, 1H), 10.21 (br, 1H).

I-92: N2-[3-Chloro-4-(4-methylsulfonylpiperazino)]phenyl-N4-(1,2,2,6,6-pentamethylpiperidin-4-yl)-5-trifluoromethyl-2,4-pyrimidinediamine LCMS: purity: 91.02%; MS (m/e): 603.91 (MH+); $^1$H NMR (DMSO-d$_6$): δ 1.05 (s, 6H), 1.08 (s, 6H), 1.61 (m, 4H), 2.21 (s, 3H), 2.93 (s, 3H), 2.97 (t, 4H), 3.30 (t, 4H), 4.54 (br, 1H), 6.40 (d, 1H), 7.03 (d, 1H), 7.64 (m, 2H), 8.16 (s, 1H); $^{19}$F NMR (282 MHz, DMSO-d$_6$): δ−60.76.

I-93: N2-(3-Chloro-4-methoxy)phenyl-5-cyano-N4-(1,2,2,6,6-pentamethylpiperidin-4-yl)-2,4-pyrimidinediamine LCMS: purity: 88.07%; MS (m/e): 429.12 (MH+); $^1$H NMR (DMSO-d$_6$): δ 1.06 (s, 6H), 1.10 (s, 6H), 1.58 (m, 4H), 2.26 (s, 3H), 3.78 (s, 3H), 4.42 (m, 1H), 6.47 (s, 1H), 6.96 (d, 1H), 7.56 (d, 1H), 7.65 (s, 1H), 8.29 (s, 1H), 9.59 (s, 1H).

I-94: 5-Cyano-N2-[4-(4-methylpiperazino)-3-trifluoromethyl]phenyl-N4-(1,2,2,6,6-pentamethylpiperidin-4-yl)-2,4-pyrimidinediamine LCMS: purity: 81.02%; MS (m/e): 531.38 (MH+).

I-95: 5-Cyano-N2-[4-(4-methylsulfonylpiperazino)-3-trifluoromethyl]phenyl-N4-(1,2,2,6,6-pentamethylpiperidin-4-yl)-2,4-pyrimidinediamine LCMS: purity: 89.22%; MS (m/e): 595.44 (MH+); $^1$H NMR (DMSO-d$_6$): δ 1.00 (s, 6H), 1.07 (s, 6H), 1.57 (m, 4H), 2.19 (s, 3H), 2.88 (t, 4H), 2.93 (s, 3H), 3.20 (t, 4H), 4.34 (br, 1H), 7.44 (d, J=8.7 Hz, 2H), 7.70 (br, 1H), 8.10 (d, 1H), 8.32 (s, 1H), 9.91 (br, 1H); $^{19}$F NMR (282 MHz, DMSO-d$_6$): δ−59.95.

I-96: 5-Fluoro-N4-(1,2,2,6,6-pentamethylpiperidin-4-yl)-N2-[4-(pyridin-4-yl)-3-trifluoromethyl]phenyl-2,4-pyrimidinediamine LCMS: purity: 93.72%; MS (m/e): 503.33 (MH+); $^1$H NMR (DMSO-d$_6$): δ 1.05 (s, 6H), 1.07 (s, 6H), 1.46 (t, J=11.7 Hz, 2H), 1.70 (d, J=11.7 Hz, 2H), 2.17 (s, 3H), 4.32 (br, 1H), 7.18 (d, J=8.7 Hz, 1H), 7.29 (d, J=6.0 Hz, 3H), 7.90 (d, J=3.9 Hz, 1H), 7.99 (s, 1H), 8.27 (d, J=8.4 Hz, 1H), 8.59 (d, J=6.0 Hz, 2H), 9.46 (s, 1H); $^{19}$F NMR (282 MHz, DMSO-d$_6$): δ−164.93, −56.23.

I-97: 5-Cyano-N2-(3-cyano)phenyl-N4-(1,2,2,6,6-pentamethylpiperidin-4-yl)-2,4-pyrimidinediamine LCMS: purity: 96.00%; MS (m/e): 390.36 (MH+).

I-98: 5-Aminocarbonyl-N2-[3-chloro-4-(4-methylpiperazino)]phenyl-N4-(1,2,2,6,6-pentamethylpiperidin-4-yl)-2,4-pyrimidinediamine LCMS: purity: 78.81%; MS (m/e): 515.24 (MH+).

I-99: N2-[3-Chloro-4-(pyridin-4-yl)]phenyl-5-fluoro-N4-(1,2,2,6,6-pentamethylpiperidin-4-yl)-2,4-pyrimidinediamine LCMS: purity: 97.55%; MS (m/e): 468.86 (MH+); $^1$H NMR (DMSO-d$_6$): δ 1.08 (s, 12H), 1.47 (t, 2H), 1.69 (d, 2H), 2.17 (s, 3H), 4.36 (br, 1H), 7.26 (m, 2H), 7.41 (d, J=4.5 Hz, 2H), 7.82 (d, 1H), 7.89 (d, 1H), 7.92 (s, 1H), 8.59 (d, J=4.8 Hz, 2H), 9.37 (s, 1H); $^{19}$F NMR (282 MHz, DMSO-d$_6$): δ−165.07.

I-100: 5-Fluoro-N2-[3-(1,3-oxazol-5-yl)]phenyl-N4-(1,2,2,6,6-pentamethylpiperidin-4-yl)-2,4-pyrimidinediamine LCMS: purity: 98.93%; MS (m/e): 425.83 (MH+); $^1$H NMR (DMSO-d$_6$): δ 1.10 (s, 6H), 1.16 (s, 6H), 1.54 (t, 2H), 1.79 (d, 2H), 2.32 (s, 3H), 4.40 (br, 1H), 7.22 (m, 2H), 7.28 (m, 1H), 7.54 (s, 1H), 7.78 (s, 1H), 7.88 (m, 2H), 8.39 (s, 1H), 9.12 (s, 1H); $^{19}$F NMR (282 MHz, DMSO-d$_6$): δ−166.08.

I-101: N2-[3-Chloro-4-(4-methylpiperazino)]phenyl-5-cyano-N4-(1,2,2,6,6-pentamethylpiperidin-4-yl)-2,4-pyrimidinediamine LCMS: purity: 86.57%; MS (m/e): 497.30 (MH+); $^1$H NMR (DMSO-d$_6$): δ 1.01 (s, 6H), 1.05 (s, 6H), 1.58 (m, 4H), 2.16 (s, 3H), 2.21 (s, 3H), 2.88 (t, 4H), 4.40 (br, 1H), 6.99 (d, J=7.8 Hz, 1H), 7.37 (d, 1H), 7.61 (d, 2H), 8.28 (s, 1H), 9.75 (br, 1H).

I-102: N2-[3-Chloro-4-(4-methylsulfonylpiperazino)]phenyl-5-cyano-N4-(1,2,2,6,6-pentamethylpiperidin-4-yl)-2,4-pyrimidinediamine LCMS: purity: 92.33%; MS (m/e): 561.20 (MH+); $^1$H NMR (DMSO-d$_6$): δ 1.10 (s, 6H), 1.14 (s, 6H), 1.69 (m, 4H), 2.31 (s, 3H), 2.93 (s, 3H), 2.97 (t, 4H), 3.25 (t, 4H), 4.43 (br, 1H), 7.05 (d, J=8.7 Hz, 1H), 7.50 (br, 1H), 7.62 (m, 2H), 8.31 (s, 1H), 9.80 (br, 1H).

I-103: N2-(3,5-Dichloro)phenyl-5-fluoro-N4-(1,2,2,6,6-pentamethylpiperidin-4-yl)-2,4-pyrimidinediamine LCMS: purity: 92.70%; MS (m/e): 426.09 (MH+); $^1$H NMR (DMSO-d$_6$): δ 1.09 (br, 6H), 1.36 (br, 6H), 1.70 (br, 4H), 2.19 (br, 3H), 4.38 (m, 1H), 6.99 (s, 1H), 7.31 (br, 1H), 7.74 (s, 2H), 7.93 (s, 1H), 9.38 (s, 1H); $^{19}$F NMR (282 MHz, DMSO-d$_6$): δ−164.45.

I-104: N2-(3-Bromo)phenyl-5-fluoro-N4-(1,2,2,6,6-pentamethylpiperidin-4-yl)-2,4-pyrimidinediamine LCMS: purity: 94.68%; MS (m/e): 438.16 (MH+); $^1$H NMR (DMSO-d$_6$): δ 1.36 (s, 6H), 1.46 (s, 6H), 2.00 (m, 4H), 2.68 (d, J=4.5 Hz, 3H), 4.45 (m, 1H), 7.17 (m, 2H), 7.60 (d, J=6.9 Hz, 1H), 7.80 (s, 1H), 8.06 (d, J=4.2 Hz, 1H), 8.37 (br, 1H), 9.61 (br, 1H), 9.82 (br, 1H); $^{19}$F NMR (282 MHz, DMSO-d$_6$): δ−163.38.

I-105: 5-Fluoro-N2-[3-(furan-3-yl)]phenyl-N4-(1,2,2,6,6-pentamethylpiperidin-4-yl)-2,4-pyrimidinediamine LCMS: purity: 93.01%; MS (m/e): 424.20 (MH+); $^1$H NMR (DMSO-d$_6$): δ 1.02 (s, 6H), 1.06 (s, 6H), 1.44 (t, 2H), 1.68 (d, J=11.1 Hz, 2H), 2.16 (s, 3H), 4.34 (br, 1H), 6.78 (s, 1H), 7.08-7.16 (m, 3H), 7.55 (s, 1H), 7.70 (s, 1H), 7.83 (d, J=4.2 Hz, 1H), 7.88 (d, J=9.3 Hz, 1H), 8.00 (s, 1H), 8.91 (s, 1H); $^{19}$F NMR (282 MHz, DMSO-d$_6$): δ−166.58.

I-106: N2-[3-(Benzothiophen-2-yl)]phenyl-5-fluoro-N4-(1,2,2,6,6-pentamethylpiperidin-4-yl)-2,4-pyrimidinediamine LCMS: purity: 95.74%; MS (m/e): 490.22 (MH+); $^1$H NMR (DMSO-d$_6$): δ 0.97 (s, 6H), 1.04 (s, 6H), 1.44 (t, J=10.8 Hz, 2H), 1.69 (d, J=11.7 Hz, 2H), 2.13 (s, 3H), 4.38 (br, 1H), 7.19 (d, J=6.9 Hz, 1H), 7.26 (m, 2H), 7.34 (m, 2H), 7.70 (s, 1H), 7.83 (m, 2H), 7.87 (d, J=4.2 Hz, 1H), 7.95 (t, J=6.9 Hz, 2H), 9.14 (s, 1H); $^{19}$F NMR (282 MHz, DMSO-d$_6$): δ−166.13.

I-107: 5-Fluoro-N4-(1,2,2,6,6-pentamethylpiperidin-4-yl)-N2-(3-pyridin-3-yl)phenyl-2,4-pyrimidinediamine LCMS: purity: 82.99%; MS (m/e): 435.28 (MH+); $^1$H NMR (DMSO-d$_6$): δ 0.94 (s, 6H), 1.04 (s, 6H), 1.43 (t, J=12.0 Hz, 2H), 1.66 (d, J=11.7 Hz, 2H), 2.14 (s, 3H), 4.34 (br, 1H), 7.18 (m, 2H), 7.26 (t, J=7.5 Hz, 1H), 7.45 (dd, J=4.2, 7.2 Hz, 1H), 7.74 (s, 1H), 7.85 (d, J=3.9 Hz, 1H), 7.96 (t, J=8.4 Hz, 2H), 8.52 (dd, J=1.5, 4.8 Hz, 1H), 8.76 (s, 1H), 9.08 (s, 1H); $^{19}$F NMR (282 MHz, DMSO-d$_6$): δ−166.31.

I-108: N2-(4-Bromo)phenyl-5-fluoro-N4-(1,2,2,6,6-pentamethylpiperidin-4-yl)-2,4-pyrimidinediamine LCMS: purity: 99.99%; MS (m/e): 438.18 (MH+); $^1$H NMR (DMSO-d$_6$): δ 1.42 (s, 6H), 1.44 (s, 6H), 1.83 (t, J=13.2 Hz, 2H), 2.08 (d, J=13.2 Hz, 2H), 2.74 (d, J=5.1 Hz, 3H), 4.48 (m, 1H), 7.32 (d, J=8.7 Hz, 2H), 7.59 (d, J=8.1 Hz, 1H), 7.64 (d, J=9.0 Hz, 2H), 7.92 (d, J=3.6 Hz, 1H), 8.69 (br, 1H), 9.23 (s, 1H); $^{19}$F NMR (282 MHz, DMSO-d$_6$): δ−165.79.

I-109: N2-(4-Bromo-3-trifluoromethyl)phenyl-5-fluoro-N4-(1,2,2,6,6-pentamethylpiperidin-4-yl)-2,4-pyrimidinediamine LCMS: purity: 84.86%; MS (m/e): 506.17 (MH+); $^1$H NMR (DMSO-d$_6$): δ 1.39 (s, 6H), 1.44 (s, 6H), 1.92 (t, J=12.0 Hz, 2H), 2.05 (d, J=11.4 Hz, 2H), 2.71 (d, J=4.8 Hz, 3H), 4.41 (m, 1H), 7.64 (d, J=8.4 Hz, 1H), 7.84 (br, 1H), 8.00 (m, 3H), 9.14 (br, 1H), 9.56 (br, 1H); $^{19}$F NMR (282 MHz, DMSO-d$_6$): δ−62.13.

I-110: N2-(4-Bromo-3-fluoro)phenyl-5-fluoro-N4-(1,2,2,6,6-pentamethylpiperidin-4-yl)-2,4-pyrimidinediamine LCMS: purity: 99.33%; MS (m/e): 456.08 (MH+); $^1$H NMR (DMSO-d$_6$): δ 1.39 (s, 6H), 1.48 (s, 6H), 2.02 (d, J=6.0 Hz, 4H), 2.70 (d, J=4.8 Hz, 3H), 4.48 (m, 1H), 7.28 (d, J=8.7 Hz, 1H), 7.51 (t, J=8.4 Hz, 1H), 7.86 (dd, J=2.4, 12.0 Hz, 1H), 8.04 (d, J=4.2 Hz, 1H), 8.25 (br, 1H), 9.63 (br, 1H), 9.91 (br, 1H); $^{19}$F NMR (282 MHz, DMSO-d$_6$): δ−107.54.

I-111: N2-(4-Bromo-3-methyl)phenyl-5-fluoro-N4-(1,2,2,6,6-pentamethylpiperidin-4-yl)-2,4-pyrimidinediamine LCMS: purity: 95.27%; MS (m/e): 452.01 (MH+); $^1$H NMR (DMSO-d$_6$): δ 1.33 (s, 6H), 1.46 (s, 6H), 2.00 (d, J=6.9 Hz, 4H), 2.29 (s, 3H), 2.69 (d, J=5.1 Hz, 3H), 4.43 (m, 1H), 7.40 (d, J=8.4 Hz, 2H), 7.50 (d, J=8.4 Hz, 1H), 8.05 (d, J=4.5 Hz, 1H), 8.43 (br, 1H), 9.56 (br, 1H), 9.74 (br, 1H).

I-112: 5-Fluoro-N4-(1,2,2,6,6-pentamethylpiperidin-4-yl)-N2-[4-(pyridin-3-yl)-3-trifluoromethyl]phenyl-2,4-pyrimidinediamine LCMS: purity: 98.94%; MS (m/e): 503.43 (MH+); $^1$H NMR (DMSO-d$_6$): δ 1.05 (s, 6H), 1.07 (s, 6H), 1.46 (t, J=12.0 Hz, 2H), 1.70 (d, J=11.7 Hz, 2H), 2.16 (s, 3H), 4.32 (br, 1H), 7.19 (d, J=8.4 Hz, 1H), 7.28 (t, J=9.3 Hz, 1H), 7.44 (dd, J=4.2, 7.2 Hz, 1H), 7.69 (d, J=7.8 Hz, 1H), 7.90 (d, J=3.9 Hz, 1H), 7.99 (s, 1H), 8.27 (d, J=8.4 Hz, 1H), 8.45 (s, 1H), 8.56 (dd, J=1.5, 4.5 Hz, 1H), 9.44 (s, 1H); $^{19}$F NMR (282 MHz, DMSO-d$_6$): δ−165.04, −56.44.

I-113: 5-Fluoro-N2-[4-(furan-3-yl)-3-trifluoromethyl]phenyl-N4-(1,2,2,6,6-pentamethylpiperidin-4-yl)-2,4-pyrimidinediamine LCMS: purity: 94.65%; MS (m/e): 492.41 (MH+); $^1$H NMR (DMSO-d$_6$): δ 1.06 (s, 6H), 1.07 (s, 6H), 1.46 (t, J=12.0 Hz, 2H), 1.70 (d, J=11.4 Hz, 2H), 2.17 (s, 3H), 4.36 (br, 1H), 6.56 (s, 1H), 7.25 (d, J=8.7 Hz, 2H), 7.70 (s, 2H), 7.89 (d, J=3.9 Hz, 1H), 7.95 (s, 1H), 8.20 (d, J=8.4 Hz, 1H), 9.36 (s, 1H); $^{19}$F NMR (282 MHz, DMSO-d$_6$): δ−165.25, −57.97.

I-114: N2-[4-(Benzothiophen-2-yl)-3-trifluoromethyl]phenyl-5-fluoro-N4-(1,2,2,6,6-pentamethylpiperidin-4-yl)-2,4-pyrimidinediamine LCMS: purity: 95.12%; MS (m/e): 558.15 (MH+); $^1$H NMR (DMSO-d$_6$): δ 1.07 (s, 12H), 1.47 (t, J=11.7 Hz, 2H), 1.71 (d, J=11.1 Hz, 2H), 2.17 (s, 3H), 4.34 (br, 1H), 7.31 (d, J=7.8 Hz, 1H), 7.34-7.42 (m, 4H), 7.86 (dd, J=2.4, 5.7 Hz, 1H), 7.91 (d, J=3.6 Hz, 1H), 7.96 (dd, J=2.1, 6.3 Hz, 1H), 8.00 (s, 1H), 8.30 (d, J=8.7 Hz, 1H), 9.53 (s, 1H); $^{19}$F NMR (282 MHz, DMSO-d$_6$): δ−164.76, −57.31.

I-115: 5-Fluoro-N2-[3-fluoro-4-(pyridin-4-yl)]phenyl-N4-(1,2,2,6,6-pentamethylpiperidin-4-yl)-2,4-pyrimidinediamine LCMS: purity: 96.95%; MS (m/e): 453.31 (MH+); $^1$H NMR (DMSO-d$_6$): δ 1.08 (s, 6H), 1.10 (s, 6H), 1.49 (t, J=12.0 Hz, 2H), 1.72 (d, J=8.7 Hz, 2H), 2.19 (s, 3H), 4.42 (br, 1H), 7.32 (d, J=9.0 Hz, 1H), 7.50 (m, 4H), 7.91 (m, 2H), 8.58 (d, J=5.4 Hz, 2H), 9.51 (s, 1H); $^{19}$F NMR (282 MHz, DMSO-d$_6$): δ−165.01, −116.32.

I-116: 5-Fluoro-N2-[4-(4-methylthiophen-2-yl)-3-trifluoromethyl]phenyl-N4-(1,2,2,6,6-pentamethylpiperidin-4-yl)-2,4-pyrimidinediamine LCMS: purity: 96.63%; MS (m/e): 522.22 (MH+); $^1$H NMR (DMSO-d$_6$): δ 1.06 (s, 6H), 1.07 (s, 6H), 1.46 (t, 2H), 1.69 (d, 2H), 2.18 (s, 3H), 2.22 (s, 3H), 4.31 (br, 1H), 6.85 (s, 1H), 7.15 (s, 1H), 7.27 (d, J=8.7 Hz, 2H), 7.90 (d, 1H), 7.93 (s, 1H), 8.28 (d, 1H), 9.43 (s, 1H); $^{19}$F NMR (282 MHz, DMSO-d$_6$): δ−165.00, −57.24.

I-117: N2-[4-Bromo-3,5-bis(trifluoromethyl)]phenyl-5-fluoro-N4-(1,2,2,6,6-pentamethylpiperidin-4-yl)-2,4-pyrimidinediamine LCMS: purity: 89.13%; MS (m/e): 574.16 (MH+); $^1$H NMR (DMSO-d$_6$): δ 1.39 (s, 6H), 1.41 (s, 6H), 1.82 (t, J=12.6 Hz, 2H), 2.07 (d, J=11.7 Hz, 2H), 2.73 (d, J=4.5 Hz, 3H), 4.43 (m, 1H), 7.75 (d, J=7.2 Hz, 1H), 8.03 (d, J=3.3 Hz, 1H), 8.47 (s, 2H), 8.68 (br, 1H), 9.65 (s, 1H); $^{19}$F NMR (282 MHz, DMSO-d$_6$): δ−163.25, −61.69.

I-118: 5-Fluoro-N2-[3-fluoro-4-(pyridin-3-yl)]phenyl-N4-(1,2,2,6,6-pentamethylpiperidin-4-yl)-2,4-pyrimidinediamine LCMS: purity: 93.66%; MS (m/e): 453.17 (MH+); $^1$H NMR (DMSO-d$_6$): δ 1.08 (s, 6H), 1.10 (s, 6H), 1.49 (t, J=12.3 Hz, 2H), 1.71 (d, J=9.3 Hz, 2H), 2.18 (s, 3H), 4.40 (m, 1H), 7.30 (d, J=8.4 Hz, 1H), 7.38 (t, J=8.7 Hz, 1H), 7.45 (dd, J=5.1, 8.1 Hz, 1H), 7.50 (d, J=8.4 Hz, 1H), 7.88 (m, 3H), 8.50 (d, J=4.8 Hz, 1H), 8.66 (s, 1H), 9.44 (s, 1H); $^{19}$F NMR (282 MHz, DMSO-d$_6$): δ−165.29, −117.51.

I-119: 5-Fluoro-N2-[3-fluoro-4-(furan-3-yl)]phenyl-N4-(1,2,2,6,6-pentamethylpiperidin-4-yl)-2,4-pyrimidinediamine LCMS: purity: 95.98%; MS (m/e): 442.38 (MH+); $^1$H NMR (DMSO-d$_6$): δ 1.08 (s, 6H), 1.10 (s, 6H), 1.48 (t, J=12.3 Hz, 2H), 1.70 (d, J=9.0 Hz, 2H), 2.19 (s, 3H), 4.39 (br, 1H), 6.87 (s, 1H), 7.26 (d, J=8.1 Hz, 1H), 7.38-7.48 (m, 2H), 7.72 (s, 1H), 7.86 (m, 2H), 7.92 (s, 1H), 9.30 (s, 1H); $^{19}$F NMR (282 MHz, DMSO-d$_6$): δ−165.63, −112.69.

I-120: 5-Fluoro-N2-[3-methyl-4-(pyridin-4-yl)]phenyl-N4-(1,2,2,6,6-pentamethylpiperidin-4-yl)-2,4-pyrimidinediamine LCMS: purity: 90.89%; MS (m/e): 449.87 (MH+); $^1$H NMR (DMSO-d$_6$): δ 1.07 (s, 12H), 1.47 (t, J=12.0 Hz, 2H), 1.70 (d, J=8.4 Hz, 2H), 2.17 (s, 3H), 2.22 (s, 3H), 4.37 (br, 1H), 7.03 (d, J=8.4 Hz, 1H), 7.18 (d, J=8.4 Hz, 1H), 7.31 (d, J=5.1 Hz, 2H), 7.39 (s, 1H), 7.85 (d, J=3.6 Hz, 1H), 7.89 (d, J=9.6 Hz, 1H), 8.55 (d, J=5.1 Hz, 2H), 9.08 (s, 1H); $^{19}$F NMR (282 MHz, DMSO-d$_6$): δ−166.22.

I-121: 5-Fluoro-N2-[3-methyl-4-(pyridin-3-yl)]phenyl-N4-(1,2,2,6,6-pentamethylpiperidin-4-yl)-2,4-pyrimidinediamine LCMS: purity: 86.98%; MS (m/e): 449.34 (MH+); $^1$H NMR (DMSO-d$_6$): δ 1.07 (s, 12H), 1.47 (t, J=12.0 Hz, 2H), 1.71 (d, J=11.7 Hz, 2H), 2.17 (s, 3H), 2.19 (s, 3H), 4.40 (br, 1H), 7.00 (d, J=7.8 Hz, 1H), 7.16 (d, J=8.1 Hz, 1H), 7.39 (s, 1H), 7.42 (m, 1H), 7.71 (d, J=6.9 Hz, 1H), 7.84 (d, J=3.9 Hz, 1H), 7.88 (d, J=8.4 Hz, 1H), 8.48 (m, 2H), 9.04 (s, 1H); $^{19}$F NMR (282 MHz, DMSO-d$_6$): δ−166.42.

I-122: 5-Fluoro-N2-[4-(furan-3-yl)-3-methyl]phenyl-N4-(1,2,2,6,6-pentamethylpiperidin-4-yl)-2,4-pyrimidinediamine LCMS: purity: 96.88%; MS (m/e): 438.41 (MH+); $^1$H NMR (DMSO-d$_6$): δ 1.07 (s, 12H), 1.46 (t, J=12.6 Hz, 2H), 1.70 (d, J=9.0 Hz, 2H), 2.18 (s, 3H), 2.28 (s, 3H), 4.37 (br, 1H), 6.66 (s, 1H), 7.13 (m, 2H), 7.34 (s, 1H), 7.68 (s, 1H), 7.74

(s, 1H), 7.78 (d, J=8.1 Hz, 1H), 7.83 (d, J=3.6 Hz, 1H), 8.95 (s, 1H); $^{19}$F NMR (282 MHz, DMSO-d$_6$): δ−166.64.

I-123: 5-Fluoro-N4-(1,2,2,6,6-pentamethylpiperidin-4-yl)-N2-[4-(pyridin-4-yl)]phenyl-2,4-pyrimidinediamine LCMS: purity: 81.39%; MS (m/e): 435.22 (MH+); $^1$H NMR (DMSO-d$_6$): δ 1.09 (s, 6H), 1.12 (s, 6H), 1.49 (t, J=12.3 Hz, 2H), 1.73 (d, J=11.7 Hz, 2H), 2.20 (s, 3H), 4.39 (br, 1H), 7.25 (d, J=8.4 Hz, 1H), 7.59 (m, 4H), 7.86 (d, J=8.4 Hz, 3H), 8.54 (d, J=4.8 Hz, 2H), 9.30 (s, 1H); $^{19}$F NMR (282 MHz, DMSO-d$_6$): δ−165.83.

I-124: 5-Fluoro-N4-(1,2,2,6,6-pentamethylpiperidin-4-yl)-N2-[4-(pyridin-3-yl)]phenyl-2,4-pyrimidinediamine LCMS: purity: 88.70%; MS (m/e): 435.24 (MH+); $^1$H NMR (DMSO-d$_6$): δ 1.09 (s, 6H), 1.12 (s, 6H), 1.48 (t, J=12.0 Hz, 2H), 1.73 (d, J=9.9 Hz, 2H), 2.20 (s, 3H), 4.39 (br, 1H), 7.22 (d, J=8.7 Hz, 1H), 7.42 (dd, J=4.5, 7.8 Hz, 1H), 7.51 (d, J=8.7 Hz, 2H), 7.84 (d, J=8.4 Hz, 3H), 7.95 (d, J=8.1 Hz, 1H), 8.46 (d, J=4.8 Hz, 1H), 8.78 (s, 1H), 9.22 (s, 1H); $^{19}$F NMR (282 MHz, DMSO-d$_6$): δ−166.17.

I-125: 5-Fluoro-N2-[4-(furan-3-yl)]phenyl-N4-(1,2,2,6,6-pentamethylpiperidin-4-yl)-2,4-pyrimidinediamine LCMS: purity: 96.47%; MS (m/e): 424.27 (MH+); $^1$H NMR (DMSO-d$_6$): δ 1.08 (s, 6H), 1.10 (s, 6H), 1.47 (t, J=12.0 Hz, 2H), 1.71 (d, J=9.9 Hz, 2H), 2.20 (s, 3H), 4.38 (br, 1H), 6.81 (s, 1H), 7.18 (d, J=8.4 Hz, 1H), 7.35 (d, J=8.1 Hz, 2H), 7.69 (t, J=8.1 Hz, 3H), 7.83 (d, J=3.6 Hz, 1H), 8.00 (s, 1H), 9.05 (s, 1H); $^{19}$F NMR (282 MHz, DMSO-d$_6$): δ−166.60.

I-126: 5-Fluoro-N2-[4-(1-methyl-1H-pyrazol-4-yl)-3-trifluoromethyl]phenyl-N4-(1,2,2,6,6-pentamethylpiperidin-4-yl)-2,4-pyrimidinediamine LCMS: purity: 98.81%; MS (m/e): 506.21 (MH+); $^1$H NMR (DMSO-d$_6$): δ 1.06 (s, 6H), 1.07 (s, 6H), 1.46 (t, J=12.0 Hz, 2H), 1.70 (d, J=9.0 Hz, 2H), 2.18 (s, 3H), 3.86 (s, 3H), 4.32 (br, 1H), 7.23 (t, J=7.2 Hz, 2H), 7.43 (s, 1H), 7.75 (s, 1H), 7.88 (d, J=3.9 Hz, 1H), 7.91 (s, 1H), 8.19 (d, J=8.4 Hz, 1H), 9.32 (s, 1H); $^{19}$F NMR (282 MHz, DMSO-d$_6$): δ−165.42, −57.96.

I-127: 5-Fluoro-N2-(3-fluoro-4-methoxy)phenyl-N4-(1,2,2,6,6-pentamethylpiperidin-4-yl)-2,4-pyrimidinediamine LCMS: purity: 98.86%; MS (m/e): 406.37 (MH+); $^1$H NMR (DMSO-d$_6$): δ 1.27 (s, 12H), 1.66 (t, J=12.6 Hz, 2H), 1.92 (d, J=13.2 Hz, 2H), 3.74 (s, 3H), 4.45 (m, 1H), 6.97 (t, J=9.0 Hz, 1H), 7.22 (d, J=9.6 Hz, 1H), 7.38 (d, J=6.6 Hz, 1H), 7.70 (d, J=13.5 Hz, 1H), 7.86 (d, J=3.6 Hz, 1H), 9.01 (s, 1H); $^{19}$F NMR (282 MHz, DMSO-d$_6$): δ−166.64.

I-128: N2-(4-Chloro-3-cyano-5-ethyl)phenyl-5-fluoro-N4-(1,2,2,6,6-pentamethylpiperidin-4-yl)-2,4-pyrimidinediamine LCMS: purity: 96.61%; MS (m/e): 445.11 (MH+); $^1$H NMR (DMSO-d$_6$): δ 0.94 (s, 6H), 1.04 (s, 6H), 1.18 (t, J=7.5 Hz, 3H), 1.40 (t, 2H), 1.64 (d, J=10.8 Hz, 2H), 2.15 (s, 3H), 2.72 (q, 2H), 4.10 (m, 1H), 7.31 (s, 1H), 7.46 (s, 1H), 7.89 (d, 1H), 8.18 (s, 1H), 8.22 (s, 1H).

I-129: N2-(3,5-Dimethoxy)phenyl-5-fluoro-N4-(1,2,2,6,6-pentamethylpiperidin-4-yl)-2,4-pyrimidinediamine LCMS: purity: 98.54%; MS (m/e): 418.36 (MH+); $^1$H NMR (DMSO-d$_6$): δ 1.40 (s, 6H), 1.43 (s, 6H), 1.79 (t, J=12.9 Hz, 2H), 2.06 (d, J=12.6 Hz, 2H), 2.75 (d, 3H), 3.67 (s, 6H), 4.53 (m, 1H), 6.08 (s, 1H), 6.91 (s, 2H), 7.56 (d, 1H), 7.90 (d, J=3.6 Hz, 1H), 8.49 (br, 1H), 8.98 (s, 1H).

I-130: N2-(3,4-Dimethoxy)phenyl-5-fluoro-N4-(1,2,2,6,6-pentamethylpiperidin-4-yl)-2,4-pyrimidinediamine LCMS: purity: 97.77%; MS (m/e): 418.39 (MH+); $^1$H NMR (DMSO-d$_6$): δ 1.12 (s, 6H), 1.13 (s, 6H), 1.51 (t, J=12.3 Hz, 2H), 1.75 (d, J=10.5 Hz, 2H), 2.28 (s, 3H), 3.66 (s, 3H), 3.69 (s, 3H), 4.35 (m, 1H), 6.70 (d, J=8.1 Hz, 1H), 7.05 (s, 1H), 7.14 (d, J=8.1 Hz, 1H), 7.43 (d, J=8.7 Hz, 1H), 7.80 (d, J=3.9 Hz, 1H), 8.67 (s, 1H); $^{19}$F NMR (282 MHz, DMSO-d$_6$): δ−167.39.

I-131: N2-(3,5-Dimethyl-4-methoxy)phenyl-5-fluoro-N4-(1,2,2,6,6-pentamethylpiperidin-4-yl)-2,4-pyrimidinediamine LCMS: purity: 97.95%; MS (m/e): 416.29 (MH+); $^1$H NMR (DMSO-d$_6$): δ 1.31 (s, 6H), 1.38 (s, 6H), 1.77 (t, J=13.2 Hz, 2H), 2.01 (d, J=11.7 Hz, 2H), 2.17 (s, 6H), 2.72 (d, J=5.1 Hz, 3H), 3.59 (s, 3H), 4.42 (m, 1H), 7.13 (s, 2H), 7.95 (d, J=4.2 Hz, 1H), 8.54 (br, 1H), 9.06 (s, 1H).

I-132: N2-[3-Cyano-4-(4-methylpiperazino)]phenyl-5-fluoro-N4-(1,2,2,6,6-pentamethylpiperidin-4-yl)-2,4-pyrimidinediamine LCMS: purity: 94.97%; MS (m/e): 481.20 (MH+); $^1$H NMR (DMSO-d$_6$): δ 1.06 (s, 12H), 1.44 (t, J=11.7 Hz, 2H), 1.67 (d, J=10.2 Hz, 2H), 2.17 (s, 3H), 2.22 (s, 3H), 3.00 (t, 4H), 4.32 (br, 1H), 7.01 (d, J=8.7 Hz, 1H), 7.17 (d, J=7.5 Hz, 1H), 7.83 (m, 2H), 7.93 (s, 1H), 9.07 (s, 1H); $^{19}$F NMR (282 MHz, DMSO-d$_6$): δ−166.07.

I-133: N2-(4-Benzoylamino)phenyl-5-fluoro-N4-(1,2,2,6,6-pentamethylpiperidin-4-yl)-2,4-pyrimidinediamine LCMS: purity: 95.72%; MS (m/e): 477.46 (MH+); $^1$H NMR (DMSO-d$_6$): δ 1.40 (s, 6H), 1.44 (s, 6H), 1.80 (t, J=13.2 Hz, 2H), 2.10 (d, J=12.0 Hz, 2H), 2.73 (s, 3H), 4.50 (br, 1H), 7.49-7.64 (m, 7H), 7.91 (d, J=6.3 Hz, 3H), 8.53 (br, 1H), 9.04 (s, 1H), 10.07 (s, 1H); $^{19}$F NMR (282 MHz, DMSO-d$_6$): δ−166.82.

I-134: N2-(4-Aminocarbonylmethoxy)phenyl-5-fluoro-N4-(1,2,2,6,6-pentamethylpiperidin-4-yl)-2,4-pyrimidinediamine LCMS: purity: 89.44%; MS (m/e): 431.13 (MH+); $^1$H NMR (DMSO-d$_6$): δ 1.28 (s, 12H), 1.66 (br, 2H), 1.90 (br, 2H), 2.53 (s, 3H), 4.31 (s, 2H), 4.43 (br, 1H), 6.78 (d, J=9.0 Hz, 2H), 7.34 (br, 2H), 7.45 (s, 1H), 7.54 (d, J=8.7 Hz, 2H), 7.83 (d, J=3.6 Hz, 1H), 8.86 (s, 1H); $^{19}$F NMR (282 MHz, DMSO-d$_6$): δ−167.43.

I-135: 5-Fluoro-N2-(4-isopropoxycarbonylmethoxy) phenyl-N4-(1,2,2,6,6-pentamethylpiperidin-4-yl)-2,4-pyrimidinediamine LCMS: purity: 98.61%; MS (m/e): 474.31 (MH+); $^1$H NMR (DMSO-d$_6$): δ 1.21 (d, J=6.3 Hz, 6H), 1.38 (s, 6H), 1.40 (s, 6H), 1.80 (t, J=13.2 Hz, 2H), 2.06 (d, J=13.2 Hz, 2H), 2.74 (d, J=4.5 Hz, 3H), 4.47 (br, 1H), 4.65 (s, 2H), 4.97 (p, J=6.3 Hz, 1H), 6.79 (d, J=8.7 Hz, 2H), 7.48 (d, J=8.7 Hz, 2H), 7.94 (d, J=4.5 Hz, 2H), 8.60 (br, 1H), 9.26 (br, 1H).

I-136: 5-Fluoro-N2-(3-methylaminocarbonyl-methoxy)phenyl-N4-(1,2,2,6,6-pentamethylpiperidin-4-yl)-2,4-pyrimidinediamine LCMS: purity: 98.85%; MS (m/e): 445.24 (MH+); $^1$H NMR (DMSO-d$_6$): δ 1.17 (s, 12H), 1.56 (t, J=12.3 Hz, 2H), 1.80 (d, J=12.0 Hz, 2H), 2.34 (s, 3H), 2.63 (d, J=4.8 Hz, 3H), 4.35 (s, 2H), 4.42 (m, 1H), 6.43 (d, J=7.2 Hz, 1H), 7.04 (t, J=8.1 Hz, 1H), 7.23 (s, 1H), 7.27 (d, J=8.1 Hz, 1H), 7.44 (d, J=7.5 Hz, 1H), 7.85 (d, J=3.6 Hz, 1H), 7.92 (q, 1H), 9.00 (s, 1H); $^{19}$F NMR (282 MHz, DMSO-d$_6$): δ−166.38.

I-137: 5-Fluoro-N2-(4-isopropoxycarbonylamino) phenyl-N4-(1,2,2,6,6-pentamethylpiperidin-4-yl)-2,4-pyrimidinediamine LCMS: purity: 98.25%; MS (m/e): 459.11 (MH+); $^1$H NMR (DMSO-d$_6$): δ 1.23 (d, J=6.3 Hz, 6H), 1.39 (s, 6H), 1.40 (s, 6H), 1.80 (t, J=12.9 Hz, 2H), 2.08 (d, J=13.5 Hz, 2H), 2.74 (d, J=4.8 Hz, 3H), 4.46 (br, 1H), 4.84 (p, J=6.3 Hz, 1H), 7.29 (d, J=9.0 Hz, 2H), 7.48 (d, J=8.4 Hz, 2H), 7.81 (br, 1H), 7.92 (d, J=4.2 Hz, 1H), 8.59 (br, 1H), 9.17 (br, 1H), 9.34 (br, 1H).

I-138: N2-(3-Ethylaminocarbonylamino)phenyl-5-fluoro-N4-(1,2,2,6,6-pentamethylpiperidin-4-yl)-2,4-pyrimidinediamine LCMS: purity: 71.90%; MS (m/e): 444.20 (MH+); $^1$H NMR (DMSO-d$_6$): δ 1.02 (t, J=6.9 Hz, 3H), 1.29 (s, 12H), 1.67 (br, 2H), 1.94 (br, 2H), 2.52 (s, 3H), 3.06 (p, 2H), 4.42 (m, 1H), 5.99 (t, 1H), 6.95 (m, 2H), 7.36 (m, 1H), 7.42 (s, 1H), 7.85 (d, 1H), 8.25 (s, 1H), 8.89 (s, 1H).

I-139: 5-Fluoro-N2-(3-isopropoxycarbonylamino) phenyl-N4-(1,2,2,6,6-pentamethylpiperidin-4-yl)-2,4-pyrimidinediamine LCMS: purity: 85.68%; MS (m/e): 459.44 (MH+); $^1$H NMR (DMSO-d$_6$): δ 1.23 (d, J=6.0 Hz, 6H), 1.32 (s, 6H), 1.38 (s, 6H), 1.77 (t, J=12.6 Hz, 2H), 2.06 (d, J=11.7 Hz, 2H), 2.71 (d, J=4.5 Hz, 3H), 4.45 (br, 1H), 4.85 (p, J=6.3 Hz, 1H), 7.01 (d, 1H), 7.08 (t, J=8.1 Hz, 1H), 7.29 (d, J=7.2 Hz, 1H), 7.59 (s, 1H), 7.90 (br, 1H), 7.95 (d, J=4.5 Hz, 1H), 8.54 (br, 1H), 9.29 (br, 1H), 9.46 (s, 1H).

I-140: N2-(3-Cyano-4-fluoro)phenyl-5-fluoro-N4-(1,2,2,6,6-pentamethylpiperidin-4-yl)-2,4-pyrimidinediamine LCMS: purity: 98.21%; MS (m/e): 401.33 (MH+); $^1$H NMR (DMSO-d$_6$): δ 1.07 (s, 12H), 1.45 (t, J=12.0 Hz, 2H), 1.68 (d, J=9.9 Hz, 2H), 2.18 (s, 3H), 4.29 (m, 1H), 7.27 (d, J=8.4 Hz, 1H), 7.33 (d, J=9.0 Hz, 1H), 7.88 (d, J=3.9 Hz, 1H), 7.92 (dd, J=4.5, 9.6 Hz, 1H), 8.12 (br, 1H), 9.32 (s, 1H); $^{19}$F NMR (282 MHz, DMSO-d$_6$): δ−165.15, −119.71.

I-141: N2-(3,4-Dicyano)phenyl-5-fluoro-N4-(1,2,2,6,6-pentamethylpiperidin-4-yl)-2,4-pyrimidinediamine LCMS: purity: 87.52%; MS (m/e): 408.17 (MH+); $^1$H NMR (DMSO-d$_6$): δ 1.08 (s, 12H), 1.48 (t, J=12.0 Hz, 2H), 1.68 (d, 2H), 2.19 (s, 3H), 4.31 (m, 1H), 7.47 (d, 1H), 7.86 (d, J=9.0 Hz, 1H), 7.97 (d, J=3.6 Hz, 1H), 8.09 (d, J=8.4 Hz, 1H), 8.30 (s, 1H), 9.95 (s, 1H); $^{19}$F NMR (282 MHz, DMSO-d$_6$): δ−162.76.

I-142: N2-(3-Cyano-4-methyl)phenyl-5-fluoro-N4-(1,2,2,6,6-pentamethylpiperidin-4-yl)-2,4-pyrimidinediamine LCMS: purity: 96.37%; MS (m/e): 397.36 (MH+); $^1$H NMR (DMSO-d$_6$): δ 1.07 (s, 12H), 1.46 (t, J=11.7 Hz, 2H), 1.68 (d, J=8.7 Hz, 2H), 2.18 (s, 3H), 2.37 (s, 3H), 4.32 (m, 1H), 7.22 (m, 2H), 7.87 (m, 2H), 7.97 (s, 1H), 9.22 (s, 1H); $^{19}$F NMR (282 MHz, DMSO-d$_6$): δ−165.60.

I-143: 5-Fluoro-N2-[3-(1-methyl-1H-pyrazol-4-yl)]phenyl-N4-(1,2,2,6,6-pentamethylpiperidin-4-yl)-2,4-pyrimidinediamine LCMS: purity: 99.89%; MS (m/e): 438.23 (MH+); $^1$H NMR (DMSO-d$_6$): δ 1.04 (s, 6H), 1.10 (s, 6H), 1.48 (t, J=12.0 Hz, 2H), 1.73 (d, J=11.7 Hz, 2H), 2.22 (s, 3H), 3.84 (s, 3H), 4.35 (br, 1H), 7.02 (d, J=7.8 Hz, 1H), 7.11 (t, J=7.8 Hz, 1H), 7.18 (d, J=7.8 Hz, 1H), 7.51 (s, 1H), 7.67 (s, 1H), 7.79 (d, J=7.8 Hz, 1H), 7.84 (d, J=3.9 Hz, 1H), 7.95 (s, 1H), 8.89 (s, 1H); $^{19}$F NMR (282 MHz, DMSO-d$_6$): δ−166.68.

I-144: 5-Fluoro-N2-[4-(1-methyl-1H-pyrazol-4-yl)]phenyl-N4-(1,2,2,6,6-pentamethylpiperidin-4-yl)-2,4-pyrimidinediamine LCMS: purity: 98.67%; MS (m/e): 438.23 (MH+); $^1$H NMR (DMSO-d$_6$): δ 1.14 (s, 6H), 1.16 (s, 6H), 1.53 (t, J=12.0 Hz, 2H), 1.77 (d, J=9.6 Hz, 2H), 2.29 (s, 3H), 3.83 (s, 3H), 4.43 (br, 1H), 7.21 (d, J=8.1 Hz, 1H), 7.31 (d, J=9.0 Hz, 2H), 7.67 (d, J=8.1 Hz, 3H), 7.83 (d, J=3.9 Hz, 1H), 7.95 (s, 1H), 9.00 (s, 1H); $^{19}$F NMR (282 MHz, DMSO-d$_6$): δ−166.81.

I-145: 5-Fluoro-N2-(3-methoxy-5-trifluoromethyl) phenyl-N4-(1,2,2,6,6-pentamethylpiperidin-4-yl)-2,4-pyrimidinediamine LCMS: purity: 97.19%; MS (m/e): 456.37 (MH+); $^1$H NMR (DMSO-d$_6$): δ 1.09 (s, 12H), 1.48 (t, J=11.4 Hz, 2H), 1.68 (d, 2H), 2.21 (s, 3H), 3.75 (s, 3H), 4.37 (m, 1H), 6.69 (s, 1H), 7.24 (br, 1H), 7.52 (s, 1H), 7.74 (s, 1H), 7.88 (d, J=3.3 Hz, 1H), 9.22 (s, 1H); $^{19}$F NMR (282 MHz, DMSO-d$_6$): δ−165.17, −61.93.

I-146: N2-[3,5-Bis(trifluoromethyl)]phenyl-5-fluoro-N4-(1,2,2,6,6-pentamethylpiperidin-4-yl)-2,4-pyrimidinediamine LCMS: purity: 76.37%; MS (m/e): 494.37 (MH+); $^1$H NMR (DMSO-d$_6$): δ 1.07 (br, 6H), 1.10 (br, 6H), 1.49 (d, J=12.3 Hz, 2H), 1.71 (d, J=9.9 Hz, 2H), 2.22 (s, 3H), 4.34 (m, 1H), 7.34 (d, J=9.0 Hz, 1H), 7.46 (s, 1H), 7.95 (d, J=3.9 Hz, 1H), 8.36 (s, 2H), 9.53 (s, 1H); $^{19}$F NMR (282 MHz, DMSO-d$_6$): δ −163.81, −62.28.

I-147: 5-Fluoro-N2-(4-methoxy-3-trifluoromethyl) phenyl-N4-(1,2,2,6,6-pentamethylpiperidin-4-yl)-2,4-pyrimidinediamine LCMS: purity: 98.23%; MS (m/e): 456.38 (MH+); $^1$H NMR (DMSO-d$_6$): δ 1.03 (s, 6H), 1.06 (s, 6H), 1.43 (t, J=11.7 Hz, 2H), 1.67 (d, J=12.0 Hz, 2H), 2.17 (s, 3H), 3.79 (s, 3H), 4.30 (m, 1H), 7.04 (d, J=8.7 Hz, 1H), 7.13 (d, J=8.1 Hz, 1H), 7.77 (s, 1H), 7.82 (s, 1H), 7.96 (d, J=8.1 Hz, 1H), 8.96 (s, 1H); $^{19}$F NMR (282 MHz, DMSO-d$_6$): δ −166.49, −61.40.

I-148: N2-[3-Cyano-4-(1H-pyrrol-1-yl)]phenyl-5-fluoro-N4-(1,2,2,6,6-pentamethylpiperidin-4-yl)-2,4-pyrimidinediamine LCMS: purity: 98.60%; MS (m/e): 448.24 (MH+) $^1$H NMR (DMSO-d$_6$): δ 1.08 (s, 12H), 1.46 (t, J=12.6 Hz, 2H), 1.70 (d, J=10.5 Hz, 2H), 2.17 (s, 3H), 4.34 (br, 1H), 6.27 (s, 2H), 7.08 (s, 2H), 7.30 (d, J=8.4 Hz, 1H), 7.37 (d, J=9.0 Hz, 1H), 7.91 (d, J=3.3 Hz, 1H), 8.05 (d, J=7.5 Hz, 1H), 8.16 (s, 1H), 9.45 (s, 1H); $^{19}$F NMR (282 MHz, DMSO-d$_6$): δ −164.81.

I-149: N2-(4-Ethylaminocarbonylamino)phenyl-5-fluoro-N4-(1,2,2,6,6-pentamethylpiperidin-4-yl)-2,4-pyrimidinediamine LCMS: purity: 99.60%; MS (m/e): 444.35 (MH+); $^1$H NMR (DMSO-d$_6$): δ 1.02 (t, J=6.9 Hz, 3H), 1.08 (s, 12H), 1.47 (t, J=12.0 Hz, 2H), 1.69 (d, J=12.3 Hz, 2H), 2.20 (s, 3H), 3.06 (p, J=6.6 Hz, 2H), 4.38 (m, 1H), 5.90 (t, 1H), 7.08 (d, 1H), 7.16 (d, J=8.1 Hz, 2H), 7.54 (d, J=9.0 Hz, 2H), 7.78 (d, J=3.6 Hz, 1H), 8.16 (s, 1H), 8.81 (s, 1H); $^{19}$F NMR (282 MHz, DMSO-d$_6$): δ −167.63.

I-150: 5-Fluoro-N2-[3-fluoro-4-(1-methyl-1H-pyrazol-4-yl)]phenyl-N4-(1,2,2,6,6-pentamethylpiperidin-4-yl)-2,4-pyrimidinediamine LCMS: purity: 94.03%; MS (m/e): 456.43 (MH+); $^1$H NMR (DMSO-d$_6$): δ 1.11 (s, 6H), 1.13 (s, 6H), 1.52 (t, J=12.6 Hz, 2H), 1.73 (d, J=12.3 Hz, 2H), 2.24 (s, 3H), 3.85 (s, 3H), 4.40 (br, 1H), 7.26 (d, J=7.5 Hz, 1H), 7.34-7.46 (m, 2H), 7.72-7.82 (m, 2H), 7.86 (d, J=3.9 Hz, 1H), 7.94 (s, 1H), 9.24 (s, 1H); $^{19}$F NMR (282 MHz, DMSO-d$_6$): δ −165.88, −114.70.

I-151: 5-Fluoro-N2-[3-methyl-4-(1-methyl-1H-pyrazol-4-yl)]phenyl-N4-(1,2,2,6,6-pentamethylpiperidin-4-yl)-2,4-pyrimidinediamine LCMS: purity: 95.31%; MS (m/e): 451.97 (MH+); $^1$H NMR (DMSO-d$_6$): δ 1.11 (s, 12H), 1.51 (t, J=12.0 Hz, 2H), 1.74 (d, J=9.0 Hz, 2H), 2.24 (s, 3H), 2.28 (s, 3H), 3.85 (s, 3H), 4.38 (br, 1H), 7.09 (d, J=8.7 Hz, 1H), 7.16 (d, J=9.3 Hz, 1H), 7.30 (s, 1H), 7.51 (s, 1H), 7.73 (d, J=8.7 Hz, 1H), 7.78 (s, 1H), 7.82 (d, J=3.9 Hz, 1H), 8.89 (s, 1H); $^{19}$F NMR (282 MHz, DMSO-d$_6$): δ −166.82.

I-152: N2-(4-Cyano-3-trifluoromethyl)phenyl-5-fluoro-N4-(1,2,2,6,6-pentamethylpiperidin-4-yl)-2,4-pyrimidinediamine LCMS: purity: 96.11%; MS (m/e): 451.07 (MH+); $^1$H NMR (DMSO-d$_6$): δ 1.07 (s, 12H), 1.47 (t, J=12.0 Hz, 2H), 1.70 (d, J=12.6 Hz, 2H), 2.19 (s, 3H), 4.32 (m, 1H), 7.43 (d, J=7.2 Hz, 1H), 7.85 (d, J=8.4 Hz, 1H), 7.96 (d, J=3.9 Hz, 1H), 8.10 (s, 1H), 8.32 (d, J=9.6 Hz, 1H), 9.90 (s, 1H); $^{19}$F NMR (282 MHz, DMSO-d$_6$): δ −162.90, −61.96.

I-153: N2-(4-Bromo-3-chloro)phenyl-5-fluoro-N4-(1,2,2,6,6-pentamethylpiperidin-4-yl)-2,4-pyrimidinediamine LCMS: purity: 95.36%; MS (m/e): 472.01 (MH+); $^1$H NMR (DMSO-d$_6$): δ 1.39 (s, 6H), 1.46 (s, 6H), 2.00 (d, J=7.5 Hz, 4H), 2.70 (d, J=5.1 Hz, 3H), 4.41 (m, 1H), 7.54 (m, 2H), 7.93 (d, J=2.1 Hz, 1H), 8.02 (d, J=3.9 Hz, 1H), 8.11 (br, 1H), 9.48 (br, 1H), 9.70 (br, 1H); $^{19}$F NMR (282 MHz, DMSO-d$_6$): δ −163.64.

I-154: N2-[3-Chloro-4-(pyridin-3-yl)]phenyl-5-fluoro-N4-(1,2,2,6,6-pentamethylpiperidin-4-yl)-2,4-pyrimidinediamine LCMS: purity: 99.58%; MS (m/e): 469.08 (MH+); $^1$H NMR (DMSO-d$_6$): δ 1.09 (s, 6H), 1.10 (s, 6H), 1.49 (t, J=11.7 Hz, 2H), 1.72 (d, J=9.0 Hz, 2H), 2.20 (s, 3H), 4.39 (br, 1H), 7.24 (d, J=8.7 Hz, 1H), 7.29 (d, J=6.6 Hz, 1H), 7.45 (dd, J=5.1, 7.8 Hz, 1H), 7.81 (m, 2H), 7.90 (m, 2H), 8.53 (d, 1H), 8.56 (s, 1H), 9.35 (s, 1H); $^{19}$F NMR (282 MHz, DMSO-d$_6$): δ −165.24.

I-155: N2-[3-Chloro-4-(furan-3-yl)]phenyl-5-fluoro-N4-(1,2,2,6,6-pentamethylpiperidin-4-yl)-2,4-pyrimidinediamine LCMS: purity: 98.43%; MS (m/e): 457.94 (MH+); $^1$H NMR (DMSO-d$_6$): δ 1.11 (s, 6H), 1.13 (s, 6H), 1.51 (t, J=12.0 Hz, 2H), 1.73 (d, J=12.0 Hz, 2H), 2.24 (s, 3H), 4.38 (m, 1H), 6.79 (s, 1H), 7.28 (d, J=8.4 Hz, 1H), 7.34 (d, J=8.4 Hz, 1H), 7.68 (d, J=2.4 Hz, 1H), 7.71 (s, 1H), 7.89 (s, 2H), 7.98 (s, 1H), 9.25 (s, 1H); $^{19}$F NMR (282 MHz, DMSO-d$_6$): δ −165.47.

I-156: N2-[4-(Benzothiophen-2-yl)-3-chloro]phenyl-5-fluoro-N4-(1,2,2,6,6-pentamethylpiperidin-4-yl)-2,4-pyrimidinediamine LCMS: purity: 98.54%; MS (m/e): 524.12 (MH+); $^1$H NMR (DMSO-d$_6$): δ 1.09 (s, 6H), 1.11 (s, 6H), 1.49 (t, J=12.0 Hz, 2H), 1.72 (d, J=11.7 Hz, 2H), 2.20 (s, 3H), 4.40 (br, 1H), 7.32 (d, J=8.7 Hz, 1H), 7.37 (m, 2H), 7.47 (d, J=8.4 Hz, 1H), 7.62 (s, 1H), 7.85 (m, 2H), 7.91 (d, J=3.9 Hz, 1H), 7.93 (m, 2H), 9.43 (s, 1H); $^{19}$F NMR (282 MHz, DMSO-d$_6$): δ −164.95.

I-157: N2-[3-Chloro-4-(1-methyl-1H-pyrazol-4-yl)]phenyl-5-fluoro-N4-(1,2,2,6,6-pentamethylpiperidin-4-yl)-2,4-pyrimidinediamine LCMS: purity: 94.32%; MS (m/e): 472.17 (MH+); $^1$H NMR (DMSO-d$_6$): δ 1.09 (s, 6H), 1.10 (s, 6H), 1.48 (t, J=12.3 Hz, 2H), 1.71 (d, J=12.0 Hz, 2H), 2.20 (s, 3H), 3.86 (s, 3H), 4.39 (br, 1H), 7.25 (d, J=8.4 Hz, 1H), 7.31 (d, J=8.1 Hz, 1H), 7.68 (m, 2H), 7.86 (m, 2H), 8.00 (s, 1H), 9.20 (s, 1H); $^{19}$F NMR (282 MHz, DMSO-d$_6$): δ −165.68.

I-158: N2-(3-Bromo-4-fluoro)phenyl-5-fluoro-N4-(1,2,2,6,6-pentamethylpiperidin-4-yl)-2,4-pyrimidinediamine LCMS: purity: 98.44%; MS (m/e): 456.02 (MH+); $^1$H NMR (DMSO-d$_6$): δ 1.34 (s, 6H), 1.44 (s, 6H), 1.98 (d, J=7.8

Hz, 4H), 2.68 (d, J=4.8 Hz, 3H), 4.37 (m, 1H), 7.25 (t, J=8.7 Hz, 1H), 7.56 (m, 1H), 7.89 (d, J=6.0 Hz, 1H), 8.02 (d, J=4.5 Hz, 1H), 8.26 (br, 1H), 9.46 (br, 1H), 9.66 (br, 1H).

I-159: N2-(3-Bromo-4-methoxy)phenyl-5-fluoro-N4-(1,2,2,6,6-pentamethylpiperidin-4-yl)-2,4-pyrimidinediamine LCMS: purity: 98.53%; MS (m/e): 468.02 (MH+); $^1$H NMR (DMSO-d$_6$): δ 1.41 (s, 12H), 1.83 (t, J=13.5 Hz, 2H), 2.05 (d, J=12.9 Hz, 2H), 2.72 (s, 3H), 3.76 (s, 3H), 4.42 (m, 1H), 6.94 (d, J=9.3 Hz, 1H), 7.52 (t, J=10.5 Hz, 2H), 7.84 (d, J=2.1 Hz, 1H), 7.88 (s, 1H), 8.78 (br, 1H), 8.91 (s, 1H); $^{19}$F NMR (282 MHz, DMSO-d$_6$): δ−166.49.

I-160: N2-(3-Bromo-4-methyl)phenyl-5-fluoro-N4-(1,2,2,6,6-pentamethylpiperidin-4-yl)-2,4-pyrimidinediamine LCMS: purity: 99.17%; MS (m/e): 452.11 (MH+); $^1$H NMR (DMSO-d$_6$): δ 1.32 (s, 6H), 1.45 (s, 6H), 1.98 (m, 4H), 2.27 (s, 3H), 2.67 (d, J=4.8 Hz, 3H), 4.39 (m, 1H), 7.21 (d, J=8.4 Hz, 1H), 7.49 (d, J=8.1 Hz, 1H), 7.76 (s, 1H), 8.05 (d, J=4.8 Hz, 1H), 8.46 (br, 1H), 9.64 (br, 1H), 9.80 (br, 1H).

I-161: N2-(4-Acetamido-3-trifluoromethyl)phenyl-5-fluoro-N4-(1,2,2,6,6-pentamethylpiperidin-4-yl)-2,4-pyrimidinediamine LCMS: purity: 91.57%; MS (m/e): 483.02 (MH+); $^1$H NMR (DMSO-d$_6$): δ 1.07 (br, 12H), 1.44 (m, 2H), 1.75 (m, 2H), 1.99 (s, 3H), 4.40 (m, 1H), 7.18 (d, 1H), 7.84 (m, 2H), 8.12 (s, 1H), 9.30 (s, 1H), 9.34 (s, 1H); $^{19}$F NMR (282 MHz, DMSO-d$_6$): δ−60.43.

I-162: N2-(3-Bromo-5-trifluoromethyl)phenyl-5-fluoro-N4-(1,2,2,6,6-pentamethylpiperidin-4-yl)-2,4-pyrimidinediamine LCMS: purity: 98.76%; MS (m/e): 505.91 (MH+); $^1$H NMR (DMSO-d$_6$): δ 1.43 (s, 12H), 1.89 (t, J=12.3 Hz, 2H), 2.05 (d, J=11.4 Hz, 2H), 2.72 (d, J=4.5 Hz, 3H), 4.43 (m, 1H), 7.36 (s, 1H), 7.71 (d, J=7.2 Hz, 1H), 7.92 (s, 1H), 8.01 (s, 1H), 8.31 (s, 1H), 8.96 (br, 1H), 9.46 (s, 1H); $^{19}$F NMR (282 MHz, DMSO-d$_6$): δ−163.91, −62.22.

I-163: N2-(4-Chloro-3-cyano)phenyl-5-fluoro-N4-(1,2,2,6,6-pentamethylpiperidin-4-yl)-2,4-pyrimidinediamine LCMS: purity: 95.44%; MS (m/e): 417.16 (MH+); $^1$H NMR (DMSO-d$_6$): δ 1.27 (s, 6H), 1.28 (s, 6H), 1.66 (t, J=11.7 Hz, 2H), 1.92 (d, J=13.8 Hz, 2H), 4.39 (m, 1H), 7.51 (d, J=8.7 Hz, 2H), 7.93 (m, 2H), 8.20 (d, J=2.7 Hz, 1H), 9.50 (s, 1H); $^{19}$F NMR (282 MHz, DMSO-d$_6$): δ−164.44.

I-164: N2-[3-Cyano-4-(4-methylsulfonylpiperazino)]phenyl-5-fluoro-N4-(1,2,2,6,6-pentamethylpiperidin-4-yl)-2,4-pyrimidinediamine LCMS: purity: 97.55%; MS (m/e): 545.27 (MH+); $^1$H NMR (DMSO-d$_6$): δ 1.28 (s, 12H), 1.66 (t, J=12.0 Hz, 2H), 1.91 (d, 2H), 2.54 (s, 3H), 2.95 (s, 3H), 3.09 (t, 4H), 4.38 (br, 1H), 7.10 (d, J=8.7 Hz, 1H), 7.45 (d, 1H), 7.81 (d, J=9.0 Hz, 1H), 7.90 (d, J=3.6 Hz, 1H), 7.97 (s, 1H), 9.17 (s, 1H); $^{19}$F NMR (282 MHz, DMSO-d$_6$): δ−165.75.

I-165: 5-Chloro-N2-(4-chloro-3-cyano)phenyl-N4-(1,2,2,6,6-pentamethylpiperidin-4-yl)-2,4-pyrimidinediamine LCMS: purity: 98.54%; MS (m/e): 433.03 (MH+); $^1$H NMR (DMSO-d$_6$): δ 1.23 (s, 12H), 1.70 (t, J=12.3 Hz, 2H), 1.84 (d, J=12.3 Hz, 2H), 2.45 (s, 3H), 4.42 (m, 1H), 7.01 (d, J=6.6 Hz, 1H), 7.52 (d, J=9.0 Hz, 1H), 7.94 (dd, J=2.7, 9.0 Hz, 1H), 8.01 (s, 1H), 8.15 (d, J=2.4 Hz, 1H), 9.60 (s, 1H).

I-166: 5-Chloro-N2-(3-cyano-4-fluoro)phenyl-N4-(1,2,2,6,6-pentamethylpiperidin-4-yl)-2,4-pyrimidinediamine LCMS: purity: 98.61%; MS (m/e): 417.10 (MH+); $^1$H NMR (DMSO-d$_6$): δ 1.07 (s, 6H), 1.08 (s, 6H), 1.55 (t, J=12.0 Hz, 2H), 1.65 (d, 2H), 2.20 (s, 3H), 4.36 (m, 1H), 6.77 (d, J=8.7 Hz, 1H), 7.34 (t, J=9.3 Hz, 1H), 7.95 (m, 2H), 8.07 (d, 1H), 9.46 (s, 1H); $^{19}$F NMR (282 MHz, DMSO-d$_6$): δ−118.95.

I-167: 5-Chloro-N2-[3-cyano-4-(1H-pyrrol-1-yl)]phenyl-N4-(1,2,2,6,6-pentamethylpiperidin-4-yl)-2,4-pyrimidinediamine LCMS: purity: 96.06%; MS (m/e): 464.22 (MH+); $^1$H NMR (DMSO-d$_6$): δ 1.29 (s, 6H), 1.31 (s, 6H), 1.78 (t, J=12.3 Hz, 2H), 1.92 (d, J=13.8 Hz, 2H), 2.55 (s, 3H), 4.47 (m, 1H), 6.28 (t, J=2.1 Hz, 2H), 7.10 (t, J=2.1 Hz, 3H), 7.42 (d, J=9.0 Hz, 1H), 8.03 (m, 2H), 9.60 (s, 1H).

I-168: 5-Chloro-N2-(3-cyano-4-methyl)phenyl-N4-(1,2,2,6,6-pentamethylpiperidin-4-yl)-2,4-pyrimidinediamine LCMS: purity: 99.76%; MS (m/e): 413.18 (MH+); $^1$H NMR (DMSO-d$_6$): δ 1.07 (s, 12H), 1.54 (t, J=12.3 Hz, 2H), 1.66 (d, J=9.6 Hz, 2H), 2.18 (s, 3H), 2.38 (s, 3H), 4.39 (m, 1H), 6.74 (d, J=7.2 Hz, 1H), 7.24 (d, J=8.1 Hz, 1H), 7.92 (m, 3H), 9.38 (s, 1H).

I-169: N2-(4-Chloro-3-cyano)phenyl-N4-(1,2,2,6,6-pentamethylpiperidin-4-yl)-5-trifluoromethyl-2,4-pyrimidinediamine LCMS: purity: 99.51%; MS (m/e): 467.12 (MH+); $^1$H NMR (DMSO-d$_6$): δ 1.05 (s, 6H), 1.07 (s, 6H), 1.62 (m, 4H), 2.18 (s, 3H), 4.50 (m, 1H), 6.53 (br, 1H), 7.54 (d, J=9.0 Hz, 1H), 7.98 (dd, J=2.4, 8.7 Hz, 1H), 8.11 (s, 1H), 8.23 (s, 1H), 9.91 (br, 1H); $^{19}$F NMR (282 MHz, DMSO-d$_6$): δ−61.10.

I-170: N2-(3-Cyano-4-fluoro)phenyl-N4-(1,2,2,6,6-pentamethylpiperidin-4-yl)-5-trifluoromethyl-2,4-pyrimidinediamine LCMS: purity: 99.56%; MS (m/e): 451.17 (MH+); $^1$H NMR (DMSO-d$_6$): δ 1.33 (s, 6H), 1.36 (s, 6H), 1.94 (m, 4H), 2.69 (s, 3H), 4.63 (m, 1H), 6.96 (d, 1H), 7.43 (t, J=9.0 Hz, 1H), 7.90 (m, 1H), 8.06 (br, 1H), 8.26 (s, 1H), 9.82 (br, 1H); $^{19}$F NMR (282 MHz, DMSO-d$_6$): δ−117.03, −60.89.

I-171: N2-(3-Cyano-4-methyl)phenyl-N4-(1,2,2,6,6-pentamethylpiperidin-4-yl)-5-trifluoromethyl-2,4-pyrimidinediamine LCMS: purity: 99.36%; MS (m/e): 447.20 (MH+); $^1$H NMR (DMSO-d$_6$): δ 1.35 (s, 6H), 1.38 (s, 6H), 1.96 (m, 4H), 2.41 (s, 3H), 2.72 (s, 3H), 4.66 (m, 1H), 6.96 (d, J=8.1 Hz, 1H), 7.32 (d, J=8.4 Hz, 1H), 7.80 (dd, J=2.1, 8.4 Hz, 1H), 7.92 (s, 1H), 8.25 (s, 1H), 9.74 (br, 1H); $^{19}$F NMR (282 MHz, DMSO-d$_6$): δ−60.81.

I-172: N2-[3-Cyano-4-(1H-pyrrol-1-yl)]phenyl-N4-(1,2,2,6,6-pentamethylpiperidin-4-yl)-5-trifluoromethyl-2,4-pyrimidinediamine LCMS: purity: 99.12%; MS (m/e): 498.23 (MH+); $^1$H NMR (DMSO-d$_6$): δ 1.39 (s, 12H), 1.98 (m, 4H), 2.74 (d, J=4.8 Hz, 3H), 4.68 (m, 1H), 6.30 (t, J=2.1 Hz, 2H), 7.03 (d, J=6.9 Hz, 1H), 7.12 (t, J=2.1 Hz, 2H), 7.48 (d, J=8.7 Hz, 1H), 7.99 (dd, J=3.0, 9.3 Hz, 1H), 8.11 (s, 1H), 8.30 (s, 1H), 8.45 (s, 1H), 9.97 (br, 1H); $^{19}$F NMR (282 MHz, DMSO-d$_6$): δ−60.89.

I-173: N2-[4-(4-Cyclopropylsulfonylpiperazino)-3-trifluoromethyl]phenyl-5-fluoro-N4-(1,2,2,6,6-pentamethylpiperidin-4-yl)-2,4-pyrimidinediamine LCMS: purity: 96.79%; MS (m/e): 614.26 (MH+); $^1$H NMR (DMSO-d$_6$): δ 0.94 (m, 2H), 1.02 (d, J=8.4 Hz, 2H), 1.19 (s, 12H), 1.58 (t, J=12.3 Hz, 2H), 1.84 (d, J=12.6 Hz, 2H), 2.41 (s, 3H), 2.68 (m, 1H), 2.86 (t, 4H), 4.36 (br, 1H), 7.38 (d, 1H), 7.41 (d, J=8.1 Hz, 1H), 7.79 (s, 1H), 7.88 (d, J=3.6 Hz, 1H), 8.07 (d, J=8.7 Hz, 1H), 9.22 (s, 1H); $^{19}$F NMR (282 MHz, DMSO-d$_6$): δ−59.87, −165.61.

I-174: N2-[3-Chloro-4-(4-cyclopropylsulfonylpiperazino)]phenyl-5-fluoro-N4-(1,2,2,6,6-pentamethylpiperidin-4-yl)-2,4-pyrimidinediamine LCMS: purity: 96.45%; MS (m/e): 580.13 (MH+); $^1$H NMR (DMSO-d$_6$): δ 0.95 (m, 2H), 1.02 (d, J=7.8 Hz, 2H), 1.14 (s, 12H), 1.52 (t, J=12.0 Hz, 2H), 1.76 (d, J=10.8 Hz, 2H), 2.30 (s, 3H), 2.66 (m, 1H), 2.95 (t, 4H), 3.32 (t, 4H), 4.35 (br, 1H), 7.01 (d, J=9.0 Hz, 1H), 7.24 (d, J=6.9 Hz, 1H), 7.58 (dd, J=8.7 Hz, 1H), 7.77 (s, 1H), 7.84 (d, J=3.9 Hz, 1H), 9.03 (s, 1H); $^{19}$F NMR (282 MHz, DMSO-d$_6$): δ−166.19.

I-175: 5-Chloro-N2-[3-cyano-4-(4-methylsulfonylpiperazino)]phenyl-N4-(1,2,2,6,6-pentamethylpiperidin-4-yl)-2,4-pyrimidinediamine LCMS: purity: 92.21%; MS (m/e): 561.21 (MH+); $^1$H NMR (DMSO-d$_6$): δ 1.10 (s, 6H), 1.11 (s, 6H), 1.57 (t, J=11.7 Hz, 2H), 1.67 (d, 2H), 2.25 (s, 3H), 2.95 (s, 3H), 3.09 (t, 4H), 4.37 (br, 1H), 6.75 (d, J=8.7 Hz, 1H), 7.09 (d, J=8.7 Hz, 1H), 7.85 (dd, J=8.7 Hz, 1H), 7.93 (m, 2H), 9.28 (s, 1H).

I-176: N2-[3-Cyano-4-(4-methylsulfonylpiperazino)]phenyl-N4-(1,2,2,6,6-pentamethylpiperidin-4-yl)-5-trifluoromethyl-2,4-pyrimidinediamine LCMS: purity: 97.91%; MS (m/e): 595.25 (MH+); $^1$H NMR (DMSO-d$_6$): δ 1.36 (s, 12H), 1.92 (m, 4H), 2.71 (s, 3H), 2.96 (s, 3H), 3.14 (m, 4H), 3.30 (t, 4H), 4.66 (br, 1H), 6.92 (br, 1H), 7.15 (d, 1H), 7.78 (d, J=8.4 Hz, 1H), 8.22 (s, 1H), 8.38 (br, 1H), 9.62 (s, 1H); $^{19}$F NMR (282 MHz, DMSO-d$_6$): δ−60.70.

I-177: N2-(3-Bromo-4-trifluoromethoxy)phenyl-5-fluoro-N4-(1,2,2,6,6-pentamethylpiperidin-4-yl)-2,4-pyrimidinediamine LCMS: purity: 99.34%; MS (m/e): 521.97 (MH+); $^1$H NMR (DMSO-d$_6$): δ 1.41 (s, 12H), 1.82 (t, J=12.6 Hz, 2H), 2.08 (d, J=12.9 Hz, 2H), 2.73 (d, J=4.8 Hz, 3H), 4.43 (m, 1H), 7.32 (d, J=8.1 Hz, 1H), 7.64 (d, J=6.9 Hz, 1H), 7.74 (d, J=9.3 Hz, 1H), 7.96 (d, J=3.3 Hz, 1H), 8.02 (s, 1H), 8.69 (br, 1H), 9.36 (s, 1H); $^{19}$F NMR (282 MHz, DMSO-d$_6$): δ−164.71, −57.90.

I-178: N2-[3-Cyano-4-(4-methylpiperazino)]phenyl-N4-(1,2,2,6,6-pentamethylpiperidin-4-yl)-5-trifluoromethyl-2,4-pyrimidinediamine LCMS: purity: 87.68%; MS (m/e): 531.26 (MH+).

I-179: 5-Chloro-N2-[3-cyano-4-(4-methylpiperazino)]phenyl-N4-(1,2,2,6,6-pentamethylpiperidin-4-yl)-2,4-pyrimidinediamine LCMS: purity: 98.68%; MS (m/e): 497.39 (MH+); $^1$H NMR (DMSO-d$_6$): δ 1.40 (s, 12H), 1.86 (t, J=12.0 Hz, 2H), 2.02 (d, J=12.3 Hz, 2H), 2.72 (s, 3H), 2.86 (br, 2H), 3.15 (s, 3H), 4.50 (br, 1H), 7.16 (d, J=9.6 Hz, 1H), 7.75 (d, J=8.7 Hz, 1H), 8.01 (d, J=6.6 Hz, 1H), 8.55 (br, 1H), 9.30 (br, 1H), 9.70 (br, 1H).

I-180: 5-Fluoro-N2-[4-fluoro-3-(pyridin-3-yl)]phenyl-N4-(1,2,2,6,6-pentamethylpiperidin-4-yl)-2,4-pyrimidinediamine LCMS: purity: 98.82%; MS (m/e): 453.16 (MH+); $^1$H NMR (DMSO-d$_6$): δ 0.89 (s, 6H), 1.04 (s, 6H), 1.42 (t, J=11.1 Hz, 2H), 1.66 (d, J=9.0 Hz, 2H), 2.15 (s, 3H), 4.26 (m, 1H), 7.11 (t, J=9.3 Hz, 1H), 7.19 (d, 1H), 7.47 (dd, J=4.2, 8.7 Hz, 1H), 7.67 (d, J=4.5 Hz, 1H), 7.84 (d, J=3.9 Hz, 2H), 7.88 (d, J=8.1 Hz, 1H), 8.56 (d, J=4.2 Hz, 1H), 8.66 (s, 1H), 9.07 (s, 1H); $^{19}$F NMR (282 MHz, DMSO-d$_6$): δ−166.32.

I-181: N2-[3-(Benzothiophen-2-yl)-4-fluoro]phenyl-5-fluoro-N4-(1,2,2,6,6-pentamethylpiperidin-4-yl)-2,4-pyrimidinediamine LCMS: purity: 98.24%; MS (m/e): 508.12 (MH+); $^1$H NMR (DMSO-d$_6$): δ 0.91 (s, 6H), 1.02 (s, 6H), 1.42 (t, J=14.1 Hz, 2H), 1.67 (d, J=8.7 Hz, 2H), 2.11 (s, 3H), 4.29 (br, 1H), 7.17 (m, 2H), 7.37 (m, 2H), 7.74 (s, 1H), 7.85-7.96 (m, 4H), 9.12 (s, 1H), 10.16 (s, 1H); $^{19}$F NMR (282 MHz, DMSO-d$_6$): δ−166.14.

I-182: 5-Fluoro-N2-[4-fluoro-3-(1-methyl-1H-pyrazol-4-yl)]phenyl-N4-(1,2,2,6,6-pentamethylpiperidin-4-yl)-2,4-pyrimidinediamine LCMS: purity: 99.16%; MS (m/e): 456.20 (MH+); $^1$H NMR (DMSO-d$_6$): δ 0.97 (s, 6H), 1.06 (s, 6H), 1.43 (t, J=11.4 Hz, 2H), 1.64 (d, 2H), 2.16 (s, 3H), 3.87 (s, 3H), 4.30 (br, 1H), 6.98 (m, 1H), 7.15 (d, 1H), 7.64 (m, 1H), 7.68 (s, 2H), 7.83 (d, 1H), 7.99 (d, 1H), 8.87 (s, 1H); $^{19}$F NMR (282 MHz, DMSO-d$_6$): δ−166.72.

I-183: 5-Fluoro-N2-[3-(furan-3-yl)-4-methoxy]phenyl-N4-(1,2,2,6,6-pentamethylpiperidin-4-yl)-2,4-pyrimidinediamine LCMS: purity: 99.08%; MS (m/e): 454.21 (MH+); $^1$H NMR (DMSO-d$_6$): δ 1.04 (s, 6H), 1.10 (s, 6H), 1.48 (t, J=12.0 Hz, 2H), 1.72 (d, J=11.7 Hz, 2H), 2.24 (s, 3H), 3.79 (s, 3H), 4.30 (br, 1H), 6.78 (s, 1H), 6.85 (d, J=9.3 Hz, 1H), 7.12 (d, J=6.9 Hz, 1H), 7.56 (s, 1H), 7.68 (t, J=1.5 Hz, 1H), 7.72 (dd, J=2.4, 9.0 Hz, 1H), 7.80 (d, J=3.9 Hz, 1H), 8.02 (s, 1H), 8.67 (s, 1H); $^{19}$F NMR (282 MHz, DMSO-d$_6$): δ−167.50.

I-184: 5-Fluoro-N2-[4-methoxy-3-(1-methyl-1H-pyrazol-4-yl)]phenyl-N4-(1,2,2,6,6-pentamethylpiperidin-4-yl)-2,4-pyrimidinediamine LCMS: purity: 99.72%; MS (m/e): 468.24 (MH+); $^1$H NMR (DMSO-d$_6$): δ 1.02 (s, 6H), 1.09 (s, 6H), 1.46 (t, J=12.6 Hz, 2H), 1.71 (d, J=9.9 Hz, 2H), 2.23 (s, 3H), 3.77 (s, 3H), 3.84 (s, 3H), 4.30 (br, 1H), 6.82 (d, J=9.3 Hz, 1H), 7.10 (d, J=7.2 Hz, 1H), 7.55 (s, 1H), 7.63 (d, J=9.0 Hz, 1H), 7.69 (s, 1H), 7.79 (d, J=3.6 Hz, 1H), 7.96 (s, 1H), 8.64 (s, 1H); $^{19}$F NMR (282 MHz, DMSO-d$_6$): δ−167.61.

I-185: N2-[3-Cyano-4-(pyridin-4-yl)]phenyl-5-fluoro-N4-(1,2,2,6,6-pentamethylpiperidin-4-yl)-2,4-pyrimidinediamine LCMS: purity: 96.59%; MS (m/e): 460.23 (MH+); $^1$H NMR (DMSO-d$_6$): δ 1.41 (s, 6H), 1.45 (s, 6H), 1.82 (t, J=12.9 Hz, 2H), 2.11 (d, J=13.8 Hz, 2H), 2.74 (d, J=5.1 Hz, 3H), 4.50 (m, 1H), 7.59 (d, J=8.1 Hz, 1H), 7.70 (d, J=6.3 Hz, 2H), 7.74 (d, J=8.1 Hz, 1H), 8.02 (d, J=3.6 Hz, 1H), 8.07 (dd, J=2.4, 8.1 Hz, 1H), 8.26 (s, 1H), 8.59 (br, 1H), 8.75 (d, J=6.0 Hz, 2H), 9.66 (s, 1H); $^{19}$F NMR (282 MHz, DMSO-d$_6$): δ−163.98.

I-186: N2-[3-Cyano-4-(pyridin-3-yl)]phenyl-5-fluoro-N4-(1,2,2,6,6-pentamethylpiperidin-4-yl)-2,4-pyrimidinediamine LCMS: purity: 93.28%; MS (m/e): 460.24 (MH+); $^1$H NMR (DMSO-d$_6$): δ 1.07 (s, 6H), 1.09 (s, 6H), 1.47 (t, J=11.7 Hz, 2H), 1.69 (d, 2H), 2.17 (s, 3H), 4.36 (m, 1H), 7.32 (d, 1H), 7.47 (d, J=8.4 Hz, 1H), 7.52 (d, J=7.8 Hz, 1H), 7.92 (m, 2H), 8.10 (dd, J=2.4, 9.0 Hz, 1H), 8.20 (d, J=2.4 Hz, 1H), 8.61 (dd, J=1.5, 5.4 Hz, 1H), 8.70 (d, J=1.8 Hz, 1H), 9.49 (s, 1H); $^{19}$F NMR (282 MHz, DMSO-d$_6$): δ−164.71.

I-187: 5-Fluoro-N2-[4-methyl-3-(pyridin-4-yl)]phenyl-N4-(1,2,2,6,6-pentamethylpiperidin-4-yl)-2,4-pyrimidinediamine LCMS: purity: 98.13%; MS (m/e): 449.20 (MH+); $^1$H NMR (DMSO-d$_6$): δ 0.95 (s, 6H), 1.07 (s, 6H), 1.45 (t, J=12.3 Hz, 2H), 1.68 (d, J=9.9 Hz, 2H), 2.13 (s, 3H), 2.18 (s, 3H), 4.28 (m, 1H), 7.08 (d, J=8.1 Hz, 1H), 7.15 (d, J=8.4 Hz, 1H), 7.32 (d, J=6.0 Hz, 1H), 7.38 (d, J=1.8 Hz, 1H), 7.83 (m, 2H), 8.58 (d, J=6.3 Hz, 2H), 8.98 (s, 1H); $^{19}$F NMR (282 MHz, DMSO-d$_6$): δ−166.63.

I-188: 5-Fluoro-N2-[3-(furan-3-yl)-4-methyl]phenyl-N4-(1,2,2,6,6-pentamethylpiperidin-4-yl)-2,4-pyrimidinediamine LCMS: purity: 99.41%; MS (m/e): 438.19 (MH+); $^1$H NMR (DMSO-d$_6$): δ 1.03 (s, 6H), 1.08 (s, 6H), 1.46 (t, J=12.3 Hz, 2H), 1.70 (d, J=12.6 Hz, 2H), 2.21 (s, 3H), 2.24 (s, 3H), 4.33 (br, 1H), 6.65 (s, 1H), 7.01 (d, J=8.1 Hz, 1H), 7.14 (d, J=9.0 Hz, 1H), 7.40 (s, 1H), 7.70 (t, J=1.8 Hz, 1H), 7.77 (s, 1H), 7.82 (d, J=3.6 Hz, 2H), 8.86 (s, 1H); $^{19}$F NMR (282 MHz, DMSO-d$_6$): δ−166.97.

I-189: N2-[3-(Benzothiophen-2-yl)-4-methyl]phenyl-5-fluoro-N4-(1,2,2,6,6-pentamethylpiperidin-4-yl)-2,4-pyrimidinediamine LCMS: purity: 96.03%; MS (m/e): 504.17 (MH+); $^1$H NMR (DMSO-d$_6$): δ 0.89 (s, 6H), 1.03 (s, 6H), 1.43 (t, J=11.1 Hz, 2H), 1.65 (d, 2H), 2.10 (s, 3H), 2.33 (s, 3H), 4.30 (br, 1H), 7.12 (t, J=8.1 Hz, 2H), 7.36 (t, J=7.5 Hz, 2H), 7.40 (s, 1H), 7.68 (s, 1H), 7.84 (m, 3H), 7.94 (d, J=8.7 Hz, 1H), 9.05 (s, 1H).

I-190: 5-Fluoro-N2-[4-methyl-3-(1-methyl-1H-pyrazol-4-yl)]phenyl-N4-(1,2,2,6,6-pentamethylpiperidin-4-yl)-2,4-pyrimidinediamine LCMS: purity: 99.75%; MS (m/e): 452.21 (MH+); $^1$H NMR (DMSO-d$_6$): δ 1.02 (s, 6H), 1.10 (s, 6H), 1.48 (t, J=12.3 Hz, 2H), 1.71 (d, J=9.3 Hz, 2H), 2.23 (s, 3H), 2.24 (s, 3H), 3.86 (s, 3H), 4.32 (br, 1H), 6.98 (d, J=8.1 Hz, 1H), 7.14 (d, J=7.2 Hz, 1H), 7.39 (d, J=1.8 Hz, 1H), 7.52 (s, 1H), 7.71 (d, J=8.1 Hz, 1H), 7.81 (m, 2H), 8.83 (s, 1H); $^{19}$F NMR (282 MHz, DMSO-d$_6$): δ−167.07.

I-191: 5-Fluoro-N2-[4-fluoro-3-(pyridin-4-yl)]phenyl-N4-(1,2,2,6,6-pentamethylpiperidin-4-yl)-2,4-pyrimidinediamine LCMS: purity: 96.55%; MS (m/e): 453.17 (MH+); $^1$H NMR (DMSO-d$_6$): δ 0.89 (s, 6H), 1.05 (s, 6H), 1.43 (t, J=12.6 Hz, 2H), 1.66 (d, J=11.7 Hz, 2H), 2.15 (s, 3H), 4.26 (m, 1H), 7.11 (d, J=9.3 Hz, 1H), 7.18 (d, J=10.5 Hz, 1H), 7.49 (d, J=4.8 Hz, 2H), 7.71 (dd, J=9.0 Hz, 1H), 7.84 (d, J=3.9 Hz, 2H), 8.62 (d, J=6.0 Hz, 2H), 9.09 (s, 1H); $^{19}$F NMR (282 MHz, DMSO-d$_6$): δ−166.22, −128.13.

I-192: 5-Fluoro-N2-[4-fluoro-3-(furan-3-yl)]phenyl-N4-(1,2,2,6,6-pentamethylpiperidin-4-yl)-2,4-pyrimidinediamine LCMS: purity: 99.60%; MS (m/e): 442.17 (MH+); $^1$H NMR (DMSO-d$_6$): δ 1.00 (s, 6H), 1.07 (s, 6H), 1.45 (t, J=12.0 Hz, 2H), 1.69 (d, J=10.2 Hz, 2H), 2.19 (s, 3H), 4.31 (br, 1H), 6.78 (s, 1H), 7.02 (t, J=9.6 Hz, 1H), 7.16 (d, J=8.7 Hz, 1H), 7.66 (d, J=4.5 Hz, 1H), 7.76 (s, 1H), 7.79 (d, J=4.8 Hz, 1H), 7.83 (d, J=3.9 Hz, 1H), 7.99 (s, 1H), 8.91 (s, 1H); $^{19}$F NMR (282 MHz, DMSO-d$_6$): δ−166.60, −123.53.

I-193: 5-Fluoro-N2-[4-methoxy-3-(pyridin-4-yl)]phenyl-N4-(1,2,2,6,6-pentamethylpiperidin-4-yl)-2,4-pyrimidinediamine LCMS: purity: 98.04%; MS (m/e): 465.25 (MH+); $^1$H NMR (DMSO-d$_6$): δ 0.89 (s, 6H), 1.04 (s, 6H), 1.41 (t, J=12.0 Hz, 2H), 1.64 (d, J=10.5 Hz, 2H), 2.14 (s, 3H), 3.70 (s, 3H), 4.26 (br, 1H), 6.94 (d, J=9.3 Hz, 1H), 7.08 (d, 1H), 7.43 (d, J=6.0 Hz, 2H), 7.52 (d, 1H), 7.79 (m, 2H), 8.54 (d, J=6.0 Hz, 2H), 8.84 (s, 1H); $^{19}$F NMR (282 MHz, DMSO-d$_6$): δ−167.16.

I-194: 5-Fluoro-N2-[4-methoxy-3-(pyridin-3-yl)]phenyl-N4-(1,2,2,6,6-pentamethylpiperidin-4-yl)-2,4-pyrimidinediamine LCMS: purity: 92.67%; MS (m/e): 465.17 (MH+); $^1$H NMR (DMSO-d$_6$): δ 0.89 (s, 6H), 1.04 (s, 6H), 1.41 (t, J=13.2 Hz, 2H), 1.64 (d, J=9.6 Hz, 2H), 2.13 (s, 3H), 3.69 (s, 3H), 4.24 (br, 1H), 6.92 (d, J=9.0 Hz, 1H), 7.06 (d, 1H), 7.40 (m, 1H), 7.48 (s, 1H), 7.79 (m, 3H), 8.46 (d, 1H), 8.59 (s, 1H), 8.83 (s, 1H); $^{19}$F NMR (282 MHz, DMSO-d$_6$): δ−167.24.

I-195: N2-[3-(Benzothiophen-2-yl)-4-methoxy]phenyl-5-fluoro-N4-(1,2,2,6,6-pentamethylpiperidin-4-yl)-2,4-pyrimidinediamine LCMS: purity: 99.60%; MS (m/e): 520.17 (MH+); $^1$H NMR (DMSO-d$_6$): δ 0.94 (s, 6H), 1.05 (s, 6H), 1.44 (t, J=12.0

Hz, 2H), 1.70 (d, J=9.3 Hz, 2H), 2.16 (s, 3H), 3.86 (s, 3H), 4.29 (br, 1H), 6.98 (d, J=8.7 Hz, 1H), 7.07 (br, 1H), 7.32 (m, 2H), 7.76 (m, 2H), 7.81 (m, 2H), 7.86 (s, 1H), 7.91 (d, J=6.9 Hz, 1H), 8.83 (s, 1H); $^{19}$F NMR (282 MHz, DMSO-d$_6$): δ−167.09.

I-196: 5-Cyano-N2-[3-cyano-4-(4-methylsulfonylpiperazino)]phenyl-N4-(1,2,2,6,6-pentamethylpiperidin-4-yl)-2,4-pyrimidinediamine LCMS: purity: 87.63%; MS (m/e): 552.21 (MH+).

I-197: 5-Fluoro-N2-[4-methyl-3-(pyridin-3-yl)]phenyl-N4-(1,2,2,6,6-pentamethylpiperidin-4-yl)-2,4-pyrimidinediamine LCMS: purity: 99.11%; MS (m/e): 449.20 (MH+); $^1$H NMR (DMSO-d$_6$): δ 0.96 (s, 6H), 1.07 (s, 6H), 1.45 (t, J=12.9 Hz, 2H), 1.67 (d, J=12.3 Hz, 2H), 2.11 (s, 3H), 2.18 (s, 3H), 4.29 (m, 1H), 7.08 (d, J=8.4 Hz, 1H), 7.14 (d, J=7.2 Hz, 1H), 7.36 (d, 1H), 7.44 (dd, J=4.8 Hz, 1H), 7.73 (d, J=7.8 Hz, 1H), 7.83 (m, 2H), 8.49 (d, 1H), 8.53 (d, J=3.0 Hz, 1H), 8.97 (s, 1H); $^{19}$F NMR (282 MHz, DMSO-d$_6$): δ−166.72.

I-198: N2-(3-Cyano-4-morpholino)phenyl-5-fluoro-N4-(1,2,2,6,6-pentamethylpiperidin-4-yl)-2,4-pyrimidinediamine LCMS: purity: 98.63%; MS (m/e): 468.23 (MH+); $^1$H NMR (DMSO-d$_6$): δ 1.39 (s, 6H), 1.41 (s, 6H), 1.78 (t, J=12.6 Hz, 2H), 2.07 (d, J=12.0 Hz, 2H), 2.73 (d, J=4.8 Hz, 3H), 3.00 (t, J=4.2 Hz, 4H), 3.74 (t, J=4.2 Hz, 4H), 4.44 (m, 1H), 7.07 (d, J=8.7 Hz, 1H), 7.60 (d, J=7.2 Hz, 1H), 7.76 (dd, J=2.4, 9.0 Hz, 1H), 7.93 (d, J=3.9 Hz, 1H), 7.98 (d, J=2.4 Hz, 1H), 8.52 (d, 1H), 9.19 (s, 1H); $^{19}$F NMR (282 MHz, DMSO-d$_6$): δ−165.70.

I-199: N2-(3-Cyano-4-thiomorpholino)phenyl-5-fluoro-N4-(1,2,2,6,6-pentamethylpiperidin-4-yl)-2,4-pyrimidinediamine LCMS: purity: 98.14%; MS (m/e): 484.17 (MH+); $^1$H NMR (DMSO-d$_6$): δ 1.29 (s, 12H), 1.67 (t, 2H), 1.93 (d, 2H), 2.76 (t, J=4.5 Hz, 4H), 3.22 (t, J=4.8 Hz, 4H), 4.38 (m, 1H), 7.07 (d, J=8.7 Hz, 1H), 7.44 (br, 1H), 7.78 (d, J=11.4 Hz, 1H), 7.90 (d, J=3.9 Hz, 1H), 7.97 (s, 1H), 9.16 (s, 1H); $^{19}$F NMR (282 MHz, DMSO-d$_6$): δ−165.79.

I-200: N2-[3-Cyano-4-(pyrrolidin-1-yl)]phenyl-5-fluoro-N4-(1,2,2,6,6-pentamethylpiperidin-4-yl)-2,4-pyrimidinediamine LCMS: purity: 98.43%; MS (m/e): 452.21 (MH+); $^1$H NMR (DMSO-d$_6$): δ 1.38 (s, 12H), 1.77 (t, J=13.2 Hz, 2H), 1.92 (t, 4H), 2.05 (d, J=12.6 Hz, 2H), 2.72 (d, J=4.5 Hz, 3H), 3.43 (t, 4H), 4.39 (m, 1H), 6.70 (d, J=8.7 Hz, 1H), 7.57 (d, J=9.0 Hz, 1H), 7.70 (s, 1H), 7.90 (d, J=3.6 Hz, 1H), 8.54 (d, 1H), 8.97 (br, 1H).

I-201: 5-Fluoro-N4-(1,2,2,6,6-pentamethylpiperidin-4-yl)-N2-[3-(pyridin-4-yl)-5-trifluoromethyl]phenyl-2,4-pyrimidinediamine LCMS: purity: 99.52%; MS (m/e): 503.23 (MH+); $^1$H NMR (DMSO-d$_6$): δ 1.22 (s, 6H), 1.36 (s, 6H), 1.76 (t, J=12.9 Hz, 2H), 2.04 (d, J=17.1 Hz, 2H), 2.68 (d, J=5.1 Hz, 3H), 4.38 (m, 1H), 7.64 (s, 1H), 7.72 (d, J=7.8 Hz, 1H), 7.89 (d, J=6.3 Hz, 2H), 8.02 (d, J=3.9 Hz, 1H), 8.15 (s, 1H), 8.32 (s, 1H), 8.52 (d, 1H), 8.75 (d, J=6.3 Hz, 2H), 9.48 (s, 1H); $^{19}$F NMR (282 MHz, DMSO-d$_6$): δ−164.29, −61.86.

I-202: 5-Fluoro-N4-(1,2,2,6,6-pentamethylpiperidin-4-yl)-N2-[3-(pyridin-3-yl)-5-trifluoromethyl]phenyl-2,4-pyrimidinediamine LCMS: purity: 97.00%; MS (m/e): 503.20 (MH+); $^1$H NMR (DMSO-d$_6$): δ 1.20 (s, 6H), 1.35 (s, 6H), 1.75 (t, J=12.0 Hz, 2H), 2.04 (d, J=17.4 Hz, 2H), 2.67 (d, J=4.5 Hz, 3H), 7.55 (s, 1H), 7.58 (d, J=7.8 Hz, 1H), 7.71 (d, 1H), 8.02 (d, J=3.9 Hz, 1H), 8.07 (s, 1H), 8.17 (d, J=8.4 Hz, 1H), 8.21 (s, 1H), 8.50 (d, 1H), 8.64 (d, J=3.3 Hz, 1H), 8.91 (s, 1H), 9.44 (s, 1H); $^{19}$F NMR (282 MHz, DMSO-d$_6$): δ−164.44, −61.81.

I-203: 5-Fluoro-N2-[3-(furan-3-yl)-5-trifluoromethyl]phenyl-N4-(1,2,2,6,6-pentamethylpiperidin-4-yl)-2,4-pyrimidinediamine LCMS: purity: 99.38%; MS (m/e): 492.19 (MH+); $^1$H NMR (DMSO-d$_6$): δ 1.26 (s, 6H), 1.36 (s, 6H), 1.75 (t, J=12.6 Hz, 2H), 2.04 (d, J=14.1 Hz, 2H), 2.69 (d, J=4.8 Hz, 3H), 4.39 (br, 1H), 6.94 (s, 1H), 7.44 (s, 1H), 7.64 (d, J=6.9 Hz, 1H), 7.75 (s, 1H), 7.90 (s, 1H), 7.99 (d, J=3.3 Hz, 1H), 8.02 (s, 1H), 8.24 (s, 1H), 8.47 (br, 1H), 9.27 (s, 1H); $^{19}$F NMR (282 MHz, DMSO-d$_6$): δ−61.83.

I-204: 5-Fluoro-N2-[3-(1-methyl-1H-pyrazol-4-yl)-5-trifluoromethyl]phenyl-N4-(1,2,2,6,6-pentamethylpiperidin-4-yl)-2,4-pyrimidinediamine LCMS: purity: 99.41%; MS (m/e): 506.26 (MH+); $^1$H NMR (DMSO-d$_6$): δ 1.22 (s, 6H), 1.35 (s, 6H), 1.75 (t, J=13.2 Hz, 2H), 2.04 (d, J=17.7 Hz, 2H), 2.68 (d, J=4.8 Hz, 3H), 3.85 (s, 3H), 4.37 (br, 1H), 7.39 (s, 1H), 7.78 (m, 2H), 7.85 (s, 1H), 7.98 (s, 1H), 8.00 (d, J=3.9 Hz, 1H), 8.19 (s, 1H), 8.53 (br, 1H), 9.33 (s, 1H); $^{19}$F NMR (282 MHz, DMSO-d$_6$): δ−164.71, −61.87.

I-205: N2-[3-(Benzothiophen-2-yl)-5-trifluoromethyl]phenyl-5-fluoro-N4-(1,2,2,6,6-pentamethylpiperidin-4-yl)-2,4-pyrimidinediamine LCMS: purity: 99.25%; MS (m/e): 558.18 (MH+); $^1$H NMR (DMSO-d$_6$): δ 1.24 (s, 6H), 1.35 (s, 6H), 1.75 (t, J=12.9 Hz, 2H), 2.08 (d, J=14.7 Hz, 2H), 2.65 (d, J=4.5 Hz, 3H), 4.40 (br, 1H), 7.39 (m, 2H), 7.61 (s, 1H), 7.66 (d, 1H), 7.84 (d, 1H), 7.98 (s, 2H), 8.02 (s, 2H), 8.28 (s, 1H), 8.46 (br, 1H), 9.44 (s, 1H); $^{19}$F NMR (282 MHz, DMSO-d$_6$): δ−164.36, −62.02.

I-206: 5-Cyano-N2-[3-cyano-4-(1H-pyrrol-1-yl)]phenyl-N4-(1,2,2,6,6-pentamethylpiperidin-4-yl)-2,4-pyrimidinediamine LCMS: purity: 81.33%; MS (m/e): 455.22 (MH+).

I-207: 5-Fluoro-N4-(1,2,2,6,6-pentamethylpiperidin-4-yl)-N2-[3-(pyridin-4-yl)-4-trifluoromethoxy]phenyl-2,4-pyrimidinediamine LCMS: purity: 98.69%; MS (m/e): 519.22 (MH+); $^1$H NMR (DMSO-d$_6$): δ 0.88 (s, 6H), 1.04 (s, 6H), 1.42 (t, J=12.0 Hz, 2H), 1.65 (d, J=11.4 Hz, 2H), 2.13 (s, 3H), 4.23 (m, 1H), 7.25 (t, 2H), 7.43 (d, J=6.0 Hz, 2H), 7.69 (d, J=2.7 Hz, 1H), 7.87 (d, J=4.5 Hz, 1H), 7.96 (d, J=9.9 Hz, 1H), 8.64 (d, J=6.3 Hz, 2H), 9.30 (s, 1H); $^{19}$F NMR (282 MHz, DMSO-d$_6$): δ−165.44, −57.71.

I-208: 5-Fluoro-N4-(1,2,2,6,6-pentamethylpiperidin-4-yl)-N2-[3-(pyridin-3-yl)-4-trifluoromethoxy]phenyl-2,4-pyrimidinediamine LCMS: purity: 97.22%; MS (m/e): 518.93 (MH+); $^1$H NMR (DMSO-d$_6$): δ 0.90 (s, 6H), 1.05 (s, 6H), 1.43 (t, J=11.7 Hz, 2H), 1.66 (d, J=12.3 Hz, 2H), 2.15 (s, 3H), 4.26 (m, 1H), 7.24 (m, 2H), 7.48 (dd, J=5.1 Hz, 1H), 7.66 (d, J=2.4 Hz, 1H), 7.86 (m, 2H), 7.95 (dd, J=9.3 Hz, 1H), 8.57 (m, 2H), 9.28 (s, 1H); $^{19}$F NMR (282 MHz, DMSO-d$_6$): δ−165.54, −57.67.

I-209: 5-Fluoro-N2-[3-(furan-3-yl)-4-trifluoromethoxy]phenyl-N4-(1,2,2,6,6-pentamethylpiperidin-4-yl)-2,4-pyrimidinediamine LCMS: purity: 98.45%; MS (m/e): 508.21 (MH+); $^1$H NMR (DMSO-d$_6$): δ 0.98 (s, 6H), 1.06 (s, 6H), 1.44 (t, J=12.3 Hz, 2H), 1.68 (d, J=12.0 Hz, 2H), 2.17 (s, 3H), 4.26 (br, 1H), 6.74 (s, 1H), 7.16 (d, J=9.3 Hz, 1H), 7.22 (d, J=7.2 Hz, 1H), 7.69 (s, 1H), 7.76 (t, J=1.5 Hz, 1H), 7.87 (m, 2H), 7.92 (s, 1H), 9.13 (s, 1H); $^{19}$F NMR (282 MHz, DMSO-d$_6$): δ−165.84, −57.33.

I-210: 5-Fluoro-N2-[3-(1-methyl-1H-pyrazol-4-yl)-4-trifluoromethoxy]phenyl-N4-(1,2,2,6,6-pentamethylpiperidin-4-yl)-2,4-pyrimidinediamine LCMS: purity: 98.76%; MS (m/e): 522.36 (MH+); $^1$H NMR (DMSO-d$_6$): δ 0.98 (s, 6H), 1.07 (s, 6H), 1.46 (t, 2H), 1.72 (d, 2H), 2.19 (s, 3H), 3.87 (s, 3H), 4.31 (br, 1H), 7.13 (d, J=8.4 Hz, 1H), 7.25 (m, 1H), 7.66 (m, 2H), 7.79 (d, J=8.7 Hz, 1H), 7.85 (d, 1H), 7.93 (s, 1H), 9.09 (s, 1H); $^{19}$F NMR (282 MHz, DMSO-d$_6$): δ−165.95, −57.16.

I-211: N2-[3-(Benzothiophen-2-yl)-4-trifluoromethoxy]phenyl-5-fluoro-N4-(1,2,2,6,6-pentamethylpiperidin-4-yl)-2,4-pyrimidinediamine LCMS: purity: 98.54%; MS (m/e): 574.25 (MH+); $^1$H NMR (DMSO-d$_6$): δ 0.90 (s, 6H), 1.05 (s, 6H), 1.45 (t, 2H), 1.68 (d, 2H), 2.14 (s, 3H), 4.26 (br, 1H), 7.27 (m, 2H), 7.38 (m, 2H), 7.67 (s, 1H), 7.90 (m, 3H), 7.97 (s, 2H), 9.32 (s, 1H); $^{19}$F NMR (282 MHz, DMSO-d$_6$): δ−165.38, −57.42.

I-212: N2-[3-(4-Acetylpiperazino)-4-trifluoromethyl]phenyl-5-fluoro-N4-(1,2,2,6,6-pentamethylpiperidin-4-yl)-2,4-pyrimidinediamine MS (m/e) 552.14 (MH$^+$); $^1$H NMR (DMSO-d$_6$): δ 9.19 (s, 1H), 8.13 (s, 1H), 8.07-8.05 (d, J=6 Hz, 1H), 7.88-7.86 (d, J=3.6, 1H), 7.79 (s, 1H), 7.35-7.32 (m, 2H), 4.33 (bm, 2H), 3.50 (s, 2H), 2.76 (s, 2H), 2.71 (s, 2H), 2.36 (s, 3H), 2.03 (s, 3H), 1.83-1.79 (d, J=10.5 Hz, 2H), 1.60-1.52 (t, J=12 Hz, 2H), 1.17-1.16 (d, J=5.7 Hz, 12H).

I-213: N4-(1-Acetyl-2,2,6,6-tetramethylpiperidin-4-yl)-N2-(3-chloro-4-methoxy)phenyl-5-fluoro-2,4-pyrimidinediamine MS (m/e) 450.09 (MH$^+$); $^1$H NMR (DMSO-d$_6$): δ 9.09 (s, 1H), 7.86-7.86 (s, 1H), 7.83 (s, 1H), 7.48-7.45 (d, J=9.0 Hz, 1H), 7.24 (s, 1H), 7.01-6.98 (d, J=9.0 Hz, 1H), 4.43 (bm, 1H), 3.78 (s, 3H), 2.26-2.07 (m, 3H), 1.89-1.85 (d, J=14, 1H), 1.65 (s, 6H), 1.22-1.19 (d, J=7.2 Hz, 6H).

I-214: 5-Fluoro-N2-[3-(4-methoxycarbonylpiperazino)-4-trifluoromethyl]phenyl-N4-(1,2,2,6,6-pentamethylpiperidin-4-yl)-2,4-pyrimidinediamine MS (m/e) 568.13 (MH$^+$); $^1$H NMR (DMSO-d$_6$): δ 9.19 (s, 1H), 8.13 (s, 1H), 8.07-8.04 (d, J=8.7 Hz, 1H), 7.87 (s, 1H), 7.79 (s, 1H), 7.36-7.34 (d, J=8.4 Hz, 1H), 7.30-7.28 (d, J=7.5 Hz, 1H), 4.32 (bm, 1H), 3.61 (s, 3H), 3.45 (s, 4H), 2.73 (s, 4H), 2.32 (s, 3H), 1.80-1.77 (d, J=11.7 Hz, 2H), 1.57-1.49 (t, J=12 Hz, 2H), 1.15-1.13 (d, J=6.3 Hz, 12H).

I-215: N4-(1-Acetyl-2,2,6,6-tetramethylpiperidin-4-yl)-5-fluoro-N2-[4-(4-methylsulfonylpiperazino)-3-trifluoromethyl]phenyl-2,4-pyrimidinediamine MS (m/e) 616.16 (MH$^+$); $^1$H NMR (DMSO-d$_6$): δ 9.19 (s, 1H), 8.09 (s, 1H), 7.96-7.93 (d, J=9.0 Hz, 1H), 7.81 (s, 1H), 7.46-7.44 (d, J=8.4 Hz, 1H), 7.24 (s, 1H), 7.06-7.03 (d, J=9.0 Hz, 1H), 4.46 (bm, 1H), 3.19 (s, 4H), 2.93 (s, 3H), 2.87 (s, 4H), 2.25-2.01 (m, 3H), 1.92-1.88 (d, J=13.5 Hz, 1H), 1.66 (s, 6H), 1.21 (s, 6H).

I-216: 5-Fluoro-N2-[3-(4-methylsulfonylpiperazino)-4-trifluoromethyl]phenyl-N4-(1,2,2,6,6-pentamethylpiperidin-4-yl)-2,4-pyrimidinediamine MS (m/e) 588.12 (MH$^+$); $^1$H NMR (DMSO-d$_6$): δ 9.21 (s, 1H), 8.12 (s, 1H), 8.10-8.06 (d, J=9.3 Hz, 1H), 7.87 (s, 1H), 7.79 (s, 1H), 7.42-7.39 (d, J=9.0 Hz, 1H), 7.33-7.30 (d, J=7.8 Hz, 1H), 4.36 (bm, 1H), 3.19 (s, 4H), 2.93 (s, 3H), 2.86 (s, 4H), 2.35 (s, 3H), 1.82-1.78 (d, J=9.9 Hz, 1H), 1.60-1.51 (t, J=12.9 Hz, 2H), 1.17 (s, 12H).

I-217: N4-(1-Acetyl-2,2,6,6-tetramethylpiperidin-4-yl)-N2-(3-cyanophenyl)-5-fluoro-2,4-pyrimidinediamine MS (m/e) 411.42 (MH$^+$); $^1$H NMR (DMSO-d$_6$): δ 9.34 (d, J=12.6 Hz, 1H), 8.22-8.18 (d, J=10.8 Hz, 1H), 7.93-7.91 (d, J=5.7 Hz, 1H), 7.84 (s, 1H), 7.39-7.34 (m, 1H), 7.27 (s, 2H), 7.16-7.13 (d, J=9.0 Hz, 1H), 4.45 (bm, 1H), 2.25-2.04 (m, 3H), 1.96-1.87 (m, 1H), 1.82-1.78 (d, J=9.9 Hz, 1H), 1.60-1.66 (m, 6H), 1.20 (s, 6H).

I-218: 5-Fluoro-N4-(1,2,2,6,6-pentamethylpiperidin-4-yl)-N2-[3-(4-propylpiperazino)-4-trifluoromethyl]phenyl-2,4-pyrimidinediamine MS (m/e) 552.19 (MH$^+$); $^1$H NMR (DMSO-d$_6$): δ 9.51 (s, 1H), 9.23 (s, 1H), 8.59 (s, 1H), 8.04-8.10 (d, J=9.0 Hz, 1H), 7.93 (s, 1H), 7.87 (s, 1H), 7.60-7.57 (d, J=7.8 Hz, 1H), 7.40-7.37 (d, J=8.7 Hz, 1H), 4.42 (bm, 1H), 3.52 (bs, 2H), 3.05 (bs, 10H), 2.73 (s, 4H), 2.09-2.06 (d, J=12 Hz, 2H), 1.82-1.66 (m, 4H), 1.39 (s, 12H), 0.92 (m, 3H).

I-219: N4-(1-Acetyl-2,2,6,6-tetramethylpiperidin-4-yl)-5-fluoro-N2-[4-(4-methylpiperazino)-3-trifluoromethyl]phenyl-2,4-pyrimidinediamine MS (m/e) 552.12 (MH$^+$); $^1$H NMR (DMSO-d$_6$): δ 9.05 (s, 1H), 8.01 (s, 1H), 7.78 (s, 1H), 7.38-7.35 (d, J=9.0 Hz, 1H), 7.23 (s, 1H), 4.42 (bm, 1H), 2.76 (s, 4H), 2.41 (s, 4H), 2.19 (s, 3H), 1.99 (s, 2H), 1.67-1.58 (m, 6H), 1.20 (s, 6H).

I-220: N2-[4-Chloro-3-(3,5-dimethyl-4-propylpiperazino)]phenyl-5-fluoro-N4-(1,2,2,6,6-pentamethylpiperidin-4-yl)-2,4-pyrimidinediamine MS (m/e) 546.22 (MH⁺); ¹H NMR (DMSO-d₆): δ 9.05 (s, 1H), 7.92 (s, 1H), 7.82-7.80 (d, J=7.2 Hz, 1H), 7.58-7.56 (d, J=7.5 Hz, 1H), 7.18-7.15 (d, J=8.4 Hz, 1H), 4.47 (bm, 1H), 2.73 (s, 4H), 2.08-2.05 (d, J=11.7 Hz, 2H), 1.84-1.76 (t, J=13.2 Hz, 2H), 1.67 (s, 2H), 1.424-1.398 (d, J=7.8 Hz, 12H), 1.26 (s, 6H), 0.92 (s, 3H).

I-221: 5-Fluoro-N2-[4-(1-methylpiperidin-4-yl)]phenyl-N4-(1,2,2,6,6-pentamethylpiperidin-4-yl)-2,4-pyrimidinediamine MS (m/e) 455.15 (MH⁺); ¹H NMR (DMSO-d₆): δ 8.99 (s, 1H), 7.88-7.87 (d, J=3.6 Hz, 1H), 7.60-7.57 (d, J=8.7 Hz, 1H), 7.51-7.49 (d, J=8.1 Hz, 1H), 7.05-7.02 (d, J=8.4 Hz, 2H), 4.49 (bm, 1H), 3.45-3.41 (d, J=12 Hz, 1H), 2.99-2.96 (t, J=11.7 Hz, 2H), 2.77 (s, 3H), 2.70 (s, 4H), 2.07-2.03 (d, J=13.8 Hz, 2H), 1.94-1.77 (m, 6H), 1.39 (s, 12H).

I-222: N2-[4-(2,6-Dimethyltetrahydropyran-4-yl)]phenyl-5-fluoro-N4-(1,2,2,6,6-pentamethylpiperidin-4-yl)-2,4-pyrimidinediamine MS (m/e) 485.18 (MH⁺); ¹H NMR (DMSO-d₆): δ 8.72 (s, 1H), 8.13 (s, 1H), 7.81-7.79 (d, J=3.3 Hz, 1H), 7.60-7.55 (d, J=8.3 Hz, 1H), 7.25 (s, 1H), 7.16-7.14 (d, J=7.8 Hz, 1H), 6.81-6.79 (d, J=8.4 Hz, 1H), 4.39 (bm, 1H), 3.72-3.67 (t, J=7.8 Hz, 2H), 2.82-2.78 (d, J=10.8 Hz, 2H), 2.32 (s, 3H), 2.27-2.24 (d, J=10.8 Hz, 2H), 2.19 (s, 3H), 1.79-1.75 (d, J=10.8 Hz, 2H), 1.57-1.49 (t, J=12.6 Hz, 2H), 1.14 (s, 12H), 1.10-1.08 (d, J=6.3 Hz, 6H).

I-223: 5-Fluoro-N4-(1,2,2,6,6-pentamethylpiperidin-4-yl)-N2-(3-trifluoromethoxy)phenyl-2,4-pyrimidinediamine MS (m/e) 442.08 (MH⁺); ¹H NMR (DMSO-d₆): δ 9.34 (s, 1H), 7.93-7.92 (d, J=3.3 Hz, 1H), 7.73 (s, 1H), 7.67-7.64 (d, J=9.0 Hz, 1H), 7.49 (s, 1H), 7.30-7.24 (t, J=8.1 Hz, 1H), 6.82-6.80 (d, J=7.5 Hz, 1H), 4.43 (bm, 1H), 2.54 (s, 3H), 1.92 (bs, 2H), 1.68 (bs, 2H), 1.29 (s, 12H).

I-224: 5-Fluoro-N2-[4-(4-morpholino)-3-trifluoromethyl]phenyl-N4-(1,2,2,6,6-pentamethylpiperidin-4-yl)-2,4-pyrimidinediamine MS (m/e) 511.14 (MH⁺); ¹H NMR (DMSO-d₆): δ 9.17 (s, 1H), 8.07-8.04 (d, J=8.7 Hz, 1H), 7.87-7.86 (d, J=3.6 Hz, 1H), 7.38-7.35 (d, J=8.7 Hz, 1H), 7.28-7.26 (d, J=7.5 Hz, 1H), 6.91-6.88 (d, J=8.4 Hz, 1H), 4.36 (bm, 1H), 3.66 (s, 4H), 2.76 (s, 4H), 2.31 (s, 3H), 1.79-1.75 (d, J=11.7 Hz, 2H), 1.56-1.48 (t, J=12.6 Hz, 2H), 1.14 (s, 12H).

I-225: N2-[4-(2,6-Dimethylmorpholino)-3-trifluoromethyl]phenyl-5-fluoro-N4-(1,2,2,6,6-pentamethylpiperidin-4-yl)-2,4-pyrimidinediamine MS (m/e) 539.20 (MH⁺); ¹H NMR (DMSO-d₆): δ 9.16 (s, 1H), 8.07-8.04 (d, J=8.4 Hz, 1H), 7.85-7.84 (d, J=3.6 Hz, 1H), 7.79 (s, 1H), 7.33-7.30 (d, J=9.3 Hz, 1H), 7.21-7.18 (d, J=7.5 Hz, 1H), 4.30 (bm, 1H), 3.64 (bs, 2H), 2.70-2.67 (d, J=10.2, 2H), 2.45-2.38 (t, J=10.8 Hz, 2H), 2.19 (s, 3H), 1.70-1.66 (d, J=12.0 Hz, 2H), 1.49-1.41 (t, J=11.1 Hz, 2H), 1.05 (m, 18H).

I-226: N2-(3-Chloro-4-methoxy)phenyl-N4-(1,2,2,6,6-pentamethylpiperidin-4-yl)-2,4-pyrimidinediamine MS (m/e) 404.13 (MH⁺); ¹H NMR (DMSO-d₆): δ 8.84 (s, 1H), 7.81 (s, 1H), 7.73 (s, 1H), 7.67-7.58 (d, J=8.7 Hz, 1H), 7.01 (s, 1H), 6.95-6.92 (d, J=8.4 Hz, 1H), 5.86-5.85 (d, J=4.2 Hz, 1H), 4.25 (bm, 1H), 3.76 (s, 3H), 2.28 (s, 3H), 1.82-1.77 (d, J=12.9 Hz, 2H), 1.38-1.30 (t, J=12.9 Hz, 2H), 1.13 (m, 12H).

I-227: N2-(3-Cyanophenyl)-N4-(1,2,2,6,6-pentamethylpiperidin-4-yl)-2,4-pyrimidinediamine MS (m/e) 365.20 (MH⁺); ¹H NMR (DMSO-d₆): δ 9.28 (s, 1H), 8.12 (s, 1H), 8.05-8.02 (d, J=8.4 Hz, 1H), 7.79 (s, 1H), 7.37-7.32 (t, J=7.8 Hz, 1H), 7.27-7.24 (d, J=7.5 Hz, 1H), 7.14 (bs, 1H), 5.95-5.93 (d, J=5.7 Hz, 1H), 4.25 (bm, 1H), 2.22 (s, 3H), 1.81-1.77 (d, J=12.0 Hz, 2H), 1.35-1.31 (t, J=12.3 Hz, 2H), 1.11 (m, 12H).

I-228: N2-[4-(4-Methylsulfonylpiperazino)-3-trifluoromethyl]phenyl-N4-(1,2,2,6,6-pentamethylpiperidin-4-yl)-2,4-pyrimidinediamine MS (m/e) 570.21 (MH⁺); ¹H NMR (DMSO-d₆): δ 9.11 (s, 1H), 7.84 (s, 1H), 7.77 (s, 1H), 7.41-7.38 (d, J=8.4 Hz, 1H), 7.04 (bs, 1H), 5.91-5.89 (d, J=5.7 Hz, 1H), 4.22 (bm, 1H), 3.19 (s, 4H), 2.93 (s, 3H), 2.86 (s, 3H), 2.22 (s, 3H), 1.79-1.76 (d, J=11.7 Hz, 2H), 1.32-1.25 (t, J=12.3 Hz, 2H), 1.07 (m, 12H).

I-229: N2-[4-(4-Methylpiperazino)-3-trifluoromethyl]phenyl-N4-(1,2,2,6,6-pentamethylpiperidin-4-yl)-2,4-pyrimidinediamine MS (m/e) 506.24 (MH⁺); ¹H NMR (DMSO-d₆): δ 9.12 (s, 1H), 8.07 (s, 1H), 7.83 (s, 1H), 7.83 (s, 1H), 7.38-7.35 (d, J=8.7 Hz, 1H), 7.26 (bs, 1H), 5.95 (s, 1H), 4.22 (bm, 1H), 2.83 (s, 4H), 2.65 (bs, 3H) 2.37 (s, 3H), 2.03 (d, J=11.7 Hz, 2H), 1.65-1.45 (t, J=12.3 Hz, 2H), 1.34 (m, 12H).

I-230: N2-[4-(Cyclopropylaminocarbonyl)-3-trifluoromethyl]phenyl-5-fluoro-N4-(1,2,2,6,6-pentamethylpiperidin-4-yl)-2,4-pyrimidinediamine MS (m/e) 509.10 (MH⁺); ¹H NMR (DMSO-d₆): δ 9.41 (s, 1H), 8.33-8.31 (d, J=4.5 Hz, 1H), 8.17-8.14 (d, J=8.1 Hz, 1H), 7.93 (s, 1H), 7.43 (s, 1H), 7.26-7.24 (d, J=7.8 Hz, 1H), 4.41 (bm, 1H), 3.15 (s, 1H), 2.75 (m, 1H), 1.88-1.84 (d, J=12.9 Hz, 2H), 1.64-1.57 (t, J=10.5 Hz, 2H), 1.22 (s, 12H), 0.69-0.63 (m, 2H), 0.46 (s, 2H).

I-231: 5-Fluoro-N4-(1,2,2,6,6-pentamethylpiperidin-4-yl)-N2-(4-trifluoromethoxyphenyl)-2,4-pyrimidinediamine MS (m/e) 442.08 (MH⁺); ¹H NMR (DMSO-d₆): δ 9.24 (s, 1H), 7.88-7.87 (d, J=3.6 Hz, 1H), 7.76-7.73 (d, J=9.0 Hz, 2H), 7.37 (s, 1H), 7.14-7.12 (d, J=8.4 Hz, 1H), 4.40 (bm, 1H), 2.38 (s, 3H), 1.86-1.82 (d, J=12.6 Hz, 2H), 1.63-1.54 (t, J=12.3 Hz, 2H), 1.19 (s, 12H).

I-232: 5-Fluoro-N2-[4-(1-pyrrolidino)-3-trifluoromethyl]phenyl-N4-(1,2,2,6,6-pentamethylpiperidin-4-yl)-2,4-pyrimidinediamine MS (m/e) 495.13 (MH⁺); ¹H NMR (DMSO-d₆): δ 8.99 (s, 1H), 7.97-7.94 (d, J=9.3 Hz, 1H), 7.83-7.82 (d, J=3.9 Hz, 1H), 7.71 (s, 1H), 7.20-7.18 (d, J=8.4 Hz, 1H), 7.14-7.11 (d, J=9.3 Hz, 1H), 4.30 (bm, 1H), 3.05 (s, 4H), 2.25 (s, 3H), 1.85 (s, 4H), 1.75-1.71 (d, J=10.5 Hz, 2H), 1.53-1.45 (t, J=12.6 Hz, 2H), 1.11 (s, 12H).

I-233: 5-Fluoro-N4-(1,2,2,6,6-pentamethylpiperidin-4-yl)-N2-[4-(1-piperidino)-3-trifluoromethyl]phenyl-2,4-pyrimidinediamine MS (m/e) 509.22 (MH$^+$); $^1$H NMR (DMSO-d$_6$): δ 9.14 (s, 1H), 8.04-8.01 (d, J=8.4 Hz, 1H), 7.86-7.85 (d, J=3.6 Hz, 1H), 7.74 (s, 1H), 7.31-7.28 (d, J=8.4 Hz, 1H), 4.32 (bm, 1H), 2.71 (s, 4H), 2.33 (s, 3H), 1.81-1.77 (d, J=11.7 Hz, 2H), 1.57-1.49 (m, 8H), 1.15-1.13 (d, J=6.0 Hz, 12H).

I-234: N2-(3-Difluoromethoxyphenyl)-5-fluoro-N4-(1,2,2,6,6-pentamethylpiperidin-4-yl)-2,4-pyrimidinediamine MS (m/e) 424.08 (MH$^+$); $^1$H NMR (DMSO-d$_6$): δ 9.20 (s, 1H), 7.87-7.85 (d, J=3.9 Hz, 1H), 7.60-7.57 (d, J=8.4 Hz, 1H), 7.53 (s, 1H), 7.37-6.87 (t, J=74.4 Hz 1H), 7.27-7.24 (d, J=8.7 Hz, 1H), 7.19-7.13 (t, J=8.1 Hz, 1H), 6.64-6.1 (d, J=8.4 Hz, 1H), 4.38 (bm, 1H), 2.22 (s, 3H), 1.72-1.69 (d, J=9.3 Hz, 2H), 1.53-1.45 (t, J=12.0 Hz, 2H), 1.10 (s, 12H).

I-235: N2-(3-Difluoromethoxy-4-morpholino)phenyl-5-fluoro-N4-(1,2,2,6,6-pentamethylpiperidin-4-yl)-2,4-pyrimidinediamine MS (m/e) 509.17 (MH$^+$); $^1$H NMR (DMSO-d$_6$): δ 8.99 (s, 1H), 8.13 (s, 1H), 7.84-7.83 (d, J=3.9 Hz, 1H), 7.57-7.54 (d, J=8.1 Hz, 1H), 7.46 (s, 1H), 7.26 (s, 1H), 7.23-6.76 (t, J=65.4 Hz 1H), 6.92-6.89 (d, J=9.0 Hz, 1H), 4.38 (bm, 1H), 3.69 (s, 4H), 2.85 (s, 4H), 2.42 (s, 3H), 1.80-1.79 (d, J=11.1 Hz, 2H), 1.58-1.50 (t, J=12.0 Hz, 2H), 1.16 (s, 12H).

I-236: N2-[3-Difluoromethoxy-4-(4-methylpiperazino)]phenyl-5-fluoro-N4-(1,2,2,6,6-pentamethylpiperidin-4-yl)-2,4-pyrimidinediamine MS (m/e) 555.19 (MH$^+$); $^1$H NMR (DMSO-d$_6$): δ 9.06 (s, 1H), 7.91-7.89 (d, J=3.6 Hz, 1H), 7.57 (s, 1H), 7.48-7.45 (d, J=8.4 Hz, 1H), 7.31-6.82 (t, J=75 Hz 1H), 7.02-6.89 (d, J=9.3 Hz, 1H), 4.45 (bm, 1H), 3.48-3.27 (m, 8H), 2.86 (s, 3H), 2.72 (s, 3H), 2.10-2.05 (d, J=13.2 Hz, 2H), 1.84-1.75 (t, J=12.6 Hz, 2H), 1.42-1.40 (d, J=4.5 Hz 12H).

I-237: N2-(3-Difluoromethoxy-4-pyrrolidino)phenyl-5-fluoro-N4-(1,2,2,6,6-pentamethylpiperidin-4-yl)-2,4-pyrimidinediamine MS (m/e) 493.14 (MH$^+$); $^1$H NMR (DMSO-d$_6$): δ 8.78 (s, 1H), 7.79-7.78 (d, J=3.0 Hz, 1H), 7.53-7.50 (d, J=9.0 Hz, 1H), 7.31 (s, 1H), 7.12-6.60 (t, J=81.6 Hz 1H), 7.10 (s, 1H), 6.68-6.65 (d, J=8.7 Hz, 1H), 4.32 (bm, 1H), 3.14 (s, 4H), 2.24 (s, 3H), 1.84 (s, 4H), 1.74-1.70 (d, J=12.3 Hz, 2H), 1.52-1.44 (t, J=11.7 Hz, 2H), 1.10 (s, 12H).

I-238: N2-[3-Difluoromethoxy-4-(4-methylsulfonylpiperazino)]phenyl-5-fluoro-N4-(1,2,2,6,6-pentamethylpiperidin-4-yl)-2,4-pyrimidinediamine MS (m/e) 586.14 (MH$^+$); $^1$H NMR (DMSO-d$_6$): δ 9.03 (s, 1H), 7.87-7.86 (d, J=2.4 Hz, 1H), 7.56-7.53 (d, J=9.0 Hz, 1H), 7.46 (s, 1H), 7.39 (bs, 1H), 7.28-6.78 (t, J=76.5 Hz 1H), 6.98-6.95 (d, J=8.4 Hz, 1H), 4.43 (bm, 1H), 3.23 (s, 4H), 2.95 (s, 4H), 2.92 (s, 3H), 1.88 (bs, 2H), 1.64 (bs, J=11.7 Hz, 2H), 1.26 (s, 12H).

I-239: N2-(3-Difluoromethoxy-4-methoxy)phenyl-5-fluoro-N4-(1,2,2,6,6-pentamethylpiperidin-4-yl)-2,4-pyrimidinediamine MS (m/e) 454.11 (MH$^+$); $^1$H NMR (DMSO-d$_6$): δ 8.91 (s, 1H), 8.15 (s, 1H), 7.82-7.81 (d, J=3.9 Hz, 1H), 7.57-7.54 (d, J=8.7 Hz, 1H), 7.49 (s, 1H), 7.18-6.69 (t, J=74.7 Hz 1H), 7.16 (s, 1H), 6.95-6.92 (d, J=9.0 Hz, 1H), 4.38 (bm, 1H), 3.73 (s, 3H), 2.25 (s, 3H), 1.73-1.69 (d, J=12.0 Hz, 2H), 1.53-1.45 (t, J=12.3 Hz, 2H), 1.11 (s, 12H).

I-240: 5-Chloro-N4-(1,2,2,6,6-pentamethylpiperidin-4-yl)-N2-(3-trifluoromethoxyphenyl)-2,4-pyrimidinediamine MS (m/e) 458.07 (MH$^+$); $^1$H NMR (DMSO-d$_6$): δ 9.47 (s, 1H), 7.96 (s, 1H), 7.72 (s, 1H), 7.70 (s, 1H), 7.30-7.24 (t, J=8.1 Hz, 1H), 6.85-6.82 (d, J=8.4 Hz, 1H), 4.45 (bm, 1H), 2.26 (s, 3H), 1.72-1.56 (m, 4H), 1.12 (s, 12H).

I-241: 5-Chloro-N2-[4-(4-morpholino)-3-trifluoromethyl]phenyl-N4-(1,2,2,6,6-pentamethylpiperidin-4-yl)-2,4-pyrimidinediamine MS (m/e) 527.13 (MH$^+$); $^1$H NMR (DMSO-d$_6$): δ 9.31 (s, 1H), 8.11-8.06 (d, J=9.9 Hz, 1H), 7.92 (s, 1H), 7.72 (s, 1H), 7.38-7.35 (d, J=9.0 Hz, 1H), 6.71-6.69 (d, J=8.1 Hz, 1H), 4.38 (bm, 1H), 3.67 (s, 4H), 2.76 (s, 4H), 2.19 (s, 3H), 1.68-1.65 (d, J=8.7 Hz, 2H), 1.57-1.49 (d, J=12.0 Hz, 2H), 1.08 (s, 6H), 1.04 (s, 6H).

I-242: N4-(1,2,2,6,6-pentamethylpiperidin-4-yl)-N2-(3-trifluoromethoxyphenyl)-5-trifluoromethyl-2,4-pyrimidinediamine MS (m/e) 492.20 (MH$^+$); $^1$H NMR (DMSO-d$_6$): δ 8.73 (s, 1H), 8.50-8.45 (bd, J=13.5 Hz, 1H), 8.24 (s, 1H), 7.84-7.81 (d, J=7.8 Hz, 1H), 7.57-7.54 (d, J=7.2 Hz, 2H), 7.46 (s, 1H), 7.42-7.37 (t, J=8.1 Hz, 1H), 7.09-7.06 (d, J=8.7 Hz, 1H), 4.05 (bm, 1H), 2.66 (s, 3H), 1.96-1.92 (d, J=12.3 Hz, 2H), 1.66-1.58 (d, J=12.6 Hz, 2H), 1.38 (s, 6H), 1.12 (s, 6H).

I-243: 5-Fluoro-N2-(3-methylsulfonylamino)phenyl-N4-(1,2,2,6,6-pentamethylpiperidin-4-yl)-2,4-pyrimidinediamine MS (m/e) 451.12 (MH$^+$); $^1$H NMR (DMSO-d$_6$): δ 9.54 (s, 1H), 9.02 (s, 1H), 8.51 (s, 1H), 7.85-7.83 (d, J=3.9 Hz, 1H), 7.71-7.68 (d, J=8.1 Hz, 1H), 7.29 (s, 1H), 7.25 (s, 1H), 7.10-7.04 (d, J=7.8 Hz, 1H), 6.70-6.68 (d, J=8.1 Hz, 1H), 4.42 (bm, 1H), 2.95 (s, 3H), 2.42 (s, 3H), 1.84-1.80 (d, J=11.4 Hz, 2H), 1.61-1.52 (t, J=12.6 Hz, 2H), 1.18 (s, 12H).

I-244: N2-[4-(4-methylsulfonylpiperazino)-3-trifluoromethyl]phenyl-5-fluoro-N4-(1,2,2,6,6-pentamethylpiperidin-4-yl)-2,4-pyrimidinediamine benzylate salt MS (m/e) 588.23 (MH$^+$); $^1$H NMR (DMSO-d$_6$): δ 9.43 (s, 1H), 8.53 (s, 1H), 8.02 (s, 1H), 7.99 (s, 1H), 7.74 (s, 1H), 7.57 (bs, 1H), 7.49-7.46 (d, J=9.0 Hz, 1H), 7.27 (s, 2H), 4.39 (m, 1H), 3.20 (s, 4H), 2.93 (s, 3H), 2.87 (s, 4H), 2.74-2.72 (d, J=4.8 Hz, 3H), 2.07-2.03 (d, J=12.3 Hz, 2H), 1.83-1.74 (t, J=12.6 Hz, 2H), 1.39 (s, 6H), 1.35 (s, 3H).

I-245: N2-[4-(4,4-Difluoropiperidin-1-yl)-3-trifluoromethyl]phenyl-5-fluoro-N4-(1,2,2,6,6-pentamethylpiperidin-4-yl)-2,4-pyrimidinediamine LCMS: purity: 97.36%; MS (m/e): 545.50 (MH+); $^1$H NMR (DMSO-d$_6$): δ 1.30 (s, 12H), 1.69 (t, J=12.9 Hz, 2H), 1.97 (d, J=13.2 Hz, 2H), 2.04 (m, 4H), 2.58 (s, 3H), 2.89 (t, 4H), 4.38 (br, 1H), 7.39 (d, J=8.4 Hz, 1H), 7.46 (d, J=6.9 Hz, 1H), 7.80 (s, 1H), 7.90 (d, J=3.6 Hz, 1H), 8.01 (d, J=9.0 Hz, 1H), 9.22 (s, 1H); $^{19}$F NMR (282 MHz, DMSO-d$_6$): δ−165.54, −60.32.

I-246: N2-[4-(4-Ethylpiperazino)-3-trifluoromethyl]phenyl-5-fluoro-N4-(1,2,2,6,6-pentamethylpiperidin-4-yl)-2,4-pyrimidinediamine LCMS: purity: 99.31%; MS (m/e): 538.46 (MH+); $^1$H NMR (DMSO-d$_6$): δ 1.24 (t, J=7.2 Hz, 3H), 1.40 (s, 12H), 1.80 (t, J=12.6 Hz, 2H), 2.07 (d, J=11.1 Hz, 2H), 2.73 (d, J=4.2 Hz, 3H), 3.04 (m, 4H), 3.22 (q, J=7.8 Hz, 2H), 3.55 (m, 4H), 4.42 (br, 1H), 7.40 (d, J=8.7 Hz, 1H), 7.63 (d, J=7.8 Hz, 1H), 7.87 (s, 1H), 7.94 (d, J=3.6 Hz, 1H), 8.04 (d, J=7.8 Hz, 1H), 8.69 (br, 1H), 9.27 (s, 1H), 9.70 (br, 1H); $^{19}$F NMR (282 MHz, DMSO-d$_6$): δ−165.18, −60.01.

I-247: 5-Fluoro-N4-(1,2,2,6,6-pentamethylpiperidin-4-yl)-N2-[4-(4-propylpiperazino)-3-trifluoromethyl]phenyl-2,4-pyrimidinediamine LCMS: purity: 99.83%; MS (m/e): 552.42 (MH+); $^1$H NMR (DMSO-d$_6$): δ 0.92 (t, J=7.2 Hz, 3H), 1.40 (s, 12H), 1.68 (m, J=7.5 Hz, 2H), 1.80 (t, J=12.9 Hz, 2H), 2.08 (d, J=12.0 Hz, 2H), 2.73 (d, J=4.2 Hz, 3H), 3.07 (m, 4H), 3.09 (q, 2H), 3.52 (m, 4H), 4.42 (br, 1H), 7.39 (d, J=8.7 Hz, 1H), 7.62 (d, J=7.8 Hz, 1H), 7.87 (s, 1H), 7.93 (d, J=3.6 Hz, 1H), 8.04 (d, J=8.7 Hz, 1H), 8.68 (br, 1H), 9.26 (s, 1H), 9.70 (br, 1H); $^{19}$F NMR (282 MHz, DMSO-d$_6$): δ−165.20, −60.01.

I-248: N2-[3-Chloro-4-(4-ethylpiperazino)]phenyl-5-fluoro-N4-(1,2,2,6,6-pentamethylpiperidin-4-yl)-2,4-pyrimidinediamine LCMS: purity: 99.26%; MS (m/e): 504.20 (MH+); $^1$H NMR (DMSO-d$_6$): δ 1.25 (t, J=7.2 Hz, 3H), 1.40 (s, 6H), 1.42 (s, 6H), 1.81 (t, J=13.5 Hz, 2H), 2.07 (d, J=14.1 Hz, 2H), 2.74 (d, J=4.8 Hz, 3H), 2.94 (t, J=12.3 Hz, 2H), 3.11-3.34 (m, 6H), 3.56 (d, J=12.3 Hz, 2H), 4.47 (br, 1H), 7.08 (d, J=9.0 Hz, 1H), 7.50 (d, J=8.7 Hz, 1H), 7.61 (d, J=7.8 Hz, 1H), 7.86 (s, 1H), 7.93 (d, J=3.6 Hz, 1H), 8.64 (br, 1H), 9.12 (s, 1H), 9.48 (br, 1H); $^{19}$F NMR (282 MHz, DMSO-d$_6$): δ−165.70.

I-249: N2-[3-Chloro-4-(4-propylpiperazino)]phenyl-5-fluoro-N4-(1,2,2,6,6-pentamethylpiperidin-4-yl)-2,4-pyrimidinediamine LCMS: purity: 100%; MS (m/e): 518.24 (MH+); $^1$H NMR (DMSO-d$_6$): δ 0.93 (t, J=7.2 Hz, 3H), 1.41 (s, 6H), 1.42 (s, 6H), 1.69 (m, J=7.5 Hz, 2H), 1.81 (t, J=12.9 Hz, 2H), 2.07 (d, J=12.3 Hz, 2H), 2.74 (d, J=4.5 Hz, 3H), 2.96 (t, J=11.4 Hz, 2H), 3.12 (m, 4H), 3.31 (d, J=12.0 Hz, 2H), 3.56 (d, J=11.4 Hz, 2H), 4.47 (br, 1H), 7.07 (d, J=8.7 Hz, 1H), 7.51 (d, J=8.4 Hz, 1H), 7.62 (d, J=7.5 Hz, 1H), 7.86 (s, 1H), 7.93 (d, J=3.9 Hz, 1H), 8.66 (br, 1H), 9.13 (s, 1H), 9.56 (br, 1H); $^{19}$F NMR (282 MHz, DMSO-d$_6$): δ−165.68.

I-250: N2-[4-Chloro-3-(3,4,5-trimethylpiperazino)]phenyl-5-fluoro-N4-(1,2,2,6,6-pentamethylpiperidin-4-yl)-2,4-pyrimidinediamine LCMS: purity: 99.07%; MS (m/e): 518.15 (MH+); $^1$H NMR (DMSO-d$_6$): δ 1.35 (d, J=6.3 Hz, 6H), 1.41 (s, 6H), 1.44 (s, 6H), 1.82 (t, J=12.6 Hz, 2H), 2.08 (d, J=12.6 Hz, 2H), 2.76 (m, 5H), 2.90 (d, J=4.8 Hz, 3H), 3.48 (m, 4H), 4.47 (br, 1H), 7.18 (m, 2H), 7.65 (d, J=7.2 Hz, 1H), 7.85 (d, J=9.6 Hz, 1H), 7.93 (d, J=3.6 Hz, 1H), 8.64 (br, 1H), 9.10 (s, 1H), 9.33 (br, 1H); $^{19}$F NMR (282 MHz, DMSO-d$_6$): δ−165.52.

I-251: N2-[3-(4-Acyl-3,5-dimethylpiperazino)-4-chloro]phenyl-5-fluoro-N4-(1,2,2,6,6-pentamethylpiperidin-4-yl)-2,4-pyrimidinediamine LCMS: purity: 100%; MS (m/e): 546.22 (MH+); $^1$H NMR (DMSO-d$_6$): δ 1.34 (s, 6H), 1.36 (d, J=7.2 Hz, 6H), 1.37 (s, 6H), 1.74 (t, J=12.9 Hz, 2H), 2.02 (d, 2H), 2.05 (s, 3H), 2.64 (m, 5H), 3.31 (m, 4H), 4.47 (br, 1H), 7.17 (m, 2H), 7.50 (d, J=8.1 Hz, 1H), 7.79 (d, J=8.7 Hz, 1H), 7.90 (d, J=3.6 Hz, 1H), 9.08 (s, 1H); $^{19}$F NMR (282 MHz, DMSO-d$_6$): δ−165.90.

I-252: 5-Fluoro-N2-(4-hydroxyl)phenyl-N4-(1,2,2,6,6-pentamethylpiperidin-4-yl)-2,4-pyrimidinediamine MS (m/e): 374.38 (MH+); $^1$H NMR (DMSO-d$_6$): δ 1.39 (s, 12H), 1.78 (t, J=12.6 Hz, 2H), 2.06 (d, J=12.3 Hz, 2H), 2.72 (s, 3H), 4.46 (br, 1H), 6.59 (d, J=8.4 Hz, 2H), 7.37 (d, J=9.3 Hz, 2H), 7.42 (m, 1H), 7.82 (d, J=3.9 Hz, 1H), 8.70 (s, 1H), 8.91 (s, 1H); $^{19}$F NMR (282 MHz, DMSO-d$_6$): δ−168.00; LCMS: purity: 98.99%.

I-254: N2-(3-Chloro-4-methoxy)phenyl-5-fluoro-N4-(2,2,6,6-tetramethylpiperidin-4-yl)-2,4-pyrimidinediamine LCMS: purity: 99.64%; MS (m/e): 408.12 (MH+); $^1$H NMR (DMSO-d$_6$): δ 1.37 (s, 6H), 1.43 (s, 6H), 1.58 (t, J=12.6 Hz, 2H), 1.95 (d, J=10.5 Hz, 2H), 3.77 (s, 3H), 4.45 (br, 1H), 6.99 (d, J=9.0 Hz, 1H), 7.45 (dd, J=2.4, 9.0 Hz, 1H), 7.60 (d, 1H), 7.74 (d, J=2.4 Hz, 1H), 7.82 (d, J=12.6 Hz, 1H), 7.91 (d, J=3.6 Hz, 1H), 8.70 (d, J=10.8 Hz, 1H), 9.07 (s, 1H); $^{19}$F NMR (282 MHz, DMSO-d$_6$): δ−166.17.

I-255: 5-Fluoro-N2-[4-(4-methylpiperazino)-3-trifluoromethyl]phenyl-N4-(2,2,6,6-tetramethylpiperidin-4-yl)-2,4-pyrimidinediamine LCMS: purity: 98.77%; MS (m/e): 510.35 (MH+); $^1$H NMR (DMSO-d$_6$): δ 1.38 (s, 6H), 1.44 (s, 6H), 1.59 (t, J=12.6 Hz, 2H), 1.98 (d, J=13.2 Hz, 2H), 2.84 (s, 3H), 3.01 (br, 4H), 3.31 (br, 4H), 4.46 (br, 1H), 7.38 (d, J=9.0 Hz, 1H), 7.54 (br, 1H), 7.85 (s, 1H), 7.92 (s, 1H), 8.05 (d, J=9.3 Hz, 1H), 8.80 (br, 1H), 9.27 (br, 1H); $^{19}$F NMR (282 MHz, DMSO-d$_6$): δ−165.28, −60.03.

I-256: N2-[3-Chloro-4-(4-methylpiperazino)]phenyl-5-fluoro-N4-(2,2,6,6-tetramethylpiperidin-4-yl)-2,4-pyrimidinediamine LCMS: purity: 93.57%; MS (m/e): 475.88 (MH+); $^1$H NMR (DMSO-d$_6$): δ 1.38 (s, 6H), 1.45 (s, 6H), 1.58 (t, J=12.9 Hz, 2H), 1.97 (d, J=12.3 Hz, 2H), 2.88 (s, 3H), 2.91 (m, 2H), 3.20 (m, 2H), 3.27 (m, 2H), 3.49 (m, 2H), 4.47 (br, 1H), 7.07 (d, J=8.7 Hz, 1H), 7.52 (d, J=8.7 Hz, 1H), 7.58 (d, J=8.1 Hz, 1H), 7.80 (br, 1H), 7.85 (s, 1H), 7.92 (d, J=3.9 Hz, 1H), 8.75 (d, 1H), 9.14 (s, 1H), 9.66 (br, 1H).

I-257: 5-Fluoro-N2-[4-(4-methylsulfonylpiperazino)-3-trifluoromethyl]phenyl-N4-(2,2,6,6-tetramethylpiperidin-4-yl)-2,4-pyrimidinediamine LCMS: purity: 98.98%; MS (m/e): 574.50 (MH+); $^1$H NMR (DMSO-$d_6$): δ 1.33 (s, 6H), 1.40 (s, 6H), 1.52 (t, J=12.6 Hz, 2H), 1.94 (d, J=10.2 Hz, 2H), 2.87 (t, 4H), 2.93 (s, 3H), 3.20 (br, 4H), 4.42 (br, 1H), 7.46 (d, J=8.1 Hz, 1H), 7.51 (d, J=8.1 Hz, 1H), 7.80 (s, 1H), 7.92 (d, J=3.6 Hz, 1H), 8.02 (d, J=8.7 Hz, 1H), 9.24 (s, 1H); $^{19}$F NMR (282 MHz, DMSO-$d_6$): δ −165.53, −59.87.

I-258: N2-[3-Chloro-4-(4-methylsulfonylpiperazino)]phenyl-5-fluoro-N4-(2,2,6,6-tetramethylpiperidin-4-yl)-2,4-pyrimidinediamine LCMS: purity: 95.07%; MS (m/e): 540.17 (MH+); $^1$H NMR (DMSO-$d_6$): δ 1.37 (s, 6H), 1.45 (s, 6H), 1.57 (t, J=12.9 Hz, 2H), 1.96 (d, J=12.9 Hz, 2H), 2.93 (s, 3H), 2.96 (t, 4H), 3.25 (t, 4H), 4.46 (br, 1H), 7.05 (d, J=8.7 Hz, 1H), 7.54 (m, 2H), 7.77 (s, 1H), 7.81 (br, 1H), 7.91 (d, J=3.6 Hz, 1H), 8.64 (d, J=10.8 Hz, 1H), 9.11 (s, 1H); $^{19}$F NMR (282 MHz, DMSO-$d_6$): δ −166.00.

I-259: 5-Fluoro-N4-(1,2,2,6,6-pentamethylpiperidin-4-yl)-N2-[3-trifluoromethyl-4-(1,3,5-trimethyl-3,7-diazabicyclo[3.3.1]nonan-7-yl)]phenyl-2,4-pyrimidinediamine LCMS: purity: 94.37%; MS (m/e): 592.40 (MH+); $^1$H NMR (DMSO-$d_6$): δ 0.93 (s, 6H), 1.38 (s, 12H), 1.56 (s, 2H), 1.78 (t, J=12.0 Hz, 2H), 2.04 (d, J=9.9 Hz, 2H), 2.69 (s, 3H), 2.83-2.93 (m, 7H), 3.02 (t, J=10.2 Hz, 2H), 3.49 (d, J=11.1 Hz, 2H), 4.42 (br, 1H), 7.54 (d, J=9.0 Hz, 1H), 7.60 (d, 1H), 7.94 (d, J=3.6 Hz, 1H), 8.00 (s, 1H), 8.05 (d, J=8.4 Hz, 1H), 9.28 (s, 1H), 9.75 (br, 1H); $^{19}$F NMR (282 MHz, DMSO-$d_6$): δ −164.90, −60.01.

I-260: 5-Fluoro-N4-(1,2,2,6,6-pentamethylpiperidin-4-yl)-N2-[4-(1,3,5-trimethyl-3,7-diazabicyclo[3.3.1]nonan-7-yl)]phenyl-2,4-pyrimidinediamine LCMS: purity: 90.74%; MS (m/e): 523.84 (MH+); $^1$H NMR (DMSO-$d_6$): δ 0.96 (s, 6H), 1.33 (s, 6H), 1.40 (s, 7H), 1.52 (d, J=12.6 Hz, 1H), 1.84 (t, J=12.3 Hz, 2H), 2.04 (d, J=12.3 Hz, 2H), 2.41 (d, J=10.8 Hz, 2H), 2.69 (d, J=5.1 Hz, 3H), 2.73 (d, J=5.1 Hz, 3H), 2.83 (t, J=10.5 Hz, 2H), 3.46 (d, J=11.7 Hz, 4H), 4.41 (br, 1H), 7.01 (d, J=9.0 Hz, 2H), 7.43 (d, J=8.7 Hz, 2H), 8.03 (d, J=4.2 Hz, 1H), 8.38 (br, 1H), 8.78 (br, 2H), 9.68 (br, 1H).

I-261: 5-Fluoro-N2-[4-morpholine-3-trifluoromethyl]phenyl-N4-(1,2,2,7,7-pentamethylazepan-4-yl)-2,4-pyrimidinediamine LCMS: purity: 90%; MS (m/e): 525 (MH+); $^1$H NMR (CD$_3$OD): δ 7.94 (m, 2H), 7.55 (m, 2H), 4.89 (m, 4H), 3.20-1.33 (m, 14H), 1.31 (m, 12H).

I-262: 5-Fluoro-N2-[3-chloro-4-methoxy]phenyl-N4-(1,2,2,7,7-pentamethylazepan-4-yl)-2,4-pyrimidinediamine LCMS: purity: 90%; MS (m/e): 436 (MH+); $^1$H NMR (CD$_3$OD): δ 7.87 (m, 2H), 7.69 (d, J=5.7 Hz, 1H), 7.27 (m, 1H), 7.69 (d, J=9.0 Hz, 1H), 4.63 (s, 3H), 3.58-1.65 (m, 10H), 1.35 (m, 12H).

I-263: 5-Fluoro-N2-[4-(methyl)-3-cyano]phenyl-N4-(1,2,2,7,7-pentamethylazepan-4-yl)-2,4-pyrimidinediamine LCMS: purity: 90%; MS (m/e): 411 (MH+); $^1$H NMR (CD$_3$OD): δ 7.98 (m, 2H), 7.55 (m, 2H), 2.65-1.65 (m, 13H), 1.38 (m, 12H).

I-264: 5-Fluoro-N2-[4-methylsulfonylpiperazin-lyl-3-trifluoromethyl]phenyl-N4-(1,2,2,7,7-pentamethylazepan-4-yl)-2,4-pyrimidinediamine LCMS: purity: 90%; MS (m/e): 602 (MH+); $^1$H NMR (CD$_3$OD): δ 8.19 (s, 1H), 7.93 (m, 1H), 7.54 (m, 2H), 3.79-1.46 (m, 21H), 1.35 (m, 12H).

I-265: 5-Fluoro-N2-[3,5-dichloro]phenyl-N4-(1,2,2,7,7-pentamethylazepan-4-yl)-2,4-pyrimidinediamine LCMS: purity: 90%; MS (m/e): 441 (MH+); $^1$H NMR (CD$_3$OD): δ 8.41 (d, J=3.0 Hz, 1H), 7.80 (d, J=3.3 Hz, 1H), 7.69 (m, 1H), 6.93 (m, 1H), 5.21-1.87 (m, 10H), 1.36 (m, 12H).

I-266: 5-Fluoro-N2-[3,4,5-trimethoxy]phenyl-N4-(1,2,2,7,7-pentamethylazepan-4-yl)-2,4-pyrimidinediamine LCMS: purity: 90%; MS (m/e): 462 (MH+); $^1$H NMR (CD$_3$OD): δ 8.27 (d, J=3.0 Hz, 1H), 7.85 (d, J=3.0 Hz, 1H), 7.21 (s, 1H), 5.20-1.35 (m, 19H), 1.31 (m, 12H).

I-267: 5-Fluoro-N2-[3,4-dimethoxy]phenyl-N4-(1,2,2,7,7-pentamethylazepan-4-yl)-2,4-pyrimidinediamine LCMS: purity: 90%; MS (m/e): 432 (MH+); $^1$H NMR (CD$_3$OD): δ 8.21 (m, 2H), 7.88 (m, 1H), 6.99 (m, 1H), 5.20-1.35 (m, 16H), 1.30 (m, 12H).

I-268: 5-Fluoro-N2-[4-methoxy-3-trifluoromethyl]phenyl-N4-(1,2,2,7,7-pentamethylazepan-4-yl)-2,4-pyrimidinediamine LCMS: purity: 90%; MS (m/e): 470 (MH+); $^1$H NMR (CD$_3$OD): δ 8.34 (m, 2H), 7.88 (m, 1H), 7.11 (m, 1H), 5.25-1.30 (m, 13H), 1.28 (m, 12H).

I-269: 5-Fluoro-N2-[3-methoxy]phenyl-N4-(1,2,2,7,7-pentamethylazepan-4-yl)-2,4-pyrimidinediamine LCMS: purity: 90%; MS (m/e): 456 (MH+); $^1$H NMR (CD$_3$OD): δ 8.11 (m, 2H), 7.71 (m, 2H), 6.82 (m, 1H), 5.25-1.30 (m, 13H), 1.27 (m, 12H).

I-270: 5-Fluoro-N2-[4-methylpiperizine-3-trifluoromethyl]phenyl-N4-(1,2,2,7,7-pentamethylazepan-4-yl)-2,4-pyrimidinediamine LCMS: purity: 90%; MS (m/e): 538 (MH+); $^1$H NMR (CD$_3$OD): δ 8.37 (m, 2H), 7.98 (m, 1H), 6.90 (m, 1H), 3.80-1.38 (m, 21H), 1.29 (m, 12H).

I-271: 5-Fluoro-N2-[6-morpholine-5-trifluoromethyl]pyridinyl-N4-(1,2,2,6,6-pentamethylpiperidin-4-yl)-2,4-pyrimidinediamine LCMS: purity: 90%; MS (m/e): 512 (MH+); $^1$H NMR (CD$_3$OD): δ 8.22 (d, J=3.0 Hz, 1H), 7.89 (d, J=3.0 Hz, 1H), 6.97 (m, 1H), 4.80-1.38 (m, 16H), 1.24 (m, 12H).

I-272: 5-Bromo-N2-[4-methoxy-3-trifluoromethyl]phenyl-N4-(1,2,2,6,6-pentamethylpiperidin-4-yl)-2,4-pyrimidinediamine LCMS: purity: 90%; MS (m/e): 517 (MH+); $^1$H NMR (CD$_3$OD): δ 8.44 (m, 2H), 7.90 (m, 1H), 7.21 (m, 1H), 4.90-1.39 (m, 11H), 1.23 (m, 12H).

I-273: 5-Fluoro-N2-[6-(4-methylpiperizin-1-yl)-5-trifluoromethyl]pyridine-3-yl]-N4-(1,2,2,6,6-pentamethylpiperidin-4-yl)-2,4-pyrimidinediamine LCMS: purity: 90%; MS (m/e): 525 (MH+); $^1$H NMR (CD$_3$OD): δ 8.11 (d, J=3.0 Hz, 1H), 7.60 (d, J=3.0 Hz, 1H), 7.01 (m, 1H), 3.50-1.40 (m, 19H), 1.20 (m, 12H).

I-274: 5-Bromo-N2-[3,4-dimethoxy]phenyl-N4-(1,2,2,6,6-pentamethylpiperidin-4-yl)-2,4-pyrimidinediamine LCMS: purity: 90%; MS (m/e): 479 (MH+); $^1$H NMR (CD$_3$OD): δ 8.24 (m, 2H), 7.50 (m, 1H), 7.17 (m, 1H), 4.90-1.42 (m, 14H), 1.25 (m, 12H).

I-275: 5-Bromo-N2-[3-trifluoromethoxy]phenyl-N4-(1,2,2,6,6-pentamethylpiperidin-4-yl)-2,4-pyrimidinediamine LCMS: purity: 90%; MS (m/e): 503 (MH+); $^1$H NMR (CD$_3$OD): δ 8.11 (m, 2H), 7.60 (m, 2H), 6.95 (m, 1H), 3.90-1.38 (m, 8H), 1.29 (m, 12H).

I-276: 5-Bromo-N2-[3,4,5-trimethoxy]phenyl-N4-(1,2,2,6,6-pentamethylpiperidin-4-yl)-2,4-pyrimidinediamine LCMS: purity: 90%; MS (m/e): 509 (MH+); $^1$H NMR (CD$_3$OD): δ 8.11 (d, J=3.0 Hz, 1H), 7.81 (d, J=3.0 Hz, 1H), 7.00 (m, 1H), 4.91-1.35 (m, 17H), 1.24 (m, 12H).

I-277: 5-Bromo-N2-[4-methyl-3-cyano]phenyl-N4-(1,2,2,6,6-pentamethylpiperidin-4-yl)-2,4-pyrimidinediamine LCMS: purity: 90%; MS (m/e): 458 (MH+); $^1$H NMR (CD$_3$OD): δ 8.11 (m, 2H), 7.81 (m, 2H), 3.91-1.35 (m, 11H), 1.20 (m, 12H).

I-278: 5-Fluoro-N2-(4-methyl-cyano)phenyl-N4-(1,2,2,5,5-pentamethylpyrrolidin-3-yl)-2,4-pyrimidinediamine LCMS: purity: 99.26%; MS (m/e): 355.45 (MH+); $^1$H NMR (DMSO-d6): δ 1.20-1.50 (m, 12H), 1.75-1.80 (m, 2H), 2.30 (s, 3H), 2.58 (s, 3H), 4.36 (t, J=12.1 Hz, 1H), 6.93 (d, J=7.5 Hz, 1H), 7.08 (m, 2H), 7.63 (d, J=7.5 Hz, 1H), 7.90 (d, J=3.9 Hz, 1H), 9.17 (s, 1H).

I-279: 5-Fluoro-N2-(3,5-dichloro)phenyl-N4-(1,2,2,5,5-pentamethylpyrrolidin-3-yl)-2,4-pyrimidinediamine LCMS: purity: 94.65%; MS (m/e): 413.34 (MH+); $^1$H NMR (DMSO-d6): δ 1.26 (m, 6H), 1.52 (m, 6H), 1.64 (m, 1H), 1.80-1.85 (m, 1H), 2.27 (s, 3H), 4.50 (t, J=12.0 Hz, 1H), 7.06 (s, 1H), 7.25 (d, J=8.7 Hz, 2H), 7.70 (s, 1H), 7.95 (s, 1H), 9.36 (s, 1H); 19F NMR (282 MHz, DMSO-d6): δ−165.25, −57.97.

I-280: 5-Fluoro-N2-(3-chloro-4-methoxy)phenyl-N4-(1,2,2,5,5-pentamethylpyrrolidin-3-yl)-2,4-pyrimidinediamine LCMS: purity: 99.01%; MS (m/e): 408.91 (MH+); $^1$H NMR (DMSO-d6): δ 1.20-1.50 (m, 12H), 1.80-1.85 (m, 2H), 2.30 (s, 3H), 3.73 (s, 1H), 4.33 (t, J=12.1 Hz, 1H), 6.88 (d, J=7.5 Hz, 1H), 6.93 (d, J=7.5 Hz, 1H), 7.08 (m, 1H), 7.63 (d, J=7.8 Hz, 1H), 7.90 (d, J=3.9 Hz, 1H), 9.17 (s, 1H).

I-281: 5-Fluoro-N2-(3,4-dimethoxy)phenyl-N4-(1,2,2,5,5-pentamethylpyrrolidin-3-yl)-2,4-pyrimidinediamine LCMS: purity: 98.26%; MS (m/e): 404.49 (MH+); $^1$H NMR (DMSO-d6): δ 1.25-1.55 (m, 12H), 1.78-1.82 (m, 2H), 2.22 (s, 3H), 3.73 (s, 3H), 3.85 (s, 3H), 4.54 (t, J=11.8 Hz, 1H), 6.90 (d, J=7.5 Hz, 1H), 6.96 (d, J=7.5 Hz, 1H), 7.11 (m, 1H), 7.53 (d, J=7.5 Hz, 1H), 7.99 (d, J=3.8 Hz, 1H), 9.17 (s, 1H).

I-282: 5-Fluoro-N2-(3,4,5-trimethoxy)phenyl-N4-(1,2,2,5,5-pentamethylpyrrolidin-3-yl)-2,4-pyrimidinediamine LCMS: purity: 96.88%; MS (m/e): 434.52 (MH+); $^1$H NMR (DMSO-d6): δ 1.22-1.50 (m, 12H), 1.80-1.85 (m, 2H), 2.20 (s, 3H), 3.74 (s, 6H), 3.79 (s, 3H), 4.38 (t, J=12.4 Hz, 1H), 6.53 (m, 2H), 7.11 (m, 1H), 8.05 (d, J=3.8 Hz, 1H), 9.22 (s, 1H).

I-283: 5-Fluoro-N2-(4-methoxy-3-trifluoromethyl)phenyl-N4-(1,2,2,5,5-pentamethylpyrrolidin-3-yl)-2,4-pyrimidinediamine LCMS: purity: 97.25%; MS (m/e): 442.17 (MH+); $^1$H NMR (DMSO-d6): δ 0.95-1.10 (m, 6H), 1.15-1.20 (m, 6H), 1.60 (d, J=7.2 Hz, 1H), 1.85 (d, J=7.5 Hz, 1H), 2.30 (s, 3H), 3.73 (s, 3H), 4.49 (t, J=12.4 Hz, 1H), 6.54 (m, 1H), 6.70 (m, 2H), 7.11 (m, 1H), 8.05 (d, J=4.1 Hz, 1H), 9.22 (s, 1H).

I-284: 5-Fluoro-N2-(3-trifluoromethoxy)phenyl-N4-(1,2,2,5,5-pentamethylpyrrolidin-3-yl)-2,4-pyrimidinediamine LCMS: purity: 96.88%; MS (m/e): 428.44 (MH+); $^1$H NMR (DMSO-d6): δ 0.87 (s, 3H), 1.06-1.09 (m, 9H), 1.85-1.93 (m, 2H), 2.14 (s, 3H), 4.55-4.58 (dd, J=11.8 Hz, 1H), 6.53 (s, 1H), 6.77-6.80 (d, J=7.5 Hz, 1H), 7.08-7.11 (d, 7.4 Hz, 1H), 7.27-7.30 (t, J=12.1 Hz, 1H), 7.50-7.52 (d, J=8.1 Hz, 1H), 7.89-7.91 (m, 1H), 8.00 (s, 1H), 9.37 (s, 1H).

I-285: 5-Fluoro-N2-[4-(4-methylpiperazin-1-yl)-3-(trifluoromethyl)]phenyl-N4-(1,2,2,5,5-pentamethylpyrrolidin-3-yl)-2,4-pyrimidinediamine LCMS: purity: 95.20%; MS (m/e): 510.59 (MH+); $^1$H NMR (DMSO-d6): δ 0.92 (s, 3H), 1.10-1.15 (m, 9H), 1.75-1.85 (m, 2H), 2.10 (s, 3H), 2.25 (s, 3H), 2.50 (d, J=10.8 Hz, 4H), 3.73 (d, J=11.2 Hz, 4H), 4.54 (m, 1H), 6.56 (m, 2H), 6.72 (m, 1H), 7.28 (s, 1H), 8.11 (d, J=4.5 Hz, 1H), 9.27 (s, 1H).

I-286: 5-Fluoro-N2-[4-(4-methylsulfonyl)piperazin-1-yl)-3-(trifluoromethyl)]phenyl-N4-(1,2,2,5,5-pentamethylpyrrolidin-3-yl)-2,4-pyrimidinediamine LCMS: purity: 97.82%; MS (m/e): 574.34 (MH+); $^1$H NMR (DMSO-d6): δ 0.93 (s, 3H), 1.10-1.12 (m, 9H), 1.75-1.85 (m, 2H), 2.15 (s, 3H), 2.55 (d, J=12.0 Hz, 4H), 2.90 (s, 3H), 3.75 (d, J=11.8 Hz, 4H), 4.44 (br, 1H), 6.60 (m, 2H), 6.75 (m, 1H), 7.32 (s, 1H), 8.01 (d, J=4.3 Hz, 1H), 9.12 (s, 1H).

I-287: 5-Fluoro-N2-[4-morpholino-3-(trifluoromethyl)]phenyl-N4-(1,2,2,5,5-pentamethylpyrrolidin-3-yl)-2,4-pyrimidinediamine LCMS: purity: 96.20%; MS (m/e): 497.54 (MH+); $^1$H NMR (DMSO-d6): δ 0.88-1.08 (m, 12H), 1.75-1.85 (m, 2H), 2.15 (s, 3H), 2.77 (m, 4H), 3.66 (m, 4H), 4.44 (br, 1H), 6.53 (m, 2H), 6.77 (m, 1H), 7.42 (s, 1H), 8.01 (d, J=3.86 Hz, 1H), 9.26 (s, 1H).

I-288: 5-Fluoro-N2-[5-chloro-6-(4-methylpiperazin-1-yl)]pyridine-3-yl-N4-(1,2,2,6,6-pentamethylpiperidin-4-yl)-2,4-pyrimidinediamine LCMS: purity: 96.83%; MS (m/e): 492.05 (MH+); $^1$H NMR (DMSO-d6): δ 1.40 (s, 6H), 1.42 (s, 6H), 1.82 (t, J=12.7 Hz, 2H), 2.07 (d, J=11.2 Hz, 2H), 2.73 (s, 3H), 4.51 (br, 1H), 7.26 (d, J=7.5 Hz, 1H), 7.55 (s, 1H), 7.63 (d, J=7.5 Hz, 1H), 7.90 (d, J=3.9 Hz, 1H), 9.32 (s, 1H).

I-289: 5-Fluoro-N2-[5-chloro-6-(4-(methylsulfonyl)piperazin-1-yl)]pyridin-3-yl-N4-(1,2,2,6,6-pentamethylpiperidin-4-yl)-2,4-pyrimidinediamine LCMS: purity: 95.86%; MS (m/e): 556.11 (MH+); $^1$H NMR (DMSO-d6): δ 1.30 (s, 6H), 1.40 (s, 6H), 1.79 (t, J=12.6 Hz, 2H), 2.12 (d, J=12.0 Hz, 2H), 2.66 (m, 4H), 2.75 (s, 3H), 2.95 (s, 3H), 3.66 (m, 4H), 4.43 (s, 1H), 7.32 (d, J=7.2 Hz, 1H), 7.65 (s, 1H), 7.77 (d, J=7.5 Hz, 1H), 8.09 (d, J=4.1 Hz, 1H), 9.44 (s, 1H).

I-290: 5-Fluoro-N2-[5-chloro-6-(4-morpholino)]pyridine-3-yl-N4-(1,2,2,6,6-pentamethylpiperidin-4-yl)-2,4-pyrimidinediamine LCMS: purity: 99.26%; MS (m/e): 479.01 (MH+); $^1$H NMR (DMSO-d6): δ 1.10 (s, 6H), 1.26 (s, 6H), 1.69 (t, J=12.0 Hz, 2H), 2.00 (d, J=11.8 Hz, 2H), 2.65 (s, 3H), 2.86 (m, 4H), 3.76 (m, 4H), 4.23 (br, 1H), 7.42 (d, J=7.5 Hz, 1H), 7.55 (s, 1H), 7.87 (d, J=7.5 Hz, 1H), 8.19 (d, J=4.1 Hz, 1H), 9.28 (s, 1H).

I-291: Methyl 3-[4-(2-(3,4-dimethoxyphenylamino)-5-fluoropyrimidine-4-ylamino)-2,2,6,6-tetramethylpiperidin-1-yl]propanoate LCMS: purity: 94.62%; MS (m/e): 490.58 (MH+); $^1$H NMR (DMSO-d6): δ 1.40 (s, 6H), 1.46 (s, 6H), 1.90 (m, 2H), 2.12 (d, J=12.0 Hz, 2H), 2.45 (t, J=12.0 Hz, 2H), 2.80 (t, J=11.8 Hz, 2H), 3.71 (s, 3H), 3.82 (s, 3H), 3.85 (s, 3H), 4.50 (m, 1H), 6.90 (d, J=7.5 Hz, 1H), 6.99 (d, J=7.5 Hz, 1H), 7.09 (m, 1H), 7.53 (d, J=7.5 Hz, 1H), 8.05 (d, J=3.8 Hz, 1H), 9.21 (s, 1H).

I-292: Methyl 3-[4-(2-(3,5-dimethoxyphenylamino)-5-fluoropyrimidine-4-ylamino)-2,2,6,6-tetramethylpiperidin-1-yl]propanoate LCMS: purity: 95.45%; MS (m/e): 490.58 (MH+); $^1$H NMR (DMSO-d6): δ 1.32 (s, 6H), 1.47 (s, 6H), 1.85 (m, 2H), 2.32 (d, J=11.8 Hz, 2H), 2.46 (t, J=11.9 Hz, 2H), 2.77 (t, J=11.8 Hz, 2H), 3.73 (s, 6H), 3.84 (s, 3H), 4.49 (m, 1H), 6.59 (d, J=7.2 Hz, 1H), 6.89 (d, J=7.5 Hz, 1H), 7.16 (m, 1H), 7.54 (d, J=7.5 Hz, 1H), 8.12 (d, J=3.8 Hz, 1H), 9.32 (s, 1H).

I-293: Methyl 3-[4-(2-(3-chloro-4-methoxyphenylamino)-5-fluoropyrimidine-4-ylamino)-2,2,6,6-tetramethylpiperidin-1-yl]propanoate LCMS: purity: 98.88%; MS (m/e): 495.00 (MH+); $^1$H NMR (DMSO-d6): δ 1.45 (s, 6H), 1.50 (s, 6H), 1.85 (m, 2H), 2.22 (d, J=12.0 Hz, 2H), 2.43 (t, J=12.0 Hz, 2H), 2.80 (t, J=11.5 Hz, 2H), 3.75 (s, 3H), 3.85 (s, 3H), 4.42 (m, 1H), 6.90 (d, J=7.2 Hz, 1H), 6.99 (d, J=6.9 Hz, 1H), 7.09 (m, 1H), 7.53 (d, J=7.5 Hz, 1H), 8.05 (d, J=4.1 Hz, 1H), 9.21 (s, 1H).

I-294: Methyl 3-[4-(2-(3,5-dichlorophenylamino)-5-fluoropyrimidine-4-ylamino)-2,2,6,6-tetramethylpiperidin-1-yl]propanoate LCMS: purity: 97.87%; MS (m/e): 499.42 (MH+); $^1$H NMR (DMSO-d6): δ 1.48 (m, 12H), 1.78 (m, 2H), 2.32 (m, 2H), 2.46 (m, 2H), 2.77 (t, J=11.8 Hz, 2H), 3.82 (s, 3H), 4.35 (m, 1H), 6.60 (d, J=7.7 Hz, 1H), 6.99 (d, J=7.5 Hz, 1H), 7.01 (s, 1H), 7.54 (d, J=7.2 Hz, 1H), 8.12 (d, J=3.8 Hz, 1H), 9.32 (s, 1H).

I-295: Methyl 3-[4-(2-(4-methoxy-3-trifluoromethyl)phenylamino)-5-fluoropyrimidine-4-ylamino)-2,2,6,6-tetramethylpiperidin-1-yl]propanoate LCMS: purity: 98.27%; MS (m/e): 528.25 (MH+); $^1$H NMR (DMSO-d6): δ 1.35 (s, 6H), 1.43 (s, 6H), 1.77 (m, 2H), 2.32 (d, J=11.8 Hz, 2H), 2.33 (t, J=12.1 Hz, 2H), 2.75 (t, J=11.5 Hz, 2H), 3.75 (s, 3H), 3.85 (s, 3H), 4.42 (m, 1H), 6.54 (m, 1H), 6.70 (m, 2H), 7.11 (m, 1H), 8.05 (d, J=4.1 Hz, 1H), 9.22 (s, 1H).

I-296: Methyl 2-[4-(2-(3-cyano-4-methylphenylamino)-5-fluoropyrimidine-4-ylamino)-2,2,6,6-tetramethylpiperidin-1-yl]propanoate LCMS: purity: 97.23%; MS (m/e): 469.57 (MH+); $^1$H NMR (DMSO-d6): δ 1.40 (s, 6H), 1.50 (s, 6H), 1.87 (m, 2H), 2.30-2.37 (m, 7H), 2.77 (t, J=11.7 Hz, 2H), 3.75 (s, 3H), 4.45 (m, 1H), 6.55 (m, 1H), 6.75 (m, 2H), 7.13 (m, 1H), 8.15 (d, J=4.2 Hz, 1H), 9.20 (s, 1H).

I-297: (E,Z)-Methyl 3-[4-(2-(3,4-dimethoxyphenylamino)-5-fluoropyrimidine-4-ylamino)-2,2,6,6-tetramethylpiperidin-1-yl]acrylate LCMS: purity: 95.54%; MS (m/e): 488.57 (MH+); $^1$H NMR (DMSO-d6): δ 1.40 (s, 6H), 1.46 (s, 6H), 1.90 (m, 2H), 2.12 (d, J=12.0 Hz, 2H), 3.72 (s, 3H), 3.82 (s, 3H), 3.85 (s, 3H), 4.50 (m, 1H), 4.85 (d, J=5.7 Hz, 1H), 6.90 (d, J=7.5 Hz, 1H), 6.99 (d, J=7.5 Hz, 1H), 7.09 (m, 1H), 7.26 (d, J=5.5 Hz, 1H), 7.53 (d, J=7.5 Hz, 1H), 8.15 (d, J=3.8 Hz, 1H), 9.43 (s, 1H).

I-298: (E,Z)-Methyl 3-[4-(2-(3,5-dimethoxyphenylamino)-5-fluoropyrimidine-4-ylamino)-2,2,6,6-tetramethylpiperidin-1-yl]acrylate LCMS: purity: 94.37%; MS (m/e): 488.57 (MH+); $^1$H NMR (DMSO-d6): δ 1.32 (s, 6H), 1.43 (s, 6H), 1.85 (m, 2H), 2.32 (d, J=11.8 Hz, 2H), 3.78 (s, 6H), 3.82 (s, 3H), 4.42 (m, 1H), 4.79 (d, J=5.2 Hz, 1H), 6.59 (d, J=7.2 Hz, 1H), 6.89 (d, J=7.5 Hz, 1H), 7.16 (m, 1H), 7.32 (d, J=5.4 Hz, 1H), 7.54 (d, J=7.5 Hz, 1H), 8.12 (d, J=3.8 Hz, 1H), 9.32 (s, 1H).

I-299: (E,Z)-Methyl 3-[4-(2-(3-chloro-4-methoxyphenylamino)-5-fluoropyrimidine-4-ylamino)-2,2,6,6-tetramethylpiperidin-1-yl]acrylate LCMS: purity: 99.20%; MS (m/e): 492.99 (MH+); $^1$H NMR (DMSO-d6): δ 1.45 (s, 6H), 1.50 (s, 6H), 1.88 (m, 2H), 2.22 (d, J=12.0 Hz, 2H), 3.75 (s, 3H), 3.85 (s, 3H), 4.45 (m, 1H), 4.88 (d, J=5.0 Hz, 1H), 6.90 (d, J=7.2 Hz, 1H), 6.99 (d, J=6.9 Hz, 1H), 7.09 (m, 1H), 7.33 (d, J=5.1 Hz, 1H), 7.53 (d, J=7.5 Hz, 1H), 8.05 (d, J=4.1 Hz, 1H), 9.21 (s, 1H).

I-300: (E,Z)-Methyl 3-[4-(2-(3,5-dichlorophenylamino)-5-fluoropyrimidine-4-ylamino)-2,2,6,6-tetramethylpiperidin-1-yl]acrylate LCMS: purity: 95.36%; MS (m/e): 497.41 (MH+); $^1$H NMR (DMSO-d6): δ 1.48 (s, 6H), 1.52 (s, 6H), 1.78 (m, 2H), 2.34 (m, 2H), 3.90 (s, 3H), 4.35 (m, 1H), 4.91 (d, J=5.3 Hz, 1H), 6.60 (d, J=7.7 Hz, 1H), 6.99 (d, J=7.5 Hz, 1H), 7.01 (s, 1H), 7.22 (d, J=5.0 Hz, 1H), 7.54 (d, J=7.2 Hz, 1H), 8.12 (d, J=3.8 Hz, 1H), 9.32 (s, 1H).

I-301: (E,Z)-Methyl 3-[4-(2-(4-methoxy-3-trifluoromethylphenylamino)-5-fluoropyrimidine-4-ylamino)-2,2,6,6-tetramethylpiperidin-1-yl]acrylate LCMS: purity: 98.34%; MS (m/e): 526.54 (MH+); $^1$H NMR (DMSO-d6): δ 1.35 (s, 6H), 1.43 (s, 6H), 1.77 (m, 2H), 2.02 (d, J=11.8 Hz, 2H), 3.67 (s, 3H), 3.89 (s, 3H), 4.42 (m, 1H), 4.79 (d, J=4.8 Hz, 1H), 6.58 (m, 1H), 6.70 (m, 2H), 7.11 (m, 1H), 7.28 (d, J=5.0 Hz, 1H), 8.15 (d, J=4.1 Hz, 1H), 9.42 (s, 1H).

I-302: 3-[4-(2-(3,5-Dimethoxyphenylamino)-5-fluoropyrimidine-4-ylamino)-2,2,6,6-tetramethylpiperidin-1-yl]propanoicacid LCMS: purity: 95.86%; MS (m/e): 476.56 (MH+); $^1$H NMR (DMSO-d6): δ 1.32 (s, 6H), 1.47 (s, 6H), 1.86 (m, 2H), 2.31 (d, J=11.8 Hz, 2H), 2.45 (t, J=11.7 Hz, 2H), 2.75 (t, J=12.0 Hz, 2H), 3.73 (s, 6H), 4.45 (m, 1H), 6.56 (d, J=7.2 Hz, 1H), 6.85 (d, J=7.5 Hz, 1H), 7.06 (m, 1H), 7.55 (d, J=7.5 Hz, 1H), 8.10 (d, J=3.8 Hz, 1H), 9.12 (s, 1H).

I-303: 3-[4-(2-(3-Chloro-4-methoxyphenylamino)-5-fluoropyrimidine-4-ylamino)-2,2,6,6-tetramethylpiperidin-1-yl]propanoicacid LCMS: purity: 98.56%; MS (m/e): 480.98 (MH+); $^1$H NMR (DMSO-d6): δ 1.45 (s, 6H), 1.50 (s, 6H), 1.85 (m, 2H), 2.22 (d, J=12.0 Hz, 2H), 2.43 (t, J=12.0 Hz, 2H), 2.80 (t, J=11.5 Hz, 2H), 3.75 (s, 3H), 4.42 (m, 1H), 6.90 (d, J=7.2 Hz, 1H), 6.99 (d, J=6.9 Hz, 1H), 7.09 (m, 1H), 7.53 (d, J=7.2 Hz, 1H), 8.05 (d, J=4.1 Hz, 1H), 9.21 (s, 1H).

I-304: 3-[4-(2-(3,5-Dichlorophenylamino)-5-fluoropyrimidine-4-ylamino)-2,2,6,6-tetramethylpiperidin-1-yl]propanoicacid LCMS: purity: 97.31%; MS (m/e): 485.39 (MH+); $^1$H NMR (DMSO-d6): δ 1.48 (s, 6H), 1.52 (s, 6H), 1.77 (m, 2H), 2.31 (m, 2H), 2.46 (m, 2H), 2.77 (t, J=11.8 Hz, 2H), 4.35 (m, 1H), 6.60 (d, J=7.7 Hz, 1H), 6.99 (d, J=7.5 Hz, 1H), 7.01 (s, 1H), 7.54 (d, J=7.2 Hz, 1H), 8.12 (d, J=3.8 Hz, 1H), 9.32 (s, 1H).

I-305: 3-[4-(2-(4-Methoxy-3-trifluoromethyl)phenylamino)-5-fluoropyrimidine-4-ylamino)-2,2,6,6-tetramethylpiperidin-1-yl]propanoicacid LCMS: purity: 98.22%; MS (m/e): 514.24 (MH+); $^1$H NMR (DMSO-d6): δ 1.35 (s, 6H), 1.43 (s, 6H), 1.77 (m, 2H), 2.32 (d, J=11.8 Hz, 2H), 2.33 (t, J=12.1 Hz, 2H), 2.75 (t, J=11.5 Hz, 2H), 3.75 (s, 3H), 4.42 (m, 1H), 6.54 (m, 1H), 6.70 (m, 2H), 7.11 (m, 1H), 8.05 (d, J=4.1 Hz, 1H), 9.22 (s, 1H).

I-306: 3-[4-(2-(3-Cyano-4-methylphenylamino)-5-fluoropyrimidine-4-ylamino)-2,2,6,6-tetramethylpiperidin-1-yl]propanoicacid LCMS: purity: 96.27%; MS (m/e): 455.54 (MH+); $^1$H NMR (DMSO-d$_6$): δ 1.40 (s, 6H), 1.50 (s, 6H), 1.87 (m, 2H), 2.30-2.37 (m, 7H), 2.77 (t, J=11.7 Hz, 2H), 4.45 (m, 1H), 6.55 (m, 1H), 6.75 (m, 2H), 7.13 (m, 1H), 8.15 (d, J=4.2 Hz, 1H), 9.20 (s, 1H).

I-307: N2-(3,5-dimethoxyphenyl)-5-fluoro-N4-(1,2,2,6,6-pentamethylpiperidin-4-yl)pyrimidine-2,4-diamine MS (m/e) 418.56 (MH+); $^1$H NMR (DMSO-d6): δ 8.95 (s, 1H), 7.89 (s, 1H), 7.49 (bs, 1H), 6.95 (s, 2H), 6.09 (s, 1H), 4.53 (bm, 2H), 3.69 (s, 6H), 2.76 (s, 3H), 2.02-1.91 (d, 2H), 1.82-1.65 (t, 2H), 1.42-1.29 (d, 12H).

I-308: N4-benzyl-N2-(3,5-dimethoxyphenyl)-5-fluoro-N4-(1,2,2,6,6-pentamethylpiperidin-4-yl)pyrimidine-2,4-diamine MS (m/e) 508.27 (MH+); $^1$H NMR (CDCl$_3$): δ 8.09 (s, 1H), 7.65 (d, 1H), 7.35 (m, 5H), 6.61 (s, 2H), 6.35 (s, 1H), 5.39 (bm, 1H), 5.05 (s, 2H), 3.75 (s, 6H), 2.65 (s, 3H), 1.61 (t, 10H), 1.21 (s, 6H).

I-309: N4-benzyl-N2-(3-(difluoromethoxy)-4-methoxyphenyl)-5-fluoro-N4-(1,2,2,6,6-pentamethylpiperidin-4-yl)pyrimidine-2,4-diamine MS (m/e) 544.27 (MH+); $^1$H NMR (CDCl$_3$): δ 8.15 (d, 1H), 7.82 (d, 1H), 7.51 (s, 1H), 7.39 (m, 6H), 6.83 (m, 2H), 4.85 (s, 2H), 4.59 (bm, 1H), 3.89 (s, 3H), 2.69 (s, 3H), 1.65 (m, 10H), 1.29 (s, 6H).

I-310: N4-benzyl-5-fluoro-N2-(4-(4-(methylsulfonyl)piperazin-1-yl)-3-(trifluoromethyl)phenyl)-N4-(1,2,2,6,6-pentamethylpiperidin-4-yl)pyrimidine-2,4-diamine MS (m/e) 678.32 (MH+); $^1$H NMR (CDCl$_3$): δ 8.05 (s, 1H), 7.85 (d, 1H), 7.29 (m, 8H), 4.86 (s, 2H), 4.19 (bm, 1H), 3.35 (t, 4H), 2.97 (t, 4H), 2.79 (s, 3H), 2.69 (s, 3H), 1.65 (m, 10H), 1.24 (s, 6H).

I-311: N4-benzyl-5-fluoro-N2-(4-(4-methylpiperazin-1-yl)-3-(trifluoromethyl)phenyl)-N4-(1,2,2,6,6-pentamethylpiperidin-4-yl)pyrimidine-2,4-diamine MS (m/e) 614.32 (MH+); $^1$H NMR (CDCl$_3$): δ 8.39 (s, 1H), 7.87 (m, 2H), 7.39 (m, 7H), 4.78 (s, 2H), 4.19 (bm, 1H), 3.59-2.99 (m, 8H), 2.82 (s, 3H), 2.75 (s, 3H), 1.69 (d, 2H), 1.44 (s, 8H), 1.29 (s, 6H).

I-312: N4-benzyl-5-fluoro-N2-(4-morpholino-3-(trifluoromethyl)phenyl)-N4-(1,2,2,6,6-pentamethylpiperidin-4-yl)pyrimidine-2,4-diamine MS (m/e) 601.28 (MH+); $^1$H NMR (CDCl$_3$): δ 8.45 (s, 1H), 7.89 (d, 1H), 7.65 (d, 1H), 7.39 (m, 6H), 4.75 (s, 2H), 4.29 (bm, 1H), 3.82 (t, 4H), 2.89 (t, 4H), 2.75 (s, 3H), 1.69 (d, 2H), 1.41 (s, 8H), 1.22 (s, 6H).

I-313: 5-(4-(benzyl(1,2,2,6,6-pentamethylpiperidin-4-yl)amino)-5-fluoropyrimidin-2-ylamino)-2-methylbenzonitrile MS (m/e) 487.24 (MH+); $^1$H NMR (CDCl$_3$): δ 8.09 (s, 1H), 7.89 (d, 1H), 7.61 (s, 1H), 7.43 (m, 6H), 7.11 (d, 1H), 4.89 (s, 2H), 4.21 (bm, 1H), 2.69 (s, 3H), 2.45 (s, 3H), 1.59 (m, 10H), 1.28 (s, 6H).

I-314: N2-(3,5-dimethoxyphenyl)-5-fluoro-N4-(naphthalen-2-ylmethyl)-N4-(1,2,2,6,6-pentamethylpiperidin-4-yl)pyrimidine-2,4-diamine MS (m/e) 558.30 (MH+); $^1$H NMR (CDCl$_3$): δ 8.41 (s, 1H), 7.84 (m, 4H), 7.74 (s, 1H), 7.49 (m, 3H), 6.75 (s, 2H), 6.11 (s, 1H), 5.19 (s, 2H), 4.85 (bm, 1H), 3.76 (s, 6H), 2.62 (s, 3H), 1.59 (d, 2H), 1.48 (s, 8H), 1.29 (s, 6H).

I-315: 5-(5-fluoro-4-((naphthalen-2-ylmethyl)(1,2,2,6,6-pentamethylpiperidin-4-yl)amino)pyrimidin-2-ylamino)-2-methylbenzonitrile MS (m/e) 537.28 (MH+); $^1$H NMR (CDCl$_3$): δ 8.45 (s, 1H), 8.09 (s, 1H), 7.92 (d, 1H), 7.85 (m, 3H), 7.71 (s, 1H), 7.49 (m, 4H), 7.09 (d, 1H), 5.09 (s, 2H), 4.29 (bm, 1H), 2.69 (s, 3H), 2.43 (s, 3H), 1.69 (d, 2H), 1.41 (s, 8H), 1.29 (s, 6H).

I-316: N2-(3-(difluoromethoxy)-4-methoxyphenyl)-5-fluoro-N4-(naphthalen-2-ylmethyl)-N4-(1,2,2,6,6-pentamethylpiperidin-4-yl)pyrimidine-2,4-diamine MS (m/e) 594.28 (MH+); $^1$H NMR (CDCl$_3$): δ 8.19 (s, 1H), 7.81 (m, 4H), 7.75 (s, 1H), 7.55 (m, 4H), 6.71 (d, 1H), 6.51 (s, 1H), 5.05 (s, 2H), 4.69 (bm, 1H), 3.81 (s, 3H), 2.69 (s, 3H), 1.69 (d, 2H), 1.45 (s, 8H), 1.29 (s, 6H).

I-317: N4-(biphenyl-4-ylmethyl)-N2-(3,5-dimethoxyphenyl)-5-fluoro-N4-(1,2,2,6,6-pentamethylpiperidin-4-yl)pyrimidine-2,4-diamine MS (m/e) 584.32 (MH+); $^1$H NMR (CDCl$_3$): δ 8.01 (s, 1H), 7.74 (d, 1H), 7.59 (m, 5H), 7.49 (d, 2H), 7.39 (d, 2H), 6.75 (s, 2H), 6.21 (s, 1H), 5.19 (s, 2H), 4.95 (bm, 1H), 3.76 (s, 6H), 2.68 (s, 3H), 1.59 (d, 2H), 1.48 (s, 8H), 1.29 (s, 6H).

I-318: 5-(4-((biphenyl-4-ylmethyl)(1,2,2,6,6-pentamethylpiperidin-4-yl)amino)-5-fluoropyrimidin-2-ylamino)-2-methylbenzonitrile MS (m/e) 563.32 (MH+); $^1$H NMR (CDCl$_3$): δ 8.01 (s, 1H), 7.91 (d, 1H), 7.61 (m, 5H), 7.43 (t, 2H), 7.39 (m, 4H), 7.15 (d, 1H), 4.89 (bs, 3H), 2.69 (s, 3H), 2.45 (s, 3H), 1.69 (d, 2H), 1.58 (s, 8H), 1.25 (s, 6H).

I-319: N4-(biphenyl-4-ylmethyl)-N2-(3-(difluoromethoxy)-4-methoxyphenyl)-5-fluoro-N4-(1,2,2,6,6-pentamethylpiperidin-4-yl)pyrimidine-2,4-diamine MS (m/e) 620.33 (MH+); $^1$H NMR (CDCl$_3$): δ 8.34 (s, 1H), 7.85 (d, 1H), 7.59 (m, 5H), 7.45 (m, 2H), 7.35 (m, 3H), 6.81 (d, 1H), 6.51 (s, 1H), 4.95 (s, 2H), 4.69 (bm, 1H), 3.81 (s, 3H), 2.69 (s, 3H), 1.69 (d, 2H), 1.55 (s, 8H), 1.29 (s, 6H).

I-320: 5-(5-fluoro-4-((1,2,2,6,6-pentamethylpiperidin-4-yl)(quinolin-2-ylmethyl)amino)pyrimidin-2-ylamino)-2-methylbenzonitrile MS (m/e) 538.28 (MH+)$^1$H NMR (CDCl$_3$): δ 8.21 (s, 2H), 8.15 (d, 1H), 7.95 (d, 1H), 7.85 (m, 2H), 7.71 (t, 1H), 7.55 (t, 2H), 7.49 (d, 1H), 7.09 (d, 1H), 5.09 (s, 2H), 4.69 (bm, 1H), 2.65 (s, 3H), 2.43 (s, 3H), 1.89 (d, 2H), 1.49 (s, 8H), 1.39 (s, 6H).

I-321: N2-(3-(difluoromethoxy)-4-methoxyphenyl)-5-fluoro-N4-(1,2,2,6,6-pentamethylpiperidin-4-yl)-N4-(quinolin-2-ylmethyl)pyrimidine-2,4-diamine MS (m/e) 595.31 (MH+); $^1$H NMR (CDCl$_3$): δ 8.24 (s, 1H), 8.15 (d, 1H), 7.95 (d, 1H), 7.80 (d, 1H), 7.65 (m, 2H), 7.55 (t, 1H), 7.43 (m, 2H), 7.17 (d, 1H), 6.89 (d, 1H), 6.55 (s, 1H), 5.19 (s, 2H), 5.15 (bm, 1H), 3.85 (s, 3H), 2.63 (s, 3H), 1.89 (d, 2H), 1.49 (s, 8H), 1.39 (s, 6H).

I-322: N2-(3,5-dimethoxyphenyl)-5-fluoro-N4-(1,2,2,6,6-pentamethylpiperidin-4-yl)-N4-(quinolin-2-ylmethyl)pyrimidine-2,4-diamine MS (m/e) 559.31 (MH+); $^1$H NMR (CDCl$_3$): δ 8.29 (s, 1H), 8.16 (d, 1H), 7.98 (d, 1H), 7.83 (d, 1H), 7.63 (m, 2H), 7.55 (t, 1H), 7.43 (d, 1H), 6.43 (s, 2H), 6.15 (s, 1H), 5.29 (bm, 1H), 5.21 (s, 2H), 3.79 (s, 3H), 2.63 (s, 3H), 1.89 (d, 2H), 1.49 (s, 8H), 1.39 (s, 6H).

I-323: N4-((6-bromobenzo[d][1,3]dioxol-5-yl)methyl)-N2-(3,5-dimethoxyphenyl)-5-fluoro-N4-(1,2,2,6,6-pentamethylpiperidin-4-yl)pyrimidine-2,4-diamine MS (m/e) 630.21 (MH+); $^1$H NMR (CDCl$_3$): δ 8.19 (d, 1H), 7.45 (d, 1H), 7.29 (s, 1H), 7.07 (s, 1H), 6.84 (s, 2H), 6.74 (s, 1H), 5.97 (s, 2H), 4.74 (bm, 1H), 3.72 (s, 6H), 2.65 (s, 3H), 1.69 (d, 2H), 1.47 (s, 8H), 1.29 (s, 6H).

I-324: 5-(4-(((6-bromobenzo[d][1,3]dioxol-5-yl)methyl)(1,2,2,6,6-pentamethylpiperidin-4-yl)amino)-5-fluoropyrimidin-2-ylamino)-2-methylbenzonitrile MS (m/e) 610.17 (MH+); $^1$H NMR (CDCl$_3$): δ 8.49 (s, 1H), 8.12 (bs, 1H), 7.91 (d, 1H), 7.65 (d, 1H), 7.13 (s, 1H), 7.03 (s, 1H), 6.79 (s, 1H), 5.98 (s, 2H), 4.77 (s, 3H), 2.65 (s, 3H), 2.43 (s, 3H), 1.89 (d, 2H), 1.49 (s, 8H), 1.39 (s, 6H).

I-325: 4'-(((2-(3,5-dimethoxyphenylamino)-5-fluoro-pyrimidin-4-yl)(1,2,2,6,6-pentamethylpiperidin-4-yl) amino)methyl)biphenyl-2-carbonitrile MS (m/e) 609.35 (MH+); $^1$H NMR (CDCl$_3$): δ 8.41 (s, 1H), 7.91 (d, 1H), 7.72 (d, 1H), 7.63 (t, 1H), 7.51 (d, 2H), 7.43 (d, 2H), 6.84 (s, 2H), 6.13 (s, 1H), 4.97 (s, 2H), 4.63 (bm, 1H), 3.76 (s, 6H), 2.62 (s, 3H), 1.62 (d, 2H), 1.48 (s, 8H), 1.32 (s, 6H).

I-326: 4'-(((2-(3-cyano-4-methylphenylamino)-5-fluoropyrimidin-4-yl)(1,2,2,6,6-pentamethylpiperi-din-4-yl)amino)methyl)biphenyl-2-carbonitrile MS (m/e) 588.32 (MH+); $^1$H NMR (CDCl$_3$): δ 8.35 (s, 1H), 8.01 (bs, 1H), 7.91 (d, 1H), 7.75 (d, 1H), 7.65 (t, 1H), 7.55 (d, 3H), 7.43 (d, 4H), 7.15 (d, 1H), 4.89 (s, 2H), 4.25 (bm, 1H), 2.69 (s, 3H), 2.45 (s, 3H), 1.69 (d, 2H), 1.58 (s, 8H), 1.25 (s, 6H).

I-327: 5-Fluoro-N2-(3-hydroxyl)phenyl-N4-(1,2,2,6,6-pentamethylpiperidin-4-yl)-2,4-pyrimidinediamine LCMS: purity: 99.26%; MS (m/e): 374.48 (MH+); $^1$H NMR (DMSO-d6): δ 1.40 (s, 6H), 1.42 (s, 6H), 1.82 (t, J=12.9 Hz, 2H), 2.07 (d, J=11.4 Hz, 2H), 2.73 (s, 3H), 4.51 (br, 1H), 6.30 (d, J=8.4 Hz, 1H), 6.93 (t, J=7.8 Hz, 1H), 7.08 (m, 2H), 7.63 (d, J=7.5 Hz, 1H), 7.90 (d, J=3.9 Hz, 1H), 8.71 (br, 1H), 9.03 (s, 1H), 9.17 (br, 1H); $^{19}$F NMR (282 MHz, DMSO-d6): δ−166.27.

I-328: 5-Fluoro-N2-[4-(furan-3-yl)-3-trifluorom-ethyl]phenyl-N4-(1,2,2,6,6-pentamethylpiperidin-4-yl)-2,4-pyrimidinediamine LCMS: purity: 94.65%; MS (m/e): 492.41 (MH+); $^1$H NMR (DMSO-d6): δ 1.06 (s, 6H), 1.07 (s, 6H), 1.46 (t, J=12.0 Hz, 2H), 1.70 (d, J=11.4 Hz, 2H), 2.17 (s, 3H), 4.36 (br, 1H), 6.56 (s, 1H), 7.25 (d, J=8.7 Hz, 2H), 7.70 (s, 2H), 7.89 (d, J=3.9 Hz, 1H), 7.95 (s, 1H), 8.20 (d, J=8.4 Hz, 1H), 9.36 (s, 1H); 19F NMR (282 MHz, DMSO-d6): δ−165.25, −57.97.

I-329: 5-Fluoro-N4-(1,2,2,6,6-pentamethylpiperidin-4-yl)-N2-(1,1,2,2-tetrafluoro-ethoxyphen-3-yl)-2,4-pyrimidinediamine MS (m/e) 472.12 (MH+); $^1$H NMR (DMSO-d6): δ 9.23 (s, 1H), 7.88-7.87 (d, J=3.9 Hz, 1H), 7.82-7.79 (d, J=7.5 Hz, 1H), 7.49 (s, 1H), 7.32-7.30 (d, J=7.8 Hz, 1H), 7.24-7.18 (t, J=8.1 Hz, 1H), 6.9-6.56 (t, J=48.3, 3H), 4.39 (m, 1H), 2.42 (s, 3H), 1.79-1.75 (d, J=10.5 Hz, 2H), 1.57-1.49 (t, J=12.3 Hz, 2H), 1.14 (s, 12H).

I-330: N2-(4-Morpholino-3-trifluoromethyl)phenyl-N4-(1,2,2,6,6-pentamethylpiperidin-4-yl)-5-trifluo-romethyl-2,4-pyrimidinediamine MS (m/e) 561.17 (MH+); $^1$H NMR (DMSO-d6): δ 9.73 (bs, 1H), 8.47 (s, 1H), 8.01-7.98 (d, J=9.0 Hz, 1H), 7.67 (bs, 1H), 7.47-7.44 (d, J=8.7 Hz, 1H), 6.97-6.95 (d, J=7.5 Hz, 1H), 4.65 (bs, 1H), 3.68 (bs, 4H), 2.79 (bs, 4H), 2.74-2.72 (m, J=4.8 Hz, 3H), 1.99-1.85 (m, 4H), 1.38-1.31 (m, 12H).

I-331: 5-Fluoro-N4-(1,2,2,6,6-pentamethylpiperidin-4-yl)-N2-(4-thiomorpholino-3-trifluoromethyl)phe-nyl-2,4-pyrimidinediamine MS (m/e) 527.13 (MH+); $^1$H NMR (DMSO-d6): δ☐ 0.14 (s, 1H), 8.07-8.05 (d, J=8.7 Hz, 1H), 7.86-7.85 (d, J=3.9 Hz, 1H), 7.78 (s, 1H), 7.33-7.30 (d, J=9.0 Hz, 1H), 7.25-7.22 (d, J=8.1 Hz, 1H), 4.37 (bs, 1H), 2.99 (bs, 4H), 2.69 (bs, 4H), 2.24 (s, 3H), 1.74-1.71 (d, J=9.6 Hz, 2H), 1.53-1.44 (t, J=12.0 Hz, 2H), 1.11-1.08 (m, 12H).

I-332: N2-(3-Chloro-4-methyl)phenyl-5-fluoro-N4-(1,2,2,6,6-pentamethylpiperidin-4-yl)-2,4-pyrim-idinediamine MS (m/e) 406.14 (MH+); $^1$H NMR (DMSO-d6): δ 9.00 (s, 1H), 7.86-7.84 (d, J=3.9 Hz, 1H), 7.73 (s, 1H), 7.60-7.58 (d, J=8.1 Hz, 1H), 7.26-7.24 (d, J=8.4 Hz, 1H), 7.10-7.07 (d, J=8.1 Hz, 1H), 4.39 (bs, 1H), 2.26 (s, 3H), 2.21 (s, 3H), 1.75-1.72 (d, J=10.2 Hz, 2H), 1.55-1.47 (t, J=12.3 Hz, 2H), 1.13 (s, 12H);

I-333: N2-(3-Chloro-4-fluoro)phenyl-5-fluoro-N4-(1,2,2,6,6-pentamethylpiperidin-4-yl)-2,4-pyrim-idinediamine MS (m/e) 410.11 (MH+); $^1$H NMR (DMSO-d6): δ 9.18 (s, 1H), 7.90-7.85 (m, 2H), 7.63-7.59 (m, 1H), 7.28-7.25 (d, J=8.7 Hz, 1H), 7.20-7.14 (t, J=9.3 Hz, 1H), 4.35 (bs, 1H), 2.22 (s, 3H), 1.73-1.69 (d, J=9.3 Hz, 2H), 1.53-1.45 (t, J=12.0 Hz, 2H), 1.10 (s, 12H).

I-334: N2-(3-Chloro-4-trifluoromethoxy)phenyl-5-fluoro-N4-(1,2,2,6,6-pentamethylpiperidin-4-yl)-2,4-pyrimidinediamine MS (m/e) 476.08 (MH+); $^1$H NMR (DMSO-d6): δ 9.37 (s, 1H), 7.95 (s, 1H), 7.90-7.89 (d, J=3.3 Hz, 1H), 7.72-7.69 (d, J=9.0 Hz, 1H), 7.35-7.29 (t, J=8.1 Hz, 2H), 4.35 (bs, 1H), 2.25 (s, 3H), 1.75-1.72 (d, J=9.9 Hz, 2H), 1.55-1.46 (t, J=12.3 Hz, 2H), 1.11 (s, 12H).

I-335: N2-(3-Chloro-4-morpholino)phenyl-5-fluoro-N4-(1,2,2,6,6-pentamethylpiperidin-4-yl)-2,4-pyrim-idinediamine MS (m/e) 477.16 (MH+); $^1$H NMR (DMSO-d6): δ 9.01 (s, 1H), 7.84-7.83 (d, J=3.6 Hz, 1H), 7.75 (s, 1H), 7.59-7.56 (d, J=8.7 Hz, 1H), 7.24-7.22 (d, J=8.1 Hz, 1H), 6.98-6.96 (d, J=8.7 Hz, 1H), 4.34 (bs, 1H), 3.72 (s, 4H), 2.85 (s, 4H), 2.28 (s, 3H), 1.77-1.73 (d, J=10.5 Hz, 2H), 1.56-1.47 (t, J=12.3 Hz, 2H), 1.13 (s, 12H).

I-336: N2-(3,4-Dichloro)phenyl-5-fluoro-N4-(1,2,2,6,6-pentamethylpiperidin-4-yl)-2,4-pyrimidinedi-amine MS (m/e) 426.33 (MH+); $^1$H NMR (DMSO-d6): δ 8.65 (s, 1H), 7.97 (s, 1H), 7.21 (s, 1H), 7.59-7.56 (m, 1H), 7.54-7.50 (m, 1H), 7.26-7.20 (t, J=10.2, 1H), 4.41 (bs, 1H), 2.12-2.10 (d, J=13.2 Hz, 2H), 1.86-1.77 (t, J=11.7 Hz, 2H), 1.36 (m, 6H), 1.02 (s, 6H).

I-337: N2-(3-Chloro-4-trifluoromethyl)phenyl-5-fluoro-N4-(1,2,2,6,6-pentamethylpiperidin-4-yl)-2,4-pyrimidinediamine MS (m/e) 460.09 (MH+); $^1$H NMR (DMSO-d6): δ 9.66-9.64 (d, J=4.5 Hz, 1H), 7.99 (bs, 2H), 7.79 (bs, 1H), 7.59-7.62 (m, 2H), 4.43 (bs, 1H), 1.96 (bs, 2H), 1.82 (bs, 2H), 1.34 (bs, 12H).

I-338: N2-[3-Chloro-4-(pyrimin-2-yl)oxy]phenyl-5-fluoro-N4-(1,2,2,6,6-pentamethylpiperidin-4-yl)-2,4-pyrimidinediamine MS (m/e) 486.09 (MH+); $^1$H NMR (DMSO-d6): δ 9.19 (s, 1H), 8.61 (s, 1H), 8.59 (s, 1H), 7.88 (s, 1H), 7.87 (s, 1H), 7.72-7.69 (d, J=8.7 Hz, 1H), 7.26-7.24 (m, 2H), 7.15-7.12 (d, J=9.0 Hz, 1H), 4.39 (bs, 1H), 2.24 (s, 3H), 1.76-1.72 (d, J=12.0 Hz, 2H), 1.56-1.47 (t, J=12.3 Hz, 2H), 1.11 (s, 12H).

I-339: N2-[3-Chloro-4-(2-furoylamino)]phenyl-5-fluoro-N4-(1,2,2,6,6-pentamethylpiperidin-4-yl)-2,4-pyrimidinediamine MS (m/e) 501.11 (MH+); $^1$H NMR (DMSO-d6): δ 9.66 (s, 1H), 9.24 (s, 1H), 7.92 (s, 2H), 7.85 (s, 1H), 7.74 (s, 1H), 7.35 (s, 2H), 7.27 (s, 1H), 6.69 (s, 1H), 4.43 (bs, 1H), 2.41 (s, 3H), 1.84 (bs, 2H), 1.62 (bs, 2H), 1.22 (s, 12H).

I-340: 5-Chloro-N2-(3,5-dimethoxy)phenyl-N4-(1,2,2,6,6-pentamethylpiperidin-4-yl)-2,4-pyrimidinediamine MS (m/e) 434.16 (MH+); $^1$H NMR (DMSO-d6): δ 9.03 (s, 1H), 7.91 (s, 1H), 6.92 (s, 2H), 6.85-6.83 (d, J=7.5 Hz, 1H), 6.09 (s, 1H), 4.55 (bs, 1H), 3.66 (s, 6H), 2.42 (s, 3H), 1.80-1.64 (m, 4H), 1.21 (s, 12H).

I-341: 5-Chloro-N2-(3-difluoromethoxy-4-methoxy)phenyl-N4-(1,2,2,6,6-pentamethylpiperidin-4-yl)-2,4-pyrimidinediamine MS (m/e) 470.13 (MH+); $^1$H NMR (DMSO-d6): δ 9.06 (s, 1H), 8.13 (s, 1H), 7.89 (s, 1H), 7.57 (s, 1H), 7.54 (s, 1H), 7.19-6.71 (t, J=69.3 Hz, 1H), 6.95 (s, 1H), 6.69 (s, 1H), 4.44 (bs, 1H), 3.75 (s, 3H), 2.29 (s, 3H), 1.74-1.69 (d, J=12.3 Hz, 2H), 1.64-1.56 (t, J=12.3 Hz, 2H), 1.14 (s, 12H).

I-342: 5-Fluoro-N2-[3-methoxy-5-(1H-1,2,3,4-tetrazol-1-yl)]phenyl-N4-(1,2,2,6,6-pentamethylpiperidin-4-yl)-2,4-pyrimidinediamine MS (m/e) 456.19 (MH+); $^1$H NMR (DMSO-d6): δ 0.02 (s, 1H), 9.29 (s, 1H), 8.13 (s, 1H), 7.90-7.89 (d, J=3.9 Hz, 1H), 7.80 (s, 1H), 7.52 (s, 1H), 7.28-7.26 (d, J=7.8 Hz, 1H), 6.97 (s, 1H), 4.33 (bs, 1H), 3.79 (s, 3H), 2.21 (s, 3H), 1.73-1.69 (d, J=11.7 Hz, 2H), 1.52-1.43 (d, J=12.3 Hz, 2H), 1.08 (s, 6H), 0.96 (s, 6H).

I-343: 5-Fluoro-N2-(4-methoxy-3-trifluoromethoxy)phenyl-N4-(1,2,2,6,6-pentamethylpiperidin-4-yl)-2,4-pyrimidinediamine MS (m/e) 472.16 (MH+); $^1$H NMR (DMSO-d6): δ 8.98 (s, 1H), 7.85-7.83 (d, J=3.6 Hz, 1H), 7.68 (s, 1H), 7.62-7.59 (d, J=9.0 Hz, 1H), 7.26-7.24 (d, J=7.2 Hz, 1H), 7.05-7.02 (d, J=9.0 Hz, 1H), 4.38 (bs, 1H), 3.77 (s, 3H), 2.33 (s, 3H), 1.80-1.76 (d, J=11.7 Hz, 2H), 1.59-1.51 (t, J=11.1 Hz, 2H), 1.16 (s, 121-1).

I-344: N2-(3,4-Bis-difluoromethoxy)phenyl-5-fluoro-N4-(1,2,2,6,6-pentamethylpiperidin-4-yl)-2,4-pyrimidinediamine MS (m/e) 490.12 (MH+); $^1$H NMR (DMSO-d6): δ 9.21 (s, 1H), 7.88-7.87 (d, J=3.9 Hz, 1H), 7.73-7.70 (d, J=8.7 Hz, 1H), 7.33 (s, 1H), 7.29-6.81 (t, J=73.5 Hz, 1H), 7.25-6.76 (t, J=76.2 Hz, 1H), 7.12-7.09 (d, J=8.7 Hz, 1H), 4.37 (bs, 1H), 2.31 (s, 3H), 1.79-1.75 (d, J=12.0 Hz, 2H), 1.58-1.50 (t, J=12.3 Hz, 2H), 1.15 (s, 12H).

I-345: 5-Fluoro-N2-(2-methoxypyrid-5-yl)-N4-(1,2,2,6,6-pentamethylpiperidin-4-yl)-2,4-pyrimidinediamine MS (m/e) 389.0 (MH+); $^1$H NMR (DMSO-d6): δ 8.92 (s, 1H), 8.40 (s, 1H), 7.85 (s, 2H), 7.46 (bs, 1H), 6.67-6.64 (d, J=8.7 Hz, 1H), 4.39 (bs, 1H), 3.78 (s, 3H), 2.61 (s, 3H), 1.96 (bs, 2H), 1.74 (bs, 2H), 1.33 (s, 12H).

I-346: N2-(3-Chloro-4-isopropoxy)phenyl-5-fluoro-N4-(1,2,2,6,6-pentamethylpiperidin-4-yl)-2,4-pyrimidinediamine MS (m/e) 450.15 (MH+); $^1$H NMR (DMSO-d6): δ 8.95 (s, 1H), 8.14 (s, 1H), 7.84-7.82 (d, J=3.9 Hz, 1H), 7.71 (s, 1H), 7.55-7.52 (d, J=8.7 Hz, 1H), 7.23-7.20 (d, J=7.8 Hz, 1H), 6.96-6.93 (d, J=9.0 Hz, 1H), 4.48-4.34 (m, 2H), 2.27 (s, 3H), 1.75-1.71 (d, J=12.6 Hz, 2H), 1.55-1.47 (t, J=12.0 Hz, 2H), 1.25 (s, 6H), 1.11 (s, 12H).

I-347: 5-Fluoro-N4-(1,2,2,6,6-pentamethylpiperidin-4-yl)-N2-(3,4,5-trifluoro)phenyl-2,4-pyrimidinediamine MS (m/e) 412.15 (MH+); $^1$H NMR (DMSO-d6): δ 9.43 (s, 1H), 7.92 (s, 1H), 7.62-7.56 (m, 2H), 7.47-7.45 (d, J=6.9 Hz, 1H), 4.37 (s, 1H), 2.35 (s, 3H), 1.82-1.78 (d, J=12 Hz, 2H), 1.62-1.54 (t, J=12.6 Hz, 2H), 1.17 (s, 121-1).

I-348: N2-[3-(2,5-Dimethyl-pyrrol-1-yl)-4-methoxy]phenyl-5-fluoro-N4-(1,2,2,6,6-pentamethylpiperidin-4-yl)-2,4-pyrimidinediamine MS (m/e) 481.28 (MH+); $^1$H NMR (DMSO-d6): δ 8.90 (s, 1H), 7.87 (s, 1H), 7.83-7.82 (d, J=3.6 Hz, 1H), 7.34-7.33 (d, J=2.4 Hz, 1H), 7.22-7.20 (d, J=8.1 Hz, 1H), 7.0-6.96 (d, J=9.0 Hz, 1H), 4.37 (s, 1H), 3.62 (s, 3H), 2.29 (s, 3H), 1.86 (s, 6H), 1.78-1.74 (d, J=11.7 Hz, 2H), 1.58-1.50 (t, J=12.0 Hz, 2H), 1.15 (s, 6H), 1.1 (s, 6H).

I-349: 5-Fluoro-N2-[3-methoxy-4-(pyrrol-1-yl)]phenyl-N4-(1,2,2,6,6-pentamethylpiperidin-4-yl)-2,4-pyrimidinediamine MS (m/e) 453.20 (MH+); $^1$H NMR (DMSO-d6): δ 9.06 (s, 1H), 7.88-7.87 (d, J=3.6 Hz, 1H), 7.70-7.67 (d, J=8.4 Hz, 1H), 7.34-7.31 (d, J=7.5 Hz, 1H), 7.23 (s, 1H), 7.04-7.01 (d, J=9.0 Hz, 1H), 6.88 (s, 2H), 6.12 (s, 2H), 4.42 (s, 1H), 3.71 (s, 3H), 2.37 (s, 3H), 1.85-1.82 (d, J=11.1 Hz, 2H), 1.63-1.54 (t, J=12.6 Hz, 2H), 1.19 (s, 12H).

I-350: N2-(3-Difluoromethoxy-4-methoxy)phenyl-N4-(1,2,2,6,6-pentamethylpiperidin-4-yl)-5-trifluoromethyl-2,4-pyrimidinediamine MS (m/e) 504.16 (MH+); $^1$H NMR (DMSO-d6): δ 9.5 (s, 1H), 8.18 (s, 1H), 7.42 (bs, 2H), 7.23-6.85 (t, J=74.7 Hz, 1H), 7.03 (s, 1H), 4.65 (s, 1H), 3.77 (s, 3H), 2.69 (bs, 2H), 1.90 (bs, 2H), 1.34 (s, 12H).

I-351: 5-Chloro-N2-[3-chloro-4-(2-furoylamino)]phenyl-N4-(1,2,2,6,6-pentamethylpiperidin-4-yl)-2,4-pyrimidinediamine MS (m/e) 517.16 (MH+); $^1$H NMR (DMSO-d6): δ 9.69 (s, 1H), 9.38 (s, 1H), 7.95 (s, 1H), 7.90 (s, 1H), 7.81 (s, 2H), 7.37-7.34 (d, J=9.0 Hz, 1H), 7.26 (s, 1H), 6.77-6.75 (d, J=8.4 Hz, 1H), 6.68 (s, 1H), 4.47 (s, 1H), 2.23 (s, 3H), 1.72-1.68 (d, J=11.7 Hz, 2H), 1.63-1.55 (t, J=12 Hz, 2H), 1.12 (s, 12H).

I-352: 5-Chloro-N2-[4-(2-furoylamino)-3-methoxy]phenyl-N4-(1,2,2,6,6-pentamethylpiperidin-4-yl)-2,4-pyrimidinediamine MS (m/e) 513.20 (MH+); $^1$H NMR (DMSO-d6): δ9.11 (s, 1H), 8.99 (s, 1H), 7.91 (s, 1H), 7.88 (s, 1H), 7.74-7.63 (m, 2H), 7.24-7.23 (d, J=3.0 Hz, 1H), 7.10 (s, 1H), 6.7 (s, 1H), 6.67 (s, 1H), 4.48 (s, 1H), 3.79 (s, 3H), 2.24 (s, 3H), 1.73-1.69 (d, J=11.7 Hz, 2H), 1.63-1.55 (t, J=12.3 Hz, 2H), 1.11 (s, 12H).

I-353: N2-[3-methoxy-4-(2-furoylamino)]phenyl-N4-(1,2,2,6,6-pentamethylpiperidin-4-yl)-5-fluoro-2,4-pyrimidinediamine MS (m/e) 497.21 (MH+); $^1$H NMR (DMSO-d6): δ 8.99 (s, 1H), 8.97 (s, 1H), 7.88 (s, 2H), 7.62 (s, 2H), 7.40-7.38 (d, J=6.9 Hz, 1H), 7.23-7.22 (d, J=3.0 Hz, 1H), 7.15 (s, 1H), 6.67-6.66 (m, 1H), 4.45 (s, 1H), 3.79 (s, 3H), 2.54 (s, 3H), 1.98-1.93 (d, J=12.6 Hz, 2H), 1.73-1.65 (t, J=12 Hz, 2H), 1.30 (s, 12H).

I-354: N2-(3,5-Difluoro)phenyl-5-fluoro-N4-(1,2,2,6,6-pentamethylpiperidin-4-yl)-2,4-pyrimidinediamine MS (m/e) 394.18 (MH+); $^1$H NMR (DMSO-d6): δ 9.48 (s, 1H), 7.92-7.91 (d, J=3.6 Hz, 1H), 7.43-7.41 (m, 2H), 6.64-6.58 (t, J=9 Hz, 1H), 4.43 (s, 1H), 2.36 (s, 3H), 1.83-1.79 (d, J=11.7 Hz, 2H), 1.63-1.55 (t, J=12.6 Hz, 2H), 1.18 (s, 12H).

I-355: 5-Fluoro-N2-[4-(2-furoylamino)-3-trifluoromethyl]phenyl-N4-(1,2,2,6,6-pentamethylpiperidin-4-yl)-2,4-pyrimidinediamine MS (m/e) 535 (MH+); $^1$H NMR (DMSO-d6): δ 9.73 (s, 1H), 9.36 (s, 1H), 8.26-8.22 (d, J=10.2 Hz, 1H), 7.89 (s, 2H), 7.29-7.22 (m, 3H), 6.66 (m, 1H), 4.37 (s, 1H), 2.20 (s, 3H), 1.74-1.71 (d, J=9.3 Hz, 2H), 1.53-1.45 (t, J=11.7 Hz, 2H), 1.10 (s, 12H).

I-356: N2-[3-Methoxy-5-(1,2,3,4-tetrazol-1-yl)]phenyl-N4-(1,2,2,6,6-pentamethylpiperidin-4-yl)-5-trifluoromethyl-2,4-pyrimidinediamine MS (m/e) 506.23 (MH+); $^1$H NMR (DMSO-d6): δ 10.05 (s, 1H), 9.78 (s, 1H), 8.23 (s, 1H), 7.73 (s, 1H), 7.49 (s, 1H), 7.09 (s, 1H), 6.49-6.46 (d, J=7.8 Hz, 1H), 4.50 (s, 1H), 3.81 (s, 3H), 2.19 (s, 3H), 1.65-1.53 (m, 4H), 1.07 (s, 6H), 0.89 (s, 6H).

I-357: 5-Fluoro-N4-(1,2,2,6,6-pentamethylpiperidin-4-yl)-N2-(3-tetrazol-1-yl)phenyl-2,4-pyrimidinediamine MS (m/e) 426.25 (MH+); $^1$H NMR (DMSO-d6): δ 10.02 (s, 1H), 9.39 (s, 1H), 8.14 (s, 1H), 8.11 (s, 1H), 7.91-7.88 (m, 2H), 7.44-7.30 (m, 3H), 4.32 (s, 1H), 2.32 (s, 3H), 1.83-1.79 (d, J=11.7 Hz, 2H), 1.58-1.51 (d, J=9.9 Hz, 2H), 1.34 (s, 6H), 1.16 (s, 6H), 1.03 (s, 6H).

I-358: 5-Fluoro-N2-[3-methoxy-5-(5-methyl-tetrazol-1-yl)]phenyl-N4-(1,2,2,6,6-pentamethylpiperidin-4-yl)-2,4-pyrimidinediamine MS (m/e) 470.23 (MH+); $^1$H NMR (DMSO-d6): δ 9.31 (s, 1H), 7.90-7.89 (d, J=2.7 Hz, 1H), 7.54-7.52 (d, J=7.8 Hz, 2H), 7.36-7.34 (d, J=6.9 Hz, 1H), 6.75 (s, 1H), 4.30 (s, 1H), 3.76 (s, 3H), 2.49 (s, 3H), 2.31 (s, 3H), 1.78-1.74 (d, J=11.4 Hz, 2H), 1.58-1.50 (d, J=11.7 Hz, 2H), 1.15 (s, 6H), 1.01 (s, 6H).

I-359: N2-(3-Difluoromethoxy-4-methoxy)phenyl-5-fluoro-N4-(1,2,2,6,6-pentamethylpiperidin-4-yl)-2,4-pyrimidinediamine, citrate salt MS (m/e) 454.19 (MH+); $^1$H NMR (DMSO-d6): δ 8.94 (s, 1H), 7.87-7.86 (d, J=3.9 Hz, 2H), 7.51 (s, 1H), 7.48-7.45 (m, 2H), 7.19-6.69 (t, J=62.7 Hz, 1H), 6.95 (s, 1H), 4.42 (s, 1H), 3.75 (s, 3H), 2.62 (s, 3H), 2.56-2.53 (m, 3H), 2.01-1.97 (d, J=12.6 Hz, 2H), 1.77-1.68 (d, J=13.2 Hz, 2H), 1.34 (s, 12H).

I-360: 5-Fluoro-N2-(3-isopropoxy-4-methoxy)phenyl-N4-(1,2,2,6,6-pentamethylpiperidin-4-yl)-2,4-pyrimidinediamine MS (m/e) 446.25 (MH+); $^1$H NMR (DMSO-d6): δ 8.69 (s, 1H), 7.83-7.81 (d, J=3.9 Hz, 1H), 7.37-7.34 (d, J=8.7 Hz, 1H), 7.31-7.28 (d, J=7.8 Hz, 1H), 7.07 (s, 1H), 6.74-6.71 (d, J=9 Hz, 1H), 4.44-4.36 (m, 2H), 3.66 (s, 3H), 1.92-1.88 (d, J=12 Hz, 2H), 1.68-1.60 (t, J=12 Hz, 2H), 1.23 (s, 18H).

I-361: 5-Fluoro-N2-[4-(3,5-dimethylpyrazol-1-yl)-3-methoxy]phenyl-N4-(1,2,2,6,6-pentamethylpiperidin-4-yl)-2,4-pyrimidinediamine MS (m/e) 482.26 (MH+); $^1$H NMR (DMSO-d6): δ 9.15 (s, 1H), 7.88-7.87 (d, J=3.6 Hz, 1H), 7.77-7.74 (d, J=8.4 Hz, 1H), 7.29-7.26 (d, J=7.8 Hz, 1H), 7.22 (s, 1H), 6.96-6.93 (d, J=8.7 Hz, 1H), 5.90 (s, 1H), 4.41 (s, 1H), 3.66 (s, 3H), 2.24 (s, 3H), 2.11 (s, 3H), 1.96 (s, 3H), 1.77-1.74 (d, J=11.1 Hz, 2H), 1.55-1.47 (t, J=12 Hz, 2H), 1.13 (s, 12H).

I-362: N2-{3-Chloro-4-[2-(pyridine-2-yl)-ethylaminocarbonyl]}phenyl-5-fluoro-N4-(1,2,2,6,6-pentamethylpiperidin-4-yl)-2,4-pyrimidinediamine MS (m/e) 540.23 (MH+); $^1$H NMR (DMSO-d6): δ 9.38 (s, 1H), 8.48-8.47 (d, J=4.2 Hz, 1H), 8.30-8.26 (t, J=5.7 Hz, 1H), 7.96-7.95 (d, J=3.9 Hz, 1H), 7.78 (s, 1H), 7.71-7.58 (m, 3H), 7.28-7.26 (d, J=7.5 Hz, 1H), 7.22-7.18 (m, 2H), 4.45 (s, 1H), 3.58-3.51 (q, J=6.6 Hz, 2H), 2.98-2.93 (t, J=6.9 Hz, 2H), 2.65 (bs, 3H), 2.04-2.00 (d, J=11.4 Hz, 2H), 1.80-1.71 (t, J=13.2 Hz, 2H), 1.38 (s, 12H).

I-363: N2-(3,5-Dimethoxy)phenyl-N4-(1,2,2,6,6-pentamethylpiperidin-4-yl)-5-trifluoromethyl-2,4-pyrimidinediamine MS (m/e) 468.24 (MH+); $^1$H NMR (DMSO-d6): δ 9.39 (s, 1H), 8.16 (s, 1H), 6.91 (s, 2H), 6.39-6.36 (d, J=8.4 Hz, 1H), 6.14 (s, 1H), 4.61 (s, 1H), 3.67 (s, 6H), 2.22 (s, 3H), 1.62-1.59 (m, 4H), 1.09 (s, 6H), 1.07 (s, 6H).

I-364: 5-Cyano-N2-(3,5-dimethoxy)phenyl-N4-(1,2,2,6,6-pentamethylpiperidin-4-yl)-2,4-pyrimidinediamine MS (m/e) 425.25 (MH+); $^1$H NMR (DMSO-d6): δ 9.72 (bs, 1H), 8.53 (bs, 1H), 8.33 (s, 1H), 7.80 (s, 1H), 6.88 (s, 2H), 6.20 (s, 1H), 4.62 (s, 1H), 3.69 (s, 6H), 2.71 (s, 3H), 1.93 (m, 4H), 1.36 (s, 12H).

I-365: 5-Cyano-N2-[3-methoxy-5-(5-methyl-tetrazol-1-yl)]phenyl-N4-(1,2,2,6,6-pentamethylpiperidin-4-yl)-2,4-pyrimidinediamine MS (m/e) 477.25 (MH+); $^1$H NMR (DMSO-d6): δ 9.98 (s, 1H), 8.36 (s, 1H), 7.60-7.56 (m, 2H), 7.44 (s, 1H), 6.90 (s, 1H), 4.39 (s, 1H), 3.77 (s, 3H), 2.56 (s, 3H), 2.30 (s, 3H), 1.68 (bs, 4H), 1.14 (bs, 6H), 0.96 (s, 6H).

I-366: 5-Cyano-N2-(3-difluoromethoxy-4-methoxy)phenyl-N4-(1,2,2,6,6-pentamethylpiperidin-4-yl)-2,4-pyrimidinediamine MS (m/e) 461.22 (MH+); $^1$H NMR (DMSO-d6): δ 9.80 (s, 1H), 8.54 (s, 1H), 8.33 (s, 1H), 7.78-7.75 (d, J=8.1 Hz, 1H), 7.44 (bs, 2H), 7.23-6.74 (t, J=74.4 Hz, 1H), 7.04-7.01 (d, J=9 Hz, 1H), 4.51 (s, 1H), 3.77 (s, 3H), 2.73 (s, 3H), 2.06-2.01 (d, J=15 Hz, 2H), 1.90-1.81 (t, J=13.2 Hz, 2H), 1.38-1.33 (m, 12H).

I-367: 5-Fluoro-N2-{4-[(pyridine-3-yl)methylaminocarbonyl]phenyl-N4-(1,2,2,6,6-pentamethylpiperidin-4-yl)-2,4-pyrimidinediamine MS (m/e) 492.27 (MH+); $^1$H NMR (DMSO-d6): δ 9.47 (s, 1H), 8.93 (s, 1H), 8.63 (s, 1H), 8.57-8.55 (d, J=5.1 Hz, 1H), 7.98-7.94 (m, 2H), 7.74 (bs, 4H), 7.57 (m, 1H), 4.52-4.50 (d, J=5.7 Hz, 1H), 2.76-2.75 (d, J=4.5 Hz, 3H), 2.14-2.09 (d, J=14.4 Hz, 2H), 1.87-1.78 (t, J=12.9 Hz, 2H), 1.45 (s, 6H), 1.41 (s, 6H).

I-368: N2-{3-Chloro-4-[2-(4-morpholino)ethoxy]}phenyl-5-fluoro-N4-(1,2,2,6,6-pentamethylpiperidin-4-yl)-2,4-pyrimidinediamine MS (m/e) 521.26 (MH+); $^1$H NMR (DMSO-d6): δ 8.94 (s, 1H), 7.85 (s, 1H), 7.74 (s, 1H), 7.52-7.49 (d, J=9 Hz, 1H), 7.28 (bs, 1H), 6.98-6.95 (d, J=9 Hz, 1H), 4.36 (s, 1H), 4.08-4.05 (t, J=5.7 Hz, 2H), 3.56 (bs, 4H), 2.69-2.66 (t, J=5.7 Hz, 2H), 1.79 (bs, 2H), 1.56 (bs, 2H), 1.18 (bs, 12H).

I-369: 5-Fluoro-N2-[4-methoxy-3-(1,3-oxazol-5-yl)]phenyl-N4-(1,2,2,6,6-pentamethylpiperidin-4-yl)-2,4-pyrimidinediamine MS (m/e) 455.26 (MH+); $^1$H NMR (DMSO-d6): δ 8.93 (s, 1H), 8.54 (s, 1H), 8.39 (s, 1H), 7.89-7.88 (d, J=3.6 Hz, 1H), 7.82 (s, 1H), 7.66-7.62 (d, J=8.7 Hz, 1H), 7.62-7.48 (m, 2H), 7.01-6.98 (d, J=9 Hz, 1H), 4.39 (s, 1H), 3.87 (s, 3H), 2.70 (s, 3H), 2.6-2.02 (d, J=12.6 Hz, 2H), 1.8-1.71 (d, J=13.2 Hz, 2H), 1.36 (s, 6H), 1.28 (s, 6H).

I-370: N2-[3-Methoxy-5-(5-methyl-tetrazol-1-yl)]phenyl-N4-(1,2,2,6,6-pentamethylpiperidin-4-yl)-5-trifluoromethyl-2,4-pyrimidinediamine MS (m/e) 520.22 (MH+); $^1$H NMR (DMSO-d6): δ 9.78 (s, 1H), 8.21 (s, 1H), 7.56 (s, 1H), 7.46 (s, 1H), 6.86 (s, 1H), 6.50-6.47 (d, J=8.4 Hz, 1H), 4.49 (s, 1H), 3.77 (s, 3H), 2.56 (s, 3H), 2.18 (s, 3H), 1.61 (bs, 4H), 1.07 (s, 6H), 0.9 (s, 6H).

I-371: N2-(3,5-Dimethoxy)phenyl-5-fluoro-N4-(1H-2,2,6,6-tetramethylpiperidin-4-yl)-2,4-pyrimidinediamine MS (m/e) 404.19 (MH+); $^1$H NMR (DMSO-d6): δ 9.13 (s, 1H), 8.64 (s, 1H), 7.94-7.92 (d, J=3.9 Hz, 1H), 7.8-7.75 (bs, 2H), 7.88 (s, 2H), 6.10 (s, 1H), 4.54 (s, 1H), 3.67 (s, 6H), 1.96-1.92 (d, J=13.2 Hz, 2H), 1.62-1.54 (t, J=12.9 Hz, 2H), 1.45 (s, 6H), 1.37 (s, 6H).

I-372: 5-Fluoro-N2-[3-methoxy-5-(5-methyl-tetrazol-1-yl)]phenyl-N4-(1H-2,2,6,6-tetramethylpiperidin-4-yl)-2,4-pyrimidinediamine MS (m/e) 456.25 (MH+); $^1$H NMR (DMSO-d6): δ 9.37 (s, 1H), 7.93-7.92 (d, J=3.6 Hz, 1H), 7.52 (bs, 3H), 6.76 (s, 1H), 4.42 (s, 1H), 3.75 (s, 3H), 2.55 (s, 3H), 1.86-1.82 (d, J=12 Hz, 2H), 1.5-1.42 (t, J=13.2 Hz, 2H), 1.26 (s, 6H), 1.21 (s, 6H).

I-373: 5-Cyano-N2-{3-chloro-4-[2-(4-morpholino)ethoxy]}phenyl-N4-(1,2,2,6,6-pentamethylpiperidin-4-yl)-2,4-pyrimidinediamine MS (m/e) 528.37 (MH+); $^1$H NMR (DMSO-d6): δ 9.9 (s, 1H), 8.6 (bs, 1H), 7.83-7.76 (m, 2H), 7.5-7.48 (d, J=9 Hz, 1H), 7.13 (s, 1H), 4.54 (bs, 1H), 4.36 (bs, 2H), 3.98 (bs, 2H), 3.57 (m, 8H), 2.73 (s, 3H), 2.02-1.98 (d, J=11.7, 2H), 1.92-1.83 (t, J=12.9 Hz, 2H), 1.39 (bs, 12H).

I-375: N2-[3,5-bis(2,2,2-trifluoroethoxy)]phenyl-5-fluoro-N4-(2,2,6,6-tetramethylpiperidin-4-yl)-2,4-pyrimidinediamine LCMS: purity: 95.86%; MS (m/e): 540.44 (MH+); $^1$H NMR (DMSO-d$_6$): δ 1.22 (s, 6H), 1.34 (s, 6H), 1.41 (t, J=12.6 Hz, 2H), 1.82 (d, J=12.9 Hz, 2H), 4.50 (br, 1H), 4.65 (q, J=9.0 Hz, 4H), 6.37 (s, 1H), 7.08 (s, 2H), 7.40 (d, J=8.1 Hz, 1H), 7.89 (d, J=3.6 Hz, 1H), 8.25 (d, J=0.9 Hz, 1H), 9.07 (s, 1H); $^{19}$F NMR (282 MHz, DMSO-d$_6$): δ −180.81, −88.41 (t, J=7.6 Hz).

I-378: N2-[3,5-bis(2,2,2-trifluoroethoxy)]phenyl-5-fluoro-N4-(1,2,2,6,6-pentamethylpiperidin-4-yl)-2,4-pyrimidinediamine LCMS: purity: 98.48%; MS (m/e): 554.50 (MH+); $^1$H NMR (DMSO-d$_6$): δ 1.24 (s, 12H), 1.63 (t, 2H), 1.84 (d, 2H), 3.30 (s, 3H), 4.43 (br, 1H), 4.66 (q, J=8.7 Hz, 4H), 6.37 (s, 1H), 7.08 (d, J=2.4 Hz, 2H), 7.40 (d, 1H), 7.90 (d, J=3.9 Hz, 1H), 9.06 (s, 1H); $^{19}$F NMR (282 MHz, DMSO-d$_6$): δ−180.90, −88.41 (t, J=9.0 Hz).

I-379: N2-(4,5-dimethoxy-2-methyl)phenyl-5-fluoro-N4-(2,2,6,6-tetramethylpiperidin-4-yl)-2,4-pyrimidinediamine LCMS: purity: 98.52%; MS (m/e): 418.36 (MH+); $^1$H NMR (DMSO-d$_6$): δ 1.13 (s, 6H), 1.32 (s, 6H), 1.52 (t, J=15.0 Hz, 2H), 1.78 (d, 2H), 2.09 (s, 3H), 3.67 (s, 3H), 3.72 (s, 3H), 6.83 (s, 2H), 7.81 (d, 1H), 8.00 (br, 1H), 8.62 (br, 1H).

I-380: N2-(4,5-dimethoxy-2-methyl)phenyl-5-fluoro-N4-(1,2,2,6,6-pentamethylpiperidin-4-yl)-2,4-pyrimidinediamine LCMS: purity: 95.52%; MS (m/e): 432.24 (MH+); $^1$H NMR (DMSO-d$_6$): δ 1.10 (s, 6H), 1.34 (s, 6H), 1.73 (t, J=12.9 Hz, 2H), 1.91 (d, J=13.8 Hz, 2H), 2.09 (s, 3H), 2.67 (d, J=4.8 Hz, 3H), 3.66 (s, 3H), 3.72 (s, 3H), 4.17 (br, 1H), 6.81 (d, J=2.4 Hz, 2H), 7.93 (d, 1H), 8.68 (br, 1H).

I-381: N2-(2-cyano-4,5-dimethoxy)phenyl-5-fluoro-N4-(1,2,2,6,6-pentamethylpiperidin-4-yl)-2,4-pyrimidinediamine LCMS: purity: 98.98%; MS (m/e): 444.43 (MH+); $^1$H NMR (DMSO-d$_6$): δ 1.40 (s, 6H), 1.44 (s, 6H), 1.90 (t, J=12.6 Hz, 2H), 2.12 (d, J=13.8 Hz, 2H), 2.76 (s, 3H), 3.85 (s, 3H), 3.90 (s, 3H), 4.33 (br, 1H), 7.03 (s, 1H), 7.39 (s, 1H), 8.10 (s, 1H), 8.71 (br, 1H), 8.83 (br, 1H); $^{19}$F NMR (282 MHz, DMSO-d$_6$): δ−171.52.

I-382: N2-(2-cyano-4,5-dimethoxy)phenyl-5-fluoro-N4-(2,2,6,6-tetramethylpiperidin-4-yl)-2,4-pyrimidinediamine LCMS: purity: 95.15%; MS (m/e): 430.38 (MH+); $^1$H NMR (DMSO-d$_6$): δ 1.42 (s, 6H), 1.50 (s, 6H), 1.73 (t, J=13.5 Hz, 2H), 2.02 (d, J=12.3 Hz, 2H), 3.90 (s, 3H), 3.95 (s, 3H), 4.65 (br, 1H), 7.16 (s, 1H), 7.48 (s, 1H), 8.00 (d, 1H), 8.84 (d, 1H), 9.10 (d, 1H).

I-383: N2-(3,5-dihydroxy)phenyl-5-fluoro-N4-(2,2,6,6-tetramethylpiperidin-4-yl)-2,4-pyrimidinediamine LCMS: purity: 99.13%; MS (m/e): 376.40 (MH+); $^1$H NMR (DMSO-d$_6$): δ 1.36 (s, 6H), 1.46 (s, 6H), 1.57 (t, J=12.9 Hz, 2H), 1.96 (d, J=12.0 Hz, 2H), 4.56 (br, 1H), 5.81 (s, 1H), 6.55 (d, J=1.8 Hz, 2H), 7.59 (br, 1H), 7.76 (d, 1H), 7.89 (d, J=3.3 Hz, 1H), 8.56 (d, 1H), 8.88 (br, 1H), 8.94 (br, 1H).

I-384: N2-(3,5-dihydroxy)phenyl-5-fluoro-N4-(1,2,2,6,6-pentamethylpiperidin-4-yl)-2,4-pyrimidinediamine LCMS: purity: 99.40%; MS (m/e): 390.40 (MH+). $^1$H NMR (DMSO-d$_6$): δ 1.40 (s, 6H), 1.41 (s, 6H), 1; 80 (t, J=12.9 Hz, 2H), 2.07 (d, J=11.7 Hz, 2H), 2.72 (d, J=5.1 Hz, 3H), 4.48 (br, 1H), 5.84 (s, 1H), 6.51 (s, 2H), 7.79 (br, 1H), 7.92 (d, J=3.9 Hz, 1H), 8.57 (br, 1H), 9.00 (br, 2H).

I-385: N2-[3,5-bis(2-methoxyethoxy)]phenyl-5-fluoro-N4-(1,2,2,6,6-pentamethylpiperidin-4-yl)-2,4-pyrimidinediamine LCMS: purity: 83.13%; MS (m/e): 506.53 (MH+); $^1$H NMR (DMSO-d$_6$): δ 1.18 (s, 6H), 1.20 (s, 6H), 1.56 (t, 2H), 1.77 (d, 2H), 3.28 (s, 6H), 3.60 (t, 4H), 3.98 (t, 4H), 4.45 (br, 1H), 6.06 (s, 1H), 6.54 (br, 1H), 6.91 (d, J=1.8 Hz, 2H), 7.27 (d, 1H), 7.85 (d, J=3.6 Hz, 1H), 8.89 (s, 1H); $^{19}$F NMR (282 MHz, DMSO-d$_6$): δ−181.51.

I-386: N2-(2-chloro-4,5-dimethoxy)phenyl-5-fluoro-N4-(1,2,2,6,6-pentamethylpiperidin-4-yl)-2,4-pyrimidinediamine LCMS: purity: 99.02%; MS (m/e): 452.40 (MH+); $^1$H NMR (DMSO-d$_6$): δ 1.09 (s, 6H), 1.28 (s, 6H), 1.59 (br, 2H), 1.87 (br, 2H), 3.70 (s, 3H), 3.73 (s, 3H), 4.20 (br, 1H), 6.98 (s, 1H), 7.08 (s, 1H), 7.32 (br, 1H), 7.79 (d, 1H), 8.19 (s, 1H).

I-387: 5-aminocarbonyl-N2-[3-methoxy-5-(5-methyl-1H-tetrazol-1-yl)]phenyl-N4-(2,2,6,6-tetramethylpiperidin-4-yl)-2,4-pyrimidinediamine LCMS: purity: 97.81%; MS (m/e): 481.41 (MH+); $^1$H NMR (DMSO-d$_6$): δ 1.10 (s, 6H), 1.16 (s, 8H), 1.87 (d, J=12.9 Hz, 2H), 2.56 (s, 3H), 3.76 (s, 3H), 4.38 (br, 1H), 6.85 (d, J=1.8 Hz, 1H), 7.24 (br, 1H), 7.58 (d, 2H), 7.84 (br, 1H), 8.23 (s, 1H), 8.54 (s, 1H), 9.20 (d, 1H), 9.78 (br, 1H).

I-388: 5-fluoro-N2-[3-methoxy-5-(tetrazol-1-yl)]phenyl-N4-(2,2,6,6-tetramethylpiperidin-4-yl)-2,4-pyrimidinediamine LCMS: purity: 97.53%; MS (m/e): 442.05 (MH+); $^1$H NMR (DMSO-d$_6$): δ 1.19 (s, 12H), 1.39 (t, J=12.6 Hz, 2H), 1.81 (d, J=12.9 Hz, 2H), 3.78 (s, 3H), 4.40 (br, 1H), 6.98 (d, J=1.8 Hz, 1H), 7.48 (m, 2H), 7.80 (s, 1H), 7.93 (d, J=3.6 Hz, 1H), 8.26 (s, 1H), 9.36 (s, 1H), 10.04 (s, 1H); $^{19}$F NMR (282 MHz, DMSO-d$_6$): δ−180.18.

I-389: 5-aminocarbonyl-N2-[3-methoxy-5-(tetrazol-1-yl)]phenyl-N4-(2,2,6,6-tetramethylpiperidin-4-yl)-2,4-pyrimidinediamine LCMS: purity: 98.18%; MS (m/e): 467.59 (MH+); $^1$H NMR (DMSO-d$_6$): δ 1.12 (s, 6H), 1.17 (s, 8H), 1.90 (d, J=12.0 Hz, 2H), 3.80 (s, 3H), 4.41 (br, 1H), 7.07 (s, 1H), 7.23 (br, 1H), 7.50 (s, 1H), 7.86 (s, 2H), 8.23 (s, 1H), 8.56 (s, 1H), 9.20 (d, J=8.1 Hz, 1H), 9.77 (s, 1H), 10.07 (s, 1H).

I-390: 5-aminocarbonyl-N2-[3-methoxy-5-(tetrazol-1-yl)]phenyl-N4-(1,2,2,6,6-pentamethylpiperidin-4-yl)-2,4-pyrimidinediamine LCMS: purity: 86.92%; MS (m/e): 481.57 (MH+); $^1$H NMR (DMSO-d$_6$): δ 0.92 (s, 6H), 1.09 (s, 6H), 1.28 (t, J=12.9 Hz, 2H), 1.85 (d, J=11.4 Hz, 2H), 2.23 (s, 3H), 3.80 (s, 3H), 4.29 (br, 1H), 7.06 (d, J=1.8 Hz, 1H), 7.18 (br, 1H), 7.51 (s, 1H), 7.86 (s, 2H), 8.54 (s, 1H), 9.14 (d, J=7.8 Hz, 1H), 9.73 (s, 1H), 10.06 (s, 1H).

I-391: 5-fluoro-N4-(2,2,6,6-tetramethylpiperidin-4-yl)-N2-[3-(tetrazol-1-yl)]phenyl-2,4-pyrimidinediamine LCMS: purity: 84.43%; MS (m/e): 412.36 (MH+); $^1$H NMR (DMSO-d$_6$): δ 1.19 (s, 6H), 1.22 (s, 6H), 1.41 (t, J=12.3 Hz, 2H), 1.84 (d, J=12.9 Hz, 2H), 4.42 (br, 1H), 7.32 (d, J=7.8 Hz, 1H), 7.45 (m, 2H), 7.85 (d, J=7.8 Hz, 1H), 7.93 (d, J=3.6 Hz, 1H), 8.16 (s, 1H), 8.21 (s, 1H), 9.42 (s, 1H), 10.03 (s, 1H); $^{19}$F NMR (282 MHz, DMSO-d$_6$): δ−180.31.

I-392: 5-aminocarbonyl-N4-(2,2,6,6-tetramethylpiperidin-4-yl)-N2-[3-(tetrazol-1-yl)]phenyl-2,4-pyrimidinediamine LCMS: purity: 89.34%; MS (m/e): 437.35 (MH+); $^1$H NMR (DMSO-d$_6$): δ 0.99 (s, 14H), 1.79 (d, J=11.7 Hz, 2H), 4.35 (br, 1H), 7.20 (br, 1H), 7.40 (m, 2H), 7.83 (br, 1H), 8.02 (d, 1H), 8.15 (s, 1H), 8.53 (s, 1H), 9.13 (d, 1H), 9.81 (s, 1H), 10.04 (s, 1H).

I-393: 5-cyano-N4-(2,2,6,6-tetramethylpiperidin-4-yl)-N2-[3-(tetrazol-1-yl)]phenyl-2,4-pyrimidinediamine LCMS: purity: 96.99%; MS (m/e): 419.34 (MH+); $^1$H NMR (DMSO-d$_6$): δ 1.07 (s, 6H), 1.15 (s, 6H), 1.42 (t, J=12.3 Hz, 2H), 1.72 (d, J=12.3 Hz, 2H), 4.45 (br, 1H), 7.48 (d, J=5.1 Hz, 2H), 7.66 (d, J=8.1 Hz, 1H), 7.89 (br, 1H), 8.09 (s, 1H), 8.22 (s, 1H), 8.39 (s, 1H), 10.06 (s, 1H), 10.10 (br, 1H).

I-394: N2-[3,5-bis(2-methoxyethoxy)]phenyl-5-fluoro-N4-(2,2,6,6-tetramethylpiperidin-4-yl)-2,4-pyrimidinediamine LCMS: purity: 75.11%; MS (m/e): 492.65 (MH+); $^1$H NMR (DMSO-d$_6$): δ 1.31 (s, 8H), 1.43 (s, 6H), 1.90 (d, J=9.6 Hz, 2H), 3.28 (s, 6H), 3.59 (t, 4H), 3.98 (t, J=4.5 Hz, 4H), 4.54 (br, 1H), 6.07 (s, 1H), 6.90 (d, J=1.8 Hz, 2H), 7.45 (d, J=6.0 Hz, 1H), 7.89 (d, J=3.3 Hz, 1H), 8.17 (s, 1H), 8.94 (s, 1H); $^{19}$F NMR (282 MHz, DMSO-d$_6$): δ−181.42.

I-395: 5-fluoro-N2-[4-methoxy-3-(5-propyl-1H-tetrazol-1-yl)]phenyl-N4-(1,2,2,6,6-pentamethylpiperidin-4-yl)-2,4-pyrimidinediamine LCMS: MS (m/e): 498.43 (MH+); $^1$H NMR (DMSO-d$_6$): δ 0.87 (t, J=7.2 Hz, 3H), 1.28 (s, 6H), 1.38 (s, 6H), 1.65 (m, J=7.2 Hz, 2H), 1.78 (t, J=12.6 Hz, 2H), 2.03 (d, J=12.3 Hz, 2H), 2.64 (t, J=7.5 Hz, 2H), 2.71 (d, J=4.8 Hz, 3H), 3.74 (s, 3H), 4.36 (br, 1H), 7.24 (d, J=9.0 Hz, 1H), 7.68 (d, J=2.1 Hz, 1H), 7.81 (dd, J=2.1, 8.7 Hz, 1H), 7.99 (d, J=4.2 Hz, 2H), 8.60 (d, 1H), 9.43 (s, 1H); $^{19}$F NMR (282 MHz, DMSO-d$_6$): δ−180.12.

I-396: 5-fluoro-N2-[3-(5-methyl-1H-tetrazol-1-yl)]phenyl-N4-(1,2,2,6,6-pentamethylpiperidin-4-yl)-2,4-pyrimidinediamine LCMS: purity: 94.45%; MS (m/e): 440.36 (MH+); $^1$H NMR (DMSO-d$_6$): δ 1.28 (s, 6H), 1.38 (s, 6H), 1.80 (t, J=12.9 Hz, 2H), 2.06 (d, J=12.9 Hz, 2H), 2.56 (s, 3H), 2.70 (d, J=5.1 Hz, 3H), 4.40 (br, 1H), 7.18 (d, J=7.5 Hz, 1H), 7.46 (t, J=8.1 Hz, 1H), 7.82 (d, J=8.1 Hz, 1H), 7.87 (m, 2H), 8.00 (d, J=4.2 Hz, 1H), 8.60 (br, 1H), 9.58 (s, 1H); $^{19}$F NMR (282 MHz, DMSO-d$_6$): δ−179.72.

I-397: 5-fluoro-N2-[3-methyl-4-(1H-tetrazol-1-yl)]phenyl-N4-(1,2,2,6,6-pentamethylpiperidin-4-yl)-2,4-pyrimidinediamine LCMS: purity: 82.26%; MS (m/e): 440.34 (MH+); $^1$H NMR (DMSO-d$_6$): δ 1.09 (s, 12H), 1.49 (t, 2H), 1.70 (d, 2H), 2.03 (s, 3H), 2.20 (s, 3H), 4.39 (br, 1H), 7.26 (m, 2H), 7.57 (s, 1H), 7.89 (d, J=3.9 Hz, 1H), 7.96 (d, J=7.8 Hz, 1H), 9.34 (s, 1H), 9.71 (s, 1H); $^{19}$F NMR (282 MHz, DMSO-d$_6$): δ−180.48.

I-398: 5-fluoro-N2-[4-methyl-3-(1H-tetrazol-1-yl)]phenyl-N4-(1,2,2,6,6-pentamethylpiperidin-4-yl)-2,4-pyrimidinediamine LCMS: purity: 78.48%; MS (m/e): 440.37 (MH+); $^1$H NMR (DMSO-d$_6$): δ 0.94 (s, 6H), 1.09 (s, 6H), 1.47 (t, J=12.3 Hz, 2H), 1.69 (d, J=11.7 Hz, 2H), 1.99 (s, 3H), 2.21 (s, 3H), 4.25 (br, 1H), 7.27 (d, J=8.7 Hz, 2H), 7.75 (d, 1H), 7.87 (m, 2H), 9.28 (s, 1H), 9.82 (s, 1H); $^{19}$F NMR (282 MHz, DMSO-d$_6$): δ−180.83.

I-399: 5-fluoro-N2-[3-(5-methylthio-1H-tetrazol-1-yl)]phenyl-N4-(1,2,2,6,6-pentamethylpiperidin-4-yl)-2,4-pyrimidinediamine LCMS: purity: 97.52%; MS (m/e): 472.33 (MH+); $^1$H NMR (DMSO-d$_6$): δ 1.01 (s, 6H), 1.17 (s, 6H), 1.56 (t, J=13.2 Hz, 2H), 1.82 (d, J=10.5 Hz, 2H), 2.34 (s, 3H), 2.76 (s, 3H), 4.30 (br, 1H), 7.07 (d, J=7.8 Hz, 1H), 7.43 (m, 2H), 7.85 (d, J=8.1 Hz, 1H), 7.92 (d, J=3.3 Hz, 1H), 8.01 (s, 1H), 9.49 (s, 1H); $^{19}$F NMR (282 MHz, DMSO-d$_6$): δ−180.20.

I-400: 5-fluoro-N2-[4-(1H-tetrazol-1-yl)]phenyl-N4-(1,2,2,6,6-pentamethylpiperidin-4-yl)-2,4-pyrimidinediamine LCMS: purity: 75.39%; MS (m/e): 426.33 (MH+); $^1$H NMR (DMSO-d$_6$): δ 1.13 (s, 6H), 1.16 (s, 6H), 1.54 (t, J=12.3 Hz, 2H), 1.78 (d, J=14.1 Hz, 2H), 2.27 (s, 3H), 4.39 (br, 1H), 7.33 (d, 1H), 7.64 (d, J=8.7 Hz, 2H), 7.90 (d, J=3.9 Hz, 1H), 7.94 (d, J=8.7 Hz, 2H), 9.42 (s, 1H), 9.93 (s, 1H); $^{19}$F NMR (282 MHz, DMSO-d$_6$): δ−180.55.

I-401: 5-fluoro-N2-[4-methoxy-3-(2,2,2-trifluoroethoxy)]phenyl-N4-(1,2,2,6,6-pentamethylpiperidin-4-yl)-2,4-pyrimidinediamine LCMS: purity: 93.50%; MS (m/e): 486.34 (MH+); $^1$H NMR (DMSO-d$_6$): δ 1.32 (s, 6H), 1.38 (s, 6H), 1.78 (t, J=12.0 Hz, 2H), 2.02 (d, J=13.5 Hz, 2H), 2.71 (d, 3H), 3.74 (s, 3H), 4.41 (br, 1H), 4.60 (q, J=8.8 Hz, 2H), 6.91 (d, J=8.7 Hz, 1H), 7.19 (s, 1H), 7.25 (d, 1H), 7.95 (d, 1H), 8.60 (br, 1H), 9.24 (br, 1H); $^{19}$F NMR (282 MHz, DMSO-d$_6$): δ−90.07.

I-402: 5-cyano-N2-[3-methoxy-5-(5-methyl-1H-tetrazol-1-yl)]phenyl-N4-(2,2,6,6-tetramethylpiperidin-4-yl)-2,4-pyrimidinediamine LCMS: purity: 98.13%; MS (m/e): 463.46 (MH+); $^1$H NMR (DMSO-d$_6$): δ 1.14 (s, 6H), 1.22 (s, 6H), 1.51 (t, J=12.6 Hz, 2H), 1.76 (d, J=11.7 Hz, 2H), 2.56 (s, 3H), 3.76 (s, 3H), 4.49 (br, 1H), 6.91 (d, J=1.8 Hz, 1H), 7.45 (br, 1H), 7.54 (s, 1H), 7.75 (d, J=8.1 Hz, 1H), 8.20 (s, 1H), 8.38 (s, 1H), 10.07 (br, 1H).

I-403: 5-cyano-N2-[3-methoxy-5-(1H-tetrazol-1-yl)]phenyl-N4-(2,2,6,6-tetramethylpiperidin-4-yl)-2,4-pyrimidinediamine LCMS: purity: 99.18%; MS (m/e): 449.42 (MH+); $^1$H NMR (DMSO-d$_6$): δ 1.20 (s, 6H), 1.32 (s, 6H), 1.62 (t, J=12.6 Hz, 2H), 1.88 (d, J=10.2 Hz, 2H), 3.81 (s, 3H), 4.50 (br, 1H), 7.16 (s, 1H), 7.46 (s, 1H), 7.74 (br, 2H), 7.85 (d, J=7.5 Hz, 1H), 8.42 (s, 1H), 8.52 (d, 1H), 10.08 (s, 1H).

I-404: 5-cyano-N2-[3-methoxy-5-(1H-tetrazol-1-yl)]
phenyl-N4-(1,2,2,6,6-pentamethylpiperidin-4-yl)-2,
4-pyrimidinediamine LCMS: purity: 91.72%; MS (m/e): 463.88 (MH+); $^1$H NMR (DMSO-d$_6$): δ 0.85 (s, 6H), 1.05 (s, 6H), 1.62 (m, 4H), 2.16 (s, 3H), 3.80 (s, 3H), 4.40 (br, 1H), 6.51 (s, 1H), 7.12 (s, 1H), 7.48 (br, 2H), 7.72 (s, 1H), 8.36 (s, 1H), 10.05 (s, 1H).

I-405: 5-cyano-N2-[3-(1H-tetrazol-1-yl)]phenyl-N4-
(1,2,2,6,6-pentamethylpiperidin-4-yl)-2,4-pyrimidinediamine LCMS: purity: 80.97%; MS (m/e): 433.46 (MH+); $^1$H NMR (DMSO-d$_6$): δ 0.92 (s, 6H), 1.11 (s, 6H), 1.60-1.72 (m, 4H), 2.25 (s, 3H), 4.43 (br, 1H), 7.48 (d, J=3.9 Hz, 2H), 7.59 (m, 2H), 7.92 (s, 1H), 8.08 (s, 1H), 8.38 (s, 1H), 10.06 (s, 1H).

I-406: 5-aminocarbonyl-N2-[3,5-bis(2,2,2-trifluoroethoxy)]phenyl-N4-(1,2,2,6,6-pentamethylpiperidin-4-yl)-2,4-pyrimidinediamine LCMS: purity: 94.41%; MS (m/e): 579.28 (MH+); $^1$H NMR (DMSO-d$_6$): δ 1.09 (s, 12H), 1.26 (t, J=11.4 Hz, 2H), 1.82 (d, J=12.0 Hz, 2H), 2.22 (s, 3H), 4.37 (br, 1H), 4.67 (q, J=9.0 Hz, 4H), 6.44 (s, 1H), 7.14 (s, 2H), 8.13 (s, 1H), 8.51 (s, 1H), 9.14 (d, 1H), 9.47 (s, 1H); $^{19}$F NMR (282 MHz, DMSO-d$_6$): δ−88.39 (t, J=7.6 Hz).

I-407: 5-fluoro-N2-[3-methoxy-4-(5-methyl-1H-tetrazol-1-yl)]phenyl-N4-(1,2,2,6,6-pentamethylpiperidin-4-yl)-2,4-pyrimidinediamine LCMS: purity: 98.87%; MS (m/e): 470.34 (MH+); $^1$H NMR (DMSO-d$_6$): δ 1.21 (s, 12H), 1.61 (t, J=12.0 Hz, 2H), 1.87 (d, J=12.9 Hz, 2H), 2.33 (s, 3H), 2.40 (s, 3H), 3.73 (s, 3H), 4.43 (br, 1H), 7.24 (d, J=8.4 Hz, 1H), 7.36 (s, 1H), 7.45 (d, 1H), 7.83 (d, J=8.4 Hz, 1H), 7.93 (d, J=3.9 Hz, 1H), 9.36 (s, 1H); $^{19}$F NMR (282 MHz, DMSO-d$_6$): δ−180.18.

I-408: 5-aminocarbonyl-N2-[3,5-bis(2,2,2-trifluoroethoxy)]phenyl-N4-(2,2,6,6-tetramethylpiperidin-4-yl)-2,4-pyrimidinediamine LCMS: purity: 99.89%; MS (m/e): 565.51 (MH+); $^1$H NMR (DMSO-d$_6$): δ 1.19 (s, 8H), 1.31 (s, 6H), 1.91 (d, J=12.3 Hz, 2H), 4.51 (br, 1H), 4.67 (q, J=8.7 Hz, 4H), 6.45 (s, 1H), 7.14 (d, J=2.4 Hz, 2H), 7.20 (br, 1H), 7.83 (br, 1H), 8.26 (s, 1H), 8.52 (s, 1H), 9.22 (d, J=7.8 Hz, 1H), 9.53 (s, 1H).

I-409: N2-[4-ethoxy-3-(5-ethyl-1H-tetrazol-1-yl)]
phenyl-5-fluoro-N4-(1,2,2,6,6-pentamethylpiperidin-4-yl)-2,4-pyrimidinediamine LCMS: purity: 99.89%; MS (m/e): 498.51 (MH+); $^1$H NMR (DMSO-d$_6$): δ 0.94 (s, 6H), 1.09 (s, 6H), 1.13 (t, J=6.9 Hz, 3H), 1.22 (t, J=7.5 Hz, 3H), 1.47 (t, J=12.3 Hz, 2H), 1.68 (d, J=11.7 Hz, 2H), 2.21 (s, 3H), 2.68 (q, J=7.5 Hz, 2H), 4.00 (q, J=6.9 Hz, 2H), 4.27 (br, 1H), 7.15 (d, J=9.3 Hz, 1H), 7.22 (d, J=8.1 Hz, 1H), 7.79 (d, J=2.7 Hz, 1H), 7.84 (m, 2H), 9.12 (s, 1H); $^{19}$F NMR (282 MHz, DMSO-d$_6$): δ−181.40.

I-410: N2-[3,4-bis(trifluoromethyl)]phenyl-5-fluoro-N4-(1,2,2,6,6-pentamethylpiperidin-4-yl)-2,4-pyrimidinediamine LCMS: purity: 99.93%; MS (m/e): 495.37 (MH+); $^1$H NMR (DMSO-d$_6$): δ 1.23 (s, 12H), 1.63 (t, J=13.2 Hz, 2H), 1.87 (d, 2H), 3.14 (s, 3H), 4.36 (br, 1H), 7.40 (d, J=9.0 Hz, 1H), 7.50 (d, 1H), 7.79 (dd, J=2.4, 9.3 Hz, 1H), 7.90 (s, 1H), 7.93 (d, J=3.6 Hz, 1H), 9.48 (s, 1H); $^{19}$F NMR (282 MHz, DMSO-d$_6$): δ−179.74, −73.88, −73.22.

I-411: 5-cyano-N2-[3,5-bis(2,2,2-trifluoroethoxy)]
phenyl-N4-(1,2,2,6,6-pentamethylpiperidin-4-yl)-2,
4-pyrimidinediamine LCMS: purity: 98.55%; MS (m/e): 561.55 (MH+); $^1$H NMR (DMSO-d$_6$): δ 1.37 (s, 12H), 1.88 (m, 2H), 1.98 (m, 2H), 2.70 (s, 3H), 4.57 (br, 1H), 4.71 (q, J=8.7 Hz, 4H), 6.54 (s, 1H), 7.04 (s, 2H), 7.90 (br, 1H), 8.37 (s, 1H), 8.54 (br, 1H), 9.89 (br, 1H); $^{19}$F NMR (282 MHz, DMSO-d$_6$): δ−88.35.

I-412: N2-[3-(cyclopropylaminocarbonylmethoxy)-
4-methoxy]phenyl-5-fluoro-N4-(1,2,2,6,6-pentamethylpiperidin-4-yl)-2,4-pyrimidinediamine LCMS: purity: 94.01%; MS (m/e): 501.36 (MH+); $^1$H NMR (DMSO-d$_6$): δ 0.46 (m, 2H), 0.63 (m, 2H), 1.19 (s, 12H), 1.57 (t, J=12.6 Hz, 2H), 1.82 (d, J=11.4 Hz, 2H), 2.39 (s, 3H), 2.66 (m, J=3.3 Hz, 1H), 3.70 (s, 3H), 4.32 (s, 2H), 4.40 (br, 1H), 6.76 (d, J=8.7 Hz, 1H), 7.08 (s, 1H), 7.24 (d, J=7.5 Hz, 1H), 7.40 (d, J=8.7 Hz, 1H), 7.80 (d, J=3.9 Hz, 1H), 7.93 (s, 1H), 8.75 (s, 1H); $^{19}$F NMR (282 MHz, DMSO-d$_6$): δ−182.44.

I-413: N2-[3-(2-methoxyethoxy)-4-methoxy]phenyl-
5-fluoro-N4-(1,2,2,6,6-pentamethylpiperidin-4-yl)-2,
4-pyrimidinediamine LCMS: purity: 98.30%; MS (m/e): 462.40 (MH+); $^1$H NMR (DMSO-d$_6$): δ 1.34 (s, 12H), 1.72 (t, 2H), 1.98 (d, 2H), 2.65 (s, 3H), 3.29 (s, 3H), 3.62 (t, J=4.5 Hz, 2H), 3.68 (s, 3H), 3.98 (t, J=4.5 Hz, 2H), 4.42 (br, 1H), 6.74 (d, J=8.7 Hz, 1H), 7.05 (s, 1H), 7.34 (d, J=8.7 Hz, 1H), 7.41 (br, 1H), 7.84 (d, J=3.6 Hz, 1H), 8.71 (s, 1H); $^{19}$F NMR (282 MHz, DMSO-d$_6$): δ−182.51.

I-414: 5-fluoro-N2-[3-(5-methyl-1H-tetrazol-1-yl)]
phenyl-N4-(2,2,6,6-tetramethylpiperidin-4-yl)-2,4-pyrimidinediamine LCMS: purity: 93.62%; MS (m/e): 426.34 (MH+); $^1$H NMR (DMSO-d$_6$): δ 1.17 (s, 12H), 1.37 (t, J=12.3 Hz, 2H), 1.79 (d, J=10.2 Hz, 2H), 2.55 (s, 3H), 4.37 (br, 1H), 7.12 (d, J=7.5 Hz, 1H), 7.42 (m, 2H), 7.92 (m, 3H), 8.25 (s, 1H), 9.43 (s, 1H); $^{19}$F NMR (282 MHz, DMSO-d$_6$): δ−180.33.

I-415: N2-[4-ethoxy-3-(5-ethyl-1H-tetrazol-1-yl)]
phenyl-5-fluoro-N4-(2,2,6,6-tetramethylpiperidin-4-yl)-2,4-pyrimidinediamine LCMS: purity: 94.92%; MS (m/e): 484.37 (MH+); $^1$H NMR (DMSO-d$_6$): δ 1.13 (s, 6H), 1.15 (s, 6H), 1.13 (m, 3H), 1.22 (t, J=7.5 Hz, 3H), 1.32 (t, J=12.3 Hz, 2H), 1.74 (d, J=12.3 Hz, 2H), 2.68 (q, J=7.5 Hz, 2H), 4.00 (q, J=6.9 Hz, 2H), 4.36 (br, 1H), 7.16 (d, J=9.0 Hz, 1H), 7.31 (d, J=8.7 Hz, 1H), 7.80 (m, 2H), 7.85 (d, J=3.6 Hz, 1H), 8.26 (s, 1H), 9.13 (s, 1H); $^{19}$F NMR (282 MHz, DMSO-d$_6$): δ−181.31.

I-416: 5-fluoro-N2-[3-(5-methylthio-1H-tetrazol-1-yl)]phenyl-N4-(2,2,6,6-tetramethylpiperidin-4-yl)-2,
4-pyrimidinediamine LCMS: purity: 96.71%; MS (m/e): 458.26 (MH+); $^1$H NMR (DMSO-d$_6$): δ 1.16 (s, 6H), 1.23 (s, 6H), 1.43 (t, J=12.9

Hz, 2H), 1.85 (d, J=12.9 Hz, 2H), 2.75 (s, 3H), 4.34 (br, 1H), 7.08 (d, J=7.5 Hz, 1H), 7.44 (t, J=8.1 Hz, 1H), 7.50 (d, J=7.8 Hz, 1H), 7.80 (d, J=7.8 Hz, 1H), 7.94 (d, J=3.6 Hz, 1H), 8.03 (s, 1H), 8.18 (s, 1H), 9.53 (s, 1H); $^{19}$F NMR (282 MHz, DMSO-d$_6$): δ−180.13.

I-417: 5-fluoro-N2-[4-methoxy-3-(pyridin-4-yl-methoxy)]phenyl-N4-(1,2,2,6,6-pentamethylpiperidin-4-yl)-2,4-pyrimidinediamine LCMS: purity: 97.46%; MS (m/e): 495.41 (MH+); $^1$H NMR (DMSO-d$_6$): δ 1.18 (s, 6H), 1.20 (s, 6H), 1.58 (t, 2H), 1.80 (d, 2H), 2.39 (s, 3H), 3.72 (s, 3H), 4.39 (br, 1H), 5.07 (s, 2H), 6.77 (d, J=8.4 Hz, 1H), 7.16 (s, 1H), 7.23 (br, 1H), 7.40 (d, J=5.7 Hz, 2H), 7.80 (t, 1H), 8.11 (s, 1H), 8.55 (d, J=5.7 Hz, 2H), 8.72 (s, 1H); $^{19}$F NMR (282 MHz, DMSO-d$_6$): δ−182.45.

I-418: 5-fluoro-N2-[4-methoxy-3-(pyridin-3-yl-methoxy)]phenyl-N4-(1,2,2,6,6-pentamethylpiperidin-4-yl)-2,4-pyrimidinediamine LCMS: purity: 98.01%; MS (m/e): 495.42 (MH+); $^1$H NMR (DMSO-d$_6$): δ 1.21 (s, 12H), 1.60 (t, J=12.6 Hz, 2H), 1.86 (d, J=12.0 Hz, 2H), 2.44 (s, 3H), 3.69 (s, 3H), 4.39 (br, 1H), 5.04 (s, 2H), 6.76 (d, J=8.7 Hz, 1H), 7.21 (s, 1H), 7.27 (d, 1H), 7.40 (m, 2H), 7.81 (m, 2H), 8.51 (d, J=4.8 Hz, 1H), 8.63 (s, 1H), 8.74 (s, 1H); $^{19}$F NMR (282 MHz, DMSO-d$_6$): δ−182.45.

I-419: 5-cyano-N2-[3,5-bis(2,2,2-trifluoroethoxy)]phenyl-N4-(2,2,6,6-tetramethylpiperidin-4-yl)-2,4-pyrimidinediamine LCMS: MS (m/e): 547.31 (MH+); $^1$H NMR (DMSO-d$_6$): δ 1.16 (s, 6H), 1.27 (s, 6H), 1.44 (t, J=12.6 Hz, 2H), 1.73 (d, J=11.4 Hz, 2H), 4.58 (br, 1H), 4.68 (q, J=8.7 Hz, 4H), 6.50 (s, 1H), 7.06 (s, 2H), 7.62 (d, 1H), 8.26 (s, 1H), 8.34 (s, 1H), 9.80 (br, 1H); $^{19}$F NMR (282 MHz, DMSO-d$_6$): δ−88.36 (t, J=9.2 Hz).

I-420: 5-aminocarbonyl-N2-[4-ethoxy-3-(5-ethyl-1H-tetrazol-1-yl)]phenyl-N4-(1,2,2,6,6-pentamethylpiperidin-4-yl)-2,4-pyrimidinediamine LCMS: purity: 81.96%; MS (m/e): 523.64 (MH+); $^1$H NMR (DMSO-d$_6$): δ 0.89 (s, 6H), 1.06 (s, 6H), 1.14 (t, J=6.9 Hz, 3H), 1.18 (t, J=7.8 Hz, 2H), 1.22 (t, J=7.5 Hz, 3H), 1.79 (d, J=12.6 Hz, 2H), 2.17 (s, 3H), 2.68 (q, J=7.2 Hz, 2H), 4.02 (q, J=6.0 Hz, 2H), 4.20 (br, 1H), 7.17 (d, J=9.3 Hz, 2H), 7.78 (s, 2H), 7.96 (d, J=9.0 Hz, 1H), 8.49 (s, 1H), 9.17 (br, 1H), 9.57 (br, 1H).

I-421: N2-{4-methoxy-3-[2-(N,N-dimethylamino)ethoxy]}phenyl-5-fluoro-N4-(1,2,2,6,6-pentamethylpiperidin-4-yl)-2,4-pyrimidinediamine LCMS: MS (m/e): 475.39 (MH+); $^1$H NMR (DMSO-d$_6$): δ 1.39 (s, 12H), 1.81 (t, J=12.6 Hz, 2H), 2.05 (d, J=12.3 Hz, 2H), 2.74 (d, J=5.1 Hz, 3H), 2.88 (s, 6H), 3.48 (t, 2H), 3.72 (s, 3H), 4.21 (t, J=4.5 Hz, 2H), 4.45 (d, J=4.5 Hz, 2H), 6.84 (d, J=9.0 Hz, 1H), 7.16 (s, 1H), 7.39 (d, J=8.7 Hz, 1H), 7.68 (br, 1H), 7.89 (d, J=3.6 Hz, 1H), 8.69 (s, 1H), 8.95 (br, 1H), 9.69 (br, 1H).

I-422: 5-bromo-N2-(3,5-dimethoxyphenyl)-N4-(1,2,2,6,6-pentamethylpiperidin-4-yl)pyrimidine-2,4-diamine MS (m/e) 479.15 (MH$^+$); $^1$H NMR (DMSO-d$_6$): δ 9.01 (s, 1H), 7.99 (s, 1H), 6.92 (d, 2H), 6.35 (d, 1H), 6.19 (d, 1H), 4.49 (m, 1H), 3.63 (s, 6H), 2.19 (s, 3H), 1.69-1.59 (d, 2H), 1.57-1.48 (t, 2H), 1.08 (s, 12H).

I-423: N2-(3,5-dimethoxyphenyl)-5-methoxy-N4-(1,2,2,6,6-pentamethylpiperidin-4-yl)pyrimidine-2,4-diamine MS (m/e) 430.28 (MH$^+$); $^1$H NMR (DMSO-d$_6$): δ 8.59 (s, 1H), 7.58 (s, 1H), 6.98 (s, 2H), 6.43 (s, 1H), 5.99 (s, 1H), 4.41 (m, 1H), 3.73 (s, 3H), 3.63 (s, 6H), 2.21 (s, 3H), 1.65-1.59 (d, 2H), 1.49-1.41 (t, 2H), 1.15 (s, 12H).

I-424: 5-methoxy-N2-(3-methoxy-5-(5-methyl-1H-tetrazol-1-yl)phenyl)-N4-(1,2,2,6,6-pentamethylpiperidin-4-yl)pyrimidine-2,4-diamine MS (m/e) 482.15 (MH$^+$); $^1$H NMR (DMSO-d$_6$): δ 10.41 (s, 1H), 8.65 (s, 1H), 7.66 (s, 1H), 7.42 (s, 1H), 7.25 (s, 1H), 7.03 (s, 1H), 4.43 (m, 1H), 3.82 (s, 3H), 3.77 (s, 3H), 2.68 (s, 3H), 2.55 (s, 3H), 1.99-1.85 (m, 4H), 1.41-1.19 (d, 12H).

I-425: N2-(3,5-dimethoxyphenyl)-5-methyl-N4-(1,2,2,6,6-pentamethylpiperidin-4-yl)pyrimidine-2,4-diamine MS (m/e) 414.28 (MH$^+$); $^1$H NMR (DMSO-d$_6$): δ 8.82 (s, 1H), 8.05 (s, 1H), 7.72 (s, 1H), 6.69 (s, 2H), 6.32 (s, 1H), 4.59 (m, 1H), 3.71 (s, 6H), 2.73 (s, 3H), 1.99 (bs, 7H), 1.39 (s, 6H), 1.28 (s, 6H);

I-426: 2-(6-(dimethylamino)pyridin-3-yl)-5-(5-fluoro-4-(1,2,2,6,6-pentamethylpiperidin-4-ylamino)pyrimidin-2-ylamino)benzonitrile MS (m/e) 503.31 (MH$^+$); $^1$H NMR (DMSO-d$_6$): δ 8.87 (s, 1H), 8.21 (dd, 1H), 8.14 (d, 2H), 7.99 (d, 1H), 7.69 (m, 2H), 7.41 (d, 1H), 6.79 (d, 1H), 4.49 (m, 1H), 3.15 (s, 6H), 2.71 (s, 3H), 2.23-2.05 (d, 2H), 1.89-1.75 (t, 2H), 1.45-1.32 (d, 12H).

I-427: 5-(5-fluoro-4-(1,2,2,6,6-pentamethylpiperidin-4-ylamino)pyrimidin-2-ylamino)-2-(6-morpholinopyridin-3-yl)benzonitrile MS (m/e) 545.31 (MH$^+$); $^1$H NMR (DMSO-d$_6$): δ 8.27 (d, 1H), 8.15 (s, 2H), 8.04 (d, 2H), 7.92 (d, 1H), 7.73 (m, 2H), 7.41 (d, 1H), 6.91 (d, 1H), 4.41 (m, 1H), 3.75 (t, 4H), 3.59 (t, 4H), 2.39 (s, 3H), 1.89-1.77 (d, 2H), 1.65-1.55 (t, 2H), 1.25-1.17 (d, 12H).

I-428: 2-(6-(dimethylamino)pyridin-3-yl)-5-(5-fluoro-4-(2,2,6,6-tetramethylpiperidin-4-ylamino)pyrimidin-2-ylamino)benzonitrile MS (m/e) 489.28 (MH$^+$); $^1$H NMR (DMSO-d$_6$): δ 8.74 (d, 1H), 8.21 (d, 1H), 8.16 (d, 1H), 7.96 (d, 1H), 7.89 (m, 2H), 7.69 (m, 2H), 7.42 (d, 1H), 6.79 (d, 1H), 4.52 (m, 1H), 3.08 (s, 6H), 2.05-1.96 (d, 2H), 1.65-1.52 (t, 2H), 1.49-1.32 (d, 12H).

I-429: 5-(5-fluoro-4-(2,2,6,6-tetramethylpiperidin-4-ylamino)pyrimidin-2-ylamino)-2-(6-morpholinopyridin-3-yl)benzonitrile MS (m/e) 531.33 (MH$^+$); $^1$H NMR (DMSO-d$_6$): δ 9.41 (s, 1H), 8.21 (m, 4H), 7.92 (d, 1H), 7.53 (d, 1H), 7.43 (d, 1H),

I-430: N2-(3,5-dimethoxyphenyl)-N4-(1,2,2,6,6-pentamethylpiperidin-4-yl)-5-((trimethylsilyl)ethynyl)pyrimidine-2,4-diamine

MS (m/e) 496.31 (MH$^+$); $^1$H NMR (DMSO-d$_6$): δ 9.31 (s, 1H), 8.01 (s, 1H), 6.95 (s, 2H), 6.12 (s, 1H), 5.78 (d, 1H), 4.49 (m, 1H), 3.65 (s, 6H), 2.21 (s, 3H), 1.73-1.69 (d, 2H), 1.85-1.51 (t, 2H), 1.15 (s, 12H), 0.21 (s, 9H);

I-431: 5-fluoro-N2-(3-methoxy-5-(2-morpholinoethoxy)phenyl)-N4-(1,2,2,6,6-pentamethylpiperidin-4-yl)pyrimidine-2,4-diamine

MS (m/e) 517.33 (MH$^+$); $^1$H NMR (DMSO-d$_6$): δ 8.85 (s, 1H), 8.15 (s, 1H), 7.55 (d, 1H), 6.95 (s, 1H), 6.88 (s, 1H), 6.09 (s, 1H), 4.51 (m, 1H), 4.05 (t, 2H), 3.83 (t, 4H), 3.71 (s, 3H), 3.55 (t, 4H), 2.69 (t, 2H), 2.21 (s, 3H), 2.09-2.01 (d, 2H), 1.89-1.79 (t, 2H), 1.43 (s, 12H).

I-432: 5-fluoro-N2-(3-methoxy-5-(2-morpholinoethoxy)phenyl)-N4-(2,2,6,6-tetramethylpiperidin-4-yl)pyrimidine-2,4-diamine

MS (m/e) 503.31 (MH$^+$); $^1$H NMR (DMSO-d$_6$): δ 9.31 (s, 1H), 8.89 (d, 1H), 8.11 (d, 1H), 7.83 (bs, 1H), 7.11 (s, 1H), 6.75 (s, 1H), 6.15 (s, 1H), 4.51 (m, 1H), 4.25 (t, 4H), 3.73 (t, 2H), 3.65 (s, 3H), 3.55 (t, 4H), 2.49 (t, 2H), 1.97-1.85 (d, 2H), 1.68-1.55 (t, 2H), 1.45-1.32 (d, 12H).

I-433: N2-(3,5-dimethoxyphenyl)-5-ethynyl-N4-(1,2,2,6,6-pentamethylpiperidin-4-yl)pyrimidine-2,4-diamine

MS (m/e) 424.22 (MH$^+$); $^1$H NMR (CDCl$_3$): δ 9.35 (s, 1H), 8.05 (s, 1H), 6.82 (s, 2H), 6.15 (s, 1H), 5.59 (d, 1H), 4.71 (m, 1H), 3.75 (s, 6H), 3.49 (s, 1H), 2.67 (s, 3H), 2.21-2.12 (t, 2H), 2.05-1.95 (dd, 2H), 1.45-1.39 (d, 12H);

I-434: 5-fluoro-N2-(3-methoxy-5-(2-(pyrrolidin-1-yl)ethoxy)phenyl)-N4-(1,2,2,6,6-pentamethylpiperidin-4-yl)pyrimidine-2,4-diamine

MS (m/e) 501.31 (MH$^+$); $^1$H NMR (CDCl$_3$): δ 8.45 (s, 1H), 8.15 (s, 1H), 7.03 (s, 1H), 6.49 (s, 1H), 6.45 (d, 1H), 6.05 (s, 1H), 4.59 (m, 1H), 4.29 (t, 2H), 3.71 (s, 3H), 3.33 (t, 2H), 3.25 (t, 4H), 2.69 (s, 3H), 2.45-2.31 (t, 2H), 1.99 (bs, 6H), 1.51-1.39 (d, 12H).

I-435: 5-fluoro-N2-(3-methoxy-5-(2-(pyrrolidin-1-yl)ethoxy)phenyl)-N4-(2,2,6,6-tetramethylpiperidin-4-yl)pyrimidine-2,4-diamine

MS (m/e) 487.31 (MH$^+$); $^1$H NMR (CDCl$_3$): δ 8.75 (s, 1H), 7.68 (d, 1H), 7.23 (s, 1H), 7.12 (s, 1H), 6.51 (s, 1H), 6.15 (s, 1H), 6.05 (bs, 1H), 4.69 (m, 1H), 4.39 (t, 2H), 3.71 (s, 3H), 3.53 (t, 2H), 2.19 (m, 6H), 1.99 (m, 6H), 1.61-1.45 (d, 12H);

I-436: 3-(5-fluoro-4-(1,2,2,6,6-pentamethylpiperidin-4-ylamino)pyrimidin-2-ylamino)-5-methoxyphenol

MS (m/e) 404.24 (MH$^+$); $^1$H NMR (DMSO-d$_6$): δ 8.95 (s, 1H), 7.99 (s, 1H), 7.19 (bs, 2H), 6.69 (bs, 1H), 6.35 (bs, 1H), 4.42 (m, 2H), 4.15 (s, 3H), 2.21 (bs, 3H), 1.71-1.49 (m, 4H), 1.19 (bs, 12H).

I-437: N2-(3-(2-(1H-pyrrol-1-yl)ethoxy)-5-methoxyphenyl)-5-fluoro-N4-(1,2,2,6,6-pentamethylpiperidin-4-yl)pyrimidine-2,4-diamine

MS (m/e) 497.31 (MH$^+$); $^1$H NMR (CDCl$_3$): δ 8.35 (s, 1H), 7.62 (d, 1H), 7.03 (s, 1H), 6.72 (d, 2H), 6.61 (s, 1H), 6.49 (d, 1H), 6.15 (d, 2H), 6.09 (s, 1H), 4.69 (m, 1H), 4.29 (s, 4H), 3.71 (s, 3H), 2.77 (s, 3H), 2.59-2.41 (t, 2H), 2.05-1.95 (dd, 2H), 1.51-1.41 (d, 12H).

I-438: N2-(3-(2-(1H-pyrrol-1-yl)ethoxy)-5-methoxyphenyl)-5-fluoro-N4-(2,2,6,6-tetramethylpiperidin-4-yl)pyrimidine-2,4-diamine

MS (m/e) 483.28 (MH$^+$); $^1$H NMR (CDCl$_3$): δ 8.45 (s, 1H), 8.05 (s, 1H), 7.73 (d, 1H), 6.98 (s, 1H), 6.74 (d, 2H), 6.59 (s, 1H), 6.15 (d, 2H), 6.06 (s, 1H), 5.45 (d, 1H), 4.65 (m, 1H), 4.23 (m, 4H), 3.71 (s, 3H), 2.61 (s, 3H), 2.05-1.97 (t, 2H), 1.95-1.85 (d, 2H), 1.64-1.41 (d, 12H).

I-439: N2-(3-(2,5-dimethyl-1H-pyrrol-1-yl)-4-(2-morpholinoethoxy)phenyl)-5-fluoro-N4-(1,2,2,6,6-pentamethylpiperidin-4-yl)pyrimidine-2,4-diamine

MS (m/e) 580.37 (MH$^+$); $^1$H NMR (DMSO-d$_6$): δ 8.89 (s, 1H), 8.15 (s, 1H), 7.83 (m, 2H), 7.39 (m, 2H), 7.05 (d, 1H), 5.69 (s, 1H), 4.39 (m, 1H), 3.91 (t, 2H), 3.45 (t, 4H), 2.47 (m, 5H), 2.29 (t, 4H), 1.89 (s, 8H), 1.71-1.63 (t, 2H), 1.34-1.11 (d, 12H).

I-440: N2-(3-(2,5-dimethyl-1H-pyrrol-1-yl)-4-(2-(pyrrolidin-1-yl)ethoxy)phenyl)-5-fluoro-N4-(1,2,2,6,6-pentamethylpiperidin-4-yl)pyrimidine-2,4-diamine

MS (m/e) 564.37 (MH$^+$); $^1$H NMR (DMSO-d$_6$): δ 9.11 (s, 1H), 8.15 (s, 1H), 7.89 (d, 1H), 7.79 (dd, 1H), 7.45 (d, 1H), 7.42 (d, 1H), 7.05 (d, 1H), 5.72 (s, 1H), 4.41 (m, 1H), 4.05 (t, 2H), 3.15 (t, 2H), 2.75 (t, 4H), 2.55 (s, 3H), 1.89 (s, 8H), 1.71-1.63 (t, 2H), 1.39-1.15 (d, 12H).

I-441: N2-(3-(2,5-dimethyl-1H-pyrrol-1-yl)-4-(2-morpholinoethoxy)phenyl)-5-fluoro-N4-(2,2,6,6-tetramethylpiperidin-4-yl)pyrimidine-2,4-diamine

MS (m/e) 566.37 (MH$^+$); $^1$H NMR (DMSO-d$_6$): δ 9.05 (s, 1H), 8.11 (s, 2H), 7.89 (d, 1H), 7.72 (dd, 1H), 7.45 (m, 2H), 7.05 (d, 1H), 5.69 (s, 1H), 4.45 (m, 1H), 3.91 (t, 2H), 3.45 (t, 4H), 2.58 (t, 2H), 2.32 (t, 4H), 1.91 (m, 8H), 1.61-1.51 (t, 2H), 1.34 (bs, 12H).

I-442: N2-(3-(2,5-dimethyl-1H-pyrrol-1-yl)-4-(2-(pyrrolidin-1-yl)ethoxy)phenyl)-5-fluoro-N4-(2,2,6,6-tetramethylpiperidin-4-yl)pyrimidine-2,4-diamine

MS (m/e) 550.36 (MH$^+$); $^1$H NMR (DMSO-d$_6$): δ 9.11 (s, 1H), 8.15 (bs, 2H), 7.89 (d, 1H), 7.82 (dd, 1H), 7.51 (m, 2H), 7.05 (d, 1H), 5.72 (s, 1H), 4.47 (m, 1H), 4.05 (t, 2H), 2.97 (t, 2H), 2.62 (t, 4H), 1.99 (m, 8H), 1.63 (m, 6H), 1.39 (bs, 12H).

I-443: N2-(3-Fluoro-5-methoxy)phenyl-5-fluoro-N4-(1,2,2,6,6-pentamethylpiperidin-4-yl)-2,4-pyrimidinediamine

$^1$H NMR (DMSO-d$_6$): δ 9.17 (s, 1H), 7.87-7.86 (d, J=3.6 Hz, 1H), 7.39-7.29 (m, 2H), 6.97 (s, 1H), 6.31-6.27 (d, J=11.4

Hz, 1H), 4.43 (bs, 1H), 3.69 (s, 3H), 2.30 (s, 3H), 1.77-1.73 (d, J=12 Hz, 2H), 1.58-1.50 (t, J=12.3 Hz, 2H), 1.14 (s, 12H); (MS (m/e) 406.21 (MH+).

I-444: N2-(3-Difluoromethoxy-4-methoxy)phenyl-5-fluoro-N4-(2,2,6,6-tetramethylpiperidin-4-yl)-2,4-pyrimidinediamine MS (m/e) 440.03 (MH+); $^1$H NMR (DMSO-$d_6$): δ 9.94 (s, 1H), 8.29 (s, 1H), 7.84-7.83 (d, J=3.9 Hz, 1H), 7.52 (s, 2H), 7.3-7.27 (d, J=7.2 Hz, 1H), 7.19-6.69 (m, 2H), 4.43 (bs, 1H), 3.74 (s, 3H), 1.80-1.76 (d, J=12.6 Hz, 2H), 1.39-1.31 (m, 8H), 1.18 (m, 6H).

I-445: N2-{3-Chloro-4-[2-(4-morpholino)ethoxy]}phenyl-5-cyano-N4-(2,2,6,6-tetramethylpiperidin-4-yl)-2,4-pyrimidinediamine MS (m/e) 514.06 (MH+); $^1$H NMR (DMSO-$d_6$): δ 9.75 (s, 1H), 8.26 (bs, 1H), 7.64 (s, 1H), 7.56-7.49 (m, 3H), 7.03-7.0 (d, J=8.4 Hz, 1H), 4.50 (bs, 1H), 4.11-4.08 (t, J=5.4 Hz, 2H), 3.55 (bs, 4H), 2.7-2.66 (t, J=5.7 Hz, 2H), 2.53 (bs, 4H), 1.75-1.7 (d, J=12.6 Hz, 2H), 1.49-1.41 (t, J=12.6 Hz, 2H), 1.26 (bs, 6H), 1.19 (bs, 6H).

I-446: 5-Fluoro-N2-[3,5-dichloro]phenyl-N4-[1-(propionylhydrazine)-2,2,6,6-pentamethylpiperidin-4-yl]-2,4-pyrimidinediamine LCMS: purity: 90%; MS (m/e): 498 (MH+); $^1$H NMR (CD3OD): δ 7.81 (d, J=2.7 Hz, 1H), 7.60 (m, 2H), 6.95 (t, J=2.7 Hz, 1H), 4.55 (m, 1H), 3.10 (m, 4H), 1.55-2.00 (m, 4H), 1.38 (m, 12H).

I-447: 5-Fluoro-N2-[3,5-dichloro]phenyl-N4-[1-(2-ethylamine)-2,2,6,6-pentamethylpiperidin-4-yl]-2,4-pyrimidinediamine LCMS: purity: 90%; MS (m/e): 455 (MH+); $^1$H NMR (CD$_3$OD): δ 7.80 (d, J=2.7 Hz, 1H), 7.62 (m, 2H), 6.94 (t, J=2.7 Hz, 1H), 4.56 (m, 1H), 3.16 (m, 4H), 1.57-2.00 (m, 4H), 1.39 (m, 12H).

I-448: 5-Amide-N2-{5-[2-(methylmorphine)-3-trifluoromethyl]pyridine}-N4-(1,2,2,6,6-pentamethylpiperidin-4-yl)-2,4-pyrimidinediamine LCMS: purity: 90%; MS (m/e): 550 (MH+); $^1$H NMR (CD$_3$OD): δ 9.00 (s, 1H), 8.30 (s, 1H), 6.80 (s, 1H), 3.55 (s, 3H), 2.90-1.60 (m, 16H), 1.50 (m, 12H).

I-449: 5-Fluoro-N2-{5-[2-(methylmorphine)-3-trifluoromethyl]pyridine}-N4-(2,2,6,6-tetramethylpiperidin-4-yl)-2,4-pyrimidinediamine LCMS: purity: 90%; MS (m/e): 511 (MH+); $^1$H NMR (CD$_3$OD): δ 8.94 (s, 1H), 8.19 (d, J=2.1 Hz, 1H), 7.82 (d, J=2.1 Hz, 1H), 4.63 (m, 1H), 3.27 (s, 3H), 2.88-1.90 (m, 12H), 1.57 (m, 12H).

I-450: 5-Fluoro-N2-[4-(methylmorphine)-3-cyano]phenyl-N4-(1,2,2,6,6-pentamethylpiperidin-4-yl)-2,4-pyrimidinediamine LCMS: purity: 90%; MS (m/e): 482 (MH+); $^1$H NMR (CD$_3$OD): δ 8.60 (s, 1H), 8.50 (s, 1H), 8.21 (m, 1H), 7.77 (m, 1H), 4.57 (m, 1H), 3.52 (s, 3H), 3.07-1.73 (m, 15H), 1.44 (s, 12H).

I-451: 5-Fluoro-N2-{5-[2-(methylmorphine)-3-cyano]pyridin}-N4-(2,2,6,6-tetramethylpiperidin-4-yl)-2,4-pyrimidinediamine LCMS: purity: 90%; MS (m/e): 468 (MH+); $^1$H NMR (CD$_3$OD): δ 8.41 (s, 1H), 8.26 (d, J=2.4 Hz, 1H), 7.79 (d, J=2.4 Hz, 1H), 4.61 (m, 1H), 3.53 (s, 3H), 2.74-2.13 (m, 12H), 1.50 (m, 12H).

I-452: 5-Cyano-N2-{5-[2-(methylmorphine)-3-trifluoromethyl]pyridine}-N4-(1,2,2,6,6-pentamethylpiperidin-4-yl)-2,4-pyrimidinediamine LCMS: purity: 90%; MS (m/e): 532 (MH+); $^1$H NMR (CD$_3$OD): δ 9.01 (s, 1H), 8.33 (s, 1H), 6.60 (s, 1H), 3.58 (s, 3H), 2.98-1.87 (m, 16H), 1.51 (m, 12H).

I-453: 3-(5-fluoro-4-(2,2,6,6-tetramethylpiperidin-4-ylamino)pyrimidin-2-ylamino)-5-methoxyphenol MS (m/e) 390.24 (MH+); 1H NMR (DMSO-d6): δ 8.85 (s, 1H), 8.21 (s, 1H), 7.85 (d, 1H), 7.47 (d, 1H), 6.79 (s, 2H), 5.85 (s, 1H), 4.58 (m, 2H), 3.59 (s, 3H), 1.95-1.84 (d, 2H), 1.65-1.52 (t, 2H), 1.49-1.35 (d, 12H).

I-454: 5-fluoro-N2-[4-(5-methyl-1H-tetrazol-1-yl)]phenyl-N4-(1,2,2,6,6-pentamethylpiperidin-4-yl)-2,4-pyrimidinediamine LCMS: purity: 87.85%; MS (m/e): 440.35 (MH+); $^1$H NMR (DMSO-$d_6$): δ 1.41 (s, 6H), 1.43 (s, 6H), 1.82 (t, J=13.8 Hz, 2H), 2.11 (d, J=12.9 Hz, 2H), 2.74 (d, J=4.8 Hz, 3H), 4.49 (br, 1H), 7.46 (d, J=8.7 Hz, 2H), 7.72 (d, 1H), 7.89 (d, J=8.7 Hz, 2H), 7.98 (d, 1H), 8.58 (br, 1H), 9.57 (s, 1H).

I-455: 5-fluoro-N2-[4-methyl-3-(1H-tetrazol-1-yl)]phenyl-N4-(2,2,6,6-tetramethylpiperidin-4-yl)-2,4-pyrimidinediamine LCMS: purity: 88.71%; MS (m/e): 425.93 (MH+); $^1$H NMR (DMSO-$d_6$): δ 1.24 (s, 6H), 1.33 (s, 6H), 1.53 (t, J=12.3 Hz, 2H), 1.92 (d, J=14.7 Hz, 2H), 2.01 (s, 3H), 4.39 (br, 1H), 7.33 (d, J=8.4 Hz, 1H), 7.62 (d, 1H), 7.75 (d, J=6.0 Hz, 2H), 7.81 (s, 1H), 7.95 (d, J=3.6 Hz, 1H), 8.57 (br, 1H), 9.38 (s, 1H), 9.84 (s, 1H).

I-456: 5-aminocarbonyl-N2-[3-(5-methylthio-1H-tetrazol-1-yl)]phenyl-N4-(1,2,2,6,6-pentamethylpiperidin-4-yl)-2,4-pyrimidinediamine LCMS: purity: 96.94%; MS (m/e): 497.65 (MH+); $^1$H NMR (DMSO-$d_6$): δ 0.98 (s, 6H), 1.16 (s, 6H), 1.36 (t, 2H), 1.97 (d, 2H), 2.34 (s, 3H), 2.76 (s, 3H), 4.26 (br, 1H), 6.53 (s, 1H), 7.17 (d, J=7.5 Hz, 1H), 7.48 (t, J=7.8 Hz, 1H), 7.92 (d, J=7.5 Hz, 1H), 8.08 (s, 1H), 8.55 (s, 1H), 9.21 (d, 1H), 9.92 (s, 1H).

I-457: 5-aminocarbonyl-N2-[3-(5-methylthio-1H-tetrazol-1-yl)]phenyl-N4-(2,2,6,6-tetramethylpiperidin-4-yl)-2,4-pyrimidinediamine LCMS: purity: 84.21%; MS (m/e): 482.91 (MH+); $^1$H NMR (DMSO-$d_6$): δ 1.22 (s, 6H), 1.34 (s, 6H), 1.41 (t, J=12.6 Hz, 2H), 2.08 (d, J=9.6 Hz, 2H), 2.77 (s, 3H), 4.40 (br, 1H), 7.20 (d, J=8.7 Hz, 1H), 7.51 (t, J=8.1 Hz, 1H), 7.69 (d, 1H), 7.87 (d, J=6.9 Hz, 1H), 8.07 (s, 1H), 8.58 (s, 2H), 9.35 (d, 1H), 9.96 (s, 1H).

I-458: 5-fluoro-N2-{4-[5-(furan-2-yl)-1H-tetrazol-1-yl]}phenyl-N4-(1,2,2,6,6-pentamethylpiperidin-4-yl)-2,4-pyrimidinediamine LCMS: purity: 99.97%; MS (m/e): 492.48 (MH+); $^1$H NMR (DMSO-$d_6$): δ 1.23 (s, 12H), 1.66 (t, 2H), 1.91 (d, 2H), 4.43 (br, 1H), 6.64 (s, 2H), 7.44 (d, J=9.0 Hz, 2H), 7.52 (br, 1H), 7.94 (m, 4H), 9.57 (s, 1H); $^{19}$F NMR (282 MHz, DMSO-$d_6$): δ−180.24.

I-459: 5-cyano-N2-[4-methyl-3-(1H-tetrazol-1-yl)]phenyl-N4-(1,2,2,6,6-pentamethylpiperidin-4-yl)-2,4-pyrimidinediamine LCMS: purity: 97.43%; MS (m/e): 447.40 (MH+); $^1$H NMR (DMSO-$d_6$): δ 0.90 (s, 6H), 1.08 (s, 6H), 1.62 (m, 4H), 2.04 (s, 3H), 2.21 (s, 3H), 4.36 (br, 1H), 7.34 (d, J=8.1 Hz, 1H), 7.51 (d, 1H), 7.66 (br, 1H), 7.92 (d, 1H), 8.34 (s, 1H), 9.83 (s, 1H), 9.99 (br, 1H).

I-460: 5-cyano-N2-[4-ethoxy-3-(5-ethyl-1H-tetrazol-1-yl)]phenyl-N4-(1,2,2,6,6-pentamethylpiperidin-4-yl)-2,4-pyrimidinediamine LCMS: purity: 99.99%; MS (m/e): 505.56 (MH+); $^1$H NMR (DMSO-$d_6$): δ 0.96 (s, 6H), 1.15 (s, 6H), 1.15 (t, J=6.9 Hz, 3H), 1.21 (t, J=7.5 Hz, 3H), 1.62-1.70 (m, 4H), 2.32 (s, 3H), 2.68 (q, J=7.5 Hz, 2H), 4.04 (q, J=6.9 Hz, 2H), 4.37 (br, 1H), 7.19 (d, J=8.7 Hz, 1H), 7.53 (d, 1H), 7.65 (s, 1H), 7.87 (d, 1H), 8.32 (s, 1H), 9.91 (br, 1H).

I-461: 5-cyano-N2-[4-methyl-3-(1H-tetrazol-1-yl)]phenyl-N4-(2,2,6,6-tetramethylpiperidin-4-yl)-2,4-pyrimidinediamine LCMS: purity: 88.74%; MS (m/e): 433.48 (MH+); $^1$H NMR (DMSO-$d_6$): δ 1.12 (s, 6H), 1.20 (s, 6H), 1.48 (t, J=12.0 Hz, 2H), 1.74 (d, J=13.2 Hz, 2H), 2.04 (s, 3H), 4.45 (br, 1H), 7.36 (d, J=8.1 Hz, 1H), 7.68 (m, 2H), 7.89 (d, 1H), 8.23 (s, 1H), 8.36 (s, 1H), 9.83 (s, 1H), 10.04 (br, 1H).

I-462: 5-cyano-N2-[3-(5-methyl-1H-tetrazol-1-yl)]phenyl-N4-(1,2,2,6,6-pentamethylpiperidin-4-yl)-2,4-pyrimidinediamine LCMS: purity: 91.90%; MS (m/e): 447.21 (MH+); $^1$H NMR (DMSO-$d_6$): δ 1.24 (s, 6H), 1.38 (s, 6H), 1.86 (t, J=12.3 Hz, 2H), 2.01 (d, J=14.1 Hz, 2H), 2.57 (s, 3H), 2.70 (d, J=5.7 Hz, 3H), 4.49 (br, 1H), 7.30 (d, J=7.5 Hz, 1H), 7.50 (t, J=7.8 Hz, 1H), 7.80 (br, 1H), 7.89 (d, J=8.7 Hz, 1H), 7.95 (br, 1H), 8.42 (s, 1H), 8.51 (br, 1H), 10.11 (br, 1H).

I-463: 5-cyano-N2-[3-(5-methyl-1H-tetrazol-1-yl)]phenyl-N4-(2,2,6,6-tetramethylpiperidin-4-yl)-2,4-pyrimidinediamine LCMS: purity: 96.33%; MS (m/e): 433.21 (MH+); $^1$H NMR (DMSO-$d_6$): δ 1.22 (s, 6H), 1.33 (s, 6H), 1.62 (t, J=12.9 Hz, 2H), 1.89 (d, J=14.1 Hz, 2H), 2.56 (s, 3H), 4.50 (br, 1H), 7.29 (d, J=7.2 Hz, 1H), 7.51 (t, J=8.1 Hz, 1H), 7.83 (m, 3H), 7.91 (d, J=7.2 Hz, 1H), 8.41 (s, 1H), 8.58 (d, 1H), 10.15 (br, 1H).

I-464: 5-cyano-N2-[3-(5-methylthio-1H-tetrazol-1-yl)]phenyl-N4-(1,2,2,6,6-pentamethylpiperidin-4-yl)-2,4-pyrimidinediamine LCMS: purity: 100%; MS (m/e): 479.58 (MH+); $^1$H NMR (DMSO-$d_6$): δ 1.22 (s, 6H), 1.37 (s, 6H), 1.85 (t, J=13.5 Hz, 2H), 2.01 (d, J=14.1 Hz, 2H), 2.68 (d, 3H), 2.77 (s, 3H), 4.50 (br, 1H), 7.27 (d, J=7.5 Hz, 1H), 7.52 (t, J=8.1 Hz, 1H), 7.91 (m, 3H), 8.42 (s, 1H), 8.54 (br, 1H), 10.24 (br, 1H).

I-465: 5-cyano-N2-[3-(5-methylthio-1H-tetrazol-1-yl)]phenyl-N4-(2,2,6,6-tetramethylpiperidin-4-yl)-2,4-pyrimidinediamine LCMS: purity: 100%; MS (m/e): 465.16 (MH+); $^1$H NMR (DMSO-$d_6$): δ 1.18 (s, 6H), 1.32 (s, 6H), 1.61 (t, J=14.1 Hz, 2H), 1.89 (d, J=9.9 Hz, 2H), 2.77 (s, 3H), 4.43 (br, 1H), 7.26 (d, J=7.5 Hz, 1H), 7.53 (t, J=8.1 Hz, 1H), 7.75 (d, 1H), 7.85 (d, J=8.1 Hz, 1H), 7.94 (s, 1H), 8.42 (s, 1H), 8.52 (d, 1H), 10.26 (br, 1H).

I-466: 5-fluoro-N2-[4-fluoro-3-(1H-tetrazol-1-yl)]phenyl-N4-(1,2,2,6,6-pentamethylpiperidin-4-yl)-2,4-pyrimidinediamine LCMS: purity: 82.69%; MS (m/e): 444.15 (MH+); $^1$H NMR (DMSO-$d_6$): δ 1.27 (s, 6H), 1.38 (s, 6H), 1.77 (t, J=13.5 Hz, 2H), 2.05 (d, J=12.6 Hz, 2H), 2.68 (d, 3H), 4.37 (br, 1H), 7.46 (t, J=10.5 Hz, 1H), 7.69 (br, 1H), 7.84 (d, 1H), 7.96 (d, 1H), 8.12 (br, 1H), 8.55 (br, 1H), 9.45 (br, 1H), 9.94 (s, 1H); $^{19}$F NMR (282 MHz, DMSO-$d_6$): δ−180.06.

I-467: 5-fluoro-N2-[4-fluoro-3-(1H-tetrazol-1-yl)]phenyl-N4-(2,2,6,6-tetramethylpiperidin-4-yl)-2,4-pyrimidinediamine LCMS: purity: 98.32%; MS (m/e): 430.66 (MH+); $^1$H NMR (DMSO-$d_6$): δ 1.23 (s, 6H), 1.33 (s, 6H), 1.53 (m, 2H), 1.93 (d, J=12.9 Hz, 2H), 4.37 (br, 1H), 7.48 (t, 1H), 7.72 (br, 1H), 7.80 (d, 1H), 7.98 (d, 1H), 8.15 (br, 1H), 8.53 (br, 1H), 9.53 (br, 1H), 9.94 (s, 1H).

I-468: 5-aminocarbonyl-N2-[4-fluoro-3-(1H-tetrazol-1-yl)]phenyl-N4-(1,2,2,6,6-pentamethylpiperidin-4-yl)-2,4-pyrimidinediamine LCMS: purity: 91.33%; MS (m/e): 469.01 (MH+); $^1$H NMR (DMSO-$d_6$): δ 1.23 (s, 6H), 1.37 (s, 6H), 1.61 (t, J=11.7 Hz, 2H), 2.17 (d, J=8.1 Hz, 2H), 2.70 (d, J=5.1 Hz, 3H), 4.35 (br, 1H), 7.31 (br, 1H), 7.51 (t, J=10.2 Hz, 1H), 7.91 (m, 2H), 8.15 (br, 1H), 8.58 (s, 2H), 9.32 (br, 1H), 9.96 (s, 1H).

I-469: 5-cyano-N2-[4-ethoxy-3-(5-ethyl-1H-tetrazol-1-yl)]phenyl-N4-(2,2,6,6-tetramethylpiperidin-4-yl)-2,4-pyrimidinediamine LCMS: purity: 95.62%; MS (m/e): 491.22 (MH+); $^1$H NMR (DMSO-$d_6$): δ 1.16 (m, 12H), 1.34 (s, 6H), 1.62 (t, J=10.5 Hz, 2H), 1.86 (d, J=13.8 Hz, 2H), 2.68 (q, J=7.2 Hz, 2H), 4.02 (q, 2H), 4.42 (br, 1H), 7.24 (d, J=8.4 Hz, 1H), 7.74-7.81 (m, 4H), 8.35 (s, 1H), 8.60 (br, 1H), 9.96 (br, 1H).

I-470: 5-Fluoro-N4-(1,2,2,6,6-pentamethylpiperidin-4-yl)-N2-[3-(tetrazol-5-yl)]phenyl-2,4-pyrimidinediamine MS (m/e) 426.11 (MH$^+$); $^1$H NMR (DMSO-$d_6$): δ 8.97 (s, 1H), 7.99-7.96 (d, J=8.7 Hz, 1H), 7.91 (s, 1H), 7.83-7.82 (d, J=3.6 Hz, 1H), 7.47-7.44 (d, J=7.5 Hz, 1H), 7.13-7.08 (m, 2H), 4.4 (bs, 1H), 2.18 (s, 3H), 1.72-1.68 (d, J=12 Hz, 2H), 1.49-1.42 (d, J=11.7 Hz, 2H), 1.07 (s, 12H).

I-471: 5-Fluoro-N4-(2,2,6,6-tetramethylpiperidin-4-yl)-N2-[3-(tetrazol-5-yl)]phenyl-2,4-pyrimidinediamine MS (m/e) 412.07 (MH+); ¹H NMR (DMSO-d₆): δ 8.97 (s, 1H), 8.0-7.98 (d, J=7.5 Hz, 1H), 7.91 (s, 1H), 7.83-7.81 (d, J=3.9 Hz, 1H), 7.47-7.44 (d, J=7.5 Hz, 1H), 7.13-7.07 (m, 2H), 4.5 (bs, 1H), 1.74-1.7 (d, J=12 Hz, 2H), 1.21-1.13 (m, 8H), 1.07 (s, 12H).

I-472: 5-Cyano-N2-[3-(2,5-dimethyl-pyrrol-1-yl)-4-methoxy]phenyl-N4-(1,2,2,6,6-pentamethylpiperidin-4-yl)-2,4-pyrimidinediamine MS (m/e) 488.30 (MH+); ¹H NMR (DMSO-d₆): δ 9.86 (bs, 1H), 8.29 (s, 1H), 7.93 (s, 1H), 7.45 (bs, 1H), 7.21 (s, 1H), 7.00 (s, 1H), 4.47 (m, 1H), 3.65 (s, 3H), 2.31 (bs, 6H), 1.86 (s, 6H), 1.71-1.64 (m, 2H), 1.16-1.64 (m, 12H).

I-473: 5-Cyano-N2-(3-difluoromethoxy-4-methoxy)phenyl-N4-(2,2,6,6-tetramethylpiperidin-4-yl)-2,4-pyrimidinediamine MS (m/e) 447.72 (MH+); ¹H NMR (DMSO-d₆): δ 9.80 (bs, 1H), 8.62 (bs, 1H), 7.78 (bs, 1H), 7.47 (s, 2H), 7.23-6.74 (m, 2H), 4.58 (bs, 1H), 3.77 (s, 3H), 1.85 (m, 2H), 1.62 (m, 2H), 1.62 (s, 12H).

II-1: 5-Fluoro-N4-(1,2,2,6,6-pentamethylpiperidin-4-yl)-N2-(quinolin-6-yl)-2,4-pyrimidinediamine MS (m/e) 409.07 (MH+); ¹H NMR (DMSO-d₆): δ 9.35 (s, 1H), 8.65 (s, 1H), 8.14 (s, 1H), 8.13 (s, 1H), 8.10 (s, 1H), 8.07 (s, 1H), 7.92-7.91 (d, J=3.9 Hz, 1H), 7.82-7.79 (d, J=9.0 Hz, 1H), 7.41-7.38 (m, 1H), 7.30-7.27 (d, J=8.1 Hz, 1H), 4.46 (bm, 1H), 2.24 (s, 3H), 1.77-1.73 (d, J=12 Hz, 2H), 1.58-1.50 (t, J=12.9 Hz, 2H), 1.11 (s, 12H).

II-2: N2-(3,4-Dihydroquinolin-1H-2-one-6-yl)-5-fluoro-N4-(1,2,2,6,6-pentamethylpiperidin-4-yl)-2,4-pyrimidinediamine MS (m/e) 427.07 (MH+); ¹H NMR (DMSO-d₆): δ 9.84 (s, 1H), 8.79 (s, 1H), 7.83-7.82 (d, J=3.6 Hz, 1H), 7.54-7.51 (d, J=7.8 Hz, 1H), 7.26 (s, 2H), 6.69-6.66 (d, J=8.4 Hz, 1H), 4.39 (bm, 1H), 2.80-2.75 (t, J=7.2 Hz, 2H), 2.40-2.35 (t, J=7.8 Hz, 2H), 1.90-1.86 (d, J=10.8 Hz, 2H), 1.66-1.58 (t, J=12.3 Hz, 2H), 1.23 (s, 12H).

II-3: N2-(1H-Benzoxazin-3-one-6-yl)-5-fluoro-N4-(1,2,2,6,6-pentamethylpiperidin-4-yl)-2,4-pyrimidinediamine MS (m/e) 429.09 (MH+); ¹H NMR (DMSO-d₆): δ 10.58 (s, 1H), 8.88 (s, 1H), 7.81 (s, 1H), 7.29 (bs, 2H), 7.05 (s, 1H), 6.74-6.71 (d, J=8.7 Hz, 1H), 4.45 (s, 2H), 4.39 (bm, 1H), 1.80 (bs, 2H), 1.63 (bs, 2H), 1.23 (s, 12H).

II-4: 5-Fluoro-N2-(1-methyl-3,4-dihydroquinolin-2-one-6-yl)-N4-(1,2,2,6,6-pentamethylpiperidin-4-yl)-2,4-pyrimidinediamine MS (m/e) 441.16 (MH+); ¹H NMR (DMSO-d₆): δ 8.87 (s, 1H), 7.84-7.83 (d, J=3.6 Hz, 1H), 7.64-7.61 (d, J=9.0 Hz, 1H), 7.35 (s, 1H), 7.27-7.25 (d, J=7.2 Hz, 1H), 6.87-6.85 (d, J=8.7 Hz, 1H), 4.39 (bm, 1H), 3.19 (s, 3H), 2.80-2.75 (t, J=7.2 Hz, 2H), 2.41 (s, 2H), 1.87-1.83 (d, J=12.3 Hz, 2H), 1.63-1.55 (t, J=11.7 Hz, 2H), 1.14 (s, 12H).

II-5: N2-(1-Ethyl-3,4-dihydroquinolin-2-one-6-yl)-5-fluoro-N4-(1,2,2,6,6-pentamethylpiperidin-4-yl)-2,4-pyrimidinediamine MS (m/e) 455.16 (MH+); ¹H NMR (DMSO-d₆): δ 8.87 (s, 1H), 7.83-7.82 (d, J=3.0 Hz, 1H), 7.65-7.63 (d, J=8.4 Hz, 1H), 7.32 (s, 1H), 7.24-7.21 (d, J=8.1 Hz, 1H), 6.91-6.88 (d, J=8.4 Hz, 1H), 4.40 (bm, 1H), 3.87-3.81 (q, 2H), 2.77-2.73 (t, J=6.9 Hz, 2H), 2.35 (s, 3H), 1.82-1.78 (d, J=11.4 Hz, 2H), 1.60-1.52 (t, J=12.3 Hz, 2H), 1.14 (s, 12H), 1.12-1.07 (t, J=7.2 Hz, 3H).

II-6: 5-Fluoro-N2-(4-methyl-2H-1,4-benzoxazin-3-one-7-yl)-N4-(1,2,2,6,6-pentamethylpiperidin-4-yl)-2,4-pyrimidinediamine MS (m/e) 443.08 (MH+); ¹H NMR (DMSO-d₆): δ 9.02 (s, 1H), 8.12 (s, 1H), 7.83-7.82 (d, J=3.9 Hz, 1H), 7.53 (s, 1H), 7.31-7.28 (d, J=8.4 Hz, 1H), 7.24-7.21 (d, J=7.8 Hz, 1H), 6.93-6.90 (d, J=8.7 Hz, 1H), 4.53 (s, 3H), 4.40 (bm, 1H), 3.21 (s, 3H), 2.28 (s, 3H), 1.76 (d, J=10.2 Hz, 2H), 1.56-1.48 (t, J=11.7 Hz, 2H), 1.14 (m, 12H).

II-7: 5-Fluoro-N2-(2-methylquinolin-6-yl)-N4-(1,2,2,6,6-pentamethylpiperidin-4-yl)-2,4-pyrimidinediamine MS (m/e) 423.16 (MH+); ¹H NMR (DMSO-d₆): δ 9.28 (s, 1H), 8.05-7.97 (m, 3H), 7.93-7.91 (d, J=3.3 Hz, 1H), 7.73-7.70 (d, J=9.6 Hz, 1H), 7.39 (s, 1H), 7.29-7.26 (d, J=8.4 Hz, 1H), 4.47 (bm, 1H), 3.15 (s, 1H), 2.58 (s, 3H), 1.88 (bs, 2H), 1.67-1.61 (t, J=10.2 Hz, 2H), 1.23 (s, 12H).

II-8: N2-(2,2-Difluoro-4-methyl-2H-1,4-benzoxazin-3-one-7-yl)-5-fluoro-N4-(1,2,2,6,6-pentamethylpiperidin-4-yl)-2,4-pyrimidinediamine MS (m/e) 479.18 (MH+); ¹H NMR (DMSO-d₆): δ 9.34 (s, 1H), 7.99 (s, 1H), 7.92-7.91 (d, J=3.6 Hz, 1H), 7.49 (bs, 1H), 7.37-7.34 (d, J=8.7 Hz, 1H), 7.24-7.21 (d, J=9.3 Hz, 1H), 4.46 (m, 1H), 3.38 (s, 3H), 1.94-1.90 (d, J=12.0 Hz, 2H), 1.73-1.64 (t, J=12.3 Hz, 2H), 1.30 (s, 6H), 1.27 (s, 6H).

II-9: 5-Fluoro-N2-(2-methylbenzoimidazol-5-yl)-N4-(1,2,2,6,6-pentamethylpiperidin-4-yl)-2,4-pyrimidinediamine LCMS: purity: 96.74%; MS (m/e): 412.15 (MH+); ¹H NMR (DMSO-d₆): δ 1.05 (s, 6H), 1.07 (s, 6H), 1.44 (t, J=12.0 Hz, 2H), 1.68 (d, J=9.0 Hz, 2H), 2.18 (s, 3H), 2.40 (s, 3H), 4.39 (m, 1H), 7.05-7.23 (m, 2H), 7.53-7.67 (m, 2H), 7.80 (m, 1H), 8.74-8.80 (m, 1H), 11.81 (m, 1H); ¹⁹F NMR (282 MHz, DMSO-d₆): δ−167.52.

II-10: Methyl 3-[4-(2-(2,3-dihydrobenzo[b][1,4]dioxin-6-ylamino)-5-fluoropyrimidine-4-ylamino)-2,2,6,6-tetramethylpiperidin-1-yl]propanoate MS (m/e): 488.46 (MH+); ¹H NMR (DMSO-d6): δ 1.41 (s, 6H), 1.43 (s, 6H), 1.95 (m, 2H), 2.22 (d, J=12.2 Hz, 2H), 2.45 (t, J=11.9 Hz, 2H), 2.80 (t, J=12.0 Hz, 2H), 4.32 (m, 4H), 4.50 (m, 1H), 6.52 (m, 1H), 6.91 (m, 1H), 7.18 (m, 1H), 7.54 (d, J=7.2 Hz, 1H), 8.15 (d, J=4.1 Hz, 1H), 9.43 (s, 1H); LCMS: purity: 98.26%.

II-11: 5-Fluoro-N2-(4H-imidazo[2,1-c][1,4]-benzoxazin-7-yl)N4-(1,2,2,6,6-pentamethylpiperidin-4-yl)-2,4-pyrimidinediamine LCMS: purity: 97.24%; MS (m/e): 452.55 (MH+); $^1$H NMR (DMSO-d6): δ 1.34-1.43 (m, 12H), 1.82-1.91 (t, J=12.0 Hz, 2H), 2.04-2.09 (m, 2H), 2.75 (s, 3H), 4.52 (br, 1H), 5.42 (s, 2H), 7.23 (d, J=7.5 Hz, 1H), 7.53 (s, 1H), 7.66 (d, J=7.8 Hz, 1H), 7.77 (s, 1H), 8.15-8.18 (m, 1H), 8.82 (s, 1H), 9.89 (s, 1H).

II-12: N2-(5-chlorobenzo[d]oxazol-2-yl)-5-fluoro-N4-(1,2,2,6,6-pentamethylpiperidin-4-yl)pyrimidine-2,4-diamine MS (m/e) 434.16 (MH+); $^1$H NMR (CDCl$_3$): δ8.29 (s, 1H), 8.06 (d, 1H), 7.99 (s, 1H), 7.15 (s, 2H), 4.53 (bm, 2H), 2.76 (s, 3H), 2.45-2.26 (t, 2H), 2.12-2.02 (d, 2H), 1.56-1.46 (d, 12H).

II-13: 5-fluoro-N4-(1,2,2,6,6-pentamethylpiperidin-4-yl)-N2-(5-(trifluoromethyl)-1,3,4-thiadiazol-2-yl)pyrimidine-2,4-diamine MS (m/e) 434.18 (MH+); $^1$H NMR (DMSO-d6): δ8.06 (d, 1H), 7.85 (d, 1H), 4.59 (bm, 2H), 2.66 (s, 3H), 1.82-1.72 (d, 2H), 1.64-1.52 (d, 2H), 1.14 (d, 12H).

II-14: 5-fluoro-N2-(5-nitrothiazol-2-yl)-N4-(1,2,2,6,6-pentamethylpiperidin-4-yl)pyrimidine-2,4-diamine MS (m/e) 410.17 (MH+); $^1$H NMR (CDCl$_3$): δ8.41 (s, 2H), 8.05 (d, 1H), 4.75 (bm, 2H), 2.76 (s, 3H), 2.48-2.36 (t, 2H), 2.06-1.86 (d, 2H), 1.62-1.52 (d, 12H).

II-15: N2-(4-(4-chlorophenyl)thiazol-2-yl)-5-fluoro-N4-(1,2,2,6,6-pentamethylpiperidin-4-yl)pyrimidine-2,4-diamine MS (m/e) 473.29 (MH−); $^1$H NMR (CDCl$_3$): δ8.29 (s, 1H), 7.89 (bs, 1H), 7.65 (d, 2H), 7.35 (d, 2H), 6.65 (s, 1H), 4.75 (bm, 2H), 2.78 (s, 3H), 2.45-2.39 (t, 2H), 2.06-1.86 (d, 2H), 1.67-1.56 (d, 12H).

II-16: N2-(benzo[d]thiazol-2-yl)-5-fluoro-N4-(1,2,2,6,6-pentamethylpiperidin-4-yl)pyrimidine-2,4-diamine MS (m/e) 415.18 (MH+); $^1$H NMR (CDCl$_3$): δ8.39 (s, 1H), 8.01 (d, 1H), 7.75 (d, 1H), 7.55 (d, 1H), 7.39 (t, 1H), 7.19 (t, 1H), 6.65 (s, 1H), 4.85 (bm, 1H), 2.78 (s, 3H), 2.45-2.37 (t, 2H), 2.14-2.04 (d, 2H), 1.59-1.56 (d, 12H).

II-17: 5-fluoro-N2-(6-nitrobenzo[d]thiazol-2-yl)-N4-(1,2,2,6,6-pentamethylpiperidin-4-yl)pyrimidine-2,4-diamine MS (m/e) 460.18 (MH+); $^1$H NMR (CDCl$_3$): δ8.49 (d, 1H), 8.41 (d, 1H), 8.25 (dd, 1H), 7.95 (d, 1H), 7.75 (dd, 1H), 4.85 (bm, 2H), 2.74 (s, 3H), 2.36-2.27 (t, 2H), 2.18-2.06 (d, 2H), 1.59-1.52 (d, 12H).

II-18: N2-(6-ethoxybenzo[d]thiazol-2-yl)-5-fluoro-N4-(1,2,2,6,6-pentamethylpiperidin-4-yl)pyrimidine-2,4-diamine MS (m/e) 459.23 (MH+); $^1$H NMR (CD$_3$OD): δ7.94 (d, 1H), 7.55 (d, 1H), 7.19 (d, 1H), 6.98 (dd, 1H), 4.85 (bm, 1H), 4.15 (q, 2H), 2.84 (s, 3H), 2.38-2.21 (d, 2H), 1.98-1.88 (t, 2H), 1.65 (s, 6H), 1.49 (s, 3H), 1.39 (t, 3H).

II-19: 5-fluoro-N2-(4-methylbenzo[d]thiazol-2-yl)-N4-(1,2,2,6,6-pentamethylpiperidin-4-yl)pyrimidine-2,4-diamine MS (m/e) 429.23 (MH+); $^1$H NMR (CD$_3$OD): δ8.22 (d, 1H), 7.45 (d, 1H), 7.18 (d, 1H), 7.08 (d, 1H), 4.75 (bm, 1H), 2.74 (s, 3H), 2.59 (s, 3H), 2.09-2.01 (d, 2H), 1.95-1.81 (t, 2H), 1.69 (s, 6H), 1.52 (s, 3H).

II-20: 5-fluoro-N2-(4-methoxybenzo[d]thiazol-2-yl)-N4-(1,2,2,6,6-pentamethylpiperidin-4-yl)pyrimidine-2,4-diamine MS (m/e) 445.20 (MH+); $^1$H NMR (CD$_3$OD): δ7.99 (d, 1H), 7.25 (d, 1H), 7.19 (d, 1H), 6.94 (d, 1H), 4.85 (bm, 1H), 3.99 (s, 3H), 2.79 (s, 3H), 2.35-2.21 (d, 2H), 2.01-1.89 (t, 2H), 1.69 (s, 6H), 1.52 (s, 3H).

II-21: 5-fluoro-N2-(5-(methylthio)-1,3,4-thiadiazol-2-yl)-N4-(1,2,2,6,6-pentamethylpiperidin-4-yl)pyrimidine-2,4-diamine MS (m/e) 412.14 (MH+); $^1$H NMR (CD$_3$OD): δ8.29 (d, 1H), 4.65 (bm, 1H), 2.85 (s, 3H), 2.69 (s, 3H), 2.35-2.25 (d, 2H), 1.99-1.85 (t, 2H), 1.65 (s, 6H), 1.52 (s, 3H).

II-22: 2-(5-fluoro-4-(1,2,2,6,6-pentamethylpiperidin-4-ylamino)pyrimidin-2-ylamino)-1H-imidazole-4,5-dicarbonitrile MS (m/e) 398.21 (MH+); $^1$H NMR (CD$_3$OD): δ8.19 (d, 1H), 4.85 (bm, 1H), 2.85 (s, 3H), 2.29-2.21 (d, 2H), 1.99-1.85 (t, 2H), 1.62 (s, 6H), 1.52 (s, 3H).

II-23: 5-fluoro-N4-(1,2,2,6,6-pentamethylpiperidin-4-yl)-N2-(thiazolo[5,4-b]pyridin-2-yl)pyrimidine-2,4-diamine MS (m/e) 416.15 (MH+); $^1$H NMR (DMSO-d6): δ9.42 (d, 1H), 8.74 (d, 1H), 8.54 (d, 1H), 8.39 (d, 1H), 8.24 (d, 1H), 8.01 (t, 1H), 4.43 (bm, 1H), 2.26 (s, 3H), 1.88-1.81 (d, 2H), 1.62-1.55 (t, 2H), 1.19-1.12 (d, 12H).

II-24: N2-(3,4-dihydro-2H-pyrido[3,2-b][1,4]oxazin-6-yl)-5-fluoro-N4-(1,2,2,6,6-pentamethylpiperidin-4-yl)pyrimidine-2,4-diamine MS (m/e) 416.22 (MH+); $^1$H NMR (DMSO-d6): δ9.22 (bs, 1H), 8.99 (bs, 1H), 8.15 (d, 2H), 7.45 (bs, 1H), 7.15 (d, 1H), 4.59 (bm, 1H), 4.25 (t, 2H), 3.49 (t, 2H), 2.49 (s, 3H), 2.12-2.05 (d, 2H), 1.99-1.75 (t, 2H), 1.49 (s, 12H).

II-25: N2-(2,2-Difluoro-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine MS (m/e) 466.09 (MH+); $^1$H NMR (DMSO-d6): δ 9.43 (s, 1H), 8.29-8.28 (d, J=3.3 Hz, 1H), 7.90-7.89 (d, J=3.3 Hz, 1H), 7.41-7.38 (d, J=7.8 Hz, 1H), 4.36 (bs, 1H), 2.28 (s, 3H), 1.77-1.73 (d, J=11.1 Hz, 2H), 1.58-1.50 (t, J=12.0 Hz, 2H), 1.14 (s, 12H).

II-26: N2-(2,2-Difluoro-4-methyl-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine MS (m/e) 480.11 (MH+); $^1$H NMR (DMSO-d6): δ 9.50 (s, 1H), 8.47 (s, 1H), 8.28 (s, 1H), 7.90-7.89 (d, J=3.6 Hz, 1H), 7.40-7.37 (d, J=8.1 Hz, 1H), 4.38 (bs, 1H), 3.41 (s, 3H), 2.23 (s, 3H), 1.74-1.70 (d, J=9.6 Hz, 2H), 1.55-1.47 (t, J=12.6 Hz, 2H), 1.11 (s, 12H).

II-27: N2-(2,2-Difluoro-4-ethyl-2H-pyrido[3,2-b]-1,4-oxazin-3(4H)-one-7-yl)-5-fluoro-N4-(1,2,2,6,6-pentamethylpiperidin-4-yl)-2,4-pyrimidinediamine MS (m/e) 494.15 (MH+); $^1$H NMR (DMSO-d6): δ 9.49 (s, 1H), 8.54 (s, 1H), 8.23 (s, 1H), 7.91 (s, 1H), 7.38 (s, 1H), 4.37 (bs, 1H), 4.10-4.07 (t, J=6.6 Hz, 2H), 2.26 (s, 3H), 1.76-1.72 (d, J=12.6 Hz, 2H), 1.56-1.49 (m, 2H), 1.23-1.12 (m, 15H).

II-28: 5-Chloro-N2-(2,2-difluoro-4-methyl-2H-1,4-benzoxazin-3(4H)-one-7-yl)-N4-(1,2,2,6,6-pentamethylpiperidin-4-yl)-2,4-pyrimidinediamine MS (m/e) 495.13 (MH+); $^1$H NMR (DMSO-d6): δ 9.46 (s, 1H), 8.14 (s, 1H), 7.99-7.98 (d, J=2.4 Hz, 1H), 7.40-7.37 (d, J=9.0 Hz, 1H), 7.36-7.21 (d, J=9.0 Hz, 1H), 6.82-6.79 (d, J=8.7 Hz, 1H), 4.50 (bs, 1H), 3.38 (s, 3H), 2.23 (s, 3H), 1.70-1.56 (m, 4H), 1.13 (s, 12H).

II-29: N2-(3,4-Ethylenedioxy)phenyl-5-fluoro-N4-(1,2,2,6,6-pentamethylpiperidin-4-yl)-2,4-pyrimidinediamine MS (m/e) 416.15 (MH+); $^1$H NMR (DMSO-d6): δ 8.75 (s, 1H), 7.79 (s, 1H), 7.22 (s, 1H), 7.17-7.08 (m, 2H), 6.63-6.58 (m, 1H), 4.38 (bs, 1H), 4.14 (s, 3H), 2.29 (s, 3H), 1.76-1.72 (d, J=12 Hz, 2H), 1.57-1.48 (t, J=12.6, 2H), 1.13 (s, 12H).

II-30: 5-Fluoro-N2-(2-methyl-benzoxazol-5-yl)-N4-(1,2,2,6,6-pentamethylpiperidin-4-yl)-2,4-pyrimidinediamine MS (m/e) 412.5 (MH+); $^1$H NMR (DMSO-d6): δ 9.31 (s, 1H), 8.56 (s, 1H), 7.95-7.93 (d, J=3.6 Hz, 1H), 7.82 (s, 1H), 7.08 (s, 1H), 6.75-6.72 (d, J=8.1 Hz, 1H), 4.39 (s, 1H), 2.71 (s, 3H), 2.07 (s, 3H), 2.00 (s, 2H), 1.80-1.72 (t, J=12.0 Hz, 2H), 1.37 (s, 6H), 1.28 (s, 6H).

II-31: N2-(2,2-Difluoro-4-ethyl-benzoxazin-3-one-7-yl)-5-fluoro-N4-(1,2,2,6,6-pentamethylpiperidin-4-yl)-2,4-pyrimidinediamine MS (m/e) 493.20 (MH+); $^1$H NMR (DMSO-d6): δ 9.33 (s, 1H), 8.01 (s, 1H), 7.88 (s, 1H), 7.37-7.25 (m, 3H), 4.41 (s, 1H), 3.99 (bs, 2H), 2.25 (s, 3H), 1.74-1.70 (d, J=12.3 Hz, 2H), 1.57-1.49 (t, J=12.3 Hz, 2H), 1.14 (bs, 15H).

II-32: 5-Fluoro-N2-(3,4-methylenedioxy)phenyl-N4-(1,2,2,6,6-pentamethylpiperidin-4-yl)-2,4-pyrimidinediamine MS (m/e) 402.18 (MH+); $^1$H NMR (DMSO-d6): δ 8.86 (s, 1H), 8.14 (s, 1H), 7.80-7.79 (d, J=3.6 Hz, 1H), 7.37 (s, 1H), 7.18-7.16 (d, J=8.4 Hz, 2H), 7.07-7.04 (d, J=8.7 Hz, 1H), 6.70-6.67 (d, J=8.4 Hz, 1H), 5.88 (s, 2H), 4.37 (s, 1H), 2.25 (s, 3H), 1.74-1.71 (d, J=9.0 Hz, 2H), 1.54-1.46 (t, J=12.3 Hz, 2H), 1.12 (s, 12H).

II-33: N2-(2,2-Dimethyl-1,4-benzoxazin-4H-3-one-7-yl)-5-fluoro-N4-(1,2,2,6,6-pentamethylpiperidin-4-yl)-2,4-pyrimidinediamine MS (m/e) 457.60 (MH+); $^1$H NMR (DMSO-d6): δ 10.34 (s, 1H), 9.02 (s, 1H), 7.85-7.83 (d, J=3.9 Hz, 1H), 7.61 (s, 1H), 7.34-7.31 (d, J=8.1 Hz, 1H), 7.07-7.05 (d, J=8.4 Hz, 1H), 6.69-6.66 (d, J=8.7 Hz, 1H), 4.49 (s, 1H), 2.42 (s, 3H), 1.86-1.82 (d, J=12 Hz, 2H), 1.66-1.58 (t, J=12.3 Hz, 2H), 1.34 (s, 6H), 1.25 (s, 6H), 1.22 (s, 6H).

II-34: N2-(2,2-Dimethyl-4-methyl-1,4-benzoxazin-3-one-7-yl)-5-fluoro-N4-(1,2,2,6,6-pentamethylpiperidin-4-yl)-2,4-pyrimidinediamine MS (m/e) 471.26 (MH+); $^1$H NMR (DMSO-d6): δ 9.10 (s, 1H), 8.12 (s, 1H), 7.85 (s, 1H), 7.72 (s, 1H), 7.32 (bs, 1H), 7.11 (bs, 1H), 6.92 (m, 1H), 4.48 (s, 1H), 3.22 (s, 3H), 2.36 (s, 3H), 1.78 (bs, 2H), 1.59 (bs, 2H), 1.34 (s, 6H), 1.22 (s, 6H), 1.18 (s, 6H).

II-35: N2-(2,2-Dimethyl-4-ethyl-1,4-benzoxazin-3-one-7-yl)-5-fluoro-N4-(1,2,2,6,6-pentamethylpiperidin-4-yl)-2,4-pyrimidinediamine MS (m/e) 485.25 (MH+); $^1$H NMR (DMSO-d6): δ 9.11 (s, 1H), 7.88-7.86 (d, J=3.6 Hz, 1H), 7.70 (s, 1H), 7.39 (bs, 1H), 7.12-7.09 (d, J=9.6 Hz, 1H), 6.98-6.96 (d, J=8.7 Hz, 1H), 4.48 (s, 1H), 3.88-3.81 (q, J=6.6 Hz, 2H), 1.88 (bs, 2H), 1.67 (bs, 2H), 1.34 (s, 6H), 1.30 (s, 6H), 1.26 (s, 6H), 1.12-1.07 (t, J=6.9 Hz, 3H).

II-36: 5-Fluoro-N2-(3-methyl-benzoxazol-2-one-6-yl)-N4-(1,2,2,6,6-pentamethylpiperidin-4-yl)-2,4-pyrimidinediamine MS (m/e) 429.22 (MH+); $^1$H NMR (DMSO-d6): δ 9.10 (s, 1H), 7.88-7.86 (bs, 2H), 7.35-7.30 (bs, 2H), 7.06-7.03 (d, J=8.7 Hz, 2H), 4.43 (s, 1H), 3.28 (s, 3H), 2.43 (s, 3H), 1.89-1.85 (d, J=12 Hz, 2H), 1.66-1.57 (d, J=12.3 Hz, 2H), 1.22 (s, 12H).

II-37: N2-(2,2-Difluoro-1,3-benzodioxol-5-yl)-5-fluoro-N4-(1,2,2,6,6-pentamethylpiperidin-4-yl)-2,4-pyrimidinediamine MS (m/e) 438.12 (MH+); $^1$H NMR (DMSO-d6): δ 9.27 (s, 1H), 7.92-7.91 (d, J=3.9 Hz, 2H), 7.89 (s, 1H), 7.57-7.55 (d, J=7.2 Hz, 2H), 7.21 (s, 2H), 4.43 (s, 1H), 3.28 (s, 3H), 2.70 (s, 3H), 2.09-2.04 (d, J=13.2 Hz, 2H), 1.82-1.73 (d, J=12.6 Hz, 2H), 1.38 (s, 12H).

II-38: 5-Fluoro-N2-(1H-indazol-5-yl)-N4-(1,2,2,6,6-pentamethylpiperidin-4-yl)-2,4-pyrimidinediamine MS (m/e) 398.21 (MH+); $^1$H NMR (DMSO-d6): δ 8.95 (s, 1H), 8.14 (s, 1H), 7.84-7.83 (d, J=3.9 Hz, 1H), 7.80 (s, 1H), 7.51-7.48 (d, J=9 Hz, 1H), 7.36-7.33 (d, J=9 Hz, 1H), 7.24-7.22 (d, J=6.9 Hz, 1H), 4.49 (s, 1H), 2.35 (s, 3H), 1.81-1.78 (d, J=9.6 Hz, 2H), 1.62-1.54 (t, J=12.9 Hz, 2H), 1.17 (s, 12H).

II-39: 5-Fluoro-N2-(1-methyl-indazol-5-yl)-N4-(1,2,2,6,6-pentamethylpiperidin-4-yl)-2,4-pyrimidinediamine MS (m/e) 412.25 (MH+); $^1$H NMR (DMSO-d6): δ 8.97 (s, 1H), 8.17 (s, 1H), 7.85-7.84 (d, J=3.9 Hz, 1H), 7.80 (s, 1H), 7.75 (s, 1H), 7.51-7.42 (m, 2H), 7.28-7.26 (d, J=7.5 Hz, 1H), 4.49 (s, 1H), 3.97 (s, 3H), 2.37 (s, 3H), 1.83-1.79 (d, J=11.1 Hz, 2H), 1.65-1.56 (t, J=12.6 Hz, 2H), 1.19 (s, 12H).

II-40: 5-Fluoro-N2-(1-H-indazol-6-yl)-N4-(1,2,2,6,6-pentamethylpiperidin-4-yl)-2,4-pyrimidinediamine MS (m/e) 398.21 (MH+); $^1$H NMR (DMSO-d6): δ 9.08 (s, 1H), 7.92-7.90 (d, J=3.6 Hz, 1H), 7.87 (s, 1H), 7.52-7.50

(d, J=8.4 Hz, 1H), 7.44-7.41 (d, J=9.9 Hz, 1H), 4.44 (s, 1H), 1.93 (bs, 2H), 1.70 (bs, 2H), 1.29 (s, 12H).

II-41: 5-Fluoro-N2-(1-methyl-indazol-6-yl)-N4-(1,2,2,6,6-pentamethylpiperidin-4-yl)-2,4-pyrimidinediamine MS (m/e) 412.23 (MH+); ¹H NMR (DMSO-d6): δ 9.06 (s, 1H), 7.89-7.88 (d, J=3.6 Hz, 1H), 7.84 (s, 1H), 7.75 (s, 1H), 7.57-7.48 (m, 2H), 7.26-7.23 (d, J=8.7 Hz, 1H), 4.39 (s, 1H), 3.91 (s, 3H), 2.30 (s, 3H), 1.80-1.76 (d, J=12.3 Hz, 2H), 1.57-1.49 (t, J=12 Hz, 2H), 1.14 (s, 12H).

II-42: 5-Fluoro-N2-(3-aminocarboxylmethylene-benzoxazol-2-one-6-yl)-N4-(1,2,2,6,6-pentamethylpiperidin-4-yl)-2,4-pyrimidinediamine MS (m/e) 472.18 (MH+); ¹H NMR (DMSO-d6): δ 9.10 (s, 1H), 7.88 (s, 2H), 7.70 (s, 1H), 7.42 (s, 1H), 7.31-7.25 (m, 2H), 6.99-6.96 (d, J=8.1 Hz, 1H), 4.46 (s, 1H), 4.36 (s, 2H), 1.94 (bs, 2H), 1.69 (bs, 2H), 1.30 (s, 12H).

II-43: N2-(3,4-Dihydro-2H-1,5-benzodioxepin-7-yl)-5-fluoro-N4-(1,2,2,6,6-pentamethylpiperidin-4-yl)-2,4-pyrimidinediamine MS (m/e) 430.26 (MH+); ¹H NMR (DMSO-d6): δ8.93 (s, 1H), 7.84-7.82 (d, J=3.9 Hz, 1H), 7.44-7.74 (s, 1H), 7.31-7.28 (d, J=7.8 Hz, 1H), 7.20-7.17 (d, J=8.7 Hz, 1H), 6.76-6.73 (d, J=8.4 Hz, 1H), 4.48 (s, 1H), 4.03-3.97 (m, 4H), 2.42 (s, 3H), 2.03 (s, 3H), 1.85-1.81 (d, J=11.4 Hz, 2H), 1.66-1.58 (t, J=12 Hz, 2H), 1.24 (s, 12H).

II-44: N2-(2,2-Dimethyl-4-isopropyl-1,4-benzoxazin-3-one-7-yl)-5-fluoro-N4-(1,2,2,6,6-pentamethylpiperidin-4-yl)-2,4-pyrimidinediamine MS (m/e) 499.35 (MH+); ¹H NMR (DMSO-d6): δ 9.07 (s, 1H), 7.83-7.82 (d, J=3.6 Hz, 1H), 7.69 (s, 1H), 7.23-7.20 (d, J=9 Hz, 1H), 7.15-7.05 (m, 2H), 4.68 (m, 1H), 4.45 (s, 1H), 2.23 (s, 3H), 1.72-1.68 (d, J=10.2 Hz, 2H), 1.56-1.47 (t, J=12.3 Hz, 2H), 1.47 (s, 3H), 1.38 (s, 3H), 1.30 (s, 6H), 1.14 (s, 3H), 1.11 (s, 3H).

II-45: 5-Cyano-N2-(2,2-dimethyl-4-ethyl-1,4-benzoxazin-3-one-7-yl)-N4-(1,2,2,6,6-pentamethylpiperidin-4-yl)-2,4-pyrimidinediamine MS (m/e) 492.30 (MH+); ¹H NMR (DMSO-d6): δ 9.94 (s, 1H), 8.56 (s, 1H), 7.85-7.82 (d, J=7.2 Hz, 1H), 7.60 (bs, 1H), 7.16-7.04 (m, 2H), 4.62 (s, 1H), 3.9 (m, 2H), 2.74 (s, 3H), 2.06-1.86 (m, 4H), 1.41-1.36 (m, 18H), 1.12-1.08 (t, J=6.9 Hz, 3H).

II-46: N2-(3-Ethyl-benzoxazol-2-one-6-yl)-5-fluoro-N4-(1,2,2,6,6-pentamethylpiperidin-4-yl)-2,4-pyrimidinediamine MS (m/e) 443.25 (MH+); ¹H NMR (DMSO-d6): δ 9.07 (s, 1H), 7.88 (s, 1H), 7.84-7.83 (d, J=3.6 Hz, 1H), 7.33-7.30 (d, J=9.6 Hz, 1H), 7.23-7.21 (d, J=8.4 Hz, 1H), 7.11-7.08 (d, J=8.4 Hz, 1H), 4.43 (s, 1H), 3.82-3.75 (q, J=7.2 Hz, 2H), 2.25 (s, 3H), 1.75-1.72 (d, J=9.6 Hz, 2H), 1.54-1.46 (t, J=12 Hz, 2H), 1.25-1.20 (t, J=7.2 Hz, 3H), 1.11 (s, 12H).

II-47: 5-Fluoro-N2-(3-isopropyl-benzoxazol-2-one-6-yl)-N4-(1,2,2,6,6-pentamethylpiperidin-4-yl)-2,4-pyrimidinediamine MS (m/e) 457.54 (MH+); ¹H NMR (DMSO-d6): δ 9.06 (s, 1H), 7.87 (s, 1H), 7.31-7.17 (m, 3H), 4.43-4.39 (m, 2H), 2.26 (s, 3H), 1.75-1.72 (d, J=9.9 Hz, 2H), 1.55-1.47 (t, J=12 Hz, 2H), 1.44 (s, 3H), 1.41 (s, 3H), 1.11 (s, 12H).

II-48: N2-(2,2-Dimethyl-4-propyl-1,4-benzoxazin-3-one-7-yl)-5-fluoro-N4-(1,2,2,6,6-pentamethylpiperidin-4-yl)-2,4-pyrimidinediamine MS (m/e) 499.28 (MH+); ¹H NMR (DMSO-d6): δ 9.1 (s, 1H), 7.85 (s, 1H), 7.69 (s, 1H), 7.36-7.34 (d, J=7.2 Hz, 1H), 7.12-7.09 (d, J=8.7 Hz, 1H), 6.97-6.95 (d, J=8.7 Hz, 1H), 4.46 (s, 1H), 3.8-3.76 (t, J=6.6 Hz, 2H), 2.42 (s, 3H), 1.86-1.82 (d, J=11.1 Hz, 2H), 1.67-1.49 (m, 4H), 1.35 (s, 6H), 1.25 (s, 6H), 1.22 (s, 6H), 0.88-0.83 (t, J=7.2 Hz, 3H).

II-49: N2-{2,2-Dimethyl-4-[2-(N,N-dimethylamino)ethyl]-1,4-benzoxazin-3-one-7-yl}-5-fluoro-N4-(1,2,2,6,6-pentamethylpiperidin-4-yl)-2,4-pyrimidinediamine MS (m/e) 528.35 (MH+); ¹H NMR (DMSO-d6): δ 9.1 (s, 1H), 7.85-7.84 (d, J=3.6 Hz, 1H), 7.64 (s, 1H), 7.31-7.28 (d, J=8.4 Hz, 1H), 7.21-7.18 (d, J=8.4 Hz, 1H), 6.96-6.93 (d, J=8.7 Hz, 1H), 4.47 (s, 1H), 3.93-3.88 (t, J=7.2 Hz, 2H), 2.42-2.37 (t, J=6.6 Hz, 2H), 2.31 (s, 3H), 2.22 (s, 6H), 1.78-1.74 (d, J=11.4 Hz, 2H), 1.61-1.53 (t, J=12.3 Hz, 2H), 1.34 (s, 6H), 1.19 (s, 6H), 1.16 (s, 6H).

II-50: N2-[2,2-Dimethyl-4-ethyl-1,4-benzoxazin-3-one-7-yl]-N4-(1,2,2,6,6-pentamethylpiperidin-4-yl)-5-trifluoromethyl-2,4-pyrimidinediamine MS (m/e) 535.27 (MH+); ¹H NMR (DMSO-d6): δ 9.62 (s, 1H), 8.15 (s, 1H), 7.62 (s, 1H), 7.21-7.18 (d, J=8.1 Hz, 1H), 7.02-6.99 (d, J=7.8 Hz, 1H), 4.67 (s, 1H), 3.89-3.82 (q, J=7.2 Hz, 2H), 2.25 (s, 3H), 1.67-1.64 (m, 4H), 1.35 (s, 6H), 1.12 (s, 15H), 1.16 (s, 6H).

II-51: 5-Fluoro-N2-(1-methyl-2,3-dihydro-indol-5-yl)-N4-(1,2,2,6,6-pentamethylpiperidin-4-yl)-2,4-pyrimidinediamine MS (m/e) 412.55 (MH+); ¹H NMR (DMSO-d6): δ 8.55 (s, 1H), 7.77-7.75 (d, J=3.6 Hz, 1H), 7.33 (s, 1H), 7.26-7.23 (d, J=8.4 Hz, 1H), 7.15-7.12 (d, J=8.1 Hz, 1H), 6.34-6.31 (d, J=8.4 Hz, 1H), 4.41 (s, 1H), 3.15-3.10 (t, J=8.1 Hz, 2H), 2.79-2.74 (t, J=7.8 Hz, 2H), 2.6 (s, 3H), 2.36 (s, 3H), 1.79-1.76 (d, J=10.8 Hz, 2H), 1.61-1.53 (t, J=12 Hz, 2H), 1.18 (s, 6H), 1.16 (s, 6H).

II-52: 5-Fluoro-N2-(1-ethyl-2,3-dihydro-indol-5-yl)-N4-(1,2,2,6,6-pentamethylpiperidin-4-yl)-2,4-pyrimidinediamine MS (m/e) 427.27 (MH+); ¹H NMR (DMSO-d6): δ 8.54 (s, 1H), 7.77-7.76 (d, J=3.6 Hz, 1H), 7.29 (s, 1H), 7.24-7.19 (m, 3H), 6.34-6.32 (d, J=8.4 Hz, 1H), 4.43 (s, 1H), 3.19-3.14 (t, J=7.8 Hz, 2H), 2.99-2.95 (q, J=7.2 Hz, 2H), 2.8-2.75 (t, J=8.1 Hz, 2H), 2.79-2.74 (t, J=7.8 Hz, 2H), 2.53 (s, 3H), 2.44 (s, 3H), 1.85-1.81 (d, J=11.4 Hz, 2H), 1.70-1.61 (t, J=12 Hz, 2H), 1.25 (s, 6H), 1.21 (s, 6H), 1.1-1.05 (t, J=7.2 Hz, 3H).

II-53: 5-Fluoro-N2-(1-isopropyl-2,3-dihydro-indol-5-yl)-N4-(1,2,2,6,6-pentamethylpiperidin-4-yl)-2,4-pyrimidinediamine MS (m/e) 441.30 (MH+); $^1$H NMR (DMSO-d6): δ 9.12 (s, 1H), 8.62 (s, 1H), 7.82-7.81 (d, J=3.6 Hz, 1H), 7.5 (bs, 1H), 7.21 (bs, 2H), 6.31-6.28 (d, J=8.1 Hz, 1H), 4.45 (s, 1H), 3.71 (m, 1H), 3.22-3.17 (t, J=7.5 Hz, 2H), 2.80-2.75 (t, J=7.8 Hz, 2H), 2.7-2.69 (d, J=4.2 Hz, 2H), 2.53 (s, 3H), 2.02-1.99 (d, J=11.1 Hz, 2H), 1.92-1.84 (t, J=12.9 Hz, 2H), 1.43 (s, 6H), 1.36 (s, 6H), 1.06 (s, 3H), 1.04 (s, 3H).

II-54: N2-(2,2-Dimethyl-4-N-methyl-2H-pyrido[3,2-b]-1,4-oxazin-3-one-7-yl)-5-fluoro-N4-(1,2,2,6,6-pentamethylpiperidin-4-yl)-2,4-pyrimidinediamine MS (m/e) 472.18 (MH+); $^1$H NMR (DMSO-d6): δ 9.3 (s, 1H), 8.24 (s, 1H), 7.93-7.92 (d, J=3.3 Hz, 1H), 7.60-7.58 (d, J=7.8 Hz, 1H), 4.47 (s, 1H), 3.29 (s, 3H), 2.68 (s, 3H), 2.06-2.01 (d, J=13.8 Hz, 2H), 1.82-1.74 (t, J=12 Hz, 2H), 1.41 (bs, 18H).

II-55: N2-(2,2-Dimethyl-4-N-ethyl-2H-pyrido[3,2-b]-1,4-oxazin-3-one-7-yl)-5-fluoro-N4-(1,2,2,6,6-pentamethylpiperidin-4-yl)-2,4-pyrimidinediamine MS (m/e) 486.22 (MH+); $^1$H NMR (DMSO-d6): δ 9.31 (s, 1H), 8.60 (bs, 1H), 8.27 (s, 1H), 7.94-7.93 (d, J=3.6 Hz, 1H), 7.87 (s, 1H), 7.64-7.61 (d, J=7.8 Hz, 1H), 4.5 (s, 1H), 4.02-3.95 (q, J=6.9 Hz, 2H), 2.74 (s, 3H), 2.10-2.06 (d, J=12 Hz, 2H), 1.86-1.77 (t, J=12.3 Hz, 2H), 1.44 (s, 6H), 1.40 (s, 6H), 1.14-1.09 (t, J=6.9 Hz, 3H).

II-56: N2-(1,3-Dimethyl-1,3-dihydro-benzoimidazol-2-one-5-yl)-5-fluoro-N4-(1,2,2,6,6-pentamethylpiperidin-4-yl)-2,4-pyrimidinediamine MS (m/e) 442.21 (MH+); $^1$H NMR (DMSO-d6): δ 8.76 (s, 1H), 7.81-7.80 (d, J=3.9 Hz, 1H), 7.53-7.50 (d, J=8.7 Hz, 1H), 7.24 (s, 1H), 7.12-7.1 (d, J=7.5 Hz, 1H), 6.9-6.87 (d, J=8.1 Hz, 1H), 4.31 (s, 1H), 3.26 (s, 6H), 2.23 (s, 3H), 1.73-1.69 (d, J=10.2 Hz, 2H), 1.51-1.43 (t, J=12.3 Hz, 2H), 1.1 (s, 6H), 1.05 (s, 6H).

II-57: 5-Cyano-N2-(2,2-dimethyl-4-ethyl-1,4-benzoxazin-3-one-7-yl)-N4-(2,2,6,6-tetramethylpiperidin-4-yl)-2,4-pyrimidinediamine MS (m/e) 478.27 (MH+); $^1$H NMR (DMSO-d6): δ 9.95 (s, 1H), 8.65-8.61 (d, J=12 Hz, 1H), 7.62 (bs, 2H), 7.68 (s, 1H), 7.14-7.05 (m, 2H), 4.69 (s, 1H), 3.9-3.83 (q, J=6.6 Hz, 2H), 1.92-1.88 (d, J=11.7 Hz, 2H), 1.74-1.65 (t, J=13.2 Hz, 2H), 1.46 (s, 6H), 1.37 (s, 6H), 1.34 (s, 6H), 1.12-1.09 (t, J=6.9 Hz, 3H).

II-58: N2-(4-Ethyl-2H-1,4-benzoxazin-3-one-7-yl)-5-fluoro-N4-(1,2,2,6,6-pentamethylpiperidin-4-yl)-2,4-pyrimidinediamine MS (m/e) 457.23 (MH+); $^1$H NMR (DMSO-d6): δ 9.05 (s, 1H), 7.86-7.85 (d, J=3.3 Hz, 1H), 7.55 (s, 1H), 7.37-7.34 (d, J=7.2 Hz, 1H), 7.25-7.22 (d, J=7.5 Hz, 1H), 7.0-6.97 (d, J=8.7 Hz, 1H), 4.52 (s, 2H), 4.44 (s, 1H), 3.9-3.83 (q, J=6.6 Hz, 2H), 1.89-1.84 (d, J=13.5 Hz, 2H), 1.68-1.59 (t, J=12.6 Hz, 2H), 1.25 (bs, 12H), 1.14-1.09 (t, J=6.9 Hz, 3H).

II-59: 5-Fluoro-N2-(4-propyl-2H-1,4-benzoxazin-3-one-7-yl)-N4-(1,2,2,6,6-pentamethylpiperidin-4-yl)-2,4-pyrimidinediamine MS (m/e) 471.21 (MH+); $^1$H NMR (DMSO-d6): δ 9.03 (s, 1H), 7.84-7.83 (d, J=3.6 Hz, 1H), 7.5 (s, 1H), 7.3-7.24 (t, J=7.2 Hz, 1H), 6.97-6.94 (d, J=8.7 Hz, 1H), 4.52 (s, 2H), 4.4 (s, 1H), 3.92-3.77 (t, J=6.6 Hz, 2H), 2.3 (s, 3H), 1.77-1.74 (d, J=10.5 Hz, 2H), 1.58-1.5 (t, J=10.8 Hz, 2H), 1.15 (bs, 12H), 0.89-0.84 (t, J=7.5 Hz, 3H).

II-60: 5-Cyano-N2-(3,4-ethylenedioxy)phenyl-N4-(1,2,2,6,6-pentamethylpiperidin-4-yl)-2,4-pyrimidinediamine MS (m/e) 423.20 (MH+); $^1$H NMR (DMSO-d6): δ 9.64 (s, 1H), 8.26 (s, 1H), 7.46 (s, 1H), 7.18 (s, 1H), 7.11-7.09 (d, J=7.5 Hz, 1H), 6.68-6.65 (d, J=8.7 Hz, 1H), 4.49 (bs, 1H), 4.16 (s, 4H), 2.34 (s, 3H), 1.73-1.59 (m, 4H), 1.16 (s, 6H), 1.13 (s, 6H).

II-61: 5-Fluoro-N2-(4-isopropyl-2H-1,4-benzoxazin-3-one-7-yl)-N4-(1,2,2,6,6-pentamethylpiperidin-4-yl)-2,4-pyrimidinediamine MS (m/e) 471.21 (MH+); $^1$H NMR (DMSO-d6): δ 9.17 (s, 1H), 8.57 (s, 1H), 7.92-7.91 (d, J=3.3 Hz, 1H), 7.63-7.6 (bs, 2H), 7.13 (s, 2H), 4.64 (m, 2H), 4.43 (s, 2H), 2.75 (s, 3H), 2.08-2.04 (d, J=12.9 Hz, 2H), 1.85-1.76 (t, J=13.2 Hz, 2H), 1.43 (s, 6H), 1.4 (s, 6H).

II-62: N2-(2,2-Dimethyl-4-methyl-2H-1,4-benzothiazin-3-one-7-yl)-5-fluoro-N4-(1,2,2,6,6-pentamethylpiperidin-4-yl)-2,4-pyrimidinediamine MS (m/e) 487.20 (MH+); $^1$H NMR (DMSO-d6): δ 9.06 (s, 1H), 7.85-7.84 (d, J=3.9 Hz, 1H), 7.71 (s, 1H), 7.63-7.6 (d, J=8.7 Hz, 1H), 7.22-7.19 (d, J=8.1 Hz, 1H), 7.06-7.03 (d, J=9 Hz, 1H), 4.35 (s, 1H), 2.23 (s, 3H), 1.73-1.7 (d, J=11.4 Hz, 2H), 1.53-1.45 (t, J=12 Hz, 2H), 1.3 (s, 6H), 1.12 (s, 6H), 1.1 (s, 6H).

II-63: N2-(2,2-Dimethyl-4-ethyl-1,4-benzothiazin-3-one-7-yl)-5-fluoro-N4-(1,2,2,6,6-pentamethylpiperidin-4-yl)-2,4-pyrimidinediamine MS (m/e) 501.24 (MH+); $^1$H NMR (DMSO-d6): δ 9.09 (s, 1H), 7.89-7.88 (d, J=2.7 Hz, 1H), 7.68 (s, 1H), 7.58-7.55 (d, J=8.7 Hz, 1H), 7.42 bs, 1H), 7.12-7.1 (d, J=8.7 Hz, 1H), 4.42 (s, 1H), 3.92-3.88 (m, 2H), 2.56 (s, 3H), 1.93 (bs, 2H), 1.73 (bs, 2H), 1.3 (s, 18H), 1.21-1.08 (t, J=6.9 Hz, 3H).

II-64: N2-(2,2-Dimethyl-1,1-dioxide-4-methyl-1,4-benzothiazin-3-one-7-yl)-5-fluoro-N4-(1,2,2,6,6-pentamethylpiperidin-4-yl)-2,4-pyrimidinediamine MS (m/e) 519.18 (MH+); $^1$H NMR (DMSO-d6): δ 9.39 (s, 1H), 8.1-8.06 (m, 2H), 7.95-7.94 (d, J=3.3 Hz, 1H), 7.46 (bs, 1H), 7.4-7.37 (d, J=8.7 Hz, 1H), 4.39 (s, 1H), 3.39 (s, 3H), 1.94 (bs, 2H), 1.66 (bs, 2H), 1.4 (s, 6H), 1.29 (bs, 12H).

II-65: 5-Cyano-N2-(2,2-difluoro-4-N-ethyl-2H-pyrido[3,2-b]-1,4-oxazin-3-one-7-yl)-N4-(1,2,2,6,6-pentamethylpiperidin-4-yl)-2,4-pyrimidinediamine MS (m/e) 501.17 (MH+); $^1$H NMR (DMSO-d6): δ 10.21 (s, 1H), 8.58 (s, 1H), 8.4 (s, 1H), 8.1 (bs, 1H), 7.91 (bs, 1H), 4.58 (bs, 1H), 4.13-4.06 (t, J=6.9 Hz, 2H), 2.62 (s, 3H), 1.94-1.82 (m, 4H), 1.32 (bs, 12H), 1.23-1.18 (t, J=7.2 Hz, 3H).

II-66: N2-(2,2-Dimethyl-1,1-dioxide-4-ethyl-1,4-benzothiazin-3-one-7-yl)-5-fluoro-N4-(1,2,2,6,6-pentamethylpiperidin-4-yl)-2,4-pyrimidinediamine MS (m/e) 533.22 (MH+); $^1$H NMR (DMSO-d6): δ 9.42 (s, 1H), 8.56 (bs, 1H), 8.23 (s, 1H), 8.04-8.01 (d, J=9 Hz, 1H), 7.98-7.97 (d, J=3.9 Hz, 1H), 7.63-7.6 (d, J=8.1 Hz, 1H), 7.46-7.43 (d, J=8.7 Hz, 1H), 4.43 (s, 1H), 4.01 (m, 2H), 2.74 (s, 3H), 2.12-2.08 (d, J=11.7 Hz, 2H), 1.83-1.75 (d, J=13.5, 2H), 1.39 (s, 18H), 1.29 (t, J=6.3 Hz, 3H).

II-67: N2-(2,2-Dimethyl-1,1-dioxide-4-isopropyl-1,4-benzothiazin-3-one-7-yl)-5-fluoro-N4-(1,2,2,6,6-pentamethylpiperidin-4-yl)-2,4-pyrimidinediamine MS (m/e) 547.25 (MH+); $^1$H NMR (DMSO-d6): δ 9.42 (s, 1H), 8.15 (s, 1H), 8.11 (s, 1H), 7.94-7.93 (d, J=3.6 Hz, 1H), 7.42-7.39 (m, 2H), 4.59 (m, 1H), 4.37 (s, 1H), 2.44 (s, 3H), 1.91-1.87 (d, J=11.7 Hz, 2H), 1.66-1.57 (d, J=13.2, 2H), 1.42 (s, 3H), 1.4 (s, 3H), 1.32 (s, 6H), 1.29 (s, 12H).

II-68: N2-(2,1-spiro-Cyclobutane-4-methyl-1,4-benzoxazin-3-one-7-yl)-5-fluoro-N4-(1,2,2,6,6-pentamethylpiperidin-4-yl)-2,4-pyrimidinediamine MS (m/e) 483.23 (MH+); $^1$H NMR (DMSO-d6): δ 9.19 (s, 1H), 8.62 (s, 1H), 7.93-7.92 (d, J=3.9 Hz, 1H), 7.73 (s, 2H), 7.63-7.61 (d, J=7.5 Hz, 1H), 7.15-7.12 (d, J=8.4 Hz, 1H), 6.97-6.94 (d, J=9 Hz, 1H), 4.54 (bs, 1H), 3.23 (s, 1H), 2.76 (s, 3H), 2.2-2.7 (m, 4H), 1.91-1.75 (m, 4H), 1.48 (s, 6H), 1.41 (s, 6H).

II-69: N2-(2,1-spiro-cyclobutane-4-ethyl-1,4-benzoxazin-3-one-7-yl)-5-fluoro-N4-(1,2,2,6,6-pentamethylpiperidin-4-yl)-2,4-pyrimidinediamine MS (m/e) 497.21 (MH+); $^1$H NMR (DMSO-d6): δ 9.21 (s, 1H), 8.62 (s, 1H), 7.93-7.92 (d, J=3.6 Hz, 1H), 7.72 (s, 1H), 7.66-7.63 (d, J=8.4 Hz, 1H), 7.13-7.11 (d, J=8.7 Hz, 1H), 7.01-6.99 (d, J=8.7 Hz, 1H), 4.53 (bs, 1H), 3.88 (m, 2H), 2.76 (s, 3H), 2.19-2.07 (m, 4H), 1.87-1.75 (m, 4H), 1.48 (s, 6H), 1.41 (s, 6H), 1.12-1.08 (t, J=6.9 Hz, 3H).

II-70: 5-Cyano-N2-(3-isopropyl-benzoxazol-2-one-6-yl)-N4-(1,2,2,6,6-pentamethylpiperidin-4-yl)-2,4-pyrimidinediamine MS (m/e) 464.24 (MH+); $^1$H NMR (DMSO-d6): δ 9.95 (s, 1H), 8.34 (s, 1H), 7.77 (s, 2H), 7.31-7.27 (m, 3H), 4.49-4.42 (m, 2H), 2.66 (s, 3H), 1.95-1.83 (m, 4H), 1.45 (s, 3H), 1.43 (s, 3H), 1.35 (s, 12H).

II-71: 5-Cyano-N2-(4-ethyl-2H-1,4-benzoxazin-3-one-7-yl)-N4-(1,2,2,6,6-pentamethylpiperidin-4-yl)-2,4-pyrimidinediamine MS (m/e) 464.22 (MH+); $^1$H NMR (DMSO-d6): δ 9.86 (s, 1H), 8.3 (s, 1H), 7.49 (bs, 2H), 7.26 (s, 1H), 7.05-7.02 (d, J=9 Hz, 1H), 4.54 (s, 3H), 3.92-3.84 (q, J=6.6 Hz, 2H), 1.69 (bs, 4H), 1.14 (bs, 15H).

II-72: 5-Cyano-N2-(4-propyl-2H-1,4-benzoxazin-3-one-7-yl)-N4-(1,2,2,6,6-pentamethylpiperidin-4-yl)-2,4-pyrimidinediamine MS (m/e) 478.27 (MH+); $^1$H NMR (DMSO-d6): δ 9.79 (s, 1H), 8.29 (s, 1H), 7.43 (bs, 2H), 7.34-7.32 (d, J=8.1 Hz, 1H), 7.02-6.99 (d, J=8.7 Hz, 1H), 4.54 (s, 3H), 3.83-3.78 (t, J=7.8 Hz, 2H), 2.23 (s, 3H), 1.66-1.53 (m, 6H), 1.1 (s, 12H), 0.89-0.84 (t, J=6.3 Hz, 3H).

II-73: 5-Cyano-N2-(2,2-difluoro-4-N-ethyl-2H-pyrido[3,2-b]-1,4-oxazin-3-one-7-yl)-N4-(1H-2,2,6,6-tetramethylpiperidin-4-yl)-2,4-pyrimidinediamine MS (m/e) 487.19 (MH+); $^1$H NMR (DMSO-d6): δ 10.2 (s, 1H), 8.57 (s, 1H), 8.37 (s, 1H), 8.25 (bs, 1H), 7.74 (bs, 1H), 4.56 (bs, 1H), 4.12-4.06 (m, 2H), 1.74-1.7 (d, J=12 Hz, 2H), 1.51-1.4 (t, J=13.8 Hz, 2H), 1.27-1.16 (m, 15H).

II-74: 5-Cyano-N2-(2,2-dimethyl-4-isopropyl-1,4-benzoxazin-3-one-7-yl)-N4-(1,2,2,6,6-pentamethylpiperidin-4-yl)-2,4-pyrimidinediamine MS (m/e) 506.29 (MH+); $^1$H NMR (DMSO-d6): δ 9.86 (s, 1H), 8.29 (s, 1H), 7.64 (bs, 1H), 7.5 (s, 1H), 7.21-7.12 (m, 2H), 4.7 (m, 1H), 4.53 (bs, 1H), 2.26 (s, 3H), 1.66 (bs, 4H), 1.41 (s, 3H), 1.38 (s, 3H), 1.31 (s, 6H), 1.12 (s, 12H).

II-75: 5-Cyano-N2-(2,2-dimethyl-4-isopropyl-1,4-benzoxazin-3-one-7-yl)-N4-(1H-2,2,6,6-tetramethylpiperidin-4-yl)-2,4-pyrimidinediamine MS (m/e) 492.26 (MH+); $^1$H NMR (DMSO-d6): δ 9.9 (s, 1H), 8.31 (s, 1H), 7.65 (bs, 2H), 7.16 (s, 2H), 4.69-4.65 (m, 2H), 1.76-1.71 (d, J=13.2 Hz, 2H), 1.53-1.45 (t, J=12.3 Hz, 2H), 1.4 (s, 3H), 1.38 (s, 3H), 1.34 (s, 6H), 1.3 (s, 6H), 1.19 (s, 6H).

II-76: N2-(2,2-Dimethyl-4-cyclopropylmethylene-1,4-benzoxazin-3-one-7-yl)-5-fluoro-N4-(1,2,2,6,6-pentamethylpiperidin-4-yl)-2,4-pyrimidinediamine MS (m/e) 511.25 (MH+); $^1$H NMR (DMSO-d6): δ 9.09 (s, 1H), 7.84-7.83 (d, J=3.9 Hz, 1H), 7.72 (s, 1H), 7.26-7.23 (d, J=8.7 Hz, 1H), 7.15-7.12 (d, J=8.7 Hz, 1H), 7.05-7.02 (d, J=8.7 Hz, 1H), 4.47 (s, 1H), 3.77 (s, 3H), 2.53 (s, 2H), 2.27 (s, 3H), 1.74-1.7 (d, J=11.4 Hz, 2H), 1.58-1.5 (t, J=12.3 Hz, 2H), 1.35 (s, 6H), 1.17 (s, 6H), 1.13 (s, 6H), 0.43 (s, 2H), 0.31 (s, 2H).

II-77: N2-(4-Cyclopropylmethylene-1,4-benzoxazin-3-one-7-yl)-5-fluoro-N4-(1,2,2,6,6-pentamethylpiperidin-4-yl)-2,4-pyrimidinediamine MS (m/e) 483.23 (MH+); $^1$H NMR (DMSO-d6): δ 9.04 (s, 1H), 7.84-7.83 (d, J=3.6 Hz, 1H), 7.51 (s, 1H), 7.31-7.25 (m, 3H), 7.07-7.05 (d, J=8.4 Hz, 1H), 4.53 (s, 2H), 4.45 (bs, 1H), 3.77 (s, 3H), 1.78-1.74 (d, J=10.8 Hz, 2H), 1.58-1.5 (t, J=13.5 Hz, 2H), 1.15 (s, 13H), 0.45 (s, 2H), 0.33 (s, 2H).

II-78: N2-[2,2-Dimethyl-4-(3-fluoropropyl)-1,4-benzoxazin-3-one-7-yl]-5-fluoro-N4-(1,2,2,6,6-pentamethylpiperidin-4-yl)-2,4-pyrimidinediamine MS (m/e) 517.23 (MH+); $^1$H NMR (DMSO-d6): δ 9.12 (s, 1H), 8.11 (s, 1H), 7.89-7.88 (d, J=3.9 Hz, 1H), 7.68 (s, 1H), 7.44 (s, 1H), 7.13 (m, 1H), 6.99-6.96 (d, J=8.7 Hz, 1H), 4.57

(m, 2H), 4.41 (m, 1H), 3.93 (m, 2H), 2.56 (s, 3H), 1.94 (m, 2H), 1.88 (m, 2H), 1.72 (m, 2H), 1.35 (bs, 18H).

II-79: 5-Cyano-N2-[2,2-dimethyl-4-(2-fluoroethyl)-1,4-benzoxazin-3-one-7-yl]-N4-(1,2,2,6,6-pentamethylpiperidin-4-yl)-2,4-pyrimidinediamine MS (m/e) 510.21 (MH+); $^1$H NMR (DMSO-d6): δ 9.95 (s, 1H), 8.32 (s, 1H), 7.65 (s, 1H), 7.14-7.07 (m, 2H), 4.66 (bs, 1H), 4.59 (bs, 1H), 4.51 (bs, 1H), 4.24 (bs, 1H), 4.15 (bs, 1H), 1.83 (bs, 4H), 1.37 (s, 6H), 1.29 (bs, 12H).

II-80: N2-[2,2-Dimethyl-4-(2-fluoroethyl)-1,4-benzoxazin-3-one-7-yl]-5-fluoro-N4-(1,2,2,6,6-pentamethylpiperidin-4-yl)-2,4-pyrimidinediamine MS (m/e) 501.43 (MH+); $^1$H NMR (DMSO-d6): δ 9.08 (s, 1H), 7.83-7.82 (d, J=3.6 Hz, 1H), 7.75 (s, 1H), 7.21-7.18 (d, J=9.3 Hz, 1H), 7.13-7.1 (d, J=8.7 Hz, 1H), 7.02-6.99 (d, J=8.7 Hz, 1H), 4.65 (bs, 1H), 4.5 (m, 2H), 4.21 (bs, 1H), 4.12 (bs, 1H), 2.19 (s, 3H), 1.68-1.65 (d, J=9.9 Hz, 2H), 1.53-1.49 (d, J=12.3 Hz, 2H), 1.36 (s, 6H), 1.12 (s, 6H), 1.08 (s, 6H).

II-81: 5-Cyano-N2-[2,2-dimethyl-4-(3-fluoropropyl)-1,4-benzoxazin-3-one-7-yl]-N4-(1,2,2,6,6-pentamethylpiperidin-4-yl)-2,4-pyrimidinediamine MS (m/e) 524.25 (MH+); $^1$H NMR (DMSO-d6): δ 9.95 (s, 1H), 8.54 (s, 1H), 7.83 (s, 1H), 7.6 (s, 1H), 7.18-7.15 (d, J=8.4 Hz, 1H), 7.07-7.04 (d, J=8.7 Hz, 1H), 4.62 (bs, 1H), 4.5 (m, 1H), 4.39 (m, 1H), 3.96 (m, 2H), 2.72 (s, 3H), 2.03-1.86 (m, 6H), 1.49 (m, 18H).

II-82: N2-[4-(2-fluoroethyl)-2H-1,4-benzoxazin-3-one-7-yl]-5-fluoro-N4-(1,2,2,6,6-pentamethylpiperidin-4-yl)-2,4-pyrimidinediamine MS (m/e) 475.25 (MH+); $^1$H NMR (DMSO-d6): δ 9.41 (s, 1H), 8.6 (s, 1H), 7.98-7.96 (d, J=4.2 Hz, 1H), 7.9 (bs, 1H), 7.58 (s, 1H), 7.1 (s, 2H), 4.69 (bs, 1H), 4.6 (s, 2H), 4.52 (m, 2H), 4.25 (bs, 1H), 4.16 (bs, 1H), 2.75 (s, 3H), 2.07-2.03 (d, J=13.5 Hz, 2H), 1.86-1.78 (d, J=12.9 Hz, 2H), 1.4 (s, 12H).

II-85: N2-(5-Benzylamino-pyrid-2-yl)-N4-(1,2,2,6,6-pentamethylpiperidin-4-yl)-5-fluoro-2,4-pyrimidinediamine MS (m/e) 464.25 (MH+); $^1$H NMR (DMSO-d6): δ 8.79 (s, 1H), 8.55 (s, 1H), 8.19 (s, 1H), 7.86-7.84 (d, J=3.6 Hz, 1H), 7.67 (s, 1H), 7.55 (s, 1H), 7.31 (s, 5H), 7.23 (m, 2H), 6.58 (s, 1H), 4.43 (m, 3H), 2.70 (s, 3H), 2.06-2.02 (d, J=12.3 Hz, 2H), 1.80-1.71 (t, J=13.2 Hz, 2H), 1.37 (s, 6H), 1.30 (s, 6H).

II-86: N4-benzyl-N2-(2,3-dihydrobenzo[b][1,4]dioxin-6-yl)-5-fluoro-N4-(1,2,2,6,6-pentamethylpiperidin-4-yl)pyrimidine-2,4-diamine MS (m/e) 506.24 (MH+); $^1$H NMR (CDCl$_3$): δ 8.25 (s, 1H), 7.79 (d, 1H), 7.39 (m, 5H), 7.01 (s, 1H), 6.85 (d, 1H), 6.77 (d, 1H), 5.19 (bm, 1H), 4.89 (s, 2H), 4.22 (t, 2H), 2.79 (m, 5H), 1.75 (d, 2H), 1.48 (s, 8H), 1.32 (s, 6H).

II-87: N2-(2,3-dihydrobenzo[b][1,4]dioxin-6-yl)-5-fluoro-N4-(naphthalen-2-ylmethyl)-N4-(1,2,2,6,6-pentamethylpiperidin-4-yl)pyrimidine-2,4-diamine MS (m/e) 556.30 (MH+); $^1$H NMR (CDCl$_3$): δ 8.41 (s, 1H), 7.79 (m, 4H), 7.69 (s, 1H), 7.45 (m, 3H), 7.19 (s, 1H), 6.85 (d, 1H), 6.61 (d, 1H), 5.05 (s, 2H), 4.95 (bm, 1H), 4.19 (t, 2H), 2.95 (t, 2H), 2.69 (s, 3H), 1.69 (d, 2H), 1.45 (s, 8H), 1.29 (s, 6H).

II-88: N4-(biphenyl-4-ylmethyl)-N2-(2,3-dihydrobenzo[b][1,4]dioxin-6-yl)-5-fluoro-N4-(1,2,2,6,6-pentamethylpiperidin-4-yl)pyrimidine-2,4-diamine MS (m/e) 582.32 (MH+); $^1$H NMR (CDCl$_3$): δ 8.45 (s, 1H), 7.79 (d, 1H), 7.54 (m, 4H), 7.41 (t, 2H), 7.34 (d, 3H), 7.11 (s, 1H), 6.82 (d, 1H), 6.71 (d, 1H), 4.99 (s, 3H), 4.22 (t, 2H), 2.85 (t, 2H), 2.68 (s, 3H), 1.75 (d, 2H), 1.48 (s, 8H), 1.32 (s, 6H).

II-89: N2-(2,3-dihydrobenzo[b][1,4]dioxin-6-yl)-5-fluoro-N4-(1,2,2,6,6-pentamethylpiperidin-4-yl)-N4-(quinolin-2-ylmethyl)pyrimidine-2,4-diamine MS (m/e) 557.17 (MH+); $^1$H NMR (CDCl$_3$): δ 8.31 (s, 1H), 8.15 (d, 1H), 7.97 (d, 1H), 7.79 (d, 1H), 7.65 (m, 2H), 7.55 (t, 1H), 7.41 (d, 1H), 7.05 (s, 1H), 6.85 (d, 1H), 6.69 (d, 1H), 5.25 (bm, 1H), 5.18 (s, 2H), 4.21 (t, 2H), 2.93 (t, 2H), 2.69 (s, 3H), 1.86 (d, 2H), 1.49 (s, 8H), 1.38 (s, 6H).

II-90: N4-((6-bromobenzo[d][1,3]dioxol-5-yl)methyl)-N2-(2,3-dihydrobenzo[b][1,4]dioxin-6-yl)-5-fluoro-N4-(1,2,2,6,6-pentamethylpiperidin-4-yl)pyrimidine-2,4-diamine MS (m/e) 629.21 (MH+); $^1$H NMR (CDCl$_3$): δ 8.25 (s, 1H), 7.79 (d, 1H), 7.04 (s, 2H), 6.79 (d, 1H), 6.69 (s, 1H), 6.64 (s, 1H), 5.97 (s, 2H), 4.71 (s, 3H), 4.23 (t, 2H), 2.98 (t, 2H), 2.65 (s, 3H), 1.69 (d, 2H), 1.47 (s, 8H), 1.29 (s, 6H).

II-91: 4'-(((2-(2,3-dihydrobenzo[b][1,4]dioxin-6-ylamino)-5-fluoropyrimidin-4-yl)(1,2,2,6,6-pentamethylpiperidin-4-yl)amino)methyl)biphenyl-2-carbonitrile MS (m/e) 607.33 (MH+); $^1$H NMR (CDCl$_3$): δ 8.38 (s, 1H), 7.99 (bs, 1H), 7.81 (d, 1H), 7.76 (d, 1H), 7.63 (t, 1H), 7.51 (d, 2H), 7.49 (d, 3H), 7.12 (s, 1H), 6.84 (s, 1H), 6.71 (s, 1H), 4.97 (s, 2H), 4.83 (bm, 1H), 4.23 (t, 2H), 2.98 (t, 2H), 2.65 (s, 3H), 1.69 (d, 2H), 1.47 (s, 8H), 1.29 (s, 6H).

II-93: N2-[3,4-dihydro-2,2-dimethyl-4-(2-methoxyethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine LCMS: purity: 96.75%; MS (m/e): 516.38 (MH+); $^1$H NMR (DMSO-d$_6$): δ 1.40 (s, 12H), 1.43 (s, 6H), 1.82 (t, J=13.2 Hz, 2H), 2.08 (d, J=12.6 Hz, 2H), 2.74 (d, J=3.6 Hz, 3H), 3.21 (s, 3H), 3.50 (t, J=6.0 Hz, 2H), 4.15 (t, 2H), 4.48 (br, 1H), 7.76 (d, 1H), 7.86 (d, 1H), 7.96 (d, J=4.2 Hz, 1H), 8.25 (d, J=2.1 Hz, 1H), 8.62 (br, 1H), 9.43 (s, 1H); $^{19}$F NMR (282 MHz, DMSO-d$_6$): δ−180.65.

II-99: N2-[3,4-dihydro-2,2-dimethyl-4-(2-methoxyethyl)-3-oxo-2H-pyrido[3,2-b]-1,4-oxazin-7-yl]phenyl-5-fluoro-N4-(2,2,6,6-tetramethylpiperidin-4-yl)-2,4-pyrimidinediamine LCMS: purity: 99.24%; MS (m/e): 502.56 (MH+); $^1$H NMR (DMSO-d$_6$): δ 1.37 (s, 6H), 1.39 (s, 6H), 1.48 (s, 6H), 1.60 (t, J=12.9 Hz, 2H), 1.97 (d, J=12.6 Hz, 2H), 3.21 (s, 3H), 3.49 (t, J=6.0 Hz, 2H), 4.14 (t, J=6.0 Hz, 2H), 4.54 (br, 1H), 7.76 (d, J=8.4 Hz, 1H), 7.80 (br, 1H), 7.88 (d, J=1.8 Hz, 1H), 7.96 (d, J=3.9 Hz, 1H), 8.27 (d, J=1.8 Hz, 1H), 8.65 (d, J=13.8 Hz, 1H), 9.46 (s, 1H); $^{19}$F NMR (282 MHz, DMSO-d$_6$): δ−180.72.

II-100: 5-aminocarbonyl-N2-[3,4-dihydro-2,2-dimethyl-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine LCMS: purity: 95.86%; MS (m/e): 527.52 (MH+); $^1$H NMR (DMSO-d$_6$): δ 1.38 (s, 6H), 1.40 (s, 8H), 1.49 (s, 6H), 2.09 (d, J=12.9 Hz, 2H), 3.22 (s, 3H), 3.50 (t, J=6.0 Hz, 2H), 4.15 (t, J=6.6 Hz, 2H), 4.53 (br, 1H), 7.26 (br, 1H), 7.73 (d, J=12.6 Hz, 1H), 7.87 (d, 1H), 8.39 (s, 1H), 8.55 (s, 1H), 8.65 (d, 1H), 9.31 (d, 1H), 9.85 (br, 1H).

II-101: 5-aminocarbonyl-N2-[3,4-dihydro-2,2-dimethyl-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine LCMS: purity: 94.63%; MS (m/e): 541.41 (MH+); $^1$H NMR (DMSO-d$_6$): δ 1.41 (s, 6H), 1.42 (s, 6H), 1.44 (s, 6H), 1.68 (t, J=13.2 Hz, 2H), 2.21 (d, J=12.3 Hz, 2H), 2.76 (d, J=4.5 Hz, 3H), 3.22 (s, 3H), 3.50 (t, J=6.0 Hz, 2H), 4.16 (t, J=6.0 Hz, 2H), 4.48 (br, 1H), 7.28 (br, 1H), 7.85 (d, 1H), 8.35 (s, 1H), 8.55 (s, 1H), 8.65 (d, 1H), 9.34 (d, 1H), 9.92 (br, 1H).

II-102: N2-(2,2-dimethyl-benzo[1,3]dioxol-5-yl)-5-fluoro-N4-(2,2,6,6-tetramethylpiperidin-4-yl)-2,4-pyrimidinediamine LCMS: purity: 92.57%; MS (m/e): 416.02 (MH+); $^1$H NMR (DMSO-d$_6$): δ 1.36 (s, 6H), 1.39 (s, 6H), 1.59 (s, 8H), 1.93 (d, J=12.6 Hz, 2H), 4.50 (br, 1H), 6.67 (d, J=7.8 Hz, 1H), 6.82 (d, J=6.3 Hz, 1H), 7.20 (s, 1H), 7.79 (d, J=13.2 Hz, 1H), 7.93 (d, J=4.5 Hz, 2H), 8.63 (d, J=10.2 Hz, 1H), 9.22 (br, 1H).

II-103: N2-(2,2-dimethyl-benzo[1,3]dioxol-5-yl)-5-fluoro-N4-(1,2,2,6,6-pentamethylpiperidin-4-yl)-2,4-pyrimidinediamine LCMS: purity: 97.52%; MS (m/e): 430.47 (MH+); $^1$H NMR (DMSO-d$_6$): δ 1.12 (s, 6H), 1.14 (s, 6H), 1.52 (t, J=12.6 Hz, 2H), 1.58 (s, 6H), 1.74 (d, J=9.0 Hz, 2H), 2.29 (s, 3H), 4.36 (br, 1H), 6.58 (d, J=8.4 Hz, 1H), 6.94 (dd, J=1.8, 8.1 Hz, 1H), 7.16 (d, J=8.7 Hz, 1H), 7.23 (d, J=1.8 Hz, 1H), 7.78 (d, J=3.9 Hz, 1H), 8.76 (s, 1H); $^{19}$F NMR (282 MHz, DMSO-d$_6$): δ−182.71.

II-104: N2-[3,4-dihydro-4-(2-methoxyethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine LCMS: purity: 97.15%; MS (m/e): 488.59 (MH+); $^1$H NMR (DMSO-d$_6$): δ 1.23 (s, 12H), 1.62 (t, J=12.3 Hz, 2H), 1.85 (d, 2H), 2.43 (s, 3H), 3.22 (s, 3H), 3.51 (t, J=6.3 Hz, 2H), 4.14 (t, J=6.0 Hz, 2H), 4.43 (br, 1H), 4.67 (s, 2H), 7.40 (d, 1H), 7.72 (d, 1H), 7.88 (d, J=3.9 Hz, 1H), 8.37 (d, 1H), 9.19 (s, 1H); $^{19}$F NMR (282 MHz, DMSO-d$_6$): δ−181.19.

II-105: 5-aminocarbonyl-N2-[3,4-dihydro-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine LCMS: purity: 97.70%; MS (m/e): 499.58 (MH+); $^1$H NMR (DMSO-d$_6$): δ 1.21 (s, 6H), 1.25 (t, J=11.4 Hz, 2H), 1.35 (s, 6H), 1.95 (d, J=9.6 Hz, 2H), 3.22 (s, 3H), 3.50 (t, J=6.0 Hz, 2H), 4.14 (t, J=6.0 Hz, 2H), 4.46 (br, 1H), 4.68 (s, 2H), 7.17 (br, 1H), 7.68 (s, 1H), 7.78 (br, 1H), 8.22 (s, 1H), 8.52 (s, 2H), 9.20 (d, J=8.1 Hz, 1H), 9.65 (s, 1H).

II-106: 5-aminocarbonyl-N2-[3,4-dihydro-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine LCMS: purity: 97.03%; MS (m/e): 513.41 (MH+); $^1$H NMR (DMSO-d$_6$): δ 1.17 (s, 6H), 1.18 (s, 6H), 1.37 (t, J=12.6 Hz, 2H), 1.94 (d, J=9.6 Hz, 2H), 2.35 (s, 3H), 3.22 (s, 3H), 3.51 (t, J=5.7 Hz, 2H), 4.15 (t, J=6.0 Hz, 2H), 4.36 (br, 1H), 4.68 (s, 2H), 7.18 (br, 1H), 7.70 (s, 1H), 8.11 (s, 1H), 8.51 (s, 2H), 9.17 (d, 1H), 9.62 (s, 1H).

II-107: N2-[3,4-dihydro-4-(2-methoxyethyl)-3-oxo-2H-1,4-benzoxazin-7-yl]phenyl-5-fluoro-N4-(2,2,6,6-tetramethylpiperidin-4-yl)-2,4-pyrimidinediamine LCMS: purity: 92.21%; MS (m/e): 473.52 (MH+); $^1$H NMR (DMSO-d$_6$): δ 1.21 (s, 6H), 1.35 (s, 6H), 1.40 (t, J=12.9 Hz, 2H), 1.83 (d, J=11.4 Hz, 2H), 3.21 (s, 3H), 3.48 (t, J=5.4 Hz, 2H), 4.00 (t, 2H), 4.52 (s, 3H), 7.06 (d, J=8.4 Hz, 1H), 7.29 (d, J=8.7 Hz, 1H), 7.36 (d, 1H), 7.48 (d, 1H), 7.86 (d, J=4.2 Hz, 1H), 8.19 (s, 1H), 9.08 (s, 1H); $^{19}$F NMR (282 MHz, DMSO-d$_6$): δ−181.66.

V. II-108: N2-[3,4-dihydro-4-(2-methoxyethyl)-3-oxo-2H-1,4-benzoxazin-7-yl]phenyl-5-fluoro-N4-(1,2,2,6,6-pentamethylpiperidin-4-yl)-2,4-pyrimidinediamine LCMS: purity: 98.67%; MS (m/e): 487.58 (MH+); $^1$H NMR (DMSO-d$_6$): δ 1.24 (s, 6H), 1.26 (s, 6H), 1.64 (t, J=12.0 Hz, 2H), 1.85 (d, 2H), 3.22 (s, 3H), 3.48 (t, J=5.4 Hz, 2H), 4.01 (t, J=5.4 Hz, 2H), 4.46 (br, 1H), 4.53 (s, 2H), 7.06 (d, J=8.4 Hz, 1H), 7.24 (d, J=8.7 Hz, 1H), 7.37 (d, 1H), 7.53 (s, 1H), 7.86 (d, J=3.6 Hz, 1H), 9.08 (s, 1H); $^{19}$F NMR (282 MHz, DMSO-d$_6$): δ−181.68.

II-109: 5-aminocarbonyl-N2-[3,4-dihydro-4-(2-methoxyethyl)-3-oxo-2H-1,4-benzoxazin-7-yl]phenyl-N4-(2,2,6,6-tetramethylpiperidin-4-yl)-2,4-pyrimidinediamine LCMS: purity: 97.67%; MS (m/e): 498.56 (MH+); $^1$H NMR (DMSO-d$_6$): δ 1.26 (s, 8H), 1.38 (s, 6H), 2.00 (d, J=12.0 Hz, 2H), 3.22 (s, 3H), 3.49 (t, J=5.1 Hz, 2H), 4.02 (t, 2H), 4.54 (s, 3H), 7.10 (d, J=9.0 Hz, 1H), 7.37 (d, J=8.1 Hz, 1H), 7.51 (s, 1H), 7.78 (br, 1H), 8.51 (s, 1H), 9.21 (d, 1H), 9.57 (br, 1H).

II-110: 5-aminocarbonyl-N2-[3,4-dihydro-4-(2-methoxyethyl)-3-oxo-2H-1,4-benzoxazin-7-yl]phenyl-N4-(1,2,2,6,6-pentamethylpiperidin-4-yl)-2,4-pyrimidinediamine LCMS: purity: 97.33%; MS (m/e): 512.59 (MH+); $^1$H NMR (DMSO-d$_6$): δ 1.13 (s, 6H), 1.15 (s, 6H), 1.32 (t, J=11.7 Hz, 2H), 1.88 (d, J=10.2 Hz, 2H), 2.28 (s, 3H), 3.22 (s, 3H), 3.50 (t, J=5.7 Hz, 2H), 4.01 (t, J=5.1 Hz, 2H), 4.38 (br, 1H), 4.54 (s, 2H), 7.08 (d, J=8.7 Hz, 1H), 7.43 (d, J=9.6 Hz, 1H), 7.48 (s, 1H), 8.48 (s, 1H), 9.13 (d, J=8.1 Hz, 1H), 9.49 (br, 1H).

II-111: 5-cyano-N2-[3,4-dihydro-2,2-dimethyl-4-(2-methoxyethyl)-3-oxo-2H-pyrido[3,2-b]-1,4-oxazin-7-yl]phenyl-N4-(2,2,6,6-tetramethylpiperidin-4-yl)-2,4-pyrimidinediamine LCMS: purity: 71.48%; MS (m/e): 509.40 (MH+); $^1$H NMR (DMSO-d$_6$): δ 1.11 (s, 6H), 1.26 (s, 6H), 1.39 (s, 8H), 1.67 (d, 2H), 3.21 (s, 3H), 3.49 (t, 2H), 4.14 (t, 2H), 4.59 (br, 1H), 7.65 (d, 1H), 7.88 (s, 1H), 8.23 (s, 1H), 8.32 (s, 1H).

II-112: 5-cyano-N2-[3,4-dihydro-2,2-dimethyl-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine LCMS: purity: 97.00%; MS (m/e): 523.62 (MH+); $^1$H NMR (DMSO-d$_6$): δ 1.10 (s, 12H), 1.40 (s, 6H), 1.64 (d, 4H), 2.23 (s, 3H), 3.21 (s, 3H), 3.50 (t, J=6.0 Hz, 2H), 4.15 (t, J=5.7 Hz, 2H), 4.50 (br, 1H), 7.60 (br, 1H), 7.88 (s, 1H), 8.32 (s, 2H), 10.02 (br, 1H).

II-113: N2-[spiro(1,3-benzodioxole-2,1'-cyclopentan)-5-yl]-5-fluoro-N4-(1,2,2,6,6-pentamethylpiperidin-4-yl)-2,4-pyrimidinediamine LCMS: purity: 99.05%; MS (m/e): 456.38 (MH+); $^1$H NMR (DMSO-d$_6$): δ 1.26 (s, 12H), 1.75 (m, 6H), 1.86 (d, 2H), 1.98 (t, 4H), 4.42 (br, 1H), 6.62 (d, J=8.4 Hz, 1H), 6.88 (dd, J=2.4, 8.4 Hz, 1H), 7.33 (d, J=1.8 Hz, 2H), 7.82 (d, J=3.9 Hz, 1H), 8.85 (s, 1H); $^{19}$F NMR (282 MHz, DMSO-d$_6$): δ−182.60.

II-114: N2-[spiro(1,3-benzodioxole-2,1'-cyclohexan)-5-yl]-5-fluoro-N4-(1,2,2,6,6-pentamethylpiperidin-4-yl)-2,4-pyrimidinediamine LCMS: purity: 96.16%; MS (m/e): 470.59 (MH+); $^1$H NMR (DMSO-d$_6$): δ 1.40 (s, 12H), 1.44 (m, 2H), 1.63 (m, 4H), 1.81 (m, 6H), 2.05 (d, J=12.6 Hz, 2H), 2.72 (d, J=4.5 Hz, 3H), 4.51 (br, 1H), 6.64 (d, J=8.7 Hz, 1H), 6.82 (dd, J=2.1, 8.7 Hz, 1H), 7.33 (d, J=1.8 Hz, 1H), 7.58 (br, 1H), 7.87 (d, J=3.9 Hz, 1H), 8.65 (br, 1H), 8.95 (s, 1H).

II-115: N2-(6-chloro-1,3-benzodioxol-5-yl)-5-fluoro-N4-(1,2,2,6,6-pentamethylpiperidin-4-yl)-2,4-pyrimidinediamine LCMS: purity: 99.85%; MS (m/e): 436.05 (MH+); $^1$H NMR (DMSO-d$_6$): δ 1.14 (s, 6H), 1.25 (s, 6H), 1.60 (t, 2H), 1.84 (d, 2H), 4.24 (br, 1H), 6.00 (s, 2H), 7.05 (s, 1H), 7.31 (s, 1H), 7.36 (d, 1H), 7.82 (d, J=3.9 Hz, 1H), 8.01 (s, 1H), 8.11 (s, 1H); $^{19}$F NMR (282 MHz, DMSO-d$_6$): δ−182.45.

II-116: N2-(7-chloro-2,3-dihydro-1,4-benzodioxin-6-yl)-5-fluoro-N4-(1,2,2,6,6-pentamethylpiperidin-4-yl)-2,4-pyrimidinediamine LCMS: purity: 99.59%; MS (m/e): 450.37 (MH+); $^1$H NMR (DMSO-d$_6$): δ 0.97 (s, 6H), 1.08 (s, 6H), 1.42 (t, J=11.7 Hz, 2H), 1.65 (d, J=11.4 Hz, 2H), 2.23 (s, 3H), 4.18 (s, 5H), 6.91 (s, 1H), 7.19 (d, J=7.8 Hz, 1H), 7.28 (s, 1H), 7.78 (d, J=3.9 Hz, 1H), 7.85 (s, 1H); $^{19}$F NMR (282 MHz, DMSO-d$_6$): δ−182.44.

II-117: 5-cyano-N2-[3,4-dihydro-4-(2-methoxyethyl)-3-oxo-2H-pyrido[3,2-b]-1,4-oxazin-7-yl]phenyl-N4-(1,2,2,6,6-pentamethylpiperidin-4-yl)-2,4-pyrimidinediamine LCMS: purity: 97.95%; MS (m/e): 495.61 (MH+); $^1$H NMR (DMSO-d$_6$): δ 1.09 (s, 6H), 1.11 (s, 6H), 1.65 (m, 4H), 2.25 (s, 3H), 3.22 (s, 3H), 3.50 (t, J=6.0 Hz, 2H), 4.14 (t, J=6.0 Hz, 2H), 4.47 (br, 1H), 4.69 (s, 2H), 7.62 (m, 2H), 8.32 (s, 1H), 8.45 (br, 1H), 9.93 (br, 1H).

II-118: 5-cyano-N2-[3,4-dihydro-4-(2-methoxyethyl)-3-oxo-2H-1,4-benzoxazin-7-yl]phenyl-N4-(2,2,6,6-tetramethylpiperidin-4-yl)-2,4-pyrimidinediamine LCMS: purity: 91.25%; MS (m/e): 480.55 (MH+); $^1$H NMR (DMSO-d$_6$): δ 1.37 (s, 6H), 1.43 (s, 6H), 1.67 (t, J=12.6 Hz, 2H), 1.90 (d, J=13.8 Hz, 2H), 3.22 (s, 3H), 3.49 (t, J=5.4 Hz, 2H), 4.03 (t, 2H), 4.56 (s, 2H), 4.60 (br, 1H), 7.14 (d, J=8.7 Hz, 1H), 7.24 (d, J=8.4 Hz, 1H), 7.46 (s, 1H), 7.79 (m, 2H), 8.34 (s, 1H), 8.63 (br, 1H), 9.91 (br, 1H).

II-119: 5-cyano-N2-[3,4-dihydro-4-(2-methoxyethyl)-3-oxo-2H-1,4-benzoxazin-7-yl]phenyl-N4-(1,2,2,6,6-pentamethylpiperidin-4-yl)-2,4-pyrimidinediamine LCMS: purity: 97.63%; MS (m/e): 494.43 (MH+); $^1$H NMR (DMSO-d$_6$): δ 1.12 (s, 12H), 1.66 (m, 4H), 2.28 (s, 3H), 3.22 (s, 3H), 3.49 (t, J=5.4 Hz, 2H), 4.01 (t, 2H), 4.50 (br, 1H), 4.55 (s, 2H), 7.10 (d, J=8.7 Hz, 1H), 7.33 (d, 1H), 7.43 (s, 1H), 7.51 (br, 1H), 8.29 (s, 1H), 9.84 (br, 1H).

II-120: N2-[spiro(1,3-benzodioxole-2,1'-cyclopentan)-5-yl]-5-fluoro-N4-(2,2,6,6-tetramethylpiperidin-4-yl)-2,4-pyrimidinediamine LCMS: purity: 97.18%; MS (m/e): 442.38 (MH+); $^1$H NMR (DMSO-d$_6$): δ 1.32 (s, 6H), 1.40 (s, 6H), 1.51 (t, J=13.2 Hz, 2H), 1.74 (m, 4H), 1.90 (d, J=14.1 Hz, 2H), 1.96 (m, 4H), 4.49 (br, 1H), 6.63 (d, J=8.7 Hz, 1H), 6.84 (d, J=8.4 Hz, 1H), 7.36 (s, 1H), 7.42 (d, J=6.6 Hz, 1H), 7.84 (d, J=3.9 Hz, 1H), 8.89 (s, 1H); $^{19}$F NMR (282 MHz, DMSO-d$_6$): δ−182.60.

II-121: N2-[spiro(1,3-benzodioxole-2,1'-cyclohexan)-5-yl]-5-fluoro-N4-(2,2,6,6-tetramethylpiperidin-4-yl)-2,4-pyrimidinediamine LCMS: purity: 93.73%; MS (m/e): 456.40 (MH+); $^1$H NMR (DMSO-d$_6$): δ 1.36 (s, 6H), 1.45 (s, 6H), 1.62 (m, 8H), 1.80 (m, 4H), 1.94 (d, J=12.3 Hz, 2H), 4.54 (br, 1H), 6.64 (d, J=8.4 Hz, 1H), 6.77 (d, J=8.4 Hz, 1H), 7.41 (d, J=1.8 Hz, 1H), 7.51 (d, 1H), 7.80 (d, J=11.1 Hz, 1H), 7.86 (d, J=3.9 Hz, 1H), 8.63 (d, 1H), 8.95 (s, 1H); $^{19}$F NMR (282 MHz, DMSO-d$_6$): δ−182.55.

II-122: N2-(6-bromo-2,2-difluoro-benzo[1,3]dioxol-5-yl)-5-fluoro-N4-(1,2,2,6,6-pentamethylpiperidin-4-yl)-2,4-pyrimidinediamine LCMS: purity: 99.56%; MS (m/e): 518.41 (MH+); $^1$H NMR (DMSO-d$_6$): δ 1.19 (br, 6H), 1.32 (br, 6H), 1.67 (br, 2H), 1.94 (br, 2H), 4.21 (br, 1H), 7.56 (br, 1H), 7.85 (m, 2H), 8.24 (br, 1H); $^{19}$F NMR (282 MHz, DMSO-d$_6$): δ−181.47, −65.27.

II-123: 5-fluoro-N2-(2,2,3,3,7-pentafluoro-2,3-dihydro-1,4-benzodioxin-6-yl)-N4-(1,2,2,6,6-pentamethylpiperidin-4-yl)-2,4-pyrimidinediamine LCMS: purity: 99.90%; MS (m/e): 506.47 (MH+); $^1$H NMR (DMSO-d$_6$): δ 1.04 (s, 6H), 1.14 (s, 6H), 1.52 (t, J=12.3 Hz, 2H), 1.73 (d, J=10.5 Hz, 2H), 2.31 (s, 3H), 4.27 (d, J=9.0 Hz, 1H), 7.42 (d, J=8.1 Hz, 1H), 7.55 (d, J=10.5 Hz, 1H), 7.87 (d, J=3.9 Hz, 1H), 7.99 (d, J=7.2 Hz, 1H), 8.74 (s, 1H); $^{19}$F NMR (282 MHz, DMSO-d$_6$): δ −180.62, −140.10, −107.13 (t, J=52 Hz).

II-124: N2-[3,4-dihydro-2,2-dimethyl-4-(2-fluoroethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine LCMS: purity: 87.12%; MS (m/e): 504.37 (MH+); $^1$H NMR (DMSO-d$_6$): δ 1.41 (s, 6H), 1.43 (s, 12H), 1.83 (t, J=12.6 Hz, 2H), 2.08 (d, J=13.2 Hz, 2H), 2.74 (d, J=4.5 Hz, 3H), 4.28 (t, 1H), 4.35 (t, 1H), 4.50 (br, 1H), 4.53 (t, 1H), 4.69 (t, 1H), 7.87 (m, 2H), 7.98 (d, J=3.9 Hz, 1H), 8.25 (d, J=2.4 Hz, 1H), 8.62 (br, 1H), 9.50 (s, 1H).

II-125: 5-aminocarbonyl-N2-[3,4-dihydro-2,2-dimethyl-4-(2-fluoroethyl)-3-oxo-2H-pyrido[3,2-b]-1,4-oxazin-7-yl]phenyl-N4-(2,2,6,6-tetramethylpiperidin-4-yl)-2,4-pyrimidinediamine LCMS: MS (m/e): 515.34 (MH+); $^1$H NMR (DMSO-d$_6$): δ 1.34 (s, 6H), 1.41 (s, 8H), 1.47 (s, 6H), 2.06 (d, J=12.6 Hz, 2H), 4.27 (t, 1H), 4.35 (t, 1H), 4.52 (t, J=5.4 Hz, 2H), 4.68 (t, J=4.8 Hz, 1H), 7.24 (br, 1H), 7.86 (br, 1H), 7.94 (d, J=2.1 Hz, 1H), 8.36 (s, 1H), 8.55 (s, 1H), 9.27 (d, 1H), 9.81 (br, 1H).

II-126: N2-[3,4-dihydro-2,2-dimethyl-4-(2,2,2-trifluoroethyl)-3-oxo-2H-pyrido[3,2-b]-1,4-oxazin-7-yl]phenyl-5-fluoro-N4-(1,2,2,6,6-pentamethylpiperidin-4-yl)-2,4-pyrimidinediamine LCMS: MS (m/e): 540.32 (MH+); $^1$H NMR (DMSO-d$_6$): δ 1.40 (s, 6H), 1.43 (s, 6H), 1.44 (d, J=1.8 Hz, 6H), 1.81 (t, J=13.2 Hz, 2H), 2.08 (d, J=11.7 Hz, 2H), 2.73 (s, 3H), 4.48 (d, 1H), 4.83 (q, J=9.0 Hz, 2H), 7.66 (d, J=7.2 Hz, 1H), 7.94 (m, 2H), 8.32 (d, J=2.4 Hz, 1H), 9.42 (s, 1H); $^{19}$F NMR (282 MHz, DMSO-d$_6$): δ −180.74, −83.72 (t, J=9.2 Hz).

II-127: 5-bromo-N2-(2,3-dihydrobenzo[b][1,4]dioxin-6-yl)-N4-(1,2,2,6,6-pentamethylpiperidin-4-yl)pyrimidine-2,4-diamine MS (m/e): 477.15 (MH$^+$); $^1$H NMR (DMSO-d$_6$): δ 9.01 (s, 1H), 7.95 (s, 1H), 7.19 (s, 1H), 7.15 (d, 1H), 6.61 (d, 1H), 6.35 (d, 1H), 4.41 (m, 1H), 4.15 (s, 4H), 2.19 (s, 3H), 1.69-1.61 (d, 2H), 1.59-1.48 (t, 2H), 1.09-1.03 (s, 12H).

II-128: 7-(5-bromo-4-(1,2,2,6,6-pentamethylpiperidin-4-ylamino)pyrimidin-2-ylamino)-4-ethyl-2,2-dimethyl-2H-benzo[b][1,4]oxazin-3(4H)-one MS (m/e): 546.21 (MH$^+$); $^1$H NMR (DMSO-d$_6$): δ 9.29 (s, 1H), 7.95 (s, 1H), 7.69 (d, 1H), 7.17 (dd, 1H), 6.95 (d, 1H), 6.43 (d, 1H), 4.51 (m, 1H), 3.84 (q, 2H), 2.21 (s, 3H), 1.61 (d, 7H), 1.39 (s, 6H), 1.15-1.03 (s, 12H).

II-129: N2-(2,3-dihydrobenzo[b][1,4]dioxin-6-yl)-5-methoxy-N4-(1,2,2,6,6-pentamethylpiperidin-4-yl)pyrimidine-2,4-diamine MS (m/e) 428.25 (MH$^+$); $^1$H NMR (DMSO-d$_6$): δ 10.21 (s, 1H), 8.81 (m, 2H), 7.56 (s, 1H), 7.09 (s, 1H), 6.81 (s, 1H), 4.51 (m, 1H), 4.21 (s, 4H), 3.79 (s, 3H), 2.68 (s, 3H), 1.98 (m, 4H), 1.39-1.25 (d, 12H).

II-130: 4-ethyl-7-(5-methoxy-4-(1,2,2,6,6-pentamethylpiperidin-4-ylamino)pyrimidin-2-ylamino)-2,2-dimethyl-2H-benzo[b][1,4]oxazin-3(4H)-one MS (m/e) 497.32 (MH$^+$); $^1$H NMR (DMSO-d$_6$): δ 10.52 (s, 1H), 8.81 (s, 1H), 7.69 (s, 1H), 7.47 (d, 1H), 7.15 (dd, 1H), 7.05 (dd, 1H), 4.53 (m, 1H), 3.94 (q, 2H), 2.81 (s, 3H), 2.72 (s, 3H), 2.05 (m, 4H), 1.41 (s, 12H), 1.35 (s, 6H), 1.15 (t, 3H).

II-131: 5-fluoro-N2-(6-fluorobenzo[d]thiazol-2-yl)-N4-(1,2,2,6,6-pentamethylpiperidin-4-yl)pyrimidine-2,4-diamine MS (m/e) 433.19 (MH$^+$); $^1$H NMR (DMSO-d$_6$): δ 8.09 (d, 1H), 7.89 (d, 1H), 7.67 (m, 2H), 7.22 (m, 1H), 6.56 (s, 1H), 4.69 (m, 1H), 2.75 (s, 3H), 2.19-2.09 (d, 2H), 1.91-1.75 (t, 2H), 1.55-1.32 (d, 12H).

II-132: N2-(4-(2,3-dihydrobenzo[b][1,4]dioxin-6-yl)thiazol-2-yl)-5-fluoro-N4-(1,2,2,6,6-pentamethylpiperidin-4-yl)pyrimidine-2,4-diamine MS (m/e) 499.22 (MH$^+$); $^1$H NMR (DMSO-d$_6$): δ 8.14 (s, 1H), 7.97 (d, 1H), 7.67 (d, 1H), 7.36 (s, 1H), 7.33 (d, 1H), 7.28 (s, 1H), 6.84 (d, 1H), 4.61 (m, 1H), 4.25 (s, 4H), 3.41 (s, 3H), 1.99-1.81 (d, 2H), 1.75-1.65 (t, 2H), 1.41-1.25 (d, 12H).

II-133: 5-fluoro-N4-(1,2,2,6,6-pentamethylpiperidin-4-yl)-N2-(4-(4-(pyrrolidin-1-yl)phenyl)thiazol-2-yl)pyrimidine-2,4-diamine MS (m/e) 510.28 (MH$^+$); $^1$H NMR (DMSO-d$_6$): δ 8.16 (s, 1H), 7.96 (s, 1H), 7.69 (d, 2H), 7.51 (d, 1H), 7.04 (s, 1H), 6.54 (d, 2H), 4.63 (m, 1H), 3.25 (t, 4H), 2.39 (s, 3H), 1.99 (t, 4H), 1.89-1.81 (d, 2H), 1.69-1.55 (t, 2H), 1.29-1.24 (d, 12H).

II-134: 5-fluoro-N4-(1,2,2,6,6-pentamethylpiperidin-4-yl)-N2-(4-(trifluoromethyl)oxazol-2-yl)pyrimidine-2,4-diamine MS (m/e) 417.21 (MH$^+$); $^1$H NMR (DMSO-d$_6$): δ 8.44 (d, 1H), 8.18 (s, 1H), 7.91 (d, 1H), 7.52 (d, 1H), 4.49 (m, 1H), 2.29 (s, 3H), 1.75-1.68 (d, 2H), 1.55-1.48 (t, 2H), 1.19-1.05 (d, 12H).

II-135: N2-(4-(4-(diethylamino)phenyl)thiazol-2-yl)-5-fluoro-N4-(1,2,2,6,6-pentamethylpiperidin-4-yl)pyrimidine-2,4-diamine MS (m/e) 512.28 (MH$^+$); $^1$H NMR (DMSO-d$_6$): δ 8.18 (s, 1H), 7.49 (d, 1H), 7.66 (d, 2H), 7.54 (d, 1H), 7.21 (s, 1H), 6.64 (d, 2H), 4.63 (m, 1H), 3.32 (q, 4H), 2.39 (s, 3H), 1.89-1.78 (d, 2H), 1.69-1.55 (t, 2H), 1.25-1.14 (d, 12H), 1.11-1.05 (t, 6H).

II-136: 5-fluoro-N4-(1,2,2,6,6-pentamethylpiperidin-4-yl)-N2-(4-(pyridin-3-yl)thiazol-2-yl)pyrimidine-2,4-diamine MS (m/e) 442.21 (MH$^+$); $^1$H NMR (DMSO-d$_6$): δ 9.51 (s, 1H), 8.49 (d, 1H), 8.19 (s, 2H), 7.98 (d, 1H), 7.61 (s, 2H), 7.42

(m, 1H), 4.63 (m, 1H), 2.41 (s, 3H), 1.89-1.82 (d, 2H), 1.71-1.55 (t, 2H), 1.29-1.18 (d, 12H).

II-137: 5-fluoro-N2-(4-(3-fluoro-4-methoxyphenyl) thiazol-2-yl)-N4-(1,2,2,6,6-pentamethylpiperidin-4-yl)pyrimidine-2,4-diamine MS (m/e) 489.22 (MH$^+$); $^1$H NMR (DMSO-d$_6$): δ 8.19 (s, 1H), 7.96 (d, 1H), 7.68 (d, 1H), 7.62 (s, 1H), 7.48 (d, 1H), 7.39 (s, 1H), 7.18 (t, 1H), 4.61 (m, 1H), 3.85 (s, 3H), 2.25 (s, 3H), 1.79-1.72 (d, 2H), 1.59-1.49 (t, 2H), 1.19-1.09 (d, 12H).

II-138: N2-(4-(3,4-dimethoxyphenyl)thiazol-2-yl)-5-fluoro-N4-(1,2,2,6,6-pentamethylpiperidin-4-yl)pyrimidine-2,4-diamine MS (m/e) 501.24 (MH$^+$); $^1$H NMR (DMSO-d$_6$): δ 8.19 (s, 1H), 7.94 (d, 1H), 7.48 (d, 1H), 7.45 (s, 1H), 7.42 (s, 1H), 7.22 (s, 1H), 6.94 (d, 1H), 4.61 (m, 1H), 3.79 (s, 3H), 3.72 (s, 3H), 2.29 (s, 3H), 1.81-1.72 (d, 2H), 1.62-1.51 (t, 2H), 1.22-1.13 (d, 12H).

II-139: 5-fluoro-N4-(1,2,2,6,6-pentamethylpiperidin-4-yl)-N2-(4-(4-phenoxyphenyl)thiazol-2-yl)pyrimidine-2,4-diamine MS (m/e) 533.24 (MH$^+$); $^1$H NMR (DMSO-d$_6$): δ 8.14 (s, 1H), 7.96 (d, 1H), 7.88 (d, 2H), 7.51 (d, 1H), 7.39 (d, 3H), 7.15 (t, 1H), 7.02 (t, 4H), 4.61 (m, 1H), 2.25 (s, 3H), 1.81-1.72 (d, 2H), 1.62-1.51 (t, 2H), 1.22-1.13 (d, 12H).

II-140: 5-fluoro-N4-(1,2,2,6,6-pentamethylpiperidin-4-yl)-N2-(4-(4-(trifluoromethyl)phenyl)thiazol-2-yl) pyrimidine-2,4-diamine MS (m/e) 509.24 (MH$^+$); $^1$H NMR (DMSO-d$_6$): δ 8.21 (s, 1H), 8.09 (d, 2H), 7.96 (d, 1H), 7.74 (d, 2H), 7.69 (s, 1H), 7.51 (d, 1H), 4.59 (m, 1H), 2.41 (s, 3H), 1.79-1.72 (d, 2H), 1.59-1.47 (t, 2H), 1.15-1.05 (d, 12H).

II-141: N2-(4-(2,4-difluorophenyl)thiazol-2-yl)-5-fluoro-N4-(1,2,2,6,6-pentamethylpiperidin-4-yl)pyrimidine-2,4-diamine MS (m/e) 477.21 (MH$^+$); $^1$H NMR (DMSO-d$_6$): δ 8.11 (s, 1H), 8.01 (d, 1H), 7.63 (s, 1H), 7.34 (d, 1H), 7.29 (s, 1H), 7.19 (t, 1H), 6.56 (s, 1H), 4.59 (m, 1H), 1.89-1.85 (d, 2H), 1.77-1.61 (t, 2H), 1.39-1.15 (d, 12H);

II-142: 4-chloro-N-(4-(2-(5-fluoro-4-(1,2,2,6,6-pentamethylpiperidin-4-ylamino)pyrimidin-2-ylamino) thiazol-4-yl)phenyl)benzenesulfonamide MS (m/e) 631.18 (MH$^+$); $^1$H NMR (DMSO-d$_6$): δ 8.21 (s, 1H), 7.92 (d, 1H), 7.72 (d, 5H), 7.58 (d, 2H), 7.44 (d, 1H), 7.28 (s, 1H), 7.06 (d, 2H), 4.59 (m, 1H), 2.19 (s, 3H), 1.75-1.63 (d, 2H), 1.58-1.49 (t, 2H), 1.15-1.05 (d, 12H);

II-143: 2-(5-fluoro-4-(1,2,2,6,6-pentamethylpiperidin-4-ylamino)pyrimidin-2-ylamino)benzo[d]thiazole-6-carboxylic acid MS (m/e) 459.18 (MH$^+$); $^1$H NMR (DMSO-d$_6$): δ 11.81 (s, 1H), 8.24 (s, 1H), 8.02 (s, 1H), 7.92 (dd, 1H), 7.65 (m, 3H), 4.61 (m, 1H), 2.25 (s, 3H), 1.82-1.79 (d, 2H), 1.68-1.47 (t, 2H), 1.29-1.09 (d, 12H);

II-144: 5-fluoro-N2-(6-(methylsulfonyl)benzo[d] thiazol-2-yl)-N4-(1,2,2,6,6-pentamethylpiperidin-4-yl)pyrimidine-2,4-diamine MS (m/e) 493.18 (MH$^+$); $^1$H NMR (DMSO-d$_6$): δ 8.24 (s, 1H), 8.12 (s, 1H), 8.06 (d, 1H), 7.86 (dd, 1H), 7.76 (d, 2H), 4.59 (m, 1H), 3.21 (s, 3H), 2.39 (s, 3H), 1.85-1.82 (d, 2H), 1.65-1.58 (t, 2H), 1.29-1.21 (d, 12H).

II-145: 4-ethyl-2,2-dimethyl-7-(5-methyl-4-(1,2,2,6,6-pentamethylpiperidin-4-ylamino)pyrimidin-2-ylamino)-2H-benzo[b][1,4]oxazin-3(4H)-one MS (m/e) 481.32 (MH$^+$); $^1$H NMR (DMSO-d$_6$): δ 8.87 (s, 1H), 8.24 (d, 1H), 7.79 (s, 1H), 7.39 (s, 1H), 7.19 (d, 1H), 7.05 (d, 1H), 4.58 (m, 1H), 3.92 (q, 2H), 2.79 (s, 3H), 1.99 (bs, 7H), 1.39 (s, 12H), 1.27 (s, 6H), 1.15 (t, 3H).

II-146: N2-(2,3-dihydrobenzo[b][1,4]dioxin-6-yl)-5-methyl-N4-(1,2,2,6,6-pentamethylpiperidin-4-yl) pyrimidine-2,4-diamine MS (m/e) 412.27 (MH$^+$); $^1$H NMR (DMSO-d$_6$): δ 8.12 (s, 1H), 7.68 (s, 1H), 7.29 (s, 1H), 7.19 (d, 1H), 6.93 (dd, 1H), 6.72 (d, 1H), 4.59 (m, 1H), 4.22 (s, 4H), 2.61 (s, 3H), 1.95 (s, 7H), 1.39-1.27 (d, 12H).

II-147: 6-(5-fluoro-4-(1,2,2,6,6-pentamethylpiperidin-4-ylamino)pyrimidin-2-ylamino)quinazoline-2,4 (1H,3H)-dione MS (m/e) 442.23 (MH$^+$); $^1$H NMR (DMSO-d$_6$): δ 11.21 (s, 1H), 11.01 (s, 1H), 8.69 (d, 1H), 8.13 (d, 1H), 7.97 (d, 1H), 7.93 (s, 1H), 7.75 (dd, 1H), 7.13 (d, 1H), 4.42 (m, 1H), 2.23 (s, 3H), 2.11-2.05 (d, 2H), 1.85-1.72 (t, 2H), 1.45-1.29 (d, 12H).

II-148: 5-(5-fluoro-4-(1,2,2,6,6-pentamethylpiperidin-4-ylamino)pyrimidin-2-ylamino)isoindoline-1,3-dione MS (m/e) 427.22 (MH$^+$); $^1$H NMR (DMSO-d$_6$): δ 11.01 (s, 1H), 8.62 (s, 1H), 8.21 (s, 1H), 8.01 (dd, 1H), 7.93 (dd, 1H), 7.75 (d, 1H), 7.69 (d, 1H), 4.49 (m, 1H), 2.21 (s, 3H), 2.15-2.05 (d, 2H), 1.89-1.77 (t, 2H), 1.51-1.35 (d, 12H).

II-149: 5-(5-fluoro-4-(1,2,2,6,6-pentamethylpiperidin-4-ylamino)pyrimidin-2-ylamino)-2-methylisoindoline-1,3-dione MS (m/e) 441.24 (MH$^+$); $^1$H NMR (DMSO-d$_6$): δ 8.62 (s, 1H), 8.21 (s, 1H), 8.05 (d, 1H), 7.95 (dd, 1H), 7.77 (d, 1H), 7.63 (d, 1H), 4.49 (m, 1H), 3.01 (s, 3H), 2.24 (s, 3H), 2.15-2.05 (d, 2H), 1.89-1.77 (t, 2H), 1.49-1.37 (d, 12H).

II-150: N2-(2,3-dihydrobenzo[b][1,4]dioxin-6-yl)-N4-(1,2,2,6,6-pentamethylpiperidin-4-yl)-5-((trimethylsilyl)ethynyl)pyrimidine-2,4-diamine MS (m/e) 494.29 (MH$^+$); $^1$H NMR (DMSO-d$_6$): δ 9.21 (s, 1H), 7.95 (s, 1H), 7.19 (m, 2H), 6.62 (d, 1H), 5.78 (d, 1H), 4.49 (m, 1H), 4.15 (s, 4H), 2.21 (s, 3H), 1.73-1.69 (d, 2H), 1.51-1.38 (t, 2H), 1.15-1.05 (d, 12H), 0.25 (s, 9H).

II-151: 4-ethyl-2,2-dimethyl-7-(4-(1,2,2,6,6-pentamethylpiperidin-4-ylamino)-5-((trimethylsilyl)ethynyl) pyrimidin-2-ylamino)-2H-benzo[b][1,4]oxazin-3 (4H)-one MS (m/e) 563.32 (MH+); $^1$H NMR (DMSO-d6): δ 9.41 (s, 1H), 8.01 (s, 1H), 7.73 (s, 1H), 7.32 (dd, 1H), 7.01 (d, 1H), 5.82 (d, 1H), 4.52 (m, 1H), 3.85 (q, 2H), 2.19 (s, 3H), 1.75-1.69 (d, 2H), 1.55-1.45 (t, 2H), 1.35 (s, 6H), 1.19-1.05 (d, 15H), 0.25 (s, 9H);

II-152: 4-ethyl-7-(5-ethynyl-4-(1,2,2,6,6-pentamethylpiperidin-4-ylamino)pyrimidin-2-ylamino)-2,2-dimethyl-2H-benzo[b][1,4]oxazin-3(4H)-one MS (m/e) 491.32 (MH$^+$); $^1$H NMR (CDCl$_3$): δ 9.49 (s, 1H), 8.05 (s, 1H), 7.72 (s, 1H), 7.41 (dd, 1H), 6.99 (d, 1H), 5.85 (d, 1H), 4.71 (m, 1H), 3.95 (q, 2H), 3.51 (s, 1H), 2.75 (s, 3H), 2.39-2.32 (t, 2H), 2.05-1.98 (dd, 2H), 1.45 (s, 18H), 1.25 (t, 3H).

II-153: 5-(5-fluoro-4-(2,2,6,6-tetramethylpiperidin-4-ylamino)pyrimidin-2-ylamino)-2-methylisoindoline-1,3-dione MS (m/e) 427.24 (MH$^+$); $^1$H NMR (CD$_3$OD-d$_4$): δ 8.42 (s, 1H), 7.95 (d, 1H), 7.87 (d, 1H), 7.74 (d, 1H), 4.69 (m, 1H), 3.09 (s, 3H), 2.21 (m, 4H), 1.65-1.49 (d, 12H).

II-154: 6-(5-fluoro-4-(2,2,6,6-tetramethylpiperidin-4-ylamino)pyrimidin-2-ylamino)quinazoline-2,4(1H,3H)-dione MS (m/e) 428.29 (MH$^+$); $^1$H NMR (DMSO-d$_6$): δ 11.21 (s, 1H), 10.95 (s, 1H), 9.11 (s, 1H), 8.31 (s, 1H), 8.11 (s, 1H), 7.97 (dd, 1H), 7.86 (d, 1H), 7.35 (d, 1H), 7.05 (d, 1H), 4.49 (m, 1H), 1.91-1.78 (d, 2H), 1.51-1.39 (t, 2H), 1.35-1.29 (d, 12H).

II-155: 6-(5-fluoro-4-(2,2,6,6-tetramethylpiperidin-4-ylamino)pyrimidin-2-ylamino)-2,3-dihydrobenzo[b][1,4]dioxine-2-carboxylic acid MS (m/e) 446.27 (MH$^+$); $^1$H NMR (DMSO-d$_6$): δ 8.55 (bs, 2H), 8.16 (s, 1H), 7.87 (d, 1H), 7.46 (d, 1H), 7.35 (s, 1H), 7.02 (dd, 1H), 6.64 (d, 1H), 4.69 (t, 1H), 4.52 (m, 1H), 4.23 (bs, 2H), 1.99-1.85 (d, 2H), 1.69-1.53 (t, 2H), 1.45-1.36 (d, 12H).

II-156: N2-(2,3-dihydrobenzo[b][1,4]dioxin-6-yl)-5-ethynyl-N4-(1,2,2,6,6-pentamethylpiperidin-4-yl)pyrimidine-2,4-diamine MS (m/e) 422.31 (MH$^+$); $^1$H NMR (CDCl$_3$): δ 9.41 (s, 1H), 7.99 (s, 1H), 7.51 (d, 1H), 7.32 (d, 1H), 7.19 (dd, 1H), 5.98 (d, 1H), 4.69 (m, 1H), 4.29 (s, 4H), 3.47 (s, 1H), 2.61 (s, 3H), 2.41-2.32 (t, 2H), 2.05-1.99 (d, 2H), 1.49 (s, 12H).

II-157: 6-(5-fluoro-4-(1,2,2,6,6-pentamethylpiperidin-4-ylamino)pyrimidin-2-ylamino)-2,3-dihydrobenzo[b][1,4]dioxine-2-carboxylic acid MS (m/e) 460.27 (MH$^+$); $^1$H NMR (DMSO-d$_6$): δ 8.85 (s, 1H), 8.16 (s, 1H), 7.82 (d, 1H), 7.36 (m, 2H), 7.05 (d, 1H), 6.64 (d, 1H), 4.61 (t, 1H), 4.47 (m, 1H), 4.19 (d, 2H), 2.61 (s, 3H), 1.91-1.85 (d, 2H), 1.79-1.63 (t, 2H), 1.38-1.16 (d, 12H).

II-158: (6-(5-fluoro-4-(1,2,2,6,6-pentamethylpiperidin-4-ylamino)pyrimidin-2-ylamino)-2,3-dihydrobenzo[b][1,4]dioxin-2-yl)(4-methylpiperazin-1-yl)methanone MS (m/e) 542.37 (MH$^+$); $^1$H NMR (DMSO-d$_6$): δ 9.23 (bs, 1H), 8.19 (d, 1H), 7.22 (s, 1H), 7.06 (d, 1H), 6.89 (dd, 1H), 5.32 (d, 1H), 4.49 (m, 2H), 4.15 (d, 2H), 3.45 (m, 4H), 3.05 (m, 4H), 2.75 (s, 3H), 2.31 (s, 3H), 2.25-2.15 (d, 2H), 1.97-1.83 (t, 2H), 1.53 (s, 12H).

II-159: 6-(5-fluoro-4-(2,2,6,6-tetramethylpiperidin-4-ylamino)pyrimidin-2-ylamino)-2,3-dihydrobenzo[b][1,4]dioxine-2-carboxamide MS (m/e) 445.23 (MH$^+$); $^1$H NMR (DMSO-d$_6$): δ 8.92 (s, 1H), 8.12 (s, 1H), 7.83 (d, 1H), 7.46 (bs, 2H), 7.45 (d, 1H), 7.05 (dd, 1H), 6.65 (d, 1H), 4.63 (m, 1H), 4.52 (m, 1H), 4.25 (dd, 1H), 4.13 (m, 2H), 2.01-1.95 (d, 2H), 1.62-1.55 (t, 2H), 1.47-1.42 (s, 12H).

II-160: (6-(5-fluoro-4-(2,2,6,6-tetramethylpiperidin-4-ylamino)pyrimidin-2-ylamino)-2,3-dihydrobenzo[b][1,4]dioxin-2-yl)(4-methylpiperazin-1-yl)methanone MS (m/e) 528.31 (MH$^+$); $^1$H NMR (DMSO-d$_6$): δ 9.03 (s, 1H), 8.89 (d, 1H), 8.11 (s, 1H), 7.26 (s, 1H), 7.05 (d, 1H), 6.75 (d, 1H), 5.23 (d, 1H), 4.49 (m, 2H), 4.35 (m, 1H), 4.13 (m, 2H), 3.45 (m, 4H), 3.05 (m, 4H), 2.81 (s, 3H), 2.01-1.85 (d, 2H), 1.71-1.55 (t, 2H), 1.47-1.35 (s, 12H).

II-161: 5-Cyano-N2-[4-(2-fluoroethyl)-2H-1,4-benzoxazin-3-one-7-yl]-N4-(1,2,2,6,6-pentamethylpiperidin-4-yl)-2,4-pyrimidinediamine MS (m/e) 482.19 (MH$^+$); $^1$H NMR (DMSO-d$_6$): δ 9.93 (bs, 1H), 8.51 (bs, 1H), 8.35 (s, 1H), 7.85 (bs, 1H), 7.59 (s, 1H), 7.13 (s, 2H), 4.68 (m, 1H), 4.61 (s, 3H), 4.52 (m, 1H), 4.25 (m, 1H), 4.17 (m, 1H), 2.75 (s, 3H), 2.02-1.75 (m, 4H), 1.39 (s, 12H).

II-162: 5-Cyano-N2-(3-isopropyl-benzoxazol-2-one-6-yl)-N4-(2,2,6,6-tetramethylpiperidin-4-yl)-2,4-pyrimidinediamine MS (m/e) 450.68 (MH$^+$); $^1$H NMR (DMSO-d$_6$): δ 9.91 (bs, 1H), 8.33 (s, 1H), 7.78 (s, 2H), 7.68 (bs, 1H), 7.31-7.26 (m, 2H), 4.54 (bs, 1H), 4.44 (m, 1H), 1.81 (m, 2H), 1.74 (s, 1H), 1.57 (m, 2H), 1.44 (s, 3H), 1.41 (s, 3H), 1.29 (s, 12H).

II-163: N2-(3-Cyclopropylmethylene-benzoxazol-2-one-6-yl)-5-fluoro-N4-(1,2,2,6,6-pentamethylpiperidin-4-yl)-2,4-pyrimidinediamine MS (m/e) 469.10 (MH$^+$); $^1$H NMR (DMSO-d$_6$): δ 9.08 (s, 1H), 7.87-7.83 (m, 2H), 7.36-7.33 (d, J=9.3 Hz, 1H), 7.23-7.21 (d, J=7.8 Hz, 1H), 7.16-7.13 (d, J=7.5 Hz, 1H), 4.35 (bs, 1H), 3.66-3.64 (d, J=6.6 Hz, 1H), 2.23 (s, 3H), 1.74-1.70 (m, 2H), 1.54-1.45 (m, 2H), 1.1 bs, 12H), 0.51 (m, 2H), 0.37 (m, 2H).

II-164: 5-Cyano-N2-[2,2-dimethyl-4-(2-fluoroethyl)-1,4-benzoxazin-3-one-7-yl]-N4-(2,2,6,6-tetramethylpiperidin-4-yl)-2,4-pyrimidinediamine MS (m/e) 496.12 (MH$^+$); $^1$H NMR (DMSO-d$_6$): δ 9.92 (s, 1H), 8.32 (s, 1H), 7.71 (s, 1H), 7.62-7.59 (m, 1H), 7.17-7.07 (m, 2H), 4.68 (m, 2H), 4.52 (bs, 1H), 4.23 (bs, 1H), 4.16 (bs, 1H), 1.73-1.69 (d, J=12.9 Hz, 2H), 1.52-1.43 (t, J=12 Hz, 2H), 1.36 (s, 6H), 1.33 (s, 6H), 1.18 (s, 6H).

II-165: N2-(2,1-spiro-cyclobutane-4-isopropyl-1,4-benzoxazin-3-one-7-yl)-5-fluoro-N4-(1,2,2,6,6-pentamethylpiperidin-4-yl)-2,4-pyrimidinediamine MS (m/e) 511.13 (MH$^+$); $^1$H NMR (DMSO-d$_6$): δ 9.08 (s, 1H), 7.84-7.83 (d, J=3.6 Hz, 1H), 7.77 (s, 1H), 7.22-7.15 (m, 2H), 7.08-7.05 (d, J=9 Hz, 1H), 4.68 (m, 1H), 4.46 (bs, 1H), 2.39 (m, 2H), 2.22 (s, 3H), 2.15-2.05 (q, J=8.7 Hz, 2H), 1.84 (m, 2H), 1.72-1.68 (d, J=11.4 Hz, 2H), 1.55-1.47 (t, J=12 Hz, 2H), 1.42 (s, 3H), 1.39 (s, 3H), 1.16 (s, 6H), 1.1 (s, 6H).

II-166: N2-(2,1-spiro-cyclobutane-4-propyl-1,4-benzoxazin-3-one-7-yl)-5-fluoro-N4-(1,2,2,6,6-pentamethylpiperidin-4-yl)-2,4-pyrimidinediamine MS (m/e) 511.13 (MH$^+$); $^1$H NMR (DMSO-d$_6$): δ 9.07 (s, 1H), 7.84-7.82 (d, J=3.6 Hz, 1H), 7.77 (s, 1H), 7.22-7.15 (m, 2H), 6.96-6.93 (d, J=8.7 Hz, 1H), 4.46 (bs, 1H), 3.81-377 (t, J=6.9 Hz, 2H), 2.44 (m, 2H), 2.22 (s, 3H), 2.17-2.1 (m, 2H), 1.88 (m, 2H), 1.71-1.68 (d, J=8.7 Hz, 2H), 1.54-1.47 (m, 3H), 1.16 (s, 6H), 1.1 (s, 6H), 0.88-0.83 (t, J=7.2 Hz, 3H).

II-167: 5-Fluoro-N2-{3-[2-(morpholino)ethyl]-benzoxazol-2-one-6-yl}-N4-(1,2,2,6,6-pentamethylpiperidin-4-yl)-2,4-pyrimidinediamine MS (m/e) 528.12 (MH$^+$); $^1$H NMR (DMSO-d$_6$): δ 9.04 (bs, 1H), 8.13 (s, 1H), 7.84 (s, 1H), 7.34-7.31 (d, J=8.4 Hz, 1H), 7.2-7.17 (d, J=7.5 Hz, 1H), 7.1-7.08 (d, J=7.8 Hz, 1H), 4.4 (bs, 1H), 3.87 (m, 2H), 3.47 (bs, 4H), 2.58 (bs, 2H), 2.4 (bs, 4H), 2.2 (s, 3H), 1.73-1.7 (d, J=11.4 Hz, 2H), 1.53-1.44 (t, J=12.9 Hz, 2H), 1.1 (s, 12H).

II-168: 5-Fluoro-N2-{3-[2-(morpholino)ethyl]-benzoxazol-2-one-6-yl}-N4-(2,2,6,6-tetramethylpiperidin-4-yl)-2,4-pyrimidinediamine MS (m/e) 514.07 (MH$^+$); $^1$H NMR (DMSO-d$_6$): δ 9.08 (bs, 1H), 8.22 (s, 1H), 7.86 (s, 2H), 7.36-7.33 (d, J=6.9 Hz, 1H), 7.3-7.27 (d, J=8.7 Hz, 1H), 7.12-7.09 (d, J=9 Hz, 1H), 4.46 (bs, 1H), 3.89 (m, 2H), 3.47 (bs, 4H), 2.58 (bs, 2H), 2.4 (bs, 4H), 1.85-1.81 (d, J=12.3 Hz, 2H), 1.46-1.37 (t, J=12 Hz, 2H), 1.34 (s, 6H), 1.23 (s, 6H).

II-169: 5-Cyano-N2-{3-[2-(morpholino)ethyl]-benzoxazol-2-one-6-yl}-N4-(1,2,2,6,6-pentamethylpiperidin-4-yl)-2,4-pyrimidinediamine MS (m/e) 535.12 (MH$^+$); $^1$H NMR (DMSO-d$_6$): δ 9.85 (bs, 1H), 8.11 (s, 1H), 7.77 (s, 1H), 7.44 (bs, 1H), 7.35-7.32 (d, J=8.7 Hz, 1H), 7.18-7.15 (d, J=8.4 Hz, 1H), 4.5 (bs, 1H), 3.89 (m, 2H), 3.47 (bs, 4H), 2.58 (m, 2H), 2.4 (bs, 4H), 2.6 (s, 3H), 1.67-1.59 (m, 4H), 1.1 (s, 6H), 1.06 (s, 6H).

II-170: 5-Cyano-N2-{3-[2-(morpholino)ethyl]-benzoxazol-2-one-6-yl}-N4-(2,2,6,6-tetramethylpiperidin-4-yl)-2,4-pyrimidinediamine MS (m/e) 521.08 (MH$^+$); $^1$H NMR (DMSO-d$_6$): δ 9.88 (bs, 1H), 7.79 (s, 1H), 7.58 (bs, 1H), 7.31-7.28 (d, J=9.0 Hz, 1H), 7.19-7.17 (d, J=8.4 Hz, 1H), 4.56 (bs, 1H), 3.89 (m, 2H), 3.47 (bs, 4H), 2.58 (m, 2H), 2.39 (bs, 4H), 1.76-1.72 (d, J=12.6 Hz, 2H), 1.49-1.41 (t, J=12.9 Hz, 2H), 1.26 (s, 6H), 1.18 (s, 6H).

II-171: 5-Cyano-N2-[4-(2-fluoroethyl)-2H-1,4-benzoxazin-3-one-7-yl]-N4-(2,2,6,6-tetramethylpiperidin-4-yl)-2,4-pyrimidinediamine MS (m/e) 468.05 (MH$^+$); $^1$H NMR (DMSO-d$_6$): δ 9.85 (bs, 1H), 7.6 (bs, 1H), 7.49 (s, 1H), 7.28-7.26 (d, J=8.4 Hz, 1H), 7.11-7.08 (d, J=8.4 Hz, 1H), 4.67 (bs, 1H), 4.58 (s, 2H), 4.51 (bs, 1H), 4.24 (bs, 1H), 4.16 (bs, 1H), 1.79-1.75 (d, J=12.3 Hz, 2H), 1.53-1.45 (t, J=12.9 Hz, 8H), 1.32 (s, 6H), 1.17 (s, 6H).

II-172: 5-Fluoro-N2-[3-(2-fluoroethyl)-benzoxazol-2-one-6-yl]-N4-(1,2,2,6,6-pentamethylpiperidin-4-yl)-2,4-pyrimidinediamine MS (m/e) 461.02 (MH$^+$); $^1$H NMR (DMSO-d$_6$): δ 9.29 (bs, 1H), 8.58 (s, 1H), 7.95-7.94 (d, J=4.2 Hz, 1H), 7.84 (bs, 1H), 7.75 (bs, 1H), 7.28-7.25 (d, J=10.5 Hz, 1H), 7.17-7.14 (d, J=8.4 Hz, 1H), 4.78 (bs, 1H), 4.62 (bs, 1H), 4.47 (m, 1H), 4.16 (bs, 1H), 4.07 (bs, 1H), 2.74 (s, 3H), 2.1-2.06 (d, J=13.5 Hz, 2H), 1.85-1.76 (t, J=12.6 Hz, 2H), 1.39 (s, 12H).

II-173: N2-(3-Ethyl-benzoxazol-2-one-5-yl)-5-Fluoro-N4-(1,2,2,6,6-pentamethylpiperidin-4-yl)-2,4-pyrimidinediamine MS (m/e) 442.5 (MH$^+$); $^1$H NMR (DMSO-d$_6$): δ 8.9 (s, 1H), 7.83-7.82 (d, J=3.6 Hz, 1H), 7.67-7.64 (d, J=8.7 Hz, 1H), 7.32 (s, 1H), 7.18-7.15 (d, J=8.3 Hz, 1H), 7.09-7.06 (d, J=9 Hz, 1H), 4.38 (bs, 1H), 3.79-3.73 (q, J=6.9 Hz, 2H), 2.2 (s, 3H), 1.7-1.67 (d, J=11.7 Hz, 2H), 1.5-1.42 (t, J=12 Hz, 2H), 1.28-1.23 (t, J=7.2 Hz, 3H), 1.08 (s, 6H), 1.05 (s, 6H).

II-174: N2-(3-Ethyl-benzoxazol-2-one-5-yl)-5-fluoro-N4-(2,2,6,6-tetramethylpiperidin-4-yl)-2,4-pyrimidinediamine MS (m/e) 428.5 (MH$^+$); $^1$H NMR (DMSO-d$_6$): δ 8.9 (s, 1H), 7.85-7.84 (d, J=3.6 Hz, 1H), 7.64-7.61 (d, J=8.1 Hz, 1H), 7.32 (s, 1H), 7.29-7.26 (d, J=8.4 Hz, 1H), 7.11-7.08 (d, J=9 Hz, 1H), 4.45 (bs, 1H), 3.8-3.73 (q, J=6.9 Hz, 2H), 1.79-1.75 (d, J=13.2 Hz, 2H), 1.36-1.27 (m, 11H), 1.16 (s, 6H).

II-175: 5-Fluoro-N2-[7-Nitro-1,2,4-triazolo(3,4-c)][1,4]-benzoxazin-N4-(1,2,2,6,6-pentamethylpiperidin-4-yl)-2,4-pyrimidinediamine LCMS: purity: 90%; MS (m/e): 453 (MH$^+$); $^1$H NMR (CD$_3$OD): δ 9.21 (s, 1H), 8.00 (m, 1H), 7.75 (m, 1H), 7.21 (m, 1H), 6.93 (m, 1H), 5.47 (m, 1H), 4.75 (m, 1H), 4.59 (m, 1H), 2.86 (s, 3H), 2.50-1.90 (m, 4H), 1.50 (m, 12H).

II-176: 5-fluoro-N4-(1,2,2,6,6-pentamethylpiperidin-4-yl)-N2-(2,2,6-trifluoro-benzo[1,3]dioxol-5-yl)-2,4-pyrimidinediamine LCMS: purity: 99.13%; MS (m/e): 456.31 (MH+); $^1$H NMR (DMSO-d$_6$): δ 1.12 (br, 6H), 1.25 (br, 6H), 1.60 (br, 2H), 1.85 (br, 2H), 4.26 (br, 1H), 7.45 (br, 1H), 7.53 (d, J=9.6 Hz, 1H), 7.81 (d, J=6.6 Hz, 1H), 7.85 (d, J=3.9 Hz, 1H), 8.59 (s, 1H); $^{19}$F NMR (282 MHz, DMSO-d$_6$): δ−181.65, −141.10, −65.19.

II-177: 5-cyano-N2-[3,4-dihydro-2,2-dimethyl-4-(2-fluoroethyl)-3-oxo-2H-pyrido[3,2-b]-1,4-oxazin-7-yl]phenyl-N4-(2,2,6,6-tetramethylpiperidin-4-yl)-2,4-pyrimidinediamine LCMS: purity: 99.79%; MS (m/e): 497.47 (MH+); $^1$H NMR (DMSO-d$_6$): δ 1.22 (s, 6H), 1.34 (s, 6H), 1.41 (s, 6H), 1.52 (t, 2H), 1.76 (d, 2H), 4.27 (t, 1H), 4.35 (t, 1H), 4.52 (t, 1H), 4.59 (br, 1H), 4.68 (t, 1H), 7.74 (br, 1H), 7.89 (s, 1H), 8.31 (s, 1H), 8.35 (s, 1H), 10.08 (br, 1H).

II-178: N2-[3,4-dihydro-2,2-dimethyl-4-(2-fluoroethyl)-3-oxo-2H-pyrido[3,2-b]-1,4-oxazin-7-yl]phenyl-5-fluoro-N4-(2,2,6,6-tetramethylpiperidin-4-yl)-2,4-pyrimidinediamine LCMS: purity: 81.64%; MS (m/e): 490.18 (MH+); $^1$H NMR (DMSO-$d_6$): δ 1.37 (s, 6H), 1.41 (s, 6H), 1.48 (s, 6H), 1.60 (t, J=12.0 Hz, 2H), 1.97 (d, J=11.4 Hz, 2H), 4.26 (t, 1H), 4.34 (t, 1H), 4.52 (t, 1H), 4.68 (t, 1H), 4.90 (br, 1H), 7.70 (d, 1H), 7.81 (d, J=13.5 Hz, 1H), 7.94 (m, 2H), 8.25 (d, J=2.1 Hz, 1H), 8.63 (d, 1H), 9.42 (s, 1H).

II-179: 5-Cyano-N2-(3-cyclopropylmethylene-benzoxazol-2-one-6-yl)-N4-(1,2,2,6,6-pentamethylpiperidin-4-yl)-2,4-pyrimidinediamine MS (m/e) 476.16 (MH$^+$); $^1$H NMR (DMSO-$d_6$): δ 9.86 (bs, 1H), 8.13 (s, 1H), 7.78 (s, 1H), 7.43 (bs, 1H), 7.37-7.34 (d, J=8.7 Hz, 1H), 7.22-7.20 (d, J=8.4 Hz, 1H), 4.43 (bs, 1H), 3.69-3.66 (d, J=6.9 Hz, 1H), 2.2 (s, 3H), 1.66-1.51 (m, 4H), 1.08 (s, 6H), 1.02 (s, 6H), 0.51 (m, 2H), 0.38 (m, 2H).

II-180: 5-Cyano-N2-(3-cyclopropylmethylene-benzoxazol-2-one-6-yl)-N4-(2,2,6,6-tetramethylpiperidin-4-yl)-2,4-pyrimidinediamine MS (m/e) 462.12 (MH$^+$); $^1$H NMR (DMSO-$d_6$): δ 9.87 (bs, 1H), 8.31 (s, 1H), 7.78 (s, 1H), 7.55 (bs, 1H), 7.34-7.31 (d, J=8.4 Hz, 1H), 7.24-7.21 (d, J=8.7 Hz, 1H), 4.54 (bs, 1H), 3.69-3.66 (d, J=6.9 Hz, 1H), 1.75-1.71 (d, J=11.7 Hz, 2H), 1.46-1.38 (t, J=12 Hz, 2H), 1.24 (s, 6H), 1.16 (s, 6H), 0.51 (m, 2H), 0.38 (m, 2H).

II-181: 5-Fluoro-N2-[4-(2-fluoroethyl)-2H-1,4-benzoxazin-3-one-7-yl]-N4-(2,2,6,6-tetramethylpiperidin-4-yl)-2,4-pyrimidinediamine MS (m/e) 461.02 (MH$^+$); $^1$H NMR (DMSO-$d_6$): δ 9.03 (bs, 1H), 7.85 (bs, 1H), 7.53 (s, 1H), 7.29 (bs, 2H), 7.04-7.01 (d, J=8.7 Hz, 2H), 4.67 (bs, 1H), 4.55 (s, 2H), 4.51 (bs, 1H), 4.22 (bs, 1H), 4.14 (bs, 1H), 1.8-1.76 (d, J=12 Hz, 2H), 1.39-1.3 (m, 8H), 1.17 (s, 6H).

III-1: N2-(3-Chloro-4-methoxy)phenyl-5-fluoro-N4-(1-methylpiperidin-4-yl)-2,4-pyrimidinediamine LCMS: purity: 98.82%; MS (m/e): 366.09 (MH+); $^1$H NMR (DMSO-$d_6$): δ 1.59 (dq, J=2.7, 10.5 Hz, 2H), 1.80 (d, J=11.7 Hz, 2H), 1.97 (t, J=11.1 Hz, 2H), 2.15 (s, 3H), 2.77 (d, J=11.7 Hz, 2H), 3.76 (s, 3H), 3.83 (m, 1H), 6.99 (d, J=9.0 Hz, 1H), 7.28 (d, J=8.1 Hz, 1H), 7.37 (dd, J=1.8, 9.1 Hz, 1H), 7.82 (d, J=3.6 Hz, 1H), 8.01 (d, J=2.4 Hz, 1H), 9.00 (s, 1H); $^{19}$F NMR (282 MHz, DMSO-$d_6$): δ−166.70.

III-2: N2-(3-Cyano)phenyl-5-fluoro-N4-(1-methylpiperidin-4-yl)-2,4-pyrimidinediamine LCMS: purity: 97.70%; MS (m/e): 327.16 (MH+); $^1$H NMR (DMSO-$d_6$): δ 1.60 (dq, J=12.0 Hz, 2H), 1.82 (d, J=9.3 Hz, 2H), 2.00 (t, J=11.1 Hz, 2H), 2.16 (s, 3H), 2.78 (d, J=11.7 Hz, 2H), 3.87 (m, 1H), 7.27 (d, J=7.5 Hz, 1H), 7.37-7.45 (m, 2H), 7.77 (d, J=8.1 Hz, 1H), 7.90 (d, J=3.6 Hz, 1H), 8.35 (s, 1H), 9.45 (s, 1H); $^{19}$F NMR (282 MHz, DMSO-$d_6$): δ−165.18.

III-3: 5-Fluoro-N2-[4-(4-methylpiperazino)-3-trifluoromethyl]phenyl-N4-(1-methylpiperidin-4-yl)-2,4-pyrimidinediamine LCMS: purity: 91.08%; MS (m/e): 468.29 (MH+); $^1$H NMR (DMSO-$d_6$): δ 1.59 (q, J=11.1 Hz, 2H), 1.83 (d, J=10.5 Hz, 2H), 1.91 (t, J=11.1 Hz, 2H), 2.15 (s, 3H), 2.20 (s, 3H), 2.41 (br, 4H), 2.76 (d, 2H), 2.78 (br, 4H), 3.86 (m, 1H), 7.30 (d, J=8.1 Hz, 1H), 7.40 (d, J=9.3 Hz, 1H), 7.73 (d, J=9.9 Hz, 1H), 7.84 (d, J=3.9 Hz, 1H), 8.19 (d, J=2.1 Hz, 1H), 9.24 (s, 1H); $^{19}$F NMR (282 MHz, DMSO-$d_6$): δ−59.54, −165.91.

III-4: N2-[3-Chloro-4-(4-methylpiperazino)]phenyl-5-fluoro-N4-(1-methylpiperidin-4-yl)-2,4-pyrimidinediamine LCMS: purity: 93.70%; MS (m/e): 434.02 (MH+); $^1$H NMR (DMSO-$d_6$): δ 1.60 (q, J=11.1 Hz, 2H), 1.81 (d, J=10.8 Hz, 2H), 1.98 (t, J=11.1 Hz, 2H), 2.16 (s, 3H), 2.21 (s, 3H), 2.45 (br, 4H), 2.78 (d, J=10.8 Hz, 2H), 2.88 (br, 4H), 3.85 (m, 1H), 7.01 (d, J=8.4 Hz, 1H), 7.29 (d, J=8.1 Hz, 1H), 7.37 (d, J=8.4 Hz, 1H), 7.83 (d, J=3.6 Hz, 1H), 8.04 (s, 1H), 9.06 (s, 1H); $^{19}$F NMR (282 MHz, DMSO-$d_6$): δ−166.44.

III-5: N2-(3-Chloro-4-methoxy)phenyl-5-fluoro-N4-[1-(2-hydroxyethyl)piperidin-4-yl]-2,4-pyrimidinediamine LCMS: purity: 99.32%; MS (m/e): 396.11 (MH+); $^1$H NMR (DMSO-$d_6$): δ 1.74 (m, 2H), 1.98 (d, J=13.8 Hz, 2H), 2.58 (m, 2H), 2.79 (t, 2H), 3.21 (m, 2H), 3.61 (t, J=5.7 Hz, 2H), 3.97 (br, 1H), 4.09 (br, 1H), 7.02 (d, J=9.0 Hz, 1H), 7.38 (s, 1H), 7.40 (d, J=9.0 Hz, 1H), 7.86 (d, J=3.9 Hz, 1H), 7.96 (d, J=2.4 Hz, 1H), 9.04 (s, 1H).

III-6: N2-(3-Cyano)phenyl-5-fluoro-N4-[1-(2-hydroxyethyl)piperidin-4-yl]-2,4-pyrimidinediamine LCMS: purity: 98.20%; MS (m/e): 357.30 (MH+); $^1$H NMR (DMSO-$d_6$): δ 1.76 (q, J=10.8 Hz, 2H), 1.98 (d, J=11.4 Hz, 2H), 2.62 (t, J=11.1 Hz, 2H), 2.77 (t, 2H), 3.26 (m, 2H), 3.61 (t, J=5.4 Hz, 2H), 3.98 (br, 1H), 7.28 (d, J=7.5 Hz, 1H), 7.41 (t, J=7.8 Hz, 1H), 7.55 (d, J=7.2 Hz, 1H), 7.80 (d, J=8.4 Hz, 1H), 7.93 (d, J=3.9 Hz, 1H), 8.31 (s, 1H), 9.48 (s, 1H); $^{19}$F NMR (282 MHz, DMSO-$d_6$): δ−164.95.

III-7: 5-Fluoro-N4-[1-(2-hydroxyethyl)piperidin-4-yl]-N2-[4-(4-methylpiperazino)-3-trifluoromethyl]phenyl-2,4-pyrimidinediamine LCMS: purity: 98.86%; MS (m/e): 497.93 (MH+); $^1$H NMR (DMSO-$d_6$): δ 1.84 (q, 2H), 2.11 (t, 4H), 2.88 (s, 3H), 3.04 (br, 4H), 3.16 (m, 2H), 3.46 (br, 4H), 3.58 (m, 2H), 3.74 (m, 2H), 4.02 (br, 1H), 5.34 (br, 1H), 7.44 (d, J=8.7 Hz, 2H), 7.62 (d, 1H), 7.93 (m, 2H), 9.36 (s, 1H), 9.65 (br, 1H); $^{19}$F NMR (282 MHz, DMSO-$d_6$): δ−59.93, −164.96.

III-8: N2-[3-Chloro-4-(4-methylpiperazino)]phenyl-5-fluoro-N4-[1-(2-hydroxyethyl)piperidin-4-yl]-2,4-pyrimidinediamine LCMS: purity: 97.88%; MS (m/e): 464.03 (MH+); $^1$H NMR (DMSO-$d_6$): δ 1.86 (q, J=9.0 Hz, 2H), 2.14 (t, 4H), 2.88 (s, 3H), 2.93 (br, 4H), 3.15 (m, 2H), 3.29 (br, 4H), 3.74 (m, 2H), 4.01 (br, 1H), 5.37 (br, 1H), 7.12 (d, J=8.1 Hz, 1H), 7.46 (d, J=8.7 Hz, 1H), 7.61 (d, 1H), 7.92 (d, J=3.3 Hz, 1H), 7.98

(s, 1H), 9.21 (s, 1H), 9.31 (br, 1H), 9.69 (br, 1H); $^{19}$F NMR (282 MHz, DMSO-d$_6$): δ−165.49.

III-9: N2-(3,5-dimethoxy)phenyl-5-fluoro-N4-[1-(pyridin-4-yl)methylpiperidin-4-yl]-2,4-pyrimidinediamine LCMS: purity: 86.39%; MS (m/e): 439.37 (MH+); $^1$H NMR (DMSO-d$_6$): δ 1.81 (d, 2H), 2.16 (br, 2H), 3.01 (br, 2H), 3.50 (br, 2H), 3.69 (s, 6H), 4.38 (br, 2H), 6.10 (s, 1H), 6.90 (s, 2H), 7.53 (m, 2H), 7.92 (d, 1H), 8.70 (m, 2H), 9.14 (br, 1H), 9.82 (br, 1H).

III-10: 5-fluoro-N2-[3-methoxy-5-(5-methyl-1H-tetrazol-1-yl)]phenyl-N4-[1-(pyridin-4-yl)methylpiperidin-4-yl]-2,4-pyrimidinediamine LCMS: purity: 92.51%; MS (m/e): 491.62 (MH+); $^1$H NMR (DMSO-d$_6$): δ 1.58 (br, 2H), 1.76 (br, 4H), 2.56 (s, 3H), 3.77 (s, 5H), 6.50 (s, 1H), 6.76 (s, 1H), 7.31 (d, 2H), 7.40 (m, 2H), 7.76 (s, 1H), 7.88 (d, 1H), 8.49 (d, 2H), 9.43 (s, 1H).

IV-1: 5-Fluoro-N2-[3-methoxy-5-(5-methyl-tetrazol-1-yl)]phenyl-N4-(1,2,6,-trimethylpiperidin-4-yl)-2,4-pyrimidinediamine, trans isomer MS (m/e) 477.25 (MH+); $^1$H NMR (DMSO-d6): δ 9.39 (s, 1H), 7.88 (s, 1H), 7.65 (s, 1H), 7.45 (s, 1H), 7.35-7.32 (d, J=7.8 Hz, 1H), 6.75 (s, 1H), 4.17 (s, 1H), 2.54 (s, 3H), 2.32 (s, 1H), 2.2 (s, 3H), 1.82-1.78 (d, J=12.6 Hz, 2H), 1.61-1.57 (d, J=12 Hz, 1H), 0.93-0.91 (d, J=6 Hz, 3H), 0.86-0.84 (d, J=6.9 Hz, 3H).

IV-2: N2-(3,5-Dimethoxy)phenyl-6-methyl-N4-(1,2,2,6,6-pentamethylpiperidin-4-yl)-2,4-pyrimidinediamine MS (m/e) 414.25 (MH+); $^1$H NMR (DMSO-d6): δ 8.78 (s, 1H), 8.16-8.14 (d, J=3.3 Hz, 1H), 7.02 (s, 2H), 6.86 (bs, 1H), 6.02 (s, 1H), 5.73 (s, 1H), 4.32 (s, 1H), 3.67 (s, 6H), 2.32-2.30 (d, J=5.7 Hz, 3H), 2.09 (s, 3H), 1.81-1.76 (d, J=12.3 Hz, 2H), 1.36 (m, 2H), 1.15 (s, 12H).

IV-3: N2-[3-Chloro-4-(4-methylsulfonylpiperazino)]phenyl-6-methyl-N4-(1,2,2,6,6-pentamethylpiperidin-4-yl)-2,4-pyrimidinediamine MS (m/e) 550.32 (MH+); $^1$H NMR (DMSO-d6): δ 8.66 (s, 1H), 8.14 (s, 1H), 7.61 (s, 1H), 7.45-7.43 (d, J=7.2 Hz, 1H), 7.16-7.13 (d, J=9.0 Hz, 1H), 5.96 (s, 1H), 4.27 (s, 1H), 3.27 (s, 4H), 3.00 (s, 4H), 2.94 (s, 3H), 2.73 (s, 3H), 2.26 (s, 3H), 2.06-2.02 (d, J=11.4 Hz, 2H), 1.71-1.62 (t, J=12.9 Hz, 2H), 1.37 (s, 6H), 1.27 (s, 6H).

IV-4: N2-[3-Chloro-4-(4-methylsulfonylpiperazino)]phenyl-N4-(4-diethylamino)cyclohexyl-5-fluoro-2,4-pyrimidinediamine LCMS: purity: 99.54%; MS (m/e): 554.19 (MH+); $^1$H NMR (DMSO-d$_6$): δ 1.26 (t, J=6.9 Hz, 6H), 1.47-1.65 (m, 4H), 2.03-2.11 (m, 4H), 2.94 (s, 3H), 3.01 (t, 4H), 3.08 (m, 2H), 3.26 (t, 7H), 3.85 (br, 1H), 7.17 (d, J=8.1 Hz, 1H), 7.40 (d, J=8.1 Hz, 1H), 7.90 (s, 1H), 8.00 (d, J=4.2 Hz, 1H), 8.16 (br, 1H), 9.59 (br, 1H).

IV-5: N2-(3-Chloro-4-methoxy)phenyl-N4-(4-diethylamino)cyclohexyl-5-fluoro-2,4-pyrimidinediamine LCMS: purity: 98.70%; MS (m/e): 422.17 (MH+); $^1$H NMR (DMSO-d$_6$): δ 1.24 (t, J=7.2 Hz, 6H), 1.54 (p, J=12.3 Hz, 4H), 2.06 (d, J=7.5 Hz, 4H), 3.08-3.21 (m, 5H), 3.78 (s, 3H), 3.79 (br, 1H), 7.05 (d, J=9.0 Hz, 1H), 7.34 (d, J=9.3 Hz, 1H), 7.76 (br, 1H), 7.92 (d, J=4.5 Hz, 1H), 7.97 (s, 1H), 8.81 (br, 1H), 9.36 (br, 1H); $^{19}$F NMR (282 MHz, DMSO-d$_6$): δ−170.77.

IV-6: N2-(3-Cyano)phenyl-N4-(4-diethylamino)cyclohexyl-5-fluoro-2,4-pyrimidinediamine LCMS: purity: 99.05%; MS (m/e): 383.38 (MH+); $^1$H NMR (DMSO-d$_6$): δ 1.19 (t, J=7.2 Hz, 6H), 1.42-1.64 (m, 4H), 2.05 (m, 4H), 3.05 (q, J=7.2 Hz, 5H), 3.87 (br, 1H), 7.29 (d, J=6.6 Hz, 1H), 7.41 (t, J=7.5 Hz, 1H), 7.50 (d, J=7.5 Hz, 1H), 7.74 (d, J=8.1 Hz, 1H), 7.91 (d, J=3.6 Hz, 1H), 8.40 (s, 1H), 9.51 (s, 1H); $^{19}$F NMR (282 MHz, DMSO-d$_6$): δ−165.04.

IV-7: N4-(4-Diethylamino)cyclohexyl-5-fluoro-N2-[4-(4-methylpiperazino)-3-trifluoromethyl]phenyl-2,4-pyrimidinediamine LCMS: purity: 91.40%; MS (m/e): 524.34 (MH+); $^1$H NMR (DMSO-d$_6$): δ 1.25 (t, J=7.2 Hz, 6H), 1.50 (q, J=8.7 Hz, 4H), 2.05 (m, 4H), 2.86 (s, 3H), 3.03 (br, 4H), 3.10 (m, 5H), 3.36 (br, 4H), 3.86 (br, 1H), 7.44 (d, J=9.0 Hz, 2H), 7.80 (d, J=6.6 Hz, 1H), 7.89 (d, 1H), 8.26 (s, 1H), 8.87 (br, 1H), 9.37 (s, 1H), 9.64 (br, 1H); $^{19}$F NMR (282 MHz, DMSO-d$_6$): δ−170.77, −59.81.

IV-8: N2-[3-Chloro-4-(4-methylpiperazino)]phenyl-N4-(4-diethylamino)cyclohexyl-5-fluoro-2,4-pyrimidinediamine LCMS: purity: 93.29%; MS (m/e): 490.17 (MH+); $^1$H NMR (DMSO-d$_6$): δ 1.24 (t, J=6.9 Hz, 6H), 1.46-1.62 (m, 4H), 2.07 (m, 4H), 2.87 (s, 3H), 2.95 (d, J=11.7 Hz, 2H), 3.19 (m, 7H), 3.30 (d, J=12.3 Hz, 2H), 3.51 (d, J=11.4 Hz, 2H), 3.85 (br, 1H), 7.11 (d, J=8.4 Hz, 1H), 7.43 (d, J=8.4 Hz, 1H), 7.50 (d, 1H), 7.88 (d, J=3.9 Hz, 1H), 8.08 (s, 1H), 8.95 (br, 1H), 9.24 (s, 1H), 9.76 (br, 1H); $^{19}$F NMR (282 MHz, DMSO-d$_6$): δ−165.63.

IV-9: N4-(4-Diethylamino)cyclohexyl-5-fluoro-N2-[4-(4-methylsulfonylpiperazino)-3-trifluoromethyl]phenyl-2,4-pyrimidinediamine LCMS: purity: 94.80%; MS (m/e): 588.18 (MH+); $^1$H NMR (DMSO-d$_6$): δ 1.17 (t, J=6.6 Hz, 6H), 1.45 (q, 4H), 1.99 (m, 4H), 2.88 (br, 4H), 2.93 (s, 3H), 3.00 (m, 5H), 3.20 (br, 4H), 3.85 (br, 1H), 7.38 (d, J=7.8 Hz, 1H), 7.49 (d, J=8.7 Hz, 1H), 7.79 (d, J=9.6 Hz, 1H), 7.88 (d, J=3.9 Hz, 1H), 8.20 (s, 1H), 9.32 (s, 1H); $^{19}$F NMR (282 MHz, DMSO-d$_6$): δ−165.58, −59.66.

A. Example 2

PKC Assay

The inhibition of PKC activity was measured by monitoring the production of phosphorylated peptide by fluorescence polarization at different concentrations of the inhibitor. Reactions were carried out in 96-well plate format with a total volume of 20 μL containing 20 mM HEPES, pH 7.4, 5 mM MgCl2, 0.2 mM CaCl2, 1 mM DTT, 0.02% Brij-35, 0.1 mg/mL phosphatidylserine, 0.02 mg/mL dioleoyl-sn-glycerol and 5 μM each of ATP and the peptide substrate. Compounds were first diluted serially in DMSO and then transferred to a solution containing the above concentrations of HEPES, MgCl2, CaCl2, DTT, and Brij-35 to yield 5× compound solutions in 2% DMSO, which was then added to the reaction solution. Reactions were initiated by the addition of PKC at a typical concentration as described in Table VI, and then allowed to incubate at room temperature for 20 min. At the end of this time, a combination of quench (EDTA) and detection (peptide tracer and antibody) reagents was added using the protocol of Invitrogen P2748. After a 30 min. period of incubation, the amount of phosphorylated peptide generated was measured by fluorescence polarization (Ex=485 nm, Em=535 nm) using a Tecan Polarian instrument.

TABLE VI

| | Peptide substrate | SEQ ID | Enzyme source | enzyme concentration |
|---|---|---|---|---|
| PKC theta | RFARKGSLRQKNV | Seq ID No. 1 | Upstate Biotechnologies, Temecula, CA, cat. #14-444 | 40 ng/mL |
| PKC epsilon | RFARKGSLRQKNV | Seq ID No. 1 | Upstate Biotechnologies, Temecula, CA, cat. #14-518 | 50 ng/mL |

B. Example 3

IL-2 ELISA, Human Primary T Cell, Anti-CD3+CD28+

Human primary T cell isolation and culture: Human primary T cells were prepared as follows. Whole blood was obtained from a healthy volunteer, mixed 1:1 with PBS, layered on to Ficoll Hypaque (Amersham Pharmacia Biotech, Piscataway, N.J., Catalog #17-1440-03) in 2:1 blood/PBS:ficoll ratio and centrifuged for 30 min at 4° C. at 1750 rpm. The cells at the serum:ficoll interface were recovered and washed twice with 5 volumes of PBS. These freshly isolated human peripheral blood mononuclear cells were cultured in Yssel's medium containing 40 U/mL IL2 in a flask pre-coated with 1 ug/mL αCD3 and 5 ug/mL αCD28 (Anti-Human CD3, BD Pharmingen Catalog #555336, Anti-Human CD28, Beckman Coulter Catalog #IM1376). The cells were stimulated for 3-4 days, then transferred to a fresh flask and maintained in RPMI (RPMI-1640 with L-Glutamine; Mediatech, Inc., Herndon Va., cat. #10-040-CM) with 10% FBS and 40 U/mL IL-2. The primary T-cells were then washed twice with PBS to remove the IL-2.

Primary T cell stimulation and IL2 ELISA: Human primary T cells (100,000 cells per well) were pre-incubated with or without test compound in Yssel's medium for 1 hr at 37° C. Cells were then stimulated by transferring them to round-bottom 96-well plates pre-coated with 1 ug/ml αCD3 and 5 μg/ml αCD28. For counter assay, cells were instead stimulated by adding 8× stock solutions of PMA and ionomycin in Yssels (for final concentrations of 0.5 ng/ml PMA and 0.1 uM ionomycin, both from Calbiochem). Cells were incubated at 37° C. for 24 hours before 100 uL supernatants were harvested for quantification of IL-2 by ELISA using Human IL-2 Duoset ELISA Kit from R and D Systems, Cat. # DY202E.

Table VII shows the $IC_{50}$ values for compounds tested in the assays described in Examples 2 and 3. A value of "9999" does not necessarily mean an inactive compound, it may also mean, e.g., that the compound's solubility is limited under the test conditions.

TABLE VII

| | Example 2 | | | |
|---|---|---|---|---|
| Compound # | PKC theta | PKC epsilon | PKC mu | Example 3 |
| I-1 | 0.226 | | | 3.024 |
| I-2 | 0.407 | | | 1.566 |
| I-3 | 0.005 | | | 0.108 |
| I-4 | 0.030 | | | 0.254 |
| I-5 | 0.005 | | | 0.086 |
| I-6 | 0.180 | | | 1.688 |
| I-7 | 0.016 | | | 0.530 |

TABLE VII-continued

| | Example 2 | | | |
|---|---|---|---|---|
| Compound # | PKC theta | PKC epsilon | PKC mu | Example 3 |
| I-8 | 0.213 | | | 5.814 |
| I-9 | 0.086 | | | 3.441 |
| I-10 | 0.070 | | | 1.881 |
| I-11 | 0.052 | | | 1.573 |
| I-12 | 0.022 | | | 0.341 |
| I-13 | | | | 7.677 |
| I-14 | | | | 9.839 |
| I-15 | | | | 6.848 |
| I-16 | | | | 5.275 |
| I-17 | | | | 0.963 |
| I-18 | | | | 9.437 |
| I-19 | | | | 1.229 |
| I-20 | 0.005 | | | 0.113 |
| I-21 | | | | 0.414 |
| I-22 | 0.021 | | | 0.177 |
| I-23 | | | | 1.681 |
| I-24 | | | | 1.521 |
| I-25 | | | | 4.892 |
| I-26 | 0.003 | | | 0.059 |
| I-27 | | | | 0.497 |
| I-28 | | | | 0.455 |
| I-29 | | | | 0.463 |
| I-30 | | | | 0.335 |
| I-31 | 0.005 | | | 0.091 |
| I-32 | | | | 0.328 |
| I-33 | | | | 0.532 |
| I-34 | 0.004 | | | 0.123 |
| I-35 | 0.024 | | | 0.145 |
| I-36 | | | | 0.083 |
| I-37 | | | | 0.511 |
| I-38 | 0.016 | 0.506 | 0.033 | 0.196 |
| I-39 | 0.015 | | | 0.937 |
| I-40 | | | | 0.461 |
| I-41 | | | | 2.633 |
| I-42 | | | | 1.017 |
| I-43 | | | | 0.890 |
| I-44 | | | | 2.014 |

TABLE VII-continued

| Compound # | Example 2 PKC theta | PKC epsilon | PKC mu | Example 3 |
|---|---|---|---|---|
| I-45 | | | | 2.373 |
| I-46 | | | | 14.306 |
| I-47 | | | | 0.136 |
| I-48 | | | | 0.039 |
| I-49 | | | | 0.284 |
| I-50 | | | | 0.320 |
| I-51 | | | | 1.011 |
| I-52 | | | | 0.133 |
| I-53 | | | | 1.940 |
| I-54 | | | | 3.063 |
| I-55 | | | | 1.566 |
| I-56 | | | | 2.383 |
| I-57 | | | | 0.364 |
| I-58 | | | | 2.000 |
| I-59 | | | | 0.911 |
| I-60 | | | | 0.524 |
| I-61 | | | | 0.094 |
| I-62 | | | | 0.257 |
| I-63 | | | | 1.854 |
| I-64 | | | | 2.599 |
| I-65 | | | | 1.979 |
| I-66 | | | | 1.460 |
| I-67 | | | | 0.346 |
| I-68 | | | | 0.589 |
| I-69 | | | | 2.38592 |
| I-70 | 0.03873 | | | 0.51683 |
| I-71 | | | | 0.63237 |
| I-72 | | | | 0.99173 |
| I-73 | | | | 0.66475 |
| I-74 | | | | 0.65727 |
| I-75 | | | | 11.2594 |
| I-76 | | | | 0.59573 |
| I-77 | | | | 2.58728 |
| I-78 | | | | 0.9281 |
| I-79 | | | | 0.55205 |
| I-80 | | | | 2.69488 |
| I-81 | | | | 28.6499 |
| I-82 | | | | 3.20602 |
| I-83 | | | | 7.76346 |
| I-84 | | | | 6.84515 |
| I-85 | | | | 0.63063 |
| I-86 | | | | 4.98535 |
| I-87 | | | | 0.49475 |
| I-88 | | | | 0.28681 |
| I-89 | | | | 5.80301 |
| I-90 | | | | 2.86349 |
| I-91 | | | | 3.91275 |
| I-92 | 0.00456 | 0.27097 | | 0.20772 |
| I-93 | 0.00259 | 0.2084 | | 0.34417 |
| I-94 | 0.01168 | | | 0.443 |
| I-95 | 0.04304 | | | 0.34696 |
| I-96 | 0.00456 | 0.08167 | | 0.17724 |
| I-97 | 0.00158 | 0.17468 | | 0.28922 |
| I-98 | | | | 1.07282 |
| I-99 | | | | 0.3039 |
| I-100 | 0.03436 | | | 0.49369 |
| I-101 | 0.00551 | 0.13125 | | 0.09459 |
| I-102 | 0.01263 | 0.21838 | | 0.21743 |
| I-103 | 0.05042 | 0.41276 | | 0.12856 |
| I-104 | 0.01584 | 0.06281 | | 0.07977 |
| I-105 | 0.02599 | 0.15449 | | 0.22086 |
| I-106 | 0.23943 | | | 0.52708 |
| I-107 | | | | 0.74988 |
| I-108 | | | | 1.15012 |
| I-109 | 0.10669 | | | 0.34531 |
| I-110 | | | | 0.49078 |
| I-111 | | | | 0.49026 |
| I-112 | 0.00891 | 0.02555 | | 0.07331 |
| I-114 | | | | 1.87787 |
| I-115 | 0.02193 | | | 0.28666 |
| I-116 | | | | 1.2255 |
| I-117 | | | | 1.24553 |
| I-118 | 0.01817 | 0.01034 | | 0.23745 |
| I-119 | 0.05532 | 0.02777 | | 0.30944 |
| I-120 | 0.02953 | | | 0.36597 |
| I-121 | 0.02375 | 0.01575 | | 0.2678 |
| I-122 | 0.06073 | 0.01875 | | 0.29456 |
| I-123 | 0.0808 | | | 0.87204 |
| I-124 | 0.05573 | | | 0.53951 |
| I-125 | 0.11066 | | | 0.8922 |
| I-126 | 0.01198 | | | 0.24303 |
| I-127 | | | | 1.13681 |
| I-128 | | | | 0.87642 |
| I-129 | 0.00419 | 0.02676 | | 0.21386 |
| I-130 | | | | 1.09809 |
| I-131 | | | | 0.62857 |
| I-132 | 0.00182 | 0.01254 | | 0.06492 |
| I-133 | | | | 1.12645 |
| I-134 | | | | 2.42762 |
| I-135 | | | | 4.63932 |
| I-136 | | | | 1.55095 |
| I-137 | | | | 1.64296 |
| I-138 | | | | 3.1459 |
| I-139 | | | | 1.56736 |
| I-140 | 0.00548 | 0.15823 | | 0.22948 |
| I-141 | 0.00329 | 0.2492 | | 0.24541 |
| I-142 | 0.00292 | 0.031 | | 0.08074 |
| I-143 | | | | 1.4104 |
| I-144 | | | | 1.05959 |
| I-145 | | | | 0.89744 |
| I-146 | 0.12301 | | | 0.25221 |
| I-147 | 0.00801 | 0.11471 | | 0.16809 |
| I-148 | 0.01351 | 0.14967 | | 0.22279 |
| I-149 | | | | 4.35904 |
| I-150 | | | | 0.70064 |
| I-151 | | | | 0.63457 |
| I-152 | | | | 0.60418 |
| I-153 | 0.01016 | | | 0.20866 |
| I-154 | 0.00381 | | | 0.26087 |
| I-155 | 0.01438 | | | 0.41834 |
| I-156 | | | | 2.88612 |
| I-157 | 0.0031 | | | 0.24212 |
| I-158 | 0.02057 | | | 0.48909 |
| I-159 | 0.00729 | | | 0.29587 |
| I-160 | 0.03261 | | | 0.20193 |
| I-161 | | | | 1.04564 |
| I-162 | 0.06857 | | | 0.55342 |
| I-163 | 0.0038 | | | 0.28993 |
| I-164 | 0.00216 | | | 0.22274 |
| I-165 | 0.00256 | 0.31061 | | 0.29246 |
| I-166 | 0.00426 | 0.19791 | | 0.28056 |
| I-167 | 0.00387 | 0.19652 | | 0.2267 |
| I-168 | 0.00272 | 0.03265 | | 0.12037 |
| I-169 | | | | 0.68378 |
| I-170 | | | | 2.65067 |
| I-171 | | | | 0.68023 |
| I-172 | | | | 0.66869 |
| I-173 | 0.02656 | | | 0.37734 |
| I-174 | 0.0107 | | | 0.27043 |
| I-175 | 0.00711 | | | 0.20483 |
| I-176 | | | | 0.6551 |
| I-177 | | | | 0.76375 |
| I-178 | 0.00081 | 0.16031 | | 0.24283 |
| I-179 | 0.00149 | | | 0.09225 |
| I-180 | | | | 0.91395 |
| I-181 | | | | 1.3158 |
| I-182 | | | | 0.67471 |
| I-183 | | | | 0.90069 |
| I-184 | | | | 2.28603 |
| I-185 | 0.00765 | | | 0.29874 |
| I-186 | 0.00141 | | | 0.09241 |
| I-187 | 0.00492 | 0.05096 | | 0.30459 |
| I-188 | 0.00474 | 0.03669 | | 0.17772 |
| I-189 | | | | 1.21865 |
| I-190 | 0.01448 | | | 0.51557 |
| I-191 | | | | 0.70033 |
| I-192 | | | | 0.94146 |
| I-193 | | | | 0.6532 |
| I-194 | | | | 0.80402 |
| I-195 | | | | 1.11844 |
| I-196 | | | | 0.97094 |
| I-197 | 0.00438 | 0.06033 | | 0.23658 |

TABLE VII-continued

| Compound # | PKC theta | PKC epsilon | PKC mu | Example 3 |
|---|---|---|---|---|
| I-198 | 0.00194 | | | 0.17473 |
| I-199 | 0.00288 | 0.00958 | | 0.1347 |
| I-200 | 0.00111 | 0.04192 | | 0.18485 |
| I-201 | | | | 0.52219 |
| I-202 | | | | 0.61517 |
| I-203 | 0.09199 | | | 0.42654 |
| I-204 | 0.08285 | | | 0.43973 |
| I-205 | | | | 0.96452 |
| I-206 | | | | 1.02832 |
| I-207 | | | | 0.40243 |
| I-208 | 0.05203 | | | 0.4667 |
| I-209 | | | | 0.70618 |
| I-210 | | | | 1.2443 |
| I-211 | | | | 1.70216 |
| I-212 | | | | 0.44477 |
| I-213 | | | | 19.565 |
| I-214 | | | | 0.53974 |
| I-215 | | | | 25.5487 |
| I-216 | 0.00599 | 0.02896 | | 0.17429 |
| I-217 | | | | 9999 |
| I-218 | 0.00652 | 0.01845 | | 0.21601 |
| I-219 | | | | 20.7591 |
| I-220 | | | | 1.05395 |
| I-221 | | | | 1.26899 |
| I-222 | | | | 1.5252 |
| I-223 | 0.03168 | 0.11875 | | 0.18357 |
| I-224 | 0.02908 | 0.01897 | | 0.11246 |
| I-225 | | | | 0.75481 |
| I-226 | | | | 1.14364 |
| I-227 | | | | 0.80565 |
| I-228 | | | | 0.72025 |
| I-229 | | | | 0.58523 |
| I-230 | | | | 1.08592 |
| I-231 | | | | 1.74538 |
| I-232 | 0.0634 | 0.04201 | | 0.89448 |
| I-233 | | | | 1.59936 |
| I-234 | 0.01355 | | | 0.22243 |
| I-235 | 0.00127 | 0.01679 | | 0.15572 |
| I-236 | 0.00241 | | | 0.12148 |
| I-237 | | | | 0.88711 |
| I-238 | 0.00394 | | | 0.11498 |
| I-239 | 0.00206 | 0.05456 | | 0.09906 |
| I-240 | | | | 0.68264 |
| I-241 | | | | 0.3608 |
| I-242 | | | | 8.19235 |
| I-243 | | | | 0.68367 |
| I-244 | 0.03408 | | | 0.24762 |
| I-245 | 0.32905 | | | 0.53908 |
| I-246 | 0.00337 | 0.00994 | | 0.11667 |
| I-247 | 0.01993 | 0.06694 | | 0.1313 |
| I-248 | 0.00275 | 0.01342 | | 0.10965 |
| I-249 | 0.01368 | | | 0.13591 |
| I-250 | 1.03883 | | | 1.49513 |
| I-251 | 0.37935 | | | 0.38386 |
| I-252 | | | | 10.1847 |
| I-253 | | | | |
| I-254 | 0.0539 | | | 0.48839 |
| I-255 | | | | 0.23578 |
| I-256 | | | | 0.24592 |
| I-257 | | | | 0.42261 |
| I-258 | | | | 0.39946 |
| I-259 | | | | 2.54286 |
| I-261 | | | | 4.66898 |
| I-262 | | | | 14.8202 |
| I-263 | | | | 10.9312 |
| I-264 | | | | 4.29727 |
| I-265 | | | | 4.32121 |
| I-266 | | | | 11.2267 |
| I-267 | | | | 11.7342 |
| I-268 | | | | 31.7452 |
| I-269 | | | | 8.20434 |
| I-270 | | | | 3.45452 |
| I-271 | | | | 0.67024 |
| I-272 | | | | 0.82631 |
| I-273 | 0.00334 | 0.00487 | | 0.2166 |
| I-274 | | | | 1.21353 |
| I-275 | | | | 0.61731 |
| I-276 | | | | 1.82935 |
| I-277 | | | | 0.20563 |
| I-278 | | | | 1.27887 |
| I-279 | | | | 7.43602 |
| I-280 | | | | 2.73321 |
| I-281 | | | | 17.117 |
| I-282 | | | | 15.331 |
| I-283 | | | | 2.6975 |
| I-284 | | | | 3.03847 |
| I-285 | | | | 1.23086 |
| I-286 | | | | 2.42472 |
| I-287 | | | | 2.19232 |
| I-288 | | | | 0.37362 |
| I-289 | | | | 0.42384 |
| I-290 | | | | 0.59601 |
| I-291 | | | | 22.3238 |
| I-292 | | | | 2.47607 |
| I-293 | | | | 2.19401 |
| I-294 | | | | 4.54933 |
| I-295 | | | | 5.10319 |
| I-296 | | | | 1.03894 |
| I-297 | | | | 24.7265 |
| I-298 | | | | 1.08417 |
| I-299 | | | | 0.52204 |
| I-300 | | | | 9999 |
| I-301 | | | | 0.9513 |
| I-302 | | | | 25.0882 |
| I-303 | | | | 17.7337 |
| I-304 | | | | 9.50635 |
| I-305 | | | | 17.9108 |
| I-306 | | | | 10.523 |
| I-307 | | | | 0.32726 |
| I-308 | | | | 0.80878 |
| I-309 | | | | 0.64183 |
| I-310 | | | | 1.41344 |
| I-311 | | | | 0.80383 |
| I-312 | | | | 1.68853 |
| I-313 | | | | 0.79346 |
| I-314 | | | | 2.57092 |
| I-315 | | | | 3.38653 |
| I-316 | | | | 3.44051 |
| I-317 | | | | 2.42487 |
| I-318 | | | | 2.50777 |
| I-319 | | | | 2.8497 |
| I-320 | | | | 6.1445 |
| I-321 | | | | 5.95092 |
| I-322 | | | | 5.79495 |
| I-323 | | | | 4.70565 |
| I-324 | | | | 4.15072 |
| I-325 | | | | 3.46363 |
| I-326 | | | | 3.08028 |
| I-327 | | | | 5.08443 |
| I-328 | 0.04571 | | | 0.2879 |
| I-329 | | | | 0.9379 |
| I-330 | | | | 1.11778 |
| I-331 | | | | 0.80579 |
| I-332 | 0.03599 | | | 0.29911 |
| I-333 | | | | 0.58591 |
| I-334 | | | | 1.01377 |
| I-335 | | | | 0.563 |
| I-336 | | | | 2.0424 |
| I-337 | 0.24941 | | | 0.31147 |
| I-338 | | | | 0.36048 |
| I-339 | 0.03184 | | | 0.18823 |
| I-340 | 0.00281 | 0.01564 | | 0.15942 |
| I-341 | 0.00055 | 0.05322 | | 0.04563 |
| I-342 | 0.00095 | 0.00157 | | 0.03181 |
| I-343 | | | | 0.31481 |
| I-344 | 0.00654 | 0.04068 | | 0.20516 |
| I-345 | | | | 5.31563 |
| I-346 | | | | 0.24763 |
| I-347 | | | | 0.61698 |
| I-348 | 0.00366 | 0.10038 | | 0.17246 |
| I-349 | | | | 1.04226 |
| I-350 | 0.00341 | 0.58904 | | 0.16122 |

TABLE VII-continued

| Compound # | PKC theta | PKC epsilon | PKC mu | Example 3 |
|---|---|---|---|---|
| I-351 | | | | 0.19768 |
| I-352 | | | | 1.06858 |
| I-353 | | | | 1.53854 |
| I-354 | | | | 0.5946 |
| I-355 | | | | 0.89303 |
| I-356 | 0.00726 | 0.04298 | | 0.09605 |
| I-357 | 0.00511 | 0.00711 | | 0.06764 |
| I-358 | 0.00211 | 0.00527 | | 0.02947 |
| I-359 | | | | 0.11819 |
| I-360 | | | | 2.20048 |
| I-361 | | | | 4.66096 |
| I-362 | | | | 0.66697 |
| I-363 | 0.00417 | 0.05477 | | 0.2328 |
| I-364 | 0.0041 | 0.02783 | | 0.27048 |
| I-365 | 0.00062 | 0.00734 | | 0.05661 |
| I-366 | 0.00171 | 0.08965 | | 0.12231 |
| I-367 | | | | 3.69735 |
| I-368 | | | | 0.29666 |
| I-369 | | | | 0.62437 |
| I-370 | | | | 0.09316 |
| I-371 | | | | 0.5496 |
| I-372 | | | | 0.09213 |
| I-373 | | | | 0.54235 |
| I-375 | 0.0012 | 0.200 | | 0.35 |
| I-376 | 0.0004 | 0.935 | | 0.26 |
| I-378 | 0.0035 | 0.0429 | | 0.31 |
| I-379 | | | | 34.50 |
| I-380 | | | | 19.48 |
| I-381 | | | | 9999 |
| I-382 | | | | 9999 |
| I-383 | | | | 30.01 |
| I-384 | | | | 9.51 |
| I-385 | | | | 1.18 |
| I-386 | | | | 3.21 |
| I-387 | | | | 3.47 |
| I-388 | | | | 0.11 |
| I-389 | | | | 5.42 |
| I-390 | | | | 0.68 |
| I-391 | | | | 0.22 |
| I-392 | | | | 4.46 |
| I-393 | | | | 0.43 |
| I-394 | | | | 2.96 |
| I-395 | | | | 0.10 |
| I-396 | | | | 0.10 |
| I-397 | | | | 1.98 |
| I-398 | | | | 0.05 |
| I-399 | | | | 0.05 |
| I-400 | | | | 1.69 |
| I-401 | | | | 3.16 |
| I-402 | | | | 0.47 |
| I-403 | | | | 0.50 |
| I-404 | | | | 0.17 |
| I-405 | | | | 0.24 |
| I-406 | | | | 0.48 |
| I-407 | | | | 2.69 |
| I-408 | | | | 1.04 |
| I-409 | | | | 0.05 |
| I-410 | | | | 1.44 |
| I-411 | | | | 0.28 |
| I-412 | | | | 6.55 |
| I-413 | | | | 6.15 |
| I-414 | | | | 0.16 |
| I-415 | 0.0005 | 0.013 | | 0.06 |
| I-416 | 0.0033 | 0.013 | | 0.08 |
| I-417 | | | | 2.67 |
| I-418 | | | | 2.19 |
| I-419 | | | | 0.27 |
| I-420 | 0.0032 | 0.115 | | 0.25 |
| I-421 | | | | 4.63 |
| I-422 | 0.0102 | 0.1649 | | 0.25 |
| I-423 | | | | 3.50 |
| I-424 | | | | 1.01 |
| I-425 | | | | 1.14 |
| I-426 | | | | 0.42 |
| I-427 | | | | 0.66 |
| I-428 | | | | 0.56 |
| I-429 | | | | 0.77 |
| I-430 | | | | 4.47 |
| I-431 | | | | 0.45 |
| I-432 | | | | 1.53 |
| I-433 | | | | 2.35 |
| I-434 | | | | 0.27 |
| I-435 | | | | 0.55 |
| I-436 | | | | 0.60 |
| I-437 | | | | 0.17 |
| I-438 | | | | 0.30 |
| I-439 | | | | 0.62 |
| I-440 | | | | 0.52 |
| I-441 | | | | 1.69 |
| I-442 | | | | 1.77 |
| I-443 | | | | 0.40 |
| I-444 | 0.0011 | 0.1574 | | 0.18 |
| I-445 | | | | 0.91 |
| I-446 | | | | 1.88 |
| I-447 | | | | 0.91 |
| I-448 | | | | 2.16 |
| I-449 | | | | 0.44 |
| I-450 | 0.0025 | 0.009 | | 0.26 |
| I-451 | | | | 0.58 |
| I-452 | | | | 1.38 |
| I-453 | | | | 1.05 |
| I-454 | | | | 6.25 |
| I-455 | 0.0013 | 0.008 | | 0.07 |
| I-456 | 0.0063 | 0.049 | | 0.35 |
| I-457 | | | | 1.67 |
| I-458 | | | | 0.79 |
| I-459 | 0.0003 | 0.022 | | 0.05 |
| I-460 | 0.0004 | 0.06 | | 0.03 |
| I-461 | 0.0008 | 0.05 | | 0.23 |
| I-462 | | | | 0.27 |
| I-463 | 0.0036 | 0.125 | | 0.59 |
| I-464 | | | | 0.18 |
| I-465 | 0.0034 | 0.115 | | 0.28 |
| I-466 | | | | 0.24 |
| I-467 | | | | 0.46 |
| I-468 | | | | 2.69 |
| I-469 | 0.0015 | 0.129 | | 0.12 |
| I-470 | 0.698 | 0.941 | | 9999 |
| I-471 | 9999 | 0.982 | | 9999 |
| II-1 | 0.00966 | 0.14433 | | 0.612 |
| II-2 | | | | 1.40198 |
| II-3 | | | | 1.84906 |
| II-4 | | | | 1.72015 |
| II-5 | 0.03781 | | | 0.561 |
| II-6 | 0.00606 | | | 0.24382 |
| II-7 | 0.05318 | | | 0.47592 |
| II-8 | 0.00243 | 0.05792 | | 0.08995 |
| II-9 | | | | 12.2834 |
| II-10 | | | | 7.24282 |
| II-11 | | | | 1.32178 |
| II-12 | | | | 4.11279 |
| II-13 | | | | 11.1709 |
| II-14 | | | | 2.5729 |
| II-15 | | | | 0.83476 |
| II-16 | | | | 1.63506 |
| II-17 | | | | 0.84459 |
| II-18 | | | | 2.1191 |
| II-19 | | | | 0.88961 |
| II-20 | | | | 2.10153 |
| II-21 | | | | 9999 |
| II-22 | | | | 37.2529 |
| II-23 | | | | 9999 |
| II-24 | | | | 11.3484 |
| II-25 | | | | 2.06772 |
| II-26 | | | | 0.95104 |
| II-27 | 0.00388 | 0.0658 | | 0.20953 |
| II-28 | | | | 0.55049 |
| II-29 | 0.00157 | 0.04859 | | 0.05108 |
| II-30 | | | | 11.1016 |
| II-31 | 0.00135 | 0.02713 | | 0.02641 |
| II-32 | | | | 0.86422 |
| II-33 | | | | 0.40665 |

TABLE VII-continued

| Compound # | PKC theta | PKC epsilon | PKC mu | Example 3 |
|---|---|---|---|---|
| II-34 | 0.01571 | 0.10181 | | 0.22374 |
| II-35 | 0.00894 | 0.15896 | | 0.14182 |
| II-36 | | | | 0.67799 |
| II-37 | | | | 1.36794 |
| II-38 | | | | 0.82719 |
| II-39 | | | | 0.96696 |
| II-40 | | | | 2.97368 |
| II-41 | | | | 1.60695 |
| II-42 | | | | 12.6853 |
| II-43 | | | | 1.467 |
| II-44 | | | | 0.29834 |
| II-45 | 0.0018 | 0.17939 | | 0.10266 |
| II-46 | | | | 0.39101 |
| II-47 | | | | 0.2289 |
| II-48 | | | | 0.26308 |
| II-49 | | | | 1.24234 |
| II-50 | | | | 0.09183 |
| II-51 | | | | 4.88438 |
| II-52 | | | | 5.61464 |
| II-53 | | | | 4.73547 |
| II-54 | | | | 0.37346 |
| II-55 | | | | 0.25835 |
| II-56 | | | | 0.96812 |
| II-57 | | | | 0.14669 |
| II-58 | | | | 0.23124 |
| II-59 | | | | 0.14762 |
| II-60 | | | | 0.71727 |
| II-61 | | | | 0.16825 |
| II-62 | | | | 0.03832 |
| II-63 | | | | 0.07718 |
| II-64 | | | | 0.84883 |
| II-65 | | | | 0.2553 |
| II-66 | | | | 0.69522 |
| II-67 | | | | 0.81132 |
| II-68 | | | | 0.26114 |
| II-69 | | | | 0.16423 |
| II-70 | | | | 0.32737 |
| II-71 | | | | 0.14513 |
| II-72 | | | | 0.16827 |
| II-73 | | | | 1.18439 |
| II-74 | | | | 0.34892 |
| II-75 | | | | 0.47576 |
| II-76 | | | | 0.17773 |
| II-77 | | | | 0.10053 |
| II-78 | | | | 0.36935 |
| II-79 | | | | 0.1524 |
| II-80 | | | | 0.19897 |
| II-81 | | | | 0.56719 |
| II-82 | | | | 0.29064 |
| II-83 | | | | 19.6149 |
| II-84 | | | | 17.512 |
| II-85 | | | | 3.66237 |
| II-86 | | | | 1.26158 |
| II-87 | | | | 3.81326 |
| II-88 | | | | 2.48311 |
| II-89 | | | | 7.67211 |
| II-90 | | | | 5.57621 |
| II-91 | | | | 3.85508 |
| II-93 | | | | 2.88 |
| II-95 | 0.0042 | 0.876 | | 0.07 |
| II-97 | 0.0025 | 9999 | | 0.50 |
| II-98 | 0.0074 | 0.087 | | 0.34 |
| II-99 | | | | 3.81 |
| II-100 | | | | 10.97 |
| II-101 | | | | 3.33 |
| II-102 | | | | 5.22 |
| II-103 | | | | 3.69 |
| II-104 | | | | 2.13 |
| II-105 | | | | 27.88 |
| II-106 | | | | 4.19 |
| II-107 | | | | 0.80 |
| II-108 | | | | 0.42 |
| II-109 | | | | 6.98 |
| II-110 | | | | 0.76 |
| II-111 | | | | 2.66 |
| II-112 | | | | 1.96 |
| II-113 | | | | 2.17 |
| II-114 | | | | 2.63 |
| II-115 | | | | 1.84 |
| II-116 | | | | 1.47 |
| II-117 | | | | 1.07 |
| II-118 | | | | 0.55 |
| II-119 | | | | 0.39 |
| II-120 | | | | 1.35 |
| II-121 | | | | 1.81 |
| II-122 | | | | 2.16 |
| II-123 | | | | 0.88 |
| II-124 | | | | 1.43 |
| II-125 | | | | 1.44 |
| II-126 | | | | 0.50 |
| II-127 | | | | 0.45 |
| II-128 | 0.0005 | 0.2021 | | 0.08 |
| II-129 | | | | 10.94 |
| II-130 | 0.0101 | 9999 | | 0.72 |
| II-131 | | | | 0.99 |
| II-132 | | | | 0.84 |
| II-133 | | | | 2.22 |
| II-134 | | | | 15.96 |
| II-135 | | | | 3.60 |
| II-136 | | | | 0.91 |
| II-137 | | | | 0.46 |
| II-138 | | | | 0.71 |
| II-139 | | | | 0.91 |
| II-140 | | | | 0.59 |
| II-141 | | | | 1.00 |
| II-142 | | | | 1.03 |
| II-143 | | | | 9999 |
| II-144 | | | | 1.08 |
| II-145 | 0.0281 | 2.6883 | | 0.37 |
| II-146 | | | | 3.13 |
| II-147 | | | | 3.57 |
| II-148 | | | | 0.99 |
| II-149 | | | | 0.99 |
| II-150 | | | | 3.58 |
| II-151 | | | | 1.25 |
| II-152 | | | | 0.54 |
| II-153 | | | | 1.80 |
| II-154 | | | | 45.49 |
| II-155 | | | | 9999 |
| II-156 | | | | 5.93 |
| II-157 | | | | 9999 |
| II-158 | | | | 7.20 |
| II-159 | | | | 8.91 |
| II-160 | | | | 17.91 |
| II-162 | | | | 1.13 |
| II-163 | 0.0061 | 0.1404 | | 0.28 |
| II-165 | | | | 0.41 |
| II-166 | | | | 0.44 |
| II-167 | | | | 2.18 |
| II-168 | | | | 5.60 |
| II-169 | | | | 3.50 |
| II-170 | | | | 15.79 |
| II-171 | 0.0024 | 0.7752 | | 0.26 |
| II-172 | | | | 0.75 |
| II-173 | | | | 1.32 |
| II-174 | | | | 2.94 |
| II-175 | | | | 1.17 |
| II-176 | | | | 2.14 |
| II-177 | 0.0164 | 1.106 | | 0.56 |
| II-178 | | | | 1.41 |
| III-1 | | | | 2.38253 |
| III-2 | 0.12966 | | | 1.05963 |
| III-3 | 0.018 | | | 0.61906 |
| III-4 | 0.03236 | | | 1.6847 |
| III-5 | | | | 3.26476 |
| III-6 | 0.25543 | | | 1.55777 |
| III-7 | 0.25373 | | | 1.13795 |
| III-8 | | | | 2.6146 |
| III-9 | | | | 9999 |
| III-10 | | | | 2.22 |
| IV-1 | | | | 0.17578 |
| IV-2 | | | | 3.14409 |

TABLE VII-continued

| | Example 2 | | | |
|---|---|---|---|---|
| Compound # | PKC theta | PKC epsilon | PKC mu | Example 3 |
| IV-3 | | | | 4.39498 |
| IV-4 | | | | 7.0503 |
| IV-5 | | | | 4.6086 |
| IV-6 | | | | 4.50895 |
| IV-7 | | | | 3.61599 |
| IV-8 | | | | 4.41497 |
| IV-9 | | | | 3.45121 |

C. Example 4

Calcium Influx

HEK-FLPTREX cells are stably transfected with pcDNA5/FRT/TO+hTRPV4a, rat TRPV1-HA or rTRPA1-HA are grown in Dulbecco's Modified Eagle's Medium (DMEM) containing 10% tetracycline-free fetal bovine serum, hygromycin (50 µg/ml) and blasticidin (10 µg/ml). Cells are treated with tetracycline (0.1 µg/ml, 20 h) to induce TRP expression. DRG from thoracic and lumbar spinal cord of rats or mice are minced in cold Hank's Balanced Salt Solution (HBSS) and incubated for 60 at 37° C. in DMEM containing 1 mg/ml of collagenase type IA and 0.1 mg/ml of DNAse type IV, pelleted and incubated with 0.25% trypsin for 30 min. Neurons are pelleted, suspended in DMEM containing 10% fetal bovine serum, 10% horse serum, 100 U/ml penicillin, 0.1 mg/ml streptomycin, 2 mM glutamine, dissociated by gentle trituration until the solution appears cloudy and homogeneous and plated on glass coverslips coated with PolyOnitine/laminin. Neurons are cultured for 3-4 days before the experiment.

Cells grown on coverslips or on a 96 multiwell plate are incubated in HBSS (pH 7.4) containing Ca2+ and Mg2+, 20 mM HEPES buffer, 0.1% BSA, 100 U/ml penicillin, 100 µg/ml streptomycin, with 2.5-5 µM Fura-2AM (Invitrogen) for 20-45 min at 37° C. Cells are washed and fluorescence is measured at 340 nm and 380 nm excitation and 510 nm emission in a F-2500 spectrophotometer, or in a Flexstation 3 Microplate Reader III (for the measurement of the calcium in the cell population) or using a Zeiss Axiovert microscope, an ICCD video camera and a video microscopy acquisition program (for the measurement of the calcium influx in the single neurons). Substances are injected directly into the chamber (20 ml into 2 ml, for the spectrophotometer; 20 ml in 200 ml for the Flexstation, 50 ml in 350 ml in the chamber for the single cells).

D. Example 5

In Vivo Hyperalgesia

Mechanical pain is quantified as the number of times the hind paw is withdrawn in response to 5 applications of a 0.173 mN von Frey hair. Responses are expressed as a percentage (e.g. 3 withdrawals out of 5 are recorded as 60%) and mechanical hyperalgesia defined as increase in the percentage of withdrawal compared to basal measurement. 2) Mechanical pain is quantified using the 'up-down paradigm', determining the 50% response threshold to the von Frey filaments applied to the mid-plantar surface for 5 s or until a withdrawal response occurred. Von Frey filaments are in this range of intensities: 1.65, 2.44, 2.83, 3.22, 3.61, 3.84, 4.08.

Thermal hyperalgesia is assessed in mice using a plantar test apparatus and quantified as the latency of paw withdrawal to a radiant heat. Thermal hyperalgesia is defined as a decrease in the withdrawal latency compared to the basal measurement. After measuring basal level mice, under light halothane anesthesia (5%), are injected with testing compound into the left or right paws (5-10 µl intraplantar injection) and paw withdrawal measurements repeated at different time point. To assess PAR2TRPV1, TRPV4 and TRPA1 mediated hyperalgesia and potentiation of TRPV-mediated responses, mice are treated with PAR2-AP for 15 min followed by capsaicin, 4αPDD or HNE. To assess the role of protein kinases, the antagonists or the corresponding vehicles are injected 20-30 minutes before the challenge with agonists. The effects induced by the different treatments are evaluated within the same rat comparing the responses recorded in the right paw (receiving for example saline, or vehicle) with the responses obtained in the left paw (receiving for example PAR2-AP or 4αPDD).

Formalin induced hyperalgesia is assessed using 5% solution of formalin administered by intradermal injection into the dorsal surface of the mouse or rat forepaw to induce a painful behavior. Pain is accessed on a four-level scale related to posture: 0, normal posture; 1, with the injected paw remaining on the ground but not supporting the animal; 2, with the injected paw clearly raised; and 3, with the injected paw being licked, nibbled, or shaken. Animals are observed and scored for behavior at 3 minutes after the injection (defined as initial phase that results from the direct stimulation of nociceptors), and then at 30-60 minutes after the injection (defined as second phase that involves a period of sensitization during which inflammatory phenomena occur). The nociceptive behavioral score for each 3-min interval is calculated as the weighted average of the number of seconds spent in each behavior. 2.5% solution of formalin is administered by intraplantar injection and thermal and mechanical pain measured as described above after 30-60 min. To assess the role of protein kinases, antagonists or their vehicles (control) are injected into the right paws 20-30 minutes before formalin. Nociceptive behavior will be scored for each rats and compared to control.

We claim:
1. A compound of formula I:

N-oxide, or therapeutically acceptable salt thereof;
wherein:
X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;
$R^1$ is selected from hydrogen, lower alkyl, substituted lower alkyl, aryl, substituted aryl, heteroaryl, and substituted heteroaryl;
each $R^{2a}$, $R^{2b}$, $R^{4a}$ and $R^{4b}$ independently is selected from hydrogen and $C_{1-3}$ alkyl;
$R^3$ is selected from —Y, —C(O)—Y, —SO$_2$—Y, —(CH$_2$)$_m$—C(O)—Y, —CH=CH—C(O)—Y and —(CH$_2$)$_m$—NY$_2$, wherein each Y independently is hydrogen, hydroxy, oxy radical, alkoxy, alkyl, or substituted alkyl and m is 1, 2, or 3;
A is selected from bicyclic aryl, bicyclic heteroaryl, tricyclic aryl, tricyclic heteroaryl and each $R^5$ independently is selected from hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;
n is an integer between 0 and 3;
p is an integer between 0 and 5;
Q is N, N→O, or CR$^{7b}$; and
R$^{7b}$ is selected from hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl;
provided that:
(1) when X is fluoro, n is zero or one, and A-(R$^5$)$_p$ is of the formula:

where each of R$^{6a}$, R$^{6b}$, R$^{7a}$, R$^{7b}$ and R$^8$ is independently R$^5$;
then
R$^{6a}$ or R$^{6b}$ is not hydrogen; or
R$^{7a}$ or R$^{7b}$ is selected from, cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, substituted heteroaryl, aminocarbonylamino, alkoxycarbonylamino, piperidinyl, substituted piperidinyl, substituted morpholinyl, pyrrolidinyl, substituted pyrrolidinyl, C-substituted piperazinyl, diazabicyclo[3.3.1]nonanyl, and thiomorpholinyl; or
R$^8$ is selected from substituted alkyl but not CF$_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, substituted heteroaryl, alkoxycarbonylamino, aminocarbonyl, piperidinyl, substituted piperidinyl, substituted morpholinyl, pyrrolidinyl, substituted pyrrolidinyl, C-substituted piperazinyl, diazabicyclo[3.3.1]nonanyl, and thiomorpholinyl; and
(2) when A is tricyclic heteroaryl and X is halo, then at least one of R$^{2a}$, R$^{2b}$, R$^{4a}$ and R$^{4b}$ is not hydrogen; and
(3) when X is nitro, CF$_3$, or C(O)NH$_2$, then at least one of R$^{2a}$, R$^{2b}$, R$^{4a}$ and R$^{4b}$ is not hydrogen; and
(4) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

2. The compound of claim 1, wherein n is 1 and each of R$^{2a}$, R$^{2b}$, R$^3$, R$^{4a}$, and R$^{4b}$ is methyl.
3. The compound of claim 1, wherein A is pyridyl.
4. The compound of claim 1, wherein A is phenyl.
5. A compound according to claim 4, wherein R$^{7a}$ or R$^{7b}$ is selected from cycloalkyl, substituted cycloalkyl, acyl, cyano, aminocarbonyl, sulfonyl, sulfonylamino, and aminosulfonyl.
6. A compound according to claim 4, wherein R$^8$ is selected from substituted alkyl, substituted alkenyl, substituted alkynyl, cycloalkyl, substituted cycloalkyl, acyl, carboxyl, carboxyl ester, cyano, sulfonyl, and sulfonylamino, wherein $R^8$ is not $CF_3$ or an amino-substituted alkyl.

7. The compound of claim 1, wherein A is a bicyclic aryl or bicyclic heteroaryl selected from:

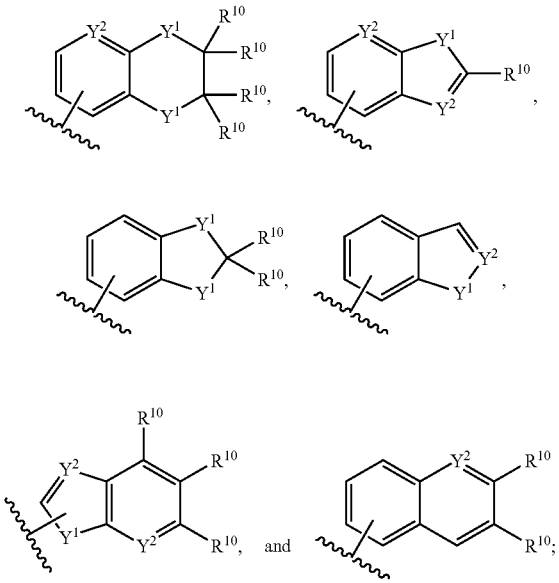

wherein:
each $Y^1$ independently is selected from —$CH_2$—, —O—, —$NR^{11}$—, —S—, and —$S(O)_2$—;
each $Y^2$ independently is selected from —CH= and —N=;
each $R^{10}$ independently is selected from hydrogen, alkyl, substituted alkyl, alkoxy, alkylthio, halo, cyano, and nitro, or two $R^{10}$ attached to the same carbon together form a $C_{4-6}$ cycloalkyl or an oxo group; and
each $R^{11}$ independently is selected from hydrogen, alkyl and substituted alkyl.

8. The compound of claim 1, wherein $R^{2a}$, $R^{2b}$, $R^{4a}$ and $R^{4b}$ each is hydrogen or methyl.

9. A compound according to claim 1, wherein X is methyl, substituted methyl or halo.

10. The compound of claim 8, wherein X is fluoro.

11. The compound of claim 1, wherein $R^1$ is hydrogen.

12. The compound of claim 1, wherein one $R^5$ is piperazinyl or C-substituted piperazinyl.

13. A compound according to claim 1, wherein X is selected from alkyl, substituted alkyl, aminocarbonyl, carboxyl ester, cyano, halo and nitro.

14. A compound having the following formula:

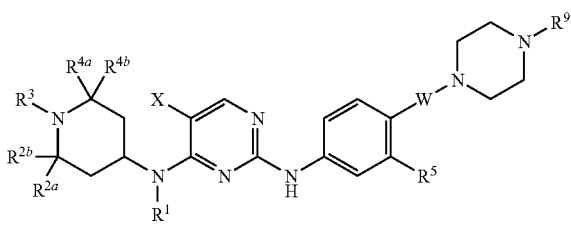

wherein:
W is a bond, —$SO_2$—, —C(O)—, or —$CH_2$—;
$R^9$ is sulfonyl;
X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;

$R^1$ is selected from hydrogen, lower alkyl, substituted lower alkyl, aryl, substituted aryl, heteroaryl, and substituted heteroaryl;

each $R^{2a}$, $R^{2b}$, $R^{4a}$ and $R^{4b}$ independently is selected from hydrogen and $C_{1-3}$ alkyl;

$R^3$ is selected from —Y, —C(O)—Y, —$SO_2$—Y, —$(CH_2)_m$—C(O)—Y, —CH=CH—C(O)—Y and —$(CH_2)_m$—$NY_2$, wherein each Y independently is hydrogen, hydroxy, oxy radical, alkoxy, alkyl, or substituted alkyl and m is 1, 2, or 3; and $R^5$ is selected from hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl.

15. A compound having the following formula:

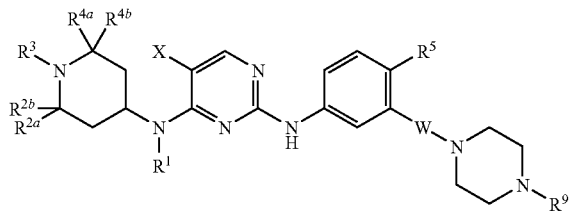

wherein:
W is a bond, —$SO_2$—, —C(O)—, or —$CH_2$—;
$R^9$ is sulfonyl;
X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;

$R^1$ is selected from hydrogen, lower alkyl, substituted lower alkyl, aryl, substituted aryl, heteroaryl, and substituted heteroaryl;

each $R^{2a}$, $R^{2b}$, $R^{4a}$ and $R^{4b}$ independently is selected from hydrogen and $C_{1-3}$ alkyl;

$R^3$ is selected from —Y, —C(O)—Y, —$SO_2$—Y, —$(CH_2)_m$—C(O)—Y, —CH=CH—C(O)—Y and —$(CH_2)_m$—$NY_2$, wherein each Y independently is hydrogen, hydroxy, oxy radical, alkoxy, alkyl, or substituted alkyl and m is 1, 2, or 3; and $R^5$ is selected from hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl.

16. A compound according to claim 1, selected from compounds of formula II:

[Structure II]

N-oxide, or therapeutically acceptable salt thereof wherein:
   X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;
   Q is N, N→O, or $CR^{7b}$;
   n is an integer between 0 and 3;
   $R^1$ is selected from hydrogen, lower alkyl, substituted lower alkyl, aryl, substituted aryl, heteroaryl, and substituted heteroaryl;
   $R^{2a}$, $R^{2b}$, $R^{4a}$ and $R^{4b}$ each independently is selected from hydrogen and $C_{1-3}$ alkyl;
   $R^3$ is selected from —Y, —C(O)—Y, —$SO_2$—Y, —$(CH_2)_m$—C(O)—Y, —CH=CH—C(O)—Y and —$(CH_2)_m$—$NY_2$, wherein each Y independently is hydrogen, hydroxy, oxy radical, alkoxy, alkyl, or substituted alkyl and m is 1, 2, or 3;
   each of $R^{6a}$, $R^{6b}$, $R^{7a}$, $R^{7b}$, and $R^8$ independently is selected from hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, sulfonyl, sulfonylamino, and aminosulfonyl;
   provided that:
   (1) when X is fluoro, and n is zero or one, then:
   $R^{6a}$ or $R^{6b}$ is not hydrogen; or
   $R^{7a}$ or $R^{7b}$ is selected from cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, substituted heteroaryl, aminocarbonylamino, alkoxycarbonylamino, piperidinyl, substituted piperidinyl, substituted morpholinyl, pyrrolidinyl, substituted pyrrolidinyl, C-substituted piperazinyl, diazabicyclo[3.3.1]nonanyl, and thiomorpholinyl; or
   $R^8$ is selected from substituted alkyl but not $CF_3$ or an amino-substituted alkyl, substituted alkenyl, substituted alkynyl, cycloalkyl, substituted cycloalkyl, acyl, carboxyl, carboxyl ester, cyano, sulfonyl, sulfonylamino, aryl, substituted aryl, heteroaryl, substituted heteroaryl, alkoxycarbonylamino, aminocarbonyl, piperidinyl, substituted piperidinyl, substituted morpholinyl, pyrrolidinyl, substituted pyrrolidinyl, C-substituted piperazinyl, diazabicyclo[3.3.1]nonanyl, and thiomorpholinyl;
   (2) when X is nitro, $CF_3$, or $C(O)NH_2$, then at least one of $R^{2a}$, $R^{2b}$, $R^{4a}$ and $R^{4b}$ not hydrogen; and (3) the compound is not 5-fluoro-N2-(4-methyl-6-(4-methylpiperazin-1-yl)pyridin-3-yl)-N4-(1,2,2,6,6-pentamethylpiperidin-4-yl)pyrimidine-2,4-diamine.

17. A method of inhibiting an activity of a Protein Kinase C theta, comprising contacting the Protein Kinase C theta with an amount of a compound effective to inhibit the activity of the Protein Kinase C theta wherein the compound is a compound of claim 16.

18. A compound according to claim 1, selected from the following compounds, N-oxides, and therapeutically acceptable salts thereof: I-342, I-356, I-357, I-358, I-365, I-370, I-372, I-374, I-387, I-388, I-389, I-391, I-392, I-393, I-394, I-395, I-397, I-398, I-399, I-400, I-402, I-403, I-404, I-405, I-407, I-409, I-414, I-415, I-416, I-420, I-424, I-454, I-455, I-456, I-457, I-458, I-459, I-460, I-461, I-462, I-463, I-464, I-465, I-466, I-467, I-468, I-469, I-470, III-10, and IV-1.

19. A method of inhibiting an activity of a Protein Kinase C theta, comprising contacting the Protein Kinase C theta with an amount of a compound effective to inhibit the activity of the Protein Kinase C theta wherein the compound is a compound of claim 18.

20. A method inhibiting an activity of a Protein Kinase C theta, comprising contacting the Protein Kinase C theta with an amount of a compound effective to inhibit the activity of the Protein Kinase C theta wherein the compound is a compound of claim 1.

21. The method of claim 20, wherein the method further comprises contacting the Protein Kinase C theta with the compound in a cell.

22. The method of claim 21, wherein said contacting occurs in vivo.

23. The method of claim 21, wherein said contacting occurs in vitro.

24. A compound according to claim 1, wherein X is cyano.

25. A compound having the following formula:

[Structure]

wherein:
   W is —$SO_2$—, —C(O)—, or —$CH_2$—;
   $R^9$ is selected from alkyl, substituted alkyl, sulfonyl, acyl, carboxyl and carboxyl ester;
   X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;
   $R^1$ is selected from hydrogen, lower alkyl, substituted lower alkyl, aryl, substituted aryl, heteroaryl, and substituted heteroaryl;
   each $R^{2a}$, $R^{2b}$, $R^{4a}$ and $R^{4b}$ independently is selected from hydrogen and $C_{1-3}$ alkyl;
   $R^3$ is selected from —Y, —C(O)—Y, —$SO_2$—Y, —$(CH_2)_m$—C(O)—Y, —CH=CH—C(O)—Y and —$(CH_2)_m$—$NY_2$, wherein each Y independently is hydrogen, hydroxy, oxy radical, alkoxy, alkyl, or substituted alkyl and m is 1, 2, or 3; and R⁵ independently is selected from hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl.

26. A compound having the following formula:

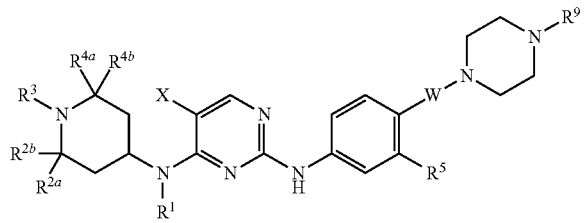

wherein:
W is a bond, —SO₂—, —C(O)—, or —CH₂—;
R⁹ is selected from alkyl, substituted alkyl, sulfonyl, acyl, carboxyl and carboxyl ester;
X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;
R¹ is selected from hydrogen, lower alkyl, substituted lower alkyl, aryl, substituted aryl, heteroaryl, and substituted heteroaryl;
each R²ᵃ, R²ᵇ, R⁴ᵃ and R⁴ᵇ independently is selected from hydrogen and C₁₋₃ alkyl;
R³ is selected from —Y, —C(O)—Y, —SO₂—Y, —(CH₂)ₘ—C(O)—Y, —CH=CH—C(O)—Y and —(CH₂)ₘ—NY₂, wherein each Y independently is hydrogen, hydroxy, oxy radical, alkoxy, alkyl, or substituted alkyl and m is 1, 2, or 3; and
R⁵ is selected from cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, substituted heteroaryl, aminocarbonylamino, alkoxycarbonylamino, piperidinyl, substituted piperidinyl, substituted morpholinyl, pyrrolidinyl, substituted pyrrolidinyl, C-substituted piperazinyl, diazabicyclo[3.3.1]nonanyl, and thiomorpholinyl.

27. A compound having the following formula:

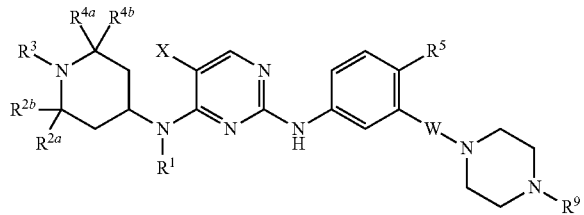

wherein:
W is —SO₂—, —C(O)—, or —CH₂—;
R⁹ is selected from alkyl, substituted alkyl, sulfonyl, acyl, carboxyl and carboxyl ester;
X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;
R¹ is selected from hydrogen, lower alkyl, substituted lower alkyl, aryl, substituted aryl, heteroaryl, and substituted heteroaryl;
each R²ᵃ, R²ᵇ, R⁴ᵃ and R⁴ᵇ independently is selected from hydrogen and C₁₋₃ alkyl;
R³ is selected from —Y, —C(O)—Y, —SO₂—Y, —(CH₂)ₘ—C(O)—Y, —CH=CH—C(O)—Y and —(CH₂)ₘ—NY₂, wherein each Y independently is hydrogen, hydroxy, oxy radical, alkoxy, alkyl, or substituted alkyl and m is 1, 2, or 3; and
R⁵ independently is selected from hydrogen, alkyl, substituted alkyl, alkoxy, substituted alkoxy, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, acylamino, alkoxycarbonylamino, aminocarbonylamino, acyl, halo, hydroxyl, carboxyl, carboxyl ester, cyano, aminocarbonyl, substituted aminocarbonyl, sulfonyl, sulfonylamino, and aminosulfonyl.

28. A compound having the following formula:

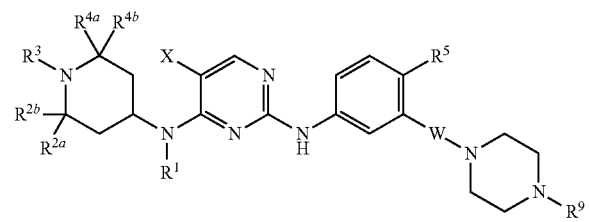

wherein:
W is a bond, —SO₂—, —C(O)—, or —CH—;
R⁹ is selected from alkyl, substituted alkyl, sulfonyl, acyl, carboxyl and carboxyl ester;
X is selected from alkyl, substituted alkyl, hydroxy, alkoxy, substituted alkoxy, amino, substituted amino, aminocarbonyl, carboxyl, carboxyl ester, cyano, fluoro, chloro, nitro, alkenyl, substituted alkenyl, alkynyl, substituted alkynyl, and trihalomethyl;
R¹ is selected from hydrogen, lower alkyl, substituted lower alkyl, aryl, substituted aryl, heteroaryl, and substituted heteroaryl;
each R²ᵃ, R²ᵇ, R⁴ᵃ and R⁴ᵇ independently is selected from hydrogen and C₁₋₃ alkyl;
R³ is selected from —Y, —C(O)—Y, —SO₂—Y, —(CH₂)ₘ—C(O)—Y, —CH=CH—C(O)—Y and —(CH₂)ₘ—NY₂, wherein each Y independently is hydrogen, hydroxy, oxy radical, alkoxy, alkyl, or substituted alkyl and m is 1, 2, or 3; and
R⁵ is selected from cycloalkyl, substituted cycloalkyl, acyl, cyano, aminocarbonyl, sulfonyl, sulfonylamino, aminosulfonyl, aryl, substituted aryl, heteroaryl other than oxadiazolyl or oxazolyl, substituted heteroaryl, aminocarbonylamino, alkoxycarbonylamino, piperidinyl, substituted piperidinyl, substituted morpholinyl, pyrrolidinyl, substituted pyrrolidinyl, C-substituted piperazinyl, diazabicyclo[3.3.1]nonanyl, and thiomorpholinyl.

29. A compound selected from the following compounds, N-oxides, and therapeutically acceptable salts thereof: I-213, I-226, I-227, I-228, I-229, I-234, I-235, I-236, I-237, I-238, I-239, I-277, I-279, I-280, I-281, I-282, I-283, I-284, I-285, I-286, I-287, I-289, I-291, I-292, I-293, I-294, I-295, I-297, I-298, I-299, I-300, I-301, I-302, I-303, I-304, I-305, I-308, I-309, I-311, I-312, I-314, I-316, I-317, I-319, I-321, I-322, I-323, I-325, I-338, I-339, I-353, I-355, I-359, I-368, I-446, and I-447.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:

```
<223> OTHER INFORMATION: Synthetic Peptide

<400> SEQUENCE: 1

Arg Phe Ala Arg Lys Gly Ser Leu Arg Gln Lys Asn Val
 1               5                  10
```